[]

US011999716B2

(12) United States Patent
Lee et al.

(10) Patent No.: US 11,999,716 B2
(45) Date of Patent: Jun. 4, 2024

(54) WDR5 INHIBITORS AND MODULATORS

(71) Applicant: Vanderbilt University, Nashville, TN (US)

(72) Inventors: Taekyu Lee, Brentwood, TN (US); Joseph R. Alvarado, Cleveland Heights, OH (US); Jianhua Tian, Nashville, TN (US); Kenneth M. Meyers, Nashville, TN (US); Changho Han, Nashville, TN (US); Jonathan J. Mills, Nashville, TN (US); Kevin B. Teuscher, Nashville, TN (US); Shaun R. Stauffer, Brentwood, TN (US); Stephen W. Fesik, Nashville, TN (US); Rocco D. Gogliotti, Kingston Springs, TN (US)

(73) Assignee: Vanderbilt University, Nashville, TN (US)

( * ) Notice: Subject to any disclaimer, the term of this patent is extended or adjusted under 35 U.S.C. 154(b) by 569 days.

(21) Appl. No.: 17/287,492

(22) PCT Filed: Oct. 24, 2019

(86) PCT No.: PCT/US2019/057877
§ 371 (c)(1),
(2) Date: Apr. 21, 2021

(87) PCT Pub. No.: WO2020/086857
PCT Pub. Date: Apr. 30, 2020

(65) Prior Publication Data
US 2023/0012362 A1    Jan. 12, 2023

Related U.S. Application Data

(60) Provisional application No. 62/749,768, filed on Oct. 24, 2018.

(51) Int. Cl.
| C07D 401/14 | (2006.01) |
| C07D 217/16 | (2006.01) |
| C07D 401/06 | (2006.01) |
| C07D 405/14 | (2006.01) |
| C07D 413/06 | (2006.01) |
| C07D 413/14 | (2006.01) |
| C07D 417/06 | (2006.01) |
| C07D 417/14 | (2006.01) |
| C07D 487/04 | (2006.01) |

(52) U.S. Cl.
CPC .......... *C07D 401/14* (2013.01); *C07D 217/16* (2013.01); *C07D 401/06* (2013.01); *C07D 405/14* (2013.01); *C07D 413/06* (2013.01); *C07D 413/14* (2013.01); *C07D 417/06* (2013.01); *C07D 417/14* (2013.01); *C07D 487/04* (2013.01)

(58) Field of Classification Search
CPC .............................. A61P 35/00; C07D 487/04
See application file for complete search history.

(56) References Cited

U.S. PATENT DOCUMENTS

| 10,246,433 | B2 * | 4/2019 | Edwards ................. A61P 35/00 |
| 10,807,959 | B2 | 10/2020 | Gogliotti et al. |
| 10,844,044 | B2 | 11/2020 | Alvarado et al. |
| 2003/0195211 | A1 | 10/2003 | Sadhu et al. |
| 2005/0124614 | A1 | 6/2005 | Gangloff et al. |
| 2008/0085890 | A1 | 4/2008 | Tsou et al. |
| 2011/0046114 | A1 | 2/2011 | Molino et al. |
| 2015/0361067 | A1 * | 12/2015 | Collins ................. C07D 413/14 544/364 |
| 2016/0347744 | A1 | 12/2016 | Corkey et al. |
| 2018/0086767 | A1 | 3/2018 | Fesik et al. |
| 2018/0265517 | A1 | 9/2018 | Marx et al. |
| 2018/0362516 | A1 | 12/2018 | Sugimoto et al. |
| 2020/0055824 | A1 | 2/2020 | Gogliotti et al. |
| 2020/0102288 | A1 | 4/2020 | Alvarado et al. |

FOREIGN PATENT DOCUMENTS

| WO | 2001081346 A2 | 11/2001 |
| WO | 2002081446 A1 | 10/2002 |
| WO | 2007122482 A1 | 11/2007 |
| WO | 2017040449 A1 | 3/2017 |
| WO | 2018068017 A1 | 4/2018 |
| WO | 2018169777 A1 | 9/2018 |
| WO | 2021026672 A1 | 2/2021 |
| WO | 2021028806 A1 | 2/2021 |

OTHER PUBLICATIONS

Balgobind et al., "The heterogeneity of pediatric MLL-rearranged acute myeloid leukemia", Leukemia, 2011, vol. 8, pp. 1239-1248.
Cao et al., "Targeting MLL1 H3K4 Methyltransferase Activity in Mixed-Lineage Leukemia", Molecular Cell, 2014, vol. 53, pp. 247-261.
Carugo et al., "In Vivo Funcitonal Platform Targeting Patient-Derived Xenografts Identifies WDR5-Myc Association as a Critical Determinant of Pancreatic Cancer", Cell Reports, 2016, vol. 16, pp. 133-147.
Caslini et al., "Interaction of MLL Amino Terminal Sequences with Menin Is Required for Transformation", Cancer Res., 2007, vol. 67, pp. 7275-7283.
Chen et al., "Upregulated WDR5 promotes proliferation, self-renewal and chemoresistance in bladder cancer via mediating H3K4 trimethylation", Scientific Reports, 2015, vol. 5, p. 8293.

(Continued)

*Primary Examiner* — Jeffrey S Lundgren
*Assistant Examiner* — Eric Tran
(74) *Attorney, Agent, or Firm* — Michael Best & Friedrich LLP

(57) ABSTRACT

Isoquinolinone compounds and derivatives inhibit WDR5 and associated protein-protein interactions, and the compounds and their pharmaceutical compositions are useful for treating disorders and conditions in a subject, such as cancer cell proliferation.

12 Claims, No Drawings

(56) References Cited

OTHER PUBLICATIONS

Dai et al., "WDR5 Expression Is Prognostic of Breast Cancer Outcome", PLoSOne, 2015, vol. 10, PMC4565643.

Dess et al., "Readily available 12-1-5 oxidant for the conversion of primary and secondary alcohols to aldehydes and ketones", J. Org. Chem., 1983, vol. 48, p. 4155.

Dias et al., "Structural analysis of the KANSL1/WDR5/KANSL2 complex reveals that WDR5 is required for efficient assembly and chromatin targeting of the NSL complex", Genes and Development, 2014, vol. 28, pp. 929-942.

Dimartino et al., "Review: MLL Rearrangements in Haematological Malignancies: Lessons from Clinical and Biological Studies", British Journal of Haematol., 1999, vol. 106, pp. 614-626.

Ee et al., "An Embryonic Stem Cell-Specific NuRD Complex Functions through Interaction with WDR5", Stem Cell Reports, 2017, vol. 8, pp. 1488-1496.

International Preliminary Report on Patentability for Application No. PCT/US19/57877 dated Apr. 27, 2021 (5 pages).

International Search Report and Written Opinion for Application No. PCT/US19/57877 dated Jan. 6, 2020 (12 pages).

Karatas et al., "Discovery of a Highly Potent, Cell-Permeable Macrocyclic Peptidomimetic (MM-589) Targeting the WD Repeat Doman 5 Protein (WDR5)-Mixed Lineage Leukemia (MLL) Protein-Protein Interaction", J. Med. Chem., 2017, vol. 60, pp. 4818-4839.

Li et al., "MOF and H4 K16 Acetylation Play Important Roles in DNA Damage Repar by Modulating Recruitment of DNA Damanage Repair Protein Mdc1", Molecular and Cellular Biology, 2010, vol. 30, pp. 5335-5347.

Littke, Fu, "Palladium-Catalyzed Coupling Reactions of Aryl Chlorides", Angew. Chem., Int. Ed., 2002, vol. 41, pp. 4176-4211.

Marschalek, "Mechanisms of leukemogenesis by MLL fusion proteins", British Journal of Haematol., 2011, vol. 152, op. 141-54.

Milne et al., "Leukemogenic MLL Fusion Proteins Bind across a Broad Region of the Hox a9 Locus, Promoting Transcription and Multiple Histone Modifications", Cancer Res., 2005, vol. 65, pp. 11367-74.

Miyaura et al., "Palladium Catalyzed Cross-Coupling Reactions of Organoboron Compounds", Chem. Rev., 1995, p. 2457.

Nakamura et al., "ALL-1 Is a Histone Methyltransferase that Assemblesl a Supercomplex of Proteins Involved in Transcriptional Regulation", Mol. Cell., 2002, vol. 10, pp. 1119-1128.

Patel et al., "On the Mechanism of Multiple Lysine Methylation by the Human Mixed Lineage Luekemia Protein-1 (MLL1) Core Complex", Biol. Chem., 2009, vol. 284, pp. 24242-56.

Pigazzi et al., "MLL Partner genes drive distinct gene expression profiles and genomic alterations in pediatric actute myeloid leukemia: an AIEOP study", Leukemia, 2011, vol. 25, pp. 560-563.

Pui et al., "Clinical heterogeneity in childhood acute lymphoblastic leukemia with 11q23 rearrangements", Leukemia, 2003, vol. 4, pp. 700-706.

Senisterra et al., "Small-molecule inhibition of MLL activity by disruption of its interaction with WDR5", Biochem J., 2013, vol. 449, pp. 151-159.

Slany, "The molecular biology of mixed lineage leukemia", Haematologica, 2009, vol. 94, pp. 984-993.

Song et al., "WDR5 Interacts with Mixed Lineage Leukemia (MLL) Protein via the Histone H3-binding Pocket", J. Biol. Chem., 2008, vol. 283, pp. 35258-64.

Sun et al., "WDR5 Supports an N-Myc Transcriptional Complex That Drives a Protumorigenic Gene Expression Signature in Neuroblastoma", Cancer Research, 2015, vol. 75, pp. 5143-5154.

Tamai et al., "11q23/MLL Acute Leukemia: Update of Clinical Aspects", J. Clin. Exp. Hematop., 2010, vol. 50, pp. 91-98.

Tan et al., "PI3K/AKT-mediated upregulation of WDR5 promotes colorectal cancer metastasis by directly targeting ZNF407", Cell Death & Disease, 2017, vol. 8, e2686, 12 pages.

Tkachuk et al., "Involvement of a Homolog of *Drosophila* Trithorax by 11q23 Chromosomal Translocations in Acute Leukemias", Cell, 1992, vol. 71, pp. 691-700.

Thomas et al., "Interaction with WDR5 Promotes Target Gene Recognition and Tumorigenesis by MYC", Molecular Cell, 2015, vol. 58, pp. 440-452.

Tian et al.,, "Discovery and Structure Based Optimization of Potent and Selective WD Repeat Domain 5 (WDR5) Inhibitors Containing a Dihydroisoquinolinone Bicyclic Core", J. Med. Chem., 2020, vol. 63, pp. 656-675.

Tomizawa et al., "Outcome of risk-based therapy for infant acute lymphoblastic leukemia with or without an MLL gene jearrangement, with emphasis on late effects: a final report of two consecutive studies, MLL96 and MLL98, of the Japan Infant Leukemia Study Group", Leukemia, 2007, vol. 21, pp. 2258-2263.

Wolff, "The Schmidt Reaction", Organic Reactions, 2011, pp. 307-336.

Yokoyama et al., "The Menin Tumor Suppressor Protein Is an Essential Oncogenic Cofactor for MLL-Associated Leukemogenesis", Cell, 2005, vol. 123, pp. 207-218.

Yokoyama et al., "Leukemia Proto-Oncoprotein MLL Forms a SET1-Like Histone Methyltransferase Complex with Menin to Regulate Hox Gene Expression", Mol. Cell Biol., 2004, vol. 24, pp. 5639-5649.

Yu et al., "MLL, a mammalian trithorax-group gene, functions as a transcriptional maintenance factor in morphogenesis", Proc. Natl. Acad. Sci., 1998, vol. 95, pp. 10632-10636.

Milne et al., "MLL Targets SET Domain Methyltransferase Activity to Hox Gene Promoters", Mol. Cell, 2002, vol. 10, pp. 1107-17.

European Patent Office. Extended European Search Report for application 19877356.6, dated May 24, 2022, 7 pages.

* cited by examiner

WDR5 INHIBITORS AND MODULATORS

RELATED APPLICATIONS

This patent application is the U.S. national stage entry, under 35 U.S.C. § 371, of International Application Number PCT/US2019/057877, filed Oct. 24, 2019, which claims priority to U.S. Provisional Application No. 62/749,768, filed Oct. 24, 2018, the entire contents of each of which are hereby incorporated by reference.

STATEMENT OF GOVERNMENT INTEREST

This invention was made with government support under Contract No. HHSN261200800001E, awarded by the NCI Experimental Therapeutics (NExT) Program. The government has certain rights in the invention.

TECHNICAL FIELD

The present invention relates generally to compounds that inhibit the binding of transcription factors, regulatory regulators, and chromatin to WDR5 and methods of use thereof. In particular embodiments, the present invention provides compositions comprising imino-azacycle-benzamide compounds and methods of use thereof to inhibit or modulate the interaction of WDR5 with chromatin, cognate transcription and other regulatory factors, including for example the histone methyltransferase MLL1, for the treatment of leukemia, solid cancers and other diseases dependent on activity of WDR5.

BACKGROUND

Mixed lineage leukemia (MLL) presents a heterogeneous group of acute myeloid leukemia and acute lymphoblastic leukemia bearing features of more than one hematopoietic cell lineage. MLL accounts for about 80% of infant acute leukemia cases (Tomizawa, D.; et. al. *Leukemia*, 2007, 21, 2258-63.) and 10% of all acute leukemia cases (Marschalek, R. *Br. J. Haematol.* 2011, 152, 141-54.). MLL leukemia patients have a poor prognosis with overall 5-year survival ratio around 35% (Dimartino, J. F.; Cleary, M. L., *Br. J. Haematol.* 1999, 106, 614-626; Pui, C., et al. *Leukemia*, 2003, 4, 700-706.; Tomizawa, D.; et. al. *Leukemia*, 2007, 21, 2258-63.).

MLL is composed of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila trithorax* (Trx) (Thachuk, D. C.; et al. *Cell*, 1992, 71, 691-700.). Wild type MLL binds to regulatory regions of homeox (HOX) genes (Milne, T. A.; et al. *Cancer Res.*, 2005, 65, 11367-74.) through the amino terminal fragment while the catalytic C-terminal domain catalyzes the Histone 3 lysine 4 (H3K4) methylation via interaction with WDR5 and up regulates target gene transcription (Nakamura, T.; et al. *Mol. Cell*, 2002, 10, 1119-28; Yokoyama, A. et al. *Mol. Cell Biol.*, 2004, 24, 5639-49.; Milne, T. A.; et al. *Mol. Cell*, 2002, 10, 1107-17). Wild type MLL in conjunction with WDR5 is required for maintenance HOX genes expression and is widely expressed not only during embryo development but also in adult tissues including myeloid and lymphoid cells (Yu, B. D.; et al. *Proc. Natl. Acad. Sci.*, 1998, 95, 10632-10636.). Reciprocal translocations of MLL gene result in-frame fusion of the 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, C., et al. *Leukemia*, 2003, 4, 700-706; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, C.; et al. *Cancer Res.*, 2007, 67, 7275-83.; Yokoyama, A.; et al. *Cell*, 2005, 123, 207-18.). The numerous chromosomal translocations of MLL gene and partner genes add to the complexity of MLL leukemia treatment. Although HOX9 and MEIS1 overexpression are commonly observed among MLL leukemia patients, each rearrangement leads to distinct dysregulated target gene expression patterns and downstream events (Slany, R. K., *Haematologica*, 2009, 94, 984-993). Clinical studies reveal that MLL of different chromosomal translocations are associated with different prognosis and are treated differently under current protocols (Tamai, H., et al. *J. Clin. Exp. Hematop.*, 2010, 50, 91-98; Balgobind, B. V., et al. *Leukemia*, 2011, 8, 1239-1248; Pigazzi, M.; et al. *Leukemia*, 2011, 25, 560-563).

Intrinsic histone methyltransferase (HMT) activity of MLL1 is extremely low and requires a complex assembly of WDR5, RbBP5, ASH2L, and DPY30 protein partners for effective H3K4 trimethylation, the so-called WRAD complex (Patel, A.; et al. *J. Biol. Chem.*, 2009, 284, 24242-56). The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, F.; et al. *Molecular Cell*, 2014, 53, 247-61., Karatas, H.; et al. *J. Med. Chem.*, 2017, 60, 4818-4839.). In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. In addition to the highly characterized WDR5-MLL1 interaction, disruption of WDR5 with other transcription factors/ epigenetic writers or displacement from chromatin itself could have a desirable benefit as a cancer treatment strategy. For example, WDR5 acts as a scaffold protein with the following chromatin complexes/structures, including histone H3 (via R2 residues, e.g. see Song, J.-J., et al. *J. Biol. Chem.* 2008, 283, 35258-64), NSL/MOF (Li, X., et al. *Molecular and Cellular Biology*, 2010, 30, 5335-47., Dias, J., et al. *Genes & Development*, 2014, 28, 929-942.), C/EBP☐ p30 (Senisterra, G., et al. *Biochem. 1*, 2013, 449, 151-159.), c-MYC (Thomas, L. R.; et al. *Molecular Cell*, 2015, 58, 440-52, herein incorporated by reference in its entirety), and the NuRD complex (Ee, L.-S., et al. *Stem Cell Reports*, 2017, 8, 1488-96.). In addition, WDR5 expression levels have been reported to be correlative and connected to patient prognosis in several other cancer types, including neuroblastoma (Sun, Y. et al. *Cancer Research*, 2015, 75, 5143-54.), breast cancer (Dai, X. et al. *PLoSOne,* 2015, 10, PMC4565643), bladder cancer (Chen, X. et al. *Scientific Reports,* 2015, 5, 8293.), and colorectal cancer (Tan, X. et al. *Cell Death & Disease,* 2017, 8, PMC5386518). In addition, in an unbiased shRNA screen in human xenografts, WDR5 was identified as an important target in pancreatic cancer (Carugo, A. et al. Cell Reports, 2016, 16, 133-147.). Based on the growing number of complexes identified, which utilize WDR5 to maintain tumor fitness and growth, the emerging importance of WDR5 in several cancer types is not unexpected. In the case of the c-MYC-WDR5 interaction, the MYC oncoprotein utilizes a molecularly defined interaction with WDR5 to bind to its target genes on chromatin. MYC is overexpressed in a majority of malignancies and contributes to an estimated 70,000-100,000 cancer deaths per year in the United States. Thus, disruption of WDR5 from chromatin as a strategy to displace MYC from its target genes may provide a beneficial strategy to treat MYC-driven tumors.

SUMMARY

The molecules described herein can inhibit or modulate the interaction of WDR5 with chromatin, cognate transcription and other regulatory factors, including for example the histone methyltransferase MLL1, and can provide a therapeutic approach to treat cancers associated with such interactions (e.g., the MLL1-WDR5 interaction).

In one aspect, the invention provides compounds of formula (I),

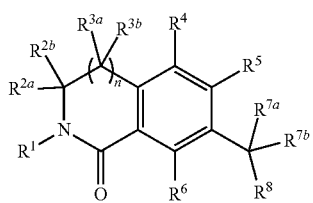

(I)

or a pharmaceutically acceptable salt thereof, wherein:

n is 0, 1, or 2;

$R^1$ is $G^1$ or $-(CR^aR^b)_p-G^1$;

p is 1, 2, or 3;

$G^1$ is a 6- to 12-membered aryl, a 5- to 12-membered heteroaryl, a 4- to 12-membered heterocyclyl, or a $C_{3-10}$carbocyclyl attached to the parent molecular moiety and optionally fused to a 6-membered arene or to a 5- to 6-membered heteroarene, wherein $G^1$ is optionally substituted with 1-5 substituents independently selected from the group consisting of halogen, $C_{1-6}$alkyl, $C_{1-6}$haloalkyl, $C_{2-6}$alkenyl, $C_{2-6}$alkynyl, oxo, $-OR^{1a}$, $-N(R^{1a})_2$, $-SR^{1a}$, cyano, $-C(O)OR^{1a}$, $-C(O)N(R^{1a})_2$, $-C(O)R^{1a}$, $-SOR^{1b}$, $-SO_2R^{1b}$, $-SO_2N(R^{1a})_2$, $-NR^{1a}C(O)R^{1a}$, $-NR^{1a}C(O)OR^{1a}$, $-NR^{1a}C(O)N(R^{1a})_2$, $-NR^{1a}S(O)_2R^{1b}$, $-NR^{1a}S(O)_2N(R^{1a})_2$, $-OC_{1-3}$alkylene-Y-$R^{1a}$, and -$L^1$-$G^{1a}$;

$R^{1a}$, at each occurrence, is independently hydrogen, $C_{1-6}$alkyl, $C_{1-6}$haloalkyl, $G^{1a}$, or $-C_{1-6}$alkylene-$G^{1a}$; wherein alternatively two $R^{1a}$, together with a common nitrogen atom to which the $R^{1a}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, $-OH$, and $-OC_{1-4}$alkyl;

$R^{1b}$, at each occurrence, is independently $C_{1-6}$alkyl, $C_{1-6}$haloalkyl, $G^{1a}$, or $-C_{1-6}$alkylene-$G^{1a}$;

Y is $-C(O)O-$, $-C(O)N(R^{1a})-$, $-C(O)-$, $-SO_2-$, or $-SO_2N(R^{1a})-$;

$L^1$ is a bond or $C_{1-3}$alkylene;

$G^{1a}$, at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $-N(R^{1c})_2$, $-SR^{1c}$, cyano, $-C(O)OR^{1c}$, $-C(O)N(R^{1c})_2$, $-C(O)R^{1c}$, $-SOR^{1d}$, $-SO_2R^{1d}$, $-SO_2N(R^{1c})_2$, $-NR^{1c}C(O)R^{1c}$, $-NR^{1c}C(O)OR^{1c}$, $-NR^{1c}C(O)N(R^{1c})_2$, $-NR^{1c}S(O)_2R^{1d}$, and $-NR^{1c}S(O)_2N(R^{1d})_2$;

$R^a$, at each occurrence, is independently hydrogen, $C_{1-4}$alkyl, $C_{1-4}$haloalkyl, $-C_{1-6}$alkylene-$R^{aa}$, $G^{1b}$, or $-C_{1-6}$alkylene-$G^{1b}$, wherein each $C_{1-6}$alkylene is optionally substituted with 1-4 halogen;

$R^{aa}$, at each occurrence, is independently $-OR^{1e}$, $-N(R^{1e})_2$, $-SR^{1e}$, cyano, $-C(O)OR^{1e}$, $-C(O)N(R^{1e})_2$, $-C(O)R^{1e}$, $-SOR^{1f}$, $-SO_2R^{1f}$, $-SO_2N(R^{1e})_2$, $-NR^{1e}C(O)R^{1e}$, $-NR C(O)OR^{1e}$, $-NR^{1e}C(O)N(R^{1e})_2$, $-NR^{1e}S(O)_2R^{1f}$, or $-NR^{1e}S(O)_2N(R^{1e})_2$;

$G^{1b}$, at each occurrence, is independently a $C_{3-6}$carbocyclyl or a 4- to 10-membered heterocyclyl, wherein the $C_{3-6}$carbocyclyl and 4- to 10-membered heterocyclyl are optionally substituted with 1-4 substituents independently selected from the group consisting of halogen, $C_{1-4}$alkyl, $C_{1-4}$haloalkyl, oxo, $-OR^{1e}$, $-N(R^{1e})_2$, $-SR^{1e}$, cyano, $-C(O)OR^{1e}$, $-C(O)N(R^{1e})_2$, $-C(O)R^{1e}$, $-SOR^{1f}$, $-SO_2R^{1f}$, $-SO_2N(R^{1e})_2$, $-NR^{1e}C(O)R^{1e}$, $-NR^{1e}C(O)OR^{1e}$, $-NR^{1e}C(O)N(R^{1e})_2$, $-NR^{1e}S(O)_2R^{1f}$, and $-NR^{1e}S(O)_2N(R^{1e})_2$;

$R^b$ is hydrogen or $C_{1-4}$alkyl;

or alternatively one $R^a$ and one $R^b$ together with the carbon atom to which they are attached form a 3-8 membered saturated or partially unsaturated carbocyclic or heterocyclic ring;

or alternatively one $R^a$ and one $R^b$ are taken together to form an oxo group;

$R^{2a}$, $R^{2b}$, $R^{3a}$, and $R^{3b}$ are independently hydrogen, halogen, $C_{1-4}$alkyl, $C_{1-4}$haloalkyl, or $-OC_{1-4}$alkyl; or alternatively any two of $R^{2a}$, $R^{2b}$, $R^{3a}$, and $R^{3b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$haloalkyl, and $-OC_{1-4}$alkyl;

or alternatively one $R^{3a}$ and one $R^{3b}$ are taken together to form an oxo group;

$R^4$ is hydrogen, halogen, $C_{1-6}$alkyl, $C_{1-6}$haloalkyl, $C_{1-6}$haloalkenyl, $-OR^{4a}$, $-SR^{4a}$, $-N(R^{4a})_2$, $-S(O)R^{4b}$, $-S(O)_2R^{4b}$, $-S(O)_2N(R^{4a})_2$, $-C(O)N(R^{4a})_2$, $-C(O)R^{4a}$, $-NR^{4a}C(O)R^{4a}$, $-NR^{4a}-C(O)OR^{4a}$, $-NR^{4a}C(O)N(R^{4a})_2$, $-NR^{4a}S(O)_2R^{4b}$, $-NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or $-C_{1-3}$alkylene-$G^2$;

$R^{4b}$ is $C_{1-6}$alkyl, $C_{1-6}$haloalkyl, $G^2$, or $-C_{1-3}$alkylene-$G^2$;

$G^2$, at each occurrence, is independently a $C_{3-10}$carbocyclyl, a 6- to 12-membered aryl, a 5- to 12-membered heteroaryl, or a 4- to 12-membered heterocyclyl, wherein $G^2$ is optionally substituted with 1-5 substituents independently selected from the group consisting of halogen, $C_{1-6}$alkyl, $C_{1-6}$haloalkyl, oxo, $-OR^{4c}$, —N(R$^{4c}$)$_2$, cyano, —C(O)OR$^{4c}$, —C(O)N(R$^{4c}$)$_2$, —C(O)R$^{4c}$, —SOR$^{4d}$, —SO$_2$R$^{4d}$, —SO$_2$N(R$^{4c}$)$_2$, —NR$^{4c}$C(O)R$^{4c}$, —NR$^{4c}$C(O)OR$^{4c}$, —NR$^{4c}$C(O)N(R$^{4c}$)$_2$, —NR$^{4c}$S(O)$_2$R$^{4d}$, —NR$^{4c}$S(O)$_2$N(R$^{4c}$)$_2$, C$_{3-8}$cycloalkyl, and —C$_{1-3}$alkylene-C$_{3-8}$cycloalkyl, wherein each C$_{3-8}$cycloalkyl is optionally substituted with 1-4 substituents independently selected from the group consisting of C$_{1-4}$alkyl and halogen;

R$^{1c}$, R$^{1e}$, and R$^{4c}$, at each occurrence, are independently hydrogen, C$_{1-6}$alkyl, C$_{1-6}$haloalkyl, C$_{3-8}$cycloalkyl, or —C$_{1-6}$alkylene-C$_{3-8}$cycloalkyl, wherein each C$_{3-8}$cycloalkyl is optionally substituted with 1-4 substituents independently selected from the group consisting of C$_{1-4}$alkyl and halogen, wherein alternatively two R$^{1c}$, two R$^{1e}$, and/or two R$^{4c}$, together with a common nitrogen atom to which the R$^{1c}$, R$^{1e}$, and/or R$^{4c}$ attach form a 4- to 8-membered saturated or partially unsaturated heterocyclic ring, optionally substituted with 1-4 substituents independently selected from the group consisting of C$_{1-4}$alkyl, C$_{1-4}$haloalkyl, oxo, —OH, and —OC$_{1-4}$alkyl;

R$^{1a}$, R$^{1f}$ and R$^{5d}$, at each occurrence, are independently C$_{1-6}$alkyl, C$_{1-6}$haloalkyl, C$_{3-8}$cycloalkyl, or C$_{1-6}$alkylene-C$_{3-8}$cycloalkyl, wherein each C$_{3-8}$cycloalkyl is optionally substituted with 1-4 substituents independently selected from the group consisting of C$_{1-4}$alkyl and halogen;

R$^5$ and R$^6$ are each independently hydrogen, halogen, C$_{1-4}$alkyl, C$_{1-4}$haloalkyl, or —OC$_{1-4}$alkyl;

R$^{7a}$ and R$^{7b}$ are independently selected from the group consisting of hydrogen, halogen, C$_{1-4}$alkyl, and C$_{1-4}$haloalkyl, or R$^{7a}$ and R$^{7b}$ are taken together to form an oxo group;

R$^8$ is

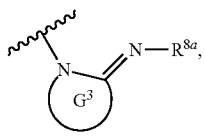

imidazolyl, triazolyl,

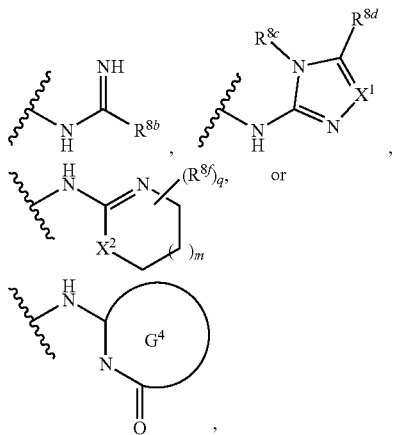

wherein the imidazolyl and triazolyl are optionally fused to a 6-membered arene and the optionally fused imidazolyl and triazolyl are optionally substituted with 1-3 substituents independently selected from the group consisting of halogen, cyano, C$_{1-4}$alkyl, C$_{1-4}$haloalkyl, NH$_2$, —NH(C$_{1-4}$alkyl), —N(C$_{1-4}$alkyl)$_2$, C$_{3-8}$cycloalkyl, and —C$_{1-3}$alkylene-C$_{3-8}$cycloalkyl, wherein each C$_{3-8}$cycloalkyl is optionally substituted with 1-4 substituents independently selected from the group consisting of halogen, C$_{1-4}$alkyl, C$_{1-4}$haloalkyl, OH, and —OC$_{1-4}$alkyl;

X$^1$ is N or CR$^{8e}$;
X$^2$ is C(R$^{8f}$)$_2$, O, or NR$^{8f}$;
m is 0, 1, or 2;
q is 0, 1, 2, 3, or 4;

G$^3$ is a 5- to 12-membered heterocyclic ring system containing a first nitrogen at the point of attachment and optionally 1-4 additional heteroatoms selected from the group consisting of oxygen, nitrogen, and sulfur, G$^3$ having the imine substituent =NR$^{8a}$ adjacent to the first nitrogen and being optionally substituted with 1-4 substituents independently selected from the group consisting of halogen, oxo, C$_{1-6}$alkyl, C$_{1-6}$haloalkyl, G$^{3a}$, and —C$_{1-3}$alkylene-G$^{3a}$;

G$^4$ is a 5- to 12-membered heterocyclic ring system attached at a first carbon atom and containing a first nitrogen bonded to the first carbon atom, G$^4$ having a first oxo substituent adjacent to the first nitrogen and being optionally substituted with 1-4 substituents independently selected from the group consisting of halogen, oxo, C$_{1-6}$alkyl, and C$_{1-6}$haloalkyl;

R$^{8a}$ is hydrogen, C$_{1-4}$alkyl, C$_{3-6}$cycloalkyl, C(O)C$_{1-4}$alkyl, or C(O)OC$_{1-4}$alkyl;

R$^{8b}$ is —N(R$^{8g}$)$_2$, C$_{1-6}$alkyl, C$_{1-6}$haloalkyl, G$^{3a}$, or C$_{1-3}$alkylene-G$^{3a}$;

R$^{8c}$, R$^{8d}$, and R$^{8e}$, are each independently hydrogen, halogen, C$_{1-4}$alkyl, C$_{1-4}$haloalkyl, C$_{3-8}$cycloalkyl, or —C$_{1-3}$alkylene-C$_{3-8}$cycloalkyl, wherein each C$_{3-8}$cycloalkyl is optionally substituted with 1-4 substituents independently selected from the group consisting of halogen, C$_{1-4}$alkyl, C$_{1-4}$haloalkyl, OH, and —OC$_{1-4}$alkyl, wherein alternatively, R$^{8d}$ and R$^{8c}$, together with the atoms to which each attaches form a 5- to 6-membered ring containing 0-2 double bonds, or R$^{8d}$ and R$^{8e}$, together with the atoms to which each attaches form a 5- to 6-membered ring containing 1-3 double bonds;

R$^{8f}$, at each occurrence, is independently hydrogen, C$_{1-4}$alkyl, C$_{1-4}$haloalkyl, G$^{3a}$, or —C$_{1-3}$alkylene-G$^{3a}$, wherein optionally two R$^{8f}$ are taken together to form an oxo group, a 3-8 membered saturated or partially unsaturated carbocyclic ring, or a 3-8 membered saturated or partially unsaturated heterocyclic ring having 1-4 heteroatoms independently selected from the group consisting of nitrogen, oxygen, or sulfur;

R$^{8g}$, at each occurrence, is independently hydrogen, C$_{1-6}$alkyl, C$_{1-6}$haloalkyl, G$^{1a}$, or —C$_{1-3}$alkylene-G$^{3a}$; and G$^{3a}$ is C$_{3-10}$carbocyclyl or a 6- to 12 membered aryl, wherein G$^{3a}$ is optionally substituted with 1-4 substituents independently selected from the group consisting of halogen, C$_{1-4}$alkyl, C$_{1-4}$haloalkyl, OH, and —OC$_{1-4}$alkyl.

In another aspect, the invention provides a pharmaceutical composition comprising a compound of formula (I), or a pharmaceutically acceptable salt thereof, and a pharmaceutically acceptable carrier.

In another aspect, the invention provides a method for the treatment of cancer, comprising administering to a subject in need thereof a therapeutically effective amount of a compound of formula (I), or a pharmaceutically acceptable salt or composition thereof.

In another aspect, the invention provides a method for inhibiting the binding of MLL1 to WDR5, comprising administering to a subject in need thereof a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of cancer.

In another aspect, the invention provides a compound of formula (I), or a pharmaceutically acceptable salt or composition thereof, for use in the inhibition of binding of MLL1 to WDR5.

In another aspect, the invention provides the use of a compound of formula (I), or a pharmaceutically acceptable salt or composition thereof, in the manufacture of a medicament for the treatment of cancer.

In another aspect, the invention provides the use of a compound of formula (I), or a pharmaceutically acceptable salt or composition thereof, in the manufacture of a medicament for the inhibition of binding of MLL1 to WDR5.

In another aspect, the invention provides a kit comprising a compound of formula (I), or a pharmaceutically acceptable salt or composition thereof, and instructions for use.

DETAILED DESCRIPTION

Disclosed herein are inhibitors of WDR5, which bind at the WDR5 interaction or WIN-site. The inhibitors can be compounds of formula (I). Compounds of formula (I) can be used to treat cancers associated with the MLL1-WDR5 interaction. In one aspect, disclosed are compounds of formula (I) as WDR5-WIN-site inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched chain hydrocarbon, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "aryl," as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term "phenyl" is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term "cycloalkyl" or "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl" or "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1] heptenyl). Exemplary monocyclic cycloalkenyl rings include cyclopentenyl, cyclohexenyl or cycloheptenyl.

The term "carbocyclyl" means a "cycloalkyl" or a "cycloalkenyl." The term "carbocycle" means a "cycloalkane" or a "cycloalkene." The term "carbocyclyl" refers to a "carbocycle" when present as a substituent.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The term "heteroaryl" is used herein to refer to a heteroarene when present as a substituent. The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. The bicyclic heteroaryl is an 8- to 12-membered ring system having a monocyclic heteroaryl ring fused to a 6-membered arene (e.g., quinolinyl), fused to a monocyclic carbocyclic ring (e.g., 6,7-dihydro-5H-cyclopenta[b]pyridinyl), fused to a monocyclic heteroarene (e.g., naphthyridinyl), or fused to a monocyclic heterocycle (e.g., 2,3-dihydrofuro[3,2-b]pyridinyl). A bicyclic heteroaryl/heteroarene group includes a 9-membered fused bicyclic aromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-c]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, and tetrahydroisoquinolinyl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, azaadamantane (1-azatricyclo[3.3.1.1³,⁷]decane), and oxa-adamantane (2-oxatricyclo[3.3.1.1³,⁷]decane). The monocyclic, bicyclic, and tricyclic heterocycles are connected to the parent molecular moiety at a non-aromatic ring atom.

The term "imino" refers to the group "=NH."

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a sub scripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups may include, for example, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed are compounds of formula (I), wherein $R^1$, $R^{2a}$, $R^{2b}$, $R^{3a}$, $R^{3b}$, $R^4$, $R^5$, $R^6$, $R^{7a}$, $R^{7b}$, $R^8$, and n are as defined herein. Embodiments of formula (I) include the following descriptions of $R^1$, $R^{2a}$, $R^{2b}$, $R^{3a}$, $R^{3b}$, $R^4$, $R^5$, $R^6$, $R^7$, $R^{7b}$, $R^8$, and n, and any combinations thereof.

In some embodiments, $R^8$ is

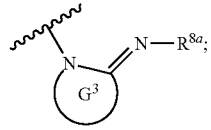

wherein $G^3$ is a 5- to 12-membered heterocyclic ring system containing a first nitrogen at the point of attachment and optionally 1-4 additional heteroatoms selected from the group consisting of oxygen, nitrogen, and sulfur, $G^3$ having the imine substituent =$NR^{8a}$ adjacent to the first nitrogen and being optionally substituted with 1-4 substituents independently selected from the group consisting of halogen, oxo, $C_{1-6}$alkyl, $C_{1-6}$haloalkyl, $G^{3a}$, and —$C_{1-3}$alkylene-$G^{3a}$; $R^{8a}$ is hydrogen, $C_{1-4}$alkyl, $C_{3-6}$cycloalkyl, $C(O)C_{1-4}$alkyl, or $C(O)OC_{1-4}$alkyl; and $G^{3a}$ is $C_{3-10}$carbocyclyl or a 6- to 12 membered aryl, wherein $G^{3a}$ is optionally substituted with 1-4 substituents independently selected from the group consisting of halogen, $C_{1-4}$alkyl, $C_{1-4}$haloalkyl, OH, and —$OC_{1-4}$alkyl. In some embodiments, the 5- to 12-membered heterocyclic ring system at $G^3$ is a 5- to 8-membered monocyclic heterocyclyl or a 8- to 12-membered fused heterocyclyl, optionally substituted as described herein. In some embodiments, the optional substituents of $G^3$ are selected from the group consisting of halogen (e.g., fluoro), $C_{1-4}$alkyl (e.g., methyl), $C_{1-4}$haloalkyl (e.g., difluoromethyl), $C_{3-8}$cycloalkyl (e.g., cyclopropyl), and $C_{1-3}$alkylene-$C_{3-8}$cycloalkyl. In the embodiments described herein, $R^8$ may be hydrogen.

In some embodiments, $R^8$ is

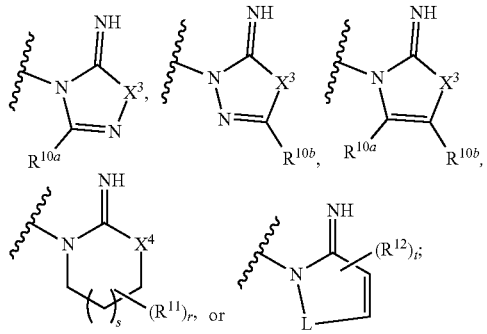

wherein $X^3$ is $NR^{13}$, O, or S; $X^4$ is $C(R^{14a})(R^{14b})$, $NR^{13}$, O, or S; $R^{10}$ and $R^{10b}$ are independently hydrogen, halogen, $C_{1-4}$alkyl, or $C_{1-4}$haloalkyl; $R^{11}$, at each occurrence, is independently halogen, $C_{1-4}$alkyl, $C_{1-4}$haloalkyl, or two $R^{11}$ optionally form an oxo; L is a $C_{1-2}$alkylene or a $C_2$alkenylene; $R^{12}$, at each occurrence, is independently halogen, $C_{1-4}$alkyl, or $C_{1-4}$haloalkyl, wherein alternatively, two $R^{12}$ on adjacent carbon atoms together are a $C_{3-4}$alkylene or a $C_4$alkenylene group that forms a fused ring with the atoms to which the two $R^{12}$ attach; $R^{13}$ is hydrogen, $C_{1-4}$alkyl, $C_{1-4}$haloalkyl, $C_{3-8}$cycloalkyl, —$C_{1-3}$alkylene-$C_{3-8}$cycloalkyl, or phenyl, each phenyl and cycloalkyl being further optionally substituted with 1-4 substituents independently selected from the group consisting of halogen, $C_{1-4}$alkyl, $C_{1-4}$haloalkyl, OH, and —$OC_{1-4}$alkyl; wherein alternatively, $R^{10b}$ and $R^{13}$ together are a $C_{3-4}$alkylene or a $C_4$alkenylene group that forms a fused ring with the atoms to which the $R^{10b}$ and $R^{13}$ attach; $R^{14a}$ and $R^{14b}$ are independently hydrogen or $C_{1-4}$alkyl; s is 0, 1, or 2; and r and t are each independently 0, 1, 2, 3, or 4, and $R^1$, $R^{2a}$, $R^{2b}$, $R^{3a}$, $R^{3b}$, $R^4$, $R^5$, $R^6$, $R^{7a}$, and n are as defined herein.

$R^8$ may be

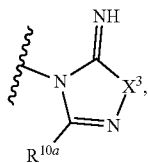

wherein $X^3$ and $R^{10a}$ are as defined herein. $X^3$ may be $NR^{13}$ or S; and $R^{10a}$ and $R^{13}$ are as defined herein. In some embodiments, $R^{10a}$ is hydrogen and $R^{13}$ is $C_{1-4}$alkyl.

$R^8$ may be

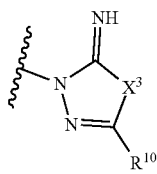

wherein $X^3$ and $R^{10b}$ are as defined herein. $X^3$ may be $NR^{13}$; and $R^{10b}$ and $R^{13}$ are as defined herein. In some embodiments, $R^{10b}$ and $R^{13}$ together are a $C_4$alkenylene group that forms a fused ring with the atoms to which the $R^{10b}$ and $R^{13}$ attach, such as where $R^8$ is

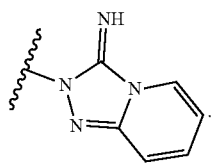 [SMILES: *n1nc2ccccn2c1=N]

$R^8$ may be

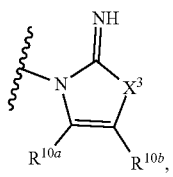

wherein $X^3$, $R^{10a}$, and $R^{10b}$ are as defined herein. $X^3$ may be $NR^{13}$, O, or S; and $R^{10a}$, $R^{10b}$, and $R^{13}$ are as defined herein. In some embodiments, $R^{10a}$ and $R^{10b}$ are independently hydrogen or halogen (e.g., fluoro); and $R^{13}$ is hydrogen, $C_{1-4}$alkyl (e.g., methyl), $C_{1-4}$haloalkyl (e.g., difluoromethyl), or $C_{3-8}$cycloalkyl (e.g., cyclopropyl). In other embodiments, $R^{10b}$ and $R^{13}$ together are a $C_{3-4}$alkylene group that forms a fused ring with the atoms to which the $R^{10b}$ and $R^{13}$ attach; and $R^{10a}$ is as defined herein (e.g., $R^8$ is

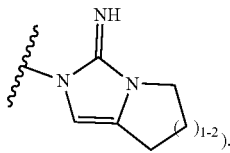

In still further embodiments, $R^{10a}$ is hydrogen.

$R^8$ may be

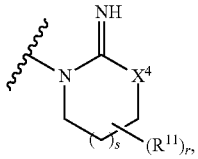

wherein $R^{11}$, $X^4$, r, and s are as defined herein. $X^4$ may be $C(R^{14a})(R^{14b})$, $NR^{13}$, O, or S; and s, r, $R^{11}$, $R^{13}$, $R^{14a}$ and $R^{14b}$ are as defined herein. In some embodiments, s is 0 or 1; r is 0, 1, or 2; $R^{11}$, at each occurrence, is independently $C_{1-4}$alkyl, or two optionally form an oxo; and $R^{13}$ is hydrogen, $C_{1-4}$alkyl (e.g., methyl), or $C_{3-8}$cycloalkyl (e.g., cyclopropyl).

$R^8$ may be

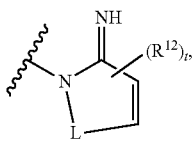

wherein L, $R^{12}$, and t are as defined herein. In some embodiments, L is a $C_{1-2}$alkylene or a $C_2$alkenylene; $R^{12}$, at each occurrence, is independently halogen, $C_{1-4}$alkyl, or $C_{1-4}$haloalkyl, wherein alternatively, two $R^{12}$ on adjacent carbon atoms together are a $C_4$alkenylene group that forms a fused ring with the atoms to which the two $R^{12}$ attach; and t is 0, 1, or 2. In further embodiments, L is a $C_{1-2}$alkylene and two $R^{12}$ on adjacent carbon atoms together are a $C_4$alkenylene group that forms a fused ring with the atoms to which the two $R^{12}$ attach (e.g.,

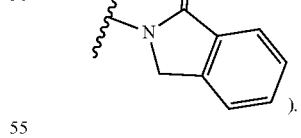

In other further embodiments, L is a $C_2$alkenylene; $R^{12}$, at each occurrence, is independently halogen, $C_{1-4}$alkyl, or $C_{1-4}$haloalkyl; and t is 0 or 1 (e.g.,

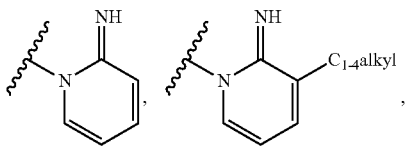

-continued
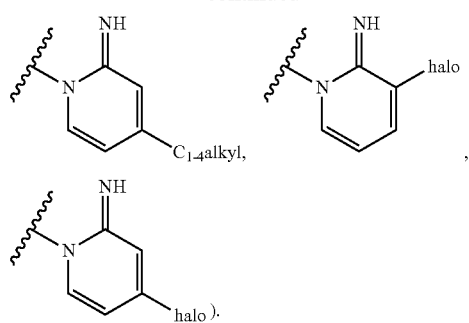
$R^8$ may be
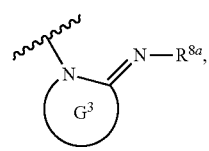
which is
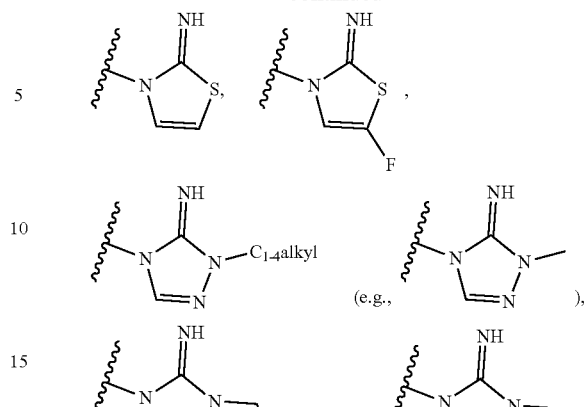
-continued
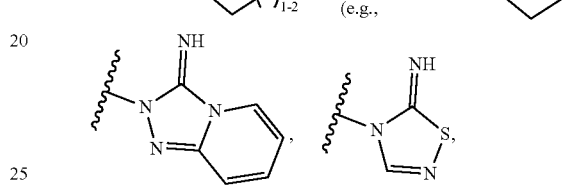
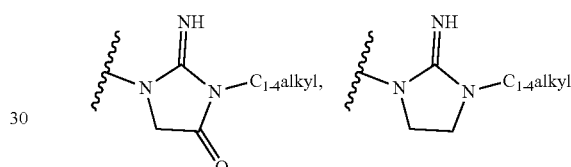
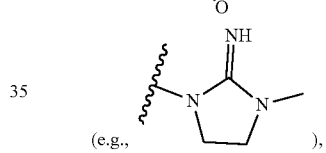
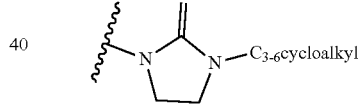
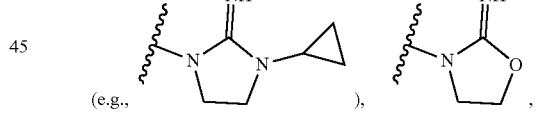
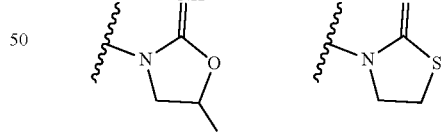
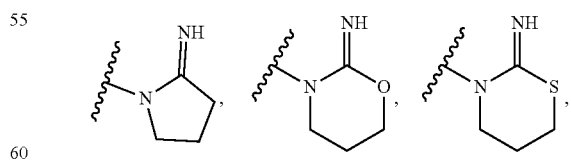
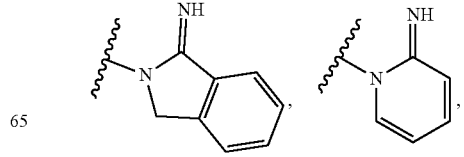

-continued

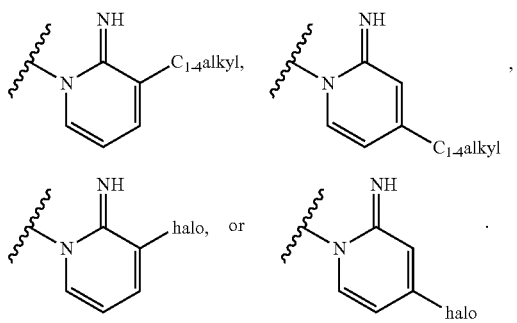

In some embodiments, $R^8$ is the optionally fused imidazolyl or triazolyl, as defined herein. In further embodiments, the optionally fused imidazolyl or triazolyl at $R^8$ are selected from the group consisting of

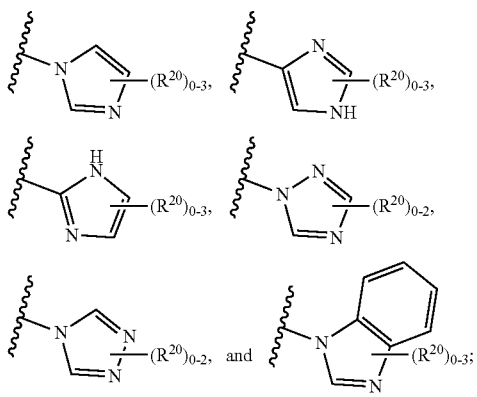

and $R^{20}$, at each occurrence, is independently halogen, cyano, $C_{1-4}$alkyl (e.g., methyl, ethyl, isopropyl), $C_{1-4}$haloalkyl, $NH_2$, —$NH(C_{1-4}alkyl)$ (e.g., —$NHCH_3$), —$N(C_{1-4}alkyl)_2$, $C_{3-8}$cycloalkyl (e.g., cyclopropyl), or —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl. In still further embodiments, the optionally fused imidazolyl or triazolyl at $R^8$ are selected from the group consisting of

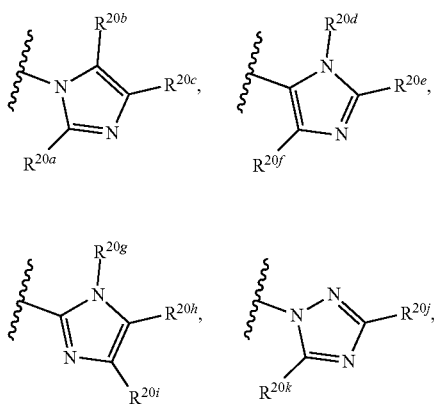

-continued

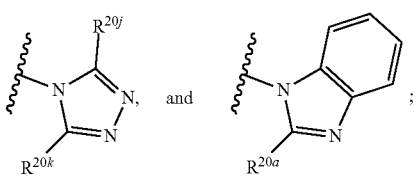

$R^{20a}$ is hydrogen, cyano, $C_{1-4}$alkyl (e.g., methyl, ethyl, isopropyl), $NH_2$, —$NH(C_{1-4}alkyl)$ (e.g., —$NHCH_3$), —$N(C_{1-4}alkyl)_2$, or $C_{3-8}$cycloalkyl (e.g., cyclopropyl); and $R^{2b}$, $R^{20c}$, $R^{20d}$, $R^{20e}$, $R^{20f}$, $R^{20g}$, $R^{20h}$, $R^{20i}$, $R^{20j}$, and $R^{20k}$, are each independently hydrogen, $C_{1-4}$alkyl (e.g., methyl, ethyl), or $C_{3-8}$cycloalkyl. In yet further embodiments, the optionally fused imidazolyl or triazolyl at $R^8$ are selected from the group consisting of

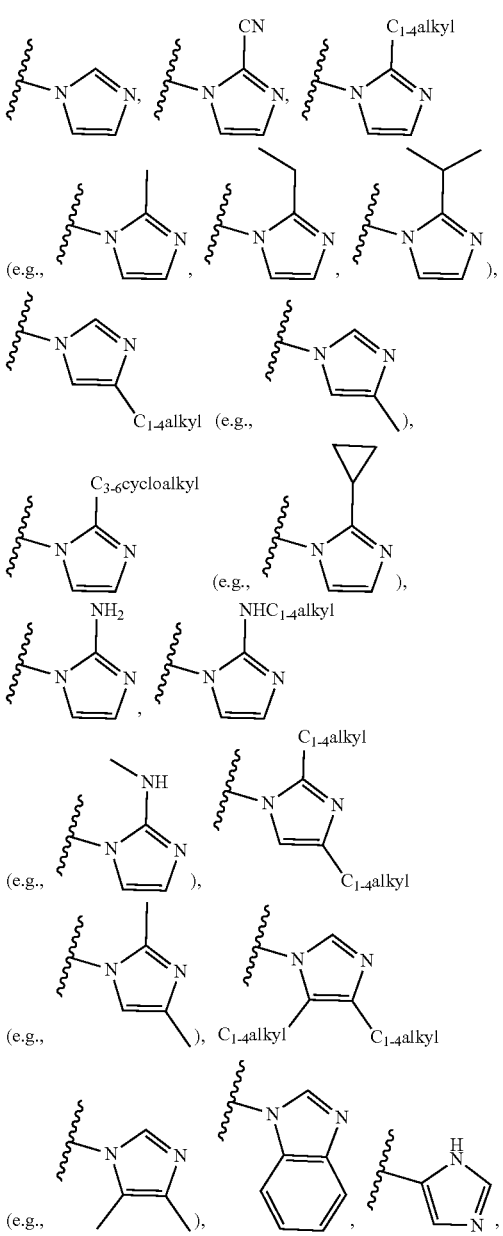

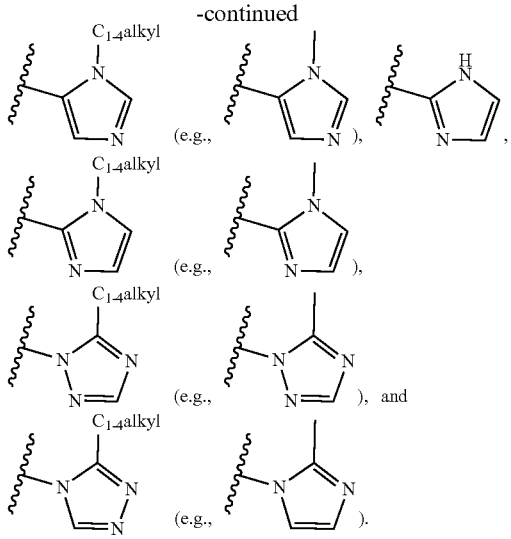

In some embodiments, R$^8$ is the imidazolyl or triazolyl as defined herein. In further embodiments, the imidazolyl or triazolyl at R$^8$ are selected from the group consisting of

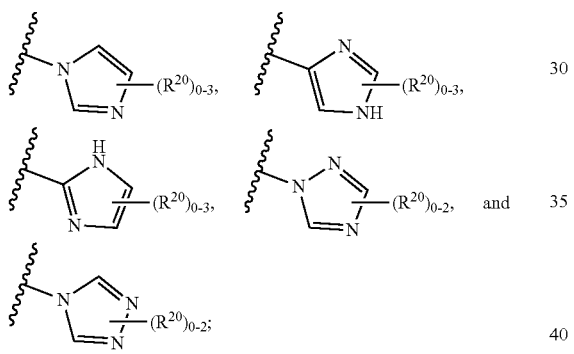

and R$^{20}$, at each occurrence, is independently halogen, C$_{1-4}$alkyl (e.g., methyl, ethyl), C$_{1-4}$haloalkyl, NH$_2$, —NH(C$_{1-4}$alkyl), —N(C$_{1-4}$alkyl)$_2$, C$_{3-8}$cycloalkyl (e.g., cyclopropyl), or —C$_{1-3}$alkylene-C$_{3-8}$cycloalkyl, wherein each C$_{3-8}$cycloalkyl is optionally substituted with 1-4 substituents independently selected from the group consisting of halogen, C$_{1-4}$alkyl, C$_{1-4}$haloalkyl, OH, and —OC$_{1-4}$alkyl. In still further embodiments, the imidazolyl or triazolyl at R$^8$ are selected from the group consisting of

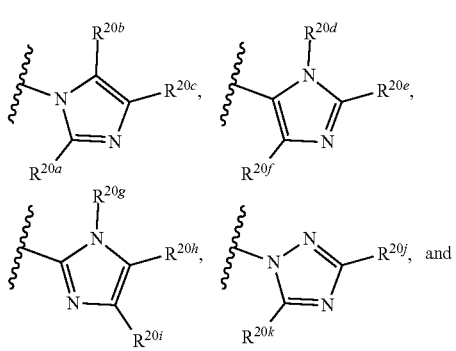

R$^{0a}$ is hydrogen, C$_{1-4}$alkyl (e.g., methyl, ethyl), NH$_2$, —NH(C$_{1-4}$alkyl), N(C$_{1-4}$alkyl)$_2$, or C$_{3-8}$cycloalkyl (e.g., cyclopropyl); and R$^{20b}$, R$^{20c}$, R$^{20d}$, R$^{20e}$, R$^{20f}$, R$^{20g}$, R$^{20h}$, R$^{20i}$, R$^{20j}$, and R$^{20k}$, are each independently hydrogen, C$_{1-4}$alkyl (e.g., methyl), or C$_{3-8}$cycloalkyl. In still further embodiments, R$^m$a is hydrogen, C$_{1-4}$alkyl (e.g., methyl, ethyl), NH$_2$, or C$_{3-8}$cycloalkyl (e.g., cyclopropyl); R$^{20b}$, R$^{20e}$, R$^{20f}$, R$^{20g}$, R$^{20h}$, R$^{20i}$, and R$^{20j}$ are each hydrogen; and R$^{20c}$, R$^{20d}$, and R$^{20k}$ are each independently hydrogen or C$_{1-4}$alkyl (e.g., methyl). In yet further embodiments, the imidazolyl or triazolyl at R$^8$ are selected from the group consisting of

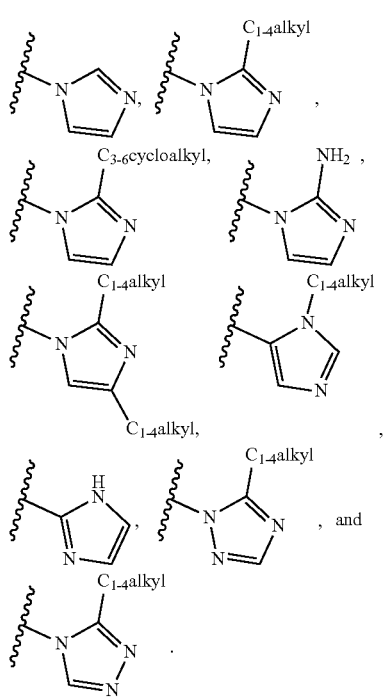

In some embodiments, R$^8$ is

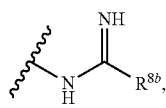

wherein R$^{8b}$ is as defined herein. In further embodiments, R$^{8b}$ is C$_{1-6}$alkyl, C$_{1-6}$haloalkyl (e.g., CF$_3$), G$^{3a}$, or C$_{1-3}$alkylene-G$^{3a}$; and G$^{3a}$ is C$_{3-6}$cycloalkyl (e.g., cyclopropyl) optionally substituted with 1-4 substituents independently selected from the group consisting of halogen and C$_{1-4}$alkyl. In still further embodiments, R$^{8b}$ is C$_{1-6}$haloalkyl (e.g., CF$_3$) or C$_{3-6}$cycloalkyl (e.g., cyclopropyl). In yet further embodiments, R$^{8b}$ is CF$_3$ or cyclopropyl.

In some embodiments, R⁸ is

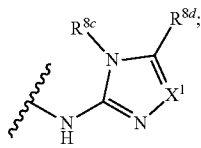

and $R^{8c}$, $R^{8d}$ and $X^1$ are as defined herein. In further embodiments, $R^{8d}$ and $R^{8c}$, together are a $C_{3-4}$alkylene or a $C_4$alkenylene group that, with the atoms to which $R^{8d}$ and $R^{8c}$ attach, form a 5- to 6-membered ring containing 0-2 double bonds and $X^1$ is as defined herein. In still further embodiments, $R^{8d}$ and $R^{8c}$, together are a $C_4$alkenylene group that, with the atoms to which $R^{8d}$ and $R^{8c}$ attach, form a 6-membered ring containing 2 double bonds; and $X^1$ is N (i.e.,

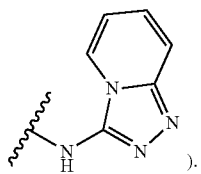

In some embodiments, R⁸ is

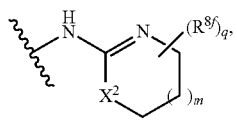

wherein $X^2$, $R^f$, q, and m are as defined herein. In further embodiments, R⁸ is

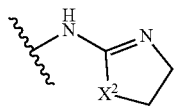

and $X^2$ is $CH_2$, O, or NH.

In some embodiments, R⁸ is

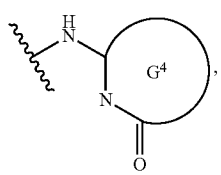

wherein $G^4$ is as defined herein. In further embodiments, $G^4$, together with the oxo substituent is a pyridone (i.e., R⁸ is

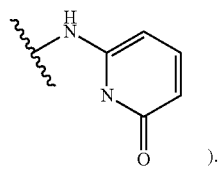 [SMILES: *Nc1cccc(=O)[nH]1]

).

$R^1$ is —$(CR^aR^b)_p$-$G^1$; and $R^a$, $R^b$, and p are as defined herein. In embodiments of the invention, $R^1$ is —$(CR^aR^b)_p$-$G^1$; and p is 1. In embodiments when p is 1, $G^1$ may be a phenyl or a 5- to 6-membered heteroaryl, wherein $G^1$ is optionally substituted as defined herein. The 5- to 6-membered heteroaryl of $G^1$ may contain 1-3 nitrogen atoms. $G^1$ further may be a phenyl, pyridinyl, pyrazolyl, or triazolyl, where $G^1$ is optionally substituted as defined herein. $G^1$ as defined herein, may be substituted with 1-3 substituents independently selected from the group consisting of halogen (e.g., fluoro, chloro), $C_{1-6}$alkyl (e.g., methyl, ethyl), $C_{1-6}$haloalkyl, —$OR^{1a}$ (e.g., $OCH_3$), —$N(R^{1a})_2$, —$SR^{1a}$, cyano, —$C(O)OR^{1a}$, —$C(O)N(R^{1a})_2$, —$C(O)R^{1a}$, —$SO_2R^{1b}$, —$NR^{1a}C(O)R^{1a}$, $C_{3-8}$cycloalkyl (e.g., cyclopropyl), and —$C_{1-3}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein $R^{1a}$ and $R^{1b}$ are as defined herein. $G^1$, as defined herein, may be substituted with 1-3 substituents independently selected from the group consisting of halogen (e.g., fluoro, chloro), $C_{1-6}$alkyl (e.g., methyl, ethyl), —$OC_{1-6}$alkyl (e.g., $OCH_3$), and $C_{3-8}$cycloalkyl (e.g., cyclopropyl). In the embodiments described herein, $G^1$ may

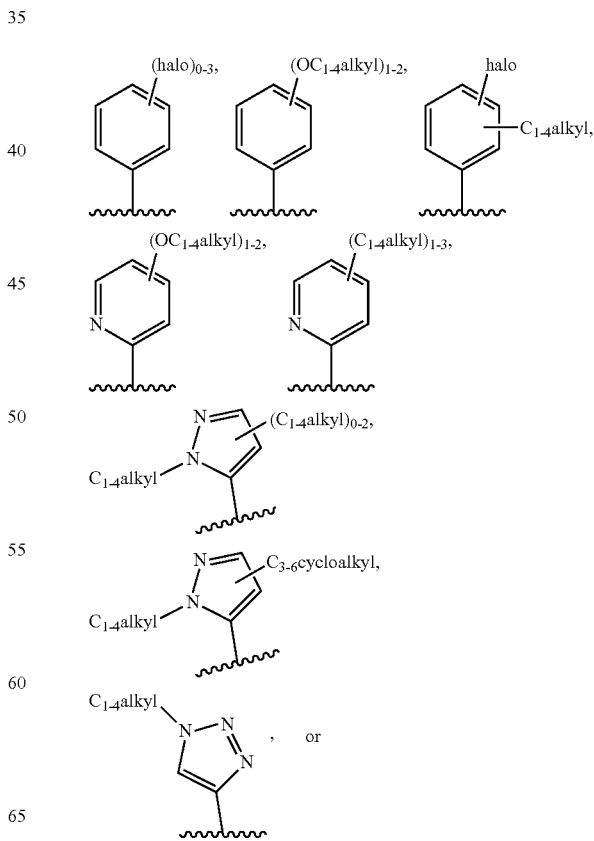

-continued

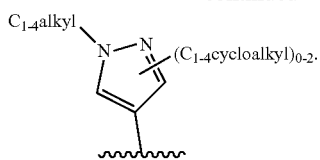

In the embodiments described herein, $G^1$ may further be

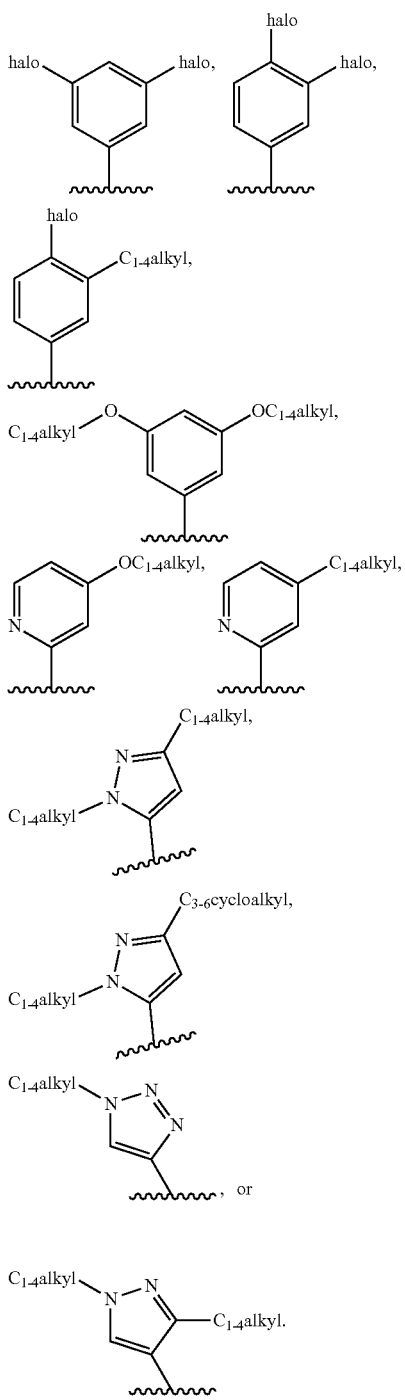

In the embodiments described herein, $G^1$ may still further be

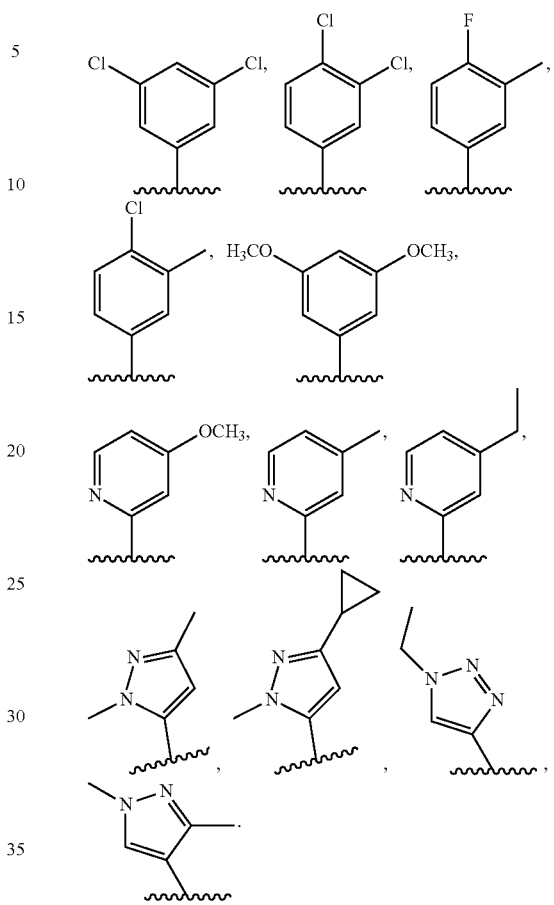

In embodiments of the invention, $R^1$ is $-(CR^aR^b)_pG^1$; p is 1; and $G^1$ is (a) phenyl, (b) naphthyl, (c) phenyl attached to the parent molecular moiety and fused to a 5- to 7-membered heterocycle containing 1-2 heteroatoms independently selected from oxygen, nitrogen, and sulfur, (d) a 5- to 6-membered heteroaryl, (e) a 8- to 12-membered fused bicyclic heteroaryl, or (f) a 4- to 8-membered heterocyclyl, wherein $G^1$ is optionally substituted as defined herein. The 5- to 6-membered heteroaryl may contain 1-3 ring heteroatoms selected from nitrogen, oxygen, and sulfur. The 8- to 12-membered fused bicyclic heteroaryl may be a monocyclic heteroaryl fused to a monocyclic heteroarene, wherein the bicyclic heteroaryl contains 1-3 ring heteroatoms selected from the group consisting of nitrogen, oxygen, and sulfur. For example, $G^1$ may be optionally substituted phenyl, naphthyl, benzo[d][1,3]dioxol-5-yl, dihydrobenzofuran-7-yl, pyridinyl, pyridazinyl, pyrazolyl, triazolyl, oxazolyl, thiazolyl, isoxazolyl, thiadiazolyl, oxadiazolyl, indolyl, quinolinyl, tetrahydropyranyl, or piperidinyl. The optional substituents may be 1-3 substituents independently selected from the group consisting of halogen, $C_{1-6}$alkyl, $C_{1-6}$haloalkyl, $C_{2-6}$alkenyl, oxo, $-OR^{1a}$, $-N(R^{1a})_2$, $-SR^{1a}$, cyano, $-C(O)OR^{1a}$, $-C(O)N(R^{1a})_2$, $-C(O)R^{1a}$, $-SO_2R^{1b}$, $-NR^{1a}C(O)R^{1a}$, $-L^1G^{1a}$, and $-OC_{1-3}$alkylene-$Y-R^{1a}$, wherein $G^{1a}$ is optionally substituted with 1-4 substituents independently selected from the group consisting of $C_{1-4}$alkyl and halogen, wherein Y is $-C(O)O$ or $-C(O)N(R^{1a})-$. The optional substituents may be halogen (e.g., F, Cl, Br), $C_{1-4}$alkyl (e.g., methyl, ethyl, isopropyl), $C_{2-4}$alkenyl (e.g., vinyl), $C_{1-4}$haloalkyl (e.g., $C_{1-4}$fluoroalkyl like CF$_3$), oxo, —OC$_{1-4}$alkyl (e.g., OCH$_3$), —OC$_{1-4}$haloalkyl (e.g., —OC$_{1-4}$fluoroalkyl like OCF$_3$), G$^{1a}$, or —OC$_{1-3}$alkylene-Y—C$_{1-3}$alkylene-G$^{1a}$, wherein G$^{1a}$ is as defined herein.

In the compounds of the invention, G$^{1a}$ may be a C$_{3-6}$cycloalkyl (e.g., cyclopropyl), a 5- to 6-membered heteroaryl (e.g. thienyl, pyridyl), or a 9- to 10-membered heteroaryl (e.g., indazolyl), wherein G$^{1a}$ is optionally substituted with 1-4 substituents independently selected from the group consisting of C$_{1-4}$alkyl and halogen. For example, in an optional G$^1$ substituent —OC$_{1-3}$alkylene-Y—R$^{1a}$, R$^{1a}$ may be G$^{1a}$ or C$_{1-3}$alkylene-G$^{1a}$, wherein G$^{1a}$ is optionally substituted pyridinyl (e.g.,

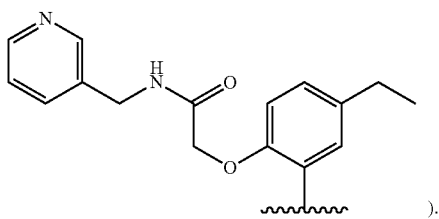 [SMILES: *c1cc(CC)ccc1OCC(=O)NCc1cccnc1]
).

In a further example, in an optional G$^1$ substituent G$^{1a}$, G$^{1a}$ may be a C$_{3-6}$cycloalkyl(e.g., cyclopropyl as in

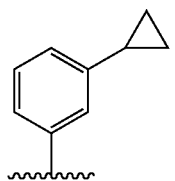
)

or a 5-membered heteroaryl (e.g. thienyl as in

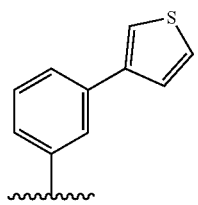
).

When p is 1, G$^1$ may be

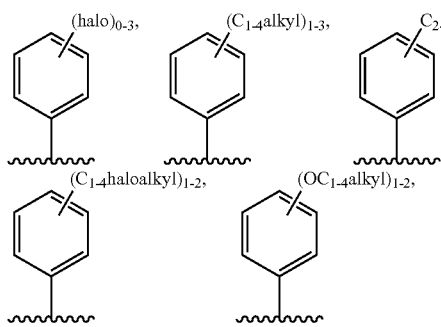

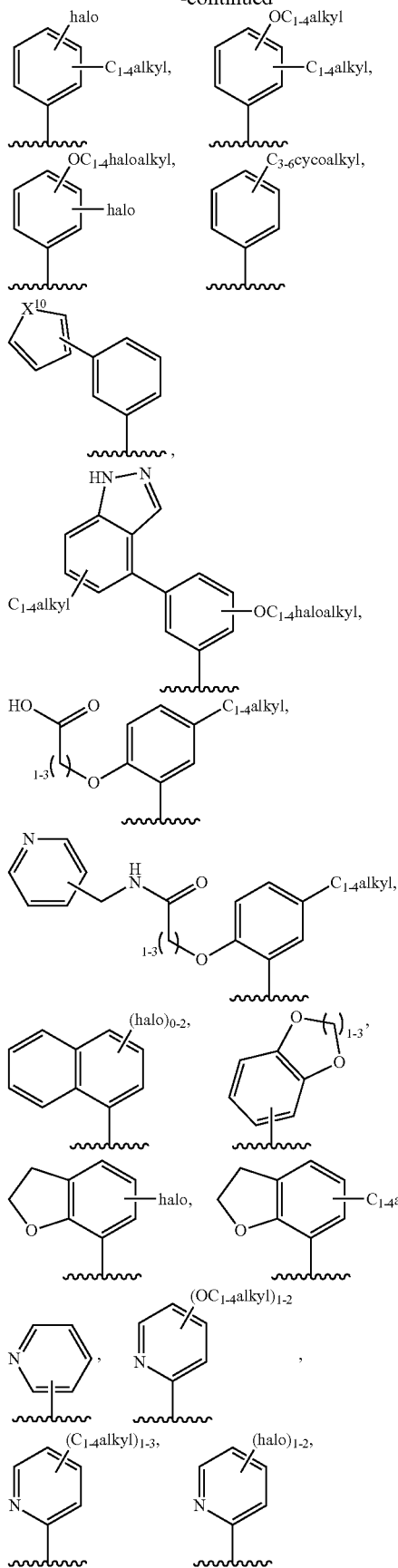

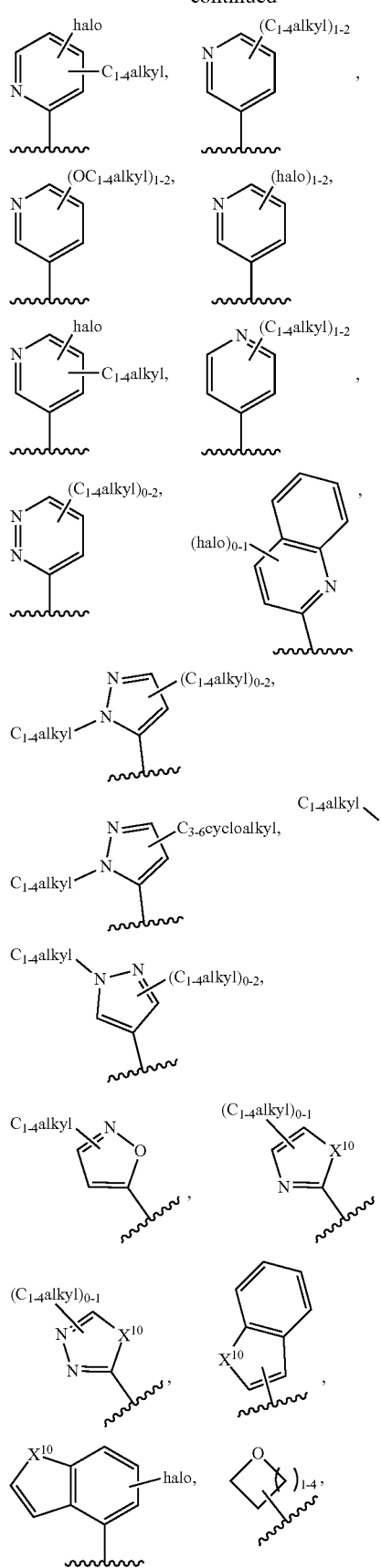
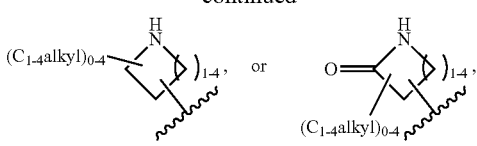
wherein $X^{10}$ is O, S, NH, or $NC_{1-4}$alkyl. When p is 1, $G^1$ may be
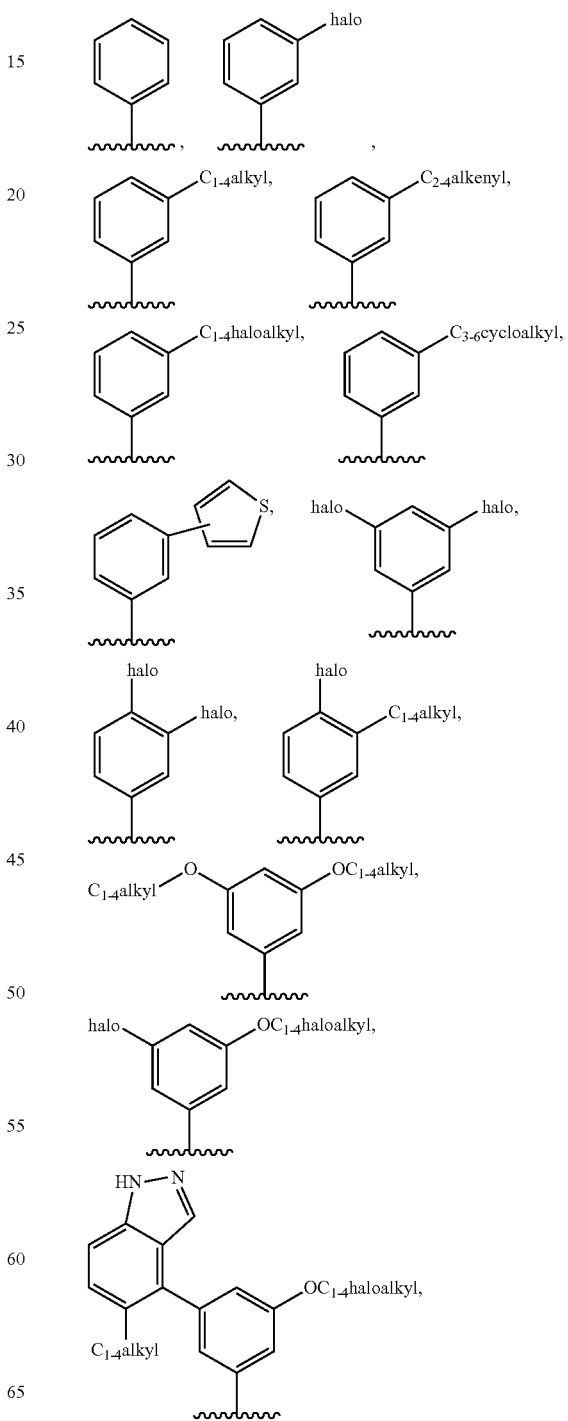

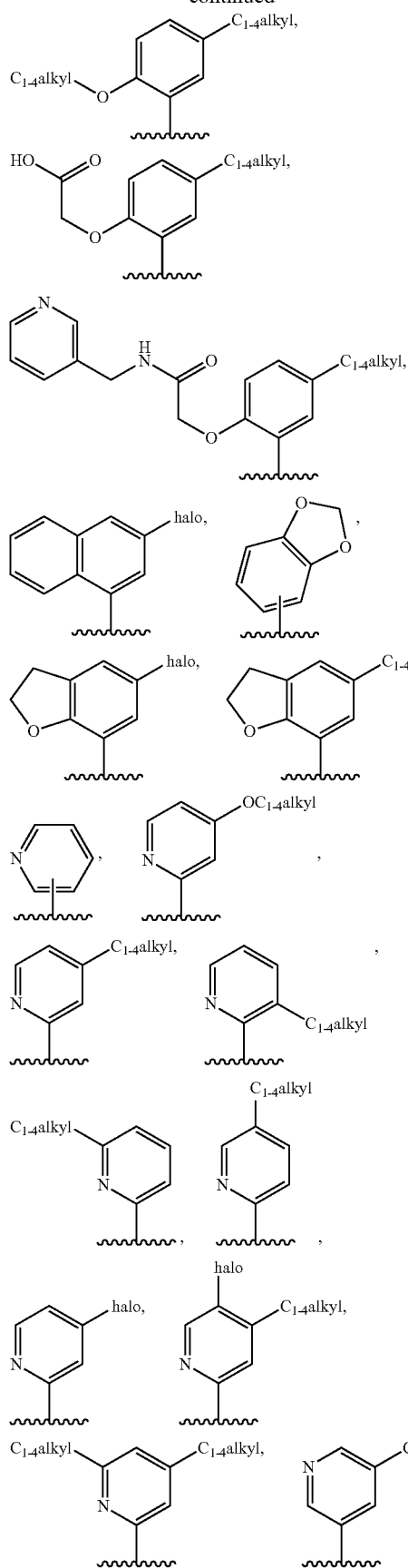
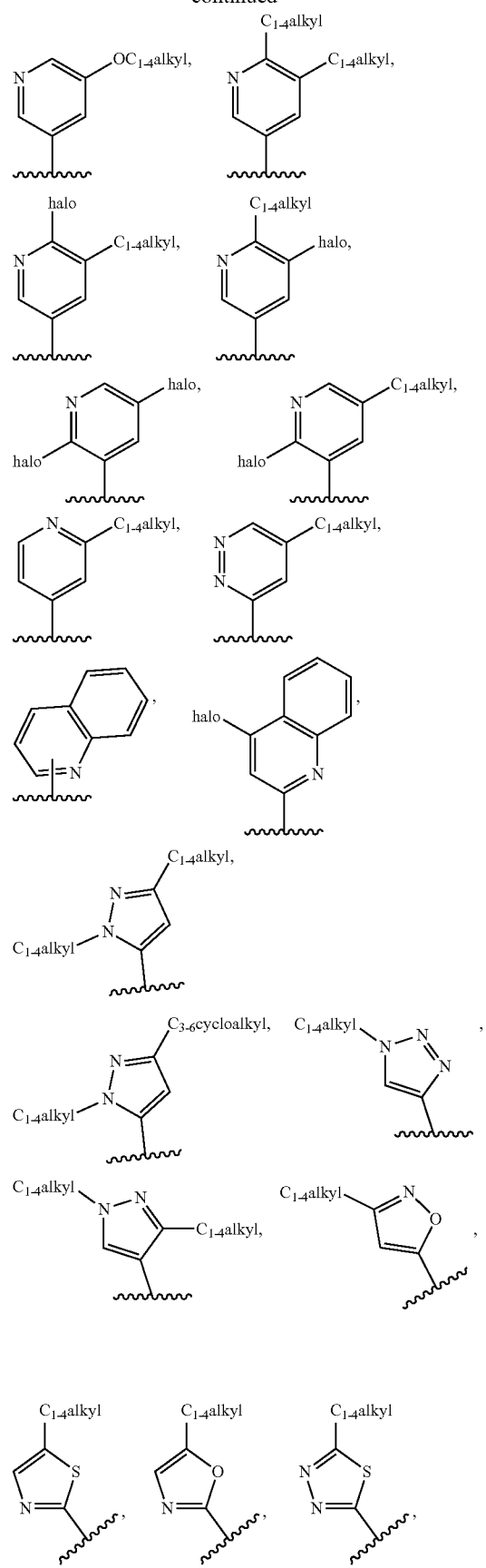

-continued
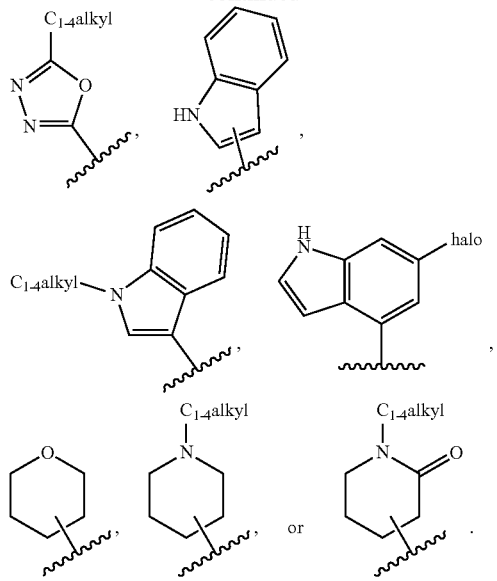
When p is 1, G¹ may be
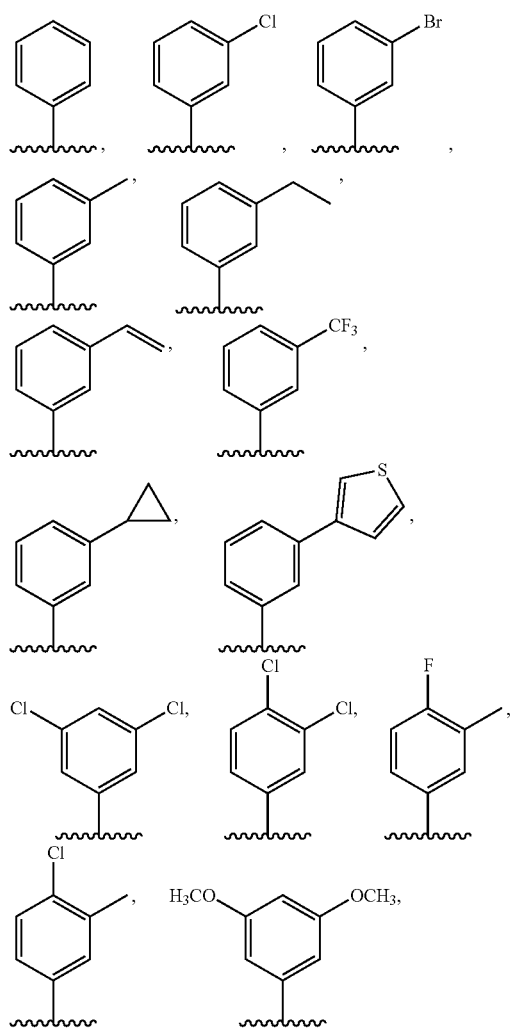
-continued
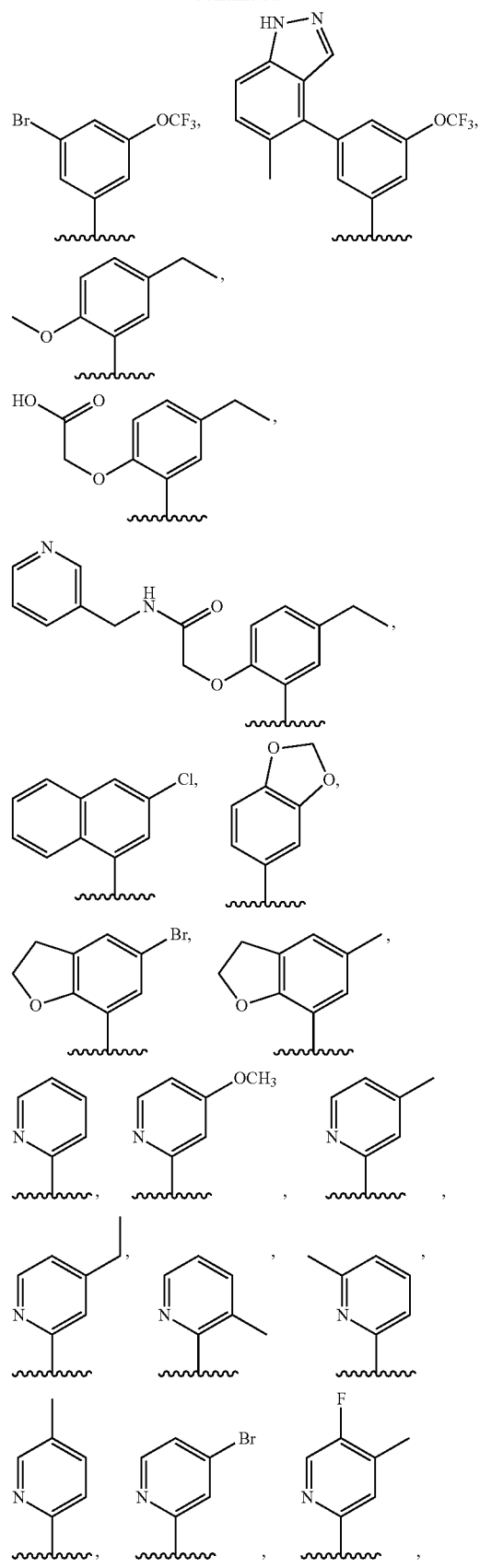

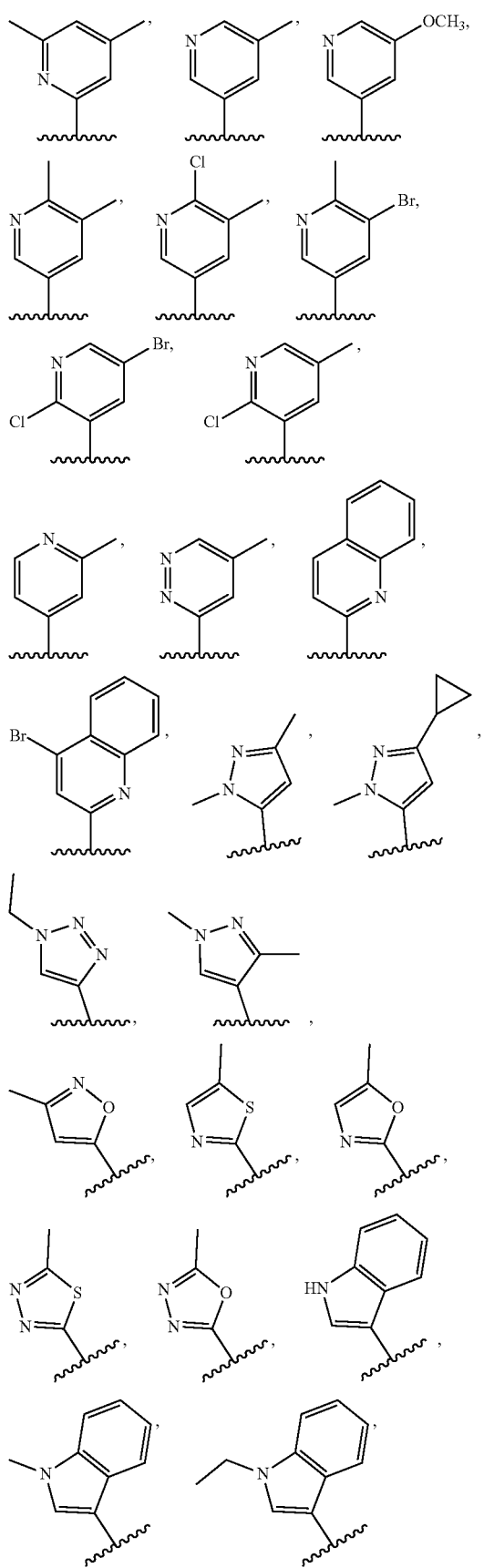

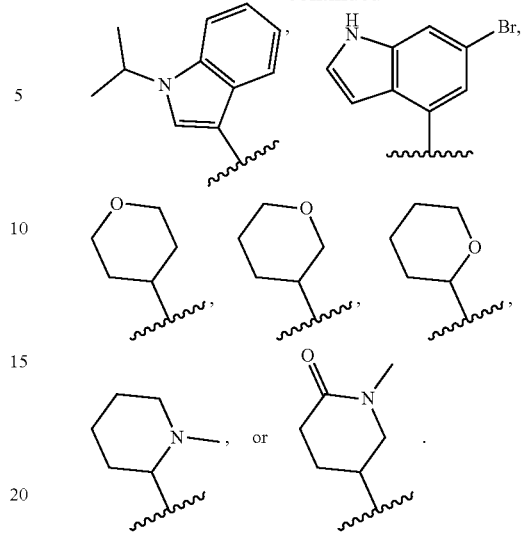

In compounds of the invention, $R^1$ may be $G^1$, wherein $G^1$ is a phenyl or 5- to 6-membered heteroaryl, wherein $G^1$ is optionally substituted with 1-5 substituents independently selected from the group consisting of halogen, $C_{1-6}$alkyl, $C_{1-6}$haloalkyl, —$OR^{1a}$, —$N(R^{1a})_2$, —$SR^{1a}$, cyano, —C(O)$OR^{1a}$, —C(O)N($R^{1a}$)$_2$, —C(O)$R^{1a}$, —$SOR^{1b}$, —$SO_2R^{1b}$, —$SO_2N(R^{1a})_2$, —$NR^{1a}$C(O)$R^{1a}$, —$NR^{1a}$C(O)$OR^{1a}$, —$NR^{1a}$C(O)N($R^{1a}$)$_2$, —$NR^{1a}$S(O)$_2R^{1b}$, —$NR^{1a}$S(O)$_2$N($R^{1a}$)$_2$, and -$L^1$-$G^{1a}$. The 5- to 6-membered heteroaryl at $G^1$ may be a pyridinyl. The phenyl or pyridinyl may be optionally substituted with 1-3 substituents independently selected from the group consisting of halogen, $C_{1-6}$alkyl, $C_{1-6}$haloalkyl, —$OR^{1a}$, and $G^{1a}$. The phenyl or pyridinyl may each be optionally substituted with 1-2 substituents independently selected from the group consisting of halogen, —$OC_{1-4}$haloalkyl, $OCH_2C_{3-6}$cycloalkyl, and phenyl. Thus, when $R^1$ is $G^1$, $G^1$ may be

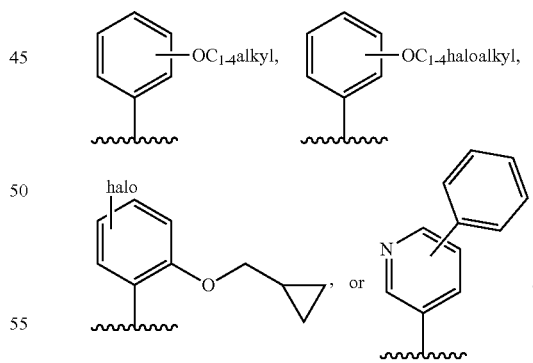

When $R^1$ is $G^1$, $G^1$ may be

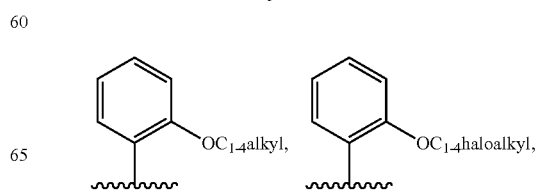

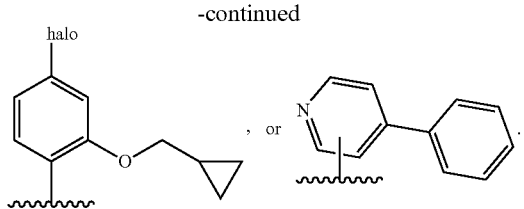

When R¹ is G¹, G¹ may be

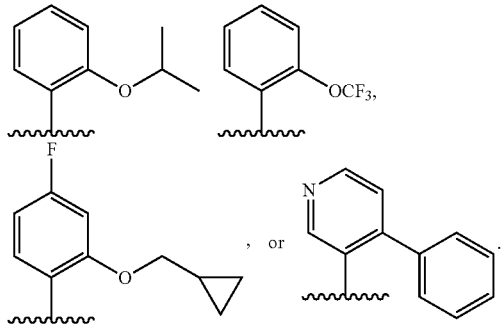

In the embodiments described herein, $R^a$ may be hydrogen, $C_{1-4}$alkyl (e.g., methyl), or $G^{1b}$, wherein $G^{1b}$ is as defined herein (e.g., cyclopropyl).

In the embodiments described herein are further embodiments, wherein $R^b$ is hydrogen.

The carbon atom to which $R^a$ and $R^b$ attach may have either R or S stereochemistry.

In some embodiments, $R^4$ is hydrogen, $-OR^{4a}$, or $G^2$, wherein $R^{4a}$ and $G^2$ are as defined herein.

In some embodiments, $R^4$ is hydrogen.

In some embodiments, $R^4$ is $-OR^{4a}$. In the embodiments herein, $R^{4a}$ may be $C_{1-6}$haloalkyl, $G^2$, or $-C_{1-3}$alkylene-$G^2$, wherein $G^2$ is as defined herein. $R^{4a}$ may be $G^2$, wherein $G^2$ may be a $C_{3-10}$carbocyclyl optionally substituted with 1-4 substituents independently selected from the group consisting of $C_{1-4}$alkyl and halogen. $R^{4a}$ may be $G^2$, wherein $G^2$ may be a $C_{3-8}$cycloalkyl optionally substituted with 1-4 substituents independently selected from the group consisting of $C_{1-4}$alkyl and halogen. $R^{4a}$ may be $-C_{1-3}$alkylene-$G^2$, wherein $G^2$ may be a $C_{3-10}$carbocyclyl optionally substituted with 1-4 substituents independently selected from the group consisting of $C_{1-4}$alkyl and halogen. $R^{4a}$ may be $-C_{1-3}$alkylene-$G^2$, wherein $G^2$ may be a $C_{3-8}$cycloalkyl optionally substituted with 1-4 substituents independently selected from the group consisting of $C_{1-4}$alkyl and halogen.

In some embodiments, $R^4$ is $G^2$; and $G^2$ is a $C_{3-10}$carbocyclyl, a 6- to 12-membered aryl, or a 5- to 12-membered heteroaryl, and optionally substituted as defined herein. $R^4$ may be $G^2$, wherein $G^2$ may be a $C_{3-8}$cycloalkyl, a phenyl, or a 5- to 6-membered heteroaryl, and optionally substituted as defined herein. The 5- to 6-membered heteroaryl of $G^2$ may contain 1-3 heteroatoms independently selected from the group consisting of oxygen and nitrogen. $R^4$ may be $G^2$, wherein $G^2$ may be cyclopropyl, phenyl, pyridinyl, pyrazolyl, imidazolyl, or isoxazoyl, and $G^2$ is optionally substituted as defined herein. $R^4$ may be $G^2$, wherein $G^2$ may be cyclopropyl, phenyl, pyridinyl, pyrimidinyl, pyrazolyl, imidazolyl, or isoxazoyl, and $G^2$ is optionally substituted as defined herein. For example, $G^2$ may be substituted with 1-4 substituents independently selected from the group consisting of halogen, $C_{1-6}$alkyl, and $C_{1-6}$haloalkyl. In further embodiments, $R^4$ may be hydrogen, $-OC_{1-6}$haloalkyl, $-OC_{3-6}$cycloalkyl, $-O-C_{1-3}$alkylene-$C_{3-6}$cycloalkyl, $C_{3-6}$cycloalkyl, phenyl,

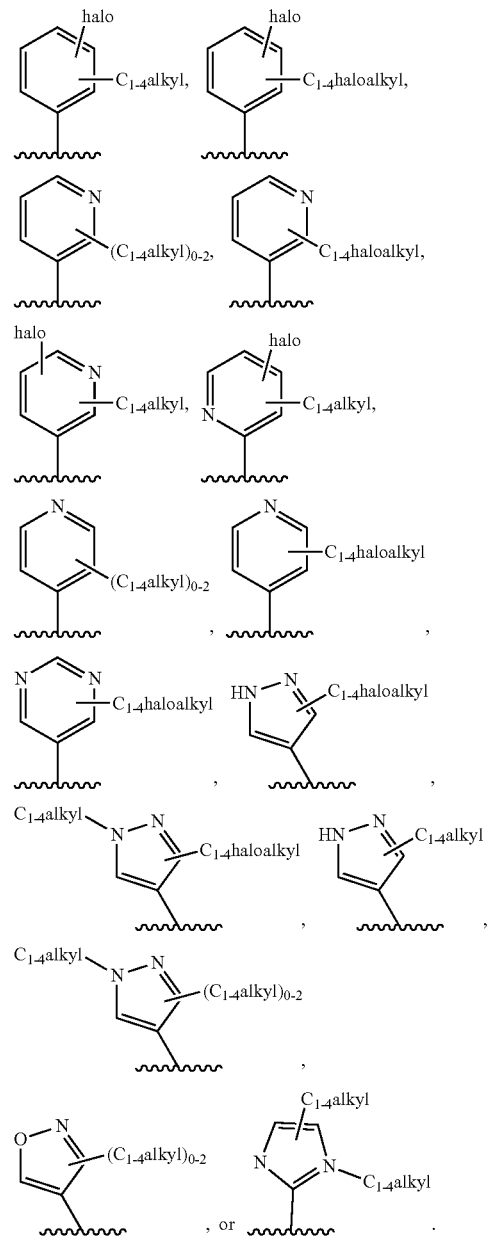

In further embodiments, $R^4$ may be hydrogen, $-OC_{1-6}$haloalkyl, $-OC_{3-6}$cycloalkyl, $-OC_{1-3}$alkylene-$C_{3-6}$cycloalkyl, $C_{3-6}$cycloalkyl, phenyl,

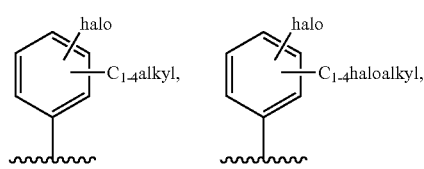

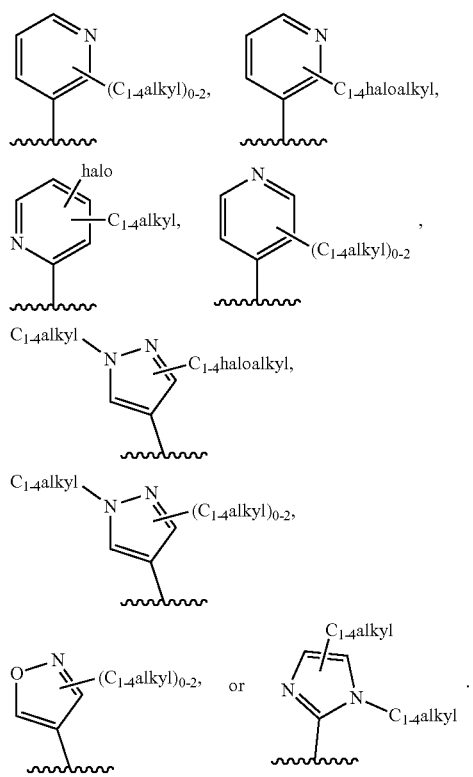
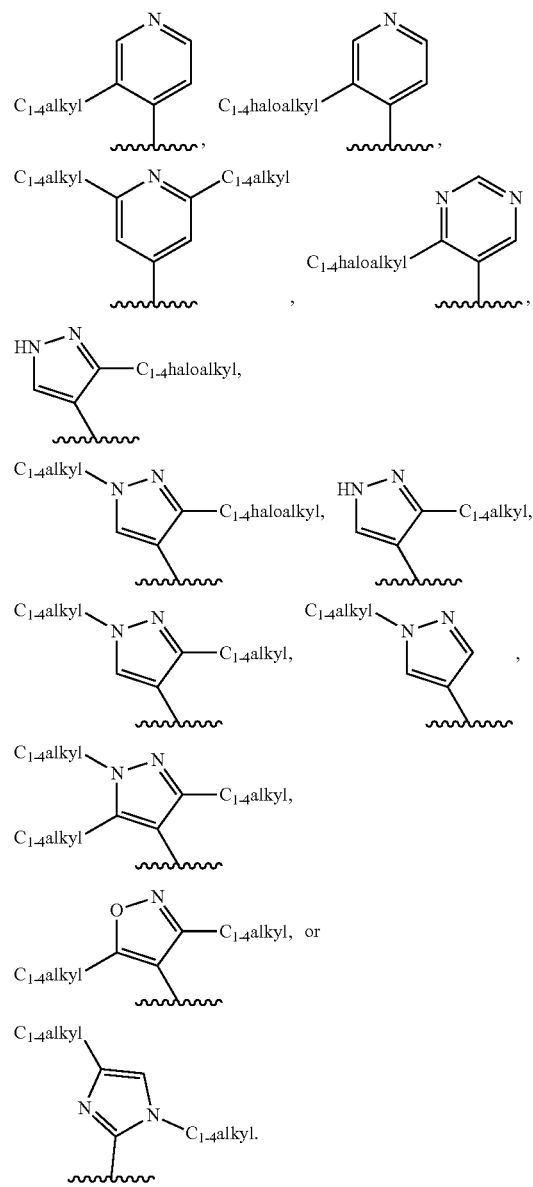
In still further embodiments, R[4] may be hydrogen, —OC$_{1-2}$haloalkyl, —OC$_{3-4}$cycloalkyl, —OC$_{1-3}$alkylene-C$_{3-4}$cycloalkyl, C$_{3-4}$cycloalkyl, phenyl,
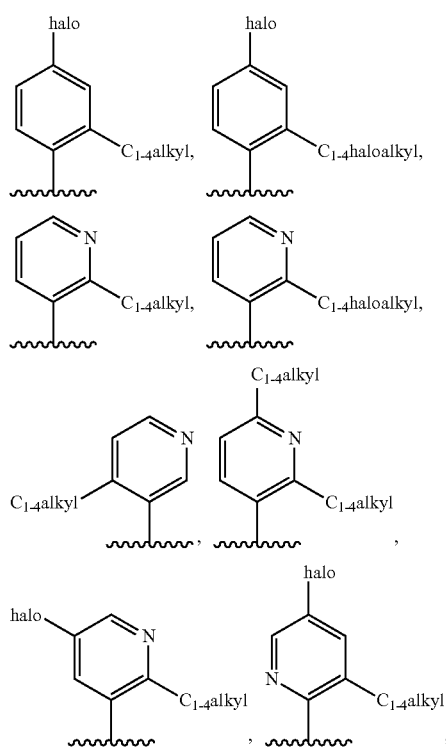
In still further embodiments, R[4] may be hydrogen, —OC$_{1-2}$haloalkyl, —OC$_{3-4}$cycloalkyl, —O—C$_{1-3}$alkylene-C$_{3-4}$cycloalkyl, C$_{3-4}$cycloalkyl, phenyl,
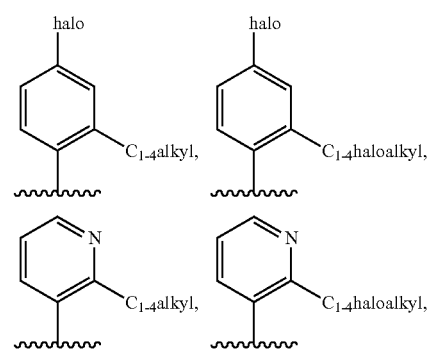

-continued
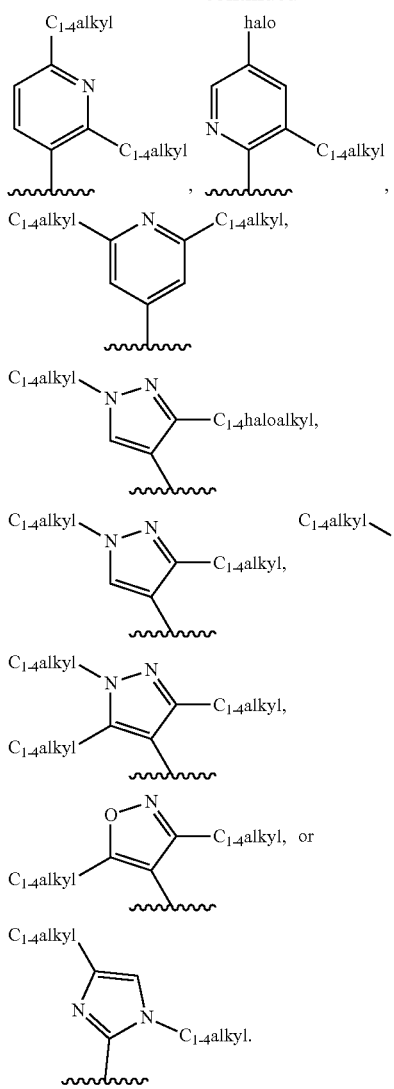
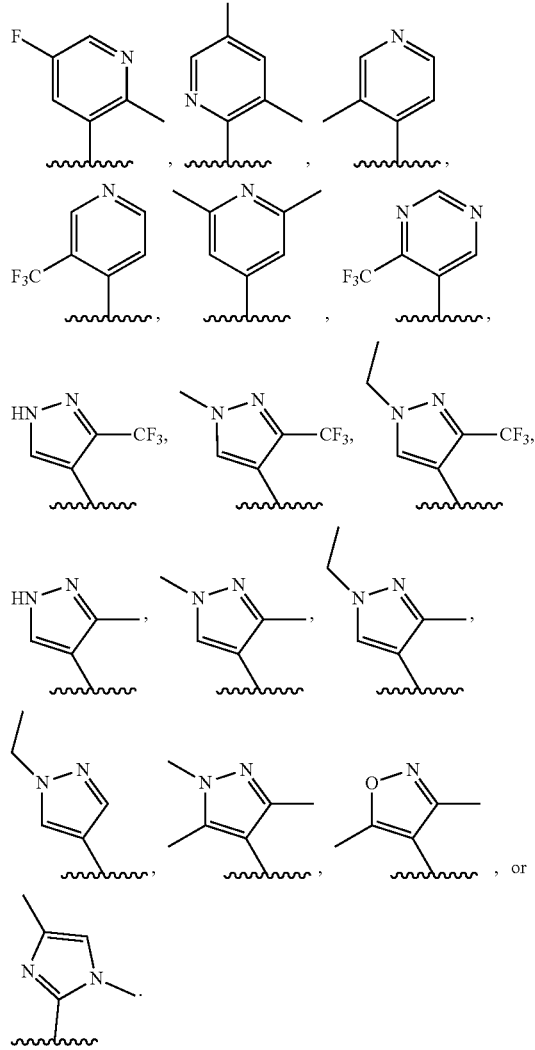
In yet further embodiments, $R^4$ may be hydrogen, —OCH$_2$CF$_3$, —O-cyclobutyl, —O—CH$_2$-cyclopropyl, cyclopropyl, phenyl,
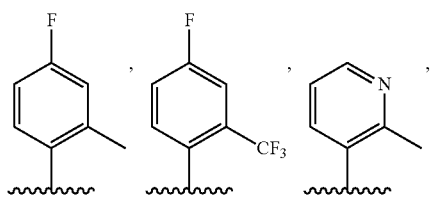
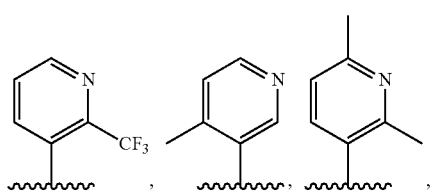
In yet further embodiments, $R^4$ may be hydrogen, —OCH$_2$CF$_3$, —O-cyclobutyl, —O—CH$_2$-cyclopropyl, cyclopropyl, phenyl,
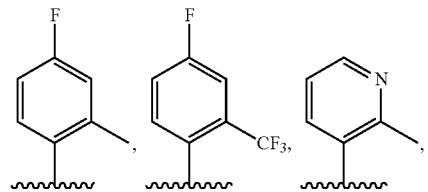
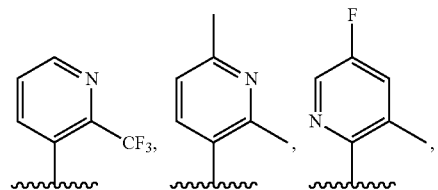

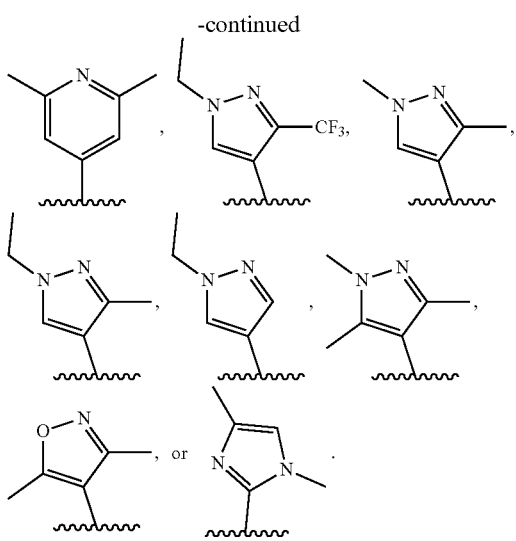

In yet further embodiments, R⁴ may be

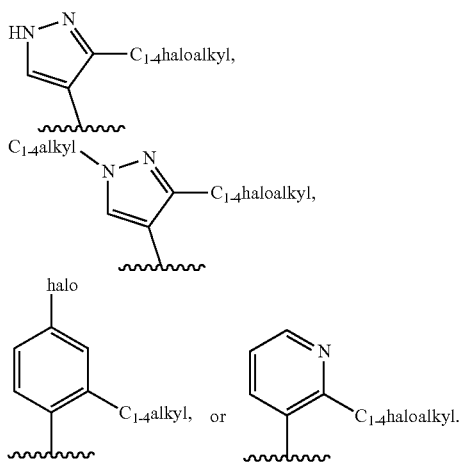

In yet further embodiments, R⁴ may be

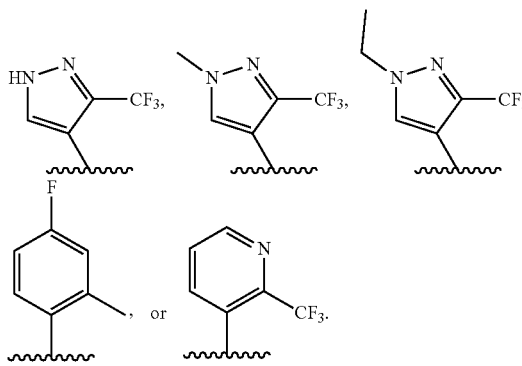

$R^{1a}$, $R^{1c}$, $R^{1e}$, $R^{4a}$, and $R^{4c}$ may independently be hydrogen, $C_{1-6}$alkyl, or $C_{1-6}$haloalkyl.

$R^{1b}$, $R^{1d}$, $R^{1f}$, $R^{4b}$, and $R^{4d}$ may independently be $C_{1-6}$alkyl or $C_{1-6}$haloalkyl.

Included in the embodiments herein $R^{2a}$, $R^{2b}$, $R^{3a}$, and $R^{3b}$ may each be hydrogen.

In the embodiments herein n may be 0. In the embodiments herein n may be 1. In the embodiments herein n may be 2.

In the embodiments herein, $R^5$ may be hydrogen or halogen.

In the embodiments herein, $R^6$ may be hydrogen.

In the embodiments herein, $R^{7a}$ and $R^{7b}$ may each be hydrogen.

In the compounds of formula (I) are compounds wherein n is 1; $R^1$ is —(CR$^a$R$^b$)-G$^1$; G$^1$ is a 6 or 5-membered aromatic ring optionally containing 1-2 nitrogen atoms, wherein G$^1$ is substituted with 1-3 substituents independently selected from the group consisting of —OC$_{1-4}$alkyl, C$_{1-4}$alkyl, halogen, and C$_{3-6}$cycloalkyl; R$^a$ is C$_{1-4}$alkyl, C$_{3-6}$cycloalkyl, or hydrogen; R$^b$ is hydrogen; $R^{2a}$, $R^{2b}$, $R^{3a}$, and $R^{3b}$ are each hydrogen; R$^4$ is a 5 or 6-membered aromatic ring optionally containing 1-2 nitrogen atoms, wherein R$^4$ is substituted with 2, 1, or 3 substituents independently selected from the group consisting of C$_{1-4}$haloalkyl, C$_{1-4}$alkyl, and halogen; R$^5$ is hydrogen; R$^6$ is hydrogen; $R^{7a}$ and $R^{7b}$ are each hydrogen; and R$^8$ is a 5-membered heterocyclic ring containing 2-3 heteroatoms and 2 or 1 double bonds, wherein one of the 2-3 heteroatoms is a nitrogen and the remaining heteroatoms are independently selected from nitrogen and oxygen, wherein R$^8$ is optionally substituted with 1-3 substituents independently selected from the group consisting of C$_{1-4}$alkyl, imino, C$_{1-4}$haloalkyl, —NH(C$_{1-4}$alkyl), halogen, cyano, NH$_2$, —N(C$_{1-4}$alkyl)$_2$, C$_{3-6}$cycloalkyl, and —C$_{1-3}$alkylene-C$_{3-6}$cycloalkyl. Included are compounds wherein R$^8$ is imidazolyl or

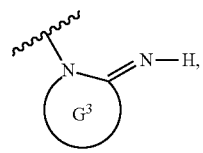

the imidazolyl being optionally substituted with 1-3 substituents independently selected from the group consisting of C$_{1-4}$alkyl, —N(C$_{1-4}$alkyl)$_2$, C$_{1-4}$haloalkyl, —NH(C$_{1-4}$alkyl), halogen, cyano, NH$_2$, C$_{3-6}$cycloalkyl, and —C$_{1-3}$alkylene-C$_{3-6}$cycloalkyl; and G$^3$ is a 5-membered heterocyclic ring containing a first nitrogen at the point of attachment and optionally 1-2 additional heteroatoms selected from the group consisting of nitrogen and oxygen, G$^3$ having the imine substituent =NH adjacent to the first nitrogen and being optionally substituted with 1-3 substituents independently selected from the group consisting of C$_{1-4}$alkyl, C$_{1-4}$haloalkyl, C$_{3-6}$cycloalkyl, and —C$_{1-3}$alkylene-C$_{3-6}$cycloalkyl. Further included are compounds wherein R$^8$ is

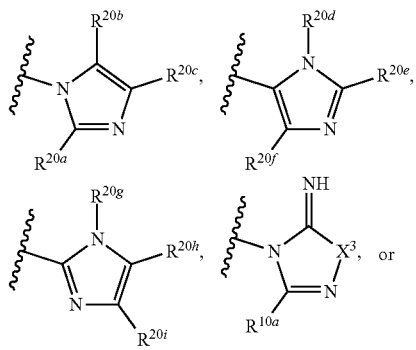

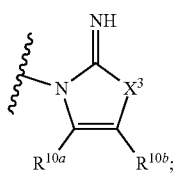

$X^3$ is $NR^{13}$ or O; $R^{10a}$ and $R^{10b}$ are independently hydrogen, $C_{1-4}$alkyl, or $C_{1-4}$haloalkyl; $R^{13}$ is $C_{1-4}$alkyl, $C_{1-4}$haloalkyl, $C_{3-6}$cycloalkyl, or —$C_{1-3}$alkylene-$C_{3-6}$cycloalkyl; $R^{20a}$ is hydrogen, $C_{1-4}$alkyl, —NH($C_{1-4}$alkyl), $NH_2$, —N($C_{1-4}$alkyl)$_2$, or $C_{3-6}$cycloalkyl; and $R^{20b}$, $R^{20c}$, $R^{20d}$, $R^{20e}$, $R^{20f}$, $R^{20g}$, $R^{20h}$, and $R^{20i}$, are each independently hydrogen, $C_{1-4}$alkyl, or $C_{3-6}$cycloalkyl. Further included are compounds wherein $R^8$ is

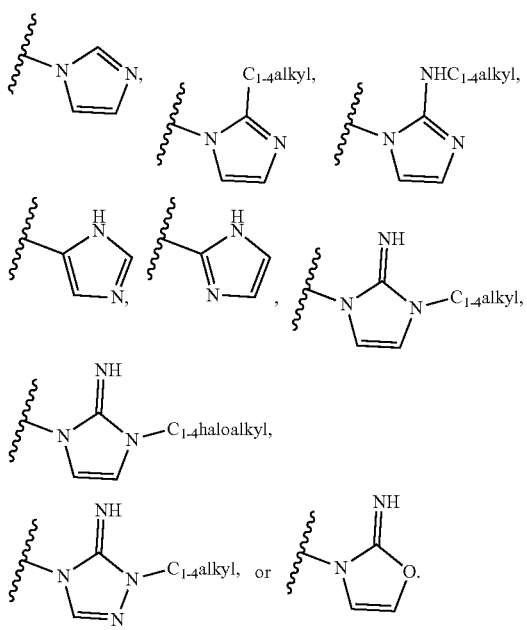

Also included in any of these groups or subgroups of compounds are further compounds wherein $G^1$ is pyridinyl, phenyl, pyridazinyl, or pyrazolyl, and substituted with 1-3 substituents independently selected from the group consisting of —$OC_{1-4}$alkyl, $C_{1-4}$alkyl, halogen, and $C_{3-6}$cycloalkyl. Further included are compounds wherein $G^1$ is

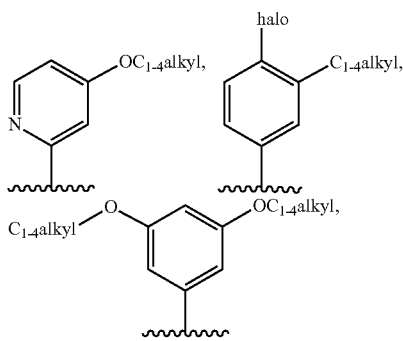

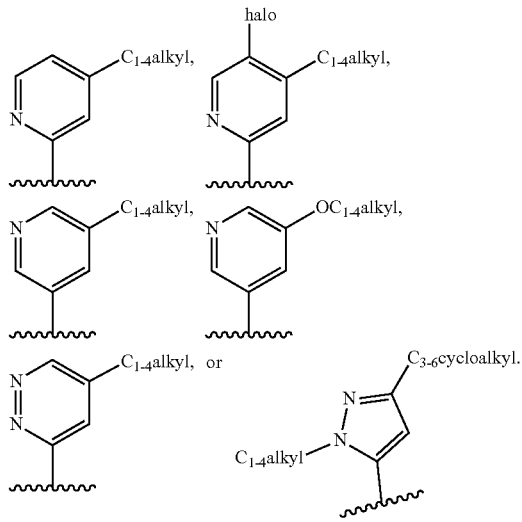

Also included in any of these groups or subgroups of compounds, or combinations thereof, are further compounds wherein $R^4$ is pyrazolyl, phenyl, or pyridinyl, and substituted with 2, 1, or 3 substituents independently selected from the group consisting of $C_{1-4}$haloalkyl, $C_{1-4}$alkyl, and halogen. Further included are compounds wherein $R^4$ is

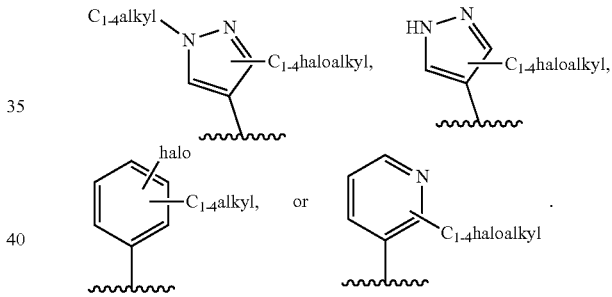

Still further included are compounds wherein $R^4$ is

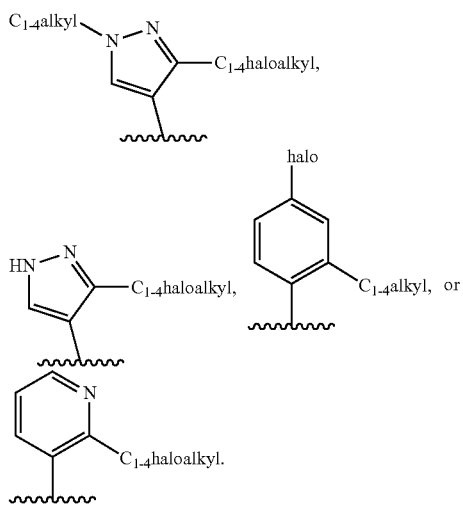

In certain embodiments, the compound of formula (I) is selected from the group consisting of the compounds in Table 1, or a pharmaceutically acceptable salt thereof.
TABLE 1
Exemplary compounds.
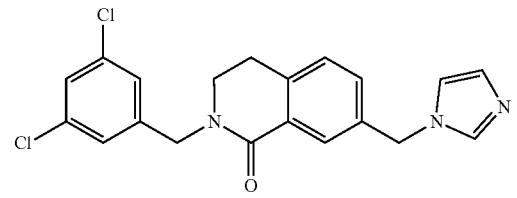 [SMILES: O=C1c2cc(Cn3ccnc3)ccc2CCN1Cc1cc(Cl)cc(Cl)c1]
I-1
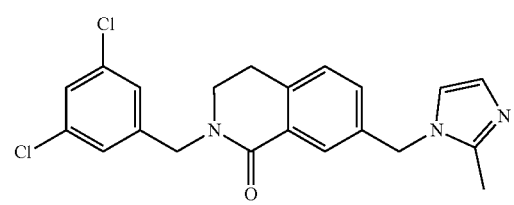 [SMILES: Cc1nccn1Cc1ccc2c(c1)C(=O)N(Cc1cc(Cl)cc(Cl)c1)CC2]
I-2
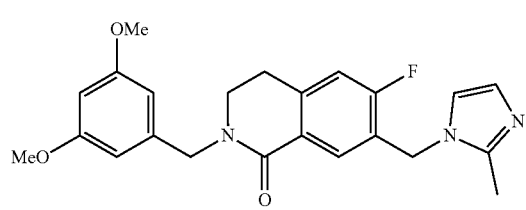 [SMILES: COc1cc(CN2CCc3cc(F)c(Cn4ccnc4C)cc3C2=O)cc(OC)c1]
I-3
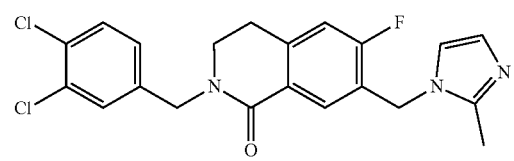 [SMILES: Cc1nccn1Cc1cc2c(cc1F)CCN(Cc1ccc(Cl)c(Cl)c1)C2=O]
I-4
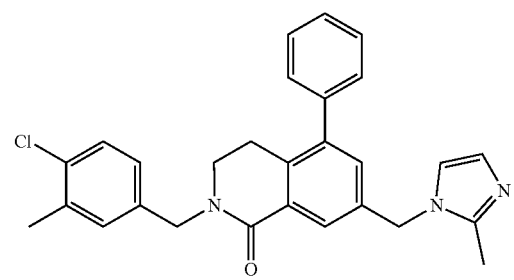 [SMILES: Cc1cc(CN2CCc3c(cc(Cn4ccnc4C)cc3-c3ccccc3)C2=O)ccc1Cl]
I-5
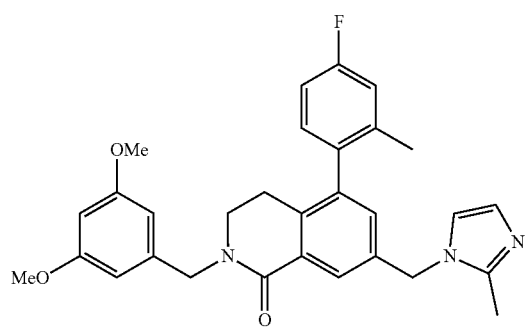 [SMILES: COc1cc(CN2CCc3c(cc(Cn4ccnc4C)cc3-c3ccc(F)cc3C)C2=O)cc(OC)c1]
I-6
TABLE 1-continued
Exemplary compounds.
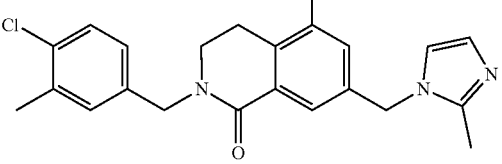
I-7
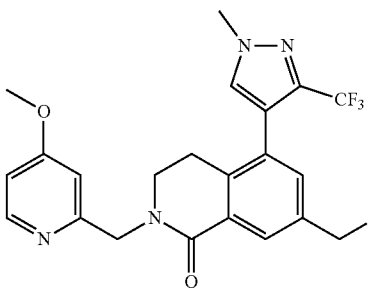
I-8
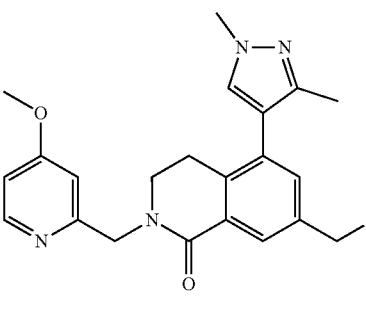
I-9
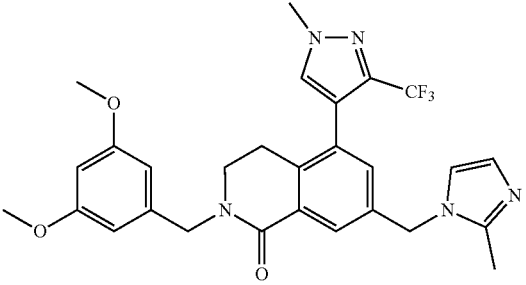 [SMILES: COc1cc(CN2CCc3c(cc(Cn4ccnc4C)cc3-c3cn(C)nc3C(F)(F)F)C2=O)cc(OC)c1]
I-10
I-11

TABLE 1-continued
Exemplary compounds.
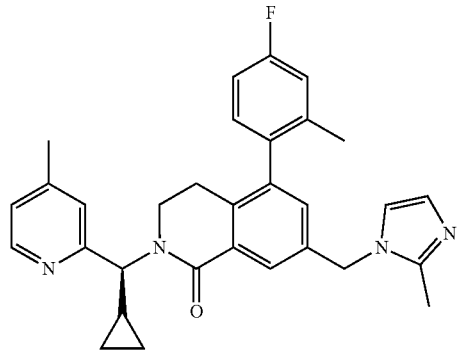 [SMILES: Cc1ccnc([C@H](C2CC2)N2CCc3c(cc(Cn4ccnc4C)cc3-c3ccc(F)cc3C)C2=O)c1]
I-12
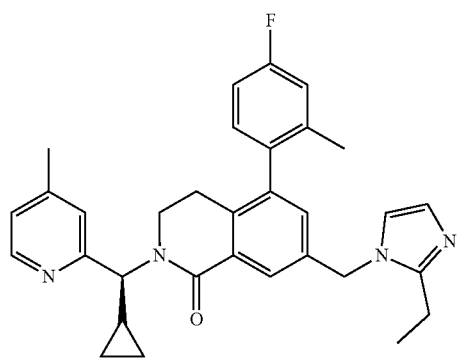 [SMILES: CCc1nccn1Cc1cc2c(c(-c3ccc(F)cc3C)c1)CCN([C@H](c1cc(C)ccn1)C1CC1)C2=O]
I-13
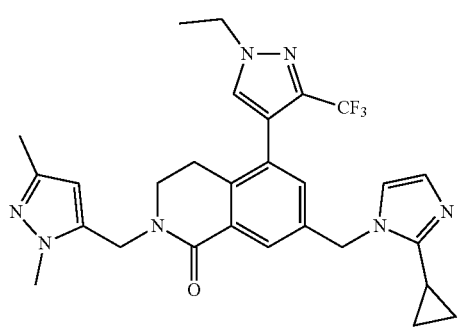 [SMILES: CCn1cc(-c2cc(Cn3ccnc3C3CC3)cc3c2CCN(Cc2cc(C)nn2C)C3=O)c(C(F)(F)F)n1]
I-14
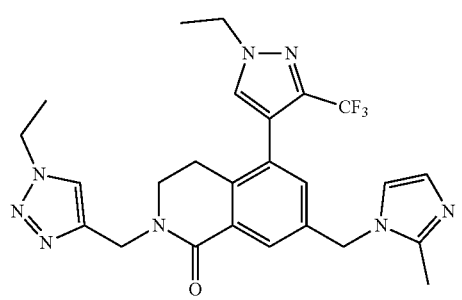 [SMILES: CCn1cc(CN2CCc3c(cc(Cn4ccnc4C)cc3-c3cn(CC)nc3C(F)(F)F)C2=O)nn1]
I-15
TABLE 1-continued
Exemplary compounds.
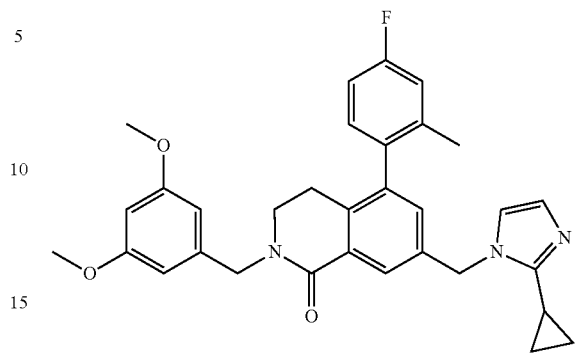
I-16
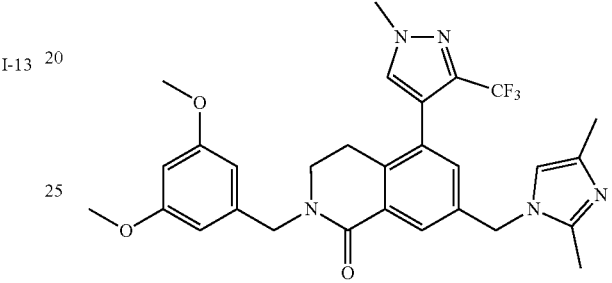
I-17
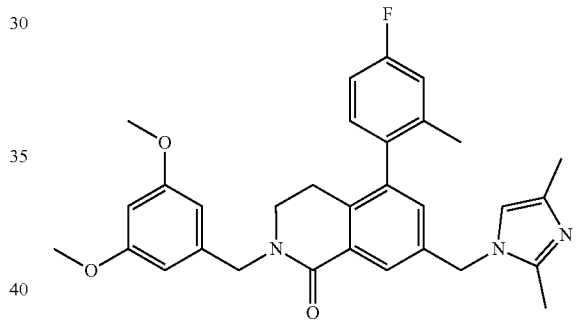
I-18
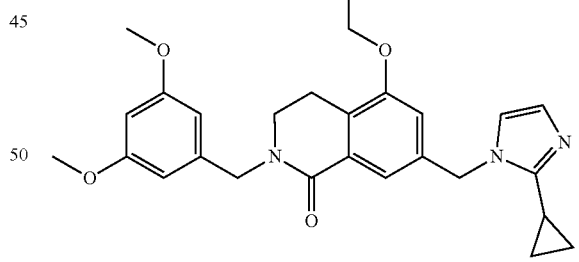
I-19
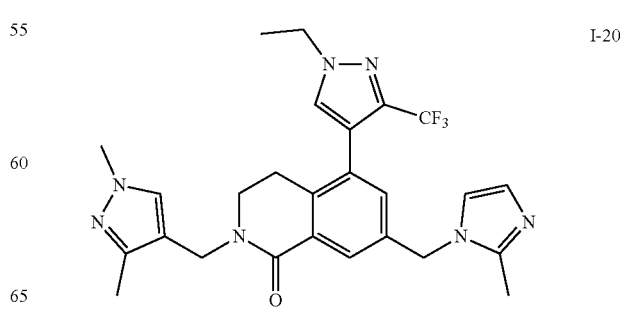
I-20

TABLE 1-continued
Exemplary compounds.
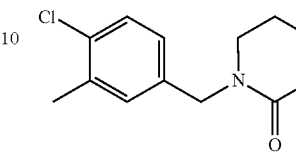 I-21
 I-22
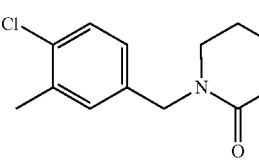 I-23
 I-24
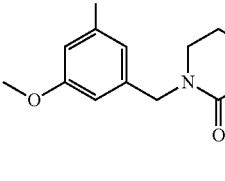 I-25
 I-26
TABLE 1-continued
Exemplary compounds.
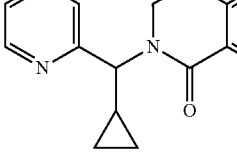 I-27
 I-28
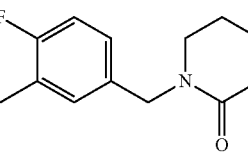 I-29
 I-30
I-31

TABLE 1-continued
Exemplary compounds.
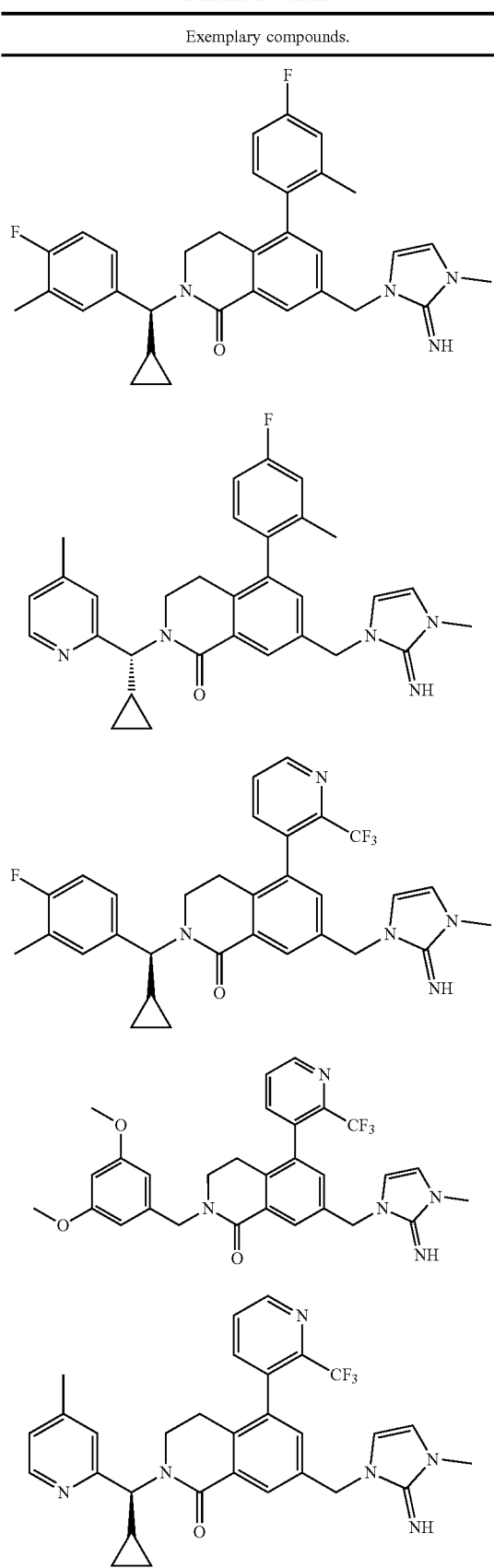
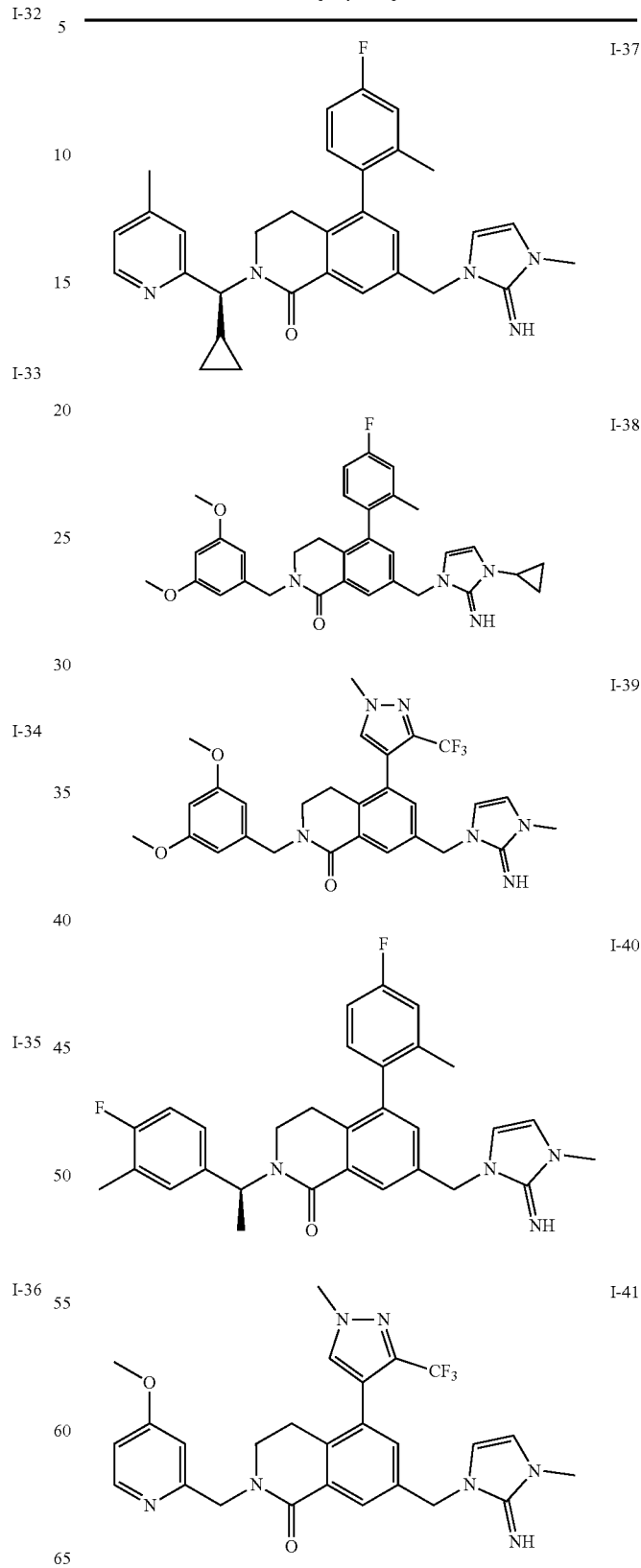

TABLE 1-continued
Exemplary compounds.
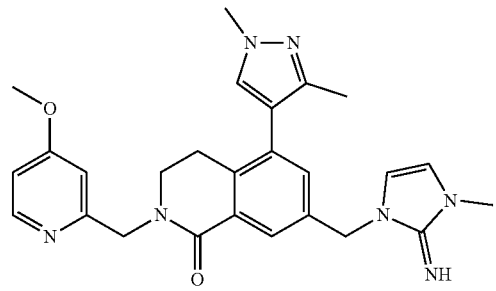 I-42
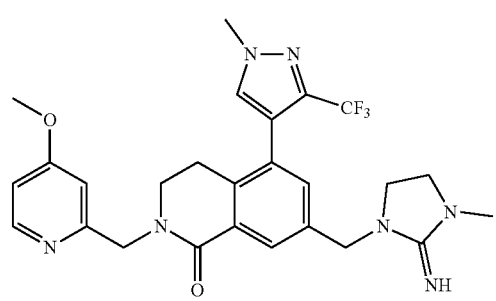 [SMILES: COc1ccnc(CN2CCc3c(cc(CN4CCN(C)C4=N)cc3-c3cn(C)nc3C(F)(F)F)C2=O)c1] I-43
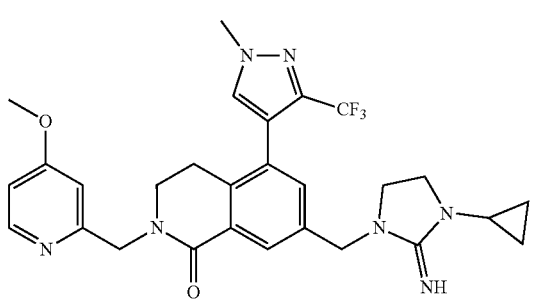 [SMILES: COc1ccnc(CN2CCc3c(cc(CN4CCN(C5CC5)C4=N)cc3-c3cn(C)nc3C(F)(F)F)C2=O)c1] I-44
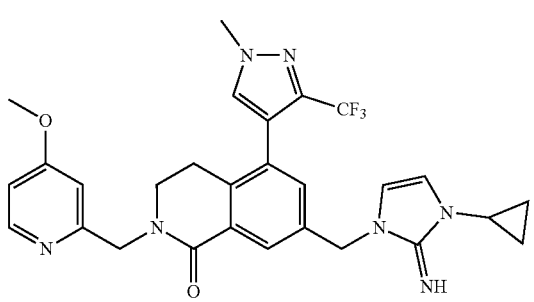 [SMILES: COc1ccnc(CN2CCc3c(cc(Cn4ccn(C5CC5)c4=N)cc3-c3cn(C)nc3C(F)(F)F)C2=O)c1] I-45
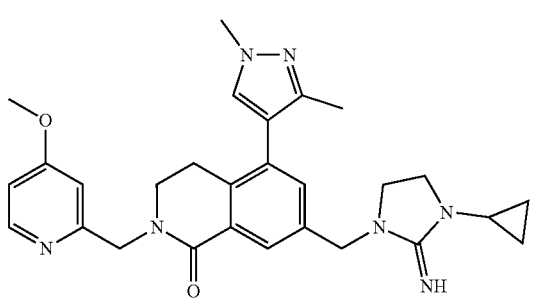 [SMILES: COc1ccnc(CN2CCc3c(cc(CN4CCN(C5CC5)C4=N)cc3-c3cn(C)nc3C)C2=O)c1] I-46
TABLE 1-continued
Exemplary compounds.
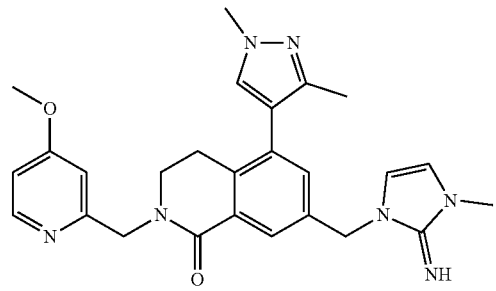 I-47
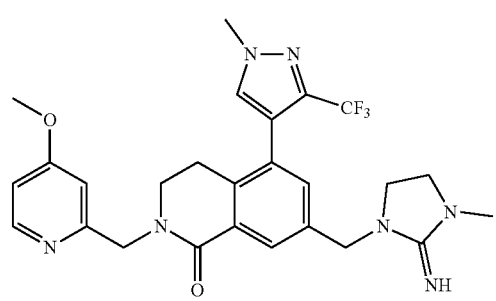 [SMILES: COc1ccnc(CN2CCc3c(cc(CN4CCN(C)C4=N)cc3-c3cn(C)nc3C(F)(F)F)C2=O)c1] I-48
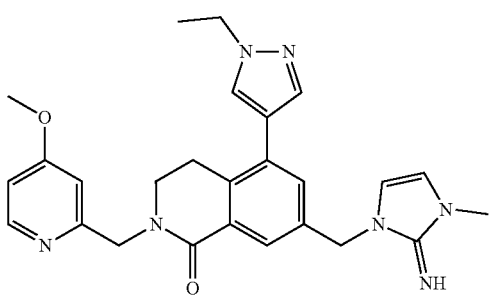 I-49
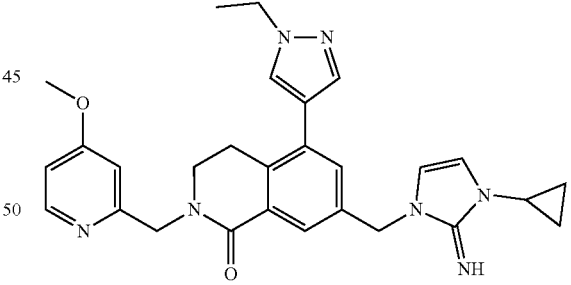 I-50
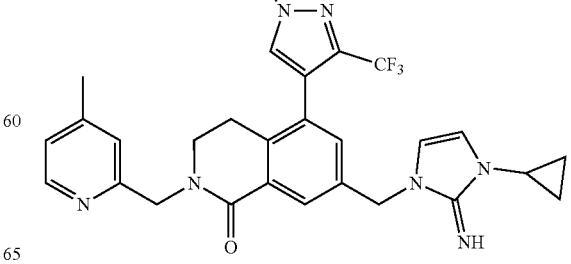 I-51

TABLE 1-continued
Exemplary compounds.
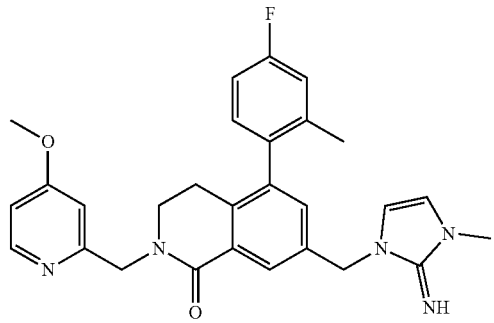 I-52
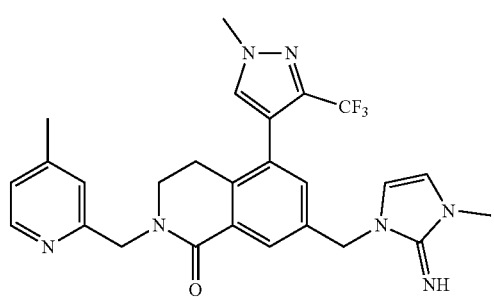 [SMILES: Cc1ccnc(CN2CCc3c(cc(Cn4ccn(C)c4=N)cc3-c3cn(C)nc3C(F)(F)F)C2=O)c1] I-53
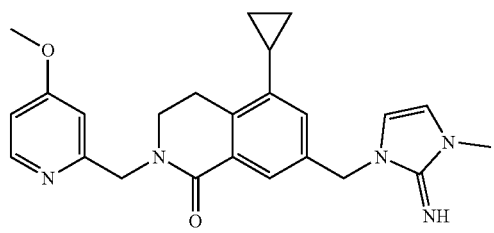 [SMILES: COc1ccnc(CN2CCc3c(cc(Cn4ccn(C)c4=N)cc3C3CC3)C2=O)c1] I-54
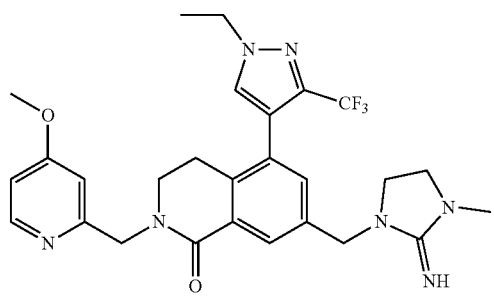 [SMILES: CCn1cc(-c2cc(CN3CCN(C)C3=N)cc3c2CCN(Cc2cc(OC)ccn2)C3=O)c(C(F)(F)F)n1] I-55
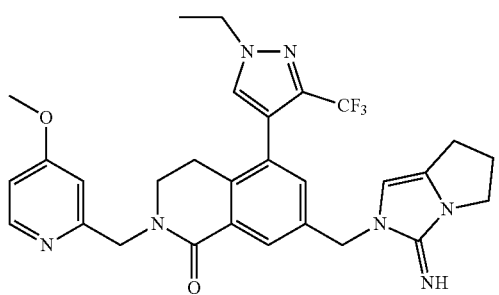 [SMILES: CCn1cc(-c2cc(Cn3cc4n(c3=N)CCC4)cc3c2CCN(Cc2cc(OC)ccn2)C3=O)c(C(F)(F)F)n1] I-56
TABLE 1-continued
Exemplary compounds.
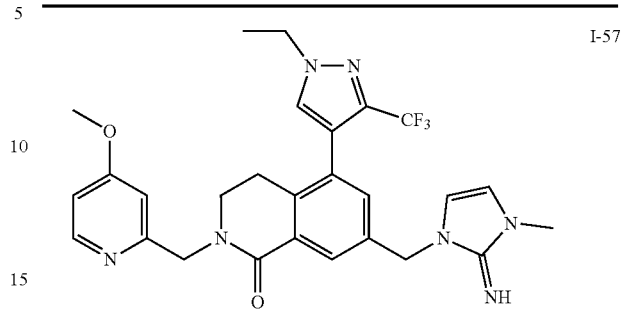 I-57
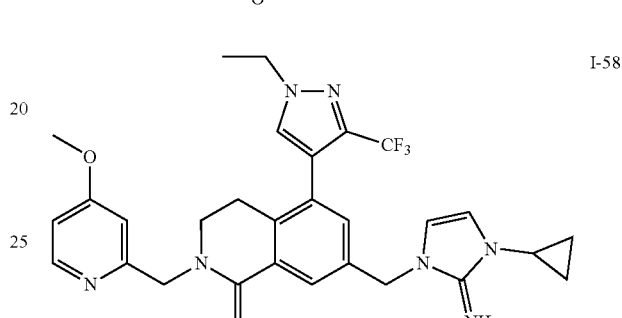 I-58
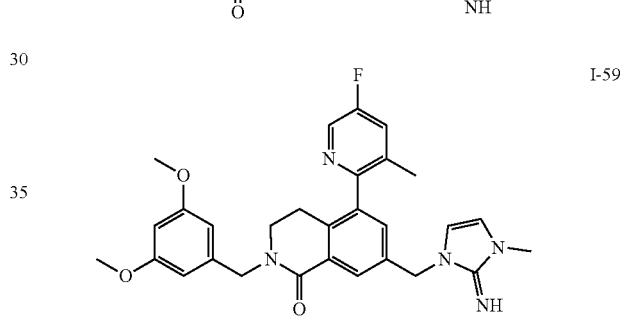 I-59
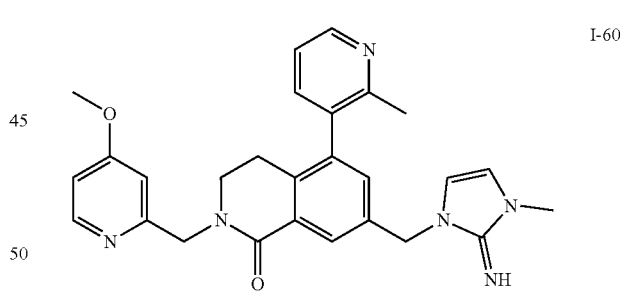 I-60
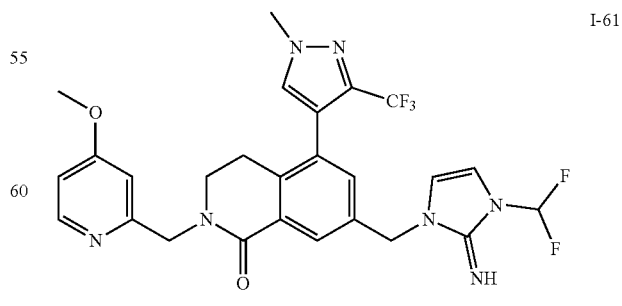 I-61

TABLE 1-continued
Exemplary compounds.
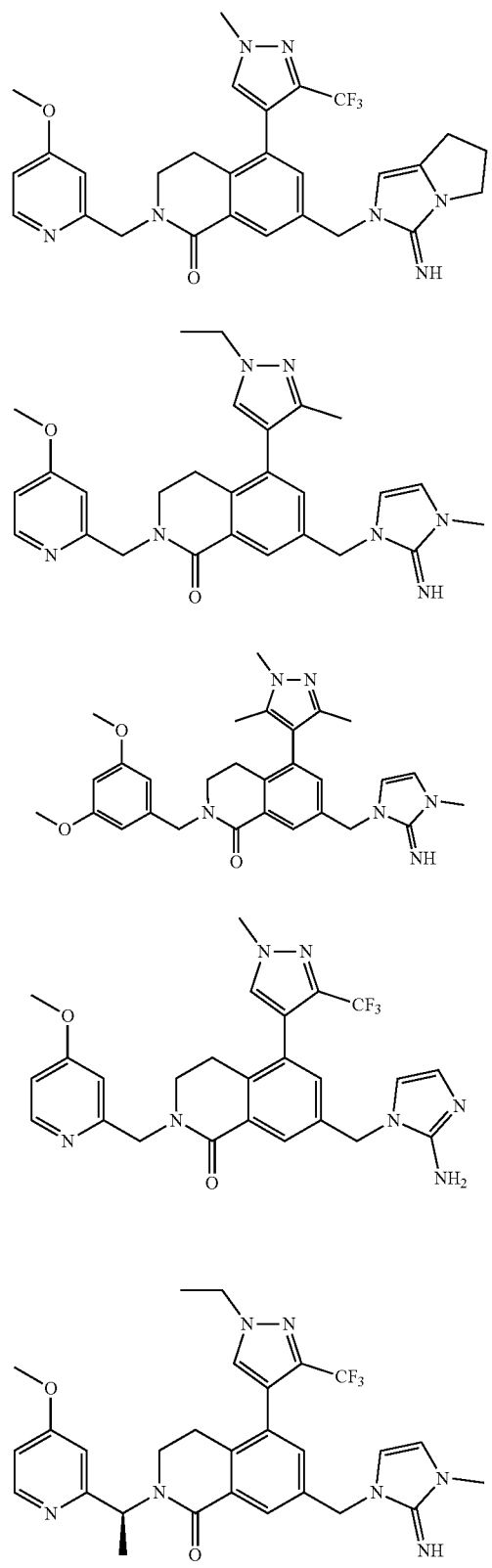
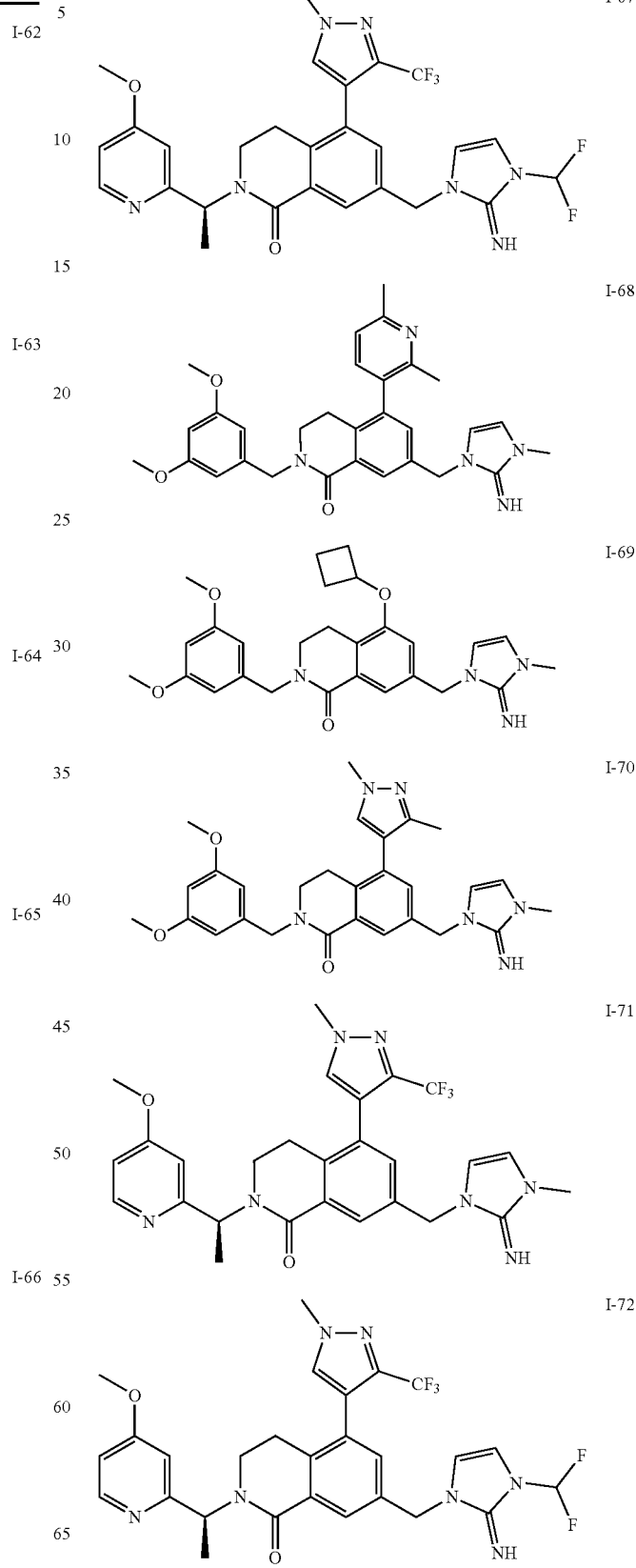

TABLE 1-continued
Exemplary compounds.
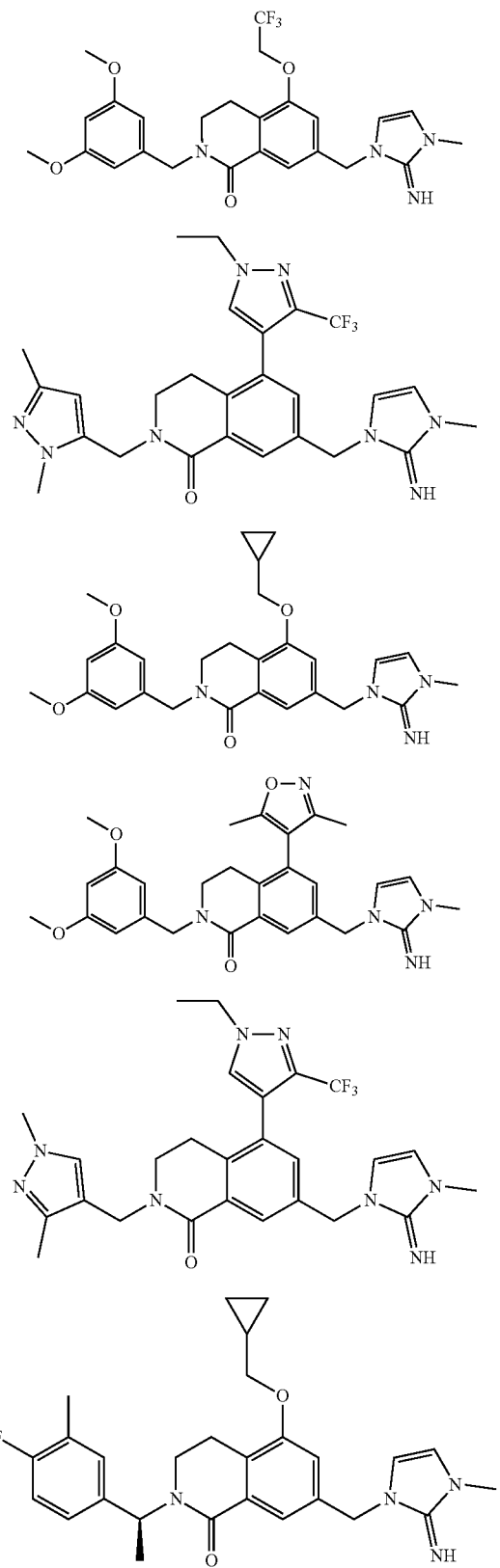
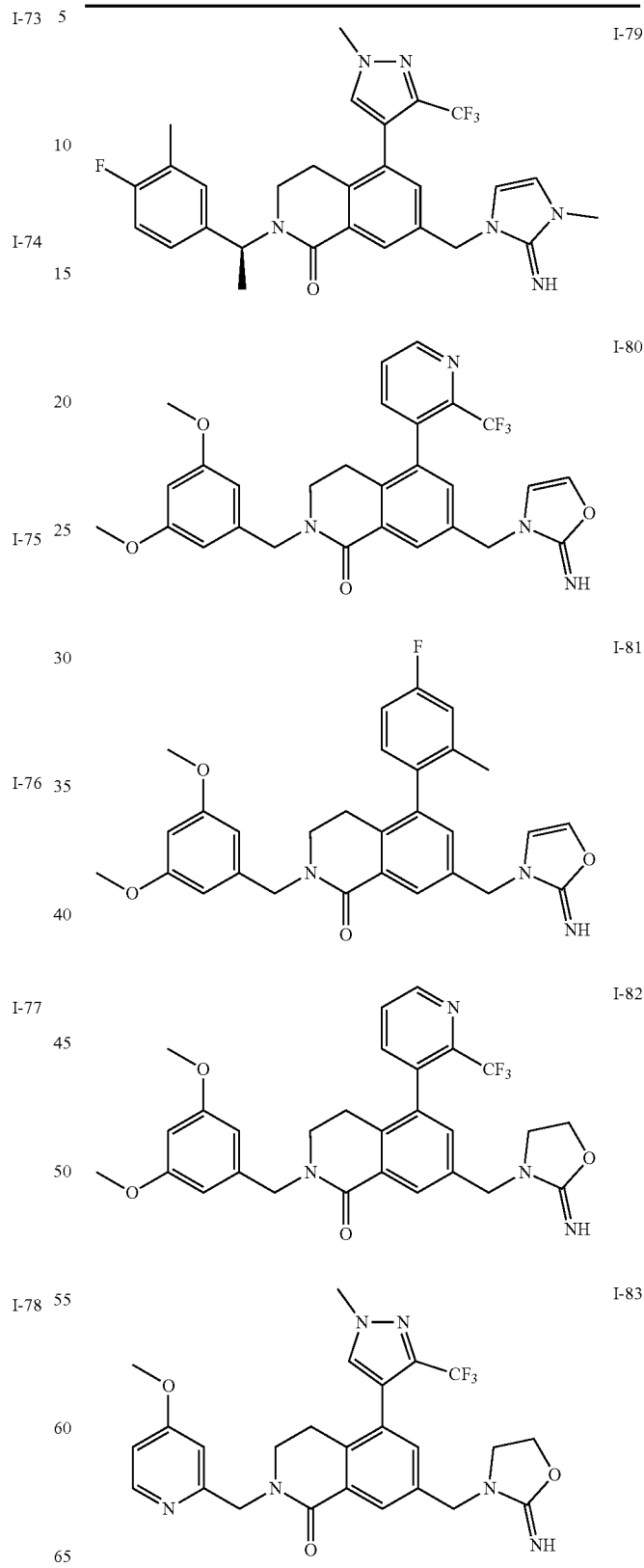

TABLE 1-continued
Exemplary compounds.
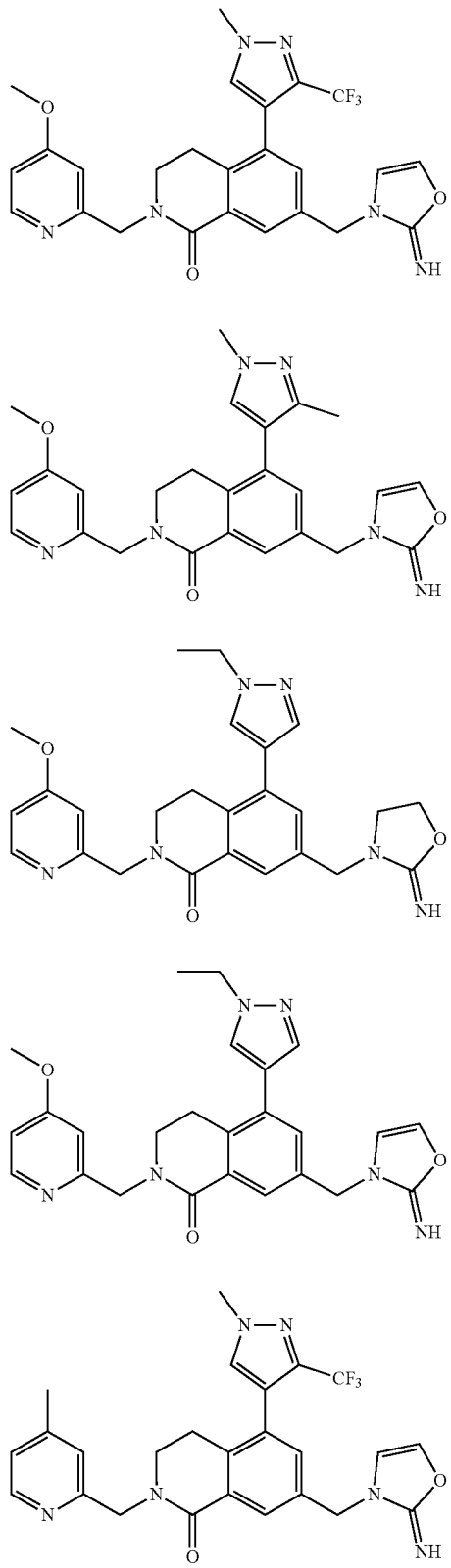
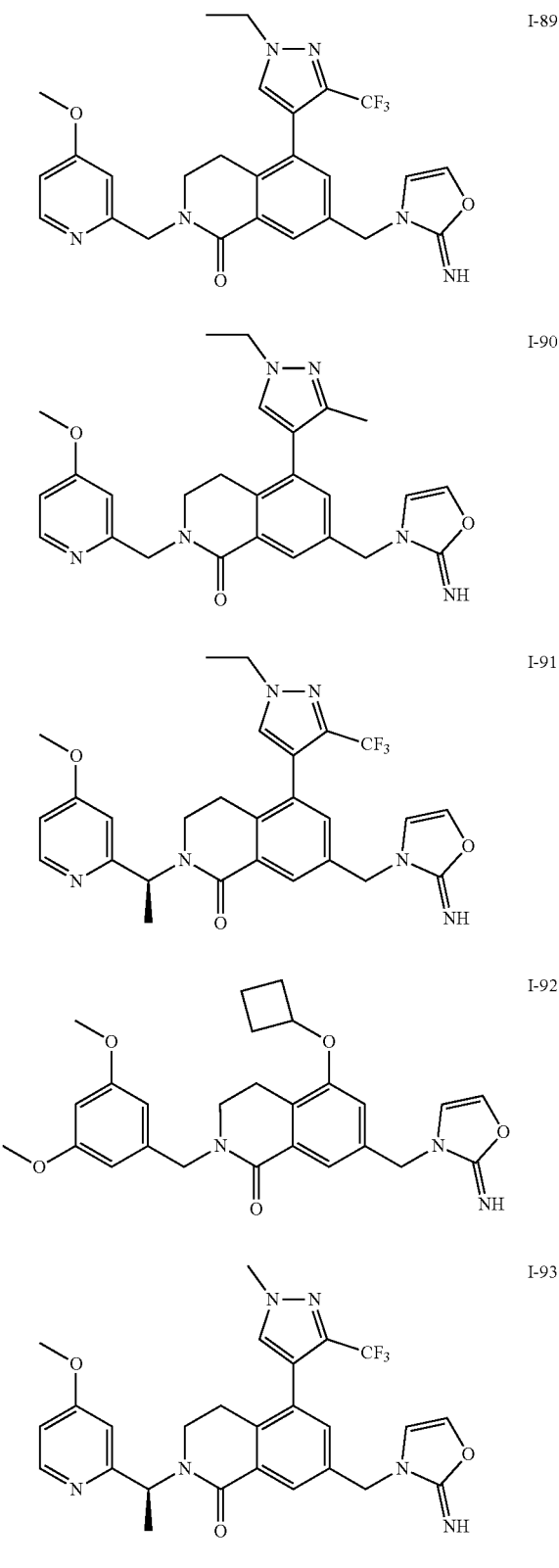

TABLE 1-continued

Exemplary compounds.

TABLE 1-continued
Exemplary compounds.
I-104
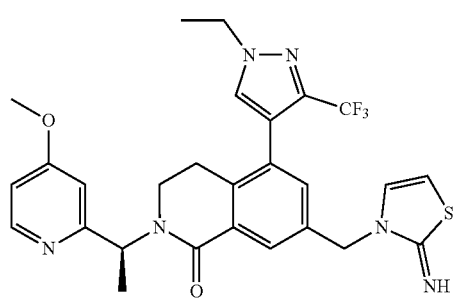
I-105
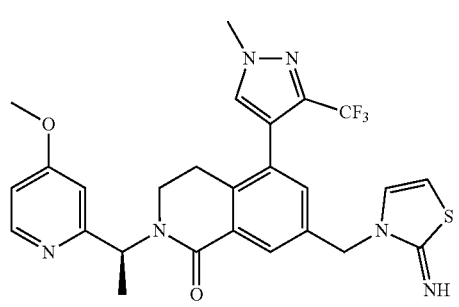 [SMILES: COc1ccnc([C@H](C)N2CCc3c(cc(Cn4ccsc4=N)cc3-c3cn(C)nc3C(F)(F)F)C2=O)c1]
I-106
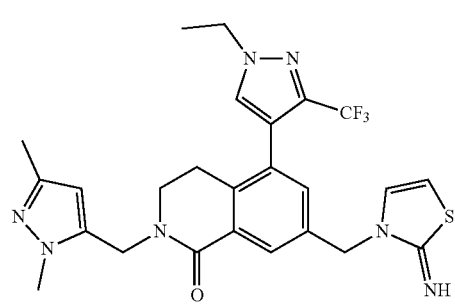 [SMILES: CCn1cc(-c2cc(Cn3ccsc3=N)cc3c2CCN(Cc2cc(C)nn2C)C3=O)c(C(F)(F)F)n1]
I-107
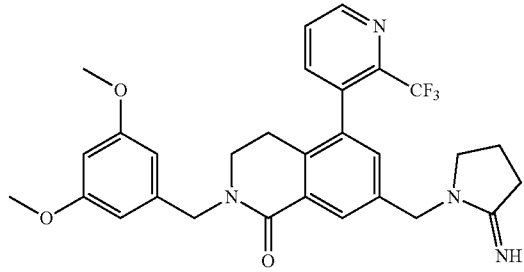 [SMILES: COc1cc(CN2CCc3c(cc(CN4CCCC4=N)cc3-c3cccnc3C(F)(F)F)C2=O)cc(OC)c1]
I-108
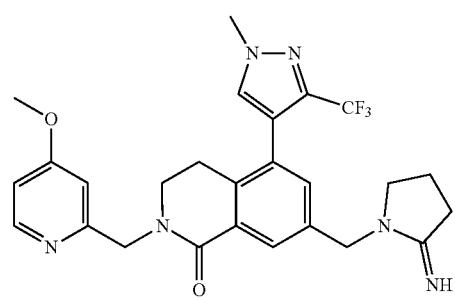 [SMILES: COc1ccnc(CN2CCc3c(cc(CN4CCCC4=N)cc3-c3cn(C)nc3C(F)(F)F)C2=O)c1]
TABLE 1-continued
Exemplary compounds.
I-109
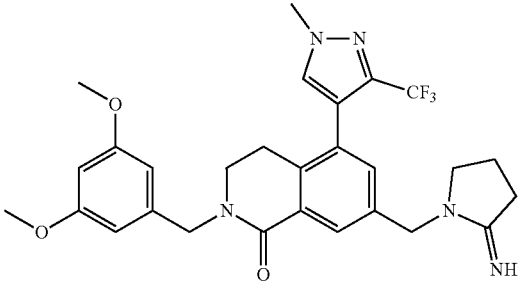 [SMILES: COc1cc(CN2CCc3c(cc(CN4CCCC4=N)cc3-c3cn(C)nc3C(F)(F)F)C2=O)cc(OC)c1]
I-110
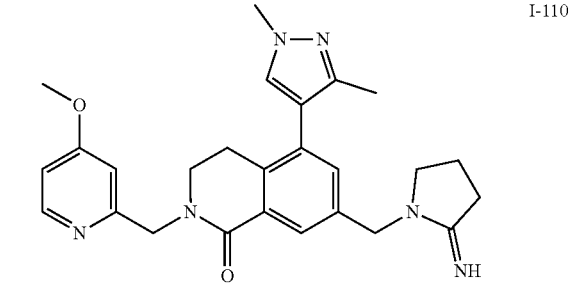
I-111
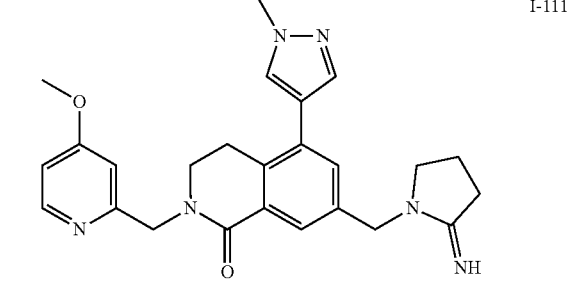
I-112
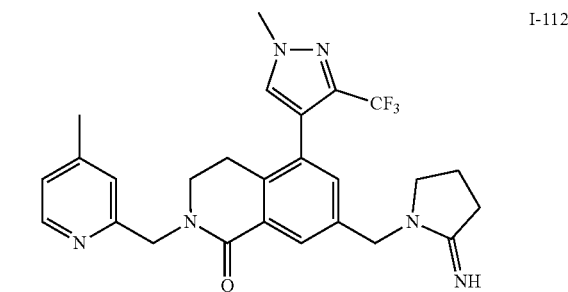
I-113
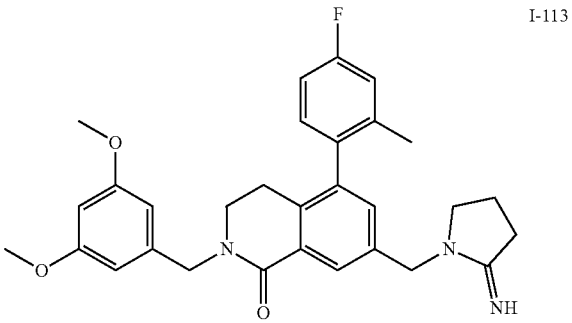

TABLE 1-continued
Exemplary compounds.
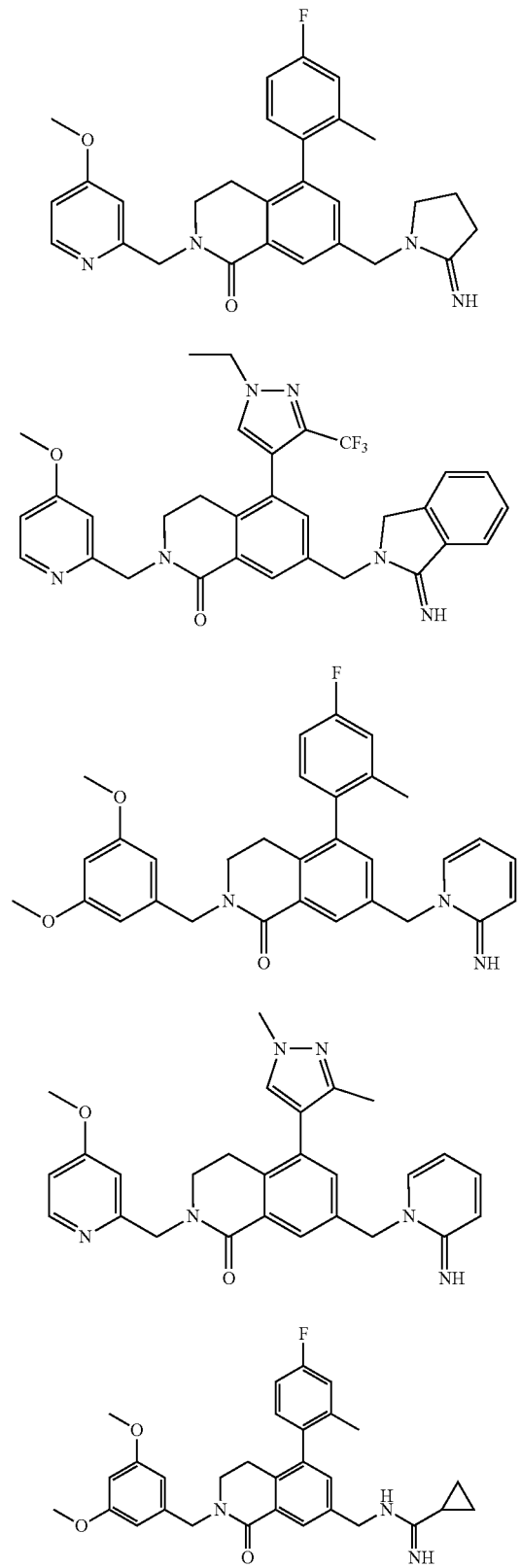
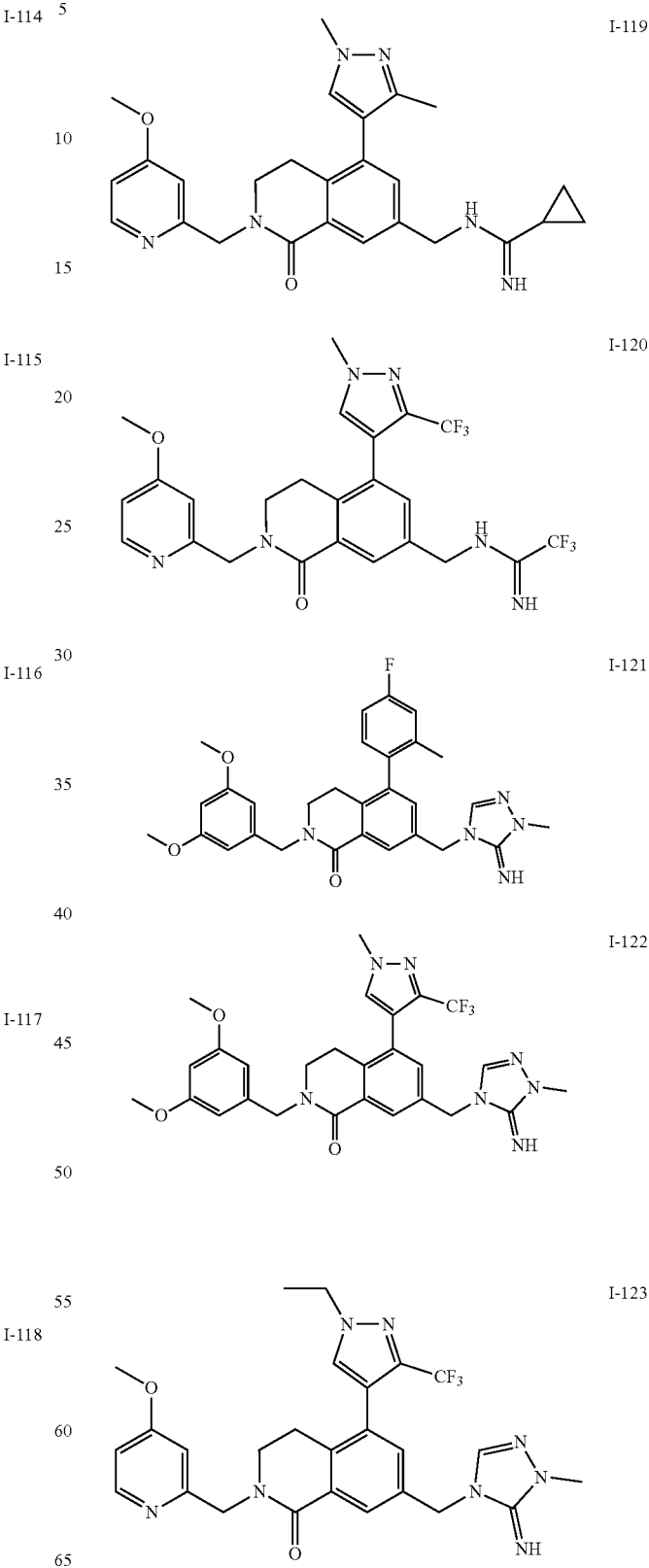

TABLE 1-continued
Exemplary compounds.
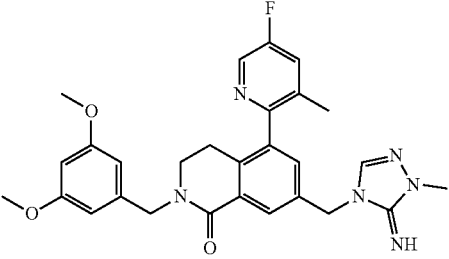 I-124
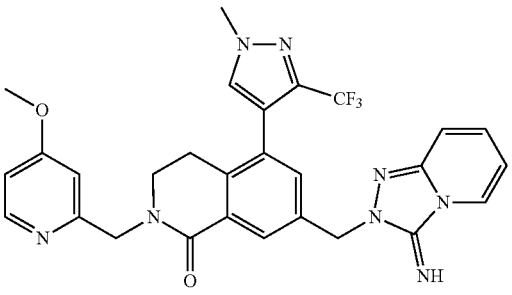 [SMILES: COc1ccnc(CN2CCc3c(cc(Cn4nc5ccccn5c4=N)cc3-c3cn(C)nc3C(F)(F)F)C2=O)c1] I-125
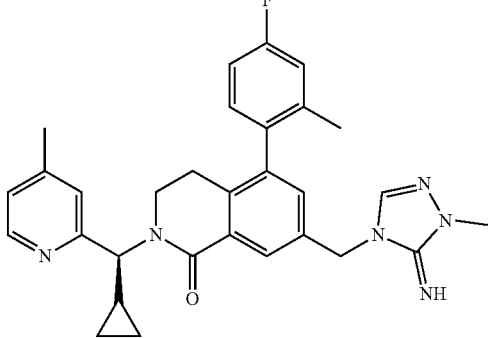 I-126
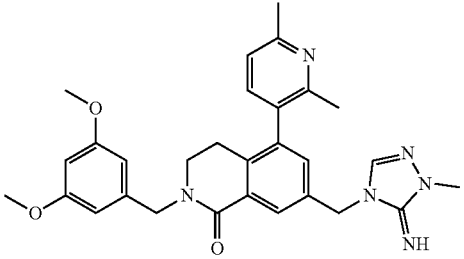 I-127
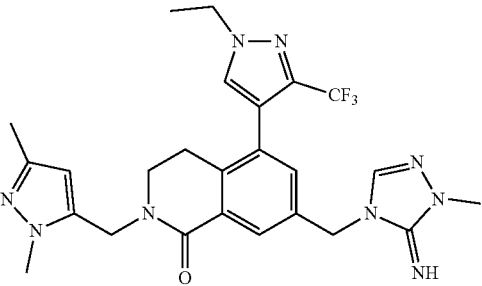 [SMILES: CCn1cc(-c2cc(Cn3cnn(C)c3=N)cc3c2CCN(Cc2cc(C)nn2C)C3=O)c(C(F)(F)F)n1] I-128
TABLE 1-continued
Exemplary compounds.
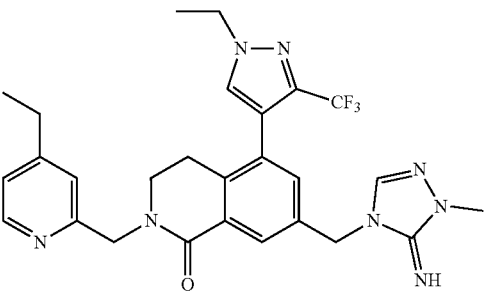 [SMILES: CCc1ccnc(CN2CCc3c(cc(Cn4cnn(C)c4=N)cc3-c3cn(CC)nc3C(F)(F)F)C2=O)c1] I-129
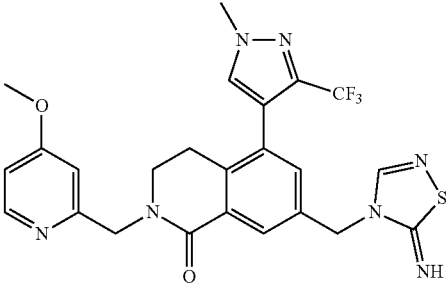 [SMILES: COc1ccnc(CN2CCc3c(cc(Cn4cnsc4=N)cc3-c3cn(C)nc3C(F)(F)F)C2=O)c1] I-130
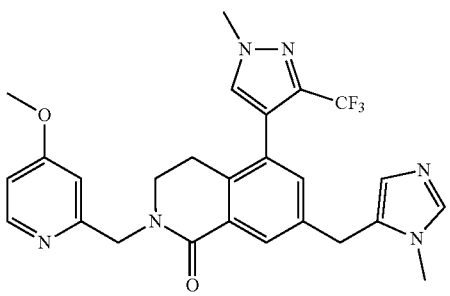 [SMILES: COc1ccnc(CN2CCc3c(cc(Cc4cncn4C)cc3-c3cn(C)nc3C(F)(F)F)C2=O)c1] I-131
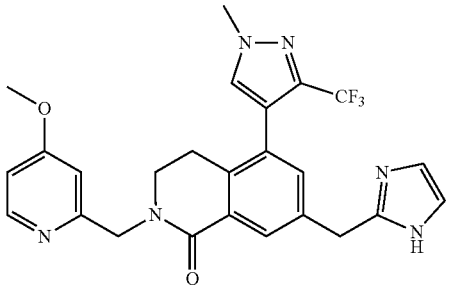 [SMILES: COc1ccnc(CN2CCc3c(cc(Cc4ncc[nH]4)cc3-c3cn(C)nc3C(F)(F)F)C2=O)c1] I-132
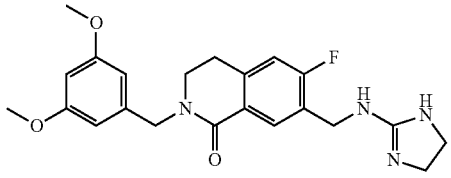 [SMILES: COc1cc(CN2CCc3cc(F)c(CNC4=NCCN4)cc3C2=O)cc(OC)c1] I-133

TABLE 1-continued
Exemplary compounds.
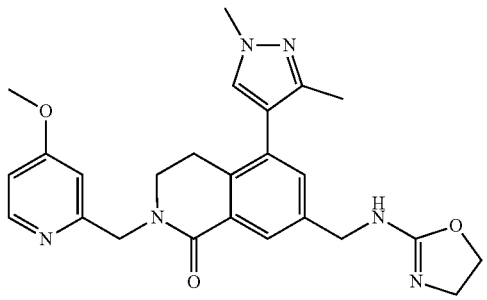 [SMILES: COc1ccnc(CN2CCc3c(cc(CNC4=NCCO4)cc3-c3cn(C)nc3C)C2=O)c1]
I-134
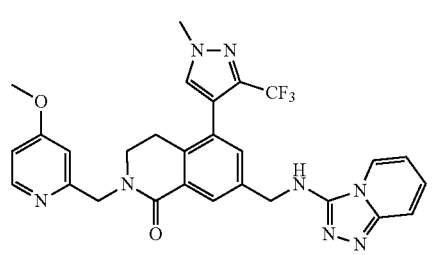 [SMILES: COc1ccnc(CN2CCc3c(cc(CNc4nnc5ccccn45)cc3-c3cn(C)nc3C(F)(F)F)C2=O)c1]
I-135
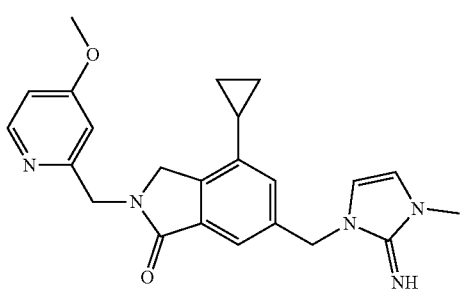 [SMILES: COc1ccnc(CN2Cc3c(cc(Cn4ccn(C)c4=N)cc3C3CC3)C2=O)c1]
I-136
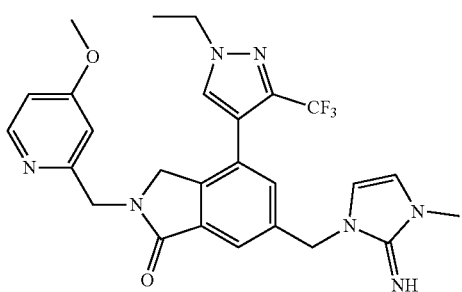 [SMILES: CCn1cc(-c2cc(Cn3ccn(C)c3=N)cc3c2CN(Cc2cc(OC)ccn2)C3=O)c(C(F)(F)F)n1]
I-137
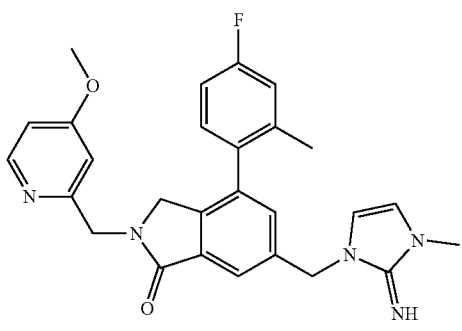 [SMILES: COc1ccnc(CN2Cc3c(cc(Cn4ccn(C)c4=N)cc3-c3ccc(F)cc3C)C2=O)c1]
I-138
TABLE 1-continued
Exemplary compounds.
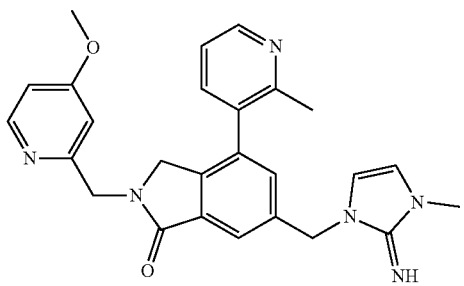 [SMILES: COc1ccnc(CN2Cc3c(cc(Cn4ccn(C)c4=N)cc3-c3cccnc3C)C2=O)c1]
I-139
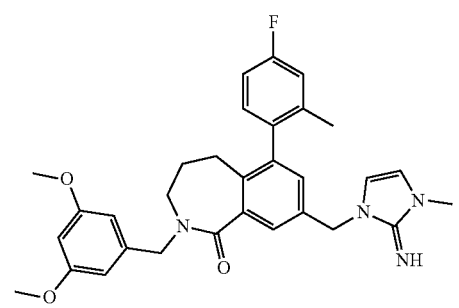
I-140
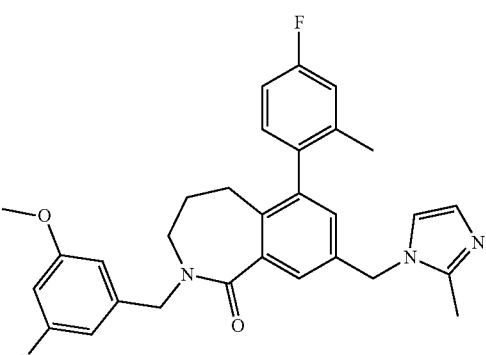
I-141
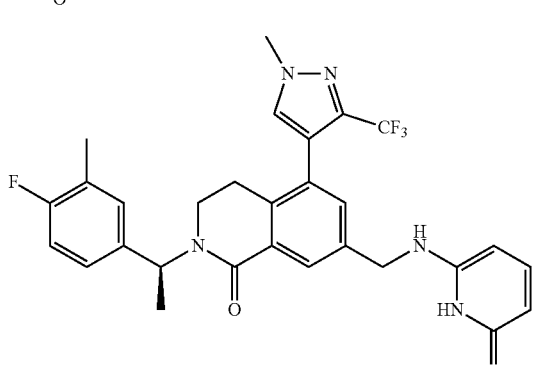
I-142
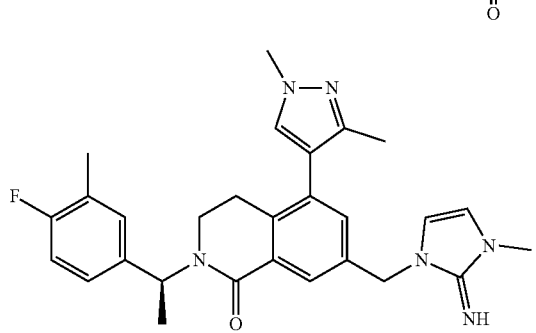
I-143

TABLE 1-continued
Exemplary compounds.
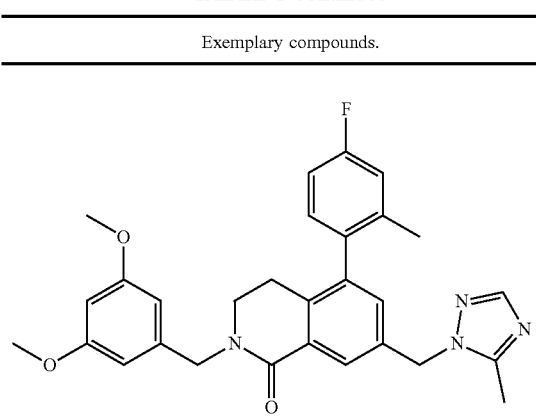
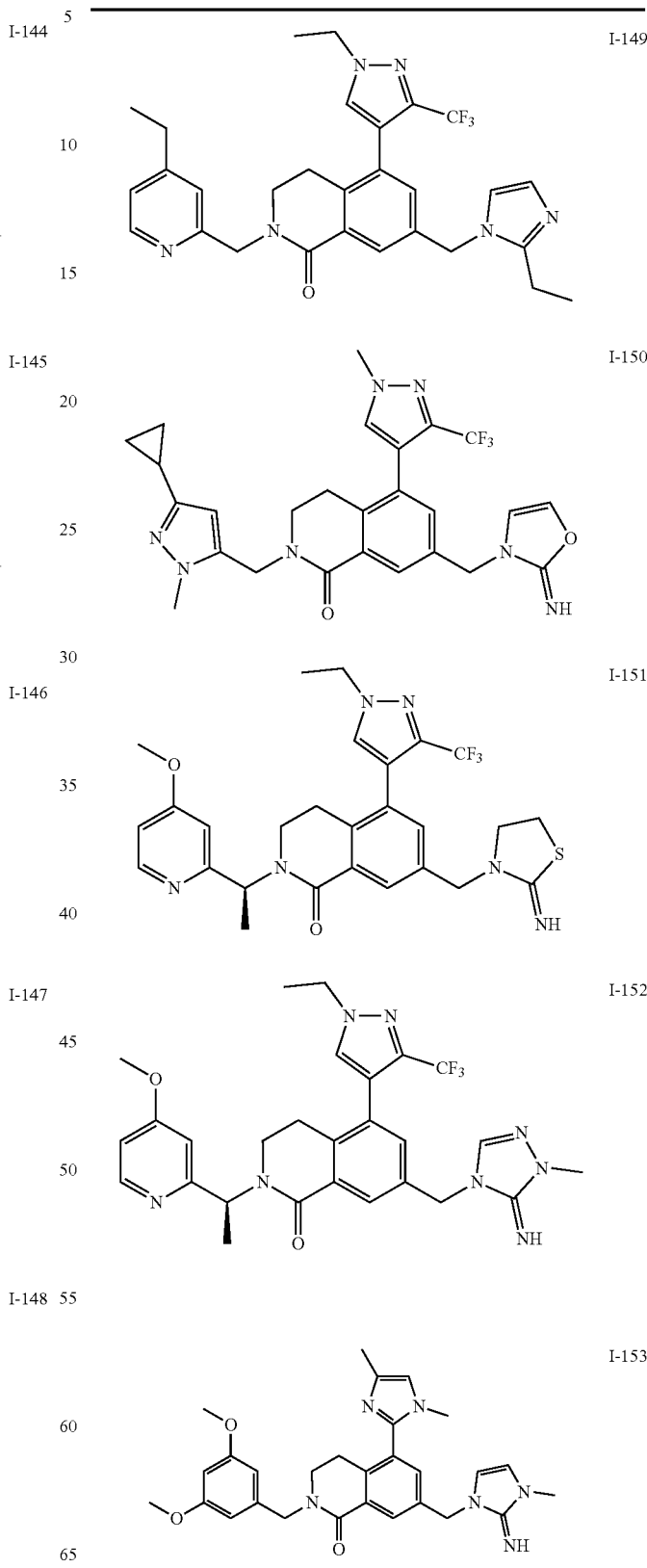

TABLE 1-continued
Exemplary compounds.
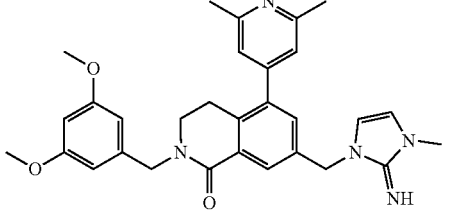 I-154
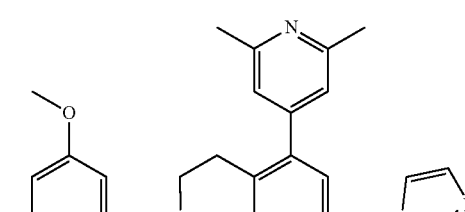 I-155
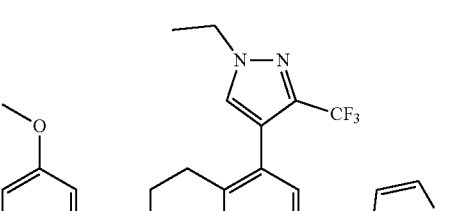 I-156
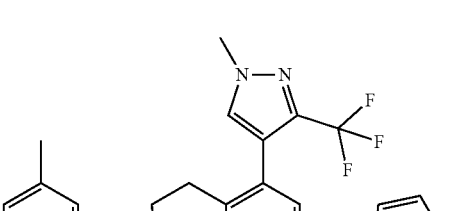 I-157
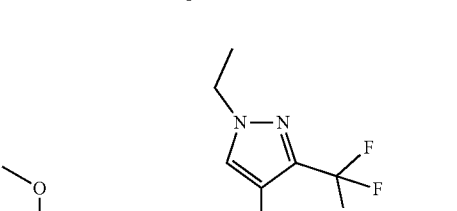 I-158
TABLE 1-continued
Exemplary compounds.
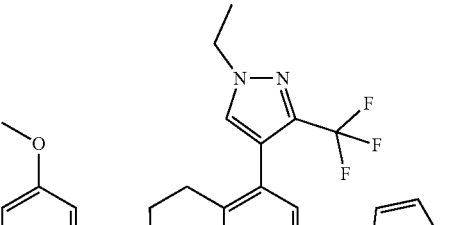 I-159
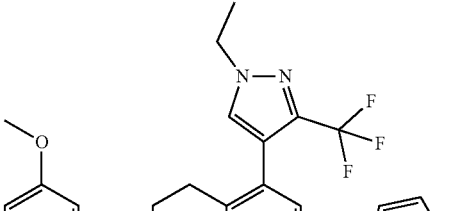 I-160
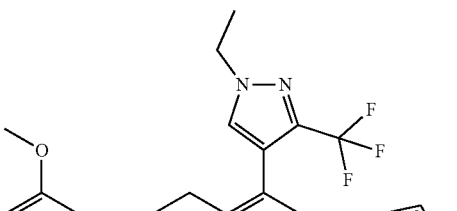 I-161
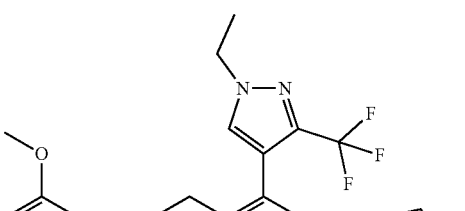 I-162

TABLE 1-continued
Exemplary compounds.
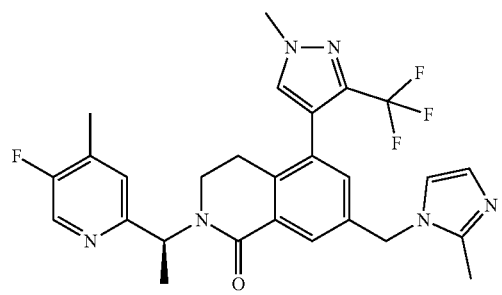 [SMILES: Cc1cc([C@H](C)N2CCc3c(cc(Cn4ccnc4C)cc3-c3cn(C)nc3C(F)(F)F)C2=O)ncc1F] I-163
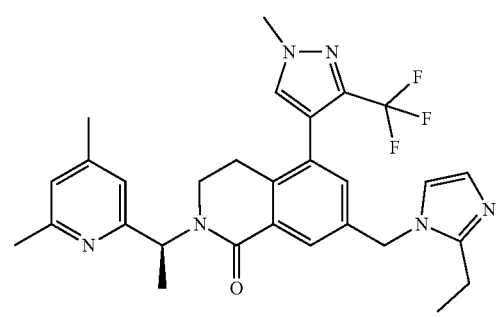 [SMILES: CCc1nccn1Cc1cc2c(c(-c3cn(C)nc3C(F)(F)F)c1)CCN([C@@H](C)c1cc(C)cc(C)n1)C2=O] I-164
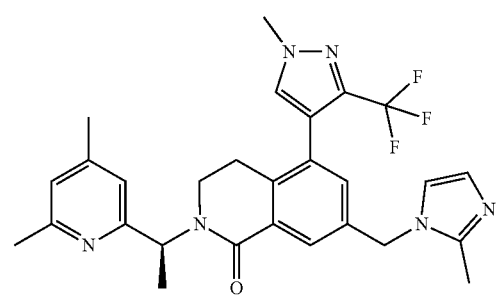 [SMILES: Cc1cc(C)nc([C@H](C)N2CCc3c(cc(Cn4ccnc4C)cc3-c3cn(C)nc3C(F)(F)F)C2=O)c1] I-165
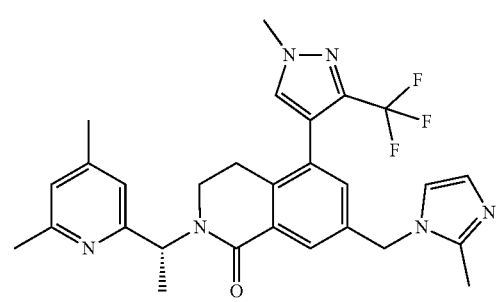 [SMILES: Cc1cc(C)nc([C@@H](C)N2CCc3c(cc(Cn4ccnc4C)cc3-c3cn(C)nc3C(F)(F)F)C2=O)c1] I-166
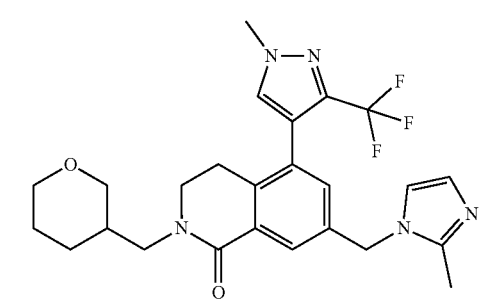 [SMILES: Cc1nccn1Cc1cc2c(c(-c3cn(C)nc3C(F)(F)F)c1)CCN(CC1CCCOC1)C2=O] I-167
TABLE 1-continued
Exemplary compounds.
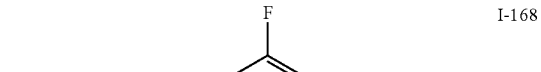 I-168
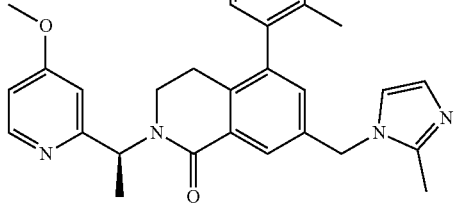 I-169
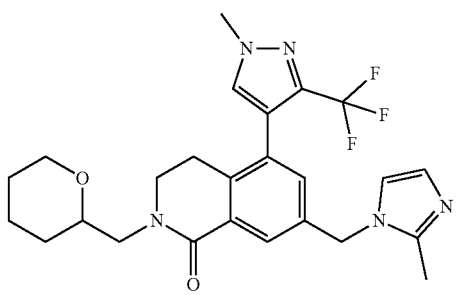 I-170
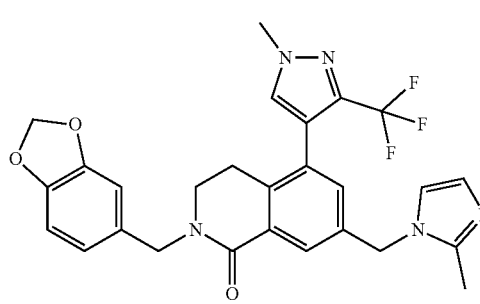 I-171
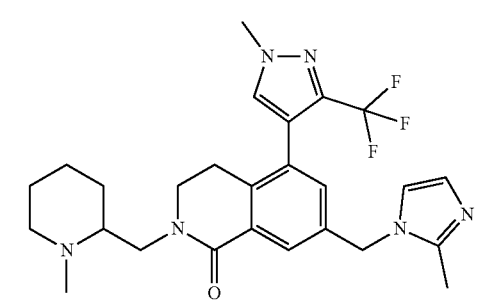 I-172

TABLE 1-continued

Exemplary compounds.

TABLE 1-continued
Exemplary compounds.
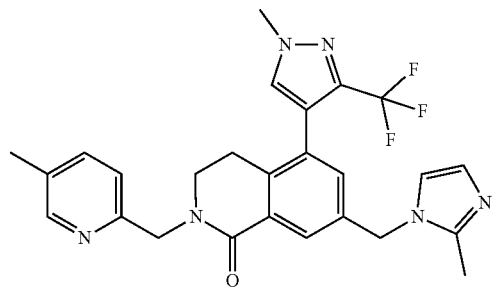 [SMILES: Cc1ccc(CN2CCc3c(cc(Cn4ccnc4C)cc3-c3cn(C)nc3C(F)(F)F)C2=O)nc1] I-183
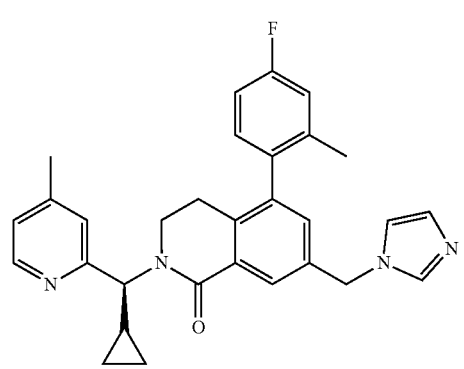 [SMILES: Cc1ccnc([C@H](C2CC2)N2CCc3c(cc(Cn4ccnc4)cc3-c3ccc(F)cc3C)C2=O)c1] I-184
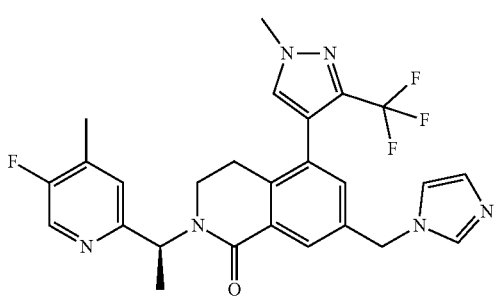 [SMILES: Cc1cc([C@H](C)N2CCc3c(cc(Cn4ccnc4)cc3-c3cn(C)nc3C(F)(F)F)C2=O)ncc1F] I-185
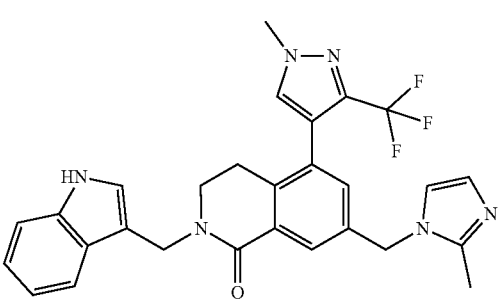 [SMILES: Cc1nccn1Cc1cc2c(c(-c3cn(C)nc3C(F)(F)F)c1)CCN(Cc1c[nH]c3ccccc13)C2=O] I-186
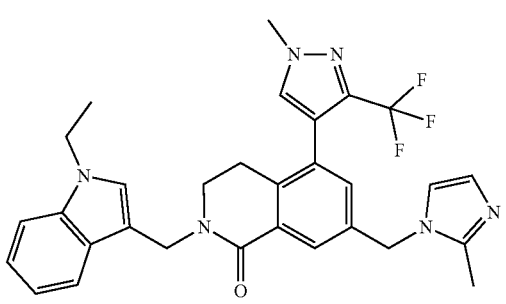 [SMILES: CCn1cc(CN2CCc3c(cc(Cn4ccnc4C)cc3-c3cn(C)nc3C(F)(F)F)C2=O)c2ccccc21] I-187
TABLE 1-continued
Exemplary compounds.
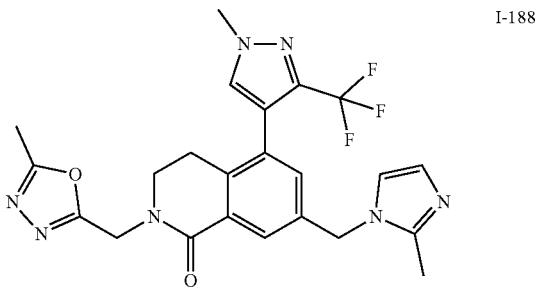 I-188
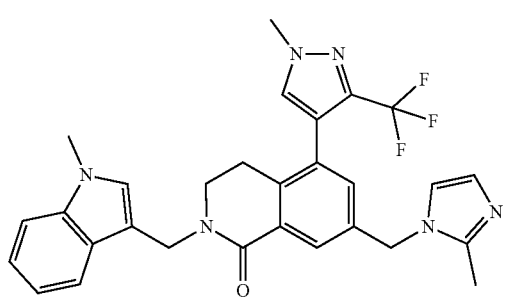 I-189
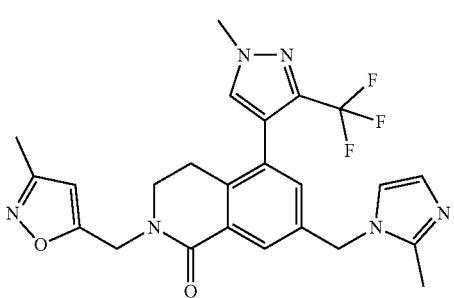 [SMILES: Cc1cc(CN2CCc3c(cc(Cn4ccnc4C)cc3-c3cn(C)nc3C(F)(F)F)C2=O)on1] I-190
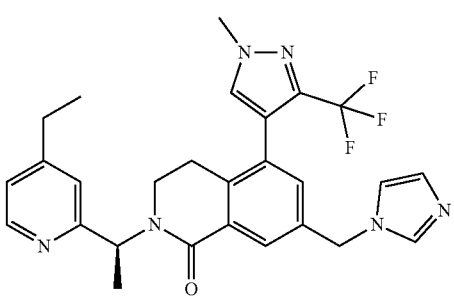 [SMILES: CCc1ccnc([C@H](C)N2CCc3c(cc(Cn4ccnc4)cc3-c3cn(C)nc3C(F)(F)F)C2=O)c1] I-191
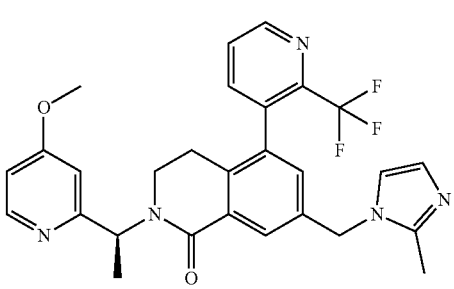 [SMILES: COc1ccnc([C@H](C)N2CCc3c(cc(Cn4ccnc4C)cc3-c3cccnc3C(F)(F)F)C2=O)c1] I-192

TABLE 1-continued
Exemplary compounds.
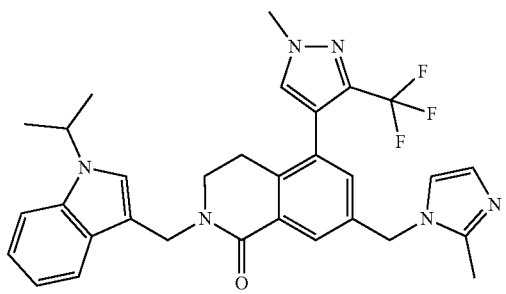 [SMILES: Cc1nccn1Cc1cc2c(c(-c3cn(C)nc3C(F)(F)F)c1)CCN(Cc1cn(C(C)C)c3ccccc13)C2=O] I-193
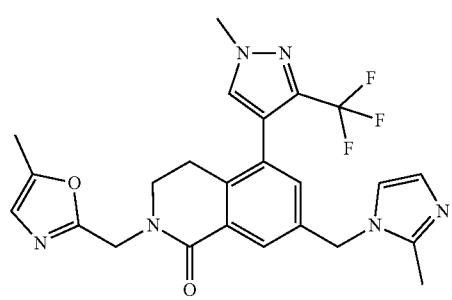 I-194
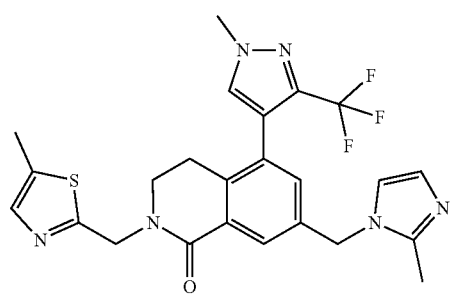 I-195
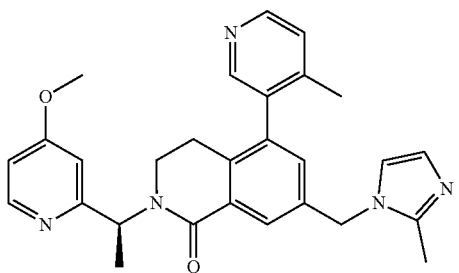 [SMILES: COc1ccnc([C@H](C)N2CCc3c(cc(Cn4ccnc4C)cc3-c3cnccc3C)C2=O)c1] I-196
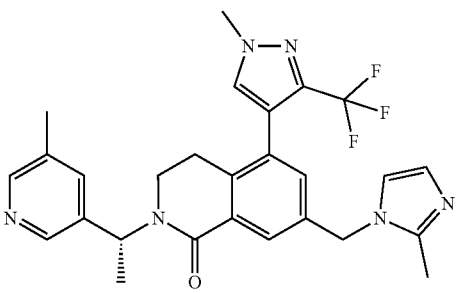 [SMILES: Cc1cncc([C@@H](C)N2CCc3c(cc(Cn4ccnc4C)cc3-c3cn(C)nc3C(F)(F)F)C2=O)c1] I-197
TABLE 1-continued
Exemplary compounds.
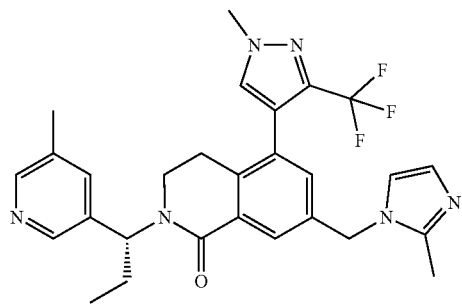 [SMILES: CC[C@H](c1cncc(C)c1)N1CCc2c(cc(Cn3ccnc3C)cc2-c2cn(C)nc2C(F)(F)F)C1=O] I-198
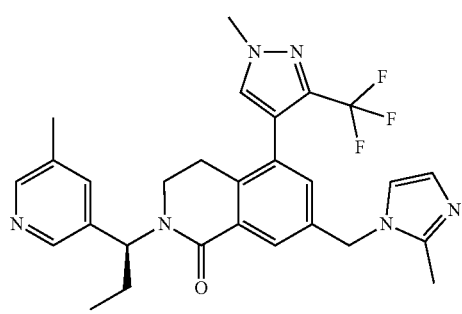 [SMILES: CC[C@@H](c1cncc(C)c1)N1CCc2c(cc(Cn3ccnc3C)cc2-c2cn(C)nc2C(F)(F)F)C1=O] I-199
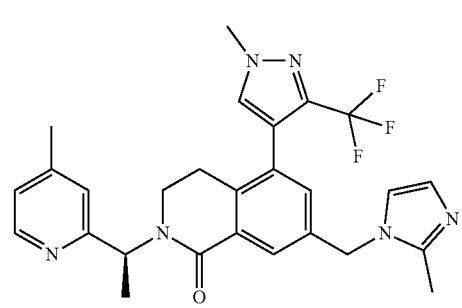 I-200
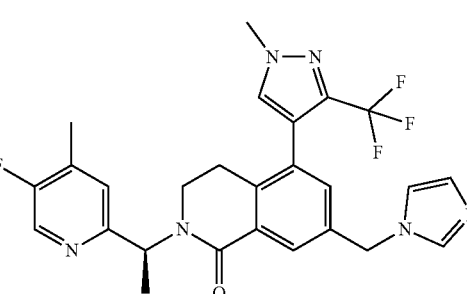 I-201
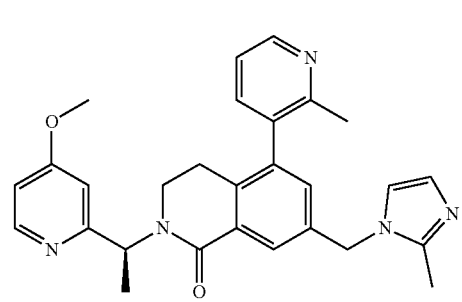 [SMILES: COc1ccnc([C@H](C)N2CCc3c(cc(Cn4ccnc4C)cc3-c3cccnc3C)C2=O)c1] I-202

TABLE 1-continued
Exemplary compounds.
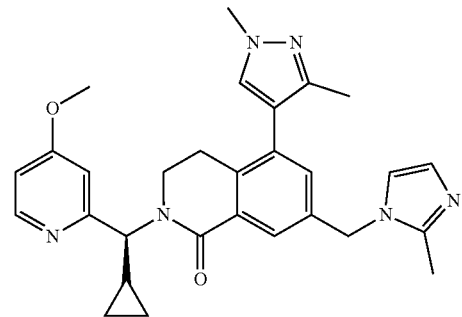 [SMILES: COc1ccnc([C@H](C2CC2)N2CCc3c(cc(Cn4ccnc4C)cc3-c3cn(C)nc3C)C2=O)c1] I-203
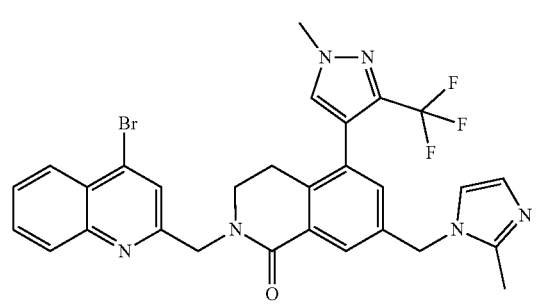 [SMILES: Cc1nccn1Cc1cc2c(c(-c3cn(C)nc3C(F)(F)F)c1)CCN(Cc1cc(Br)c3ccccc3n1)C2=O] I-204
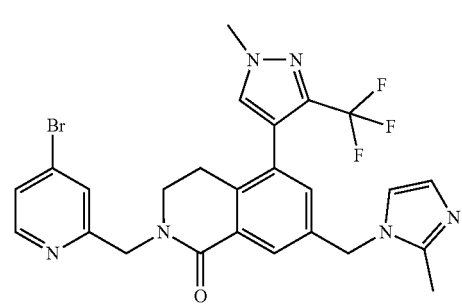 [SMILES: Cc1nccn1Cc1cc2c(c(-c3cn(C)nc3C(F)(F)F)c1)CCN(Cc1cc(Br)ccn1)C2=O] I-205
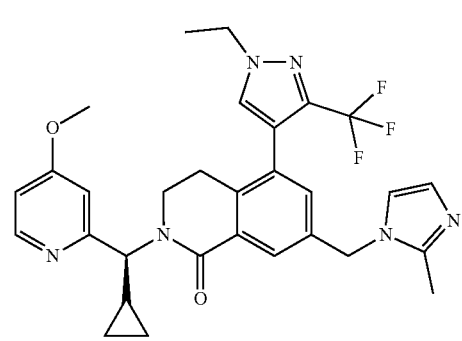 [SMILES: CCn1cc(-c2cc(Cn3ccnc3C)cc3c2CCN([C@H](c2cc(OC)ccn2)C2CC2)C3=O)c(C(F)(F)F)n1] I-206
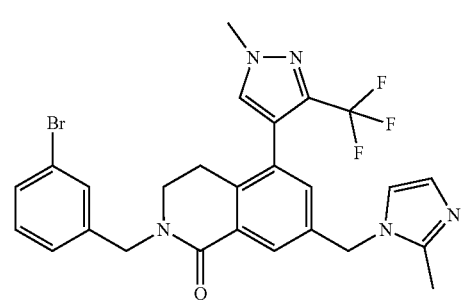 I-207
TABLE 1-continued
Exemplary compounds.
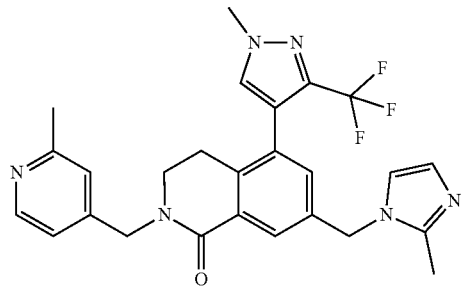 [SMILES: Cc1cc(CN2CCc3c(cc(Cn4ccnc4C)cc3-c3cn(C)nc3C(F)(F)F)C2=O)ccn1] I-208
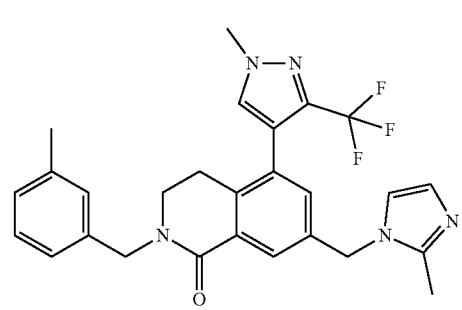 I-209
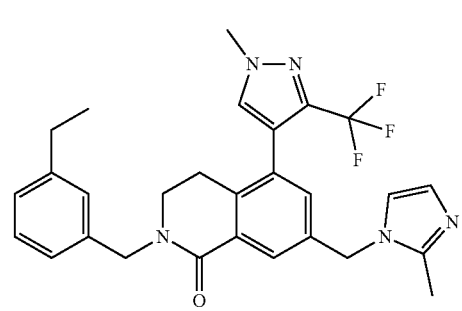 [SMILES: CCc1cccc(CN2CCc3c(cc(Cn4ccnc4C)cc3-c3cn(C)nc3C(F)(F)F)C2=O)c1] I-210
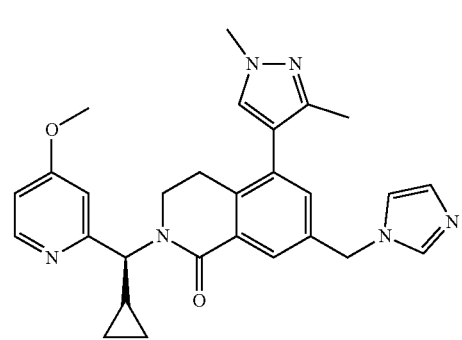 [SMILES: COc1ccnc([C@H](C2CC2)N2CCc3c(cc(Cn4ccnc4)cc3-c3cn(C)nc3C)C2=O)c1] I-211
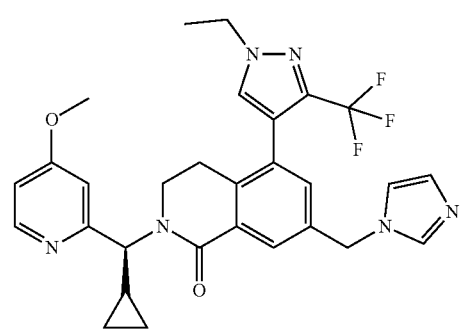 I-212

TABLE 1-continued

Exemplary compounds.

| | |
|---|---|
| I-213 | I-218 |
| I-214 | I-219 |
| I-215 | I-220 |
| I-216 | I-221 |
| I-217 | I-222 |

TABLE 1-continued
Exemplary compounds.
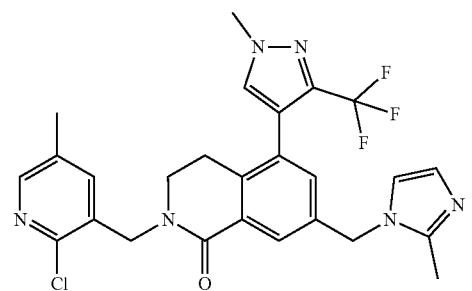 [SMILES: Cc1cnc(Cl)c(CN2CCc3c(cc(Cn4ccnc4C)cc3-c3cn(C)nc3C(F)(F)F)C2=O)c1]
I-223
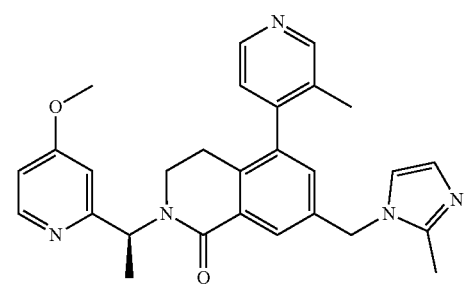 [SMILES: COc1ccnc([C@H](C)N2CCc3c(cc(Cn4ccnc4C)cc3-c3ccncc3C)C2=O)c1]
I-224
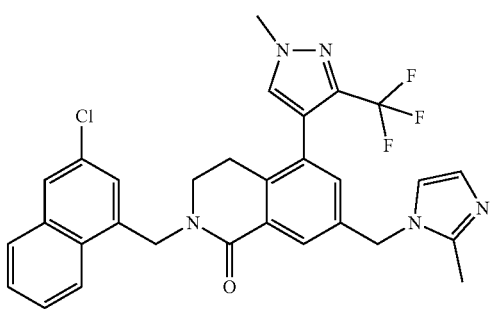 [SMILES: Cc1nccn1Cc1cc2c(c(-c3cn(C)nc3C(F)(F)F)c1)CCN(Cc1cc(Cl)cc3ccccc13)C2=O]
I-225
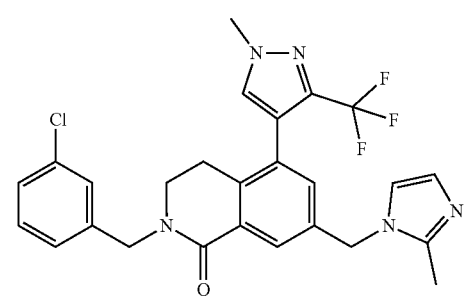 [SMILES: Cc1nccn1Cc1cc2c(c(-c3cn(C)nc3C(F)(F)F)c1)CCN(Cc1cccc(Cl)c1)C2=O]
I-226
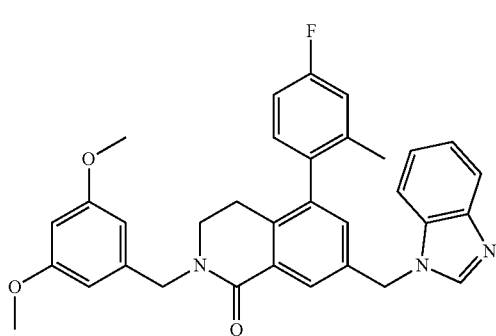 [SMILES: COc1cc(CN2CCc3c(cc(Cn4cnc5ccccc54)cc3-c3ccc(F)cc3C)C2=O)cc(OC)c1]
I-227
TABLE 1-continued
Exemplary compounds.
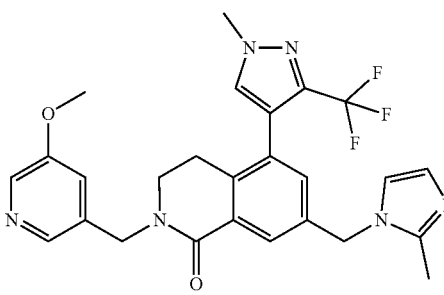
I-228
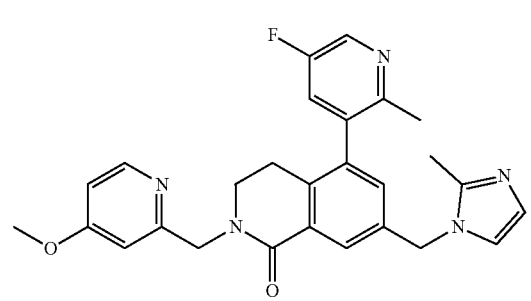 [SMILES: COc1ccnc(CN2CCc3c(cc(Cn4ccnc4C)cc3-c3cc(F)cnc3C)C2=O)c1]
I-229
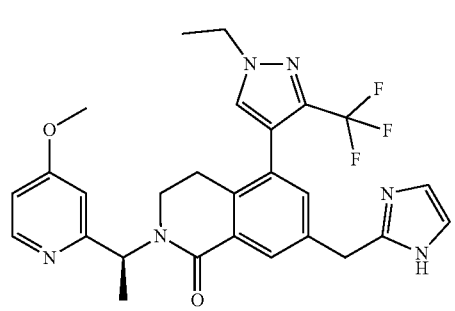 [SMILES: CCn1cc(-c2cc(Cc3ncc[nH]3)cc3c2CCN([C@@H](C)c2cc(OC)ccn2)C3=O)c(C(F)(F)F)n1]
I-230
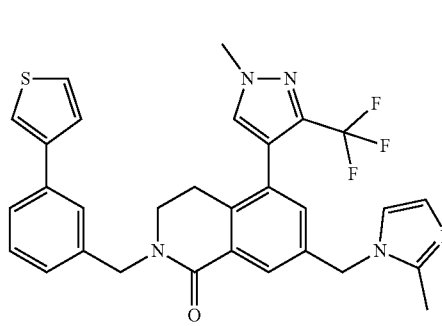
I-231
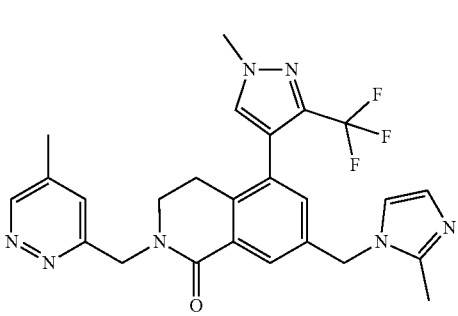 [SMILES: Cc1cnnc(CN2CCc3c(cc(Cn4ccnc4C)cc3-c3cn(C)nc3C(F)(F)F)C2=O)c1]
I-232

TABLE 1-continued
Exemplary compounds.
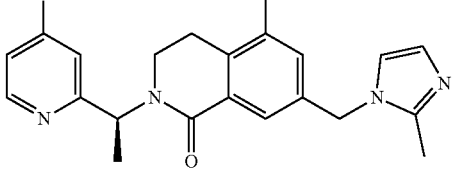
I-233
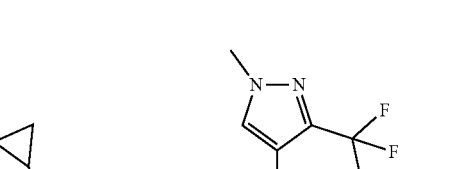
I-234
I-235
I-236
I-237
TABLE 1-continued
Exemplary compounds.
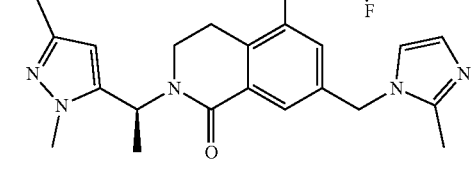
I-238
I-239
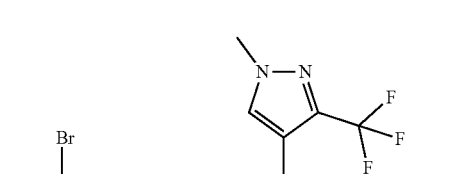
I-240
I-241
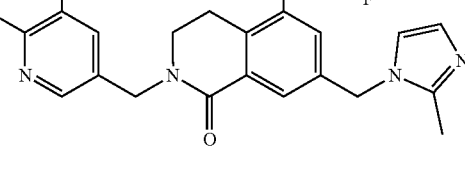
I-242

TABLE 1-continued
Exemplary compounds.
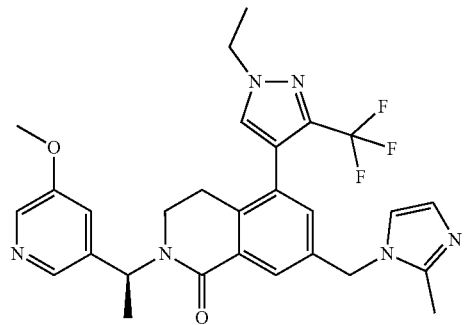 [SMILES: CCn1cc(-c2cc(Cn3ccnc3C)cc3c2CCN([C@@H](C)c2cncc(OC)c2)C3=O)c(C(F)(F)F)n1]
I-243
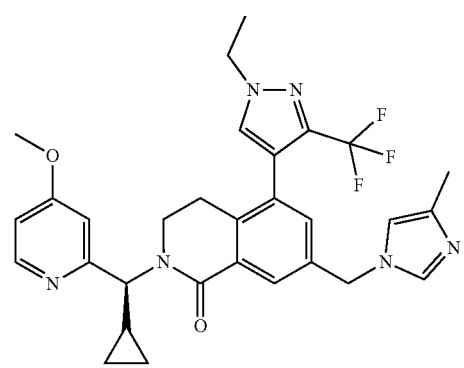 [SMILES: CCn1cc(-c2cc(Cn3cnc(C)c3)cc3c2CCN([C@H](c2cc(OC)ccn2)C2CC2)C3=O)c(C(F)(F)F)n1]
I-244
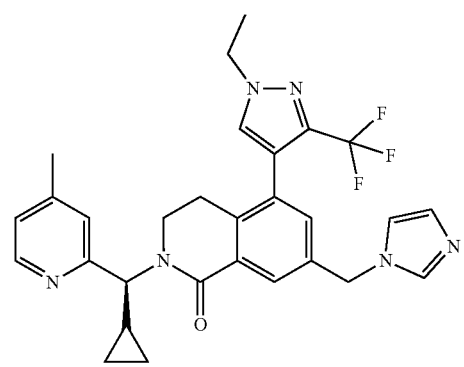
I-245
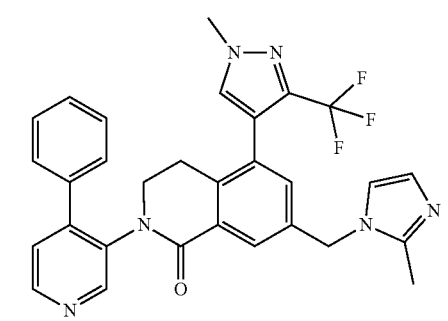 [SMILES: Cc1nccn1Cc1cc2c(c(-c3cn(C)nc3C(F)(F)F)c1)CCN(c1cnccc1-c1ccccc1)C2=O]
I-246
TABLE 1-continued
Exemplary compounds.
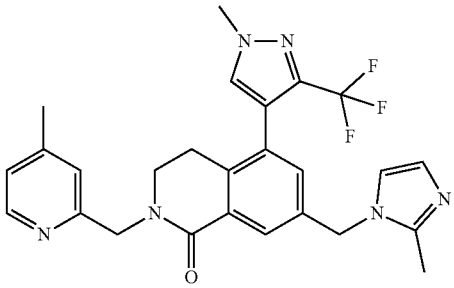
I-247
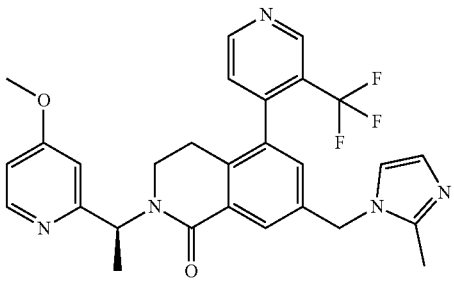 [SMILES: COc1ccnc([C@H](C)N2CCc3c(cc(Cn4ccnc4C)cc3-c3ccncc3C(F)(F)F)C2=O)c1]
I-248
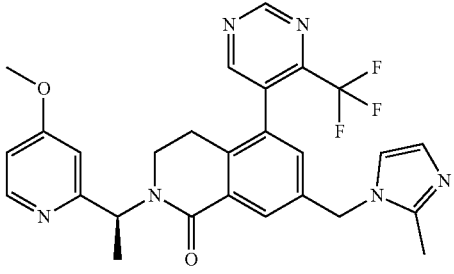 [SMILES: COc1ccnc([C@H](C)N2CCc3c(cc(Cn4ccnc4C)cc3-c3cncnc3C(F)(F)F)C2=O)c1]
I-249
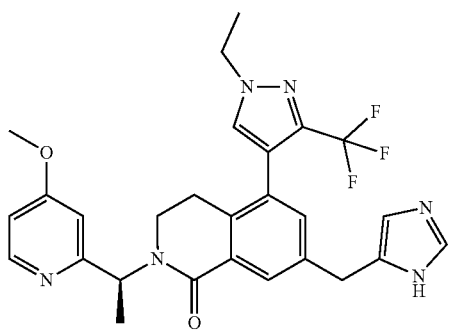 [SMILES: CCn1cc(-c2cc(Cc3cnc[nH]3)cc3c2CCN([C@@H](C)c2cc(OC)ccn2)C3=O)c(C(F)(F)F)n1]
I-250
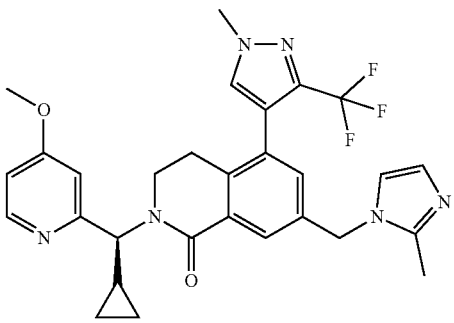 [SMILES: COc1ccnc([C@H](C2CC2)N2CCc3c(cc(Cn4ccnc4C)cc3-c3cn(C)nc3C(F)(F)F)C2=O)c1]
I-251

TABLE 1-continued

Exemplary compounds.

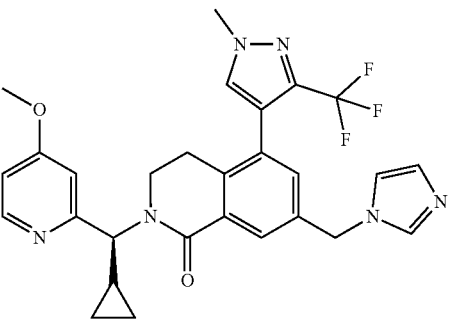 [SMILES: COc1ccnc([C@H](C2CC2)N2CCc3c(cc(Cn4ccnc4)cc3-c3cn(C)nc3C(F)(F)F)C2=O)c1] I-252

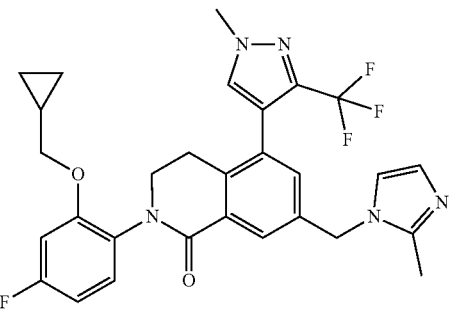 [SMILES: Cc1nccn1Cc1cc2c(c(-c3cn(C)nc3C(F)(F)F)c1)CCN(c1ccc(F)cc1OCC1CC1)C2=O] I-253

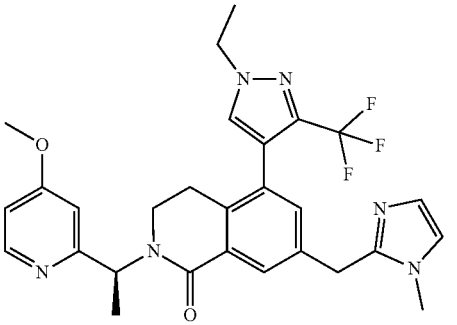 [SMILES: CCn1cc(-c2cc(Cc3nccn3C)cc3c2CCN([C@@H](C)c2cc(OC)ccn2)C3=O)c(C(F)(F)F)n1] I-254

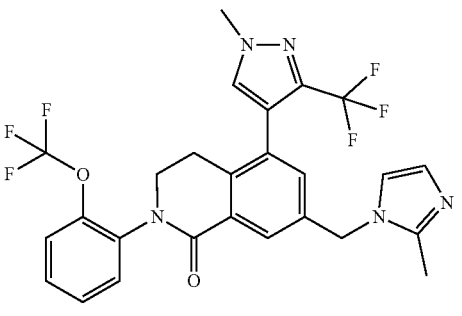 [SMILES: Cc1nccn1Cc1cc2c(c(-c3cn(C)nc3C(F)(F)F)c1)CCN(c1ccccc1OC(F)(F)F)C2=O] I-255

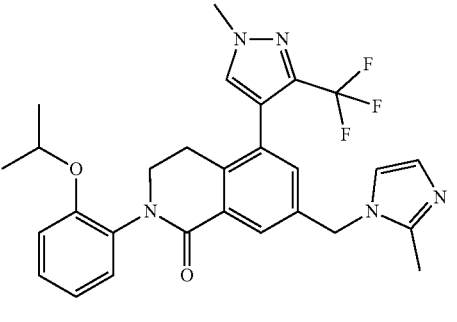 [SMILES: Cc1nccn1Cc1cc2c(c(-c3cn(C)nc3C(F)(F)F)c1)CCN(c1ccccc1OC(C)C)C2=O] I-256

TABLE 1-continued

Exemplary compounds.

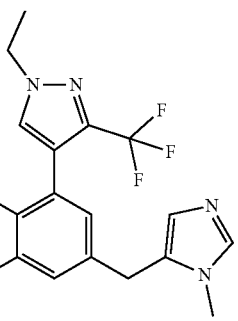 I-257

Compound names are assigned by using Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. Binding to WDR5

The disclosed compounds may bind to WDR5 and prevent the association of MLL1 or other transcription factors and proteins dependent on WDR5. The compounds may bind to WDR5 and prevent oncogenic processes associated with MLL1, c-MYC, or other oncogenic proteins dependent on WDR5.

Compounds of formula (I) can bind to WDR5 resulting in a $K_i$ ranging from about 0.01 nM to about 250 μM. The compounds may have a $K_i$ of about 250 μM, about 200 μM, about 150 μM, about 100 μM, about 90 μM, about 80 μM, about 70 μM, about 60 μM, about 50 μM, about 40 μM, about 30 μM, about 20 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) can bind to WDR5 resulting in a $K_i$ of less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

B. General Synthesis

Compounds of formula (I) may be prepared by synthetic processes or by metabolic processes. Preparation of the compounds by metabolic processes includes those occurring in the human or animal body (in vivo) or processes occurring in vitro.

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein. Compounds of formula (I) may be also prepared by metabolic processes. Preparation of the compounds by metabolic processes includes those occurring in the human or animal body (in vivo) or processes occurring in vitro.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, Scheme 1

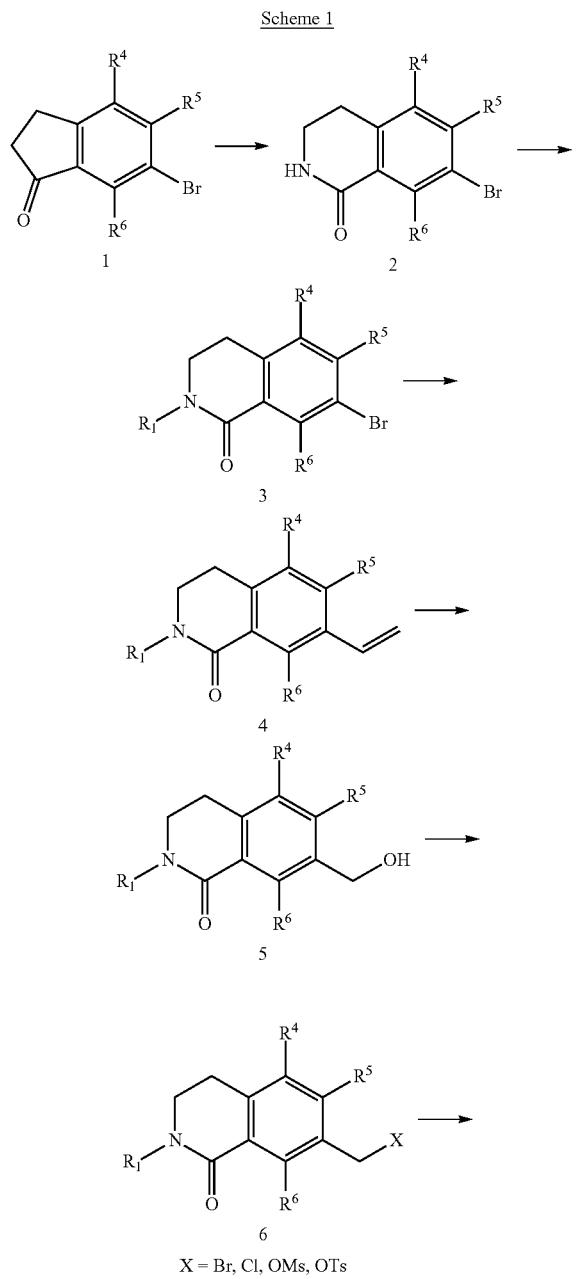

X = Br, Cl, OMs, OTs

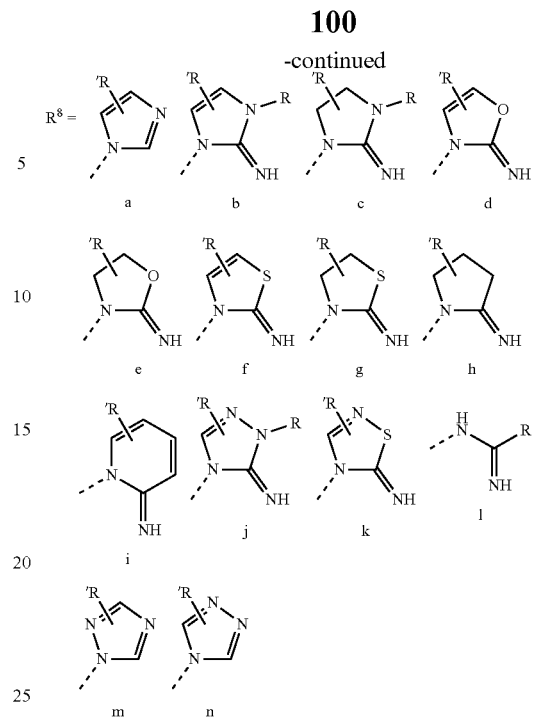

In some embodiments, provided compounds of this invention may be prepared as shown in Scheme 1. Appropriately substituted 6-bromo-dihydroindan-1-one 1 is converted to 7-bromo-dihydroisoquinolin-1-one 2 using the Schmidt reaction protocol (Wolff, H. "The Schmidt Reaction". Organic Reactions (2011), 307-336) using $NaN_3$ under the acidic reaction condition. The corresponding lactam NH of 2 can be alkylated by appropriate $R^1$ group at a number of conditions that are routine for those skilled in the art to give intermediate 3. The commercially available vinyl boronic acid or potassium trifluoro(vinyl)borate can be coupled with intermediates 3 to provide vinyl adduct 4 via e.g., Suzuki-Miyaura coupling protocol (Miyaura, N., Suzuki, A., *Chem. Rev.* (1995), 2457) in the presence of a catalytic Pd species including, but not limited to, $PdCl_2(dppf)$ or $Pd(PPh_3)_4$, and with appropriate bases such as $Na_2CO_3$, $Cs_2CO_3$, $K_2CO_3$, $Ba(OH)_2$ or $Et_3N$. Subsequent ozonolysis of compound 4 followed by hydride reduction using, but not limited to, $NaBH_4$ or $NaCNBH_3$ to prepare alcohol 5. Hydroxy group of Formula 5 may be activated by converting to bromide, chloride, mesylate or tosylate group by a number of conditions that are routine for those skilled in the art of organic synthesis. Intermediate 6 can be reacted with variety of nucleophiles such as optionally substituted imidazole (a), 1,3-dihydro-2H-imidazol-2-imine (b), imidazolidin-2-imine (c), oxazol-2-imine (d), oxazolidine-2-imine (e), thiazol-2-imine (f), thiazolidin-2-imine (g), pyrrolidin-2-imine (h), 2-aminopyridine (i), 2,4-dihydro-1,2,4-triazol-3-imine (j), 1,2,4-thiadiazol-5-imine (k), amidine (l), or 1,2,4-triazole (m and n) in the presence of appropriate bases, such as DIEA, TEA, $Cs_2CO_3$, $K_2CO_3$, LiOH or NaOH, to yield corresponding products of Formula 7a-n, respectively.

Scheme 2

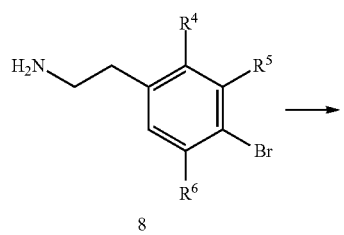

8

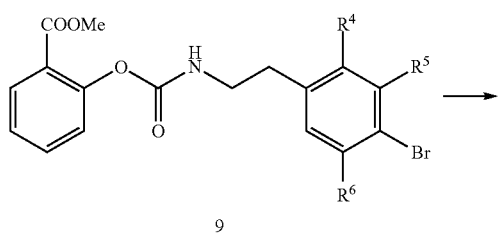

9

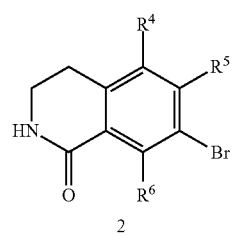

2

Alternatively, intermediate of formula 2 can be prepared by procedures illustrated in Scheme 2. Suitably substituted phenethylamine 8 can be converted to carbonate 9 using dimethyl 2,2'-(carbonylbis(oxy))dibenzoate in the presence of an organic base such as $Et_3N$ or $(i-Pr)_2EtN$. Carbonate 9 may undergo the Fredel-Crafts acylation reaction under acidic conditions to yield intermediate 2, which can be utilized in protocols illustrated in Scheme 1 to generate compounds of formula 7a-n.

Scheme 3

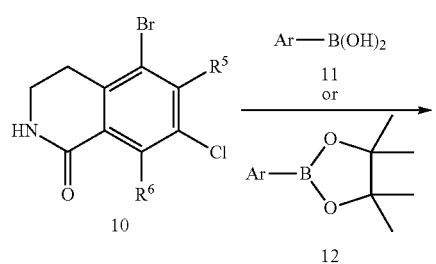
10

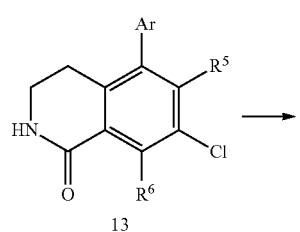
13

-continued

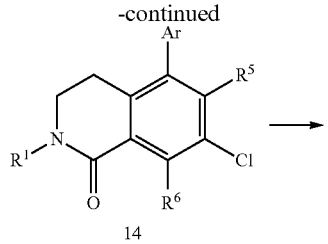
14

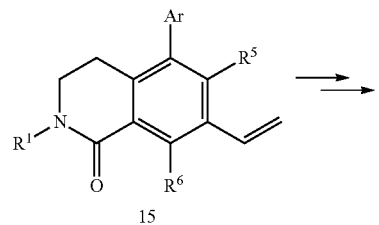
15

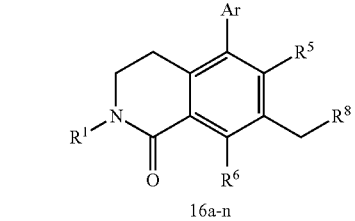
16a-n

In some embodiments, compounds of formula 16a-n containing an aryl or heteroaryl substituent at $R^4$ may be synthesized by procedures illustrated in Scheme 3 using dihydroisoquinolinone 10, which can be prepared by following protocols described in Scheme 1 or 2, as a starting material. A variety of boronic acids 11 or borates 12, which are commercially available or can be prepared, can be selectively coupled with intermediates 10 by reacting with the bromine atom via e.g., Suzuki-Miyaura coupling protocol to afford biaryl adducts 13 (Miyaura, N., Suzuki, A., *Chem. Rev.* (1995), 2457) in the presence of a catalytic Pd species, such as $Pd(PPh_3)_4$, $PdCl_2(dppf)$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. Installation of desirable $R^1$ moieties using the alkylation protocol described in Scheme 1 may allow formation of intermediate 14, which can be converted to vinyl intermediate 15 by palladium-catalyzed cross coupling protocol developed by Fu (Littke, A. F., Fu, G. C. "Palladium-Catalyzed Coupling Reactions of Aryl Chlorides" *Angew. Chem., Int. Ed.* (2002) 41, 4176-4211) using vinyl boronic acid or potassium trifluoro(vinyl)borate in the presence of a catalytic Pd species including, but not limited to, $Pd(t-Bu_3P)_2$ in an appropriate solvent such as 1,4-dioxane. Intermediate 15 can be subjected in subsequent reactions illustrated in Scheme 1 to generate compounds of formula 16a-n.

Scheme 4

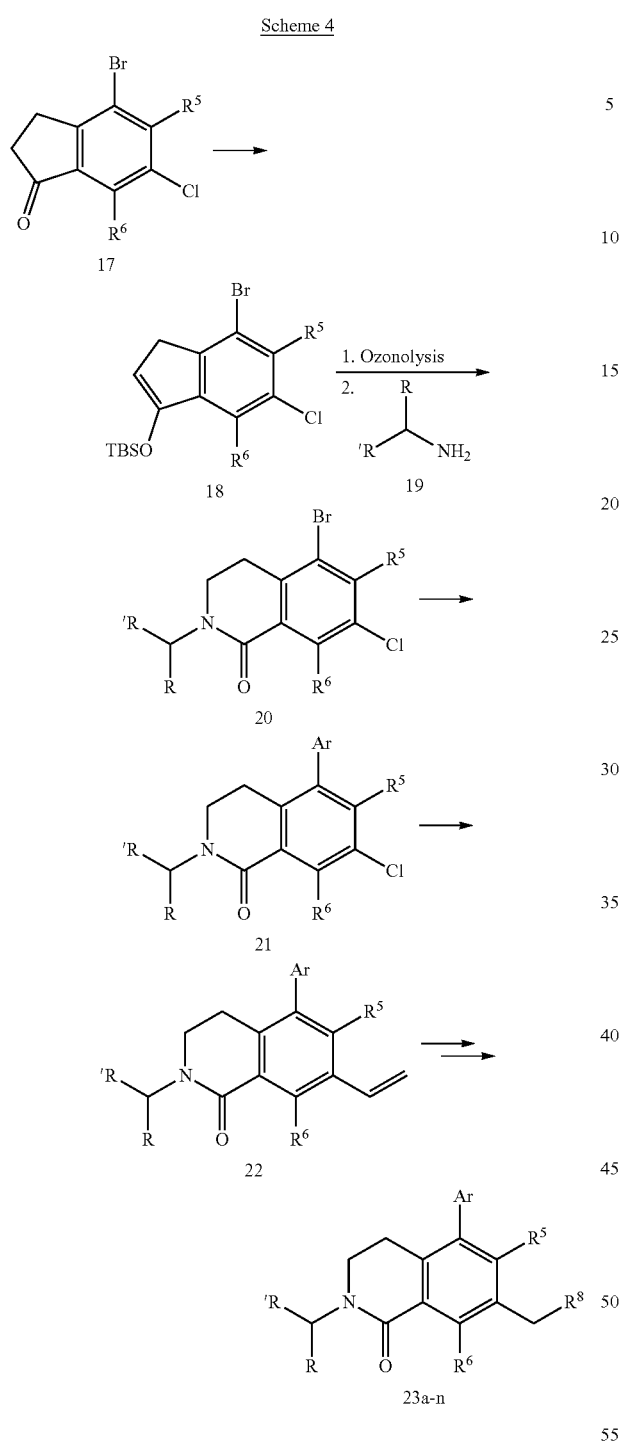

Scheme 5

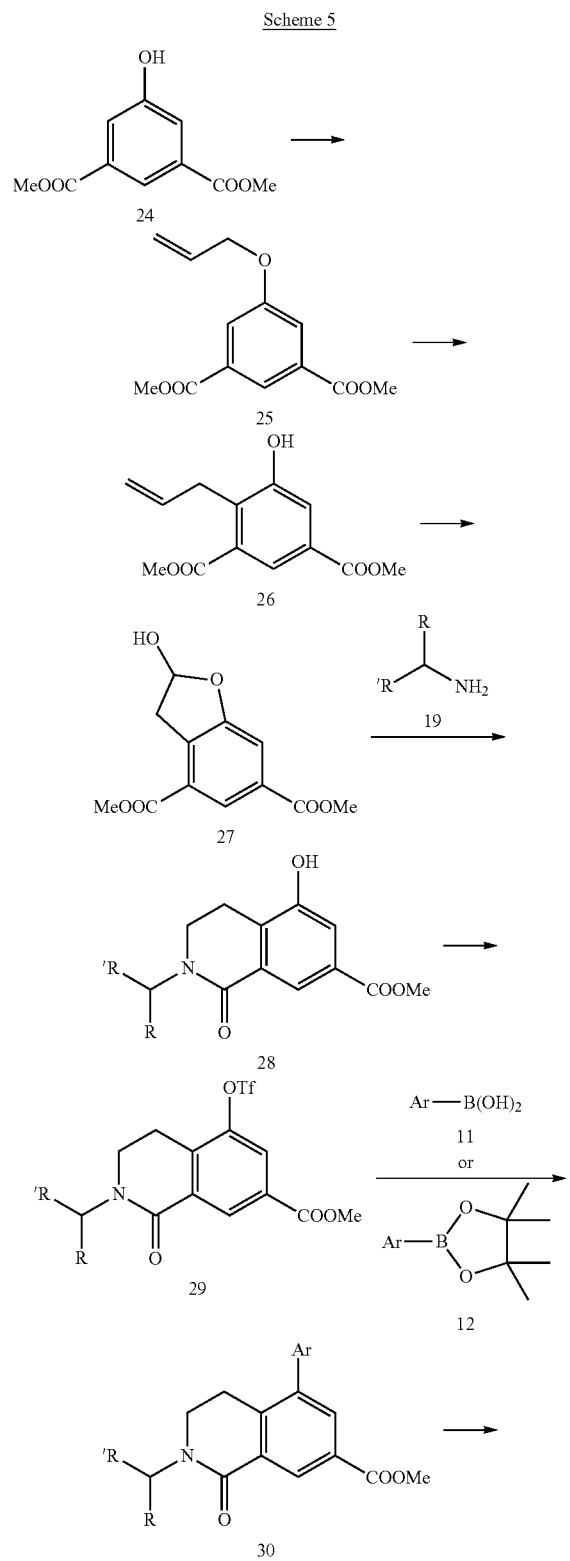

rine atom of compound 21 can be converted to the vinyl group of formula 22 using the palladium-catalyzed cross coupling reaction described in Scheme 3. Intermediate 22 can be elaborated using the subsequent reaction sequence shown in Scheme 1 to prepare compounds of formula 23a-n.

Scheme 4 depicts a route to produce compounds of Formula 23a-n that contain branched $R^1$ moieties. Optionally substituted 4-bromo-6-chlorodihydroindan-1-one 17 can be converted to silyl-enol-ether 18 by a number of conditions that are routine for those skilled in the art of organic synthesis. Intermediate 18 can be subjected to ozonolysis followed by in situ reductive amination reaction with primary amines of formula 19 and a reducing agent including, but not limited, $NaBH(OAc)_3$ or $NaCNBH_3$ to yield intermediate 20. Suzuki-Miyaura coupling protocol outlined in Scheme 3 can be utilized to generate biaryl compounds of formula 21 from intermediate 20. The chlo-

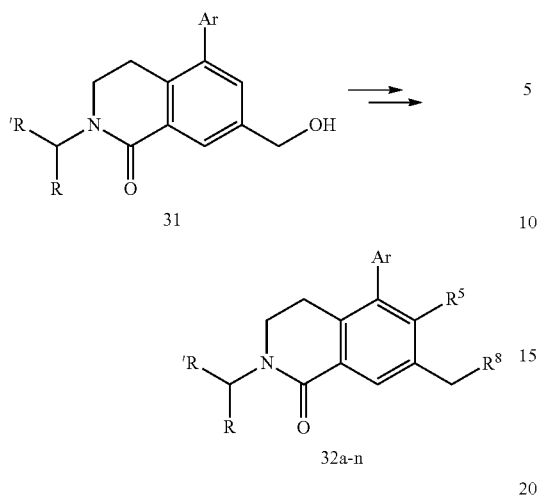

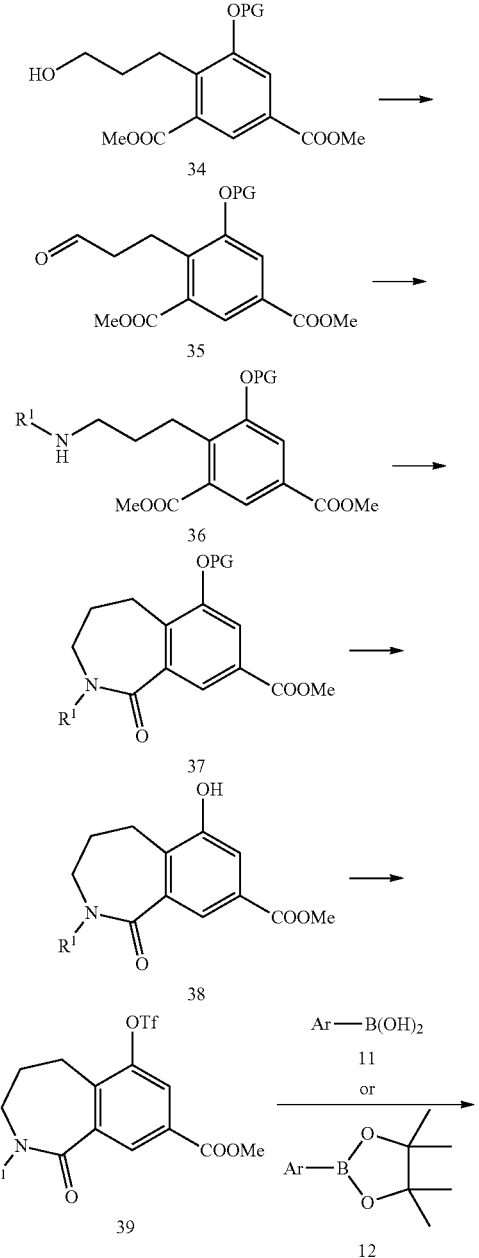

In some embodiments, compounds of Formula 32a-n may be synthesized by procedures illustrated in Scheme 5 using dimethyl 5-hydroxyisophthalate 24 as a starting material. The phenol moiety of 24 can be allylated using, but not limited to, allyl bromide with appropriate bases, such as $Cs_2CO_3$, $K_2CO_3$, $Et_3N$ or $(i-Pr)_2EtN$. The resulting allylphenylether 25 may be subjected under the aromatic Claisen rearrangement protocol (Hiersemann, M., Nubbemeyer, U. (2007) "The Claisen Rearrangement" Wiley-VCH. ISBN 3-527-30825-3) that is routine for those skilled in the art of organic synthesis to produce intermediate 26. Subsequent ozonolysis followed by dimethyl sulfide treatment may give hemiacetal 27. It can be then coupled with primary amines of formula 19 under the reductive amination condition described above followed by spontaneous cyclization to yield dihydroisoquinolinone 28. After activation of phenol moiety of 28 to triflate, the intermediate 29 may be coupled with a variety of boronic acids 11 or borates 12 under the Suzuki-Miyaura coupling protocol outlined in Scheme 3 to afford biaryl intermediate 30. The methyl ester functional group of 30 can be converted to an alcohol under various reduction conditions that are routine for those skilled in the art of organic synthesis. Finally, alcohol 31 can further elaborated to produce compounds of formula 32a-n using the reaction sequence illustrated in Scheme 1

Scheme 6

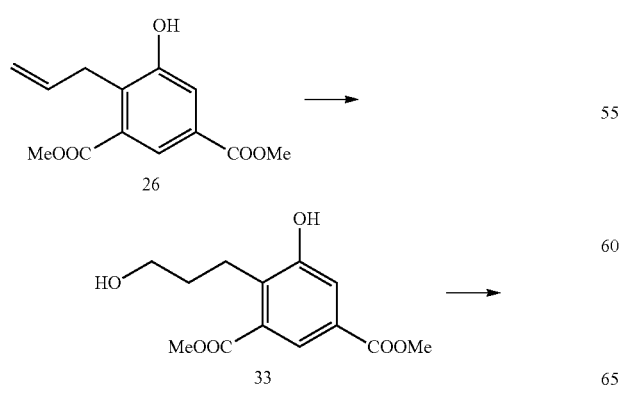

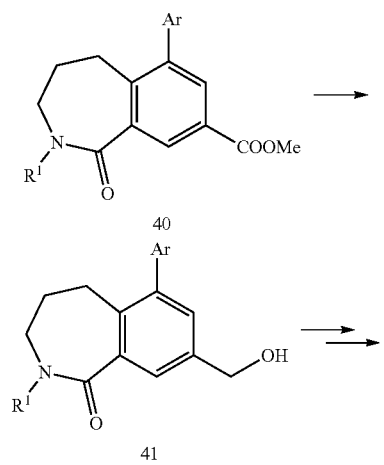

-continued

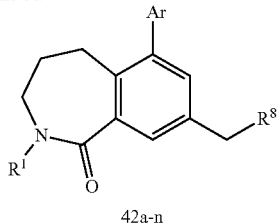

42a-n

Exemplary method for preparing compounds of Formula 42a-n containing the benzoazepinone core unit is shown in Scheme 6 and proceeds from compounds of Formula 26. Oxidative hydroboration reaction can be applied using, but not limited to, $BH_3$ in THF followed by $H_2O_2$ treatment to generate intermediates of Formula 33. The phenol group of 33 can be selectively protected with a benzyl group using benzyl bromide and base such as $Cs_2CO_3$, $K_2CO_3$, $Et_3N$ or $(i-Pr)_2EtN$ or other proper protecting groups under appropriate conditions that are routine for those skilled in the art. Subsequent oxidation of the primary alcohol of 34 to an aldehyde group using, but not limited to, Dess-Martin perio- dinane (Dess, D. B., Martin, J. C. "Readily accessible 12-I-5 oxidant for the conversion of primary and secondary alcohols to aldehydes and ketones". J. Org. Chem. (1983) 48, 4155) followed by the reductive amination protocol described in Scheme 4 can afford compounds of Formula 36. Benzoazepinone 37 can be synthesized via thermal intramolecular cyclization of intermediate 36 using amidine bases such as DBU and DBN. Removal of the phenol protecting group under conditions that are routine for those skilled in the art can produce versatile intermediate 38, which can be subjected to same reaction sequence from intermediate 28 to 32a-n depicted in Scheme 5 to afford compounds of formula 42a-n.

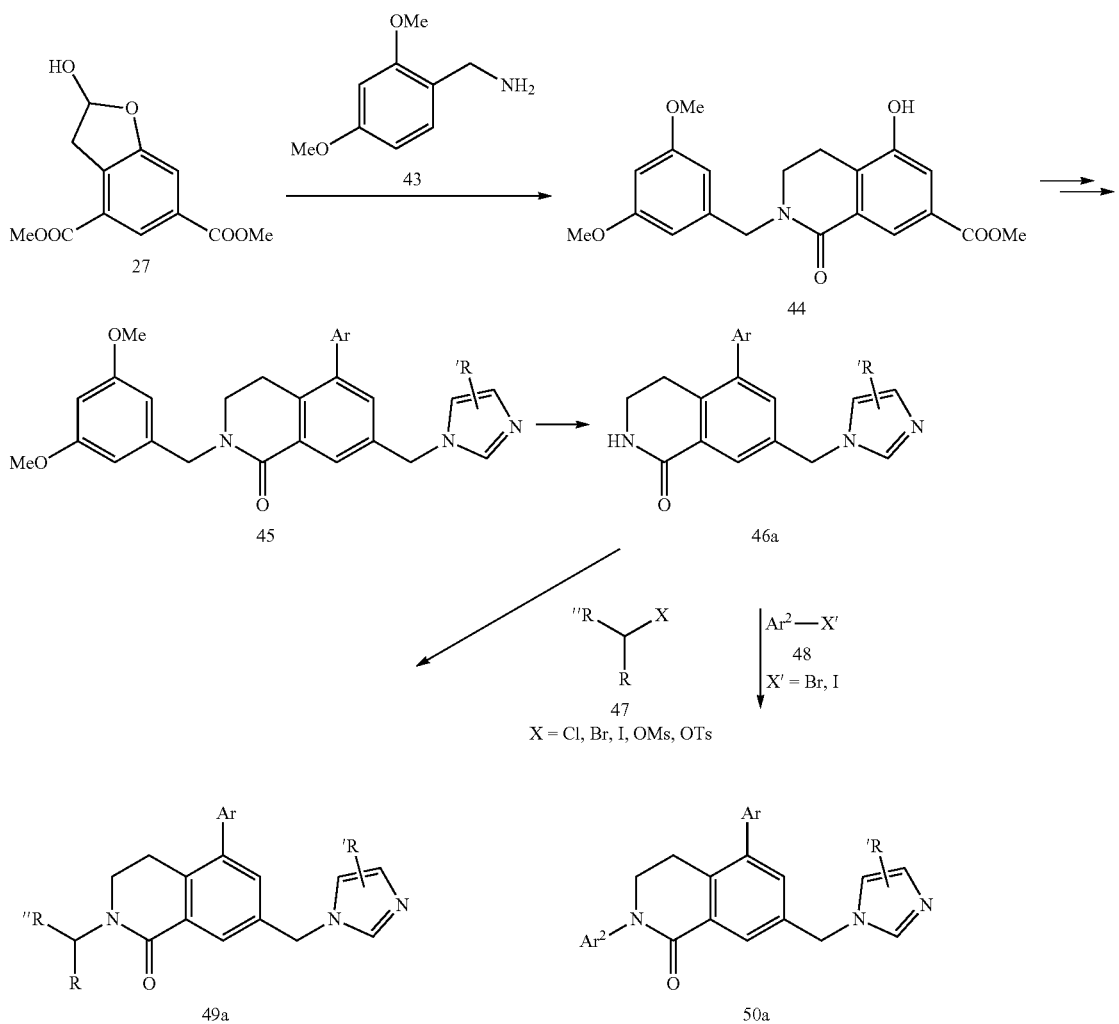

Scheme 7 depicts a synthetic route to prepare compounds of Formula 49a and 50a. Hemiacetal 27 can be coupled with (2,4-dimethoxyphenyl)methanamine 43 under the reductive amination condition described above to give intermediate 44, which was subjected to the reaction sequence illustrated in Scheme 5 to afford intermediate 45. The dimethoxybenzyl moiety of 45 can be removed using, but not limited to, TFA to prepare lactam 46a. The corresponding lactam NH of 46a can be alkylated by appropriate reagent 47 at a number of conditions that are routine for those skilled in the art to give compounds of formula 49a. The NH group of formula 46a can undergo cross-coupling reactions with a variety of aryl or heteroaryl halides of formula 48, wherein X is Br or I in the presence of a catalytic Pd species, such as Pd(OAc)$_2$ or Pd$_2$(dba)$_3$ and a suitable ligand such as Xantphos or BrettPhos and a base such as Na$_2$CO$_3$, Cs$_2$CO$_3$, or K$_2$CO$_3$ to generate compounds of Formula 50a. Alternatively, compounds of formula 50a can also be produced using the Ullman coupling conditions in the presence of CuI and a suitable ligand such as (trans)-1,2-N,N'-dimethylaminocyclohexane or L-Proline and a base such as Cs$_2$CO$_3$, K$_2$CO$_3$ or K$_2$PO$_4$ in a suitable solvent such as toluene or DMF.

Scheme 8.

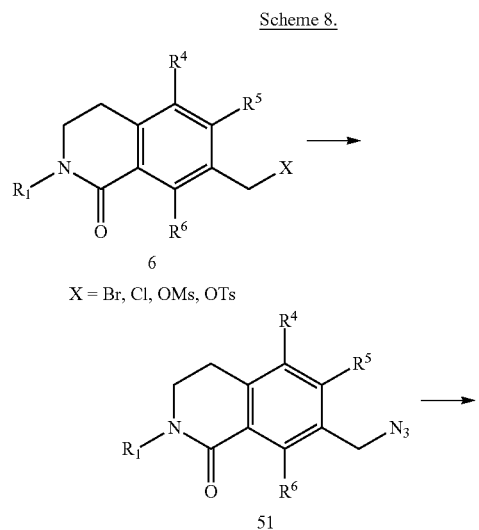

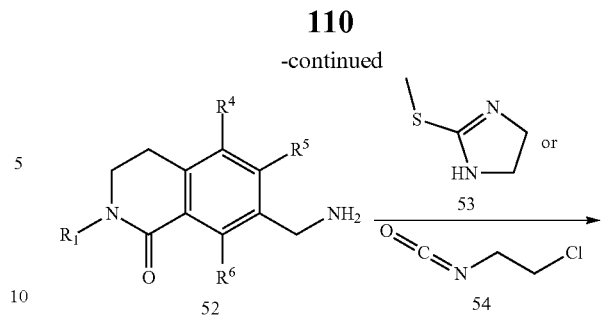

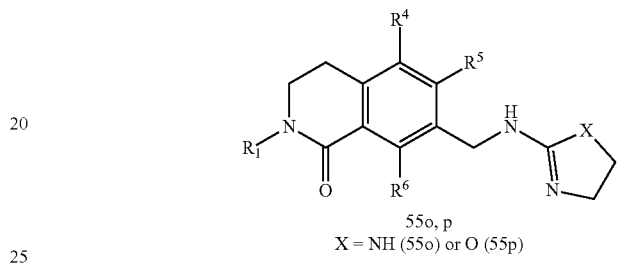

Compounds of formula 55o and 55p may be synthesized by procedures illustrated in Scheme 8 using bromide 6 as a starting material. The bromo group of 1 can be converted to the corresponding azide intermediate followed by reduction under the catalytic hydrogenation condition using, but not limited to, Raney-Nickel or Pd/C to give the corresponding amine 52. Dihydro-imidazol-2-amine 55o and dihydrooxazol-2-amine 55p can be produced by treatment of amine 52 with appropriate agents, but not limited to, methylthiodihydroimidazole 53 or 2-chloroethyl isocyanate 54 in an alcoholic or polar aprotic solvent with heat, respectively.

Scheme 9.

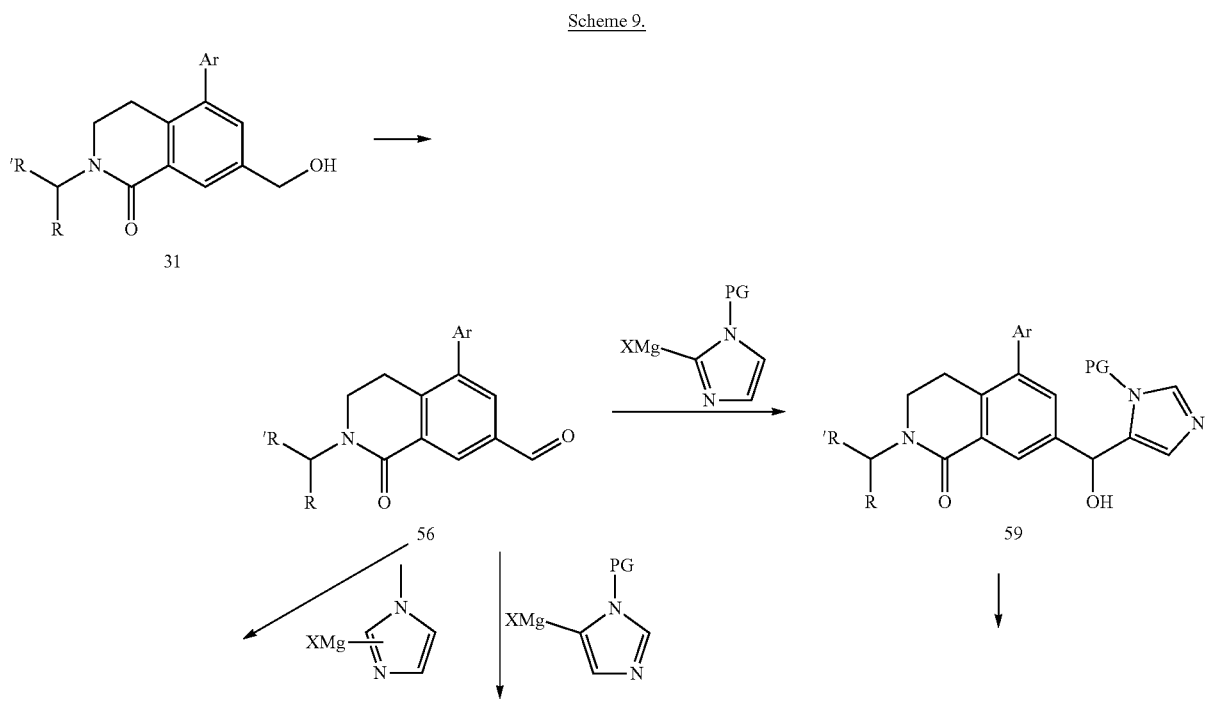

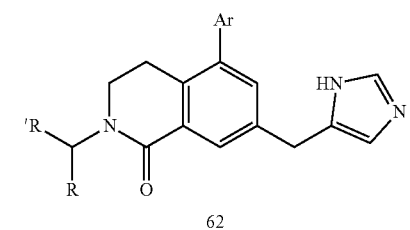
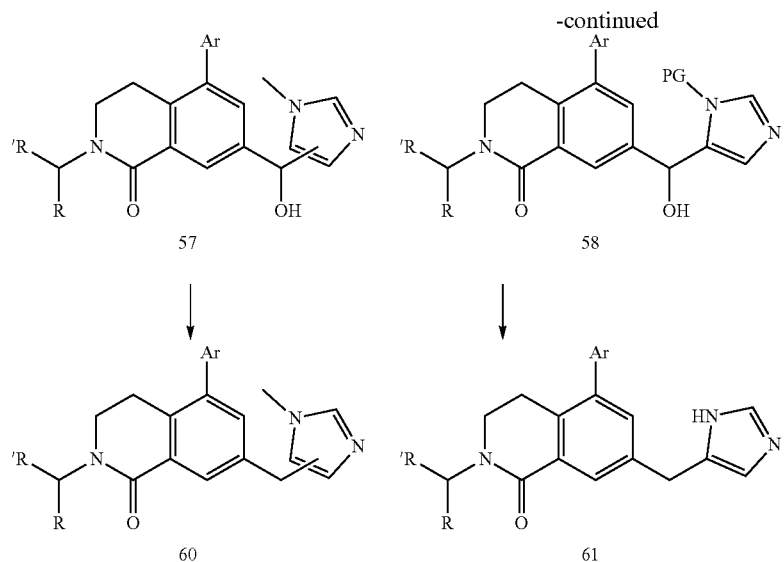

Exemplary methods for preparing compounds of Formula 60-62 containing the imidazolyl $R^8$ group are shown in Scheme 9 and proceed from intermediate 31. The primary alcohol group can be oxidized by appropriate reagents at a number of conditions that are routine for those skilled in the art to give aldehyde 56. A variety of N-substituted imidazolyl Grignard reagents such as (1-methyl-1H-imidazol-2-yl)magnesium iodide, (1-trityl-1H-imidazol-5-yl)magnesium iodide or (1-trityl-1H-imidazol-2-yl)magnesium iodide, but not limited to, can react with aldehyde 56 to generate corresponding secondary alcohols 57-59. Compounds of formula 60-62 can be produced by reduction of alcohols 57-59 using, but not limited to, triethylsilane and TFA in a polar aprotic solvent such as 1,2-dichloroethane with heat.

Precursor reagents and intermediates for core aryl or phenyl structure were either commercially available or prepared using known methods in the literature. Procedures towards key intermediates are detailed within specified examples or below.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

C. Examples

Abbreviations

The following abbreviations are employed in the Examples and elsewhere herein:
DCM=dichloromethane
EDC=1-Ethyl-3-(3-dimethyl aminopropyl)carbodiimide
TEA=triethylamine
DMF=dimethylformamide
DMSO=dimethylsulfoxide
THF=tetrahydrofuran
$K_2CO_3$=potassium carbonate
$Cs_2CO_3$=cesium carbonate
ether=diethyl ether
NaOH=sodium hydroxide
KOH=potassium hydroxide
EtOAc=ethyl acetate
$Na_2CO_3$=sodium carbonate
$NaHCO_3$=sodium bicarbonate
$MgSO_4$=magnesium sulfate
$CH_2Cl_2$=methylene chloride
MeOH=methanol
EtOH=ethanol
Hex=hexanes
HCl=hydrochloric acid
$Pd(PPh_3)_4$=tetrakis(triphenylphosphine)palladium(0)
$Pd(OAc)_2$=Palladium(II) acetate
$Pd(t-Bu_3P)_2$=Bis(tri-tert-butylphosphine)palladium(0)
TFA=trifluoroacetic acid
$Et_3N$=triethylamine
DIPEA=N,N-diisopropylethylamine
NaH=sodium hydride
$NaN_3$=sodium azide
SPhos=2-Dicyclohexylphosphino-2',6'-dimethoxybiphenyl
TBAF=tetrabutyl ammonium fluoride
NBS=N-bromo succinimide
AIBN=Azobisisobutyronitrile
min=minute(s)
h or hr=hour(s)
mL or ml=milliliter
g=gram(s)
mg=milligram(s)
mmol=millimole(s)
RT or r.t.=room temperature
LRMS=low resolution mass spectrometry
NMR=nuclear magnetic resonance
$[M+H]^+$=the protonated mass of the free base of the compound
$R_T$=retention time (in minutes)

Microwave assisted reactions are performed in a single-mode reactor: Emrys™ Optimizer microwave reactor (Personal Chemistry A.B., currently Biotage).

Hydrogenation reactions are performed using an atmospheric balloon or using a Parr hydrogenation shaker apparatus.

Normal phase flash silica gel-based column chromatography is performed using ready-to-connect cartridges from ISCO, on irregular silica gel, particle size 15-40 µm on a Combi-flash Companion chromatography system from ISCO.

Low resolution mass spectra are obtained on an Agilent 1200 series 6130 mass spectrometer. Analytical HPLC is performed on an HP1100 with UV detection at 214 and 254 nm along with ELSD detection, LC/MS (J-Sphere80-C18, 3.0×50 mm, 4.1 min gradient, 5%[0.05% TFA/$CH_3CN$]: 95%[0.05% TFA/$H_2O$] to 100%[0.05% TFA/$CH_3CN$]. Preparative RP-HPLC purification is performed on a custom HP1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient.

For LC-MS characterization of the compounds of the present invention, the following methods are used.

Method 1: The HPLC measurement is performed using an Agilent 1200 system comprising a binary pump with degasser, an autosampler, a column oven, a diode-array detector (DAD) and a column as specified in the respective methods below. Flow from the column is split to a SQ mass spectrometer and Polymer Labs ELSD. The MS detector is configured with an ES ionization source. Nitrogen is used as the nebulizer gas. The source temperature is maintained at 350° C. Data acquisition is performed with Agilent Chemstation software. Reversed phase HPLC is carried out on a Kinetex C18 column (2.6 µm, 2.1×30 µm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 2: Using method 1 instrument and column conditions. The gradient conditions used are: 95% A (water+0.1% TFA), 5% B (acetonitrile), to 95% B in 2.0 minutes, returning to initial conditions at 2.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 3: Using method 1 instrument and column conditions. The gradient conditions used are: 50% A (water+0.1% TFA), 50% B (acetonitrile), to 95% B in 2.0 minutes, returning to initial conditions at 2.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

$^1$H NMR spectra are recorded either on a Bruker DPX-400 or on a Bruker AV-500 spectrometer with standard pulse sequences, operating at 400 MHz and 500 MHz respectively.

Chemical shifts (δ) are reported in parts per million (ppm) downfield from tetramethylsilane (TMS), which is used as internal standard. Coupling constants (J-values) are reported in Hz.

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

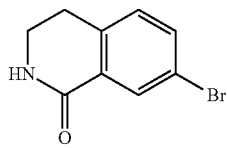

Intermediate 1

7-Bromo-3,4-dihydroisoquinolin-1(2H)-one

To a solution of 6-bromo-1-indanone (1.0 g, 4.74 mmol) in DCM (30 mL) and methanesulfonic acid (15 mL) at 0° C. was added NaN₃ (432 mg, 6.63 mmol). The resulting mixture was warmed to room temperature and stirred overnight. The excess acid was neutralized with Na₂CO₃/water. The resulting mixture was extracted with DCM. The combined organic layers were dried (Na₂SO₄) and concentrated. The residue was purified by flash chromatography (Combi-flash Rf, Hex/EtOAc=0-90% gradient) to afford the title compound (100 mg, 9%). ¹H NMR (400 MHz, CDCl₃) δ 8.23 (d, J=2.0 Hz, 1H), 7.58 (dd, J=2.0, 8.0 Hz, 1H), 7.13 (d, J=8.0 Hz, 1H), 5.88 (brs, 1H), 3.59 (m, 2H), 2.99 (t, J=6.4 Hz, 2H).

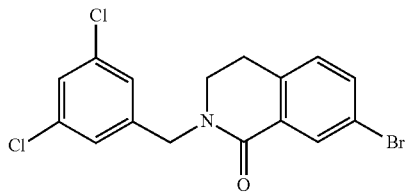 [SMILES: O=C1c2cc(Br)ccc2CCN1Cc1cc(Cl)cc(Cl)c1]

Intermediate 2

7-Bromo-2-(3,5-dichlorobenzyl)-3,4-dihydroisoquinolin-1(2H)-one

To a solution of Intermediate 1 (49 mg, 0.22 mmol) in DMF (1 mL) at 0° C. was added NaH (11.6 mg, 0.29 mmol). After stirring for 30 min, 3,5-dichloro-benzylbromide (70 mg, 0.29 mmol) was added. The resulting mixture was allowed to warm to room temperature and was stirred for 4 h. The reaction was quenched with NH₄Cl (sat. aq.) and extracted with EtOAc. The combined organic layers were dried (Na₂SO₄) and concentrated. The residue was purified by flash chromatography (Combi-flash Rf, Hex/EtOAc=0-20% gradient) to afford the title compound (72.5 mg, 86%). ¹H NMR 400 MHz, CDCl₃) δ 8.29 (d, J=2.0 Hz, 1H), 7.59 (dd, J=2.0, 8.0 Hz, 1H), 7.31 (m, 1H), 7.23 (d, J=1.6 Hz, 2H), 7.09 (d, J=8.0 Hz, 1H), 4.74 (s, 2H), 3.52 (t, J=6.4 Hz, 2H), 2.96 (t, J=6.4 Hz, 2H).

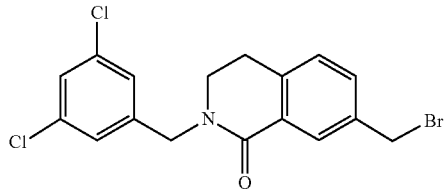 [SMILES: O=C1c2cc(CBr)ccc2CCN1Cc1cc(Cl)cc(Cl)c1]

Intermediate 3

7-(Bromomethyl)-2-(3,5-dichlorobenzyl)-3,4-dihydroisoquinolin-1(2H)-one

Step A. Preparation of 2-(3,5-dichlorobenzyl)-7-vinyl-3,4-dihydroisoquinolin-1(2H)-one. To a solution of Intermediate 2 (72 mg, 0.19 mmol) in EtOH (2.5 mL) was added potassium trifluoro(vinyl)borate (33.5 mg, 0.25 mmol), Et₃N (35 µL, 0.25 mmol), and PdCl₂(dppf) (2.8 mg, 0.0038 mmol). The mixture was heated at 80° C. overnight. The solvent was removed under reduced pressure. The residue was purified by flash chromatography (Combi-flash Rf, Hex/EtOAc=0-20% gradient) to afford 2-(3,5-dichlorobenzyl)-7-vinyl-3,4-dihydroisoquinolin-1(2H)-one (52 mg, 82%). LC-MS: >89% 254 nm, R_T=1.35 min, MS (ES) 332 [M+H]⁺.

Step B. Preparation of 2-(3,5-dichlorobenzyl)-7-(hydroxymethyl)-3,4-dihydroisoquinolin-1(2H)-one. Ozone was bubbled through a solution of 2-(3,5-dichlorobenzyl)-7-vinyl-3,4-dihydroisoquinolin-1(2H)-one (52 mg, 0.15 mmol) in EtOH (6 mL)/DCM (6 mL) at −78° C. The reaction was closely monitored by LC-MS. Once the starting material was consumed, NaBH₄ (44 mg, 1.1 mmol) was added. The reaction mixture was allowed to warm to room temperature and was stirred for 2 h. The solvent was removed under reduced pressure. The residue was taken up in EtOAc and washed with water. The organic layer was dried (Na₂SO₄) and concentrated. The residue was purified on by flash chromatography (Combi-flash Rf, Hex/EtOAc=0-60% gradient) to afford the title compound (35 mg, 64%). ¹H NMR 400 MHz, CDCl₃) δ 8.13 (d, J=1.6 Hz, 1H), 7.51 (dd, J=1.6, 7.6 Hz, 1H), 7.30 (m, 1H), 7.42 (m, 3H), 4.76 (s, 2H), 3.53 (t, J=6.4 Hz, 2H), 3.01 (t, J=6.4 Hz, 2H).

Step C. Preparation of 7-(bromomethyl)-2-(3,5-dichlorobenzyl)-3,4-dihydroisoquinolin-1(2H)-one. To a solution of 2-(3,5-dichlorobenzyl)-7-(hydroxymethyl)-3,4-dihydroisoquinolin-1(2H)-one (35 mg, 0.1 mmol) in DCM (2.5 mL) at 0° C. was added PBr₃ (20 µL, 0.22 mmol). The reaction was allowed to warm to room temperature and stirred overnight. The reaction mixture was neutralized with NaHCO₃ (sat.) and extracted with Et₂O. The combined organic layers were dried (Na₂SO₄) and concentrated to provide the desired product (40 mg, quantitative), which was used without further purification. LC-MS: >92% 254 nm, R_T=1.34 min, MS (ES) 398 [M+H]⁺.

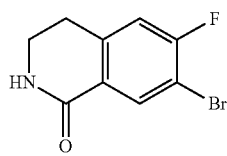

Intermediate 4

7-Bromo-6-fluoro-3,4-dihydroisoquinolin-1(2H)-one

Step A. Preparation of (E)-1-bromo-2-fluoro-4-(2-nitrovinyl)benzene. To a solution of NH₄OAc (1.04 g, 13.5 mmol) in AcOH (10 mL) was added CH₃NO₂ (2.09 mL, 38.9 mmol), 4-bromo-3-fluorobenzaldehyde (1.14 g, 5.6 mmol). The reaction mixture was heated in a sealed tube at 100° C. for 5 h. The reaction mixture was neutralized with Na₂CO₃ (s)/NaHCO₃ (sat.), and extracted with EtOAc. The combined organic layers were dried (Na₂SO₄) and concentrated. The residue was purified by flash chromatography (Combi-flash Rf, Hex/EtOAc=0-30% gradient) to afford the title compound (890 mg, 64%). $^1$H NMR 400 MHz, CDCl₃) δ 7.93 (d, J=13.6 Hz, 1H), 7.68 (dd, J=6.8, 8.0 Hz, 1H), 7.58 (d, J=13.6 Hz, 1H), 7.32 (dd, J=2.0, 8.8 Hz, 1H), 7.24 (dd, J=2.0, 8.8 Hz, 1H).

Step B. Preparation of 2-(4-bromo-3-fluorophenyl)ethan-1-amine. To a suspension of NaBH₄ (825.4 mg, 21.7 mmol) in THF (15 mL) at 0° C. was added dropwise BF₃·OEt₂ (2.95 mL, 23.9 mmol). The mixture was allowed to warm to room temperature and was stirred for 10 min. Then (E)-1-bromo-2-fluoro-4-(2-nitrovinyl)benzene (890 mg, 3.62 mmol) was added as a solution in THF (6 mL). The resulting mixture was heated under reflux overnight, and then quenched cautiously with water. After acidifying to pH≈1-2 with 1M HCl, the mixture was refluxed for 3 h and then extracted with Et₂O. The aqueous layer was separated, basified with K₂CO₃ (s) to pH≈12, and extracted with Et₂O. The combined organic layers were dried (Na₂SO₄) and concentrated. The residue was purified by flash chromatography (Combi-flash Rf, DMC/MeOH=0-10% gradient) to afford the title compound (650 mg, 71%). $^1$H NMR 400 MHz, CDCl₃) δ 7.37 (t, J=8.0 Hz, 1H), 6.90 (dd, J=2.0, 9.2 Hz, 1H), 6.80 (dd, J=2.0, 8.0 Hz, 1H), 2.99 (t, J=7.2 Hz, 2H), 2.78 (t, J=7.2 Hz, 2H).

Step C. Preparation of methyl 2-(((4-bromo-3-fluorophenethyl)carbamoyl)oxy) benzoate. To a solution of 2-(4-bromo-3-fluorophenyl)ethan-1-amine (650 mg, 2.55 mmol) in THF (10 mL) at rt was added dimethyl 2,2'-(carbonylbis(oxy))dibenzoate (855 mg, 2.55 mmol) and Et₃N (391 μL, 2.81 mmol). The reaction mixture was stirred overnight and concentrated. The residue was purified by flash chromatography (Combi-flash Rf, Hex/EtOAc=0-50% gradient) to afford the title compound (724 mg, 72%). LC-MS: >90% 254 nm, R$_T$=1.17 min, MS (ES) 418 [M+Na].

Step D. Preparation of 7-bromo-6-fluoro-3,4-dihydroisoquinolin-1(2H)-one. To a solution of methyl 2-(((4-bromo-3-fluorophenethyl)carbamoyl)oxy)benzoate (180 mg, 0.45 mmol) in DCM (2.25 mL) at rt was added trifluoromethanesulfonic acid (398 μL, 4.5 mmol). After stirring for 30 min, the reaction was quenched with NaHCO₃ (sat.). The mixture was then extracted with EtOAc. The combined organic layers were dried (Na₂SO₄), and concentrated. The residue was purified by flash chromatography (Combi-flash Rf, Hex/EtOAc=0-90% gradient) to afford the title compound (98 mg, 89%). $^1$H NMR 400 MHz, CDCl₃) δ 8.29 (d, J=7.2 Hz, 1H), 6.99 (d, J=8.4 Hz, 1H), 6.05 (brs, 1H), 3.58 (m, 2H), 2.97 (t, J=6.8 Hz, 2H).

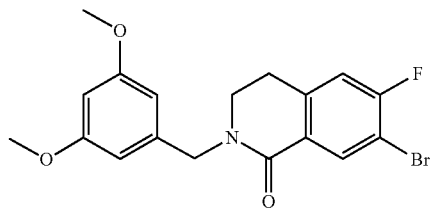 [SMILES: COc1cc(CN2CCc3cc(F)c(Br)cc3C2=O)cc(OC)c1]

Intermediate 5

7-Bromo-2-(3,5-dimethoxybenzyl)-6-fluoro-3,4-dihydroisoquinolin-1(2H)-one

The title compound (251 mg, 96%) was prepared from the procedure described in Intermediate 2 using 7-bromo-6-fluoro-3,4-dihydroisoquinolin-1(2H)-one (Intermediate 4) and 3,5-dimethoxy-benzylbromide. $^1$H NMR (400 MHz, CDCl₃) δ 8.35 (d, J=7.2 Hz, 1H), 6.93 (d, J=8.4 Hz, 1H), 6.45 (s, 2H), 6.38 (s, 1H), 4.70 (s, 2H), 3.77 (s, 6H), 3.49 (t, J=6.4 Hz, 2H), 2.90 (t, J=6.4 Hz, 2H).

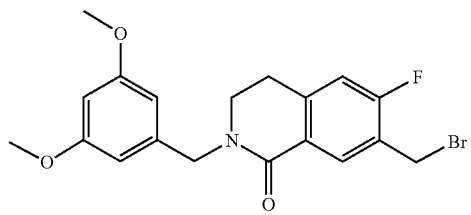 [SMILES: COc1cc(CN2CCc3cc(F)c(CBr)cc3C2=O)cc(OC)c1]

Intermediate 6

7-(Bromomethyl)-2-(3,5-dimethoxybenzyl)-6-fluoro-3,4-dihydroisoquinolin-1(2H)-one Step A. Preparation of 2-(3,5-dimethoxybenzyl)-6-fluoro-7-vinyl-3,4-dihydroisoquinolin-1(2H)-one. To a solution of 7-bromo-2-(3,5-dimethoxybenzyl)-6-fluoro-3,4-dihydroisoquinolin-1(2H)-one (251 mg, 0.64 mmol) in EtOH (10 mL) was added potassium trifluoro(vinyl)borate (132.4 mg, 0.96 mmol), Et₃N (268 μL, 1.92 mmol), and PdCl₂(dppf) (14 mg, 0.019 mmol). The mixture was heated in a sealed tube at 85° C. overnight. The solvent was removed under reduced pressure. The residue was purified by flash chromatography (Combi-flash Rf, Hex/EtOAc=0-40% gradient) to afford the title compound (210 mg, 95%). LC-MS: >95% 254 nm R$_T$=1.19 min, MS (ES) 342 [M+H]⁺.

Step B. Preparation of 2-(3,5-dimethoxybenzyl)-6-fluoro-7-(hydroxymethyl)-3,4-dihydroisoquinolin-1(2H)-one. The title compound (147 mg, 68%) was prepared from the procedure described in Intermediate 3, Step B substituting 2-(3,5-dimethoxybenzyl)-6-fluoro-7-vinyl-3,4-dihydroisoquinolin-1(2H)-one for 2-(3,5-dichlorobenzyl)-7-vinyl-3,4-dihydroisoquinolin-1(2H)-one. LC-MS: >85% 254 nm, R$_T$=0.94 min, MS (ES) 346 [M+H].

Step C. Preparation of 7-(bromomethyl)-2-(3,5-dimethoxybenzyl)-6-fluoro-3,4-dihydroisoquinolin-1(2H)-one. To a solution of 2-(3,5-dimethoxybenzyl)-6-fluoro-7-(hydroxymethyl)-3,4-dihydroisoquinolin-1(2H)-one (93 mg, 0.27 mmol) in CH₂Cl₂ (6 mL) at 0° C. was added PPh₃ (142 mg, 0.54 mmol) and CBr₄ (179 mg, 0.54 mmol). The mixture was stirred at this temperature for 3 h, and then concentrated. The residue was purified by flash chromatography (Combi-flash Rf, Hex/EtOAc=0-40% gradient) to afford the title compound (79 mg, 70%). ¹H NMR 400 MHz, CDCl₃) δ 8.19 (d, J=8.0 Hz, 1H), 6.88 (d, J=9.6 Hz, 1H), 6.46 (s, 2H), 6.38 (s, 1H), 4.71 (s, 2H), 4.53 (s, 2H), 3.77 (s, 6H), 3.49 (t, J=6.8 Hz, 2H), 2.93 (t, J=6.8 Hz, 2H).

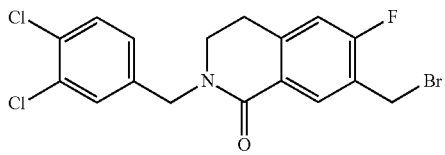 [SMILES: O=C1c2cc(CBr)c(F)cc2CCN1Cc1ccc(Cl)c(Cl)c1]

Intermediate 7

7-(Bromomethyl)-2-(3,4-dichlorobenzyl)-6-fluoro-3,4-dihydroisoquinolin-1(2H)-one The title compound was prepared from the procedure described in Intermediate 2 using 7-bromo-6-fluoro-3,4-dihydroisoquinolin-1(2H)-one (Intermediate 4) and 3,4-dichloro-benzylbromide followed by the procedure described in Intermediate 6, Step A-C substituting 2-(3,4-dichlorobenzyl)-6-fluoro-7-(hydroxymethyl)-3,4-dihydroisoquinolin-1(2H)-one for 2-(3,5-dimethoxybenzyl)-6-fluoro-7-(hydroxymethyl)-3,4-dihydroisoquinolin-1(2H)-one. ¹H NMR (400 MHz, CDCl₃) δ 8.21 (d, J=7.6 Hz, 1H), 7.42 (m, 2H), 7.19 (dd, J=2.0, 8.0 Hz, 1H), 6.92 (d, J=9.6 Hz, 1H), 4.74 (s, 2H), 4.55 (s, 2H), 3.52 (t, J=6.4 Hz, 2H), 2.98 (t, J=6.4 Hz, 2H).

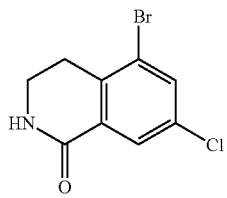

Intermediate 8

5-Bromo-7-chloro-3,4-dihydroisoquinolin-1(2H)-one

Step A. Preparation of (E)-2-bromo-4-chloro-1-(2-nitrovinyl)benzene. To a solution of NH₄OAc (1.13 g, 14.65 mmol) in AcOH (10 mL) was added CH₃NO₂ (2.09 mL, 38.9 mmol), 2-bromo-4-chlorobenzaldehyde (1.31 g, 6.1 mmol). The reaction mixture was heated in a sealed tube at 100° C. for 2 h, and then poured into water. The solid was filtered and dried under vacuum in the presence of P₂O₅ overnight to provide the desired product (1.43 g, 88%). ¹H NMR (400 MHz, CDCl₃) δ 8.32 (d, J=13.6 Hz, 1H), 7.71 (d, J=2.0 Hz, 1H), 7.51 (m, 2H), 7.37 (dd, J=8.4, 2.0 Hz, 1H).

Step B. Preparation of 5-bromo-7-chloro-3,4-dihydroisoquinolin-1(2H)-one. The title compound (55 mg,) was prepared from the procedure described in Intermediate 4, Step B-D substituting (E)-2-bromo-4-chloro-1-(2-nitrovinyl)benzene for (E)-1-bromo-2-fluoro-4-(2-nitrovinyl)benzene at Step B. ¹H NMR (400 MHz, CDCl₃) δ 8.06 (d, J=2.0 Hz, 1H), 7.70 (d, J=2.8 Hz, 1H), 6.03 (brs, 1H), 3.58 (m, 2H), 3.07 (t, J=6.4 Hz, 2H).

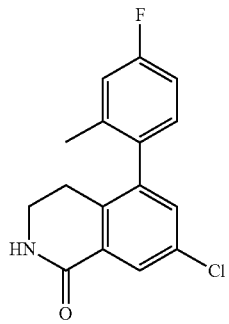 [SMILES: Cc1cc(F)ccc1-c1cc(Cl)cc2c1CCNC2=O]

Intermediate 9

7-Chloro-5-(4-fluoro-2-methylphenyl)-3,4-dihydroisoquinolin-1(2H)-one

To a mixture of 5-bromo-7-chloro-3,4-dihydroisoquinolin-1(2H)-one (Intermediate 8, 113 mg, 0.43 mmol), 4-fluoro-2-methylphenyl-boronic acid (86.2 mg, 0.56 mmol), and Et₃N (180 μL, 1.29 mmol) in EtOH (4.3 mL) was added PdCl₂(dppf) (9 mg, 0.012 mmol). The resulting mixture was degassed and back filled with Argon gas, and heated at 85° C. overnight. The solvent was removed under reduced pressure. The residue was purified by flash chromatography (Combi-flash Rf, Hex/EtOAc=10-90% gradient) to afford the title compound (78 mg, 63%). ¹H NMR (400 MHz, CDCl₃) δ 8.11 (d, J=2.4 Hz, 1H), 7.29 (d, J=2.4 Hz, 1H), 7.00 (m, 3H), 6.04 (brs, 1H), 3.45 (m, 2H), 2.60 (m, 2H), 2.06 (s, 3H).

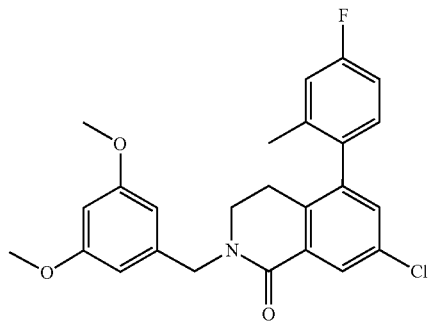 [SMILES: COc1cc(CN2CCc3c(cc(Cl)cc3-c3ccc(F)cc3C)C2=O)cc(OC)c1]

Intermediate 10

7-Chloro-2-(3,5-dimethoxybenzyl)-5-(4-fluoro-2-methylphenyl)-3,4-dihydroisoquinolin-1(2H)-one The title compound (119 mg, 99%) was prepared from the procedure described in Intermediate 2 using 7-chloro-5-(4-fluoro-2-methylphenyl)-3,4-dihydroisoquinolin-1(2H)-one and 3,5-dimethoxy-benzylbromide. ¹H NMR (400 MHz, CDCl₃) δ 8.16 (d, J=2.4 Hz, 1H), 6.95 (m, 3H), 6.45 (d, J=2.4 Hz, 2H), 6.38 (t, J=2.4 Hz, 1H), 4.70 (dd, J=14.8, 23.6 Hz, 2H), 3.76 (s, 6H), 3.37 (t, J=6.4 Hz, 2H), 2.52 (m, 2H), 2.04 (s, 3H).

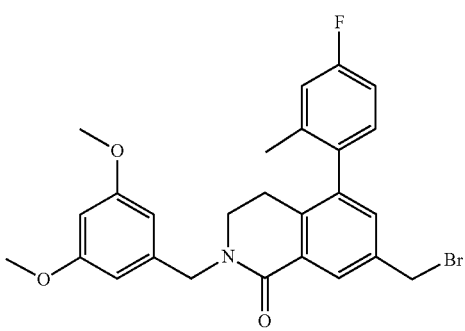 [SMILES: COc1cc(CN2CCc3c(cc(CBr)cc3-c3ccc(F)cc3C)C2=O)cc(OC)c1]

Intermediate 11

7-(Bromomethyl)-2-(3,5-dimethoxybenzyl)-5-(4-fluoro-2-methylphenyl)-3,4-dihydroisoquinolin-1(2H)-one Step A. Preparation of 2-(3,5-dimethoxybenzyl)-5-(4-fluoro-2-methylphenyl)-7-vinyl-3,4-dihydroisoquinolin-1(2H)-one. To a mixture of 7-chloro-2-(3,5-dimethoxybenzyl)-5-(4-fluoro-2-methylphenyl)-3,4-dihydroisoquinolin-1(2H)-one (119 mg, 0.27 mmol), potassium vinyltrifluoroborate (112 mg, 0.81 mmol), 1 M $Cs_2CO_3$ (1.2 mL, 1.2 mmol), and 1,4-dioxane (2.4 mL) was added $Pd(t-Bu_3P)_2$ (27.6 mg, 0.054 mmol) under Ar. The resulting mixture was heated at 90° C. for 2 h, and then partitioned between EtOAc and water. The organic layer was dried ($Na_2SO_4$) and concentrated. The residue was purified by flash chromatography (Combi-flash Rf, Hex/EtOAc=0-40% gradient) to afford the title compound (105 mg, 88%). $^1$H NMR (400 MHz, CDCl$_3$) δ 8.24 (d, J=2.0 Hz, 1H), 7.30 (d, J=2.0 Hz, 1H), 7.04 (dd, J=6.0, 8.4 Hz, 1H), 6.94 (m, 2H), 6.46 (m, 2H), 6.75 (dd, J=11.2, 17.6 Hz, 1H), 6.36 (t, J=2.4 Hz, 1H), 5.84 (d, J=17.6 Hz, 1H), 5.31 (d, J=11.2 Hz, 1H), 4.71 (dd, J=7.6, 16.4 Hz, 2H), 3.76 (s, 6H), 3.37 (t, J=6.8 Hz, 2H), 2.57 (m, 2H), 2.04 (s, 3H).

Step B. Preparation of 2-(3,5-dimethoxybenzyl)-5-(4-fluoro-2-methylphenyl)-7-(hydroxymethyl)-3,4-dihydroisoquinolin-1(2H)-one. To a mixture of 2-(3,5-dimethoxybenzyl)-5-(4-fluoro-2-methylphenyl)-7-vinyl-3,4-dihydroisoquinolin-1(2H)-one (105 mg, 0.24 mmol), pyridine (39 μL, 0.48 mmol), water (1 mL), and 1,4-dioxane (3 mL) at room temperature was added $OsO_4$ (4% wt. in water, 38 μL, 0.06 mmol) followed by $NaIO_4$ (205.3 mg, 0.96 mmol). After stirring overnight, the reaction mixture was cooled to 0° C., then MeOH (3 mL) was added followed by $NaBH_4$ (107 mg, 2.81 mmol). The ice bath was removed and the reaction was stirred at room temperature for 45 min. The solvent was removed under reduced pressure and the residue was taken in EtOAc and washed with water. The organic layer was dried ($Na_2SO_4$) and concentrated. The residue was purified by flash chromatography (Combi-flash Rf, Hex/EtOAc=10-90% gradient) to afford the title compound (80 mg, 75%). $^1$H NMR (400 MHz, CDCl$_3$) δ 8.16 (d, J=2.0 Hz, 1H), 7.32 (d, J=2.0 Hz, 1H), 7.03 (dd, J=5.6, 8.0 Hz, 1H), 6.94 (m, 2H), 6.47 (m, 2H), 6.36 (t, J=2.4 Hz, 1H), 4.73 (m, 4H), 3.76 (s, 6H), 3.38 (t, J=6.4 Hz, 2H), 2.56 (m, 2H), 2.04 (s, 3H).

Step C. Preparation of 7-(bromomethyl)-2-(3,5-dimethoxybenzyl)-5-(4-fluoro-2-methylphenyl)-3,4-dihydroisoquinolin-1(2H)-one. The title compound (95 mg crude, quantitative; used without further purification) was prepared from the procedure described in Intermediate 3, Step C substituting 2-(3,5-dimethoxybenzyl)-5-(4-fluoro-2-methylphenyl)-7-(hydroxymethyl)-3,4-dihydroisoquinolin-1(2H)-one for 2-(3,5-dichlorobenzyl)-7-(hydroxymethyl)-3,4-dihydroisoquinolin-1(2H)-one. $^1$H NMR (400 MHz, CDCl$_3$) δ 8.20 (d, J=2.0 Hz, 1H), 7.32 (d, J=2.0 Hz, 1H), 7.04 (dd, J=6.0, 8.4 Hz, 1H), 6.94 (m, 2H), 6.46 (d, J=2.0 Hz, 2H), 6.37 (t, J=2.0 Hz, 1H), 4.71 (d, J=14.8 Hz, 1H), 4.70 (d, J=14.8 Hz, 1H), 4.54 (s, 2H), 3.77 (s, 6H), 3.38 (t, J=6.4 Hz, 2H), 2.58 (m, 2H), 2.04 (s, 3H).

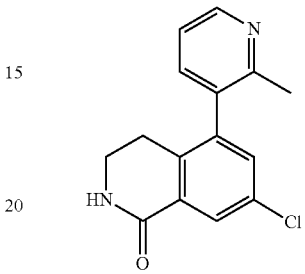

Intermediate 12

7-Chloro-5-(2-methylpyridin-3-yl)-3,4-dihydroisoquinolin-1(2H)-one

The title compound (70 mg, 28%; containing some impurities; used without further purification) was prepared from the procedure described in Intermediate 9 substituting (2-methylpyridin-3-yl)boronic acid for 4-fluoro-2-methylphenyl-boronic acid. $^1$H NMR (400 MHz, CDCl$_3$) δ 8.56 (m, 1H), 8.12 (d, J=2.4 Hz, 1H), 7.41 (m, 1H), 7.30 (d, J=2.0 Hz, 1H), 7.23 (m, 1H), 6.76 (brs, 1H), 3.47 (m, 2H), 2.61 (t, J=6.8 Hz, 2H), 2.31 (s, 3H).

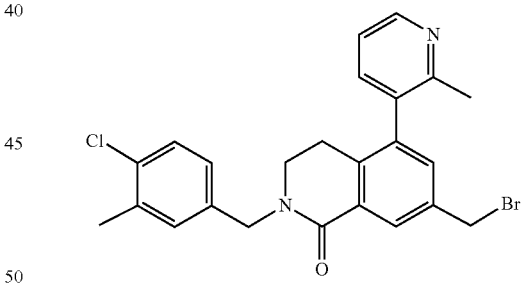

Intermediate 13

7-(Bromomethyl)-2-(4-chloro-3-methylbenzyl)-5-(2-methylpyridin-3-yl)-3,4-dihydroisoquinolin-1(2H)-one Step A. Preparation of 5-(2-methylpyridin-3-yl)-7-vinyl-3,4-dihydroisoquinolin-1(2H)-one. To a mixture of 7-chloro-5-(2-methylpyridin-3-yl)-3,4-dihydroisoquinolin-1(2H)-one (intermediate 12, 70 mg, 0.26 mmol), potassium vinyltrifluoroborate (108 mg, 0.78 mmol), 1 M $Cs_2CO_3$ (1.0 mL), and 1,4-dioxane (2.0 mL) was added $Pd(t-Bu_3P)_2$ (27 mg, 0.052 mmol) under argon atmosphere. The resulting mixture was heated at 90° C. for 2 h, and then partitioned between EtOAc and water. The organic layer was dried (Na$_2$SO$_4$) and concentrated. The residue was purified by flash chromatography (Combi-flash Rf, DCM/MeOH=0-10% gradient) to afford the title compound (64 mg, 92%). $^1$H NMR (400 MHz, CDCl$_3$) δ 8.56 (m, 1H), 8.21 (d, J=2.0 Hz, 1H), 7.44 (dd, J=1.6, 7.6 Hz, 1H), 7.35 (d, J=2.0 Hz, 1H), 7.22 (m, 1H), 6.75 (dd, J=10.8, 17.6 Hz, 1H), 5.95 (brs, 1H), 5.85 (d, J=17.6 Hz, 1H), 5.33 (d, J=10.8 Hz, 1H), 3.48 (m, 2H), 2.64 (t, J=6.4 Hz, 2H), 2.34 (s, 3H).

Step B. Preparation of 2-(4-chloro-3-methylbenzyl)-5-(2-methylpyridin-3-yl)-7-vinyl-3,4-dihydroisoquinolin-1(2H)-one. To a solution of 5-(2-methylpyridin-3-yl)-7-vinyl-3,4-dihydroisoquinolin-1(2H)-one (64 mg, 0.24 mmol) in DMF (2 mL) at 0° C. was added NaH (10.6 mg, 0.26 mmol). After stirring for 30 min, 4-chloro-3-methyl-benzylbromide (53 mg, 0.24 mmol) was added. The resulting mixture was stirred at 0° C. for 1 h. The reaction was quenched with NH$_4$Cl (sat.) and extracted with EtOAc. The combined organic layers were dried (Na$_2$SO$_4$) and concentrated. The residue was purified by flash chromatography (Combi-flash Rf, Hex/EtOAc=0-60% gradient) to afford the title compound (60 mg, 63%). $^1$H NMR (400 MHz, CDCl$_3$) δ 8.55 (m, 1H), 8.29 (d, J=2.0 Hz, 1H), 7.41 (dd, J=1.6, 7.6 Hz, 1H), 7.33 (s, 1H), 7.28 (m, 1H), 7.21 (m, 2H), 7.11 (m, 1H), 6.77 (dd, J=10.8, 17.6 Hz, 1H), 5.87 (d, J=17.6 Hz, 1H), 5.34 (d, J=10.8 Hz, 1H), 4.73 (d, J=14.4 Hz, 1H), 4.71 (d, J=14.4 Hz, 1H), 3.39 (t, J=6.4 Hz, 2H), 2.58 (m, 2H), 2.36 (s, 3H), 2.32 (s, 3H).

Step C. Preparation of 7-(bromomethyl)-2-(4-chloro-3-methylbenzyl)-5-(2-methylpyridin-3-yl)-3,4-dihydroisoquinolin-1(2H)-one. The title compound (43 mg, 97%) was prepared from the procedure described in Intermediate 3, Step B-C substituting 2-(4-chloro-3-methylbenzyl)-5-(2-methylpyridin-3-yl)-7-vinyl-3,4-dihydroisoquinolin-1(2H)-one for 2-(3,5-dichlorobenzyl)-7-(hydroxymethyl)-3,4-dihydroisoquinolin-1(2H)-one in Step B. LC-MS: >95% 254 nm, R$_T$=1.01 min, MS (ES) 469 [M+H]$^+$.

J=17.3, 1.6 Hz, 1H), 5.32 (dq, J=10.6, 1.4 Hz, 1H), 4.62 (dt, J=5.4, 1.5 Hz, 2H), 3.94 (s, 6H); LC-MS: >95% (215, 254 nm), R$_T$=1.083 min, MS (ES) 251 [M+H]$^+$.

Step B. Preparation of dimethyl 4-allyl-5-hydroxyisopthalate. Dimethyl 4-allyl-5-hydroxyisoptalate (10 g, 40 mmol) was added to a microwave reaction vessel which was then sealed and heated at 200° C. for 16 h under neat conditions. The resultant tan mixture was directly purified by column chromatography (Combi-flash Rf, Hex/EtOAc=0-40% gradient) to provide the title compound (8.6 g, 34 mmol, 85%) as a white solid. $^1$H NMR (400 MHz, Chloroform-d) δ 8.10 (d, J=1.7 Hz, 1H), 7.71 (d, J=1.7 Hz, 1H), 6.01 (ddt, J=16.5, 12.2, 5.3 Hz, 1H), 5.77 (s, 1H), 5.20-5.00 (m, 2H), 3.93 (s, 3H), 3.91 (s, 3H), 3.82 (dt, J=6.1, 1.7 Hz, 2H); LC-MS: >95% (215, 254 nm), R$_T$=0.951 min, MS (ES) 251 [M+H]$^+$.

Step C. Preparation of dimethyl 2-hydroxy-2,3-dihydrobenzofuran-4,6-dicarboxylate. Ozone was bubbled through a solution of dimethyl 4-allyl-5-hydroxyisophtalate (8.6 g, 34.3 mmol, 1 equiv) in dichloromethane (0.34 L, 0.1 M) at −78° C. until the reaction mixture reached homogeneity and a light blue appearance. After the solution was purged with oxygen and argon, dimethyl sulfide (7.6 mL, 102.9 mmol, 3 equiv) was added to the colorless solution. The reaction mixture was allowed to warm to 23° C. and stirred for 4 hours. Next, water was added and the mixture was extracted with dichloromethane (3×50 mL). The combined organic phases were dried over Na$_2$CO$_3$ and concentrated in vacuo. The residue was purified by flash chromatography (Combi-flash Rf, Hex/EtOAc=0-50% gradient) to afford the title compound (7.3 g, 28.9 mmol, 84%) as a white solid. $^1$H NMR (400 MHz, Chloroform-d) δ 8.21 (d, J=1.4 Hz, 1H), 7.61 (d, J=1.4 Hz, 1H), 6.19-6.15 (m, 1H), 3.97 (d, J=5.1 Hz, 1H), 3.91 (s, 6H), 3.64 (dd, J=18.5, 6.2 Hz, 1H), 3.48 (dd, J=18.5, 2.4 Hz, 1H).

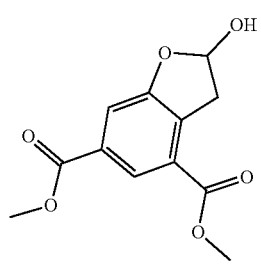 [SMILES: COC(=O)c1cc2c(c(C(=O)OC)c1)CC(O)O2]

Intermediate 14

Dimethyl 2-hydroxy-2,3-dihydrobenzofuran-4,6-dicarboxylate

Step A. Preparation of dimethyl 5-(allyloxy)isophthalate. Allyl bromide (4.9 mL, 6.9 g, 57.1 mmol, 1.5 equiv) was added to a heterogeneous mixture of dimethyl 5-hydroxyisopthalate (8.0 g, 38.1 mmol) and K$_2$CO$_3$ (16.8 g, 3.2 equiv) in acetone (0.13 L, 0.3 M); then placed in a preheated reaction block. The reaction mixture was refluxed at 75° C. for 12 h. The resultant solids were filtered off and washed with EtOAc. The organic layers were concentrated in vacuo to give the title compound (9.3 g, 37.2 mmol, 97%) as a white solid and used without further purification. $^1$H NMR (400 MHz, Chloroform-d) δ 8.28 (t, J=1.5 Hz, 1H), 7.76 (d, J=1.4 Hz, 2H), 6.05 (ddt, J=17.3, 10.5, 5.2 Hz, 1H), 5.44 (dq,

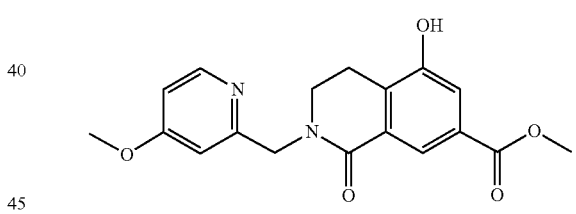

Intermediate 15

Methyl 5-hydroxy-24(4-methoxypyridin-2-yl)methyl)-1-oxo-1,2,3,4-tetrahydroisoquinoline-7-carboxylate NaCNBH$_3$ (2.5 g, 39.7 mmol, 2.5 equiv) was added to a solution of (4-methoxypyridin-2-yl)methanamine (4.4 g, 31.7 mmol, 2 equiv) and dimethyl 2-hydroxy-2,3-dihydrobenzofuran-4,6-dicarboxylate (Intermediate 14, 4 g, 15.9 mmol, 1 equiv) in dichloromethane/methanol (0.16 L, 0.1 M, 1:1) at 23° C. and allowed to stir for 12 h. Water was then added and the mixture was extracted with dichloromethane (3×50 mL). The combined organic phases were dried over Na$_2$CO$_3$ and concentrated in vacuo. The residue was purified by flash chromatography (Combi-flash Rf, CH$_2$Cl$_2$/MeOH 0-3% gradient) to afford the title compound (4.8 g, 14 mmol, 88%) as a tan solid. $^1$H NMR (400 MHz, Chloroform-δ 8.36 (dd, J=5.9, 2.3 Hz, 1H), 8.27 (d, J=1.5 Hz, 1H), 7.61 (d, J=1.6 Hz, 1H), 6.95 (d, J=2.4 Hz, 1H), 6.76 (dd, J=5.9, 2.5

Hz, 1H), 4.87 (s, 2H), 3.86 (s, 3H), 3.83 (s, 3H), 3.64 (t, J=6.7 Hz, 2H), 3.01 (t, J=6.7 Hz, 2H), 2.64 (s, 1H). LC-MS: >95% (215, 254 nm), $R_T$=0.623 min, MS (ES) 343 [M+H]$^+$.

4.85 (s, 2H), 4.01 (s, 3H), 3.92 (s, 3H), 3.83 (s, 3H), 3.59 (t, J=6.6 Hz, 2H), 2.82 (t, J=6.5 Hz, 2H); $^{19}$F NMR (376 MHz, Chloroform-d) 6-60.28; LC-MS: >95% (215, 254 nm), $R_T$=0.089 min, MS (ES) 475 [M+H]$^+$.

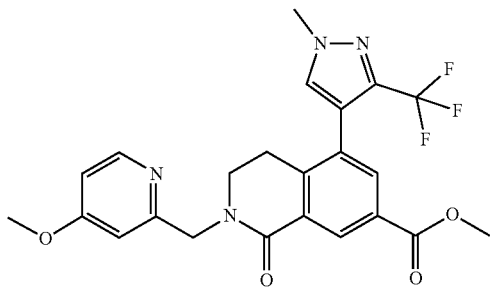

Intermediate 16

Methyl 2-((4-methoxypyridin-2-yl)methyl)-5-(1-methyl-3-(trifluoromethyl)-1H-pyrazol-4-yl)-1-oxo-1,2,3,4-tetrahydroisoquinoline-7-carboxylate Step A. Preparation of methyl 2-((4-methoxypyridin-2-yl)methyl)-1-oxo-5-(((trifluoromethyl)sulfonyl)oxy)-1,2,3,4-tetrahydroisoquinoline-7-carboxylate). Phenyl triflimide (6.0 g, 16.8 mmol, 1.2 equiv) was added to a mixture of methyl 5-hydroxy-2-((4-methoxypyridin-2-yl)methyl)-1-oxo-1,2,3,4-tetrahydroisoquinoline-7-carboxylate (Intermediate 15, 4.8 g, 14.0 mmol, 1 equiv) and triethylamine (5.7 mL, 4.3 g, 42.1 mmol, 3 equiv) in tetrahydrofuran/dichloromethane (0.14 L, 0.1 M, 5:1) at 23° C. and allowed to stir for 14 h. Saturated aqueous NaHCO$_3$ was added and the mixture was extracted with dichloromethane (3×50 mL). The combined organic phases were dried over Na$_2$CO$_3$ and concentrated in vacuo. The residue was purified by flash chromatography (Combi-flash Rf, CH$_2$Cl$_2$/MeOH=0-1.5% gradient) to afford the title compound (5.4 g, 11.4 mmol, 81%) as a white solid. $^1$H NMR (400 MHz, Chloroform-d) δ 8.81 (d, J=1.6 Hz, 1H), 8.36 (d, J=5.7 Hz, 1H), 8.04 (d, J=1.6 Hz, 1H), 6.90 (d, J=2.5 Hz, 1H), 6.74 (dd, J=5.8, 2.5 Hz, 1H), 4.85 (s, 2H), 3.96 (s, 3H), 3.83 (s, 3H), 3.74 (t, J=6.6 Hz, 2H), 3.12 (t, J=6.6 Hz, 2H). $^{19}$F NMR (376 MHz, Chloroform-d) 6-73.19; LC-MS: >95% (254 nm), $R_T$=0.819 min, MS (ES) 475 [M+H]$^+$.

Step B. Preparation of methyl 2-((4-methoxypyridin-2-yl)methyl)-5-(1-methyl-3-(trifluoromethyl)-1H-pyrazol-4-yl)-1-oxo-1,2,3,4-tetrahydroisoquinoline-7-carboxylate. Pd(PPh$_3$)$_4$ (0.16 g, 0.14 mmol, 0.04 equiv) and potassium carbonate (2.9 g, 8.9 mmol, 2.5 equiv) were added to a solution of methyl 2-((4-methoxypyridin-2-yl)methyl)-1-oxo-5-(((trifluoromethyl)sulfonyl)oxy)-1,2,3,4-tetrahydroisoquinoline-7-carboxylate (1.7 g, 3.5 mmol, 1 equiv) and (1-methyl-3-(trifluoromethyl)-1H-pyrazol-4-yl)boronic acid (0.8 g, 4.1 mmol, 1.2 equiv) in dioxane/H$_2$O (83 mL, 0.04 M, 4:1) and degassed for 20 min. The reaction mixture was then placed in a preheated heating block and stirred for 14 h at 80° C. At 23° C., brine was added to the mixture and extracted with EtOAc (3×40 mL). The combined organic layers were dried over Na$_2$SO$_4$ and concentrated in vacuo. The residue was purified by flash chromatography (Combi-flash Rf, DCM/MeOH=0-3% gradient) to afford the title compound (1.5 g, 3.2 mmol, 90%) as a tan solid. $^1$H NMR (400 MHz, Chloroform-d) δ 8.82 (d, J=1.9 Hz, 1H), 8.34 (d, J=5.8 Hz, 1H), 8.02 (d, J=1.9 Hz, 1H), 7.37 (d, J=1.1 Hz, 1H), 6.92 (d, J=2.5 Hz, 1H), 6.73 (dd, J=5.8, 2.5 Hz, 1H),

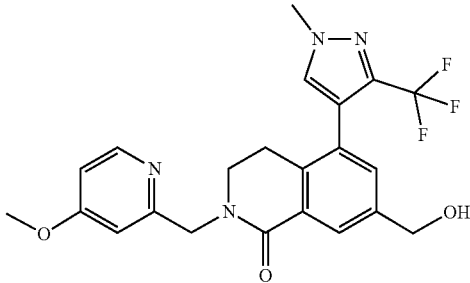 [SMILES: COc1ccnc(CN2CCc3c(cc(CO)cc3-c3cn(C)nc3C(F)(F)F)C2=O)c1]

Intermediate 17

7-(Hydroxymethyl)-2-((4-methoxypyridin-2-yl)methyl)-5-(1-methyl-3-(trifluoromethyl)-1H-pyrazol-4-yl)-3,4-dihydroisoquinolin-1(2H)-one)

Sodium borohydride (1.7 g, 47.4 mmol, 15 equiv) was added to a solution of methyl 2-((4-methoxypyridin-2-yl)methyl)-5-(1-methyl-3-(trifluoromethyl)-1H-pyrazol-4-yl)-1-oxo-1,2,3,4-tetrahydroisoquinoline-7-carboxylate (1.5 g, 3.2 mmol, 1 equiv) in ethanol (63 mL, 0.05 M) at 23° C. The reaction mixture was then placed in a preheated heating block and stirred for 12 h at 78° C. Ethanol was then removed in vacuo. Water was added to the resultant residue and extracted with ethyl acetate (3×30 mL). The combined organic layers were dried over Na$_2$SO$_4$ and concentrated in vacuo to give the crude title compound (1.4 g, 3.1 mmol, 95%) as a colorless oil. $^1$H NMR (400 MHz, Chloroform-d) δ 8.33 (d, J=5.8 Hz, 1H), 8.15 (d, J=1.9 Hz, 1H), 7.39 (d, J=1.9 Hz, 1H), 7.34 (s, 1H), 6.72 (dd, J=5.8, 2.5 Hz, 1H), 4.84 (s, 2H), 4.74 (s, 2H), 3.99 (s, 3H), 3.81 (s, 3H), 3.55 (t, J=6.5 Hz, 2H), 2.76 (t, J=6.6 Hz, 2H); $^{19}$F NMR (376 MHz, Chloroform-d) 6-60.17; LC-MS: >95% (215, 254 nm), $R_T$=0.739 min, MS (ES) 447 [M+H]$^+$.

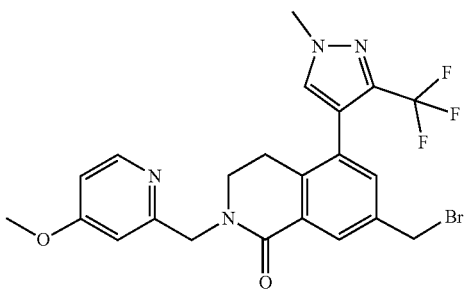 [SMILES: COc1ccnc(CN2CCc3c(cc(CBr)cc3-c3cn(C)nc3C(F)(F)F)C2=O)c1]

Intermediate 18

7-(Bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one Methanesulfonyl chloride (0.14 mL, 0.21 g, 1.8 mmol, 1.1 equiv) was added to a solution of 7-(hydroxymethyl)-2-((4-methoxypyridin-2-yl)methyl)-5-(1-methyl-3-(trifluoromethyl)-1H-pyrazol-4-yl)-3,4-dihydroisoquinolin-1(2H)-one (0.7 g, 1.6 mmol, 1 equiv) and N,N-diisopropylethylamine (0.44 mL, 0.32 g, 3.2 mmol, 2 equiv) in dichloromethane (16 mL, 0.1 M) at −10° C. and stirred for 10 minutes. Saturated aqueous NaHCO₃ was then added to the mixture and extracted with dichloromethane (3×10 mL). The combined organic layers were dried over Na₂SO₄ and concentrated in vacuo to give crude (2-((4-methoxypyridin-2-yl)methyl)-5-(1-methyl-3-(trifluoromethyl)-1H-pyrazol-4-yl)-1-oxo-1,2,3,4-tetrahydroisoquinolin-7-yl)methyl methanesulfonate.

Lithium bromide (0.35 g, 4 mmol, 2.5 equiv) was added to a solution of crude (2-((4-methoxypyridin-2-yl)methyl)-5-(1-methyl-3-(trifluoromethyl)-1H-pyrazol-4-yl)-1-oxo-1,2,3,4-tetrahydroisoquinolin-7-yl)methyl methanesulfonate (0.16 mmol, 1 equiv) in THF (3.2 mL, 0.5 M) at 23° C. The reaction mixture was then placed in a preheated heating block and stirred for 1 h at 75° C. Water was then added to the mixture and extracted with ethyl acetate (3×5 mL). The combined organic layers were dried over Na₂SO₄ and concentrated in vacuo. The residue was purified by flash chromatography (Combi-flash Rf, DCM/MeOH=0-9% gradient) to afford the title compound (0.75 g, 1.4 mmol, 91% over two steps) was obtained as a white solid. LC-MS, >95% (254 nm), $R_T$=0.895 min, m/z=509 [M+H]⁺.

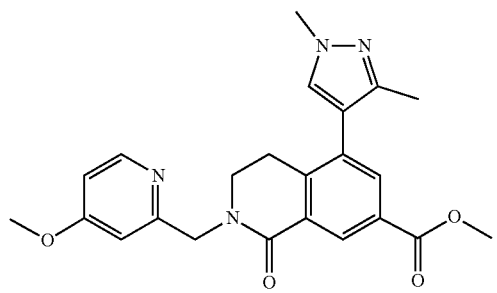

Intermediate 19

Methyl 5-(1,3-dimethyl-1H-pyrazol-4-yl)-2-((4-methoxypyridin-2-yl)methyl)-1-oxo-1,2,3,4-tetrahydroisoquinoline-7-carboxylate The title compound (0.72 g, 1.7 mmol, 82%) was prepared following the procedure described Intermediate 16 using (1,3-dimethyl-1H-pyrazol-4-yl)boronic acid (0.56 g, 2.5 mmol, 1.2 equiv).

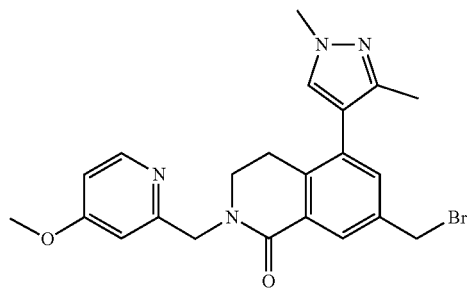 [SMILES: COc1ccnc(CN2CCc3c(cc(CBr)cc3-c3cn(C)nc3C)C2=O)c1]

Intermediate 20

7-(Bromomethyl)-5-(1,3-dimethyl-1H-pyrazol-4-yl)-24(4-methoxypyridin-2-yl)methyl)-3,4-dihydroisoquinolin-1(2H)-one The title compound (0.62, 1.4 mmol, 85%) was prepared following the procedure described in Intermediate 17 and 18 using methyl 5-(1,3-dimethyl-1H-pyrazol-4-yl)-2-((4-methoxypyridin-2-yl)methyl)-1-oxo-1,2,3,4-tetrahydroisoquinoline-7-carboxylate.

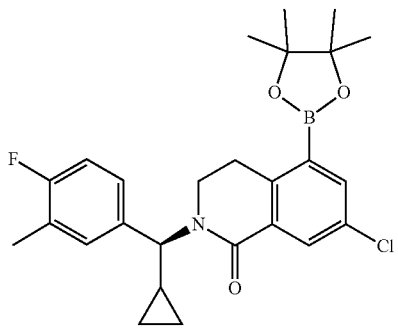 [SMILES: Cc1cc([C@H](C2CC2)N2CCc3c(B4OC(C)(C)C(C)(C)O4)cc(Cl)cc3C2=O)ccc1F]

Intermediate 21

(S)-7-Chloro-2-(cyclopropyl(4-fluoro-3-methylphenyl)methyl)-5-(4,4,5,5-tetramethyl-1,3,2-dioxaborolan-2-yl)-3,4-dihydroisoquinolin-1(2H)-one To a solution of (S)-5-bromo-7-chloro-2-(cyclopropyl(4-fluoro-3-methylphenyl)methyl)-3,4-dihydroisoquinolin-1(2H)-one (100 mg, 0.24 mmol) in 1,4-dioxane (4 mL) was added KOAc (71 mg, 0.72 mmol), bis(pinacolato)diboron (91.5 mg, 0.36 mmol), and PdCl₂(dppf) (18 mg, 0.024 mmol). The resulting mixture was thoroughly degassed and back filled with Argon gas, and then heated at 85° C. overnight. The mixture was filtered and the filtrate was concentrated. The residue was purified by flash chromatography (Combi-flash Rf, Hex/EtOAc=0-20% gradient) to afford the title compound (70 mg, 62%). ¹H NMR (400 MHz, CDCl₃) δ 8.21 (d, J=2.4 Hz, 1H), 7.88 (d, J=2.4 Hz, 1H), 7.28 (m, 2H), 6.96 (t, J=9.2 Hz, 1H), 5.15 (d, J=10.0 Hz, 1H), 3.57 (m, 1H), 3.31 (m, 2H), 3.05 (m, 1H), 2.27 (s, 3H), 1.33 (s, 12H), 1.30 (m, 1H), 0.86 (m, 1H), 0.59 (m, 2H), 0.52 (m, 1H).

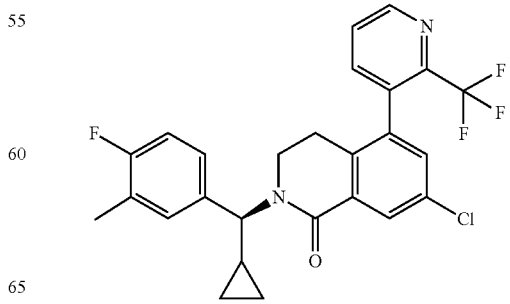

Intermediate 22

(S)-7-Chloro-2-(cyclopropyl(4-fluoro-3-methylphenyl)methyl)-5-(2-(trifluoromethyl)pyridin-3-yl)-3,4-dihydroisoquinolin-1(2H)-one To a mixture of (S)-7-chloro-2-(cyclopropyl(4-fluoro-3-methylphenyl)methyl)-5-(4,4,5,5-tetramethyl-1,3,2-dioxaborolan-2-yl)-3,4-dihydroisoquinolin-1(2H)-one (Intermediate 21, 70 mg, 0.15 mmol), 3-bromo-2-(trifluoromethyl)pyridine (52 mg, 0.23 mmol), 2M $Na_2CO_3$ (150 µL 0.3 mmol), toluene (2 mL), and EtOH (2 mL) was added $Pd(PPh_3)_4$ (10.4 mg, 0.009 mmol). The resulting mixture was degassed and back filled with Argon gas, and heated at 85° C. overnight. The solvent was removed under reduced pressure. The residue was purified by reverse phase HPLC (Phenomenex Gemini C18, $H_2O/CH_3CN$ gradient from 0-95% $CH_3CN$, 0.1% TFA) to yield the title compound (44 mg, 60%). $^1H$ NMR (400 MHz, $CDCl_3$) δ 8.78 (m, 1H), 8.24 (d, J=2.0 Hz, 1H), 7.57 (m, 2H), 7.28 (m, 3H), 6.94 (m, 1H), 5.15 (d, J=10.0 Hz, 1H), 3.47 (m, 1H), 3.18 (m, 1H), 2.38 (m, 2H), 2.24 (s, 3H), 1.29 (m, 1H), 0.86 (m, 1H), 0.60 (m, 2H), 0.51 (m, 1H).

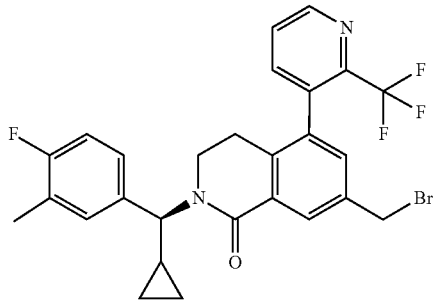 [SMILES: Cc1cc([C@H](C2CC2)N2CCc3c(cc(CBr)cc3-c3cccnc3C(F)(F)F)C2=O)ccc1F]

Intermediate 23

(S)-7-(Bromomethyl)-2-(cyclopropyl(4-fluoro-3-methylphenyl)methyl)-5-(2-(trifluoromethyl)pyridin-3-yl)-3,4-dihydroisoquinolin-1(2H)-one Step A. Preparation of (S)-2-(cyclopropyl(4-fluoro-3-methylphenyl)methyl)-5-(2-(trifluoromethyl)pyridin-3-yl)-7-vinyl-3,4-dihydroisoquinolin-1(2H)-one. The title compound (40 mg, 92%) was prepared from the procedure described in Intermediate 11, Step A. $^1H$ NMR (400 MHz, $CDCl_3$) δ 8.76 (m, 1H), 8.31 (m, 1H), 7.64 (m, 1H), 7.58 (m, 1H), 7.34 (s, 1H), 7.28 (m, 2H), 6.94 (m, 1H), 6.77 (dd, J=10.8, 17.6 Hz, 1H), 5.83 (d, J=17.6 Hz, 1H), 5.34 (d, J=10.8 Hz, 1H), 5.18 (d, J=10.0 Hz, 1H), 3.47 (m, 1H), 3.18 (m, 1H), 2.46 (m, 2H), 2.25 (s, 3H), 1.30 (m, 1H), 0.86 (m, 1H), 0.60 (m, 2H), 0.52 (m, 1H).

Step B. Preparation of (S)-2-(cyclopropyl(4-fluoro-3-methylphenyl)methyl)-7-(hydroxymethyl)-5-(2-(trifluoromethyl)pyridin-3-yl)-3,4-dihydroisoquinolin-1(2H)-one. The title compound (25 mg, 62%) was prepared from the procedure described in Intermediate 11, Step B substituting (S)-2-(cyclopropyl (4-fluoro-3-methylphenyl)methyl)-5-(2-(trifluoromethyl)pyridin-3-yl)-7-vinyl-3,4-dihydroisoquinolin-1(2H)-one for 2-(3,5-dimethoxybenzyl)-5-(4-fluoro-2-methylphenyl)-7-vinyl-3,4-dihydroisoquinolin-1(2H)-one. LC-MS: >95% 254 nm, $R_T$=1.20 min, MS (ES) 485 $[M+H]^+$.

Step C. Preparation of (S)-7-(bromomethyl)-2-(cyclopropyl(4-fluoro-3-methylphenyl)methyl)-5-(2-(trifluoromethyl)pyridin-3-yl)-3,4-dihydroisoquinolin-1 (2H)-one. The title compound (22 mg crude, used without further purification) was prepared from the procedure described in Intermediate 3, Step C substituting (S)-2-(cyclopropyl(4-fluoro-3-methylphenyl)methyl)-7-(hydroxymethyl)-5-(2-(trifluoromethyl)pyridin-3-yl)-3,4-dihydroisoquinolin-1 (2H)-one for 2-(3,5-dichlorobenzyl)-7-(hydroxymethyl)-3,4-dihydroisoquinolin-1(2H)-one. LC-MS: >90% 254 nm, $R_T$=1.44 min, MS (ES) 547 $[M+H]^+$.

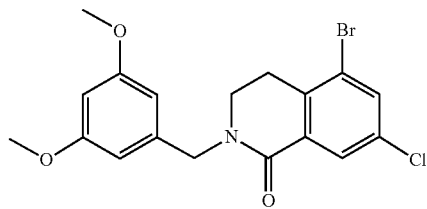 [SMILES: COc1cc(CN2CCc3c(Br)cc(Cl)cc3C2=O)cc(OC)c1]

Intermediate 24

5-Bromo-7-chloro-2-(3,5-dimethoxybenzyl)-3,4-dihydroisoquinolin-1(2H)-one

The title compound was prepared from the procedure described in Intermediate 10 substituting 5-bromo-7-chloro-3,4-dihydroisoquinolin-1(2H)-one for 7-chloro-5-(4-fluoro-2-methylphenyl)-3,4-dihydroisoquinolin-1(2H)-one.

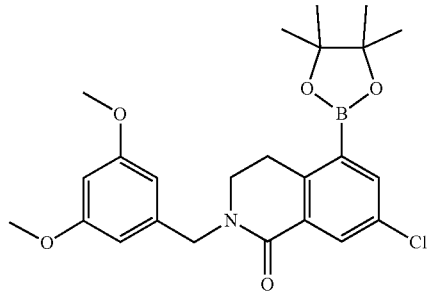 [SMILES: COc1cc(CN2CCc3c(B4OC(C)(C)C(C)(C)O4)cc(Cl)cc3C2=O)cc(OC)c1]

Intermediate 25

7-Chloro-2-(3,5-dimethoxybenzyl)-5-(4,4,5,5-tetramethyl-1,3,2-dioxaborolan-2-yl)-3,4-dihydroisoquinolin-1(2H)-one The title compound was prepared from the procedure described in intermediate 21 substituting 5-bromo-7-chloro-2-(3,5-dimethoxybenzyl)-3,4-dihydroisoquinolin-1(2H)-one (Intermediate 24) for (5)-5-bromo-7-chloro-2-(cyclopropyl(4-fluoro-3-methylphenyl)methyl)-3,4-dihydroisoquinolin-1(2H)-one. $^1H$ NMR (400 MHz, $CDCl_3$) δ 8.22 (d, J=2.4 Hz, 1H), 7.88 (d, J=2.4 Hz, 1H), 6.47 (d, J=2.4 Hz, 2H), 6.38 (m, 1H), 4.72 (s, 2H), 3.77 (s, 6H), 3.45 (t, J=6.4 Hz, 2H), 3.24 (t, J=6.4 Hz, 2H), 1.33 (s, 12H).

131

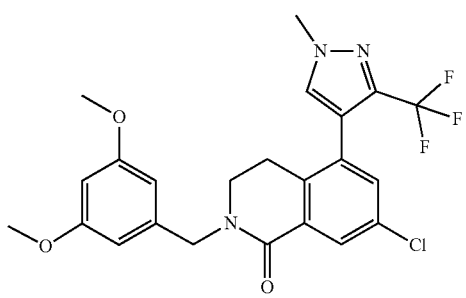 [SMILES: COc1cc(CN2CCc3c(cc(Cl)cc3-c3cn(C)nc3C(F)(F)F)C2=O)cc(OC)c1]

Intermediate 26

7-Chloro-2-(3,5-dimethoxybenzyl)-5-(1-methyl-3-(trifluoromethyl)-1H-pyrazol-4-yl)-3,4-dihydroisoquinolin-1(2H)-one The title compound (160 mg, 78%) was prepared from the procedure described in Intermediate 22 using 7-chloro-2-(3,5-dimethoxybenzyl)-5-(4,4,5,5-tetramethyl-1,3,2-dioxaborolan-2-yl)-3,4-dihydroisoquinolin-1(2H)-one (Intermediate 25) and 4-bromo-1-methyl-3-(trifluoromethyl)-1H-pyrazole. $^1$H NMR (400 MHz, CDCl$_3$) δ 8.19 (s, 1H), 7.34 (s, 1H), 6.46 (s, 2H), 6.38 (s, 1H), 4.72 (s, 2H), 4.01 (s, 3H), 3.77 (s, 6H), 3.39 (t, J=6.4 Hz, 2H), 2.69 (t, J=6.4 Hz, 2H).

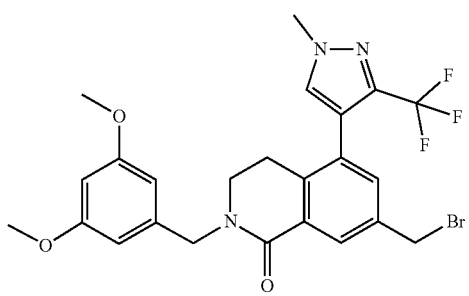 [SMILES: COc1cc(CN2CCc3c(cc(CBr)cc3-c3cn(C)nc3C(F)(F)F)C2=O)cc(OC)c1]

Intermediate 27

7-(Bromomethyl)-2-(3,5-dimethoxybenzyl)-5-(1-methyl-3-(trifluoromethyl)-1H-pyrazol-4-yl)-3,4-dihydroisoquinolin-1(2H)-one The title compound (135 mg) was prepared from the procedure described in Intermediate 23, Step A-C substituting 7-chloro-2-(3,5-dimethoxybenzyl)-5-(1-methyl-3-(trifluoromethyl)-1H-pyrazol-4-yl)-3,4-dihydroisoquinolin-1(2H)-one (Intermediate 26) for (5)-7-Chloro-2-(cyclopropyl(4-fluoro-3-methylphenyl)methyl)-5-(2-(trifluoromethyl)pyridin-3-yl)-3,4-dihydroisoquinolin-1(2H)-one. LC-MS: >92% 254 nm, R$_T$=1.28 min, MS (ES) 538 [M+H]$^+$.

132

Intermediate 28

(S)-5-Bromo-7-chloro-2-(cyclopropyl(4-methylpyridin-2-yl)methyl)-3,4-dihydroisoquinolin-1(2H)-one Step A. Preparation of ((7-bromo-5-chloro-1H-inden-3-yl)oxy)(tert-butyl)dimethylsilane. tert-Butyldimethylsilyl trifluoromethanesulfonate (1.48 mL, 6.46 mmol) was added dropwise to a solution of 4-bromo-6-chloro-1-indanone (1321.1 mg, 5.38 mmol) in CH$_2$Cl$_2$ (35.0 mL) in the presence of Et$_3$N (1.13 mL, 8.07 mmol) at 0° C. The reaction mixture was allowed to warm to room temperature and stirred overnight. Sat. aq. NH$_4$Cl (35.0 mL) was added to quench the reaction. The reaction mixture was extracted with CH$_2$Cl$_2$ (3×50.0 mL). The combined organics were dried over Na$_2$SO$_4$ and filtered. Then, the combined organics were concentrated under reduced pressure. The residue was purified by flash chromatography (Combi-flash Rf, Hex/EtOAc=0-10% gradient) to afford the title compound (1730 mg, 89% yield). $^1$H NMR (400 MHz, CDCl$_3$) δ 7.36 (s, 1H), 7.28 (s, 1H), 5.52 (t, J=2.4 Hz, 1H), 2.07 (d, J=2.4 Hz, 2H), 1.02 (s, 9H), 0.26 (s, 6H).

Step B. Preparation of (S)-5-bromo-7-chloro-2-(cyclopropyl(4-methylpyridin-2-yl)methyl)-3,4-dihydroisoquinolin-1(2H)-one. Ozone was bubbled through a solution of ((7-bromo-5-chloro-1H-inden-3-yl)oxy)(tert-butyl)dimethylsilane (500.0 mg, 1.39 mmol) in CH$_2$Cl$_2$ (50.0 mL) at −78° C. Once the starting material was consumed, PPh$_3$ (546.8 mg, 2.08 mmol) was added. The reaction was allowed to warm to 0° C. and stirred for 45 min. Then, (5)-cyclopropyl(4-methylpyridin-2-yl)methanamine dihydrochloride (392 mg, 1.67 mmol) was added as a solution of free base in CH$_2$Cl$_2$ (5.0 mL) followed by NaBH(OAc)$_3$ (539.0 mg, 2.78 mmol). The ice bath was removed and the resulting mixture was stirred at room temperature overnight. The solvent was removed under reduced pressure. The residue was taken up in toluene (5.0 mL) and heated to reflux for 2 h. The reaction mixture was concentrated under reduced pressure and the residue was purified by flash chromatography (Combi-flash Rf, Hex/EtOAc=0-70% gradient) to afford the title compound (507 mg, 89% yield). LCMS: R$_T$=1.550 min, MS (ES) 406.7 [M+H]$^+$. $^1$H NMR (400 MHz, Chloroform-d) δ 8.45 (d, J=5.1 Hz, 1H), 8.04 (d, J=1.9 Hz, 1H), 7.64 (d, J=2.2 Hz, 1H), 7.29 (s, 1H), 7.05 (s, 1H), 4.97 (d, J=8.2 Hz, 1H), 3.81 (m, 2H), 3.01 (m, 2H), 2.09 (s, 3H), 1.75-1.62 (m, 1H), 0.84-0.76 (m, 1H), 0.66 (m, 1H), 0.52 (m, 2H).

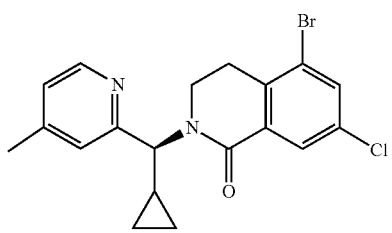 [SMILES: Cc1ccnc([C@H](C2CC2)N2CCc3c(Br)cc(Cl)cc3C2=O)c1]

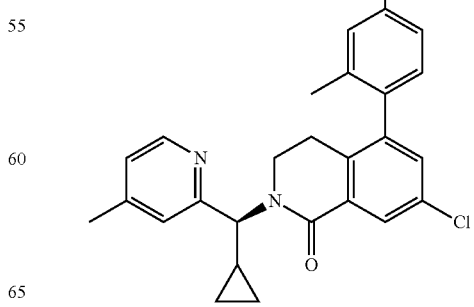

Intermediate 29

(S)-7-chloro-2-(cyclopropyl(4-methylpyridin-2-yl)methyl)-5-(4-fluoro-2-methylphenyl)-3,4-dihydroisoquinolin-1(2H)-one Pd(PPh$_3$)$_4$ (72.1 mg, 0.06 mmol) was added to a mixture of (S)-5-bromo-7-chloro-2-(cyclopropyl(4-methylpyridin-2-yl)methyl)-3,4-dihydroisoquinolin-1(2H)-one (507 mg, 1.25 mmol), 4-fluoro-2-methylphenyl-boronic acid (288 mg, 1.87 mmol), K$_2$CO$_3$ (690 mg, 4.99 mmol), 1,4-dioxane (10.0 mL), and H$_2$O (2.0 mL). The resulting mixture was degassed for 5 min., and heated at 80° C. overnight. The solvent was removed under reduced pressure. The residue was purified by flash chromatography (Combi-flash Rf, Hex/EtOAc=0-100% gradient) to afford the title compound (422 mg, 77% yield). LCMS: R$_T$=1.759 min, MS (ES) 435.9 [M+H]$^+$.

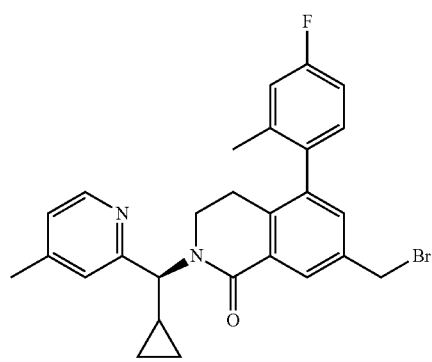 [SMILES: Cc1ccnc([C@H](C2CC2)N2CCc3c(cc(CBr)cc3-c3ccc(F)cc3C)C2=O)c1]

Intermediate 30

(S)-7-(Bromomethyl)-2-(cyclopropyl(4-methylpyridin-2-yl)methyl)-5-(4-fluoro-2-methylphenyl)-3,4-dihydroisoquinolin-1(2H)-one Step A. Preparation of (S)-2-(cyclopropyl(4-methylpyridin-2-yl)methyl)-5-(4-fluoro-2-methylphenyl)-7-vinyl-3,4-dihydroisoquinolin-1(2H)-one. Pd(t-Bu$_3$P)$_2$ (99.2 mg, 0.19 mmol) was added to a mixture of (S)-7-chloro-2-(cyclopropyl(4-methylpyridin-2-yl)methyl)-5-(4-fluoro-2-methylphenyl)-3,4-dihydroisoquinolin-1(2H)-one (422.0 mg, 0.97 mmol), potassium vinyltrifluoroborate (389.9 mg, 2.91 mmol), 1 M Cs$_2$CO$_3$ (3.9 mL), and 1,4-dioxane (10.0 mL) under argon atmosphere. The resulting mixture was heated at 90° C. overnight. H$_2$O (5.0 mL) was added to quench the reaction. The reaction mixture was extracted with EtOAc (3×20.0 mL). The combined organics were dried over Na$_2$SO$_4$, filtered and concentrated. The residue was purified by flash chromatography (Combi-flash Rf, Hex/EtOAc=0-40% gradient) to afford the title compound (356 mg, 86% yield). LCMS: R$_T$=1.701 min, MS (ES) 427.5 [M+H]$^+$.

Step B. Preparation of (S)-2-(cyclopropyl(4-methylpyridin-2-yl)methyl)-5-(4-fluoro-2-methylphenyl)-7-(hydroxymethyl)-3,4-dihydroisoquinolin-1(2H)-one. OsO$_4$, polymer-bound (53 mg, 0.21 mmol) was added to a mixture of (S)-2-(cyclopropyl(4-methylpyridin-2-yl)methyl)-5-(4-fluoro-2-methylphenyl)-7-vinyl-3,4-dihydroisoquinolin-1 (2H)-one (356 mg, 0.84 mmol), pyridine (130 µL, 1.67 mmol), H$_2$O (3.0 mL), and 1,4-dioxane (10.0 mL) at room temperature followed by NaIO$_4$ (715 mg, 3.34 mmol). After stirring overnight, the reaction mixture was cooled to 0° C., then MeOH (10.0 mL) was added followed by NaBH$_4$ (379.3 mg, 10.0 mmol). The ice bath was removed and the reaction was stirred at room temperature for 45 min. The solvent was removed under reduced pressure and the residue was taken up in EtOAc (10.0 mL) and washed with water (3.0 mL). The combined organics were dried over Na$_2$SO$_4$, filtered and concentrated. The residue was purified by flash chromatography (Combi-flash Rf, Hex/EtOAc=10-90% gradient) to afford the title compound (250.9 mg, 69% yield). LCMS: R$_T$=1.537 min, MS (ES) 431.5 [M+H]$^+$; $^1$H NMR (400 MHz, Chloroform-d) δ 8.39 (t, J=5.0 Hz, 1H), 8.13* (dd, J=22.7, 1.6 Hz, 1H), 7.28 (m, 2H), 7.08-6.85 (m, 4H), 5.37 (s, 1H), 5.08 (ddd, J=10.5, 7.9, 3.1 Hz, 1H), 4.73 (s, 1H), 3.81-3.55 (m, 2H), 2.56 (m, 2H), 2.32* (t, J=3.5 Hz, 3H), 2.03* (m, 4H), 1.72-1.57 (m, 1H), 0.81-0.71 (m, 1H), 0.66-0.57 (m, 1H), 0.56-0.45 (m, 2H) (*Indicates two atropisomers (1:1)).

Step C. Preparation of (S)-7-(bromomethyl)-2-(cyclopropyl(4-methylpyridin-2-yl)methyl)-5-(4-fluoro-2-methylphenyl)-3,4-dihydroisoquinolin-1(2H)-one. PBr$_3$ (2.0 µL, 0.19 mmol) was added to a solution of (S)-2-(cyclopropyl(4-methylpyridin-2-yl)methyl)-5-(4-fluoro-2-methylphenyl)-7-(hydroxymethyl)-3,4-dihydroisoquinolin-1(2H)-one (40.0 mg, 0.09 mmol) in THF (1.0 mL). The reaction was stirred at room temperature for 1.5 h. H$_2$O (0.5 mL) was added and the mixture was extracted with CH$_2$Cl$_2$ (3.0 mL×3). The combined organics were passed through the phase separator and concentrated to provide the title product, which was used in the next step without further purification. LCMS: R$_T$=1.774 min, MS (ES) 494.4 [M+H]$^+$.

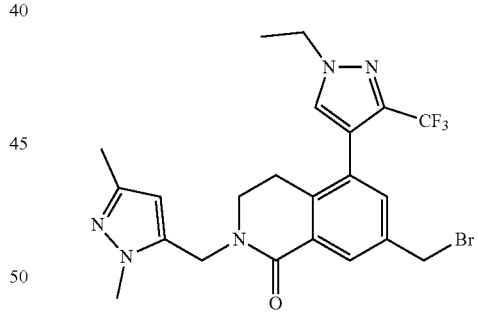

Intermediate 31

7-(Bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one The title compound was prepared following the synthetic sequence described in Intermediates 15-18 substituting (1,3-dimethyl-1H-pyrazol-5-yl)methanamine for (4-methoxypyridin-2-yl)methanamine in Intermediate 15, and (1-ethyl-3-(trifluoromethyl)-1H-pyrazol-4-yl)boronic acid for (1-methyl-3-(trifluoromethyl)-1H-pyrazol-4-yl)boronic acid in Intermediate 16.

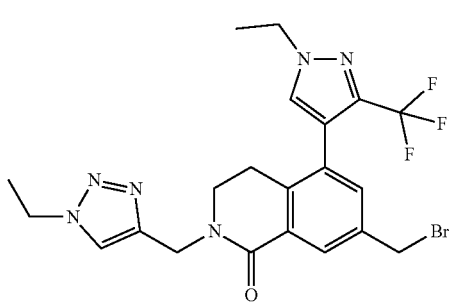 [SMILES: CCn1cc(CN2CCc3c(cc(CBr)cc3-c3cn(CC)nc3C(F)(F)F)C2=O)nn1]

Intermediate 32

7-(Bromomethyl)-2-((1-ethyl-1H-1,2,3-triazol-4-yl)methyl)-5-(1-ethyl-3-(trifluoromethyl)-1H-pyrazol-4-yl)-3,4-dihydroisoquinolin-1(2H)-one The title compound was prepared following the synthetic sequence described in Intermediates 15-18 substituting (1-ethyl-1H-1,2,3-triazol-4-yl)methanamine for (4-methoxypyridin-2-yl)methanamine in Intermediate 15, and (1-ethyl-3-(trifluoromethyl)-1H-pyrazol-4-yl)boronic acid for (1-methyl-3-(trifluoromethyl)-1H-pyrazol-4-yl)boronic acid in Intermediate 16.

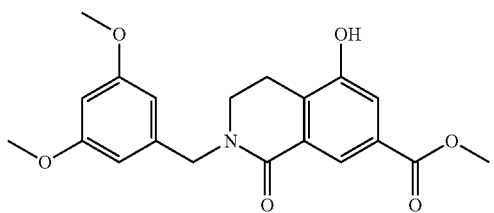

Intermediate 33

Methyl 2-(3,5-dimethoxybenzyl)-5-hydroxy-1-oxo-1,2,3,4-tetrahydroisoquinoline-7-carboxylate The title compound (2.7 g, 7.3 mmol,) was prepared following the procedure described in Intermediate 15 substituting (3,5-dimethoxyphenyl)methanamine for (4-methoxypyridin-2-yl)methanamine. LCMS method 1: $R_T$=1.42 min, MS (ES) 372.0 [M+H]$^+$.

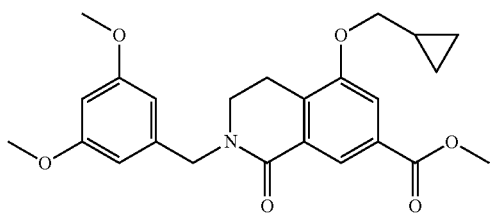

Intermediate 34

Methyl 5-(cyclopropylmethoxy)-2-(3,5-dimethoxybenzyl)-1-oxo-1,2,3,4-tetrahydroisoquinoline-7-carboxylate (Bromomethyl)cyclopropane (0.25 mL, 2.7 mmol) and potassium carbonate (0.56 g, 4.0 mmol) were added to a solution of methyl 2-(3,5-dimethoxybenzyl)-5-hydroxy-1-oxo-1,2,3,4-tetrahydroisoquinoline-7-carboxylate (0.5 g, 1.35 mmol) in 5 mL of acetone. This was heated at 75° C. for 16 hours. The reaction was filtered and the filtrate was concentrated to dryness. The residue was purified by flash chromatography (Combi-flash Rf, Hex/EtOAc=0-40% gradient) to afford the title compound (0.19 g, 32% yield). LCMS method 1: $R_T$=1.86 min, MS (ES) 426.0 [M+H]$^+$.

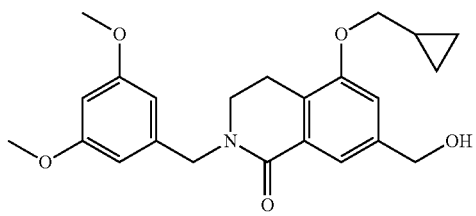 [SMILES: COc1cc(CN2CCc3c(OCC4CC4)cc(CO)cc3C2=O)cc(OC)c1]

Intermediate 35

5-(Cyclopropylmethoxy)-2-(3,5-dimethoxybenzyl)-7-(hydroxymethyl)-3,4-dihydroisoquinolin-1(2H)-one The title compound (88 mg, 0.22 mmol,) was prepared following the procedure described in Intermediate 17 from methyl 5-(cyclopropylmethoxy)-2-(3,5-dimethoxybenzyl)-1-oxo-1,2,3,4-tetrahydroisoquinoline-7-carboxylate (intermediate 34, 0.19 g, 0.44 mmol). LCMS method 1: $R_T$=1.59 min, MS (ES) 398.0 [M+H]$^+$.

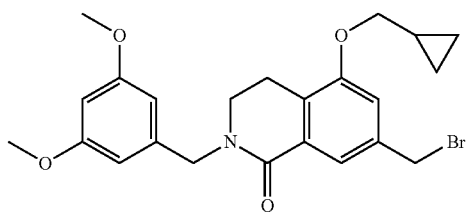 [SMILES: COc1cc(CN2CCc3c(OCC4CC4)cc(CBr)cc3C2=O)cc(OC)c1]

Intermediate 36

7-(Bromomethyl)-5-(cyclopropylmethoxy)-2-(3,5-dimethoxybenzyl)-3,4-dihydroisoquinolin-1(2H)-one Triphenylphosphine (0.12 g, 0.44 mmol) and N-bromosuccinimide (79 mg, 0.44 mmol) were added to a 0° C. solution of 5-(cyclopropylmethoxy)-2-(3,5-dimethoxybenzyl)-7-(hydroxymethyl)-3,4-dihydroisoquinolin-1(2H)-one (88 mg, 0.22 mmol) in 5 mL of THF. The reaction was allowed to warm to RT overnight. The reaction was concentrated and the residue was purified by flash chromatography (Combi-flash Rf, Hex/EtOAc=5-40% gradient) to afford the title compound (42 mg, 41% yield). LCMS method 1: $R_T$=1.96 min, MS (ES) 459.9 [M+H]$^+$.

137

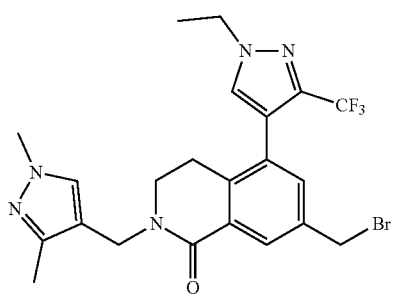 [SMILES: CCn1cc(-c2cc(CBr)cc3c2CCN(Cc2cn(C)nc2C)C3=O)c(C(F)(F)F)n1]

Intermediate 37

7-(Bromomethyl)-2-((1,3-dimethyl-1H-pyrazol-4-yl)methyl)-5-(1-ethyl-3-(trifluoromethyl)-1H-pyrazol-4-yl)-3,4-dihydroisoquinolin-1(2H)-one The title compound was prepared following the synthetic sequence described in Intermediates 15-18 substituting (1,3-dimethyl-1H-pyrazol-4-yl)methanamine for (4-methoxypyridin-2-yl)methanamine in Intermediate 15, and (1-ethyl-3-(trifluoromethyl)-1H-pyrazol-4-yl)boronic acid for (1-methyl-3-(trifluoromethyl)-1H-pyrazol-4-yl)boronic acid in Intermediate 16, Step B.

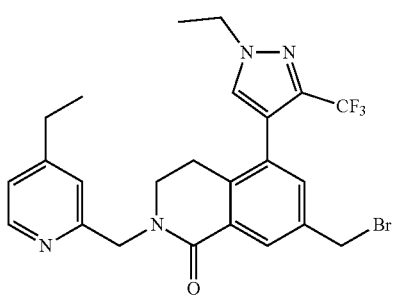 [SMILES: CCc1ccnc(CN2CCc3c(cc(CBr)cc3-c3cn(CC)nc3C(F)(F)F)C2=O)c1]

Intermediate 38

7-(Bromomethyl)-5-(1-ethyl-3-(trifluoromethyl)-1H-pyrazol-4-yl)-2-((4-ethylpyridin-2-yl)methyl)-3,4-dihydroisoquinolin-1(2H)-one The title compound was prepared following the synthetic sequence described in Intermediates 15-18 substituting (4-ethylpyridin-2-yl)methanamine for (4-methoxypyridin-2-yl)methanamine in Intermediate 15, and (1-ethyl-3-(trifluoromethyl)-1H-pyrazol-4-yl)boronic acid for (1-methyl-3-(trifluoromethyl)-1H-pyrazol-4-yl)boronic acid in Intermediate 16, Step B.

138

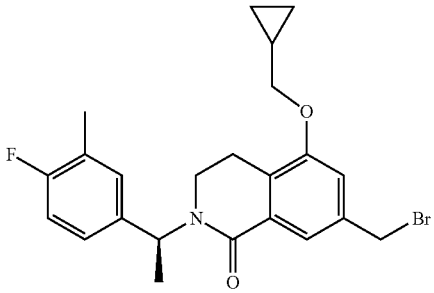 [SMILES: Cc1cc([C@H](C)N2CCc3c(OCC4CC4)cc(CBr)cc3C2=O)ccc1F]

Intermediate 39

(S)-7-(Bromomethyl)-5-(cyclopropylmethoxy)-2-(1-(4-fluoro-3-methylphenyl)ethyl)-3,4-dihydroisoquinolin-1(2H)-one The title compound was prepared following the synthetic sequence described in Intermediates 33-36 substituting (S)-1-(4-fluoro-3-methyl phenyl)ethan-1-amine for (3,5-dimethoxyphenyl)methanamine in Intermediate 33.

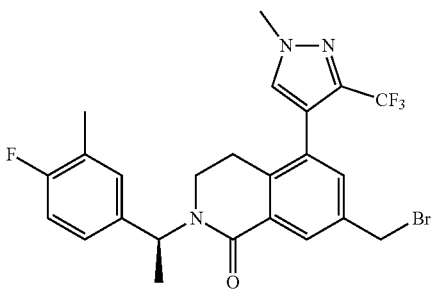 [SMILES: Cc1cc([C@H](C)N2CCc3c(cc(CBr)cc3-c3cn(C)nc3C(F)(F)F)C2=O)ccc1F]

Intermediate 40

(S)-7-(Bromomethyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one The title compound was prepared following the synthetic sequence described in Intermediates 15-18 substituting (S)-1-(4-fluoro-3-methylphenyl)ethan-1-amine for (4-methoxypyridin-2-yl)methanamine in Intermediate 15.

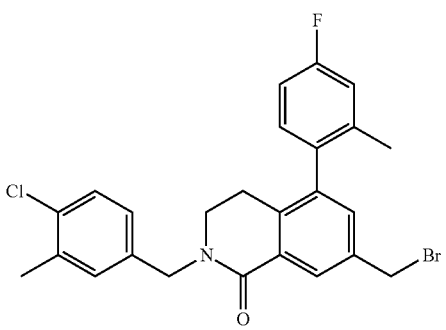 [SMILES: Cc1cc(CN2CCc3c(cc(CBr)cc3-c3ccc(F)cc3C)C2=O)ccc1Cl]

Intermediate 41

7-(Bromomethyl)-2-(4-chloro-3-methylbenzyl)-5-(4-fluoro-2-methylphenyl)-3,4-dihydroisoquinolin-1(2H)-one The title compound was prepared following the synthetic sequence described in Intermediate 13, Step A-C substituting 7-chloro-5-(4-fluoro-2-methylphenyl)-3,4-dihydroisoquinolin-1(2H)-one (Intermediate 9) for 7-chloro-5-(2-methylpyridin-3-yl)-3,4-dihydroisoquinolin-1(2H)-one (Intermediate 12) in Step A. LC-MS: >95% 254 nm, $R_T$=1.65 min, MS (ES) 486 [M+H]$^+$.

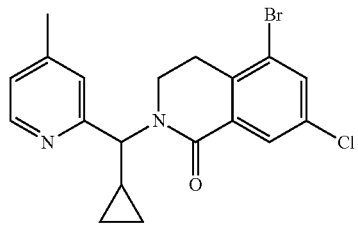 [SMILES: Cc1ccnc(C(C2CC2)N2CCc3c(Br)cc(Cl)cc3C2=O)c1]

Intermediate 42

5-Bromo-7-chloro-2-(cyclopropyl(4-methylpyridin-2-yl)methyl-3,4-dihydroisoquinolin-1(2H)-one The title compound was prepared following the procedure described in Intermediate 28 Step B using racemic cyclopropyl(4-methylpyridin-2-yl)methanamine hydrochloride. $^1$H NMR (400 MHz, CDCl$_3$) δ 8.43 (d, J=4.8 Hz, 1H), 8.06 (d, J=2.4 Hz, 1H), 7.64 (d, J=2.0 Hz, 1H), 7.23 (s, 1H), 7.02 (d, J=5.2 Hz, 1H), 5.03 (d, J=10.0 Hz, 1H), 3.82 (m, 2H), 3.04 (m, 2H), 2.34 (s, 3H), 1.67 (m, 1H), 0.79 (m, 1H), 0.63 (m, 1H), 0.51 (m, 2H).

Intermediate 43

7-(Bromomethyl)-2-(cyclopropyl(4-methylpyridin-2-yl)methyl)-5-(4-fluoro-2-methylphenyl)-3,4-dihydroisoquinolin-1(2H)-one The title compound was prepared following the synthetic sequence described in Intermediates 29 and 30. $^1$H NMR (400 MHz, CDCl$_3$) δ 8.41 (t, J=5.2 Hz, 1H), 8.16 (d, J=2.0 Hz, 1H), 7.27 (m, 2H), 6.96 (m, 4H), 5.11 (dd, J=2.8, 10.4 Hz, 1H), 4.53 (s, 2H), 3.68 (m, 2H), 2.55 (m, 2H), 2.33 (m, 3H), 2.06 (s, 1.5H), 2.00 (s, 1.5H), 1.66 (m, 1H), 0.77 (m, 1H), 0.62 (m, 1H), 0.52 (m, 2H).

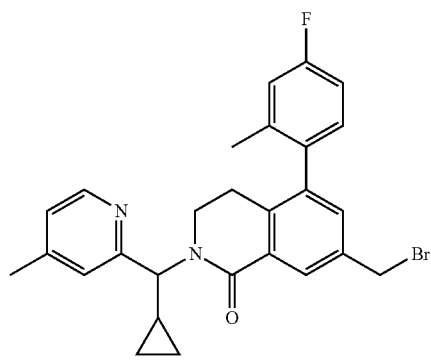

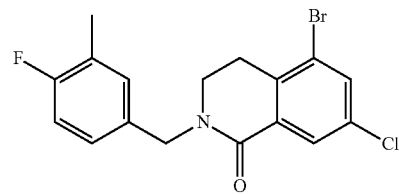 [SMILES: Cc1cc(CN2CCc3c(Br)cc(Cl)cc3C2=O)ccc1F]

Intermediate 44

5-Bromo-7-chloro-2-(4-fluoro-3-methylbenzyl)-3,4-dihydroisoquinolin-1(2H)-one

The title compound (72 mg, 76%) was prepared following the procedure described in Intermediate 28 Step B substituting 4-fluoro-3-methylbenzylamine for cyclopropyl(4-methylpyridin-2-yl)methanamine hydrochloride. $^1$H NMR (400 MHz, CDCl$_3$) δ 8.12 (d, J=2.4 Hz, 1H), 7.67 (d, J=2.0 Hz, 1H), 7.10 (m, 2H), 6.96 (m, 1H), 4.70 (s, 2H), 3.48 (t, J=6.4 Hz, 2H), 2.99 (t, J=6.4 Hz, 2H), 2.26 (s, 3H).

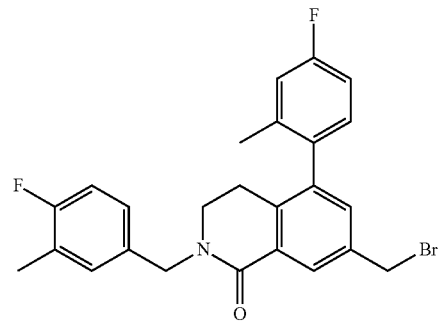 [SMILES: Cc1cc(CN2CCc3c(cc(CBr)cc3-c3ccc(F)cc3C)C2=O)ccc1F]

Intermediate 45

7-(Bromomethyl)-5-(4-fluoro-2-methylphenyl)-2-(4-fluoro-3-methylbenzyl)-3,4-dihydroisoquinolin-1(2H)-one The title compound was prepared following the synthetic sequence described in Intermediates 29 and 30. LC-MS: >92% 254 nm, $R_T$=1.53 min, MS (ES) 470 [M+H]$^+$.

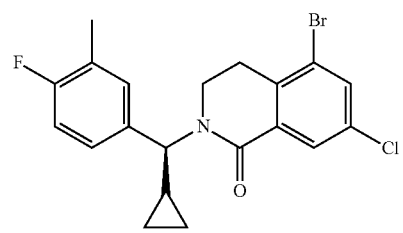 [SMILES: Cc1cc([C@H](C2CC2)N2CCc3c(Br)cc(Cl)cc3C2=O)ccc1F]

Intermediate 46

(S)-5-bromo-7-chloro-2-(cyclopropyl(4-fluoro-3-methylphenyl)methyl)-3,4-dihydroisoquinolin-1(2H)-one The title compound (183 mg, 89%) was prepared following the procedure described in Intermediate 28 Step B substituting (S)-cyclopropyl(4-fluoro-3-methylphenyl) methanamine for cyclopropyl(4-methylpyridin-2-yl)methanamine hydrochloride. $^1$H NMR (400 MHz, CDCl$_3$) δ 8.12 (d, J=2.0 Hz, 1H), 7.68 (d, J=2.0 Hz, 1H), 7.28 (m, 2H), 6.98 (t, J=9.2 Hz, 1H), 5.14 (d, J=10.0 Hz, 1H), 3.59 (m, 1H), 3.29 (m, 1H), 3.02 (m, 1H), 2.83 (m, 1H), 2.27 (s, 3H), 1.33 (m, 1H), 0.89 (m, 1H), 0.60 (m, 3H).

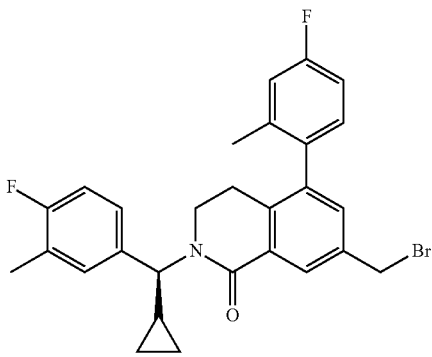 [SMILES: Cc1cc([C@H](C2CC2)N2CCc3c(cc(CBr)cc3-c3ccc(F)cc3C)C2=O)ccc1F]

Intermediate 47

(S)-7-(Bromomethyl)-2-(cyclopropyl(4-fluoro-3-methylphenyl)methyl)-5-(4-fluoro-2-methylphenyl)-3,4-dihydroisoquinolin-1(2H)-one The title compound was prepared following the synthetic sequence described in Intermediates 29 and 30. $^1$H NMR (400 MHz, CDCl$_3$) δ 8.21 (d, J=2.0 Hz, 1H), 7.29 (m, 3H), 6.95 (m, 4H), 5.18 (d, J=10.0 Hz, 1H), 4.55 (s, 2H), 3.46 (m, 1H), 3.18 (m, 1H), 2.47 (m, 2H), 2.25 (s, 3H), 2.09 (s, 1.5H), 2.02 (s, 1.5H), 1.30 (m, 1H), 0.86 (m, 1H), 0.60 (m, 2H), 0.51 (m, 1H).

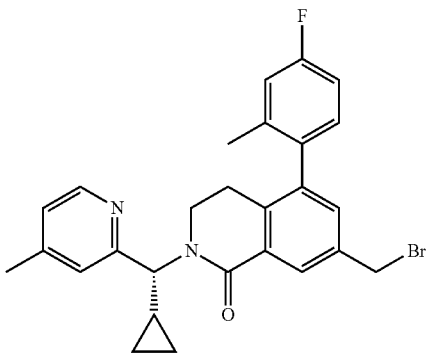 [SMILES: Cc1ccnc([C@@H](C2CC2)N2CCc3c(cc(CBr)cc3-c3ccc(F)cc3C)C2=O)c1]

Intermediate 48

(R)-7-(bromomethyl)-2-(cyclopropyl(4-methylpyridin-2-yl)methyl)-5-(4-fluoro-2-methylphenyl)-3,4-dihydroisoquinolin-1(2H)-one The title compound was prepared following the synthetic sequence described in Intermediates 28-30 substituting (R)-cyclopropyl(4-methylpyridin-2-yl)methanamine hydrochloride for (S)-cyclopropyl(4-methylpyridin-2-yl)methanamine hydrochloride. $^1$H NMR (400 MHz, CDCl$_3$) δ 8.41 (t, J=5.2 Hz, 1H), 8.16 (d, J=2.0 Hz, 1H), 7.27 (m, 2H), 6.96 (m, 4H), 5.11 (dd, J=2.8, 10.4 Hz, 1H), 4.53 (s, 2H), 3.68 (m, 2H), 2.55 (m, 2H), 2.33 (m, 3H), 2.06 (s, 1.5H), 2.00 (s, 1.5H), 1.66 (m, 1H), 0.77 (m, 1H), 0.62 (m, 1H), 0.52 (m, 2H).

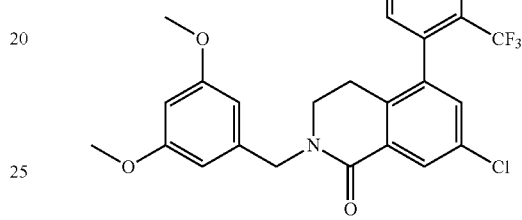

Intermediate 49

7-Chloro-2-(3,5-dimethoxybenzyl)-5-(2-(trifluoromethyl)pyridin-3-yl)-3,4-dihydroisoquinolin-1(2H)-one The title compound (131 mg, quant) was prepared from the procedure described in Intermediate 22 substituting 7-chloro-2-(3,5-dimethoxybenzyl)-5-(4,4,5,5-tetramethyl-1,3,2-dioxaborolan-2-yl)-3,4-dihydroisoquinolin-1(2H)-one for (S)-7-chloro-2-(cyclopropyl(4-fluoro-3-methyl phenyl) methyl)-5-(4,4,5,5-tetramethyl-1,3,2-dioxaborolan-2-yl)-3, 4-dihydroisoquinolin-1(2H)-one. $^1$H NMR (400 MHz, CDCl$_3$) δ 8.78 (m, 1H), 8.25 (d, J=2.4 Hz, 1H), 7.58 (m, 2H), 7.31 (s, 1H), 6.45 (d, J=2.0 Hz, 2H), 6.38 (m, 1H), 4.83 (d, J=14.8 Hz, 1H), 4.58 (d, J=14.8 Hz, 1H), 3.77 (s, 6H), 3.38 (m, 2H), 2.50 (m, 2H).

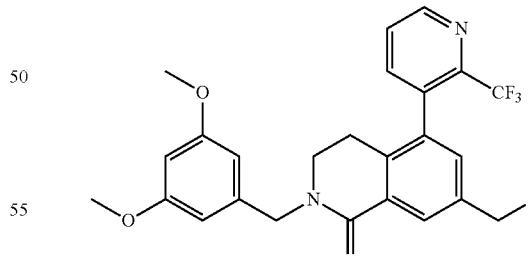

Intermediate 50

7-(Bromomethyl)-2-(3,5-dimethoxybenzyl)-5-(2-(trifluoromethyl)pyridin-3-yl)-3,4-dihydroisoquinolin-1(2H)-one The title compound was prepared from the synthetic sequence described in Intermediate 23 A-C substituting 7-chloro-2-(3,5-dimethoxybenzyl)-5-(2-(trifluoromethyl)pyridin-3-yl)-3,4-dihydroisoquinolin-1(2H)-one (Intermediate 49) for (S)-7-Chloro-2-(cyclopropyl(4-fluoro-3-methylphenyl)methyl)-5-(2-(trifluoromethyl)pyridin-3-yl)-3,4-dihydroisoquinolin-1(2H)-one. LC-MS: >90% 254 nm, $R_T$=1.23 min, MS (ES) 535 [M+H]$^+$.

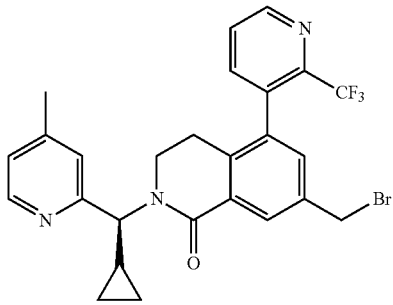 [SMILES: Cc1ccnc([C@H](C2CC2)N2CCc3c(cc(CBr)cc3-c3cccnc3C(F)(F)F)C2=O)c1]

Intermediate 51

(S)-7-(Bromomethyl)-2-(cyclopropyl(4-methylpyridin-2-yl)methyl)-5-(2-(trifluoromethyl)pyridin-3-yl)-3,4-dihydroisoquinolin-1(2H)-one The title compound (67 mg, 75%) was prepared from the synthetic sequence described in Intermediates 21-23 substituting (S)-5-bromo-7-chloro-2-(cyclopropyl(4-methylpyridin-2-yl)methyl)-3,4-dihydroisoquinolin-1(2H)-one (Intermediate 28) for (S)-5-bromo-7-chloro-2-(cyclopropyl(4-fluoro-3-methylphenyl)methyl)-3,4-dihydroisoquinolin-1(2H)-one in Intermediate 21. LC-MS, >90% 254 nm, $R_T$=1.00 min, MS (ES) 530 [M+H]$^+$.

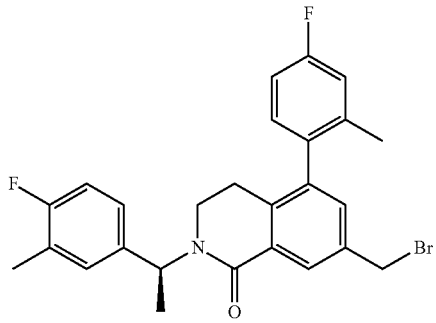 [SMILES: Cc1cc([C@H](C)N2CCc3c(cc(CBr)cc3-c3ccc(F)cc3C)C2=O)ccc1F]

Intermediate 52

(S)-7-(bromomethyl)-5-(4-fluoro-2-methylphenyl)-2-(1-(4-fluoro-3-methylphenyl)ethyl)-3,4-dihydroisoquinolin-1(2H)-one The title compound (67 mg, 75%) was prepared from the synthetic sequence described in Intermediates 28-30 substituting (S)-1-(4-fluoro-3-methylphenyl)ethan-1-amine hydrochloride for (S)-cyclopropyl(4-methylpyridin-2-yl)methanamine hydrochloride in Intermediate 28. LC-MS: >90% 254 nm, $R_T$=1.50 min, MS (ES) 484 [M+H]$^+$.

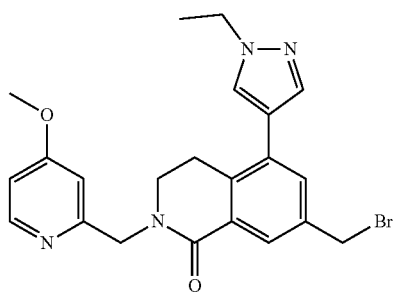 [SMILES: CCn1cc(-c2cc(CBr)cc3c2CCN(Cc2cc(OC)ccn2)C3=O)cn1]

Intermediate 53

7-(Bromomethyl)-5-(1-ethyl-1H-pyrazol-4-yl)-2-((4-methoxypyridin-2-yl)methyl)-3,4-dihydroisoquinolin-1(2H)-one The title compound was prepared from the synthetic sequence described in Intermediates 16-18 substituting (1-ethyl-1H-pyrazol-4-yl)boronic acid for (1-methyl-3-(trifluoromethyl)-1H-pyrazol-4-yl)boronic acid in Intermediate 16, Step B.

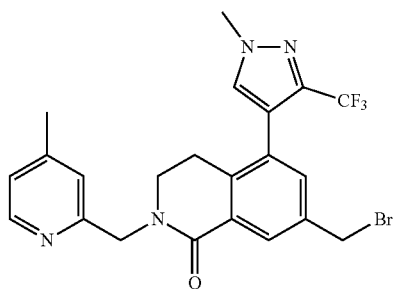 [SMILES: Cc1ccnc(CN2CCc3c(cc(CBr)cc3-c3cn(C)nc3C(F)(F)F)C2=O)c1]

Intermediate 54

7-(Bromomethyl)-5-(1-methyl-3-(trifluoromethyl)-1H-pyrazol-4-yl)-2-((4-methylpyridin-2-yl)methyl)-3,4-dihydroisoquinolin-1(2H)-one The title compound was prepared following the synthetic sequence described in Intermediates 15-18 substituting (4-methylpyridin-2-yl)methanamine for (4-methoxypyridin-2-yl)methanamine in Intermediate 15.

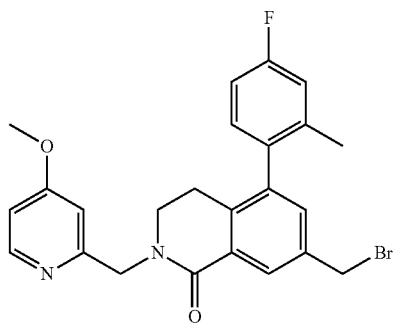 [SMILES: COc1ccnc(CN2CCc3c(cc(CBr)cc3-c3ccc(F)cc3C)C2=O)c1]

Intermediate 55

7-(Bromomethyl)-5-(4-fluoro-2-methylphenyl)-2-((4-methoxypyridin-2-yl)methyl)-3,4-dihydroisoquinolin-1(2H)-one The title compound was prepared from the synthetic sequence described in Intermediates 16-18 substituting (4-fluoro-2-methylphenyl)boronic acid for (1-methyl-3-(trifluoromethyl)-1H-pyrazol-4-yl)boronic acid in Intermediate 16, Step B.

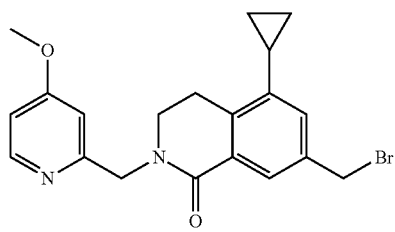 [SMILES: COc1ccnc(CN2CCc3c(cc(CBr)cc3C3CC3)C2=O)c1]

Intermediate 56

7-(Bromomethyl)-5-cyclopropyl-2-((4-methoxypyridin-2-yl)methyl)-3,4-dihydroisoquinolin-1(2H)-one The title compound was prepared from the synthetic sequence described in Intermediates 16-18 substituting cyclopropylboronic acid for (1-methyl-3-(trifluoromethyl)-1H-pyrazol-4-yl)boronic acid in Intermediate 16, Step B.

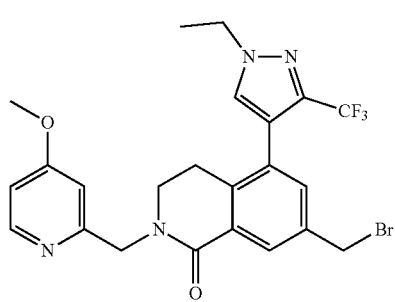 [SMILES: CCn1cc(-c2cc(CBr)cc3c2CCN(Cc2cc(OC)ccn2)C3=O)c(C(F)(F)F)n1]

Intermediate 57

7-(Bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one The title compound was prepared from the synthetic sequence described in Intermediates 16-18 substituting (1-ethyl-3-(trifluoromethyl)-1H-pyrazol-4-yl)boronic acid for (1-methyl-3-(trifluoromethyl)-1H-pyrazol-4-yl)boronic acid in Intermediate 16, Step B.

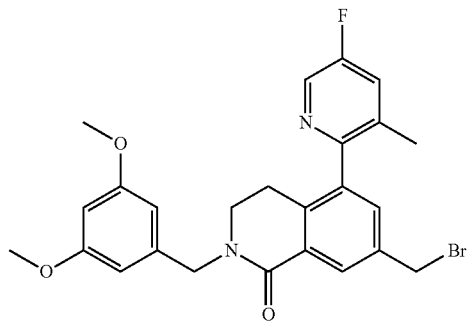 [SMILES: COc1cc(CN2CCc3c(cc(CBr)cc3-c3ncc(F)cc3C)C2=O)cc(OC)c1]

Intermediate 58

7-(Bromomethyl)-2-(3,5-dimethoxybenzyl)-5-(5-fluoro-3-methylpyridin-2-yl)-3,4-dihydroisoquinolin-1(2H)-one The title compound was prepared from the synthetic sequence described in Intermediates 22 and 23 substituting 7-chloro-2-(3,5-dimethoxybenzyl)-5-(4,4,5,5-tetramethyl-1,3,2-dioxaborolan-2-yl)-3,4-dihydroisoquinolin-1(2H)-one (Intermediate 25) and 2-bromo-5-fluoro-3-methylpyridine for (S)-7-chloro-2-(cyclopropyl(4-fluoro-3-methylphenyl)methyl)-5-(4,4,5,5-tetramethyl-1,3,2-dioxaborolan-2-yl)-3,4-dihydroisoquinolin-1(2H)-one and 3-bromo-2-(trifluoromethyl)pyridine in Intermediate 22, respectively. LC-MS, >95% 254 nm, $R_T$=1.24 min, MS (ES) 499 [M+H]$^+$.

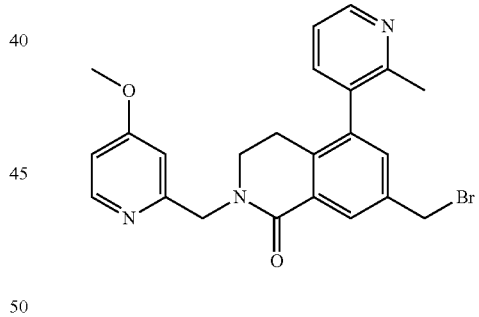

Intermediate 59

7-(Bromomethyl)-2-((4-methoxypyridin-2-yl)methyl)-5-(2-methylpyridin-3-yl)-3,4-dihydroisoquinolin-1(2H)-one The title compound was prepared from the synthetic sequence described in Intermediates 16-18 substituting (2-methylpyridin-3-yl)boronic acid for (1-methyl-3-(trifluoromethyl)-1H-pyrazol-4-yl)boronic acid in Intermediate 16, Step B.

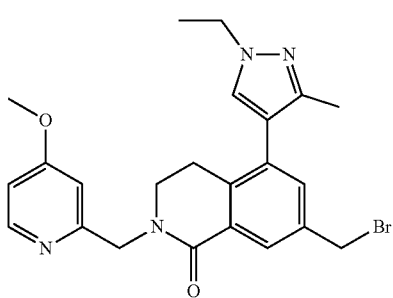 [SMILES: CCn1cc(-c2cc(CBr)cc3c2CCN(Cc2cc(OC)ccn2)C3=O)c(C)n1]

Intermediate 60

7-(Bromomethyl)-5-(1-ethyl-3-methyl-1H-pyrazol-4-yl)-2-((4-methoxypyridin-2-yl)methyl)-3,4-dihydroisoquinolin-1(2H)-one The title compound was prepared from the synthetic sequence described in Intermediates 16-18 substituting 1-ethyl-3-methyl-4-(4,4,5,5-tetramethyl-1,3,2-dioxaborolan-2-yl)-1H-pyrazole for (1-methyl-3-(trifluoromethyl)-1H-pyrazol-4-yl)boronic acid in Intermediate 16, Step B.

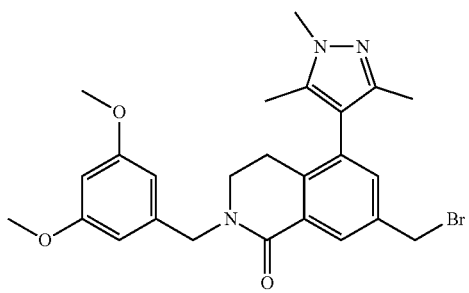 [SMILES: COc1cc(CN2CCc3c(cc(CBr)cc3-c3c(C)nn(C)c3C)C2=O)cc(OC)c1]

Intermediate 61

7-(Bromomethyl)-2-(3,5-dimethoxybenzyl)-5-(1,3,5-trimethyl-1H-pyrazol-4-yl)-3,4-dihydroisoquinolin-1(2H)-one The title compound (88 mg) was prepared from the procedure described in Intermediate 22 using 5-bromo-7-chloro-2-(3,5-dimethoxybenzyl)-3,4-dihydroisoquinolin-1(2H)-one and 1,3,5-trimethyl-4-(4,4,5,5-tetramethyl-1,3,2-dioxaborolan-2-yl)-1H-pyrazole, followed by the synthetic sequence described in Intermediate 23. LC-MS: >90% 254 nm, $R_T$=1.06 min, MS (ES) 498 [M+H]$^+$.

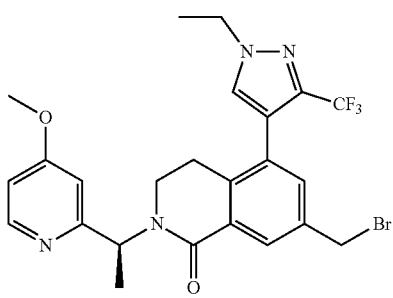 [SMILES: CCn1cc(-c2cc(CBr)cc3c2CCN([C@@H](C)c2cc(OC)ccn2)C3=O)c(C(F)(F)F)n1]

Intermediate 62

(S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound was prepared from the synthetic sequence described in Intermediates 15-18 substituting (S)-1-(4-methoxypyridin-2-yl)ethan-1-amine for (4-methoxypyridin-2-yl)methanamine in Intermediate 15 and (1-ethyl-3-(trifluoromethyl)-1H-pyrazol-4-yl)boronic acid for (1-methyl-3-(trifluoromethyl)-1H-pyrazol-4-yl)boronic acid in Intermediate 16, Step B.

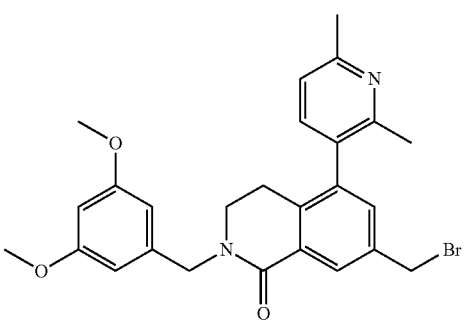 [SMILES: COc1cc(CN2CCc3c(cc(CBr)cc3-c3ccc(C)nc3C)C2=O)cc(OC)c1]

Intermediate 63

7-(Bromomethyl)-2-(3,5-dimethoxybenzyl)-5-(2,6-dimethylpyridin-3-yl)-3,4-dihydroisoquinolin-1(2H)-one The title compound was prepared from the synthetic sequence described in Intermediates 22 and 23 substituting 7-chloro-2-(3,5-dimethoxybenzyl)-5-(4,4,5,5-tetramethyl-1,3,2-dioxaborolan-2-yl)-3,4-dihydroisoquinolin-1(2H)-one (Intermediate 25) and 3-bromo-2,6-dimethylpyridine for (S)-7-chloro-2-(cyclopropyl (4-fluoro-3-methylphenyl)methyl)-5-(4,4,5,5-tetramethyl-1,3,2-dioxaborolan-2-yl)-3,4-dihydroisoquinolin-1(2H)-one and 3-bromo-2-(trifluoromethyl)pyridine in Intermediate 22, respectively. LC-MS, >95% 254 nm, $R_T$=0.94 min, MS (ES) 495 [M+H]$^+$.

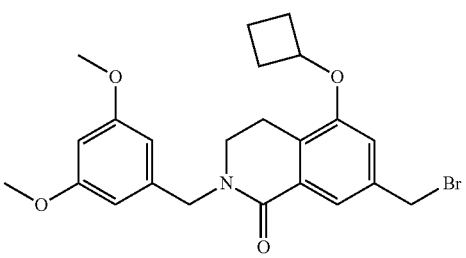 [SMILES: COc1cc(CN2CCc3c(OC4CCC4)cc(CBr)cc3C2=O)cc(OC)c1]

Intermediate 64

7-(Bromomethyl)-5-cyclobutoxy-2-(3,5-dimethoxybenzyl)-3,4-dihydroisoquinolin-1 (2H)-one The title compound was prepared from the synthetic sequence described in Intermediates 34-36 substituting bromocyclobutane for (bromomethyl)cyclopropane in Intermediate 34.

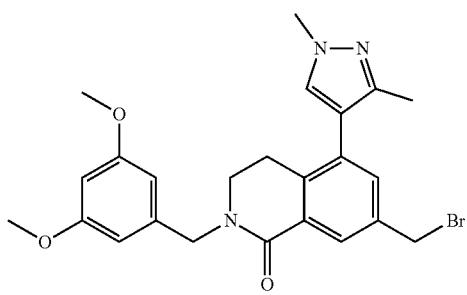 [SMILES: COc1cc(CN2CCc3c(cc(CBr)cc3-c3cn(C)nc3C)C2=O)cc(OC)c1]

Intermediate 65

7-(Bromomethyl)-2-(3,5-dimethoxybenzyl)-5-(1,3-dimethyl-1H-pyrazol-4-yl)-3,4-dihydroisoquinolin-1(2H)-one The title compound was prepared from the synthetic sequence described in Intermediates 22 and 23 substituting 7-chloro-2-(3,5-dimethoxybenzyl)-5-(4,4,5,5-tetramethyl-1,3,2-dioxaborolan-2-yl)-3,4-dihydroisoquinolin-1(2H)-one (Intermediate 25) and 4-bromo-1,3-dimethyl-1H-pyrazole for (S)-7-chloro-2-(cyclopropyl (4-fluoro-3-methylphenyl) methyl)-5-(4,4,5,5-tetramethyl-1,3,2-dioxaborolan-2-yl)-3,4-dihydroisoquinolin-1(2H)-one and 3-bromo-2-(trifluoromethyl)pyridine in Intermediate 22, respectively. $^1$H NMR (400 MHz, CDCl$_3$) δ 8.17 (d, J=2.0 Hz, 1H), 7.39 (s, 1H), 7.25 (s, 1H), 6.48 (d, J=2.0 hz, 2H), 6.38 (m, 1H), 4.72 (s, 2H), 4.54 (s, 2H), 3.88 (s, 3H), 3.77 (s, 6H), 3.40 (t, J=6.4 Hz, 2H), 2.80 (t, J=6.4 Hz, 2H), 2.15 (s, 3H).

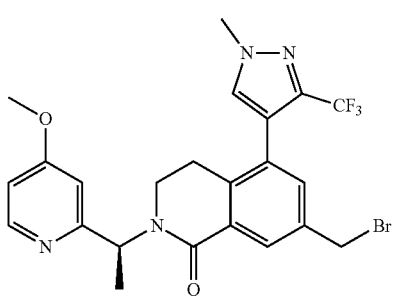 [SMILES: COc1ccnc([C@H](C)N2CCc3c(cc(CBr)cc3-c3cn(C)nc3C(F)(F)F)C2=O)c1]

Intermediate 66

(S)-7-(bromomethyl)-5-(1-methyl-3-(trifluoromethyl)-1H-pyrazol-4-yl)-2-(1-(4-methoxypyridin-2-yl)ethyl)-3,4-dihydroisoquinolin-1(2H)-one The title compound was prepared from the synthetic sequence described in Intermediates 15-18 substituting (5)-1-(4-methoxypyridin-2-yl)ethan-1-amine for (4-methoxypyridin-2-yl)methanamine in Intermediate 15.

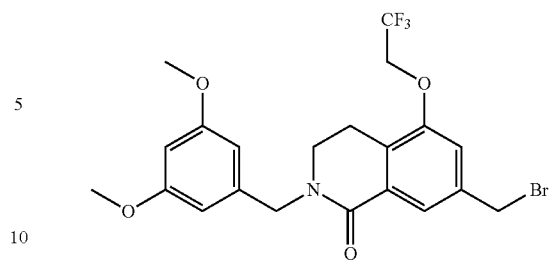

Intermediate 67

7-(Bromomethyl)-2-(3,5-dimethoxybenzyl)-5-(2,2,2-trifluoroethoxy)-3,4-dihydroisoquinolin-1(2H)-one Step A. Preparation of methyl 2-(3,5-dimethoxybenzyl)-1-oxo-5-(2,2,2-trifluoroethoxy)-1,2,3,4-tetrahydroisoquinoline-7-carboxylate. To a solution of methyl 2-(3,5-dimethoxybenzyl)-5-hydroxy-1-oxo-1,2,3,4-tetrahydroisoquinoline-7-carboxylate (0.4 g, 1.1 mmol) in 5 mL of DMF was added cesium carbonate (1.4 g, 4.3 mmol) and 2,2,2-trifluoroethyl 4-methylbenzenesulfonate (0.82 g, 3.2 mmol). This was heated at 75° C. for 16 hours. The reaction was diluted with 20 mL of EtOAc and filtered through celite. The filtrate was washed with brine and concentrated to dryness. The residue was purified by silica gel chromatography with a Teledyne ISCO Combi-Flash eluting with 0 to 50% EtOAc in hexanes to provide the title compound (0.14 g, 30% yield). LCMS method 1: R$_T$=1.78 min, MS (ES) 453.9 (M+H).

Step B. Preparation of 7-(bromomethyl)-2-(3,5-dimethoxybenzyl)-5-(2,2,2-trifluoroethoxy)-3,4-dihydroisoquinolin-1(2H)-one. The title compound (84 mg, 0.17 mmol) was prepared following the synthetic sequence described in Intermediates 35 and 36 using methyl 2-(3,5-dimethoxybenzyl)-1-oxo-5-(2,2,2-trifluoroethoxy)-1,2,3,4-tetrahydroisoquinoline-7-carboxylate. LCMS method 1: R$_T$=1.58 min, MS (ES) 426.0 [M+H]$^+$.

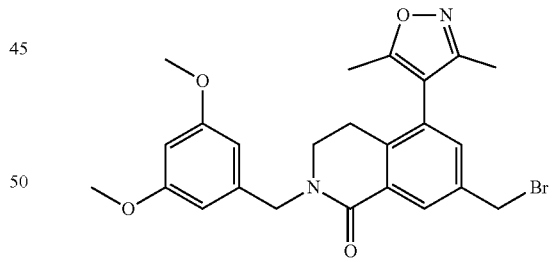

Intermediate 68

7-(Bromomethyl)-2-(3,5-dimethoxybenzyl)-5-(3,5-dimethylisoxazol-4-yl)-3,4-dihydroisoquinolin-1(2H)-one Step A. Preparation of 2-(3,5-dimethoxybenzyl)-5-hydroxy-7-(hydroxymethyl)-3,4-dihydroisoquinolin-1(2H)-one. To a solution of methyl 2-(3,5-dimethoxybenzyl)-5-hydroxy-1-oxo-1,2,3,4-tetrahydroisoquinoline-7-carboxylate (0.3 g, 0.81 mmol) in 5 mL of THF was added lithium borohydride solution (2.0 M) (4 mL, 8.1 mmol). The reaction was refluxed for 24 hours. The reaction was concentrated to dryness. The residue was diluted with EtOAc and water. The organic layer was concentrated to dryness to give the title compound (0.14 g, 0.42 mmol). LCMS method 1: $R_T$=1.23 min, MS (ES) 344.1 [M+H]$^+$.

Step B. Preparation of 7-(((tert-butyldiphenylsilyl)oxy)methyl)-2-(3,5-dimethoxybenzyl)-5-hydroxy-3,4-dihydroisoquinolin-1(2H)-one. To a solution of 2-(3,5-dimethoxybenzyl)-5-hydroxy-7-(hydroxymethyl)-3,4-dihydroisoquinolin-1(2H)-one (0.14 g, 0.42 mmol) in 10 mL of THF was added tert-butylchlorodiphenylsilane (0.26 mL, 1.0 mmol), triethylamine (0.087 mL, 0.62 mmol) and N,N-dimethylpyridin-4-amine (10 mg, 0.08 mmol). The reaction was stirred for 48 hours. The reaction was concentrated and the residue was purified by flash chromatography (Combi-flash Rf, Hex/EtOAc=0-40% gradient) to afford the title compound (0.14 g, 57% yield). LCMS method 1: $R_T$=2.27 min, MS (ES) 582.0 [M+H]$^+$.

Step C. Preparation of 7-(((tert-butyldiphenylsilyl)oxy)methyl)-2-(3,5-dimethoxybenzyl)-1-oxo-1,2,3,4-tetrahydroisoquinolin-5-yl trifluoromethanesulfonate. The title compound (0.39 g, 0.84 mmol) was prepared from 7-(((tert-butyldiphenylsilyl)oxy)methyl)-2-(3,5-dimethoxybenzyl)-5-hydroxy-3,4-dihydroisoquinolin-1(2H)-one following the procedures described in Intermediate 16 Step A. LCMS method 2: $R_T$=2.12 min, MS (ES) 713.8 [M+H]$^+$.

Step D. Preparation of 7-(((tert-butyldiphenylsilyl)oxy)methyl)-2-(3,5-dimethoxybenzyl)-5-(3,5-dimethylisoxazol-4-yl)-3,4-dihydroisoquinolin-1(2H)-one. The title compound (95 mg, 0.14 mmol) was prepared from 7-(((tert-butyldiphenylsilyl)oxy)methyl)-2-(3,5-dimethoxybenzyl)-1-oxo-1,2,3,4-tetrahydroisoquinolin-5-yl trifluoromethanesulfonate (140 mg, 0.19 mmol) and (3,5-dimethylisoxazol-4-yl)boronic acid (36 mg, 0.25 mmol) following the procedure described in Intermediate 16 Step B. LCMS method 2: $R_T$=1.83 min, MS (ES) 660.9 [M+H]$^+$.

Step E. Preparation of 2-(3,5-dimethoxybenzyl)-5-(3,5-dimethylisoxazol-4-yl)-7-(hydroxymethyl)-3,4-dihydroisoquinolin-1(2H)-one. To a solution of 7-(((tert-butyldiphenylsilyl)oxy)methyl)-2-(3,5-dimethoxybenzyl)-5-(3,5-dimethylisoxazol-4-yl)-3,4-dihydroisoquinolin-1(2H)-one (95 mg, 0.14 mmol) in 5 mL of THF was added tetrabutyl ammonium fluoride solution (2.0 M in THF) (0.14 mL, 0.28 mmol). The reaction was stirred for 16 hours at room temperature. The reaction was concentrated and residue was purified by flash chromatography (Combi-flash Rf, Hex/EtOAc=0-100% gradient) to afford the title compound (25 mg, 41% yield). LCMS method 1: $R_T$=1.46 min, MS (ES) 423.0 [M+H]$^+$.

Step F. Preparation of 7-(bromomethyl)-2-(3,5-dimethoxybenzyl)-5-(3,5-dimethylisoxazol-4-yl)-3,4-dihydroisoquinolin-1(2H)-one. The title compound (17 mg, 0.035 mmol) was prepared from 2-(3,5-dimethoxybenzyl)-5-(3,5-dimethylisoxazol-4-yl)-7-(hydroxymethyl)-3,4-dihydroisoquinolin-1(2H)-one (25 mg, 0.06 mmol) following the procedure described in Intermediate 36. LCMS method 1: $R_T$=1.77 min, MS (ES) 497.8 [M+H]$^+$.

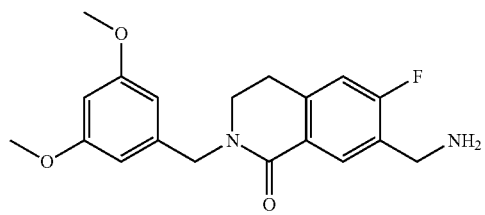 [SMILES: COc1cc(CN2CCc3cc(F)c(CN)cc3C2=O)cc(OC)c1]

Intermediate 69

7-(Aminomethyl)-2-(3,5-dimethoxybenzyl)-6-fluoro-3,4-dihydroisoquinolin-1(2H)-one Step A. Preparation of 7-(azidomethyl)-2-(3,5-dimethoxybenzyl)-6-fluoro-3,4-dihydroisoquinolin-1(2H)-one. To a solution of 7-(bromomethyl)-2-(3,5-dimethoxybenzyl)-6-fluoro-3,4-dihydroisoquinolin-1(2H)-one (79 mg, 0.19 mmol) in DMF (1 mL) was added NaN$_3$ (70 mg, 1.07 mmol). The resulting mixture was stirred at 60° C. for 2 h, and then diluted with EtOAc, washed with water/brine, dried (Na$_2$SO$_4$), and concentrated to provide the crude title compound, which was used in the next step without further purification. LC-MS: >95% 254 nm, $R_T$=1.14 min, MS (ES) 371 [M+H]$^+$.

Step B. Preparation of 7-(aminomethyl)-2-(3,5-dimethoxybenzyl)-6-fluoro-3,4-dihydroisoquinolin-1(2H)-one. To a solution of 7-(azidomethyl)-2-(3,5-dimethoxybenzyl)-6-fluoro-3,4-dihydroisoquinolin-1(2H)-one (0.19 mmol) in THF (2 mL) was added water (4 drops) and PPh$_3$ (100 mg, 0.38 mmol). After stirring at room temperature overnight, Na$_2$SO$_4$ was added. The mixture was filtered and the filtrate was concentrated. The residue was purified on ISCO (0-15% EtOAc in hexane) to provide the desired product (56 mg, 84%, over two steps): $^1$H NMR (400 MHz, CDCl$_3$) δ 8.11 (d, J=4.0 Hz, 1H), 6.84 (d, J=10.0 Hz, 1H), 6.46 (d, J=2.4 Hz, 2H), 6.37 (m, 1H), 4.72 9s, 2H), 3.92 (s, 2H), 3.77 (s, 6H), 4.80 (t, J=6.8 Hz, 2H), 2.91 (t, J=6.8 Hz, 2H).

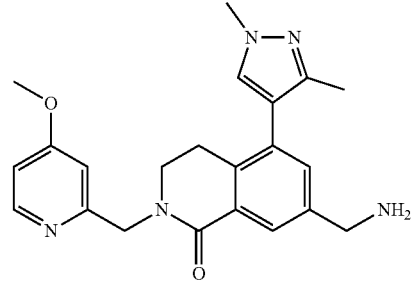 [SMILES: COc1ccnc(CN2CCc3c(cc(CN)cc3-c3cn(C)nc3C)C2=O)c1]

Intermediate 70

7-(Aminomethyl)-5-(1,3-dimethyl-1H-pyrazol-4-yl)-2-((4-methoxypyridin-2-yl)methyl)-3,4-dihydroisoquinolin-1(2H)-one Step A. Preparation of 7-(bromomethyl)-5-(1,3-dimethyl-1H-pyrazol-4-yl)-2-((4-methoxypyridin-2-yl)methyl)-3,4-dihydroisoquinolin-1(2H)-one. The title compound was prepared from the synthetic sequence described in Intermediates 16-18 substituting (1-methyl-3-(methyl)-1H-pyrazol-4-yl)boronic acid for (1-methyl-3-(trifluoromethyl)-1H-pyrazol-4-yl)boronic acid in Intermediate 16, Step B.

Step B. Preparation of 7-(azidomethyl)-5-(1,3-dimethyl-1H-pyrazol-4-yl)-2-((4-methoxypyridin-2-yl)methyl)-3,4-dihydroisoquinolin-1(2H)-one. Sodium azide (21 mg, 0.3 mmol) was added to a solution of 7-(bromomethyl)-5-(1,3-dimethyl-1H-pyrazol-4-yl)-2-((4-methoxypyridin-2-yl)methyl)-3,4-dihydroisoquinolin-1(2H)-one (100 mg, 0.22 mmol) in 4.5 mL of methanol and 0.5 mL of water. This was stirred at RT for 16 hours. The reaction was concentrated and the crude product was partitioned between water and DCM. The layers were separated and the organic layer was concentrated to dryness to provide the title compound (54 mg, 59% yield). LCMS method 1: $R_T$=1.0 min, MS (ES) 418.0 [M+H]+.

Step C. 7-(aminomethyl)-5-(1,3-dimethyl-1H-pyrazol-4-yl)-2-((4-methoxypyridin-2-yl)methyl)-3,4-dihydroisoquinolin-1(2H)-one. 10% Palladium on Carbon (10 mol %) was added to a solution of 7-(azidomethyl)-5-(1,3-dimethyl-1H-pyrazol-4-yl)-2-((4-methoxypyridin-2-yl)methyl)-3,4-dihydroisoquinolin-1(2H)-one (54 mg, 0.13 mmol) in 5 mL of methanol. The reaction was degassed and placed under a hydrogen balloon atmosphere. The reaction was stirred for 30 minutes when the catalyst was filtered off and the solution was concentrated to dryness to provide the title compound (50 mg, 98% yield).

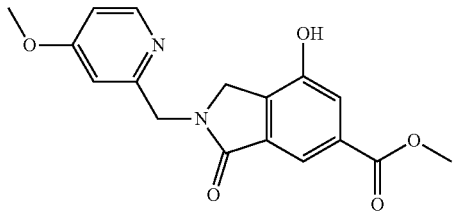

Intermediate 71

Methyl 7-hydroxy-2-((4-methoxypyridin-2-yl) methyl)-3-oxoisoindoline-5-carboxylate The title compound was isolated as a side product in the synthesis of Intermediate 15. Sodium azide (21 mg, 0.3 mmol) was added to a solution of 7-(azidomethyl)-5-(1,3-dimethyl-1H-pyrazol-4-yl)-2-((4-methoxypyridin-2-yl) methyl)-3,4-dihydroisoquinolin-1(2H)-one (100 mg, 0.22 mmol) in 4.5 mL of methanol and 0.5 mL of water. This was stirred at RT for 16 hours. The reaction was concentrated and the crude product was partitioned between water and DCM. The layers were separated and the organic layer was concentrated to dryness to provide the title compound (54 mg, 59% yield). LCMS method 1: $R_T$=1.0 min, MS (ES) 418.0 [M+H]+.

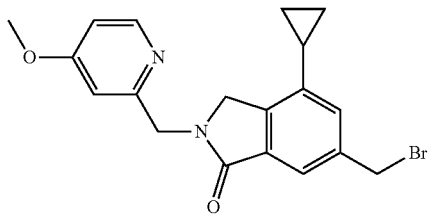 [SMILES: COc1ccnc(CN2Cc3c(cc(CBr)cc3C3CC3)C2=O)c1]

Intermediate 72

6-(Bromomethyl)-4-cyclopropyl-2-((4-methoxypyridin-2-yl)methyl)isoindolin-1-one

The title compound was prepared from the synthetic sequence described in Intermediates 16-18 substituting methyl 7-hydroxy-2-((4-methoxypyridin-2-yl)methyl)-3-oxoisoindoline-5-carboxylate (Intermediate 71) for methyl 5-hydroxy-2-((4-methoxypyridin-2-yl)methyl)-1-oxo-1,2,3,4-tetrahydroisoquinoline-7-carboxylate in Intermediate 16, Step A and cyclopropylboronic acid for (1-methyl-3-(trifluoromethyl)-1H-pyrazol-4-yl)boronic acid in Intermediate 16, Step B.

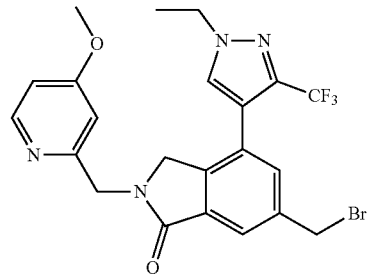 [SMILES: CCn1cc(-c2cc(CBr)cc3c2CN(Cc2cc(OC)ccn2)C3=O)c(C(F)(F)F)n1]

Intermediate 73

6-(Bromomethyl)-4-(1-ethyl-3-(trifluoromethyl)-1H-pyrazol-4-yl)-2-((4-methoxypyridin-2-yl)methyl) isoindolin-1-one The title compound was prepared from the synthetic sequence described in Intermediates 16-18 substituting methyl 7-hydroxy-2-((4-methoxypyridin-2-yl)methyl)-3-oxoisoindoline-5-carboxylate (Intermediate 71) for methyl 5-hydroxy-2-((4-methoxypyridin-2-yl)methyl)-1-oxo-1,2,3,4-tetrahydroisoquinoline-7-carboxylate in Intermediate 16, Step A and (1-ethyl-3-(trifluoromethyl)-1H-pyrazol-4-yl) boronic acid for (1-methyl-3-(trifluoromethyl)-1H-pyrazol-4-yl)boronic acid in Intermediate 16, Step B.

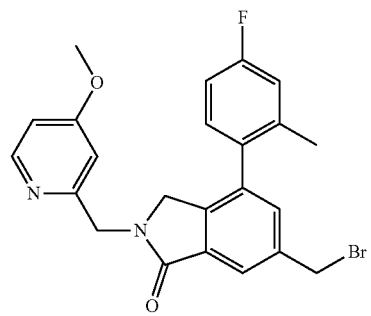 [SMILES: COc1ccnc(CN2Cc3c(cc(CBr)cc3-c3ccc(F)cc3C)C2=O)c1]

Intermediate 74

6-(Bromomethyl)-4-(4-fluoro-2-methylphenyl)-2-((4-methoxypyridin-2-yl)methyl)isoindolin-1-one The title compound was prepared from the synthetic sequence described in Intermediates 16-18 substituting methyl 7-hydroxy-2-((4-methoxypyridin-2-yl)methyl)-3-oxoisoindoline-5-carboxylate (Intermediate 71) for methyl 5-hydroxy-2-((4-methoxypyridin-2-yl)methyl)-1-oxo-1,2,3,4-tetrahydroisoquinoline-7-carboxylate in Intermediate 16, Step A and 4-fluoro-2-methyl phenyl-boronic acid for (1-methyl-3-(trifluoromethyl)-1H-pyrazol-4-yl)boronic acid in Intermediate 16, Step B.

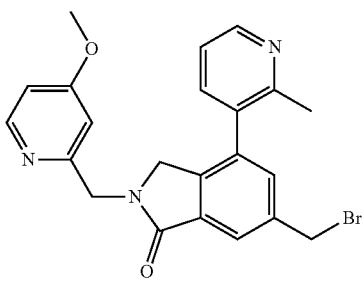 [SMILES: COc1ccnc(CN2Cc3c(cc(CBr)cc3-c3cccnc3C)C2=O)c1]

Intermediate 75

6-(Bromomethyl)-2-((4-methoxypyridin-2-yl)methyl)-4-(2-methylpyridin-3-yl)isoindolin-1-one The title compound was prepared from the synthetic sequence described in Intermediates 16-18 substituting methyl 7-hydroxy-2-((4-methoxypyridin-2-yl)methyl)-3-oxoisoindoline-5-carboxylate (Intermediate 71) for methyl 5-hydroxy-2-((4-methoxypyridin-2-yl)methyl)-1-oxo-1,2,3,4-tetrahydroisoquinoline-7-carboxylate in Intermediate 16, Step A and (2-methyl pyridin-3-yl)boronic acid for (1-methyl-3-(trifluoromethyl)-1H-pyrazol-4-yl)boronic acid in Intermediate 16, Step B.

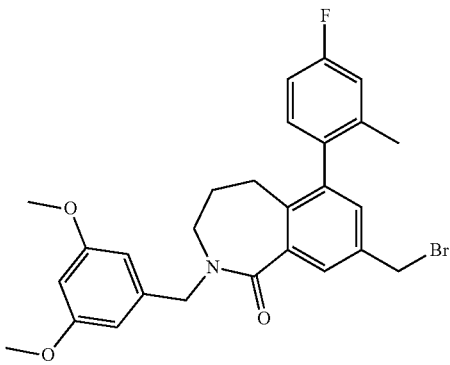 [SMILES: COc1cc(CN2CCCc3c(cc(CBr)cc3-c3ccc(F)cc3C)C2=O)cc(OC)c1]

Intermediate 76

8-(Bromomethyl)-2-(3,5-dimethoxybenzyl)-6-(4-fluoro-2-methylphenyl)-2,3,4,5-tetrahydro-1H-1-benzo[c]azepin-1-one Step A. Preparation of dimethyl 5-(allyloxy)isophthalate. To a solution of dimethyl 5-hydroxyisophthalate (5.5 g, 26.2 mmol) in acetone (100 mL) was added $K_2CO_3$ (10.9 g, 78.6 mmol), and allyl bromide (3.4 mL, 39.3 mmol). The resulting mixture was stirred at room temperature overnight. The mixture was filtered, and the solid was washed with acetone. The combined organic layers were concentrated. The residue was dissolved in EtOAc and washed with water. The organic layer was dried ($Na_2SO_4$) and concentrated to provide the desired product (6.36 g, 97%). $^1H$ NMR (400 MHz, $CDCl_3$) δ 8.29 (s, 1H), 7.78 (s, 2H), 6.05 (m, 1H), 5.45 (dd, J=1.2, 17.2 Hz, 1H), 5.33 (dd, J=1.2, 10.4 Hz, 1H), 4.63 (m, 2H), 3.95 (s, 6H).

Step B. Preparation of dimethyl 4-allyl-5-hydroxyisophthalate. Dimethyl 5-(allyloxy)isophthalate (6.1 g, 24.4 mmol) was heated in a sealed tube at 205° C. for 20 h, then cooled to room temperature to provide the desired product (6.03 g, quantitative), which was pure enough to use in the next step. $^1H$ NMR (400 MHz, $CDCl_3$) δ 8.12 (d, J=1.6 Hz, 1H), 7.68 (d, J=1.6 Hz, 1H), 6.02 (m, 1H), 5.52 (s, 1H), 5.13 (m 2H), 3.93 (s, 3H), 3.92 (s, 3H), 3.83 (m, 2H).

Step C. Preparation of dimethyl 5-hydroxy-4-(3-hydroxypropyl)isophthalate. To a solution of dimethyl 4-allyl-5-hydroxyisophthalate (0.74 g, 2.96 mmol) in THF (15 mL) was added 1 M $BH_3$ (6 mL, 6 mmol) in THF at 0° C. The reaction was stirred for 3.5 h, then 30% $H_2O_2$ (6.8 mL, 59 mmol) was added followed by addition of $NaHCO_3$ (sat.) (15 mL). The resulting mixture was allowed to warm to room temperature and stirred overnight. The mixture was extracted with EtOAc. The combined organic layers were dried ($Na_2SO_4$) and concentrated. The residue was purified by flash chromatography (Combi-flash Rf, Hex/EtOAc=0-80% gradient) to afford the title compound (700 mg, 87%). $^1H$ NMR (400 MHz, $CDCl_3$) δ 8.12 (d, J=1.6 Hz, 1H), 7.76 (brs, 1H), 7.70 (s, 1H), 4.14 (s, 3H), 4.12 (s, 3H), 3.66 (m, 2H), 3.14 (t, J=6.8 Hz, 2H), 2.35 (brs, 1H), 2.05 (m, 2H).

Step D. Preparation of dimethyl 5-(benzyloxy)-4-(3-hydroxypropyl)isophthalate. To a solution of dimethyl 5-hydroxy-4-(3-hydroxypropyl)isophthalate (0.7 g, 2.6 mmol) in acetone (26 mL) was added benzyl bromide (371 μL, 3.12 mmol), $K_2CO_3$ (1.08 g, 7.8 mmol). The resulting mixture was stirred at room temperature overnight, and then filtered. The filtrate was concentrated and the residue was taken up in EtOAc. After washing with water, the organic layer was dried ($Na_2SO_4$), concentrated. The residue was purified by flash chromatography (Combi-flash Rf, Hex/EtOAc=0-60% gradient) to afford the title compound (640 mg, 68%). $^1H$ NMR (400 MHz, $CDCl_3$) δ 8.14 (s, 1H), 7.75 (s, 1H), 7.43 (m, 5H), 5.16 (s, 2H), 3.94 (s, 3H), 3.93 (s, 3H), 3.56 (q, J=6.0 Hz, 2H), 3.15 (t, J=7.2 Hz, 2H), 1.92 (p, J=6.0 Hz, 2H).

Step E. Preparation of dimethyl 5-(benzyloxy)-4-(3-oxopropyl)isophthalate. To a solution of dimethyl 5-(benzyloxy)-4-(3-hydroxypropyl)isophthalate (556 mg, 1.55 mmol) in $CH_2Cl_2$ (12 mL) was added Dess-Martin Periodinane (988 mg, 2.33 mmol). The resulting mixture was stirred at room temperature overnight. The mixture was diluted with EtOAc, and then washed with $NaS_2O_3$ (sat.), $NaHCO_3$ (sat.). The organic layer was dried ($Na_2SO_4$) and concentrated. The residue was purified by flash chromatography (Combi-flash Rf, Hex/EtOAc=0-70% gradient) to afford the title compound (390 mg, 71%). $^1H$ NMR (400 MHz, $CDCl_3$) δ 9.79 (s, 1H), 8.14 (s, 1H), 7.75 (s, 1H), 7.41 (m, 5H), 5.16 (s, 2H), 3.94 (s, 3H), 3.92 (s, 3H), 3.34 (t, J=7.6 Hz, 2H), 2.75 (t, J=7.6 Hz, 2H).

Step F. Preparation of dimethyl 5-(benzyloxy)-4-(3-((3,5-dimethoxybenzyl)amino)propyl)isophthalate. To a solution of dimethyl 5-(benzyloxy)-4-(3-oxopropyl)isophthalate (390 mg, 1.1 mmol) in $CH_2Cl_2$ (10 mL) was added 3,5-dimethoxybenzylamine (219 mg, 1.31 mmol), $NaBH(OAc)_3$ (348 mg, 1.64 mmol). The resulting mixture was stirred at room temperature overnight. The mixture was diluted with EtOAc and washed with $NaHCO_3$ (sat.). The organic layer was dried ($Na_2SO_4$) and concentrated. The residue was purified by flash chromatography (Combi-flash Rf, Hex/EtOAc=0-90% gradient) to afford the title compound (290 mg, 52%). $^1H$ NMR (400 MHz, $CDCl_3$) δ 8.11 (s, 1H), 8.72 (s, 1H), 7.44 (d, J=6.8 Hz, 2H), 7.33 (m, 3H), 6.47 (d, J=2.4 Hz, 2H), 6.35 (m, 1H), 5.15 (s, 2H), 3.93 (s, 3H), 3.90 (s, 3H), 3.80 (s, 6H), 3.10 (m, 2H), 2.69 (t, J=7.2 Hz, 2H), 1.82 (m, 2H).

Step G. Preparation of methyl 6-(benzyloxy)-2-(3,5-dimethoxybenzyl)-1-oxo-2,3,4,5-tetrahydro-1H-benzo[c]azepine-8-carboxylate. To a solution of dimethyl 5-(benzyloxy)-4-(3-((3,5-dimethoxybenzyl)amino)propyl)isophthalate (190 mg, 0.37 mmol) in 1,4-dioxane (10 mL) was added DBU (110.5 L, 0.74 mmol). The mixture was heated in a sealed tube at 115° C. overnight. The solvent was removed under reduced pressure and the residue was taken up in EtOAc. After washing with 1 M HCl, The organic layer was dried ($Na_2SO_4$) and concentrated. The residue was purified by flash chromatography (Combi-flash Rf, Hex/EtOAc=0-90% gradient) to afford the title compound (94 mg, 54%). $^1$H NMR (400 MHz, $CDCl_3$) δ 8.03 (s, 1H), 7.72 (s, 1H), 7.37 (m, 5H), 6.53 (d, J=2.4 Hz, 2H), 6.39 (m, 1H), 5.13 (s, 2H), 4.73 (s, 2H), 3.94 (s, 3H), 3.80 (s, 6H), 3.16 (t, J=6.0 Hz, 2H), 2.93 (t, J=6.0 Hz, 2H), 1.77 9m, 2H).

Step H. Preparation of methyl 2-(3,5-dimethoxybenzyl)-6-hydroxy-1-oxo-2,3,4,5-tetrahydro-1H-benzo[c]azepine-8-carboxylate. A mixture of methyl 6-(benzyloxy)-2-(3,5-dimethoxybenzyl)-1-oxo-2,3,4,5-tetrahydro-1H-benzo[c]azepine-8-carboxylate (94 mg, 0.2 mmol) and Pd/C (12 mg, 0.011 mmol) in MeOH (2 mL) was stirred at room temperature under 1 atm hydrogen gas atmosphere overnight. The mixture was filtered and the filtrate was concentrated to provide the desired product (80 mg, quantitative). $^1$H NMR (400 MHz, $CDCl_3$) δ 7.87 (s, 1H), 7.57 (s, 1H), 6.52 (d, J=2.4 Hz, 2H), 6.39 (m, 1H), 4.73 (s, 2H), 3.87 (s, 3H), 3.82 (s, 6H), 3.16 (t, J=6.4 Hz, 2H), 2.83 (t, J=6.4 Hz, 2H), 1.77 (m, 2H).

Step I. Preparation of methyl 2-(3,5-dimethoxybenzyl)-1-oxo-6-(((trifluoromethyl)sulfonyl)oxy)-2,3,4,5-tetrahydro-1H-benzo[c]azepine-8-carboxylate. To a solution of methyl 2-(3,5-dimethoxybenzyl)-6-hydroxy-1-oxo-2,3,4,5-tetrahydro-1H-benzo[c]azepine-8-carboxylate (80 mg, 0.2 mmol) in $CH_2Cl_2$ (3 mL) was added N-phenyl-bis(trifluoromethanesulfonimide) (90 mg, 0.25 mmol), Diisopropylethylamine (54 μL, 0.31 mmol). The resulting mixture was stirred at room temperature overnight. The mixture was diluted with EtOAc and washed with water. The organic layer was dried ($Na_2SO_4$) and concentrated. The residue was purified by flash chromatography (Combi-flash Rf, Hex/EtOAc=0-60% gradient) to afford the title compound (98 mg, quantitative). $^1$H NMR (400 MHz, $CDCl_3$) δ 8.42 (s, 1H), 7.99 (s, 1H), 6.52 (d, J=2.04 Hz, 2H), 6.41 (m, 1H), 4.73 (s, 2H), 3.97 (s, 3H), 3.77 (s, 6H), 3.22 (t, J=6.4 Hz, 2H), 2.91 (t, J=6.4 Hz, 2H), 1.91 (m., 2H).

Step J. Preparation of methyl 2-(3,5-dimethoxybenzyl)-6-(4-fluoro-2-methylphenyl)-1-oxo-2,3,4,5-tetrahydro-1H-benzo[c]azepine-8-carboxylate. To a solution of methyl 2-(3,5-dimethoxybenzyl)-1-oxo-6-(((trifluoromethyl)sulfonyl)oxy)-2,3,4,5-tetrahydro-1H-benzo[c]azepine-8-carboxylate (96 mg, 0.19 mmol) in 1,4-dioxane (3 mL) was added (4-fluoro-2-methylphenyl)boronic acid (45 mg, 0.29 mmol), $Na_2CO_3$ (51 mg, 0.48 mmol), water (0.3 mL), and Pd(PPh$_3$)$_4$ (13.2 mg, 0.011 mmol). The resulting mixture was heated at 80° C. overnight, and then diluted with EtOAc and washed with water. The organic layer was dried ($Na_2SO_4$) and concentrated. The residue was purified by flash chromatography (Combi-flash Rf, Hex/EtOAc=0-70% gradient) to afford the title compound (90 mg, quantitative). $^1$H NMR (400 MHz, $CDCl_3$) δ 8.39 (s, 1H), 7.89 (s, 1H), 6.99 (m, 2H), 6.91 (m, 1H), 6.52 (s, 2H), 6.38 (m, 1H), 4.74 (m, 2H), 3.93 (s, 3H), 3.77 (s, 6H), 3.21 (m, 2H), 2.51 (m, 2H), 2.63 (m, 2H).

Step K. Preparation of 2-(3,5-dimethoxybenzyl)-6-(4-fluoro-2-methylphenyl)-8-(hydroxymethyl)-2,3,4,5-tetrahydro-1H-benzo[c]azepin-1-one. To a solution of methyl 2-(3,5-dimethoxybenzyl)-6-(4-fluoro-2-methylphenyl)-1-oxo-2,3,4,5-tetrahydro-1H-benzo[c]azepine-8-carboxylate (90 mg, 0.19 mmol) in THF (4 mL) was added 2 M LiBH$_4$ in THF (360 μL, 0.72 mmol). The reaction mixture was stirred at room temperature overnight, and then quenched with 0.5 M HCl. The resulting mixture was extracted with EtOAc. The combined organic layers were washed with NaHCO$_3$ (sat.), dried ($Na_2SO_4$), and concentrated. The residue was purified by flash chromatography (Combi-flash Rf, Hex/EtOAc=0-70% gradient) to afford the title compound (91 mg, quantitative, used without further purification). $^1$H NMR (400 MHz, $CDCl_3$) δ 7.72 (s, 1H), 7.23 (s, 1H), 6.98 (m, 2H), 6.90 (m, 1H), 6.52 (d, J=2.0 Hz, 2H), 6.38 (m, 1H), 4.72 (m, 4H), 3.78 (s, 6H), 3.21 (m, 2H), 2.50 (m, 2H), 2.00 (s, 3H), 1.60 (m, 2H).

Step L. Preparation of 8-(bromomethyl)-2-(3,5-dimethoxybenzyl)-6-(4-fluoro-2-methylphenyl)-2,3,4,5-tetrahydro-11/-benzo[c]azepin-1-one. To a solution of 2-(3,5-dimethoxybenzyl)-6-(4-fluoro-2-methylphenyl)-8-(hydroxymethyl)-2,3,4,5-tetrahydro-1H-benzo[c]azepin-1-one (92 mg crude, 0.19 mmol) in $CH_2Cl_2$ (3 mL) at 0° C. was added 1 M PBr$_3$ in $CH_2Cl_2$ (480 μL, 0.48 mmol). The mixture was stirred at this temperature overnight. After quenching with NaHCO$_3$, the resulting mixture was extracted with Et$_2$O. The combined organic layers were dried ($Na_2SO_4$) and concentrated to provide the crude desired product (105 mg, quantitative, used without further purification). LC-MS, >95% (254 nm), R$_T$=1.47 min, m/z=512 [M+Na].

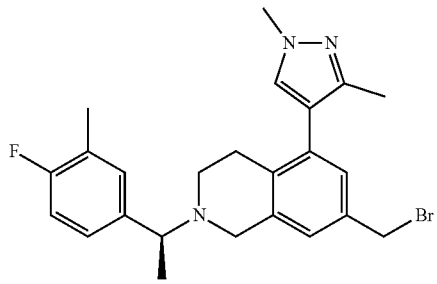 [SMILES: Cc1cc([C@H](C)N2CCc3c(cc(CBr)cc3-c3cn(C)nc3C)C2)ccc1F]

Intermediate 77

(S)-7-(bromomethyl)-5-(1,3-dimethyl-1H-pyrazol-4-yl)-2-(1-(4-fluoro-3-methylphenyl)ethyl)-3,4-dihydroisoquinolin-1(2H)-one The title compound was prepared from the synthetic sequence described in Intermediates 15-18 substituting (S)-1-(4-fluoro-3-methyl phenyl)ethan-1-amine for (4-methoxypyridin-2-yl)methanamine in Intermediate 15 and (1-methyl-3-(methyl)-1H-pyrazol-4-yl)boronic acid for (1-methyl-3-(trifluoromethyl)-1H-pyrazol-4-yl)boronic acid in Intermediate 16 step B.

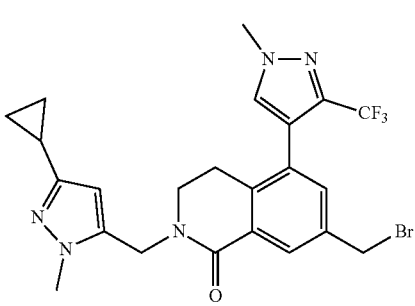 [SMILES: Cn1cc(-c2cc(CBr)cc3c2CCN(Cc2cc(C4CC4)nn2C)C3=O)c(C(F)(F)F)n1]

Intermediate 78

7-(Bromomethyl)-2-((3-cyclopropyl-1-methyl-1H-pyrazol-5-yl)methyl)-5-(1-methyl-3-(trifluoromethyl)-1H-pyrazol-4-yl)-3,4-dihydroisoquinolin-1(2H)-one The title compound was prepared following the synthetic sequence described in Intermediates 15-18 substituting (3-cyclopropyl-1-methyl-1H-pyrazol-5-yl)methanamine for (4-methoxypyridin-2-yl)methanamine in Intermediate 15.

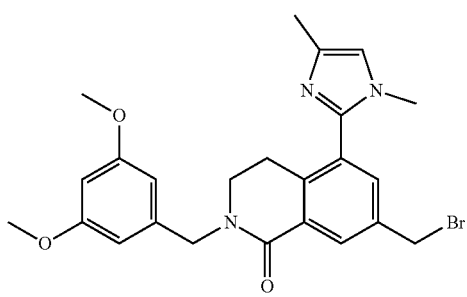 [SMILES: COc1cc(CN2CCc3c(cc(CBr)cc3-c3nc(C)cn3C)C2=O)cc(OC)c1]

Intermediate 79

7-(Bromomethyl)-2-(3,5-dimethoxybenzyl)-5-(1,4-dimethyl-1H-imidazol-2-yl)-3,4-dihydroisoquinolin-1(2H)-one Step A. Preparation of 7-chloro-2-(3,5-dimethoxybenzyl)-5-(1,4-dimethyl-1H-imidazol-2-yl)-3,4-dihydroisoquinolin-1(2H)-one. To a mixture of 7-chloro-2-(3,5-dimethoxybenzyl)-5-(4,4,5,5-tetramethyl-1,3,2-dioxaborolan-2-yl)-3,4-dihydroisoquinolin-1(2H)-one (Intermediate 25, 192 mg, 0.42 mmol), 2-bromo-1,4-dimethyl-1H-imidazole (88 mg, 0.5 mmol), $K_2CO_3$ (116 mg, 0.84 mmol), and toluene (6 mL)/water (0.5 mL) was added 4-(di-tert-butylphosphino)-N,N-dimethylaniline-dichloropalladium (9 mg, 0.013 mmol). The resulting mixture was degassed and back filled with Argon, and heated at 110° C. overnight. The solvent was removed under reduced pressure. The residue was purified by flash chromatography (Combi-flash Rf, Hex/EtOAc=10-100% gradient) to afford the title compound (94 mg, 52%). $^1$H NMR (400 MHz, CDCl$_3$) δ 8.22 (s, 1H), 7.44 (s, 1H), 6.69 (s, 1H), 6.45 (d, J=2.0 Hz, 2H), 6.37 (m, 1H), 4.71 (s, 2H), 3.77 (s, 6H), 3.47 (s, 3H), 3.42 (t, J=6.4 Hz, 2H), 2.85 (t, J=6.4 Hz, 2H), 2.23 (s, 3H).

Step B. Preparation of 7-(bromomethyl)-2-(3,5-dimethoxybenzyl)-5-(1,4-dimethyl-1H-imidazol-2-yl)-3,4-dihydroisoquinolin-1(2H)-one. The title compound (135 mg) was prepared from the procedure described in Intermediate 23, Step A-C substituting 7-chloro-2-(3,5-dimethoxybenzyl)-5-(1,4-dimethyl-1H-imidazol-2-yl)-3,4-dihydroisoquinolin-1(2H)-one for (S)-7-chloro-2-(cyclopropyl (4-fluoro-3-methylphenyl)methyl)-5-(2-(trifluoromethyl)pyridin-3-yl)-3,4-dihydroisoquinolin-1(2H)-one. LC-MS: >92% (254 nm), $R_T$=0.91 min, MS (ES) 484 [M+H]$^+$.

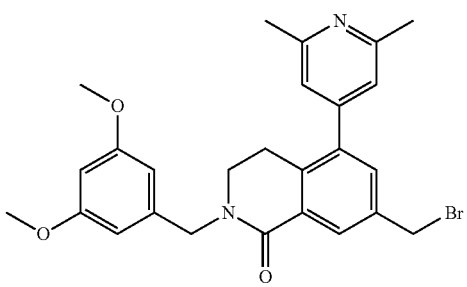 [SMILES: COc1cc(CN2CCc3c(cc(CBr)cc3-c3cc(C)nc(C)c3)C2=O)cc(OC)c1]

Intermediate 80

7-(Bromomethyl)-2-(3,5-dimethoxybenzyl)-5-(2,6-dimethylpyridin-4-yl)-3,4-dihydroisoquinolin-1(2H)-one The title compound was prepared following the synthetic sequence described in Intermediates 22 and 23 using 7-chloro-2-(3,5-dimethoxybenzyl)-5-(4,4,5,5-tetramethyl-1,3,2-dioxaborolan-2-yl)-3,4-dihydroisoquinolin-1(2H)-one (Intermediate 25) and 4-bromo-2,6-dimethylpyridine in Intermediate 22. LC-MS, >74% (254 nm), $R_T$=0.96 min, MS (ES) 495 [M+H]$^+$.

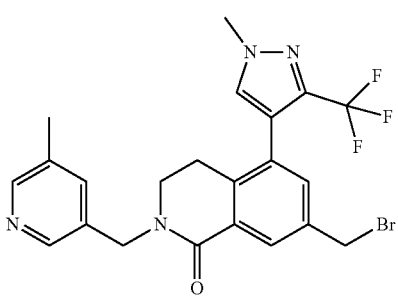 [SMILES: Cc1cncc(CN2CCc3c(cc(CBr)cc3-c3cn(C)nc3C(F)(F)F)C2=O)c1]

Intermediate 81

7-(Bromomethyl)-5-(1-methyl-3-(trifluoromethyl)-1H-pyrazol-4-yl)-2-((5-methylpyridin-3-yl)methyl)-3,4-dihydroisoquinolin-1(2H)-one The title compound was prepared following the synthetic sequence described in Intermediates 15-18 substituting (5-methylpyridin-3-yl)methanamine for (4-methoxypyridin-2-yl)methanamine in Intermediate 15. LCMS: $R_T$=1.327 min, MS (ES) 494.3 [M+H]$^+$.

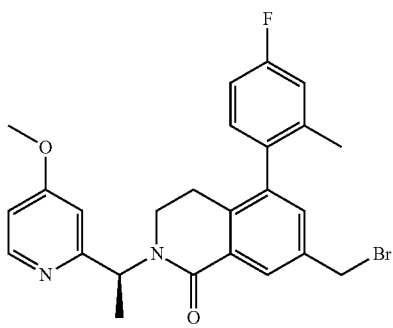 [SMILES: COc1ccnc([C@H](C)N2CCc3c(cc(CBr)cc3-c3ccc(F)cc3C)C2=O)c1]

Intermediate 82

(S)-7-(bromomethyl)-5-(4-fluoro-2-methylphenyl)-2-(1-(4-methoxypyridin-2-yl)ethyl)-3,4-dihydroisoquinolin-1(2H)-one The title compound was prepared from the synthetic sequence described in Intermediates 15-18 substituting (S)-1-(4-methoxypyridin-2-yl)ethan-1-amine for (4-methoxypyridin-2-yl)methanamine in Intermediate 15 and substituting (4-fluoro-2-methylphenyl)boronic acid for (1-methyl-3-(trifluoromethyl)-1H-pyrazol-4-yl)boronic acid in Intermediate 16 Step B.

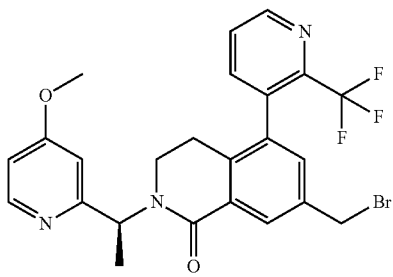 [SMILES: COc1ccnc([C@H](C)N2CCc3c(cc(CBr)cc3-c3cccnc3C(F)(F)F)C2=O)c1]

Intermediate 83

(S)-7-(Bromomethyl)-2-(1-(4-methoxypyridin-2-yl)ethyl)-5-(2-(trifluoromethyl)pyridin-3-yl)-3,4-dihydroisoquinolin-1(2H)-one The title compound was prepared from the synthetic sequence described in Intermediates 15, 16 Step A, 22, 17, and 18 substituting (S)-1-(4-methoxypyridin-2-yl)ethan-1-amine for (4-methoxypyridin-2-yl)methanamine in Intermediate 15 and substituting 3-bromo-2-(trifluoromethyl)pyridine for (1-methyl-3-(trifluoromethyl)-1H-pyrazol-4-yl)boronic acid in Intermediate 22.

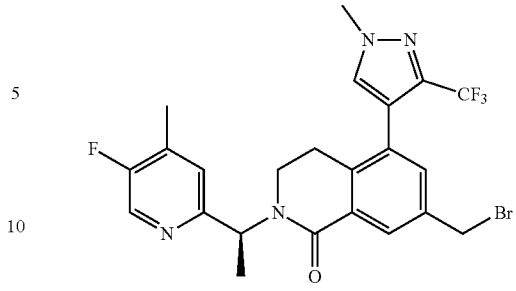

Intermediate 84

(S)-7-(Bromomethyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one The title compound was prepared from the synthetic sequence described in Intermediates 15-18 substituting (5)-1-(5-fluoro-4-methylpyridin-2-yl)ethan-1-amine for (4-methoxypyridin-2-yl)methanamine in Intermediate 15. LCMS: $R_T$=1.421 min, MS (ES) 522.4 [M+H]$^+$.

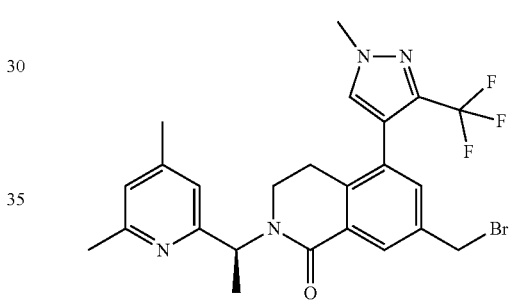

Intermediate 85

(S)-7-(Bromomethyl)-2-(1-(4,6-dimethylpyridin-2-yl)ethyl)-5-(1-methyl-3-(trifluoromethyl)-1H-pyrazol-4-yl)-3,4-dihydroisoquinolin-1(2H)-one The title compound was prepared from the synthetic sequence described in Intermediates 15-18 substituting (5)-1-(4,6-dimethylpyridin-2-yl)ethan-1-amine for (4-methoxypyridin-2-yl)methanamine in Intermediate 15. LCMS: $R_T$=1.850 min, MS (ES) 526.4 [M+H]$^+$.

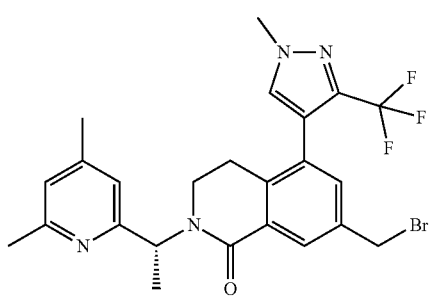 [SMILES: Cc1cc(C)nc([C@@H](C)N2CCc3c(cc(CBr)cc3-c3cn(C)nc3C(F)(F)F)C2=O)c1]

Intermediate 86

(R)-7-(Bromomethyl)-2-(1-(4,6-dimethylpyridin-2-yl)ethyl)-5-(1-methyl-3-(trifluoromethyl)-1H-pyrazol-4-yl)-3,4-dihydroisoquinolin-1(2H)-one The title compound was prepared from the synthetic sequence described in Intermediates 15-18 substituting (R)-1-(4,6-dimethylpyridin-2-yl)ethan-1-amine for (4-methoxypyridin-2-yl)methanamine in Intermediate 15. LCMS: $R_T$=1.415 min, MS (ES) 522.4 [M+H]$^+$.

Intermediate 87

7-((2-Methyl-1H-imidazol-1-yl)methyl)-5-(1-methyl-3-(trifluoromethyl)-1H-pyrazol-4-yl)-3,4-dihydroisoquinolin-1(2H)-one To a solution of 2-(2,4-dimethoxybenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 10, 180 mg, 0.334 mmol, 1.0 equiv.) in DCM (0.45 mL) was added anisole (0.18 mL, 1.67 mmol, 5.0 equiv.) and TFA (0.9 mL). The reaction was stirred at room temperature overnight. The solvent was removed under reduced pressure and the residue was taken up in EtOAc (5 mL) and washed with saturated NaHCO$_3$ (5 mL). The organic layer was dried (MgSO$_4$), filtered and concentrated. The residue was purified by flash chromatography (Combi-flash Rf, DCM/MeOH=0-10% gradient) to yield the title compound (77 mg, 59% yield). LCMS: $R_T$=0.993 min, MS (ES) 390.0 [M+H]$^+$.

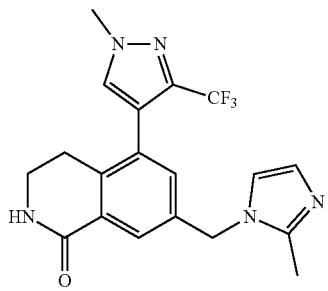 [SMILES: Cc1nccn1Cc1cc2c(c(-c3cn(C)nc3C(F)(F)F)c1)CCNC2=O]

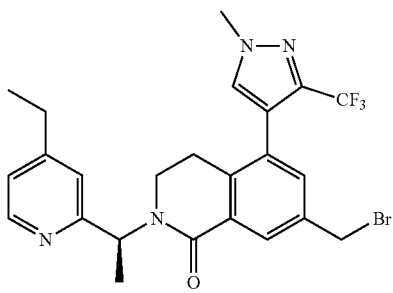 [SMILES: CCc1ccnc([C@H](C)N2CCc3c(cc(CBr)cc3-c3cn(C)nc3C(F)(F)F)C2=O)c1]

Intermediate 88

(S)-7-(Bromomethyl)-2-(1-(4-ethylpyridin-2-yl)ethyl)-5-(1-methyl-3-(trifluoromethyl)-1H-pyrazol-4-yl)-3,4-dihydroisoquinolin-1(2H)-one The title compound was prepared from the synthetic sequence described in Intermediates 15-18 substituting (S)-1-(4-ethylpyridin-2-yl)ethan-1-amine hydrochloride for (4-methoxypyridin-2-yl)methanamine in Intermediate 15. LCMS: $R_T$=1.589 min, MS (ES) 520.9 [M+H]$^+$.

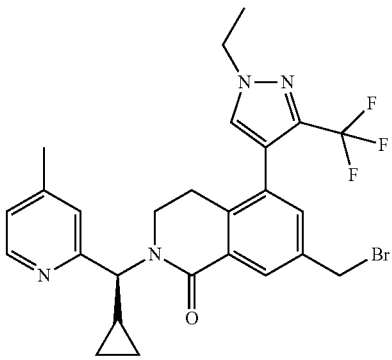 [SMILES: CCn1cc(-c2cc(CBr)cc3c2CCN([C@H](c2cc(C)ccn2)C2CC2)C3=O)c(C(F)(F)F)n1]

Intermediate 89

(S)-7-(Bromomethyl)-2-(cyclopropyl(4-methylpyridin-2-yl)methyl)-5-(1-ethyl-3-(trifluoromethyl)-1H-pyrazol-4-yl)-3,4-dihydroisoquinolin-1(2H)-one The title compound was prepared from the synthetic sequence described in Intermediates 15-18 substituting (S)-cyclopropyl (4-methylpyridin-2-yl)methanamine dihydrochloride for (4-methoxypyridin-2-yl)methanamine in Intermediate 15 and substituting (1-ethyl-3-(trifluoromethyl)-1H-pyrazol-4-yl)boronic acid for (1-methyl-3-(trifluoromethyl)-1H-pyrazol-4-yl)boronic acid in Intermediate 16 Step B.

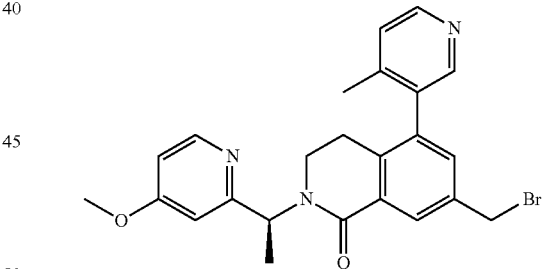

Intermediate 90

(S)-7-(Bromomethyl)-2-(1-(4-methoxypyridin-2-yl)ethyl)-5-(4-methylpyridin-3-yl)-3,4-dihydroisoquinolin-1(2H)-one The title compound was prepared from the synthetic sequence described in Intermediates 15-18 substituting (S)-1-(4-methoxypyridin-2-yl)ethan-1-amine for (4-methoxypyridin-2-yl)methanamine in Intermediate 15 and substituting (4-methylpyridin-3-yl)boronic acid for (1-methyl-3-(trifluoromethyl)-1H-pyrazol-4-yl)boronic acid in Intermediate 16 Step B. LC-MS: MS (ES) 466.4 [M+H]$^+$.

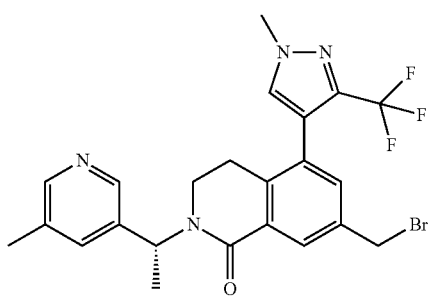 [SMILES: Cc1cncc([C@@H](C)N2CCc3c(cc(CBr)cc3-c3cn(C)nc3C(F)(F)F)C2=O)c1]

Intermediate 91

(R)-7-(Bromomethyl)-5-(1-methyl-3-(trifluoromethyl)-1H-pyrazol-4-yl)-2-(1-(5-methylpyridin-3-yl)ethyl)-3,4-dihydroisoquinolin-1(2H)-one The title compound was prepared from the synthetic sequence described in Intermediates 15-18 substituting (R)-1-(5-methyl pyridin-3-yl)ethan-1-amine for (4-methoxypyridin-2-yl)methanamine in Intermediate 15. LC-MS, >95% (254 nm), $R_T$=1.402 min, MS (ES) 508.4 [M+H]$^+$.

Intermediate 92

(R)-7-(Bromomethyl)-5-(1-methyl-3-(trifluoromethyl)-1H-pyrazol-4-yl)-2-(1-(5-methylpyridin-3-yl)propyl)-3,4-dihydroisoquinolin-1(2H)-one The title compound was prepared from the synthetic sequence described in Intermediates 15-18 substituting (R)-1-(5-methylpyridin-3-yl)propan-1-amine for (4-methoxypyridin-2-yl)methanamine in Intermediate 15. LC-MS, >95% (254 nm), $R_T$=1.446 min, MS (ES) 522.4 [M+H]$^+$.

Intermediate 93

(S)-7-(Bromomethyl)-5-(1-methyl-3-(trifluoromethyl)-1H-pyrazol-4-yl)-2-(1-(5-methylpyridin-3-yl)propyl)-3,4-dihydroisoquinolin-1(2H)-one The title compound was prepared from the synthetic sequence described in intermediates 15-18 substituting (S)-1-(5-methylpyridin-3-yl)propan-1-amine for (4-methoxypyridin-2-yl)methanamine in Intermediate 15. LC-MS, >95% (254 nm), $R_T$=1.439 min, MS (ES) 522.4 [M+H]$^+$.

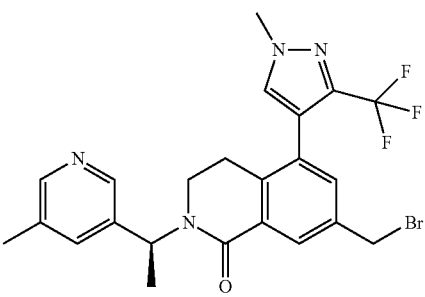 [SMILES: Cc1cncc([C@H](C)N2CCc3c(cc(CBr)cc3-c3cn(C)nc3C(F)(F)F)C2=O)c1]

Intermediate 94

(S)-7-(Bromomethyl)-5-(1-methyl-3-(trifluoromethyl)-1H-pyrazol-4-yl)-2-(1-(5-methylpyridin-3-yl)ethyl)-3,4-dihydroisoquinolin-1(2H)-one The title compound was prepared from the synthetic sequence described in Intermediates 15-18 substituting (5)-1-(5-methylpyridin-3-yl)ethan-1-amine for (4-methoxypyridin-2-yl)methanamine in Intermediate 15. LC-MS, >95% (254 nm), $R_T$=1.402 min, MS (ES) 508.4 [M+H]$^+$.

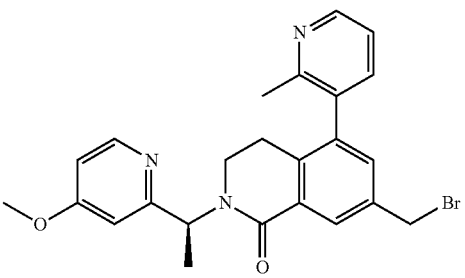 [SMILES: COc1ccnc([C@H](C)N2CCc3c(cc(CBr)cc3-c3cccnc3C)C2=O)c1]

Intermediate 95

(S)-7-(Bromomethyl)-2-(1-(4-methoxypyridin-2-yl)ethyl)-5-(2-methylpyridin-3-yl)-3,4-dihydroisoquinolin-1(2H)-one The title compound was prepared from the synthetic sequence described in Intermediates 15-18 substituting (S)-1-(4-methoxypyridin-2-yl)ethan-1-amine for (4-methoxypyridin-2-yl)methanamine in Intermediate 15 and substituting (4-methylpyridin-3-yl)boronic acid for (1-methyl-3-(trifluoromethyl)-1H-pyrazol-4-yl)boronic acid in Intermediate 16 Step B. LC-MS: MS (ES) 466.4 [M+H]$^+$.

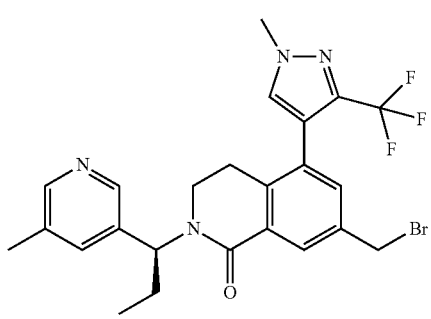

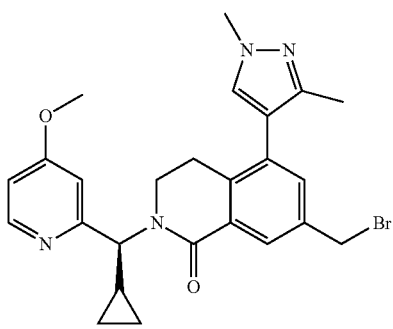 [SMILES: COc1ccnc([C@H](C2CC2)N2CCc3c(cc(CBr)cc3-c3cn(C)nc3C)C2=O)c1]

Intermediate 96

(S)-7-(Bromomethyl)-2-(cyclopropyl(4-methoxy-pyridin-2-yl)methyl)-5-(1,3-dimethyl-1H-pyrazol-4-yl)-3,4-dihydroisoquinolin-1(2H)-one The title compound was prepared from the synthetic sequence described in Intermediates 15-18 substituting (S)-cyclopropyl (4-methoxypyridin-2-yl)methanamine hydrochloride for (4-methoxypyridin-2-yl)methanamine in Intermediate 15 and substituting (1,3-dimethyl-1H-pyrazol-4-yl)boronic acid for (1-methyl-3-(trifluoromethyl)-1H-pyrazol-4-yl)boronic acid in Intermediate 16 Step B.

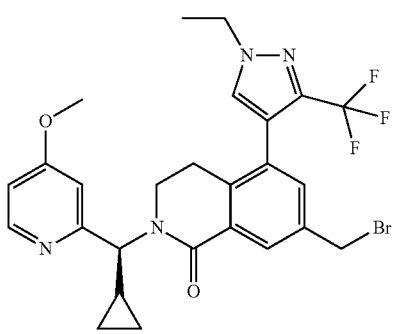 [SMILES: CCn1cc(-c2cc(CBr)cc3c2CCN([C@H](c2cc(OC)ccn2)C2CC2)C3=O)c(C(F)(F)F)n1]

Intermediate 97

(S)-7-(Bromomethyl)-2-(cyclopropyl(4-methoxy-pyridin-2-yl)methyl)-5-(1-ethyl-3-(trifluoromethyl)-1H-pyrazol-4-yl)-3,4-dihydroisoquinolin-1(2H)-one The title compound was prepared from the synthetic sequence described in Intermediates 15-18 substituting (S)-cyclopropyl (4-methoxypyridin-2-yl)methanamine hydrochloride for (4-methoxypyridin-2-yl)methanamine in Intermediate 15 and substituting (1-ethyl-3-(trifluoromethyl)-1H-pyrazol-4-yl)boronic acid for (1-methyl-3-(trifluoromethyl)-1H-pyrazol-4-yl)boronic acid in Intermediate 16 Step B.

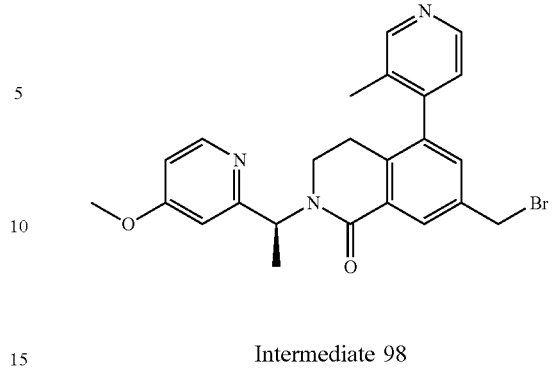

Intermediate 98

(S)-7-(Bromomethyl)-2-(1-(4-methoxypyridin-2-yl)ethyl)-5-(3-methylpyridin-4-yl)-3,4-dihydroisoquinolin-1(2H)-one The title compound was prepared from the synthetic sequence described in Intermediates 15-18 substituting (5)-1-(4-methoxypyridin-2-yl)ethan-1-amine for (4-methoxypyridin-2-yl)methanamine in Intermediate 15 and substituting (3-methylpyridin-4-yl)boronic acid for (1-methyl-3-(trifluoromethyl)-1H-pyrazol-4-yl)boronic acid in Intermediate 16 Step B. LC-MS: MS (ES) 466.4 [M+H]$^+$.

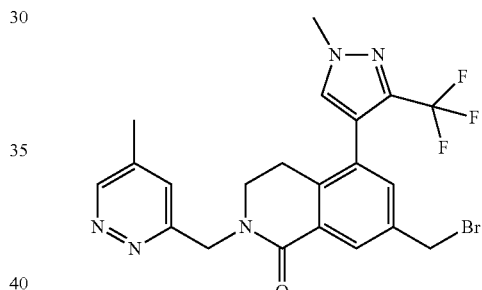

Intermediate 99

7-(Bromomethyl)-5-(1-methyl-3-(trifluoromethyl)-1H-pyrazol-4-yl)-2-((5-methylpyridazin-3-yl)methyl)-3,4-dihydroisoquinolin-1(2H)-one Step A. Preparation of dimethyl 4-(2-aminoethyl)-5-hydroxyisophthalate acetate. To a solution of dimethyl (E)-5-hydroxy-4-(2-(hydroxyimino)ethyl)isophthalate (105.3 mg, 0.39 mml, 1.0 equiv.) in acetic acid (4.0 mL), zinc (257.6 mg, 3.94 mmol, 10.0 equiv.) was added, and the resulting mixture was sonicated for 2.0 h. The reaction mixture was filtered and concentrated under the reduced pressure to yield crude title compound, which was used for the next step without further purification. LC-MS: $R_T$=0.941, MS (ES) 254.2 [M+H]$^+$.

Step B. Preparation of methyl 5-hydroxy-24(5-methylpyridazin-3-yl)methyl)-1-oxo-1,2,3,4-tetrahydroisoquinoline-7-carboxylate. The title compound (29.4 mg, 16% yield over 2 steps) was prepared from the procedure described in Intermediate 15 using 5-methylpyridazine-3-carbaldehyde (68.6 mg, 0.56 mmol, 1.0 equiv.) and dimethyl 4-(2-aminoethyl)-5-hydroxyisophthalate acetate (176.0 mg, 0.56 mmol, 1.0 equiv.) LC-MS: $R_T$=1.094, MS (ES) 328.3 [M+H]$^+$.

Step C. Preparation of 7-(bromomethyl)-5-(1-methyl-3-(trifluoromethyl)-1H-pyrazol-4-yl)-2-((5-methylpyridazin-3-yl)methyl)-3,4-dihydroisoquinolin-1(2H)-one. The title compound was prepared from the synthetic sequence described in Intermediates 16-18 substituting methyl 5-hydroxy-2-((5-methylpyridazin-3-yl)methyl)-1-oxo-1,2,3,4-tetrahydroisoquinoline-7-carboxylate for methyl 5-hydroxy-2-((4-methoxypyridin-2-yl)methyl)-1-oxo-1,2,3,4-tetrahydroisoquinoline-7-carboxylate in Intermediate 16. LC-MS: $R_T$=1.611, MS (ES) 495.3 [M+H]$^+$.

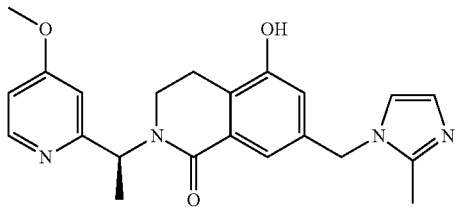 [SMILES: COc1ccnc([C@H](C)N2CCc3c(O)cc(Cn4ccnc4C)cc3C2=O)c1]

Intermediate 100

(S)-5-Hydroxy-2-(1-(4-methoxypyridin-2-yl)ethyl)-7-((2-methyl-1H-imidazol-1-yl)methyl)-3,4-dihydroisoquinolin-1(2H)-one Step A. Preparation of methyl (S)-5-((tert-butyldimethylsilyl)oxy)-2-(1-(4-methoxypyridin-2-yl)ethyl)-1-oxo-1,2,3,4-tetrahydroisoquinoline-7-carboxylate. To a solution of methyl (5)-5-hydroxy-2-(1-(4-methoxypyridin-2-yl)ethyl)-1-oxo-1,2,3,4-tetrahydroisoquinoline-7-carboxylate (5.5 g, 15.4 mmol) in DMF (30 mL) was added imidazole (2.0 eq), tert-butylchlorodimethylsilane (2.0 eq), and DMAP (0.2 eq). The reaction was stirred at RT for 20 h. The reaction mixture was poured into water and extracted with EtOAc. The organic layer was washed with brine, dried over magnesium sulfate, and concentrated. The residue was purified by flash chromatography (Combi-flash Rf, Hex/EtOAc=0-100% gradient) to afford the title compound (4.6 g, 63% yield). LC-MS Method 2: >95% 254 nm, $R_T$=1.720 min, MS (ES) 470.1 [M+H]$^+$.

Step B. preparation of (S)-5-((tert-butyldimethylsilyl)oxy)-2-(1-(4-methoxypyridin-2-yl)ethyl)-7-((2-methyl-1H-imidazol-1-yl)methyl)-3,4-dihydroisoquinolin-1(2H)-one. The title compound was prepared from the synthetic sequence described in Intermediates 17, 18 and Example 8 substituting (S)-5-((tert-butyldimethylsilyl)oxy)-2-(1-(4-methoxypyridin-2-yl)ethyl)-1-oxo-1,2,3,4-tetrahydroisoquinoline-7-carboxylate for methyl 2-((4-methoxypyridin-2-yl)methyl)-5-(1-methyl-3-(trifluoromethyl)-1H-pyrazol-4-yl)-1-oxo-1,2,3,4-tetrahydroisoquinoline-7-carboxylate in Intermediate 17.

Step C. Preparation of (S)-5-hydroxy-2-(1-(4-methoxypyridin-2-yl)ethyl)-7-((2-methyl-1H-imidazol-1-yl)methyl)-3,4-dihydroisoquinolin-1(2H)-one. To a solution of (5)-5-((tert-butyldimethyl silyl)oxy)-2-(1-(4-methoxypyridin-2-yl)ethyl)-7-((2-methyl-1H-imidazol-1-yl)methyl)-3,4-dihydroisoquinolin-1(2H)-one (0.5 g, 0.99 mmol) in THF (10 mL) was added 1.0 M TBAF solution in THF (4.0 eq). The reaction was stirred at RT for 1 h then concentrated. The residue was dissolved in DCM and washed with water and brine. The organic layer was concentrated to give the crude title compound (0.32 g, 82%), which was used without further purification.

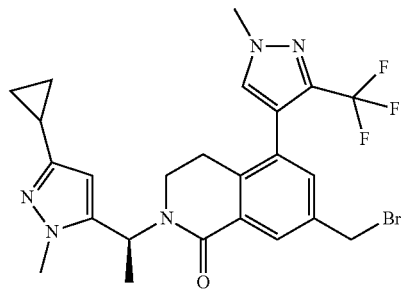 [SMILES: C[C@@H](c1cc(C2CC2)nn1C)N1CCc2c(cc(CBr)cc2-c2cn(C)nc2C(F)(F)F)C1=O]

Intermediate 101

(S)-7-(Bromomethyl)-2-(1-(3-cyclopropyl-1-methyl-1H-pyrazol-5-yl)ethyl)-5-(1-methyl-3-(trifluoromethyl)-1H-pyrazol-4-yl)-3,4-dihydroisoquinolin-1(2H)-one The title compound was prepared from the synthetic sequence described in Intermediates 15-18 substituting (5)-1-(3-cyclopropyl-1-methyl-1H-pyrazol-5-yl)ethan-1-amine for (4-methoxypyridin-2-yl)methanamine in Intermediate 15.

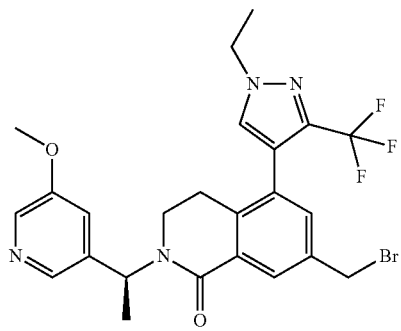 [SMILES: CCn1cc(-c2cc(CBr)cc3c2CCN([C@@H](C)c2cncc(OC)c2)C3=O)c(C(F)(F)F)n1]

Intermediate 102

(S)-7-(bromomethyl)-5-(1-ethyl-3-(trifluoromethyl)-1H-pyrazol-4-yl)-2-(1-(5-methoxypyridin-3-yl)ethyl)-3,4-dihydroisoquinolin-1(2H)-one The title compound was prepared from the synthetic sequence described in Intermediates 15-18 substituting (S)-1-(5-methoxypyridin-3-yl)ethan-1-amine dihydrochloride for (4-methoxypyridin-2-yl)methanamine in Intermediate 15 and substituting (1-ethyl-3-(trifluoromethyl)-1H-pyrazol-4-yl)boronic acid for (1-methyl-3-(trifluoromethyl)-1H-pyrazol-4-yl)boronic acid in Intermediate 16 Step B. LC-MS: >95% 254 nm, $R_T$=1.592 min, MS (ES) 538.4 [M+H]$^+$.

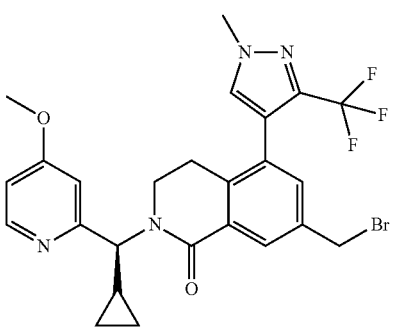 [SMILES: COc1ccnc([C@H](C2CC2)N2CCc3c(cc(CBr)cc3-c3cn(C)nc3C(F)(F)F)C2=O)c1]

Intermediate 103

(S)-7-(bromomethyl)-2-(cyclopropyl(4-methoxypyridin-2-yl)methyl)-5-(1-methyl-3-(trifluoromethyl)-1H-pyrazol-4-yl)-3,4-dihydroisoquinolin-1(2H)-one The title compound was prepared from the synthetic sequence described in Intermediates 15-18 substituting (S)-cyclopropyl (4-methoxypyridin-2-yl)methanamine for (4-methoxypyridin-2-yl)methanamine in Intermediate 15.

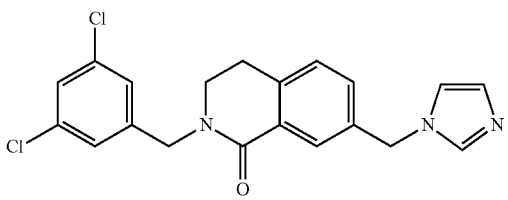 [SMILES: O=C1c2cc(Cn3ccnc3)ccc2CCN1Cc1cc(Cl)cc(Cl)c1]

Example 1

7-((1H-Imidazol-1-yl)methyl)-2-(3,5-dichlorobenzyl)-3,4-dihydroisoquinolin-1(2H)-one To a solution of 7-(bromomethyl)-2-(3,5-dichlorobenzyl)-3,4-dihydroisoquinolin-1(2H)-one (Intermediate 3, 20 mg, 0.05 mmol) in acetonitrile (3 mL) was added imidazole (10.2 mg, 0.15 mmol). The reaction mixture was heated at 80° C. in a microwave reactor for 30 min. The solvent was removed under reduced pressure. The residue was purified by flash chromatography (Combi-flash Rf, DCM/MeOH=0-10% gradient) to afford the title compound (14 mg, 72%). $^1$H NMR 400 MHz, CDCl$_3$) δ 8.07 (s, 1H), 7.58 (s, 1H), 7.30 (m, 3H), 7.24 (s, 2H), 7.11 (s, 1H), 6.93 (s, 1H), 5.17 (s, 2H), 4.75 (s, 2H), 3.53 (t, J=6.4 Hz, 2H), 3.00 (t, J=6.4 Hz, 2H); LC-MS: >95% 254 nm, R$_T$=0.97 min, MS (ES) 386 [M+H]$^+$.

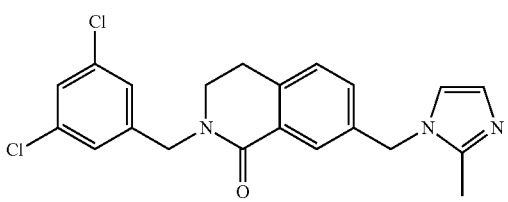 [SMILES: Cc1nccn1Cc1ccc2c(c1)C(=O)N(Cc1cc(Cl)cc(Cl)c1)CC2]

Example 2

2-(3,5-Dichlorobenzyl)-7-((2-methyl-1H-imidazol-1-yl)methyl)-3,4-dihydroisoquinolin-1(2H)-one The title compound (14.5 mg, 72%) was prepared from the procedure described in Example 1 substituting 2-methyl-1H-imidazole for imidazole. $^1$H NMR (400 MHz, CDCl$_3$) δ 8.02 (d, J=1.6 Hz, 1H), 7.30 (m, 3H), 7.17 (d, J=7.6 Hz, 1H), 7.05 (dd, J=1.6, 7.6 Hz, 1H), 6.97 (d, J=1.2 Hz, 1H), 6.87 (d, J=1.2 Hz, 1H), 5.10 (s, 2H), 4.74 (s, 2H), 3.53 (t, J=6.4 Hz, 2H), 2.99 (t, J=6.4 Hz, 2H), 2.37 (s, 3H); LC-MS, >95% (254 nm), R$_T$=0.98 min, m/z=400 [M+H]$^+$.

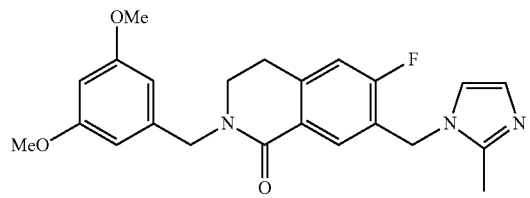 [SMILES: COc1cc(CN2CCc3cc(F)c(Cn4ccnc4C)cc3C2=O)cc(OC)c1]

Example 3

2-(3,5-Dimethoxybenzyl)-6-fluoro-7-((2-methyl-1H-imidazol-1-yl)methyl)-3,4-dihydroisoquinolin-1(2H)-one The title compound (19.6 mg, 81%) was prepared from the procedure described in Example 1 using 7-(bromomethyl)-2-(3,5-dimethoxybenzyl)-6-fluoro-3,4-dihydroisoquinolin-1(2H)-one and 2-methyl-1H-imidazole. $^1$H NMR (400 MHz, CDCl$_3$) δ 7.96 (d, J=7.6 Hz, 1H), 6.89 (m, 3H), 6.44 (s, 2H), 6.37 (s, 1H), 5.05 (s, 2H), 4.68 (s, 2H), 3.76 (s, 6H), 3.48 (t, J=6.8 Hz, 2H), 2.92 (t, J=6.8 Hz, 2H); LC-MS, >95% 254 nm, R$_T$=0.85 min, MS (ES) 410 [M+H]$^+$.

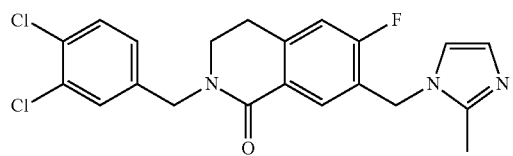 [SMILES: Cc1nccn1Cc1cc2c(cc1F)CCN(Cc1ccc(Cl)c(Cl)c1)C2=O]

Example 4

2-(3,4-Dichlorobenzyl)-6-fluoro-7-((2-methyl-1H-imidazol-1-yl)methyl)-3,4-dihydroisoquinolin-1(2H)-one The title compound (15 mg, 62%) was prepared from the procedure described in Example 1 using 7-(bromomethyl)-2-(3,4-dichlorobenzyl)-6-fluoro-3,4-dihydroisoquinolin-1(2H)-one (Intermediate 7) and 2-methyl-1H-imidazole. $^1$H NMR (400 MHz, CDCl$_3$) δ 7.94 (d, J=7.6 Hz, 1H), 7.40 (m, 2H), 7.16 (dd, J=2.0, 8.4 Hz, 1H), 6.89 (m, 3H), 5.06 (s, 2H), 4.69 (s, 2H), 3.49 (t, J=6.4 Hz, 2H), 2.95 (t, J=6.4 Hz, 2H); LC-MS, >95% (254 nm), R$_T$=0.97 min, m/z=418 [M+H]$^+$.

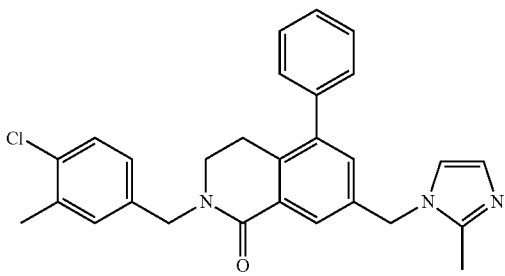 [SMILES: Cc1cc(CN2CCc3c(cc(Cn4ccnc4C)cc3-c3ccccc3)C2=O)ccc1Cl]

Example 5

2-(4-Chloro-3-methylbenzyl)-7-((2-methyl-1H-imidazol-1-yl)methyl)-5-phenyl-3,4-dihydroisoquinolin-1(2H)-one Step A. Preparation of 5-chloro-[1,1'-biphenyl]-2-carbaldehyde. To a solution of 2-bromo-4-chlorobenzaldehyde (491 mg, 2.24 mmol) in EtOH (12 mL) was added phenylboronic acid (300 mg, 2.46 mmol), PdCl$_2$(dppf) (33 mg, 0.045 mmol), and Et$_3$N (937 μL, 6.72 mmol). The resulting mixture was heated in a sealed tube under Argon atmosphere at 80° C. for 1.5 h. The solvent was removed under reduced pressure. The residue was purified by flash chromatography (Combi-flash Rf, Hex/EtOAc=0-15% gradient) to afford the title compound (430 mg, 88%). $^1$H NMR (400 MHz, CDCl$_3$) δ 9.91 (s, 1H), 7.97 (d, J=8.4 Hz, 1H), 7.48 (m, 5H), 7.37 (m, 2H).

Step B. Preparation of (E)-5-chloro-2-(2-nitrovinyl)-1,1'-biphenyl. The title compound (513 mg crude, used without further purification) was prepared from the procedure described in Intermediate 8, Step A substituting 5-chloro-[1,1'-biphenyl]-2-carbaldehyde for 2-bromo-4-chlorobenzaldehyde. $^1$H NMR (400 MHz, CDCl$_3$) δ 7.96 (d, J=13.6 Hz, 1H), 7.60 (d, J=8.4 Hz, 1H), 7.48 (m, 5H), 7.43 (m, 1H), 7.29 (m, 2H).

Step C. Preparation of 2-(5-chloro-[1,1'-biphenyl]-2-yl)ethan-1-amine. The title compound (550 mg crude, used without further purification) was prepared from the procedure described in Intermediate 4, Step B substituting (E)-5-chloro-2-(2-nitrovinyl)-1,1'-biphenyl for (E)-1-bromo-2-fluoro-4-(2-nitrovinyl)benzene. $^1$H NMR (400 MHz, CDCl$_3$) δ 7.41 (m, 4H), 7.34 (s, 2H), 7.24 (m, 2H), 2.73 (m, 4H).

Step D. Preparation of methyl 2-(((2-(5-chloro-[1,1'-biphenyl]-2-yl)ethyl)carbamoyl)oxy)benzoate. The title compound (720 mg, contaminated with starting material and used without further purification) was prepared from the procedure described in Intermediate 4, Step C substituting 2-(5-chloro-[1,1'-biphenyl]-2-yl)ethan-1-amine for 2-(4-bromo-3-fluorophenyl)ethan-1-amine. $^1$H NMR (400 MHz, CDCl$_3$) δ 7.96 (d, J=6.4 Hz, 1H), 7.53 (m, 1H), 7.40 (m, 4H), 7.31 (m, 4H), 7.26 (m, 1H), 7.09 (d, J=8.4 Hz, 1H), 5.00 (brs, 1H), 3.81 (s, 3H), 3.32 (q, J=6.8 Hz, 2H), 2.87 (t, J=6.8 Hz, 2H).

Step E. Preparation of 7-chloro-5-phenyl-3,4-dihydroisoquinolin-1(2H)-one. The title compound (300 mg, 58% over four steps) was prepared from the procedure described in Intermediate 4, Step D substituting methyl 2-(((2-(5-chloro-[1,1'-biphenyl]-2-yl)ethyl)carbamoyl)oxy)benzoate for methyl 2-(((4-bromo-3-fluorophenethyl)carbamoyl)oxy)benzoate. $^1$H NMR (400 MHz, CDCl$_3$) δ 8.10 (d, J=2.0 Hz, 1H), 7.43 (m, 4H), 7.30 (m, 2H), 6.05 (brs, 1H), 3.45 (m, 2H), 2.89 (t, J=6.4 Hz, 2H).

Step F. Preparation of 5-phenyl-7-vinyl-3,4-dihydroisoquinolin-1(2H)-one. The title compound (53 mg, 78%) was prepared from the procedure described in Intermediate 13, Step A substituting 7-chloro-5-phenyl-3,4-dihydroisoquinolin-1(2H)-one for 7-chloro-5-(2-methylpyridin-3-yl)-3,4-dihydroisoquinolin-1(2H)-one. $^1$H NMR (400 MHz, CDCl$_3$) δ 8.18 (s, 1H), 7.45 (m, 4H), 7.32 (m, 2H), 6.76 (dd, J=17.6, 11.6 Hz, 1H), 5.85 (d, J=17.6 Hz, 1H), 5.31 (d, J=11.6 Hz, 1H), 3.45 (m, 2H), 2.91 (t, J=6.4 Hz, 2H).

Step G. Preparation of 2-(4-chloro-3-methylbenzyl)-5-phenyl-7-vinyl-3,4-dihydroisoquinolin-1(2H)-one. The title compound (75 mg, 90%) was prepared from the procedure described in Intermediate 13, Step B substituting 5-phenyl-7-vinyl-3,4-dihydroisoquinolin-1(2H)-one for 5-(2-methylpyridin-3-yl)-7-vinyl-3,4-dihydroisoquinolin-1(2H)-one. $^1$H NMR (400 MHz, CDCl$_3$) δ 8.24 (s, 1H), 7.42 (m, 4H), 7.30 (m, 3H), 7.20 (s, 1H), 7.09 (d, J=8.0 Hz, 1H), 6.77 (dd, J=17.6, 11.2 Hz, 1H), 5.85 (d, J=17.6 Hz, 1H), 5.32 (d, J=11.2 Hz, 1H), 4.72 (s, 2H), 3.36 (t, J=6.4 Hz, 2H), 3.84 (t, J=6.4 Hz, 2H), 2.35 (s, 3H).

Step H. Preparation of 2-(4-chloro-3-methylbenzyl)-7-(hydroxymethyl)-5-phenyl-3,4-dihydroisoquinolin-1(2H)-one. The title compound (78 mg, quantitative) was prepared from the procedure described in Intermediate 11, Step B substituting 2-(4-chloro-3-methylbenzyl)-5-phenyl-7-vinyl-3,4-dihydroisoquinolin-1(2H)-one for 2-(3,5-dimethoxybenzyl)-5-(4-fluoro-2-methylphenyl)-7-vinyl-3,4-dihydroisoquinolin-1(2H)-one. $^1$H NMR (400 MHz, CDCl$_3$) δ 8.17 (s, 1H), 7.49 (s, 1H), 7.38 (m, 3H), 7.29 (m, 3H), 7.20 (s, 1H), 7.08 (m, 1H), 4.78 (s, 2H), 4.72 (s, 2H), 3.36 (t, J=6.4 Hz, 2H), 2.86 (t, J=6.4 Hz, 2H), 2.34 (s, 3H).

Step I. Preparation of 7-(bromomethyl)-2-(4-chloro-3-methylbenzyl)-5-phenyl-3,4-dihydroisoquinolin-1(2H)-one. The title compound (68 mg, 79%) was prepared from the procedure described in Intermediate 3, Step C substituting 2-(4-chloro-3-methylbenzyl)-7-(hydroxymethyl)-5-phenyl-3,4-dihydroisoquinolin-1(2H)-one for 2-(3,5-dichlorobenzyl)-7-(hydroxymethyl)-3,4-dihydroisoquinolin-1(2H)-one. LC-MS: >95% 254 nm, $R_T$=1.56 min, MS (ES) 454 [M+H]$^+$.

Step J. 2-(4-Chloro-3-methylbenzyl)-7-((2-methyl-1H-imidazol-1-yl)methyl)-5-phenyl-3,4-dihydroisoquinolin-1(2H)-one. The title compound (30 mg, quantitative) was prepared from the procedure described in Example 1 substituting 7-(bromomethyl)-2-(4-chloro-3-methylbenzyl)-5-phenyl-3,4-dihydroisoquinolin-1(2H)-one for 7-(bromomethyl)-2-(3,5-dichlorobenzyl)-3,4-dihydroisoquinolin-1(2H)-one and substituting 2-methyl-1H-imidazole for imidazole. $^1$H NMR (400 MHz, CDCl$_3$) δ 8.05 (s, 1H), 7.40 (m, 3H), 7.32 (m, 1H), 7.20 (m, 3H), 7.07 (m, 2H), 6.94 (s, 1H), 6.88 (s, 1H), 5.10 (s, 2H), 4.70 (s, 2H), 3.36 (t, J=6.4 Hz, 2H), 2.84 (t, J=6.4 Hz, 2H), 2.38 (s, 3H), 2.34 (s, 3H); LC-MS: >95% 254 nm, $R_T$=1.13 min, MS (ES) 456 [M+H]$^+$.

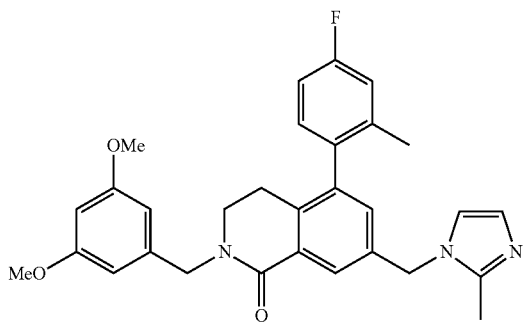 [SMILES: COc1cc(CN2CCc3c(cc(Cn4ccnc4C)cc3-c3ccc(F)cc3C)C2=O)cc(OC)c1]

Example 6

2-(3,5-Dimethoxybenzyl)-5-(4-fluoro-2-methylphenyl)-7-((2-methyl-1H-imidazol-1-yl)methyl)-3,4-dihydroisoquinolin-1(2H)-one The title compound (12 mg, 75%) was prepared from the procedure described in Example 1 using 7-(bromomethyl)-2-(3,5-dimethoxybenzyl)-5-(4-fluoro-2-methylphenyl)-3,4-dihydroisoquinolin-1(2H)-one (Intermediate 11) and 2-methyl-1H-imidazole. $^1$H NMR (400 MHz, CDCl$_3$) δ 8.06 (d, J=2.0 Hz, 1H), 6.90 (m, 6H), 6.46 (d, J=2.4 Hz, 2H), 6.37 (t, J=2.4 Hz, 1H), 5.10 (s, 2H), 4.71 (d, J=14.8 Hz, 1H), 4.70 (d, J=14.8 Hz, 1H), 3.76 (s, 6H), 3.38 (t, J=6.4 Hz, 2H), 2.63 (m, 1H), 2.59 (m, 1H), 2.36 (s, 3H), 1.97 (s, 3H); LC-MS, >95% (254 nm), R$_T$=1.06 min, m/z=500 [M+H]$^+$.

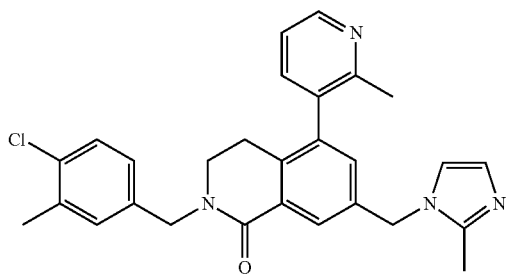 [SMILES: Cc1cc(CN2CCc3c(cc(Cn4ccnc4C)cc3-c3cccnc3C)C2=O)ccc1Cl]

Example 7

2-(4-Chloro-3-methylbenzyl)-7-((2-methyl-1H-imidazol-1-yl)methyl)-5-(2-methylpyridin-3-yl)-3,4-dihydroisoquinolin-1(2H)-one The title compound (12.6 mg, 55%) was prepared from the procedure described in Example 1, using 7-(bromomethyl)-2-(4-chloro-3-methylbenzyl)-5-(2-methylpyridin-3-yl)-3,4-dihydroisoquinolin-1(2H)-one (Intermediate 13) and 2-methyl-1H-imidazole. $^1$H NMR (400 MHz, CDCl$_3$) δ 8.53 (m, 1H), 8.09 (d, J=1.6 Hz, 1H), 7.30 (m, 2H), 7.17 (m, 2H), 7.08 (dd, J=2.0, 8.0 Hz, 1H), 6.94 (s, 1H), 6.90 (s, 1H), 6.87 (s, 1H), 5.12 (s, 2H), 4.70 (d, J=14.4 Hz, 1H), 4.68 (d, J=14.4 Hz, 1H), 3.38 (t, J=6.4 Hz, 2H), 2.56 (m, 2H), 2.37 (s, 3H), 2.35 (s, 3H), 2.24 (s, 3H); LC-MS: >95% 254 nm, R$_T$=0.83 min, MS (ES) 471 [M+H]$^+$.

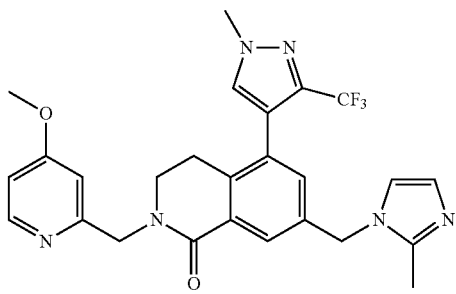 [SMILES: COc1ccnc(CN2CCc3c(cc(Cn4ccnc4C)cc3-c3cn(C)nc3C(F)(F)F)C2=O)c1]

Example 8

2-((4-Methoxypyridin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one 2-Methyl-1H-imidazole (16 mg, 0.2 mmol, 2 equiv) was added to a solution of (7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18, 50 mg, 0.1 mmol, 1 equiv) in MeCN (1 mL, 0.1 M) at 23° C. The reaction mixture was allowed to stir for 12 h at 23° C. The mixture was filtered and concentrated. The residue was purified by reverse phase HPLC (Phenomenex Gemini C18, H$_2$O/CH$_3$CN gradient from 2-35% CH$_3$CN, 0.1% TFA) to yield the title compound (42 mg, 0.082 mmol, 82%) as a white solid. $^1$H NMR (400 MHz, Methanol-d$_4$) δ 8.59-8.52 (m, 1H), 7.97 (d, J=2.0 Hz, 1H), 7.81 (d, J=1.1 Hz, 1H), 7.53 (d, J=2.1 Hz, 1H), 7.49 (d, J=2.1 Hz, 1H), 7.43 (dd, J=3.7, 1.4 Hz, 2H), 7.40 (d, J=1.9 Hz, 1H), 5.49 (s, 2H), 4.99 (s, 2H), 4.12 (s, 3H), 4.01 (s, 3H), 3.72 (t, J=6.6 Hz, 2H), 2.97 (t, J=6.6 Hz, 2H), 2.62 (s, 3H). LC-MS, >95% (254 nm), R$_T$=0.101 min, MS (ES) 511 [M+H]$^+$.

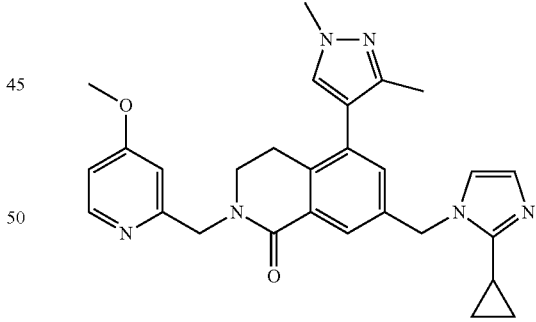

Example 9

7-((2-Cyclopropyl-1H-imidazol-1-yl)methyl)-5-(1,3-dimethyl-1H-pyrazol-4-yl)-2-((4-methoxypyridin-2-yl)methyl)-3,4-dihydroisoquinolin-1(2H)-one The title compound (22 mg, 0.046 mmol, 69%) was prepared following the procedure described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and 2-cyclopropyl-1H-imidazole (14 mg, 0.13 mmol, 2 equiv). LC-MS: >95% (254 nm), $R_T$=0.083 min, MS (ES) 483 [M+H]⁺.

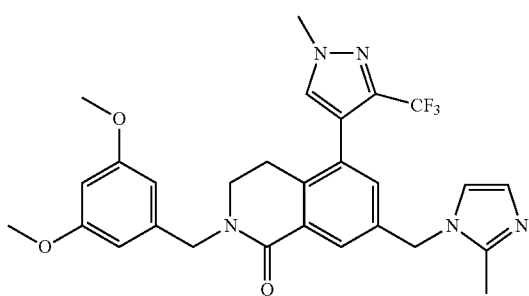 [SMILES: COc1cc(CN2CCc3c(cc(Cn4ccnc4C)cc3-c3cn(C)nc3C(F)(F)F)C2=O)cc(OC)c1]

Example 10

2-(3,5-Dimethoxybenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (18.6 mg, 73%) was prepared from the procedure described in Example 1 using 7-(bromomethyl)-2-(3,5-dimethoxybenzyl)-5-(1-methyl-3-(trifluoromethyl)-1H-pyrazol-4-yl)-3,4-dihydroisoquinolin-1(2H)-one and 2-methyl-1H-imidazole. ¹H NMR (400 MHz, CDCl₃) δ 8.08 (s, 1H), 7.29 (s, 1H), 6.95 (s, 1H), 6.92 (s, 1H), 6.86 (s, 1H), 6.46 (d, J=2.0 Hz, 2H), 6.37 (m, 1H), 5.10 (s, 2H), 4.72 (s, 2H), 4.12 (s, 3H), 3.77 (s, 6H), 3.41 (t, J=6.8 Hz, 2H), 2.72 (t, J=6.8 Hz, 2H), 2.36 (s, 3H); LC-MS, >95% (254 nm), $R_T$=1.0 min, MS (ES) 540 [M+H]⁺.

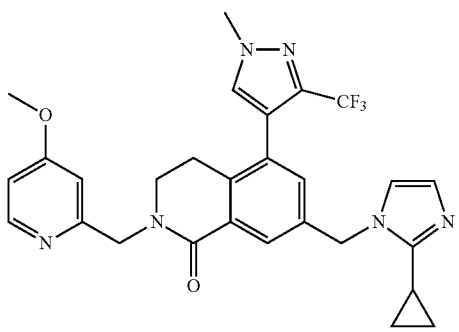 [SMILES: COc1ccnc(CN2CCc3c(cc(Cn4ccnc4C4CC4)cc3-c3cn(C)nc3C(F)(F)F)C2=O)c1]

Example 11

7-((2-Cyclopropyl-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (25 mg, 0.047 mmol, 78%) was prepared following the procedures described in Example 8 using 2-cyclopropyl-1H-imidazole (13 mg, 0.12 mmol, 2 equiv). LC-MS, >95% (254 nm), $R_T$=0.087 min, MS (ES)= 537 [M+H]⁺.

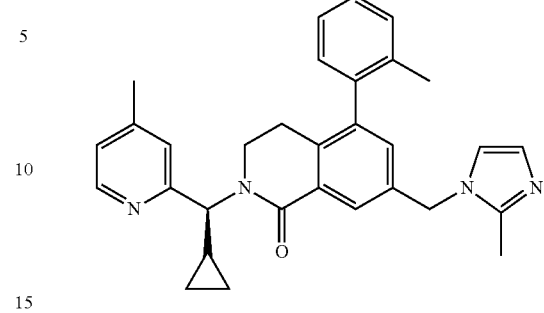

Example 12

(S)-2-(Cyclopropyl(4-methylpyridin-2-yl)methyl)-5-(4-fluoro-2-methylphenyl)-7-((2-methyl-1H-imidazol-1-yl)methyl)-3,4-dihydroisoquinolin-1(2H)-one 2-Methyl-1H-imidazole (11.5 mg, 0.14 mmol) and N,N-diisopropylethylamine (40 μL 0.23 mmol) were added to a solution of (S)-7-(bromomethyl)-2-(cyclopropyl(4-methylpyridin-2-yl)methyl)-5-(4-fluoro-2-methylphenyl)-3,4-dihydroisoquinolin-1(2H)-one (23 mg, 0.05 mmol) in CH₃CN (1.0 mL). The reaction mixture was heated at 90° C. for 12 h. The reaction mixture was cooled to room temperature and concentrated under reduced pressure. The residue was re-dissolved in DMSO (1.0 mL) and filtered. The DMSO solution was purified by reverse phase HPLC (Phenomenex Gemini C18, H₂O/CH₃CN gradient from 5-95% CH₃CN, 0.1% TFA) to yield the title compound (18.9 mg, 81% yield) as a mixture of two atropisomers (1:1). (To remove TFA, the organic layer has to be washed with sat. aq. NaHCO₃) LCMS: $R_T$=1.256 min, MS (ES) 495.6 [M+H]⁺; ¹H NMR (400 MHz, Chloroform-d) δ 8.39 (t, J=4.5 Hz, 1H), 7.99 (s, 1H), 7.24 (d, J=6.1 Hz, 1H), 7.01-6.82 (m, 7H), 5.07 (s, 2H), 5.04 (d, J=3.6 Hz, 1H), 3.77-3.57 (m, 2H), 2.54 (m, 3H), 2.35 (s, 3H), 2.32* (d, J=3.1 Hz, 3H), 1.96* (d, J=32.3 Hz, 3H), 1.69-1.57 (m, 1H), 0.76 (m, 1H), 0.61 (m, 1H), 0.55-0.44 (m, 2H). (*Indicates two atropisomers (1:1)).

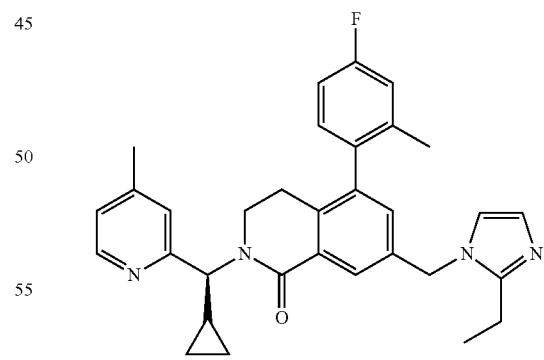

Example 13

(S)-2-(Cyclopropyl(4-methylpyridin-2-yl)methyl)-7-((2-ethyl-1H-imidazol-1-yl)methyl)-5-(4-fluoro-2-methylphenyl)-3,4-dihydroisoquinolin-1(2H)-one The title compound (19.7 mg, 83% yield) was prepared from the procedure described in Example 12 using (S)-7-

(bromomethyl)-2-(cyclopropyl(4-methylpyridin-2-yl)methyl)-5-(4-fluoro-2-methylphenyl)-3,4-dihydroisoquinolin-1(2H)-one (23.0 mg, 0.05 mmol) and 2-ethyl-1H-imidazole (13.4 mg, 0.14 mmol). LCMS: $R_T$=1.279 min, MS (ES) 509.6 [M+H]$^+$; $^1$H NMR (400 MHz, Chloroform-d) δ 8.39 (t, J=4.6 Hz, 1H), 8.00 (s, 1H), 7.24 (d, J=6.2 Hz, 1H), 7.01-6.86 (m, 5H), 6.84 (s, 2H), 5.08 (s, 2H), 5.06 (dd, J=10.3, 3.7 Hz, 1H), 3.67 (m, 2H), 2.66 (q, J=7.5 Hz, 2H), 2.52 (m, 2H), 2.32* (d, J=3.2 Hz, 3H), 1.96* (d, J=32.4 Hz, 3H), 1.63 (m, 1H), 1.28 (t, J=7.5 Hz, 3H), 0.75 (m, 1H), 0.61 (m, 1H), 0.55-0.46 (m, 2H) (*Indicates two atropisomers (1:1)).

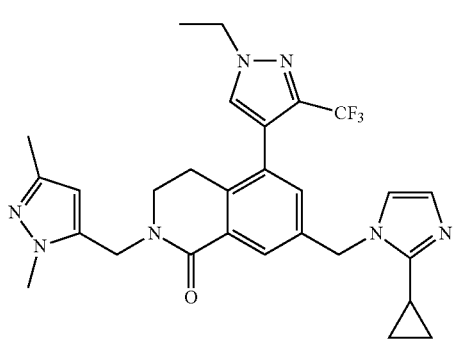 [SMILES: CCn1cc(-c2cc(Cn3ccnc3C3CC3)cc3c2CCN(Cc2cc(C)nn2C)C3=O)c(C(F)(F)F)n1]

Example 14

7-((2-Cyclopropyl-1H-imidazol-1-yl)methyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one The title compound (15 mg, 0.028 mmol) was prepared following the procedures described in Example 8 using 7-(bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one (Intermediate 31) and 2-cyclopropyl-1H-imidazole. $^1$H NMR (CDCl$_3$) δ 8.09 (d, J=1.8 Hz, 1H), 7.33 (s, 1H), 7.04 (d, J=1.8 Hz, 1H), 6.92 (d, J=1.2 Hz, 1H), 6.86 (d, J=1.2 Hz, 1H), 6.01 (s, 1H), 5.26 (s, 2H), 4.78 (s, 2H), 4.26 (q, J=7.5 Hz, 2H), 3.83 (s, 3H), 3.43 (t, J=6.6 Hz, 2H), 2.73 (t, J=6.6 Hz, 2H), 2.24 (s, 3H), 1.75-1.70 (m, 1H), 1.58 (t, J=7.5 Hz, 3H), 1.01-0.97 (m, 2H), 0.93-0.88 (m, 2H); LCMS method 1: $R_T$=1.19 min, MS (ES) 538.0 [M+H]$^+$.

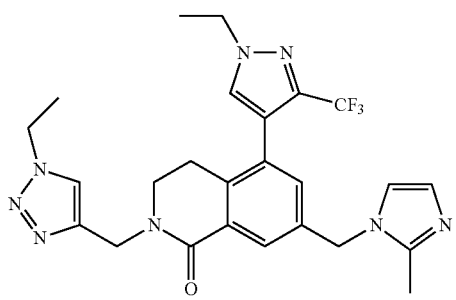 [SMILES: CCn1cc(CN2CCc3c(cc(Cn4ccnc4C)cc3-c3cn(CC)nc3C(F)(F)F)C2=O)nn1]

Example 15

2-((1-Ethyl-1H-1,2,3-triazol-4-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one The title compound (39 mg, 0.076 mmol, 78%) was prepared following the procedure described in Example 8 using 7-(bromomethyl)-2-((1-ethyl-1H-1,2,3-triazol-4-yl)methyl)-5-(1-ethyl-3-(trifluoromethyl)-1H-pyrazol-4-yl)-3,4-dihydroisoquinolin-1(2H)-one (Intermediate 32). $^1$H NMR (400 MHz, Methanol-d$_4$) δ 7.95 (dd, J=6.7, 4.5 Hz, 2H), 7.85 (t, J=2.7 Hz, 1H), 7.55 (q, J=2.3 Hz, 1H), 7.50 (t, J=2.7 Hz, 1H), 7.38 (t, J=3.0 Hz, 1H), 5.49 (s, 2H), 4.85 (s, 2H), 4.44 (q, J=6.1, 4.8 Hz, 2H), 4.30 (q, J=6.2, 5.1 Hz, 2H), 3.64-3.58 (m, 2H), 2.85 (q, J=6.0, 5.5 Hz, 2H), 2.64 (s, 3H), 1.53 (ddt, J=7.1, 5.2, 2.5 Hz, 6H); LC-MS: >95% (254 nm), $R_T$=0.783 min, MS (ES) 513 [M+H]$^+$.

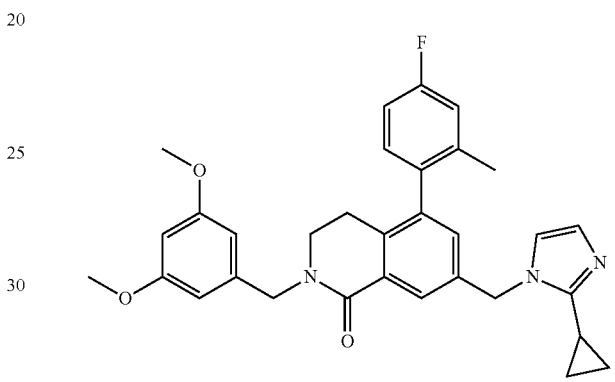

Example 16

7-((2-Cyclopropyl-1H-imidazol-1-yl)methyl)-2-(3,5-dimethoxybenzyl)-5-(4-fluoro-2-methylphenyl)-3,4-dihydroisoquinolin-1(2H)-one The title compound (15 mg, 0.028 mmol,) was prepared following the procedures described in Example 8 using 7-(bromomethyl)-2-(3,5-dimethoxybenzyl)-5-(4-fluoro-2-methylphenyl)-3,4-dihydroisoquinolin-1(2H)-one (Intermediate 11) and 2-cyclopropyl-1H-imidazole. $^1$H NMR (CDCl$_3$) δ 8.10 (d, J=1.3 Hz, 1H), 6.98-6.87 (series of m, 5H), 6.84 (d, J=1.2 Hz, 1H), 6.46 (d, J=2.1 Hz, 2H), 6.37 (t, J=2.3 Hz, 1H), 5.25 (s, 2H), 4.76-4.66 (m, 2H), 3.76 (s, 6H), 3.38 (t, J=6.6 Hz, 2H), 2.65-2.47 (m, 2H), 1.97 (s, 3H), 1.77-1.70 (m, 1H), 0.99-0.95 (m, 2H), 0.91-0.87 (m, 2H); LCMS method 1: $R_T$=1.46 min, MS (ES) 526.0 [M+H]$^+$.

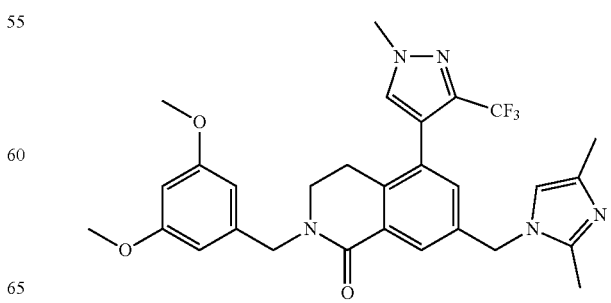

Example 17

2-(3,5-Dimethoxybenzyl)-7-((2,4-dimethyl-1H-imidazol-1-yl)methyl)-5-(1-methyl-3-(trifluoromethyl)-1H-pyrazol-4-yl)-3,4-dihydroisoquinolin-1(2H)-one The title compound (17.8 mg, 57%) was prepared from the procedure described in Example 1 using 7-(bromomethyl)-2-(3,5-dimethoxybenzyl)-5-(1-methyl-3-(trifluoromethyl)-1H-pyrazol-4-yl)-3,4-dihydroisoquinolin-1(2H)-one (Intermediate 27) and 2,4-dimethyl-1H-imidazole. $^1$H NMR (400 MHz, CDCl$_3$) δ 8.06 (s, 1H), 7.30 (s, 1H), 6.94 (s, 1H), 6.56 (s, 1H), 6.46 (d, J=2.0 Hz, 2H), 6.38 (m, 1H), 5.02 (s, 2H), 4.71 (s, 2H), 3.97 (s, 3H), 3.77 (s, 6H), 3.40 (t, J=6.8 Hz, 2H), 2.72 (t, J=6.8 Hz, 2H), 2.31 (s, 3H), 2.16 (s, 3H); LC-MS: >95% (254 nm), R$_T$=1.0 min, MS (ES) 554 [M+H]$^+$.

Example 19

7-((2-Cyclopropyl-1H-imidazol-1-yl)methyl)-5-(cyclopropylmethoxy)-2-(3,5-dimethoxybenzyl)-3,4-dihydroisoquinolin-1(2H)-one The title compound (16 mg, 0.033 mmol) was prepared following the procedure described in Example 8 using 7-(bromomethyl)-5-(cyclopropylmethoxy)-2-(3,5-dimethoxybenzyl)-3,4-dihydroisoquinolin-1(2H)-one (Intermediate 36, 75 mg, 0.16 mmol) and 2-cyclopropyl-1H-imidazole (35 mg, 0.32 mmol). $^1$H NMR (CDCl$_3$) δ 7.68 (s, 1H), 6.90 (s, 1H), 6.82 (s, 1H), 6.53 (s, 1H), 6.47 (d, J=1.9 Hz, 2H), 6.37 (t, J=2.0 Hz, 1H), 5.19 (s, 2H), 4.71 (s, 2H), 3.77 (s, 6H), 3.70 (d, J=6.7 Hz, 2H), 3.46 (t, J=6.4 Hz, 2H), 2.92 (t, J=6.4 Hz, 2H), 1.77-1.71 (m, 1H), 1.20-1.13 (m, 1H), 1.01-0.98 (m, 2H), 0.92-0.87 (m, 2H), 0.61-0.56 (m, 2H), 0.31-0.27 (m, 2H); LCMS method 1: R$_T$=1.40 min, MS (ES) 488.1 [M+H]$^+$.

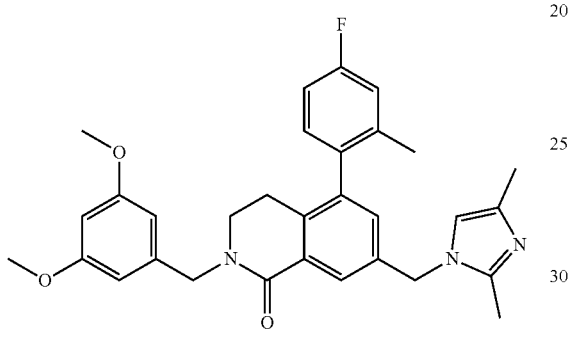

Example 18

2-(3,5-Dimethoxybenzyl)-7-((2,4-dimethyl-1H-imidazol-1-yl)methyl)-5-(4-fluoro-2-methylphenyl)-3,4-dihydroisoquinolin-1(2H)-one The title compound (23 mg, 75%) was prepared from the procedure described in Example 1 using 7-(bromomethyl)-2-(3,5-dimethoxybenzyl)-5-(4-fluoro-2-methylphenyl)-3,4-dihydroisoquinolin-1(2H)-one (Intermediate 11) and 2,4-dimethyl-1H-imidazole. $^1$H NMR (400 MHz, CDCl$_3$) δ 8.05 (s, 1H), 6.94 (m, 4H), 6.56 (s, 1H), 6.46 (d, J=2.0 Hz, 2H), 6.37 (m, 1H), 5.02 (s, 2H), 4.70 (m, 2H), 3.77 (s, 6H), 3.38 (t, J=6.4 Hz, 2H), 2.53 (m, 2H), 2.32 (s, 3H), 2.16 (s, 3H), 1.98 (s, 3H); LC-MS: >95% (254 nm), R$_T$=1.10 min, MS (ES) 514 [M+H]$^+$.

Example 20

2-((1,3-Dimethyl-1H-pyrazol-4-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one The title compound (45 mg, 0.093 mmol, 95%) was prepared following the procedure described in Example 8 using 7-(bromomethyl)-2-((1,3-dimethyl-1H-pyrazol-4-yl)methyl)-5-(1-ethyl-3-(trifluoromethyl)-1H-pyrazol-4-yl)-3,4-dihydroisoquinolin-1(2H)-one (Intermediate 37). LC-MS: >95% (254 nm), R$_T$=1.206 min, MS (ES) 512 [M+H]$^+$.

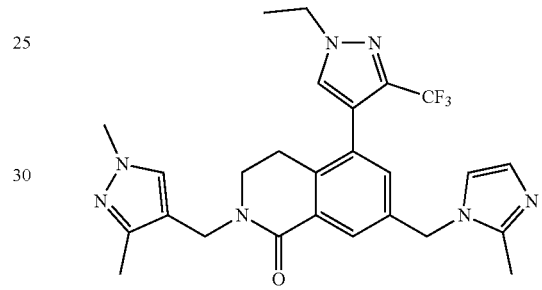

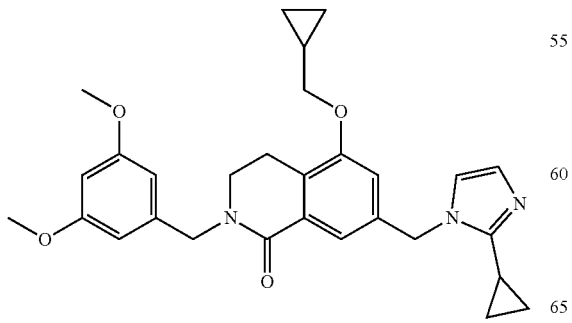

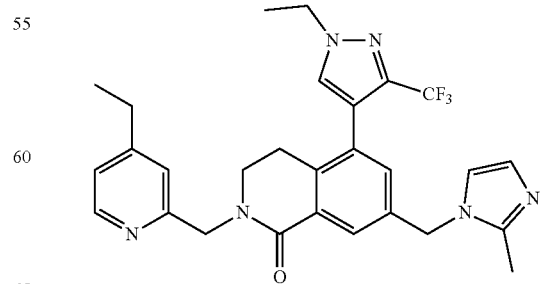

Example 21

5-(1-Ethyl-3-(trifluoromethyl)-1H-pyrazol-4-yl)-2-((4-ethylpyridin-2-yl)methyl)-7-((2-methyl-1H-imidazol-1-yl)methyl)-3,4-dihydroisoquinolin-1(2H)-one

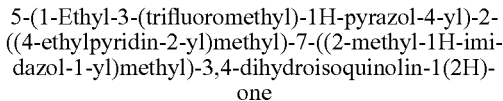

The title compound (14.5 mg, 72%) was prepared from the procedure described in Example 1 using 7-(bromomethyl)-5-(1-ethyl-3-(trifluoromethyl)-1H-pyrazol-4-yl)-2-((4-ethylpyridin-2-yl)methyl)-3,4-dihydroisoquinolin-1(2H)-one (Intermediate 38) and 2-methyl-1H-imidazole. $^1$H NMR (400 MHz, CDCl$_3$) δ 8.41 (d, J=5.2 Hz, 1H), 8.06 (s, 1H), 7.32 (s, 1H), 7.22 (s, 1H), 7.05 (d, J=5.2 Hz, 1H), 6.95 (s, 2H), 6.86 (s, 1H), 5.09 (s, 2H), 4.86 (s, 2H), 4.24 (q, J=7.6 Hz, 2H), 3.58 (t, J=6.4 Hz, 2H), 2.76 (t, J=6.4 Hz, 2H), 2.63 (q, J=7.6 Hz, 2H), 2.35 (s, 3H), 1.56 (t, J=7.6 Hz, 3H), 1.23 (t, J=7.6 Hz, 3H); LC-MS: >95% (254 nm), RT=0.80 min, MS (ES) 523.6 [M+H]$^+$.

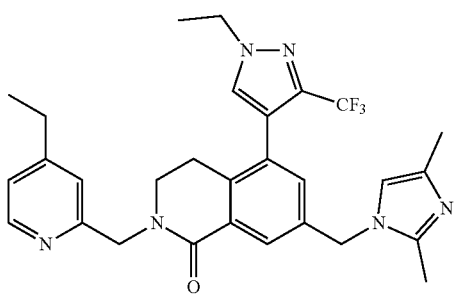 [SMILES: CCc1ccnc(CN2CCc3c(cc(Cn4cc(C)nc4C)cc3-c3cn(CC)nc3C(F)(F)F)C2=O)c1]

Example 22

7-((2,4-Dimethyl-1H-imidazol-1-yl)methyl)-5-(1-ethyl-3-(trifluoromethyl)-1H-pyrazol-4-yl)-2-((4-ethylpyridin-2-yl)methyl)-3,4-dihydroisoquinolin-1(2H)-one The title compound (14.5 mg, 72%) was prepared from the procedure described in Example 1 using 7-(bromomethyl)-5-(1-ethyl-3-(trifluoromethyl)-1H-pyrazol-4-yl)-2-((4-ethylpyridin-2-yl)methyl)-3,4-dihydroisoquinolin-1(2H)-one (Intermediate 38) and 2,4-dimethyl-1H-imidazole. $^1$H NMR (400 MHz, CDCl$_3$) δ 8.40 (d, J=5.2 Hz, 1H), 8.05 (s, 1H), 7.33 (s, 1H), 7.22 (s, 1H), 7.05 (d, J=5.2 Hz, 1H), 6.97 (s, 1H), 6.56 (s, 1H), 5.01 (s, 2H), 4.86 (s, 1H), 4.23 (q, J=7.6 Hz, 2H), 3.58 (t, J=6.4 Hz, 2H), 2.76 (t, J=6.4 Hz, 2H), 2.63 (q, J=7.6 Hz, 2H), 2.32 (s, 3H), 2.16 (s, 3H), 1.56 (t, J=7.6 Hz, 3H), 1.32 (t, J=7.6 Hz, 3H); LC-MS: >95% (254 nm), R$_T$=0.82 min, MS (ES) 537.6 [M+H]$^+$.

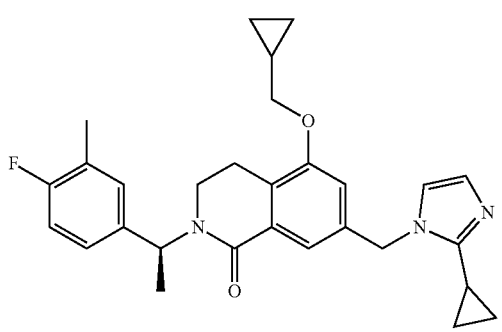 [SMILES: Cc1cc([C@H](C)N2CCc3c(OCC4CC4)cc(Cn4ccnc4C4CC4)cc3C2=O)ccc1F]

Example 23

(S)-7-((2-Cyclopropyl-1H-imidazol-1-yl)methyl)-5-(cyclopropylmethoxy)-2-(1-(4-fluoro-3-methylphenyl)ethyl)-3,4-dihydroisoquinolin-1(2H)-one The title compound (34 mg, 0.072 mmol) was prepared following the procedure described in Example 8 using (S)-7-(bromomethyl)-5-(cyclopropylmethoxy)-2-(1-(4-fluoro-3-methylphenyl)ethyl)-3,4-dihydroisoquinolin-1(2H)-one (Intermediate 39, 75 mg, 0.16 mmol) and 2-cyclopropyl-1H-imidazole (35 mg, 0.32 mmol). $^1$H NMR (CDCl$_3$) δ 7.68 (s, 1H), 7.19-7.13 (m, 2H), 6.95 (t, J=8.9 Hz, 1H), 6.91 (d, J=1.1 Hz, 2H), 6.82 (d, J=1.1 Hz, 2H), 6.53 (s, 1H), 6.14 (q, J=7.0 Hz, 1H), 5.19 (s, 2H), 3.69 (d, J=6.8 Hz, 1H), 3.36-3.29 (m, 1H), 3.12-3.05 (m, 1H), 2.93-2.86 (m, 1H), 2.74-2.66 (m, 1H), 2.25 (s, 3H), 1.78-1.71 (m, 1H), 1.55 (d, J=7.0 Hz, 3H), 1.19-1.11 (m, 1H), 1.02-0.98 (m, 2H), 0.93-0.88 (m, 2H), 0.60-0.55 (m, 2H), 0.30-0.26 (m, 2H); LCMS method 1: R$_T$=1.49 min, MS (ES) 474.1 [M+H]$^+$.

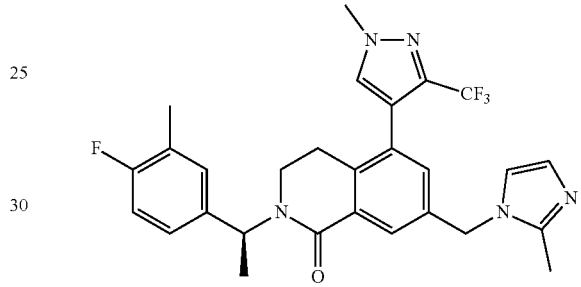

Example 24

(S)-2-(1-(4-Fluoro-3-methylphenyl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (36 mg, 0.068 mmol) was prepared following the procedures described in Example 8 using (S)-7-(bromomethyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one. LCMS method 1: R$_T$=1.41 min, MS (ES) 526.0 [M+H]$^+$.

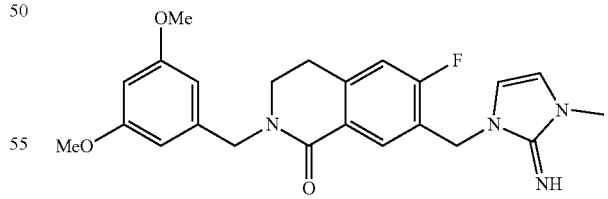

Example 25

2-(3,5-Dimethoxybenzyl)-6-fluoro-7-((2-imino-3-methyl-2,3-dihydro-1H-imidazol-1-yl)methyl)-3,4-dihydroisoquinolin-1(2H)-one The title compound (19.7 mg, 79%) was prepared from the procedure described in Example 3 substituting 1-methyl- 1H-imidazol-2-amine for 2-methyl-1H-imidazole. ¹H NMR (400 MHz, CDCl₃) δ 8.13 (d, J=7.6 Hz, 1H), 6.89 (d, J=9.6 Hz, 1H), 6.45 (m, 2H), 6.39 (m, 2H), 6.34 (m, 1H), 5.28 (s, 2H), 4.64 (s, 2H), 3.74 (s, 6H), 3.62 (s, 3H), 3.47 (t, J=6.8 Hz, 2H), 2.91 (t, J=6.8 Hz, 2H); LC-MS: >95% (254 nm), R$_T$=0.87 min, MS (ES) 425 [M+H]⁺.

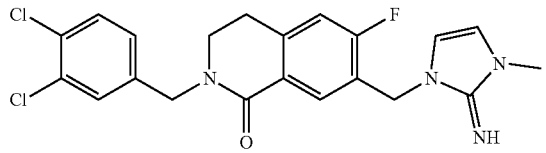 [SMILES: Cn1ccn(Cc2cc3c(cc2F)CCN(Cc2ccc(Cl)c(Cl)c2)C3=O)c1=N]

Example 26

2-(3,4-Dichlorobenzyl)-6-fluoro-7-((2-imino-3-methyl-2,3-dihydro-1H-imidazol-1-yl)methyl)-3,4-dihydroisoquinolin-1(2H)-one The title compound (15 mg, 79%) was prepared from the procedure described in Example 1 using 7-(bromomethyl)-2-(3,4-dichlorobenzyl)-6-fluoro-3,4-dihydroisoquinolin-1(2H)-one (Intermediate 7) and 1-methyl-1H-imidazol-2-amine. ¹H NMR (400 MHz, CDCl₃) δ 8.14 (d, J=7.6 Hz, 1H), 7.35 (m, 2H), 7.12 (m, 1H), 6.92 (d, J=9.6 Hz, 1H), 6.44 (m, 2H), 5.28 (s, 2H), 4.67 (s, 2H), 3.63 (s, 3H), 3.49 (t, J=6.8 Hz, 2H), 2.94 (t, J=6.8 Hz, 2H); LC-MS: >95% (254 nm), R$_T$=0.98 min, MS (ES) 433 [M+H]⁺.

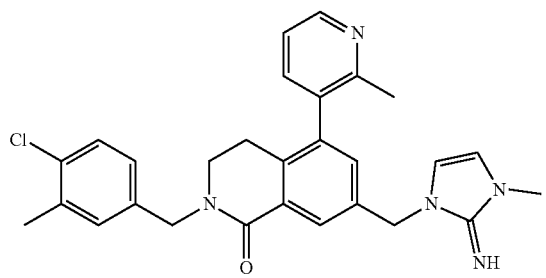 [SMILES: Cc1cc(CN2CCc3c(cc(Cn4ccn(C)c4=N)cc3-c3cccnc3C)C2=O)ccc1Cl]

Example 27

2-(4-Chloro-3-methylbenzyl)-7-((2-imino-3-methyl-2,3-dihydro-1H-imidazol-1-yl)methyl)-5-(2-methylpyridin-3-yl)-3,4-dihydroisoquinolin-1(2H)-one To a solution of 7-(bromomethyl)-2-(4-chloro-3-methylbenzyl)-5-(2-methylpyridin-3-yl)-3,4-dihydroisoquinolin-1(2H)-one (Intermediate 13, 21.9 mg, 0.044 mmol) in acetonitrile (3 mL) was added 1-methyl-1H-imidazol-2-amine (12.8 mg, 0.132 mmol). The reaction mixture was heated at 80° C. for 30 min. The solvent was removed under reduced pressure and the residue was purified by reverse phase HPLC (Phenomenex Gemini C18, H₂O/CH₃CN gradient from 15-95% CH₃CN, 0.1% TFA). The fractions containing the desired product were combined, neutralized with NaHCO₃ (sat.), and extracted with CH₂Cl₂/EtOAc (2/1, V/V). The combined organic layers were allowed to pass through a phase separator. The filtrate was concentrated, dried under vacuum to provide the title product (13 mg, 56%) as a TFA salt (To remove TFA, the organic layer has to be washed with K₂CO₃ (sat.)). ¹H NMR (400 MHz, CDCl₃) δ 8.51 (m, 1H), 8.05 (d, J=2.0 Hz, 1H), 7.38 (m, 2H), 7.28 (s, 1H), 7.17 (m, 2H), 7.06 (dd, J=2.4, 5.6 Hz, 1H), 6.49 (m, 2H), 5.31 (s, 2H), 4.68 (d, J=14.4 Hz, 1H), 4.67 (d, J=14.4 Hz, 1H), 3.60 (s, 3H), 3.38 (t, J=6.4 Hz, 2H), 2.58 (t, J=6.4 Hz, 2H), 2.34 (s, 3H), 2.25 (s, 3H); LC-MS: >95% 254 nm, R$_T$=0.86 min, MS (ES) 486 [M+H]⁺.

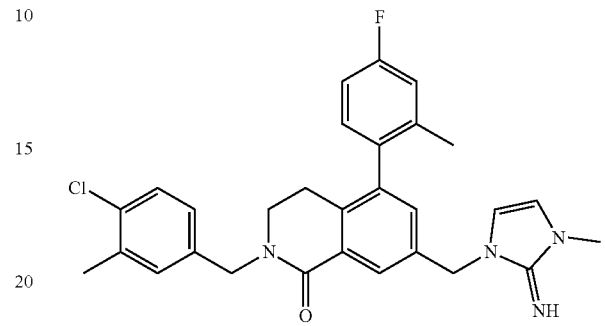

Example 28

2-(4-Chloro-3-methylbenzyl)-5-(4-fluoro-2-methylphenyl)-7-((2-imino-3-methyl-2,3-dihydro-1H-imidazol-1-yl)methyl)-3,4-dihydroisoquinolin-1(2H)-one The title compound (35 mg, 69%) was prepared from the procedure described in Example 27 substituting 7-(bromomethyl)-2-(4-chloro-3-methylbenzyl)-5-(4-fluoro-2-methylphenyl)-3,4-dihydroisoquinolin-1(2H)-one (Intermediate 41) for 7-(bromomethyl)-2-(4-chloro-3-methylbenzyl)-5-(2-methylpyridin-3-yl)-3,4-dihydroisoquinolin-1(2H)-one (Intermediate 13). ¹H NMR (400 MHz, CDCl₃) δ 8.03 (d, J=1.6 Hz, 1H), 7.30 (m, 2H), 7.17 (d, J=1.6 Hz, 1H), 7.07 (dd, J=2.0, 8.0 Hz, 1H), 6.93 (m, 3H), 6.47 (m, 2H), 5.25 (s, 2H), 4.68 (m, 2H), 3.58 (s, 3H), 3.35 (t, J=6.4 Hz, 2H), 2.60 (m, 2H), 2.34 (s, 3H), 1.99 (3H); LC-MS: >95% 254 nm, R$_T$=1.20 min, MS (ES) 503 [M+H]⁺.

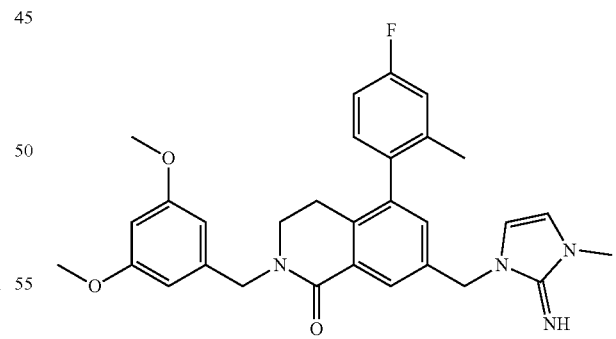

Example 29

2-(3,5-Dimethoxybenzyl)-5-(4-fluoro-2-methylphenyl)-7-((2-imino-3-methyl-2,3-dihydro-1H-imidazol-1-yl)methyl)-3,4-dihydroisoquinolin-1(2H)-one The title compound (16.0 mg, 70%) was prepared from the procedure described in Example 27 using 7-(bromomethyl)-2-(3,5-dimethoxybenzyl)-5-(4-fluoro-2-methylphenyl)-3,4-dihydroisoquinolin-1(2H)-one (Intermediate 11, 21.9 mg, 0.044 mmol) and 1-methyl-1H-imidazol-2-amine (12.8 mg, 0.132 mmol) as a TFA salt. $^1$H NMR (400 MHz, CDCl$_3$) δ 8.03 (d, J=2.0 Hz, 1H), 7.31 (d, J=2.0 Hz, 1H), 7.91 (m, 3H), 6.48 (dd, J=4.8, 2.8 Hz, 2H), 6.44 (d, J=2.0 Hz, 2H), 6.37 (t, J=2.0 Hz, 1H), 5.28 (s, 2H), 4.67 (d, J=14.8 Hz, 1H), 4.66 (d, J=14.8 Hz, 1H), 3.76 (s, 6H), 3.60 (s, 3H), 3.38 (t, J=6.4 Hz, 2H), 2.54 (m, 2H), 2.03 (s, 3H); LC-MS: >95% 254 nm, R$_T$=1.09 min, MS (ES) 515 [M+H]$^+$.

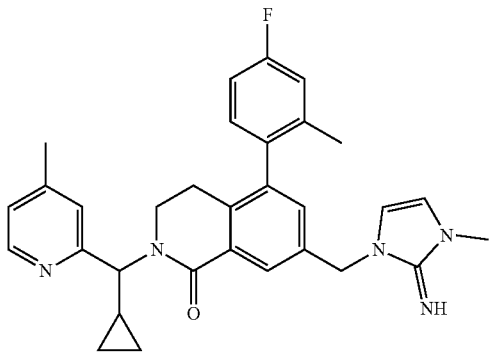 [SMILES: Cc1ccnc(C(C2CC2)N2CCc3c(cc(Cn4ccn(C)c4=N)cc3-c3ccc(F)cc3C)C2=O)c1]

Example 30

2-(Cyclopropyl(4-methylpyridin-2-yl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one The title compound (14.9 mg, 63%) was prepared following the procedure described in Example 27 using 7-(bromomethyl)-2-(cyclopropyl(4-methylpyridin-2-yl)methyl)-5-(4-fluoro-2-methylphenyl)-3,4-dihydroisoquinolin-1(2H)-one (Intermediate 43) and 1-methyl-1H-imidazol-2-amine. $^1$H NMR (400 MHz, CDCl$_3$) δ 8.40 (t, J=4.8 Hz, 1H), 7.96 (s, 1H), 7.24 (m, 2H), 6.92 (m, 4H), 6.46 (s, 2H), 5.23 (s, 2H), 5.04 (dd, J=3.2, 10.0 Hz, 1H), 3.65 (m, 2H), 3.58 (s, 3H), 2.52 (m, 2H), 2.33 (m, 3H), 2.05 (s, 1.5H), 1.97 (s, 1.5H), 1.61 (m, 1H), 0.77 (m, 1H), 0.62 (m, 1H), 0.52 (m, 2H); LC-MS: >95% 254 nm, R$_T$=0.89 min, MS (ES) 510 [M+H]$^+$.

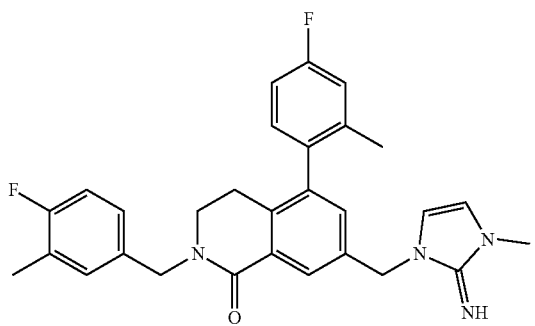 [SMILES: Cc1cc(CN2CCc3c(cc(Cn4ccn(C)c4=N)cc3-c3ccc(F)cc3C)C2=O)ccc1F]

Example 31

5-(4-Fluoro-2-methylphenyl)-2-(4-fluoro-3-methylbenzyl)-7-((2-imino-3-methyl-2,3-dihydro-1H-imidazol-1-yl)methyl)-3,4-dihydroisoquinolin-1(2H)-one The title compound (10 mg, 17%, over two steps) was prepared following the procedure described in Example 27 using 7-(bromomethyl)-5-(4-fluoro-2-methylphenyl)-2-(4-fluoro-3-methylbenzyl)-3,4-dihydroisoquinolin-1(2H)-one (Intermediate 45) and 1-methyl-1H-imidazol-2-amine. H NMR (400 MHz, CDCl$_3$) δ 8.03 (s, 1H), 7.30 (s, 1H), 7.11 (m, 2H), 6.97 (m, 4H), 6.47 (m, 2H), 5.26 (s, 2H), 4.67 (m, 2H), 3.59 (s, 3H), 3.36 (t, J=6.4 Hz, 2H), 2.57 (m, 2H), 2.24 (s, 3H), 2.00 (s, 3H); LC-MS: >95% 254 nm, R$_T$=1.12 min, MS (ES) 487 [M+H]$^+$.

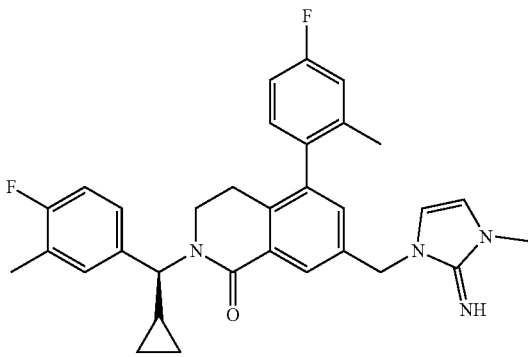 [SMILES: Cc1cc([C@H](C2CC2)N2CCc3c(cc(Cn4ccn(C)c4=N)cc3-c3ccc(F)cc3C)C2=O)ccc1F]

Example 32

(S)-2-(Cyclopropyl(4-fluoro-3-methylphenyl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one The title compound (13.6 mg, 69%) was prepared following the procedure described in Example 27 using (S)-7-(bromomethyl)-2-(cyclopropyl(4-fluoro-3-methylphenyl)methyl)-5-(4-fluoro-2-methylphenyl)-3,4-dihydroisoquinolin-1(2H)-one (Intermediate 47) and 1-methyl-1H-imidazol-2-amine. $^1$H NMR (400 MHz, CDCl$_3$) δ 8.01 (d, J=2.0 Hz, 1H), 7.27 (m, 3H), 6.91 (m, 4H), 6.48 (m, 2H), 5.27 (s, 2H), 5.12 (d, J=10.0 Hz, 1H), 3.59 (s, 3H), 3.47 (m, 1H), 3.19 (m, 1H), 2.47 (m, 2H), 2.24 (s, 3H), 2.04 (s, 1.5H), 1.98 (s, 1.5H), 1.27 (m, 1H), 0.85 (m, 1H), 0.48 (m, 3H); LC-MS: >95% 254 nm, R$_T$=1.21 min, MS (ES) 427 [M+H]$^+$.

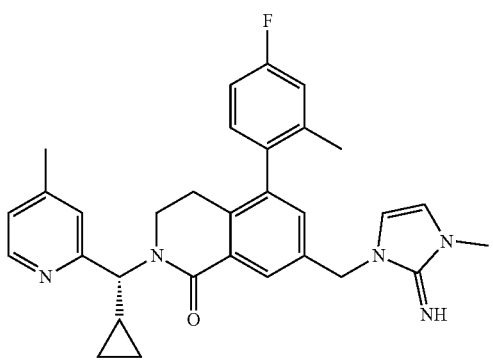

Example 33

(R)-2-(Cyclopropyl(4-methylpyridin-2-yl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one The title compound (16 mg) was prepared from the procedure described in Example using (R)-7-(bromomethyl)-2-(cyclopropyl(4-methylpyridin-2-yl)methyl)-5-(4-fluoro-2-methylphenyl)-3,4-dihydroisoquinolin-1(2H)-one (Intermediate 48) and 1-methyl-1H-imidazol-2-amine. $^1$H NMR (400 MHz, CDCl$_3$) δ 8.40 (t, J=4.8 Hz, 1H), 7.96 (s, 1H), 7.24 (m, 2H), 6.92 (m, 4H), 6.46 (s, 2H), 5.23 (s, 2H), 5.04 (dd, J=3.2, 10.0 Hz, 1H), 3.65 (m, 2H), 3.58 (s, 3H), 2.52 (m, 2H), 2.33 (m, 3H), 2.05 (s, 1.5H), 1.97 (s, 1.5H), 1.61 (m, 1H), 0.77 (m, 1H), 0.62 (m, 1H), 0.52 (m, 2H); LC-MS: >95% 254 nm, R$_T$=0.89 min, MS (ES) 510 [M+H]$^+$.

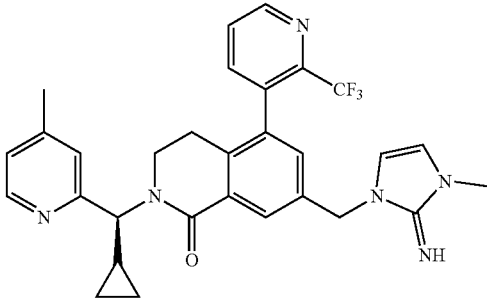 [SMILES: Cc1ccnc([C@H](C2CC2)N2CCc3c(cc(Cn4ccn(C)c4=N)cc3-c3cccnc3C(F)(F)F)C2=O)c1]

Example 34

(S)-2-(Cyclopropyl(4-fluoro-3-methylphenyl)methyl)-7-((2-imino-3-methyl-2,3-dihydro-1H-imidazol-1-yl)methyl)-5-(2-(trifluoromethyl)pyridin-3-yl)-3,4-dihydroisoquinolin-1(2H)-one The title compound (12.8 mg, 44%, over two steps) was prepared from the procedure described in Example 27 using (S)-7-(bromomethyl)-2-(cyclopropyl(4-fluoro-3-methylphenyl)methyl)-5-(2-(trifluoromethyl)pyridin-3-yl)-3,4-dihydroisoquinolin-1(2H)-one (Intermediate 23) and 1-methyl-1H-imidazol-2-amine. $^1$H NMR (400 MHz, CDCl$_3$) δ 8.73 (m, 1H), 8.07 (m, 1H), 7.70 (m, 1H), 7.56 (m, 1H), 7.32 (m, 1H), 7.25 (m, 2H), 6.95 (m, 1H), 6.48 (m, 2H), 5.27 (m, 2H), 5.12 (d, J=10.0 Hz, 1H), 3.73 (s, 3H), 3.49 (m, 1H), 3.19 (m, 1H), 2.47 (m, 2H), 2.25 (s, 3H), 1.29 (m, 1H), 0.87 (m, 1H), 0.60 (m, 2H), 0.50 (m, 1H); LC-MS: >95% 254 nm, R$_T$=1.10 min, MS (ES) 564 [M+H]$^+$.

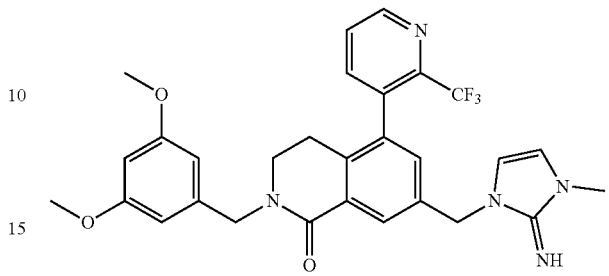

Example 35

2-(3,5-Dimethoxybenzyl)-7-((2-imino-3-methyl-2,3-dihydro-1H-imidazol-1-yl)methyl)-5-(2-(trifluoromethyl)pyridin-3-yl)-3,4-dihydroisoquinolin-1(2H)-one The title compound (13.2 mg, 60%) was prepared from the procedure described in Example 27 using 7-(bromomethyl)-2-(3,5-dimethoxybenzyl)-5-(2-(trifluoromethyl)pyridin-3-yl)-3,4-dihydroisoquinolin-1(2H)-one (Intermediate 50) and 1-methyl-1H-imidazol-2-amine. $^1$H NMR (400 MHz, CDCl$_3$) δ 8.73 (m, 1H), 8.08 (s, 1H), 7.65 (m, 1H), 7.55 (dd, J=4.8, 7.6 Hz, 1H), 7.31 (s, 1H), 6.47 (m, 4H), 6.35 (m, 1H), 5.27 (s, 2H), 4.75 (d, J=14.8 Hz, 1H), 6.59 (d, J=14.8 Hz, 1H), 3.75 (s, 6H), 3.57 (s, 3H), 3.38 (t, J=6.4 Hz, 2H), 2.53 (m, 2H); LC-MS: >95% 254 nm, R$_T$=0.93 min, MS (ES) 552 [M+H]$^+$.

Example 36

(S)-2-(Cyclopropyl(4-methylpyridin-2-yl)methyl)-7-((2-imino-3-methyl-2,3-dihydro-1H-imidazol-1-yl)methyl)-5-(2-(trifluoromethyl)pyridin-3-yl)-3,4-dihydroisoquinolin-1(2H)-one The title compound (7.9 mg, 32%, over two steps) was prepared from the procedure described in Example 27 using (S)-7-(bromomethyl)-2-(cyclopropyl(4-methylpyridin-2-yl)methyl)-5-(2-(trifluoromethyl)pyridin-3-yl)-3,4-dihydroisoquinolin-1(2H)-one (Intermediate 51) and 1-methyl-1H-imidazol-2-amine. $^1$H NMR (400 MHz, CDCl$_3$) δ 8.74 (m, 1H), 8.38 (m, 1H), 8.01 (d, J=1.6 Hz, 1H), 7.68 (dd, J=6.4, 8.0

Hz, 1H), 7.55 (m, 1H), 7.29 (s, 1H), 7.24 (s, 1H), 7.00 (m, 1H), 6.47 (m, 2H), 5.25 (m, 2H), 5.04 (dd, J=6.0, 10.0 Hz, 1H), 3.68 (m, 2H), 3.58 (s, 3H), 2.53 (m, 2H), 2.33 (s, 3H), 1.60 (m, 1H), 0.77 (m, 1H), 0.62 (m, 1H), 0.50 (m, 2H); LC-MS: >95% 254 nm, $R_T$=0.77 min, MS (ES) 547 [M+H]$^+$.

2-(3,5-dimethoxybenzyl)-5-(4-fluoro-2-methylphenyl)-3,4-dihydroisoquinolin-1(2H)-one (Intermediate 11) and 1-cyclopropyl-1H-imidazol-2-amine. $^1$H NMR (400 MHz, CDCl$_3$) δ7.99 (d, J=1.6 Hz, 1H), 7.34 (d, J=1.6 Hz, 1H), 6.95 (m, 3H), 6.43 (m, 5H), 5.27 (s, 2H), 4.69 (m, 2H), 3.77 (s, 6H), 3.39 (t, J=6.4 Hz, 2H), 3.15 (m, 1H), 2.59 (m, 2H), 2.02 (s, 3H), 1.18 (m, 2H), 0.98 (m, 2H); LC-MS: >95% 254 nm, $R_T$=1.12 min, MS (ES) 541 [M+H]$^+$.

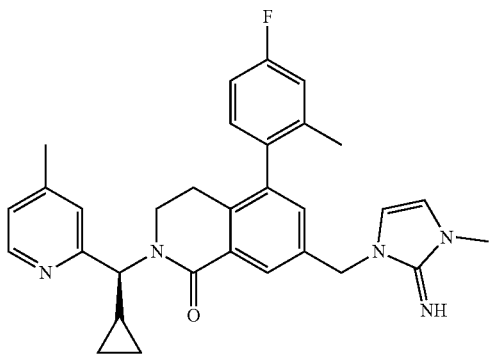

Example 37

(S)-2-(Cyclopropyl(4-methylpyridin-2-yl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one The title compound (16.6 mg, 30%, over two steps) was prepared from the procedure described in Example 27 using (S)-7-(bromomethyl)-2-(cyclopropyl(4-methylpyridin-2-yl)methyl)-5-(4-fluoro-2-methylphenyl)-3,4-dihydroisoquinolin-1(2H)-one (Intermediate 30) and 1-methyl-1H-imidazol-2-amine. $^1$H NMR (400 MHz, CDCl$_3$) δ 8.40 (t, J=4.8 Hz, 1H), 7.96 (s, 1H), 7.24 (m, 2H), 6.92 (m, 4H), 6.46 (s, 2H), 5.23 (s, 2H), 5.04 (dd, J=3.2, 10.0 Hz, 1H), 3.65 (m, 2H), 3.58 (s, 3H), 2.52 (m, 2H), 2.34 (m, 1.5H), 2.33 (s, 1.5H), 2.05 (s, 1.5H), 1.97 (s, 1.5H), 1.61 (m, 1H), 0.77 (m, 1H), 0.62 (m, 1H), 0.52 (m, 2H); LC-MS: >95% 254 nm, RT=0.89 min, MS (ES) 510 [M+H]$^+$.

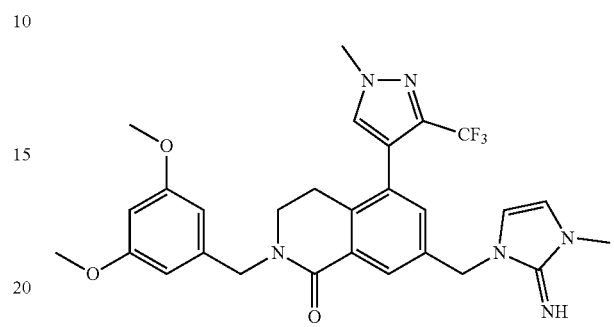

Example 39

2-(3,5-Dimethoxybenzyl)-7-((2-imino-3-methyl-2,3-dihydro-1H-imidazol-1-yl)methyl)-5-(1-methyl-3-(trifluoromethyl)-1H-pyrazol-4-yl)-3,4-dihydroisoquinolin-1(2H)-one The title compound (20.7 mg, 66%) was prepared from the procedure described in Example 27 using 7-(bromomethyl)-2-(3,5-dimethoxybenzyl)-5-(1-methyl-3-(trifluoromethyl)-1H-pyrazol-4-yl)-3,4-dihydroisoquinolin-1(2H)-one (Intermediate 27) and 1-methyl-1H-imidazol-2-amine. $^1$H NMR (400 MHz, CDCl$_3$) δ 8.01 (d, J=1.6 Hz, 1H), 7.47 (s, 1H), 7.34 (d, =1.6 Hz, 1H), 6.50 (s, 2H), 6.44 (s, 2H), 6.38 (m, 1H), 5.24 (s, 2H), 4.69 (s, 2H), 4.13 (s, 3H), 3.77 (s, 6H), 3.61 (s, 3H), 3.41 (t, J=6.4 Hz, 2H), 2.75 (t, J=6.4 Hz, 2H); LC-MS: >95% (254 nm), $R_T$=0.92 min, MS (ES) 555 [M+H]$^+$.

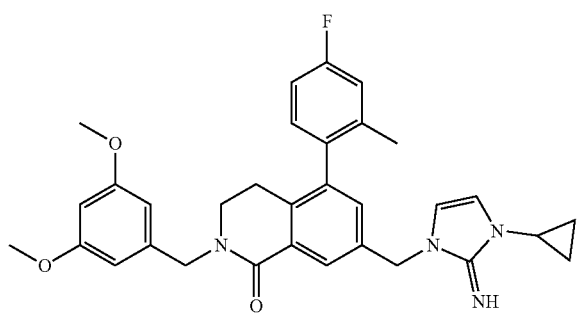 [SMILES: COc1cc(CN2CCc3c(cc(Cn4ccn(C5CC5)c4=N)cc3-c3ccc(F)cc3C)C2=O)cc(OC)c1]

Example 38

7-((3-Cyclopropyl-2-imino-2,3-dihydro-1H-imidazol-1-yl)methyl)-2-(3,5-dimethoxybenzyl)-5-(4-fluoro-2-methylphenyl)-3,4-dihydroisoquinolin-1(2H)-one The title compound (20 mg, 84%) was prepared from the procedure described in Example 27 using 7-(bromomethyl)-

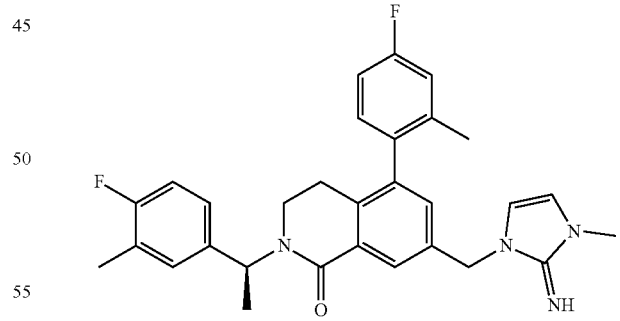

Example 40

(S)-5-(4-Fluoro-2-methylphenyl)-2-(1-(4-fluoro-3-methylphenyl)ethyl)-7-((2-imino-3-methyl-2,3-dihydro-1H-imidazol-1-yl)methyl)-3,4-dihydroisoquinolin-1(2H)-one The title compound (22.7 mg, 70%) was prepared from the procedure described in Example 27 using (S)-7-(bromomethyl)-5-(4-fluoro-2-methylphenyl)-2-(1-(4-fluoro-3-methylphenyl)ethyl)-3,4-dihydroisoquinolin-1(2H)-one (Intermediate 52) and 1-methyl-1H-imidazol-2-amine. $^1$H NMR (400 MHz, CDCl$_3$) δ 7.97 (s, 1H), 7.08 (m, 3H), 6.85 (m, 4H), 6.08 (m, 1H), 6.03 (s, 2H), 4.75 (s, 2H), 3.17 (m, 1H), 3.13 (s, 3H), 2.89 (m, 1H), 2.33 (m, 2H), 2.17 (s, 3H), 1.94 (s, 1.5H), 1.89 (s, 1.5H), 1.46 (m, 3H); LC-MS: >95% 254 nm, R$_T$=1.05 min, MS (ES) 501 [M+H]$^+$.

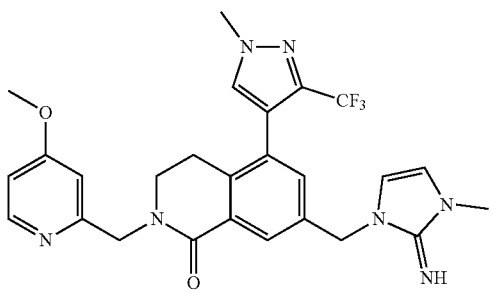 [SMILES: COc1ccnc(CN2CCc3c(cc(Cn4ccn(C)c4=N)cc3-c3cn(C)nc3C(F)(F)F)C2=O)c1]

Example 41

7-((2-Imino-3-methyl-2,3-dihydro-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (23 mg, 0.04 mmol, 68%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 1-methyl-1H-imidazol-2-amine (11 mg, 0.12 mmol, 2 equiv) for 2-methyl-1H-imidazole. LC-MS: >95% (254 nm), R$_T$=0.863 min, MS (ES) 472 [M+H]$^+$.

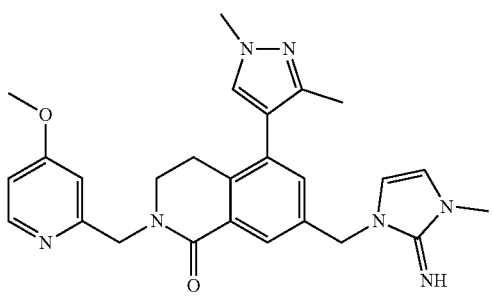

Example 42

5-(1,3-Dimethyl-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one The title compound (25 mg, 0.053 mmol, 80%) was prepared following the procedures described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and 1-methyl-1H-imidazol-2-amine (13 mg, 0.13 mmol, 2 equiv) in Step D. LC-MS: >95% (254 nm), RT=0.863 min, MS (ES) 472 [M+H]$^+$.

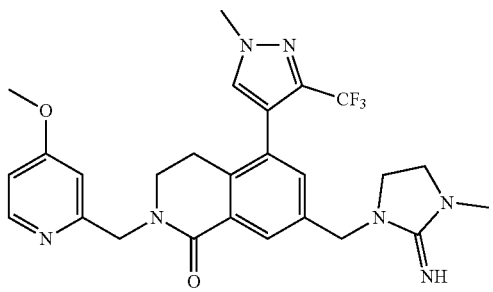 [SMILES: COc1ccnc(CN2CCc3c(cc(CN4CCN(C)C4=N)cc3-c3cn(C)nc3C(F)(F)F)C2=O)c1]

Example 43

7-((2-Imino-3-methylimidazolidin-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (18 mg, 0.031 mmol, 53%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 1-methyl-4,5-dihydro-1H-imidazol-2-amine (10 mg, 0.12 mmol, 2 equiv) in Step I. LC-MS: >95% (254 nm), R$_T$=1.079 min, MS (ES) 528 [M+H]$^+$.

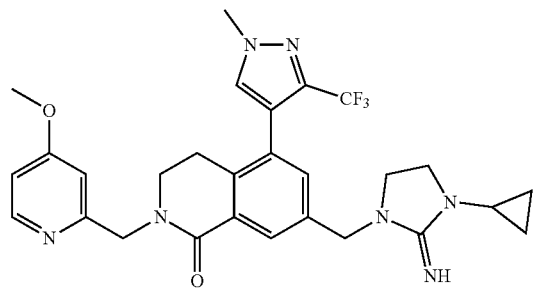 [SMILES: COc1ccnc(CN2CCc3c(cc(CN4CCN(C5CC5)C4=N)cc3-c3cn(C)nc3C(F)(F)F)C2=O)c1]

Example 44

7-((3-Cyclopropyl-2-iminoimidazolidin-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (15 mg, 0.027 mmol, 46%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 1-cyclopropyl-4,5-dihydro-1H-imidazol-2-amine (15 mg, 0.12 mmol, 2 equiv) in Step I. LC-MS: >95% (254 nm), R$_T$=1.154 min, MS (ES) 554 [M+H]$^+$.

195

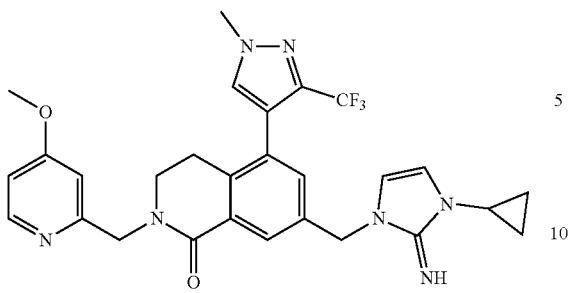

Example 45

7-((3-Cyclopropyl-2-imino-2,3-dihydro-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (24 mg, 0.042 mmol, 71%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 1-cyclopropyl-1H-imidazol-2-amine (15 mg, 0.12 mmol, 2 equiv) in Step I. LC-MS: >95% (254 nm), $R_T$=0.082 min, MS (ES) 552 [M+H]$^+$.

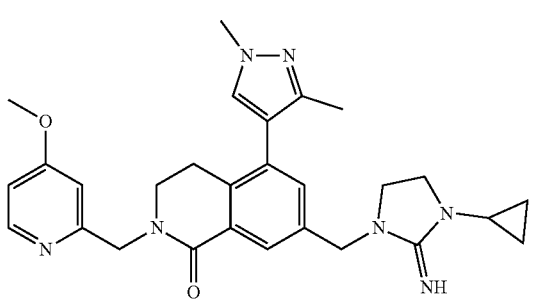

Example 46

7-((3-Cyclopropyl-2-iminoimidazolidin-1-yl)methyl)-5-(1,3-dimethyl-1H-pyrazol-4-yl)-2-((4-methoxypyridin-2-yl)methyl)-3,4-dihydroisoquinolin-1(2H)-one The title compound (20 mg, 0.04 mmol, 61%) was prepared following the procedures described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and 1-cyclopropyl-4,5-dihydro-1H-imidazol-2-amine (16 mg, 0.13 mmol, 2 equiv) in Step D. LC-MS: >95% (254 nm), $R_T$=0.083 min, MS (ES) 500 [M+H]$^+$.

196

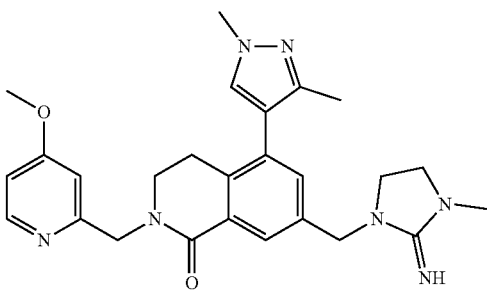

Example 47

5-(1,3-Dimethyl-1H-pyrazol-4-yl)-7-((2-imino-3-methylimidazolidin-1-yl)methyl)-2-((4-methoxypyridin-2-yl)methyl)-3,4-dihydroisoquinolin-1(2H)-one The title compound (22 mg, 0.046 mmol, 71%) was prepared following the procedures described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and 1-methyl-4,5-dihydro-1H-imidazol-2-amine (13 mg, 0.13 mmol, 2 equiv) in Step D. LC-MS: >95% (254 nm), $R_T$=0.084 min, MS (ES) 474 [M+H]$^+$.

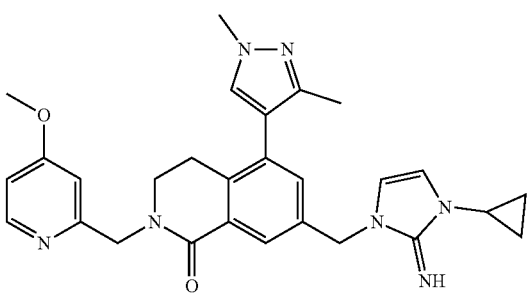 [SMILES: COc1ccnc(CN2CCc3c(cc(Cn4ccn(C5CC5)c4=N)cc3-c3cn(C)nc3C)C2=O)c1]

Example 48

7-((3-Cyclopropyl-2-imino-2,3-dihydro-1H-imidazol-1-yl)methyl)-5-(1,3-dimethyl-1H-pyrazol-4-yl)-24(4-methoxypyridin-2-yl)methyl)-3,4-dihydroisoquinolin-1(2H)-one The title compound (26 mg, 0.052 mmol, 79%) was prepared following the procedures described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and 1-cyclopropyl-1H-imidazol-2-amine (16 mg, 0.13 mmol, 2 equiv) in Step D. LC-MS: >95% (254 nm), $R_T$=0.082 min, MS (ES) 498 [M+H]$^+$.

197

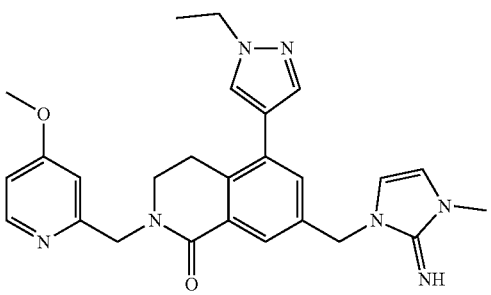

Example 49

5-(1-Ethyl-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one The title compound (45 mg, 0.095 mmol, 87%) was prepared following the procedure described in Example 8 using 7-(bromomethyl)-5-(1-ethyl-1H-pyrazol-4-yl)-2-((4-methoxypyridin-2-yl)methyl)-3,4-dihydroisoquinolin-1(2H)-one and 1-methyl-1H-imidazol-2-amine (21 mg, 0.22 mmol, 2 equiv). $^1$H NMR (400 MHz, Methanol-$d_4$) δ 8.56 (d, J=7.7 Hz, 1H), 8.11 (s, 1H), 7.92 (s, 1H), 7.87 (d, J=1.6 Hz, 1H), 7.56 (d, J=1.5 Hz, 1H), 7.45-7.41 (m, 2H), 6.99 (q, J=2.5 Hz, 2H), 5.27 (s, 2H), 5.15 (s, 2H), 4.31-4.26 (m, 2H), 4.12 (s, 3H), 3.76 (t, J=6.6 Hz, 2H), 3.58 (s, 3H), 3.25 (t, J=6.8 Hz, 2H), 1.53 (d, J=7.3 Hz, 3H); LC-MS: >95% (254 nm), $R_T$=0.946 min, MS (ES) 472 [M+H]$^+$.

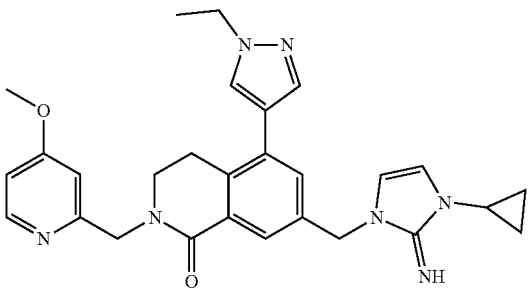 [SMILES: CCn1cc(-c2cc(Cn3ccn(C4CC4)c3=N)cc3c2CCN(Cc2cc(OC)ccn2)C3=O)cn1]

Example 50

7-((3-Cyclopropyl-2-imino-2,3-dihydro-1H-imidazol-1-yl)methyl)-5-(1-ethyl-1H-pyrazol-4-yl)-2-((4-methoxypyridin-2-yl)methyl)-3,4-dihydroisoquinolin-1(2H)-one The title compound (42 mg, 0.084 mmol, 77%) was prepared following the procedures described in Example 8 using 7-(bromomethyl)-5-(1-ethyl-1H-pyrazol-4-yl)-24(4-methoxypyridin-2-yl)methyl)-3,4-dihydroisoquinolin-1(2H)-one and 1-cyclopropyl-1H-imidazol-2-amine (27 mg, 0.22 mmol, 2 equiv). LC-MS: >95% (254 nm), $R_T$=0.087 min, MS (ES) 498 [M+H]$^+$.

198

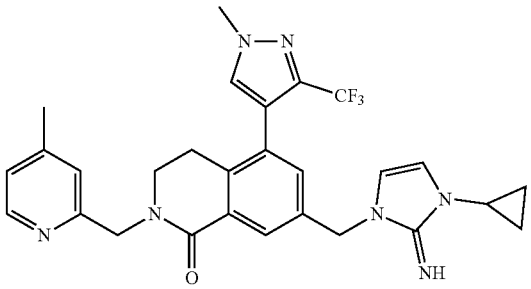 [SMILES: Cc1ccnc(CN2CCc3c(cc(Cn4ccn(C5CC5)c4=N)cc3-c3cn(C)nc3C(F)(F)F)C2=O)c1]

Example 51

7-((3-Cyclopropyl-2-imino-2,3-dihydro-1H-imidazol-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one The title compound (31 mg, 0.058 mmol, 71%) was prepared following the procedure described in Example 8 using 7-(bromomethyl)-5-(1-methyl-3-(trifluoromethyl)-1H-pyrazol-4-yl)-2-((4-methylpyridin-2-yl)methyl)-3,4-dihydroisoquinolin-1(2H)-one (Intermediate 54) and 1-cyclopropyl-1H-imidazol-2-amine (20 mg, 0.16 mmol, 2 equiv). $^1$H NMR (400 MHz, Methanol-$d_4$) δ 8.53 (d, J=5.8 Hz, 1H), 7.93 (d, J=2.0 Hz, 1H), 7.80 (s, 1H), 7.69 (s, 1H), 7.62 (dt, J=5.8, 1.2 Hz, 1H), 7.34 (d, J=2.0 Hz, 1H), 6.95 (d, J=2.6 Hz, 1H), 6.84 (d, J=2.6 Hz, 1H), 5.17 (s, 2H), 4.98 (s, 2H), 4.01 (s, 3H), 3.70 (t, J=6.6 Hz, 2H), 3.16 (dt, J=7.0, 3.5 Hz, 1H), 2.95 (t, J=6.6 Hz, 2H), 2.57 (s, 3H), 1.20-1.11 (m, 2H), 1.04 0.96 (m, 2H); $^{19}$F NMR (376 MHz, Methanol-$d_4$) δ −60.96; LC-MS: >95% (254 nm), $R_T$=0.998 min, MS (ES) 536 [M+H]$^+$.

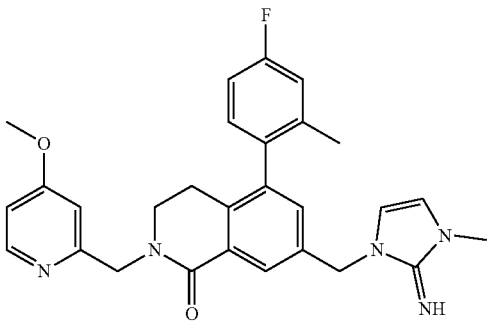

Example 52

5-(4-fluoro-2-methylphenyl)-7-((2-imino-3-methyl-2,3-dihydro-1H-imidazol-1-yl)methyl)-2-((4-methoxypyridin-2-yl)methyl)-3,4-dihydroisoquinolin-1(2H)-one The title compound was prepared (5.1 mg, 0.011 mmol) according to procedures described in Example 8 using 7-(bromomethyl)-5-(4-fluoro-2-methylphenyl)-2-((4-methoxypyridin-2-yl)methyl)-3,4-dihydroisoquinolin-1(2H)-one (Intermediate 55) and 1-methyl-1H-imidazol-2-amine. $^1$H NMR (400 MHz, Chloroform-d) δ 8.36 (d, J=5.6 Hz, 1H), 8.03 (d, J=2.0 Hz, 1H), 7.49 (d, J=2.0 Hz, 1H), 7.05-7.01 (m, 1H), 6.97-6.87 (m, 4H), 6.74 (dd, J=5.6, 2.4 Hz, 1H), 6.49-6.46 (m, 2H), 5.47 (s, 2H), 4.83-4.80 (m, 2H), 3.82 (s, 3H), 3.73 (s, 3H), 3.53 (t, J=6.8 Hz, 2H), 2.71-2.52 (m, 2H), 2.02 (s, 3H). $^{19}$F NMR (376 MHz, Chloroform-d) δ -114.93. LC-MS: >95% 254 nm, $R_T$=1.068 min, MS (ES) 486.0 [M+H]$^+$.

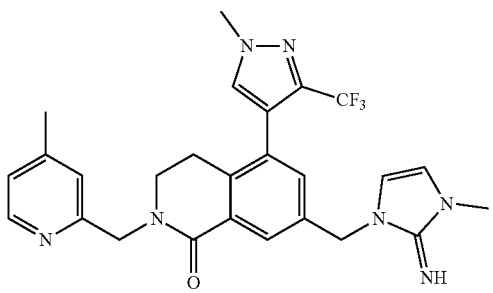 [SMILES: Cc1ccnc(CN2CCc3c(cc(Cn4ccn(C)c4=N)cc3-c3cn(C)nc3C(F)(F)F)C2=O)c1]

Example 53

7-((2-Imino-3-methyl-2,3-dihydro-1H-imidazol-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one The title compound (33 mg, 0.08 mmol, 65%) was prepared following the procedures described in Example 8 using 7-(bromomethyl)-5-(1-methyl-3-(trifluoromethyl)-1H-pyrazol-4-yl)-2-((4-methylpyridin-2-yl)methyl)-3,4-dihydroisoquinolin-1(2H)-one (Intermediate 54) and 1-methyl-1H-imidazol-2-amine. LC-MS: >95% (254 nm), $R_T$=0.942 min, MS (ES) 510 [M+H]$^+$.

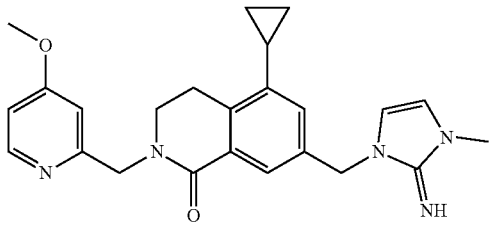

Example 54

5-Cyclopropyl-7-((2-imino-3-methyl-2,3-dihydro-1H-imidazol-1-yl)methyl)-2-((4-methoxypyridin-2-yl)methyl)-3,4-dihydroisoquinolin-1(2H)-one The title compound (11 mg, 0.026 mmol,) was prepared following the procedures described in Example 8 using 7-(bromomethyl)-5-cyclopropyl-2-((4-methoxypyridin-2-yl)methyl)-3,4-dihydroisoquinolin-1(2H)-one and 1-methyl-1H-imidazol-2-amine. $^1$H NMR (DMSO d$_6$) δ 8.33 (d, J=5.8 Hz, 1H), 7.64 (s, 1H), 7.16 (s, 1H), 6.89-6.86 (m, 1H), 6.84 (d, J=2.4 Hz, 1H), 6.44 (d, J=2.6 Hz, 1H), 6.38 (d, J=2.6 Hz, 1H), 4.74 (s, 2H), 4.71 (s, 2H), 3.81 (s, 3H), 3.62 (t, J=6.6 Hz, 2H), 3.11-3.08 (m, 5H), 1.98-1.91 (m, 1H), 0.96-0.91 (m, 2H), 0.63-0.59 (m, 2H); LCMS method 1: $R_T$=0.84 min, MS (ES) 418.0 [M+H]$^+$.

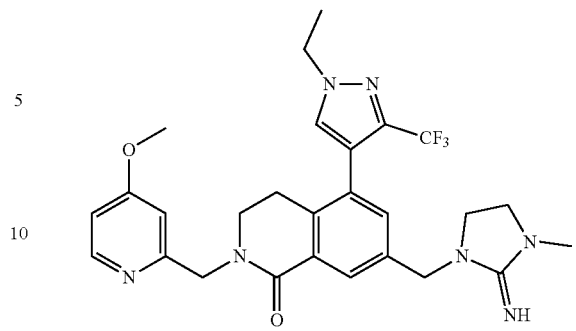

Example 55

5-(1-Ethyl-3-(trifluoromethyl)-1H-pyrazol-4-yl)-7-((2-imino-3-methylimidazolidin-1-yl)methyl)-2-((4-methoxypyridin-2-yl)methyl)-3,4-dihydroisoquinolin-1(2H)-one The title compound (19 mg, 0.035 mmol, 46%) was prepared following the procedure described in Example 8 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and 1-methyl-4,5-dihydro-1H-imidazol-2-amine (15 mg, 0.15 mmol, 2 equiv). LC-MS: >95% (254 nm), $R_T$=0.090 min, MS (ES) 542 [M+H]$^+$.

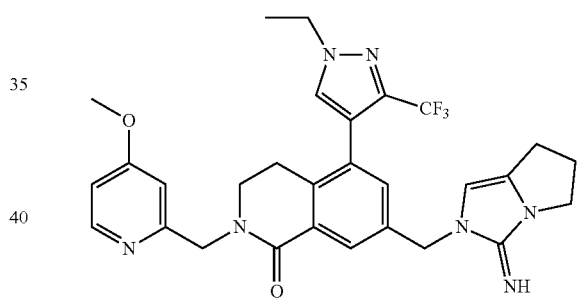

Example 56

5-(1-Ethyl-3-(trifluoromethyl)-1H-pyrazol-4-yl)-7-((3-imino-6,7-dihydro-3H-pyrrolo[1,2-c]imidazol-2(5H)-yl)methyl)-2-((4-methoxypyridin-2-yl)methyl)-3,4-dihydroisoquinolin-1(2H)-one The title compound (35 mg, 0.062 mmol, 81%) was prepared following the procedures described in Example 8 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and 6,7-dihydro-5H-pyrrolo[1,2-c]imidazol-3-amine (16 mg, 0.16 mmol, 2 equiv). $^1$H NMR (400 MHz, Methanol-d$_4$) δ 8.60-8.54 (m, 1H), 7.95 (d, J=2.0 Hz, 1H), 7.84 (d, J=1.0 Hz, 1H), 7.47-7.41 (m, 2H), 7.37 (d, J=2.0 Hz, 1H), 6.56 (t, J=1.6 Hz, 1H), 5.12 (s, 2H), 4.99 (s, 2H), 4.30 (q, J=7.3 Hz, 2H), 4.13 (s, 3H), 3.96-3.86 (m, 2H), 3.72 (t, J=6.6 Hz, 2H), 2.96 (t, J=6.6 Hz, 2H), 2.85 (td, J=7.5, 1.6 Hz, 2H), 2.58 (p, J=7.3 Hz, 2H), 1.53 (t, J=7.3 Hz, 3H); $^{19}$F NMR (376 MHz, Methanol-d$_4$) δ -61.00; LC-MS: >95% (254 nm), $R_T$=1.223 min, MS (ES) 566 [M+H]$^+$.

201

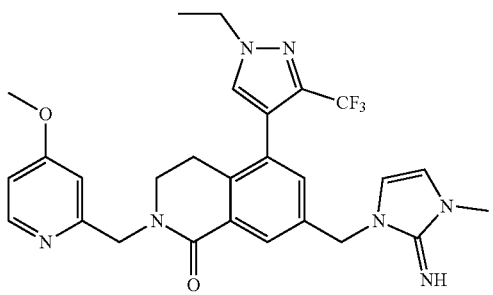

Example 57

5-(1-Ethyl-3-(trifluoromethyl)-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one The title compound (36 mg, 0.067 mmol, 87%) was prepared following the procedures described in Example 8 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and 1-methyl-1H-imidazol-2-amine (15 mg, 0.15 mmol, 2 equiv). $^1$H NMR (400 MHz, Methanol-$d_4$) δ 8.59-8.55 (m, 1H), 7.94 (d, J=2.0 Hz, 1H), 7.84 (d, J=1.0 Hz, 1H), 7.47-7.43 (m, 2H), 7.36 (d, J=2.0 Hz, 1H), 6.95 (d, J=2.5 Hz, 1H), 6.90 (d, J=2.5 Hz, 1H), 5.19 (s, 2H), 4.99 (s, 2H), 4.30 (q, J=7.3 Hz, 2H), 4.13 (s, 3H), 3.72 (t, J=6.6 Hz, 2H), 3.53 (s, 3H), 2.96 (t, J=6.6 Hz, 2H), 1.53 (t, J=7.3 Hz, 3H); LC-MS: >95% (254 nm), $R_T$=1.136 min, MS (ES) 540 [M+H]$^+$.

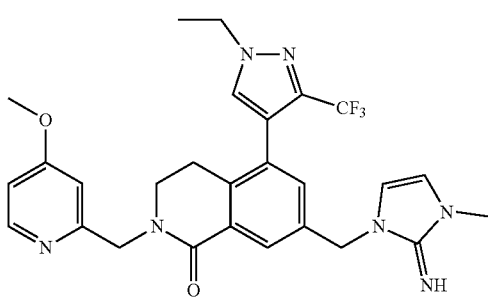

Example 58

7-((3-Cyclopropyl-2-imino-2,3-dihydro-1H-imidazol-1-yl)methyl)-5-(1-ethyl-3-(trifluoromethyl)-1H-pyrazol-4-yl)-2-((4-methoxypyridin-2-yl)methyl)-3,4-dihydroisoquinolin-1(2H)-one The title compound (33 mg, 0.058 mmol, 76%) was prepared following the procedures described in Example 8 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and 1-cyclopropyl-1H-imidazol-2-amine (19 mg, 0.15 mmol, 2 equiv). LC-MS: >95% (254 nm), $R_T$=1.212 min, MS (ES) 566 [M+H]$^+$.

202

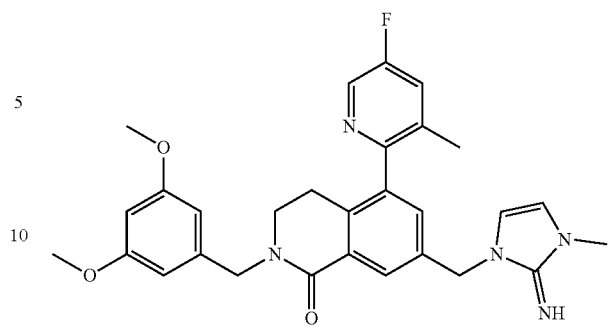

Example 59

2-(3,5-Dimethoxybenzyl)-5-(5-fluoro-3-methylpyridin-2-yl)-7-((2-imino-3-methyl-2,3-dihydro-1H-imidazol-1-yl)methyl)-3,4-dihydroisoquinolin-1(2H)-one The title compound (21.2 mg, 66%, over two steps) was prepared from the procedure described in Example 8 using 7-(bromomethyl)-2-(3,5-dimethoxybenzyl)-5-(5-fluoro-3-methylpyridin-2-yl)-3,4-dihydroisoquinolin-1(2H)-one (Intermediate 58) and 1-methyl-1H-imidazol-2-amine. $^1$H NMR (400 MHz, CDCl$_3$) δ 8.33 (d, J=2.8 Hz, 1H), 8.11 (d, J=1.6 Hz, 1H), 7.34 9m, 1H), 6.45 (d, J=2.0 Hz, 2H), 6.37 9m, 1H), 6.17 (m, 2H), 4.95 (s, 2H), 4.71 (s, 2H), 3.77 (s, 6H), 3.40 (t, J=6.4 Hz, 2H), 3.30 (s, 3H), 2.62 (m, 2H), 2.13 (s, 3H); LC-MS: >95% 254 nm, $R_T$=0.98 min, MS (ES) 516 [M+H]$^+$.

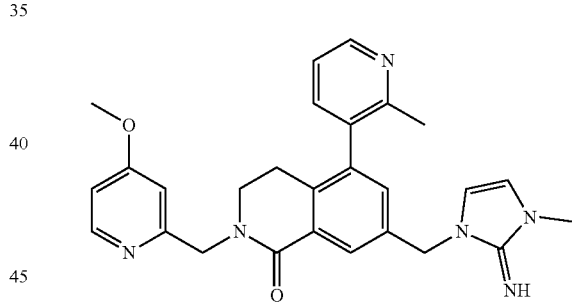

Example 60

7-((2-Imino-3-methyl-2,3-dihydro-1H-imidazol-1-yl)methyl)-2-((4-methoxypyridin-2-yl)methyl)-5-(2-methylpyridin-3-yl)-3,4-dihydroisoquinolin-1(2H)-one The title compound (6 mg, 0.013 mmol,) was prepared following the procedures described in Example 8 using 7-(bromomethyl)-24(4-methoxypyridin-2-yl)methyl)-5-(2-methylpyridin-3-yl)-3,4-dihydroisoquinolin-1(2H)-one (Intermediate 59) and 1-methyl-1H-imidazol-2-amine. $^1$H NMR (CDCl$_3$) δ 8.53 (dd, J=4.8, 1.7 Hz, 1H), 8.33 (d, J=5.6 Hz, 1H), 8.07 (d, J=1.7 Hz, 1H), 7.39 (dd, J=7.7, 1.7 Hz, 1H), 7.19-7.16 (m, 2H), 6.91 (d, J=2.4 Hz, 1H), 6.72 (dd, J=5.8, 2.5 Hz, 1H), 6.1 (s, 2H), 4.84-4.82 (m, 4H), 3.83 (s, 3H), 3.56 (t, J=6.5 Hz, 2H), 3.20 (s, 3H), 2.63-2.59 (m, 2H), 2.28 (s, 3H); LCMS method 1: $R_T$=0.15 min, MS (ES) 469.0 [M+H]$^+$.

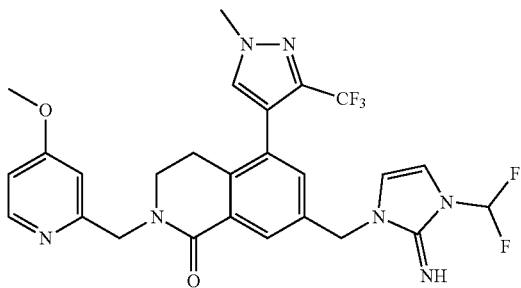 [SMILES: COc1ccnc(CN2CCc3c(cc(Cn4ccn(C(F)F)c4=N)cc3-c3cn(C)nc3C(F)(F)F)C2=O)c1]

Example 61

7-((3-(Difluoromethyl)-2-imino-2,3-dihydro-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (40 mg, 0.071 mmol, 72%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 1-(difluoromethyl)-1H-imidazol-2-amine (26 mg, 0.2 mmol, 2 equiv). LC-MS: >95% (254 nm), $R_T$=0.094 min, MS (ES) 562 [M+H]$^+$.

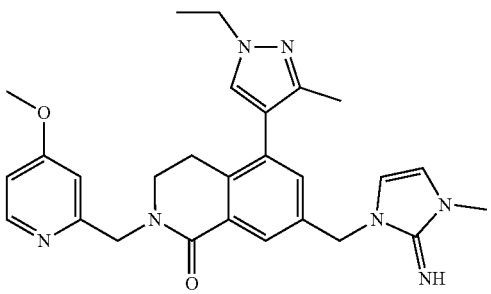

Example 63

5-(1-Ethyl-3-methyl-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one The title compound (14 mg, 0.029 mmol, 67%) was prepared following the procedure described in Example 8 using 7-(bromomethyl)-5-(1-ethyl-3-methyl-1H-pyrazol-4-yl)-2-((4-methoxypyridin-2-yl)methyl)-3,4-dihydroisoquinolin-1(2H)-one (Intermediate 60) and 1-methyl-1H-imidazol-2-amine (8 mg, 0.09 mmol, 2 equiv). $^1$H NMR (400 MHz, Methanol-d$_4$) δ 8.62-8.54 (m, 1H), 7.87 (d, J=2.0 Hz, 1H), 7.63 (s, 1H), 7.50-7.42 (m, 2H), 7.38 (d, J=2.0 Hz, 1H), 6.94 (s, 2H), 5.18 (s, 2H), 4.99 (s, 2H), 4.24-4.04 (m, 5H), 3.72 (t, J=6.6 Hz, 2H), 3.54 (s, 3H), 3.03 (t, J=6.6 Hz, 2H), 2.14 (s, 3H), 1.47 (t, J=7.3 Hz, 3H); LC-MS: >95% (254 nm), $R_T$=0.089 min, MS (ES) 486 [M+H]$^+$.

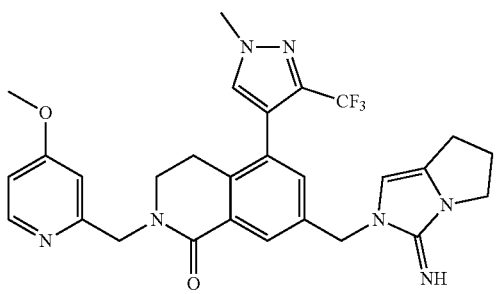 [SMILES: COc1ccnc(CN2CCc3c(cc(Cn4cc5n(c4=N)CCC5)cc3-c3cn(C)nc3C(F)(F)F)C2=O)c1]

Example 62

7-((3-Imino-6,7-dihydro-3H-pyrrolo[1,2-c]imidazol-2(5H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (42 mg, 0.076 mmol, 77%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 6,7-dihydro-5H-pyrrolo[1,2-c]imidazol-3-amine (24 mg, 0.2 mmol, 2 equiv). LC-MS: >95% (254 nm), $R_T$=1.098 min, MS (ES) 552 [M+H]$^+$.

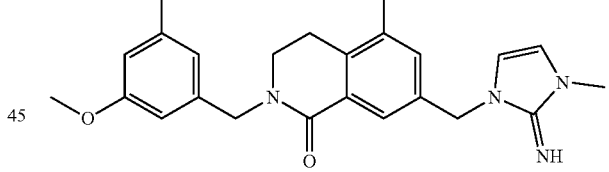

Example 64

2-(3,5-Dimethoxybenzyl)-7-((2-imino-3-methyl-2,3-dihydro-1H-imidazol-1-yl)methyl)-5-(1,3,5-trimethyl-1H-pyrazol-4-yl)-3,4-dihydroisoquinolin-1(2H)-one The title compound (8.5 mg, 18%) was prepared from the procedure described in Example 8 using 7-(bromomethyl)-2-(3,5-dimethoxybenzyl)-5-(1,3,5-trimethyl-1H-pyrazol-4-yl)-3,4-dihydroisoquinolin-1(2H)-one (Intermediate 61) and 1-methyl-1H-imidazol-2-amine. $^1$H NMR (400 MHz, CDCl$_3$) δ 8.02 (d, J=1.6 Hz, 1H), 7.18 (d, J=2.0 Hz, 1H), 6.47 (d, J=2.0 Hz, 2H), 6.38 (m, 1H), 6.19 (s, 2H), 4.94 (m, 2H), 4.75 (m, 2H), 3.77 (s, 6H), 3.76 (s, 3H), 3.39 (t, J=6.4 Hz, 2H), 3.32 (s, 3H), 2.66 (m, 2H), 2.04 (s, 3H), 2.03 (s, 3H); LC-MS: >90% 254 nm, $R_T$=0.86 min, MS (ES) 515 [M+H]$^+$.

205

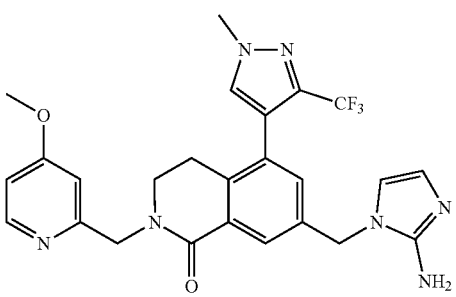 [SMILES: COc1ccnc(CN2CCc3c(cc(Cn4ccnc4N)cc3-c3cn(C)nc3C(F)(F)F)C2=O)c1]

Example 65

7-((2-Amino-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one Step A. Preparation of tert-butyl 2-imino-3-((2-((4-methoxypyridin-2-yl)methyl)-5-(1-methyl-3-(trifluoromethyl)-1H-pyrazol-4-yl)-1-oxo-1,2,3,4-tetrahydroisoquinolin-7-yl)methyl)-2,3-dihydro-1H-imidazole-1-carboxylate. The title compound (25 mg, 0.041 mmol, 83%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one) (Intermediate 18) and tert-butyl 2-amino-1H-imidazole-1-carboxylate (18 mg, 0.01 mmol, 2 equiv).

Step B. 7-((2-amino-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one. Hydrochloric acid (0.5 mL, 6 N) was added to tert-butyl 2-imino-3-((2-((4-methoxypyridin-2-yl)methyl)-5-(1-methyl-3-(trifluoromethyl)-1H-pyrazol-4-yl)-1-oxo-1,2,3,4-tetrahydroisoquinolin-7-yl)methyl)-2,3-dihydro-1H-imidazole-1-carboxylate (25 mg, 0.041 mmol, 1 equiv) in dichloromethane (0.5 mL, 0.1 M) and stirred for 12 h at 23° C. Next, the reaction mixture was concentrated. Saturated $K_2CO_3$ was then added to the residue and extracted with dichloromethane (3×1 mL). The combined organic layers were dried over $Na_2SO_4$ and concentrated in vacuo to give the title compound (12 mg, 0.023 mmol, 48%) as a white solid. $^1$H NMR (400 MHz, Methanol-$d_4$) δ 8.60-8.55 (m, 1H), 7.98 (d, J=2.0 Hz, 1H), 7.81 (d, J=1.0 Hz, 1H), 7.48-7.44 (m, 2H), 7.38 (d, J=2.0 Hz, 1H), 6.93-6.87 (m, 2H), 5.20 (s, 2H), 5.01 (s, 2H), 4.14 (s, 3H), 4.03 (s, 3H), 3.74 (t, J=6.6 Hz, 2H), 2.98 (t, J=6.6 Hz, 2H), 2.68 (s, 2H); LC-MS: >95% (254 nm), $R_T$=0.089 min, MS (ES) 512 [M+H]$^+$.

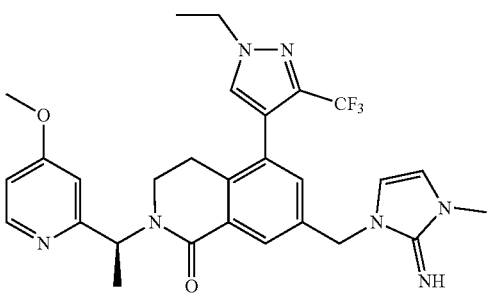 [SMILES: CCn1cc(-c2cc(Cn3ccn(C)c3=N)cc3c2CCN([C@@H](C)c2cc(OC)ccn2)C3=O)c(C(F)(F)F)n1]

206

Example 66

(S)-5-(1-Ethyl-3-(trifluoromethyl)-1H-pyrazol-4-yl)-7-((2-imino-3-methyl-2,3-dihydro-1H-imidazol-1-yl)methyl)-2-(1-(4-methoxypyridin-2-yl)ethyl)-3,4-dihydroisoquinolin-1(2H)-one The title compound (26 mg, 0.047 mmol, 84%) was prepared following the procedure described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 1-methyl-1H-imidazol-2-amine (11 mg, 0.11 mmol, 2 equiv). $^1$H NMR (400 MHz, Chloroform-d) δ 8.36 (d, J=5.7 Hz, 1H), 8.04 (d, J=2.0 Hz, 1H), 7.34 (d, J=1.1 Hz, 1H), 7.23 (d, J=2.0 Hz, 1H), 6.90 (d, J=2.5 Hz, 1H), 6.71 (dd, J=5.8, 2.5 Hz, 1H), 6.15-6.07 (m, 3H), 4.80 (s, 2H), 4.23 (q, J=7.3 Hz, 2H), 3.81 (s, 3H), 3.45 (ddd, J=13.5, 8.8, 5.2 Hz, 1H), 3.36-3.27 (m, 1H), 3.21 (s, 3H), 2.67-2.58 (m, 2H), 1.61 (d, J=7.1 Hz, 3H), 1.54 (t, J=7.3 Hz, 3H); $^{19}$F NMR (376 MHz, Chloroform-d) 6-60.04; LC-MS: >95% (254 nm), $R_T$=1.141 min, MS (ES) 554 [M+H]$^+$.

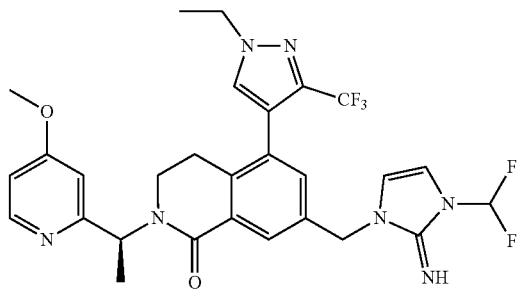 [SMILES: CCn1cc(-c2cc(Cn3ccn(C(F)F)c3=N)cc3c2CCN([C@@H](C)c2cc(OC)ccn2)C3=O)c(C(F)(F)F)n1]

Example 67

(S)-7-((3-(Difluoromethyl)-2-imino-2,3-dihydro-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound (39 mg, 0.066 mmol, 71%) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 1-(difluoromethyl)-1H-imidazol-2-amine (25 mg, 0.19 mmol, 2 equiv). $^1$H NMR (400 MHz, Chloroform-d) δ 8.36 (d, J=5.7 Hz, 1H), 8.07 (d, J=2.0 Hz, 1H), 7.34 (d, J=1.0 Hz, 1H), 7.20 (d, J=2.0 Hz, 1H), 7.13 (m, 1H), 6.90 (d, J=2.5 Hz, 1H), 6.72 (dd, J=5.7, 2.5 Hz, 1H), 6.39 (d, J=3.1 Hz, 1H), 6.17 (d, J=3.1 Hz, 1H), 6.11 (q, J=7.1 Hz, 1H), 4.69 (s, 2H), 4.24 (q, J=7.3 Hz, 2H), 3.82 (s, 3H), 3.47 (ddd, J=13.5, 8.8, 5.2 Hz, 1H), 3.34 (ddd, J=12.4, 6.7, 5.4 Hz, 1H), 2.73-2.59 (m, 2H), 1.62 (d, J=7.1 Hz, 3H), 1.55 (t, J=7.3 Hz, 3H); $^{19}$F NMR (376 MHz, Chloroform-d) δ −60.00, −98.40; LC-MS: >95% (254 nm), $R_T$=0.115 min, MS (ES) 590 [M+H]$^+$.

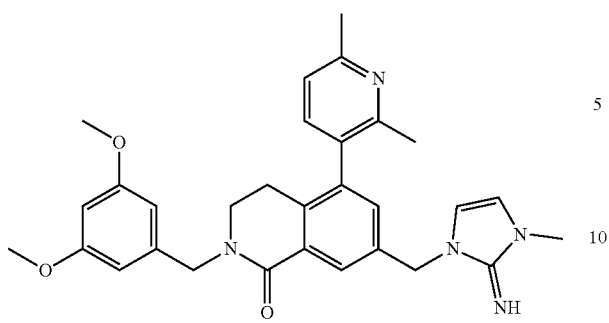

Example 68

2-(3,5-Dimethoxybenzyl)-5-(2,6-dimethylpyridin-3-yl)-7-((2-imino-3-methyl-2,3-dihydro-1H-imidazol-1-yl)methyl)-3,4-dihydroisoquinolin-1(2H)-one To a solution of 7-(bromomethyl)-2-(3,5-dimethoxybenzyl)-5-(2,6-dimethylpyridin-3-yl)-3,4-dihydroisoquinolin-1(2H)-one (Intermediate 63, 35 mg, 0.071 mmol) in acetonitrile (3 mL) was added 1-methyl-1H-imidazol-2-amine hydrochloride (19 mg, 0.142 mmol), KI (3.5 mg, 0.3 mmol), and N,N-diisopropylethylamine (37 µL, 0.213 mmol). The reaction mixture was stirred at room temperature overnight. The solvent was removed under reduced pressure and the residue was purified by reverse phase HPLC (Phenomenex Gemini C18, H$_2$O/CH$_3$CN gradient from 10-60% CH$_3$CN, 0.1% TFA). The fractions containing the desired product were combined, concentrated, basified with 0.5 M NaOH, and extracted with CHCl$_3$. The combined organic layers were dried (Na$_2$SO$_4$) and filtered. The filtrate was concentrated, dried under vacuum to yield the title compound (30.8 mg, 85%). $^1$H NMR (400 MHz, CDCl$_3$) δ 8.06 (d, J=1.6 Hz, 1H), 7.27 (m, 2H), 7.02 (d, J=8.0 Hz, 1H), 6.46 (d, J=2.8 Hz, 2H), 6.37 (m, 1H), 6.22 (s, 2H), 5.00 (m, 2H), 4.70 (m, 2H), 3.77 (s, 6H), 3.39 (m, 5H), 2.58 (m, 5H), 2.26 (s, 3H); LC-MS: >95% 254 nm, R$_T$=0.78 min, MS (ES) 513 [M+H]$^+$.

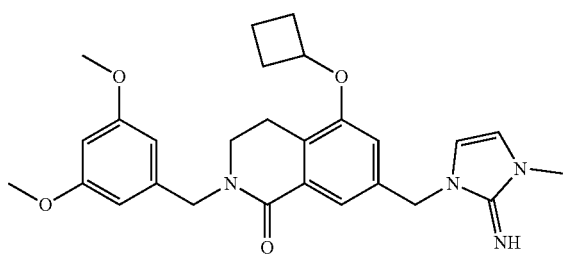

Example 69

5-Cyclobutoxy-2-(3,5-dimethoxybenzyl)-7-((2-imino-3-methyl-2,3-dihydro-1H-imidazol-1-yl)methyl)-3,4-dihydroisoquinolin-1(2H)-one The title compound (25 mg, 0.052 mmol) was prepared following the procedures described in Example 8 using 7-(Bromomethyl)-5-cyclobutoxy-2-(3,5-dimethoxybenzyl)-3,4-dihydroisoquinolin-1(2H)-one and 1-methyl-1H-imidazol-2-amine for 2-cyclopropyl-1H-imidazole. $^1$H NMR (CDCl$_3$) δ 7.61 (s, 1H), 6.75 (s, 1H), 6.46 (d, J=2.2 Hz, 2H), 6.37 (t, J=2.2 Hz, 1H), 6.09 (d, J=2.7 Hz, 1H), 6.06 (d, J=2.7 Hz, 1H), 4.72 (s, 2H), 4.71 (s, 2H), 4.65-4.57 (m, 1H), 3.76 (s, 6H), 3.43 (t, J=6.8 Hz, 2H), 3.21 (s, 3H), 2.87 (t, J=6.8 Hz, 2H), 2.44-2.37 (m, 2H), 2.15-2.05 (m, 2H), 1.87-1.79 (m, 1H), 1.73-1.61 (m, 1H); LCMS method 1: R$_T$=1.39 min, MS (ES) 477.0 [M+H]$^+$.

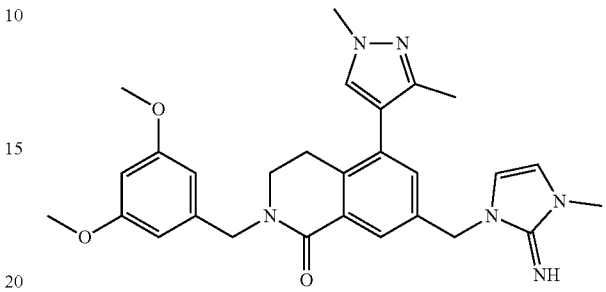

Example 70

2-(3,5-Dimethoxybenzyl)-5-(1,3-dimethyl-1H-pyrazol-4-yl)-7-((2-imino-3-methyl-2,3-dihydro-1H-imidazol-1-yl)methyl)-3,4-dihydroisoquinolin-1(2H)-one The title compound (18.2 mg, 9% over five steps) was prepared from the procedure described in Example 68 using 7-(bromomethyl)-2-(3,5-dimethoxybenzyl)-5-(1,3-dimethyl-1H-pyrazol-4-yl)-3,4-dihydroisoquinolin-1(2H)-one (Intermediate 65) and 1-methyl-1H-imidazol-2-amine. $^1$H NMR (400 MHz, CDCl$_3$) δ 8.00 (s, 1H), 7.32 (s, 1H), 7.24 (s, 1H), 6.47 (d, J=2.4 Hz, 2H), 6.38 (m, 1H), 6.25 (m, 2H), 5.04 (s, 2H), 4.71 (s, 2H), 3.89 (s, 3H), 3.77 (s, 6H), 3.40 (m, 5H), 2.80 (t, J=6.4 Hz, 2H), 2.12 (s, 3H); LC-MS: >95% 254 nm, R$_T$=0.89 min, MS (ES) 502 [M+H]$^+$.

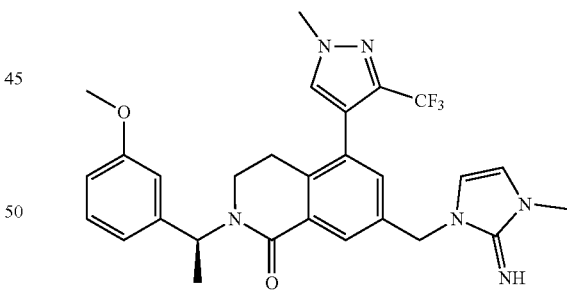

Example 71

(S)-7-((2-Imino-3-methyl-2,3-dihydro-1H-imidazol-1-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one The title compound (15 mg, 0.028 mmol, 73%) was prepared following the procedure described in Example 8 using (S)-7-(bromomethyl)-5-(1-methyl-3-(trifluoromethyl)-1H-pyrazol-4-yl)-2-(1-(4-methoxypyridin-2-yl)ethyl)-3,4-dihydroisoquinolin-1(2H)-one (Intermediate 66)

and 1-methyl-1H-imidazol-2-amine (7 mg, 0.08 mmol, 2 equiv). LC-MS: >95% (254 nm), $R_T$=0.081 min, MS (ES) 540 [M+H]⁺.

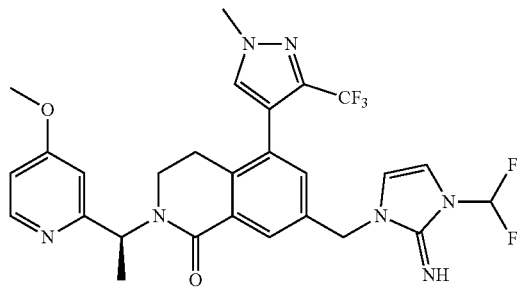 [SMILES: COc1ccnc([C@H](C)N2CCc3c(cc(Cn4ccn(C(F)F)c4=N)cc3-c3cn(C)nc3C(F)(F)F)C2=O)c1]

Example 72

(S)-7-((3-(Difluoromethyl)-2-imino-2,3-dihydro-1H-imidazol-1-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one The title compound (31 mg, 0.054 mmol, 70%) was prepared following the procedures described in Example 8 using (S)-7-(bromomethyl)-5-(1-methyl-3-(trifluoromethyl)-1H-pyrazol-4-yl)-2-(1-(4-methoxypyridin-2-yl)ethyl)-3,4-dihydroisoquinolin-1(2H)-one (Intermediate 66) and 1-(difluoromethyl)-1H-imidazol-2-amine (20 mg, 0.15 mmol, 2 equiv). LC-MS: >95% (254 nm), $R_T$=1.049 min, MS (ES) 576 [M+H]⁺.

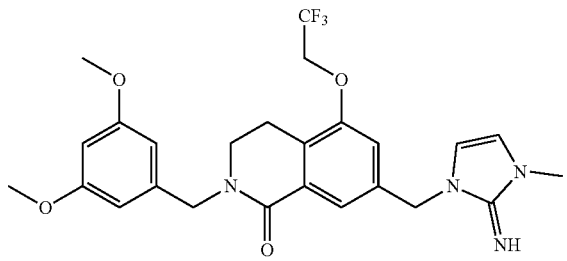

Example 73

2-(3,5-Dimethoxybenzyl)-7-((2-imino-3-methyl-2,3-dihydro-1H-imidazol-1-yl)methyl)-5-(2,2,2-trifluoroethoxy)-3,4-dihydroisoquinolin-1(2H)-one The title compound (33 mg, 0.065 mmol,) was prepared following the procedures described in Example 8 using 7-(bromomethyl)-2-(3,5-dimethoxybenzyl)-5-(2,2,2-trifluoroethoxy)-3,4-dihydroisoquinolin-1(2H)-one and 1-methyl-1H-imidazol-2-amine. ¹H NMR (CDCl₃) δ 7.87 (s, 1H), 7.68 (s, 1H), 6.63 (d, J=2.4 Hz, 1H), 6.46-6.41 (m, 3H), 6.37 (t, J=2.2 Hz, 1H), 5.38 (s, 2H), 4.70 (s, 2H), 4.55 (q, J=8.1 Hz, 2H), 3.76 (s, 6H), 3.73 (s, 3H), 3.46 (t, J=6.6 Hz, 2H), 2.93 (t, J=6.6 Hz, 2H); LCMS method 1: $R_T$=1.29 min, MS (ES) 505.0 [M+H]⁺.

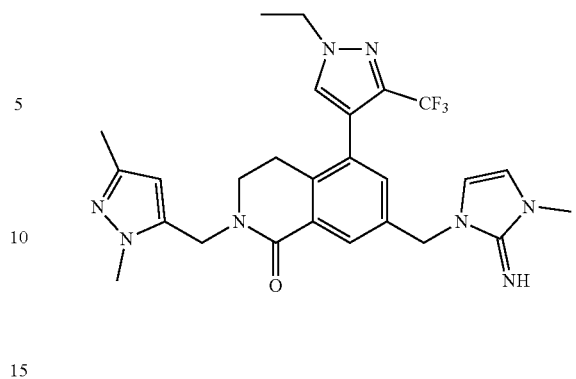

Example 74

The title compound (38 mg, 0.072 mmol, 73%) was prepared following the procedure described in Example 8 using 7-(bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one (Intermediate 31) and 1-methyl-1H-imidazol-2-amine (26 mg, 0.2 mmol, 2 equiv). ¹H NMR (400 MHz, Methanol-d₄) δ 7.93 (d, J=2.0 Hz, 1H), 7.83 (s, 1H), 7.32 (d, J=2.0 Hz, 1H), 6.97-6.90 (m, 2H), 6.15 (s, 1H), 5.19 (s, 2H), 4.82 (s, 2H), 4.28 (q, J=7.3 Hz, 2H), 3.83 (s, 3H), 3.54 (d, J=4.8 Hz, 5H), 2.83 (t, J=6.6 Hz, 2H), 2.21 (s, 3H), 1.52 (t, J=7.3 Hz, 3H); LC-MS: >95% (254 nm), $R_T$=1.178 min, MS (ES) 527 [M+H]⁺.

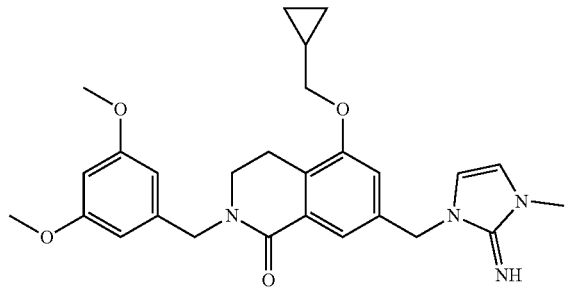

Example 75

5-(Cyclopropylmethoxy)-2-(3,5-dimethoxybenzyl)-7-((2-imino-3-methyl-2,3-dihydro-1H-imidazol-1-yl)methyl)-3,4-dihydroisoquinolin-1(2H)-one The title compound (33 mg, 0.07 mmol) was prepared following the procedures described in Example 8 using 7-(bromomethyl)-5-(cyclopropylmethoxy)-2-(3,5-dimethoxybenzyl)-3,4-dihydroisoquinolin-1(2H)-one (Intermediate 36) and 1-methyl-1H-imidazol-2-amine for 2-cyclopropyl-1H-imidazole. LCMS method 1: $R_T$=1.33 min, MS (ES) 477.0 [M+H]⁺.

211

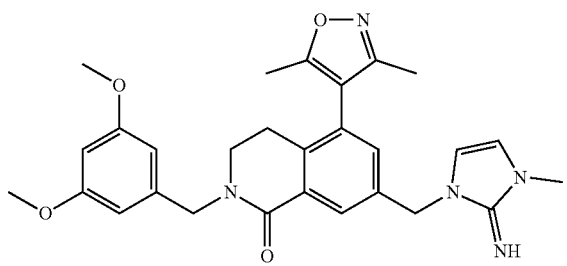

Example 76

2-(3,5-Dimethoxybenzyl)-5-(3,5-dimethylisoxazol-4-yl)-7-((2-imino-3-methyl-2,3-dihydro-1H-imidazol-1-yl)methyl)-3,4-dihydroisoquinolin-1(2H)-one The title compound (5 mg, 0.009 mmol) was prepared following the procedure described in Example 8 using 7-(bromomethyl)-2-(3,5-dimethoxybenzyl)-5-(3,5-dimethylisoxazol-4-yl)-3,4-dihydroisoquinolin-1(2H)-one (Intermediate 68, 17 mg, 0.035 mmol) and 1-methyl-1H-imidazol-2-amine (9 mg, 0.070 mmol). $^1$H NMR (CDCl$_3$) δ 8.08 (s, 1H), 7.16 (s, 1H), 6.47 (d, J=2.2 Hz, 2H), 6.37 (t, J=2.2 Hz, 1H), 6.14-6.12 (m, 2H), 4.86 (s, 2H), 4.76-4.66 (m, 2H), 3.77 (s, 6H), 3.40 (t, J=7.1 Hz, 2H), 3.23 (s, 3H), 2.67-2.63 (m, 2H), 2.21 (s, 3H), 2.07 (s, 3H); LCMS method 1: $R_T$=1.17 min, MS (ES) 502.0 [M+H]$^+$.

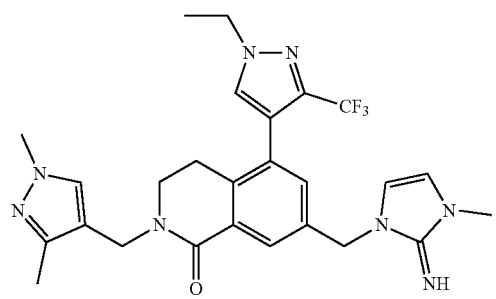 [SMILES: CCn1cc(-c2cc(Cn3ccn(C)c3=N)cc3c2CCN(Cc2cn(C)nc2C)C3=O)c(C(F)(F)F)n1]

Example 77

2-((1,3-Dimethyl-1H-pyrazol-4-yl)methyl)-5-(1-ethyl-3-(trifluoromethyl)-1H-pyrazol-4-yl)-7-((2-imino-3-methyl-2,3-dihydro-1H-imidazol-1-yl)methyl)-3,4-dihydroisoquinolin-1(2H)-one The title compound (44 mg, 0.084 mmol, 85%) was prepared following the procedures described in Example 8 using 7-(bromomethyl)-2-((1,3-dimethyl-1H-pyrazol-4-yl)methyl)-5-(1-ethyl-3-(trifluoromethyl)-1H-pyrazol-4-yl)-3,4-dihydroisoquinolin-1(2H)-one (Intermediate 37) and 1-methyl-1H-imidazol-2-amine (19 mg, 0.2 mmol, 2 equiv). LC-MS, >95% (254 nm), $R_T$=1.189 min, MS (ES) 527 [M+H]$^+$.

212

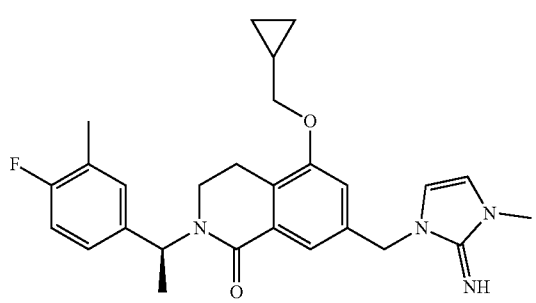 [SMILES: Cc1cc([C@H](C)N2CCc3c(OCC4CC4)cc(Cn4ccn(C)c4=N)cc3C2=O)ccc1F]

Example 78

(S)-5-(Cyclopropylmethoxy)-2-(1-(4-fluoro-3-methylphenyl)ethyl)-7-((2-imino-3-methyl-2,3-dihydro-1H-imidazol-1-yl)methyl)-3,4-dihydroisoquinolin-1(2H)-one The title compound (40 mg, 0.086 mmol,) was prepared following the procedures described in Example 8 using (S)-7-(bromomethyl)-5-(cyclopropylmethoxy)-2-(1-(4-fluoro-3-methylphenyl)ethyl)-3,4-dihydroisoquinolin-1(2H)-one and 1-methyl-1H-imidazol-2-amine. LCMS method 1: $R_T$=1.48 min, MS (ES) 463.0 [M+H]$^+$.

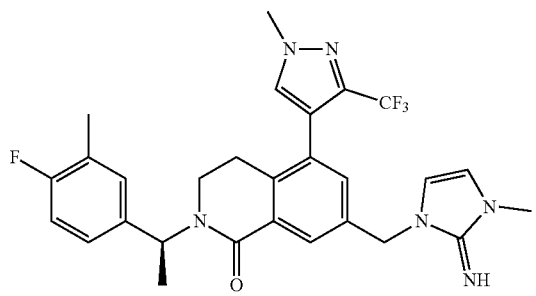 [SMILES: Cc1cc([C@H](C)N2CCc3c(cc(Cn4ccn(C)c4=N)cc3-c3cn(C)nc3C(F)(F)F)C2=O)ccc1F]

Example 79

(S)-2-(1-(4-Fluoro-3-methylphenyl)ethyl)-7-((2-imino-3-methyl-2,3-dihydro-1H-imidazol-1-yl)methyl)-5-(1-methyl-3-(trifluoromethyl)-1H-pyrazol-4-yl)-3,4-dihydroisoquinolin-1(2H)-one The title compound (56 mg, 0.1 mmol) was prepared following the procedures described in Example 8 using (S)-7-(bromomethyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one and 1-methyl-1H-imidazol-2-amine. $^1$H NMR (CDCl$_3$) δ 8.05 (d, J=1.6 Hz, 1H), 7.32 (s, 1H), 7.24 (d, J=1.8 Hz, 1H), 7.17-7.11 (m, 2H), 6.95 (t, J=8.2 Hz, 1H), 6.16-6.11 (m, 3H), 4.85 (s, 2H), 3.96 (s, 3H), 3.30-3.23 (m, 1H), 3.25 (s, 3H), 3.03-3.00 (m, 1H), 2.65-2.50 (m, 2H), 2.25 (s, 3H), 1.53 (d, J=7.1 Hz, 3H); LCMS method 1: $R_T$=1.41 min, MS (ES) 541.0 [M+H]$^+$.

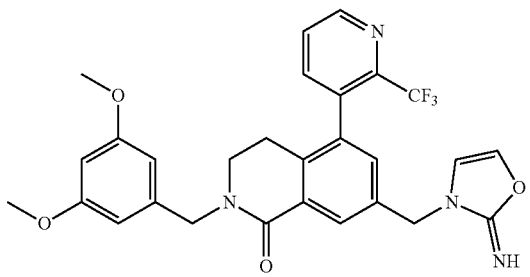 [SMILES: COc1cc(CN2CCc3c(cc(Cn4ccoc4=N)cc3-c3cccnc3C(F)(F)F)C2=O)cc(OC)c1]

Example 80

2-(3,5-Dimethoxybenzyl)-7-((2-iminooxazol-3(2H)-yl)methyl)-5-(2-(trifluoromethyl)pyridin-3-yl)-3,4-dihydroisoquinolin-1(2H)-one To a solution of 7-(bromomethyl)-2-(3,5-dimethoxybenzyl)-5-(2-(trifluoromethyl)pyridin-3-yl)-3,4-dihydroisoquinolin-1(2H)-one (Intermediate 50, 21 mg, 0.04 mmol) in acetonitrile (3 mL) was added 1,3-oxazole-2-amine (30 mg, 0.36 mmol), and N,N-diisopropylethylamine (21 µL, 0.12 mmol). The reaction mixture was stirred at 55° C. overnight. The solvent was removed under reduced pressure and the residue was purified by reverse phase HPLC (Phenomenex Gemini C18, H₂O/CH₃CN gradient from 10-60% CH₃CN, 0.1% TFA). The fractions containing the desired product were combined, concentrated, basified with NaHCO₃ (sat.), and extracted with CH₂Cl₂/EtOAc (2/1, V/V). The combined organic layers were dried (Na₂SO₄) and filtered. The filtrate was concentrated, dried under vacuum to provide the title compound (12.6 mg, 50%). ¹H NMR (400 MHz, CDCl₃) δ 8.75 (m, 1H), 8.17 (d, J=2.0 Hz, 1H), 7.62 (dd, J=1.6, 8.0 Hz, 1H), 7.55 (dd, J=4.4, 8.0 Hz, 1H), 7.28 (s, 1H), 6.63 (d, J=2.0 Hz, 1H), 6.45 (d, J=2.0 Hz, 2H), 6.37 (m, 1H), 6.33 (d, J=2.0 Hz, 1H), 4.82 (m, 3H), 4.60 (d, J=14.8 Hz, 1H), 3.77 (s, 6H), 3.39 (m, 2H), 2.53 (m, 2H); LC-MS: >95% 254 nm, R$_T$=0.94 min, MS (ES) 539 [M+H]⁺.

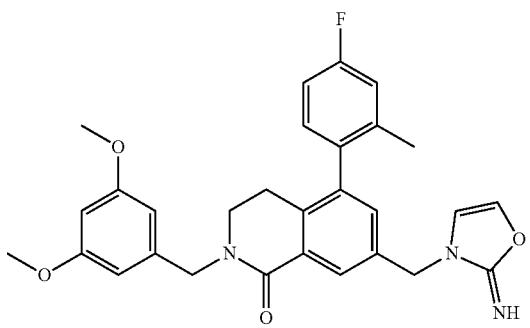 [SMILES: COc1cc(CN2CCc3c(cc(Cn4ccoc4=N)cc3-c3ccc(F)cc3C)C2=O)cc(OC)c1]

Example 81

2-(3,5-Dimethoxybenzyl)-5-(4-fluoro-2-methylphenyl)-7-((2-iminooxazol-3(2H)-yl)methyl)-3,4-dihydroisoquinolin-1(2H)-one The title compound (9.7 mg, 43%) was prepared from the procedure described in Example 80 substituting 7-(bromomethyl)-2-(3,5-dimethoxybenzyl)-5-(2-(4-fluoro-2-methylphenyl)-3,4-dihydroisoquinolin-1(2H)-one (Intermediate 11) for 7-(bromomethyl)-2-(3,5-dimethoxybenzyl)-5-(2-(trifluoromethyl)pyridin-3-yl)-3,4-dihydroisoquinolin-1(2H)-one. ¹H NMR (400 MHz, CDCl₃) δ 8.10 (d, J=2.0 Hz, 1H), 7.26 (s, 1H), 6.95 (m, 3H), 6.65 (d, J=2.0 Hz, 1H), 6.47 (d, J=2.4 Hz, 2H), 6.37 (m, 2H), 4.80 (s, 2H), 4.71 (m, 2H), 3.77 (s, 6H), 3.38 (t, J=6.4 Hz, 2H), 2.59 (m, 2H), 2.02 (s, 3H); LC-MS: >95% 254 nm, R$_T$=1.04 min, MS (ES) 502 [M+H]⁺.

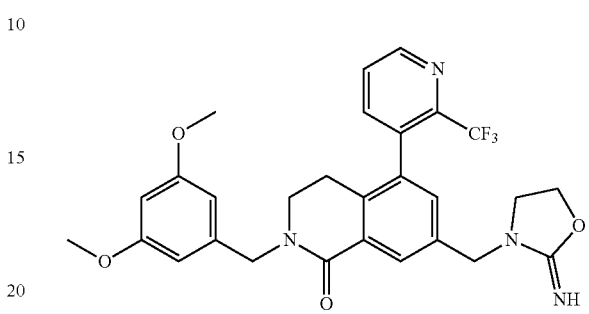

Example 82

2-(3,5-Dimethoxybenzyl)-7-((2-iminooxazolidin-3-yl)methyl)-5-(2-(trifluoromethyl)pyridin-3-yl)-3,4-dihydroisoquinolin-1(2H)-one To a solution of 7-(bromomethyl)-2-(3,5-dimethoxybenzyl)-5-(2-(trifluoromethyl)pyridin-3-yl)-3,4-dihydroisoquinolin-1(2H)-one (Intermediate 50, 36 mg, 0.067 mmol) in acetonitrile (3 mL) was added 2-amino-2-oxazoline hydrochloride (16.4 mg, 0.134 mmol), KI (56 mg, 0.335 mmol), and N,N-diisopropylethylamine (23 µL, 0.134 mmol). The reaction mixture was stirred at room temperature overnight. The solvent was removed under reduced pressure and the residue was purified on by reverse phase HPLC (Phenomenex Gemini C18, H₂O/CH₃CN gradient from 10-80% CH₃CN, 0.1% TFA). The fractions containing the desired product were combined, concentrated, basified with K₂CO₃ (sat.), and extracted with CH₂Cl₂. The combined organic layers were dried (Na₂SO₄) and filtered. The filtrate was concentrated, dried under vacuum to provide the title compound (7.9 mg, 21%). ¹H NMR (400 MHz, CDCl₃) δ 8.74 (d, J=3.6 Hz, 1H), 8.17 (s, 1H), 7.63 (d, J=3.6 Hz, 1H), 7.55 (m, 1H), 7.34 (s, 1H), 6.46 (d, J=2.4 Hz, 2H), 6.36 (m, 1H), 4.84 (d, J=14.8 Hz, 1H), 4.70 (d, J=15.2 Hz, 1H), 4.60 (d, J=14.8 Hz, 1H), 4.43 (d, J=15.2 Hz, 1H), 4.25 (m, 2H), 3.76 (s, 6H), 3.40 (m, 4H), 2.54 (m, 2H); LC-MS: >95% (254 nm), R$_T$=0.90 min, MS (ES) 541 [M+H]⁺.

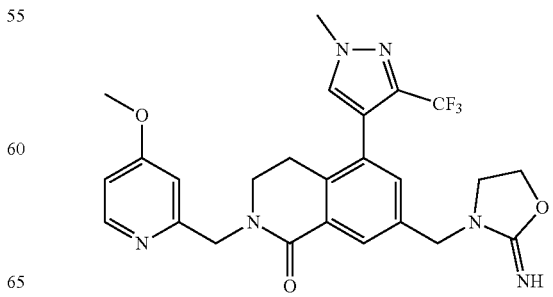

Example 83

7-((2-Iminooxazolidin-3-yl)methyl)-2-((4-methoxy-pyridin-2-yl)methyl)-5-(1-methyl-3-(trifluoromethyl)-1H-pyrazol-4-yl)-3,4-dihydroisoquinolin-1(2H)-one The title compound (16 mg, 0.031 mmol, 53%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 4,5-dihydrooxazol-2-amine (10 mg, 0.12 mmol, 2 equiv). LC-MS: >95% (254 nm), $R_T$=0.093 min, MS (ES) 515 [M+H]$^+$.

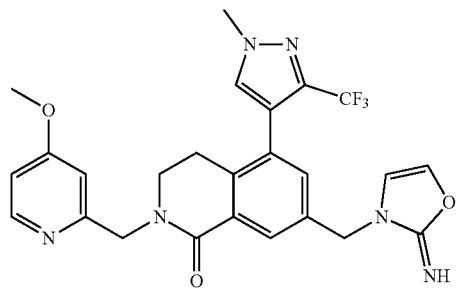 [SMILES: COc1ccnc(CN2CCc3c(cc(Cn4ccoc4=N)cc3-c3cn(C)nc3C(F)(F)F)C2=O)c1]

Example 84

7-((2-Iminooxazol-3(2H)-yl)methyl)-2-((4-methoxy-pyridin-2-yl)methyl)-5-(1-methyl-3-(trifluoromethyl)-1H-pyrazol-4-yl)-3,4-dihydroisoquinolin-1(2H)-one The title compound (24 mg, 0.047 mmol, 79%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and oxazol-2-amine (20 mg, 0.24 mmol, 4 equiv). $^1$H NMR (400 MHz, Chloroform-d) δ 8.34 (d, J=5.8 Hz, 1H), 8.09 (d, J=2.0 Hz, 1H), 7.34 (d, J=1.1 Hz, 1H), 7.31 (d, J=2.0 Hz, 1H), 6.90 (d, J=2.5 Hz, 1H), 6.72 (dd, J=5.8, 2.5 Hz, 1H), 6.62 (d, J=1.9 Hz, 1H), 6.32 (d, J=1.9 Hz, 1H), 4.84 (s, 2H), 4.75 (s, 2H), 3.99 (s, 3H), 3.82 (s, 3H), 3.57 (t, J=6.6 Hz, 2H), 2.77 (t, J=6.6 Hz, 2H). LC-MS: >95% (254 nm), $R_T$=0.103 min, MS (ES) 513 [M+H]$^+$.

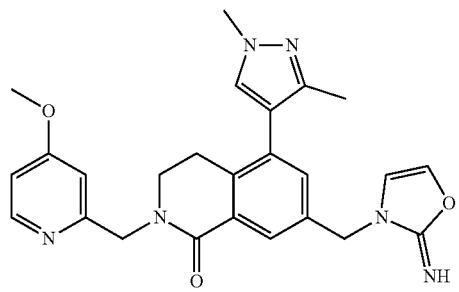 [SMILES: COc1ccnc(CN2CCc3c(cc(Cn4ccoc4=N)cc3-c3cn(C)nc3C)C2=O)c1]

Example 85

5-(1,3-Dimethyl-1H-pyrazol-4-yl)-7-((2-iminooxazol-3(2H)-yl)methyl)-2-((4-methoxypyridin-2-yl)methyl)-3,4-dihydroisoquinolin-1(2H)-one The title compound (17 mg, 0.037 mmol, 56%) was prepared following the procedures described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and oxazol-2-amine (20 mg, 0.24 mmol, 4 equiv) in Step D. LC-MS: >95% (254 nm), $R_T$=0.084 min, MS (ES) 459 [M+H]$^+$.

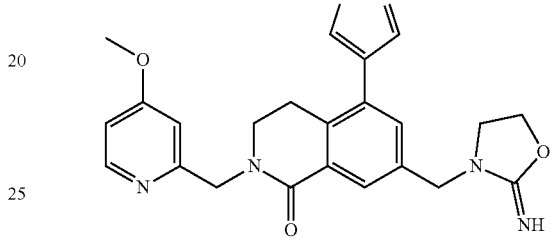

Example 86

5-(1-Ethyl-1H-pyrazol-4-yl)-7-((2-iminooxazolidin-3-yl)methyl)-2-((4-methoxypyridin-2-yl)methyl)-3,4-dihydroisoquinolin-1(2H)-one The title compound (26 mg, 0.056 mmol, 51%) was prepared following the procedures described in Example 8 using 7-(bromomethyl)-5-(1-ethyl-1H-pyrazol-4-yl)-2-((4-methoxypyridin-2-yl)methyl)-3,4-dihydroisoquinolin-1(2H)-one (Intermediate 53) and 4,5-dihydrooxazol-2-amine (19 mg, 0.22 mmol, 2 equiv). LC-MS: >95% (254 nm), $R_T$=0.20 min, MS (ES) 461 [M+H]$^+$.

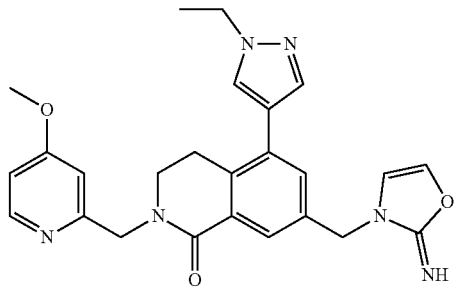 [SMILES: CCn1cc(-c2cc(Cn3ccoc3=N)cc3c2CCN(Cc2cc(OC)ccn2)C3=O)cn1]

Example 87

5-(1-Ethyl-1H-pyrazol-4-yl)-7-((2-iminooxazol-3(2H)-yl)methyl)-2-((4-methoxypyridin-2-yl)methyl)-3,4-dihydroisoquinolin-1(2H)-one The title compound (29 mg, 0.063 mmol, 57%) was prepared following the procedures described in Example 8 using 7-(bromomethyl)-5-(1-ethyl-1H-pyrazol-4-yl)-24(4-methoxypyridin-2-yl)methyl)-3,4-dihydroisoquinolin-1

(2H)-one (Intermediate 53) and oxazol-2-amine (19 mg, 0.22 mmol, 2 equiv). ¹H NMR (400 MHz, Methanol-d₄) δ 8.58-8.54 (m, 1H), 7.91 (dd, J=5.7, 1.4 Hz, 2H), 7.69 (dd, J=3.4, 1.2 Hz, 2H), 7.66 (d, J=2.0 Hz, 1H), 7.43-7.38 (m, 3H), 5.15 (s, 2H), 5.00 (s, 2H), 4.30-4.23 (m, 2H), 4.12 (s, 3H), 3.74 (t, J=6.6 Hz, 2H), 3.24 (t, J=6.6 Hz, 2H), 1.51 (t, J=7.3 Hz, 3H); LC-MS: >95% (254 nm), $R_T$=0.08 min, MS (ES) 459 [M+H]⁺.

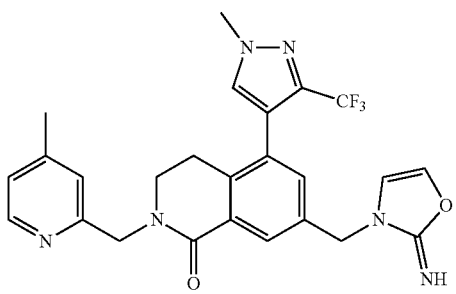 [SMILES: Cc1ccnc(CN2CCc3c(cc(Cn4ccoc4=N)cc3-c3cn(C)nc3C(F)(F)F)C2=O)c1]

Example 88

7-((2-Iminooxazol-3(2H)-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one The title compound (25 mg, 0.062 mmol, 50%) was prepared following the procedures described in Example 8 using 7-(bromomethyl)-5-(1-methyl-3-(trifluoromethyl)-1H-pyrazol-4-yl)-2-((4-methylpyridin-2-yl)methyl)-3,4-dihydroisoquinolin-1(2H)-one (Intermediate 54) and oxazol-2-amine (27 mg, 0.32 mmol, 4 equiv). ¹H NMR (400 MHz, Methanol-d₄) δ 8.57 (d, J=5.9 Hz, 1H), 8.04 (d, J=2.0 Hz, 1H), 7.83 (d, J=1.1 Hz, 1H), 7.77 (d, J=1.7 Hz, 1H), 7.74-7.67 (m, 2H), 7.48 (d, J=2.0 Hz, 1H), 7.38 (d, J=1.7 Hz, 1H), 5.18 (s, 2H), 5.02 (s, 2H), 4.03 (s, 3H), 3.74 (t, J=6.6 Hz, 2H), 2.99 (t, J=6.6 Hz, 2H), 2.61 (d, J=0.8 Hz, 3H); LC-MS: >95% (254 nm), $R_T$=0.844 min, MS (ES) 497 [M+H]⁺.

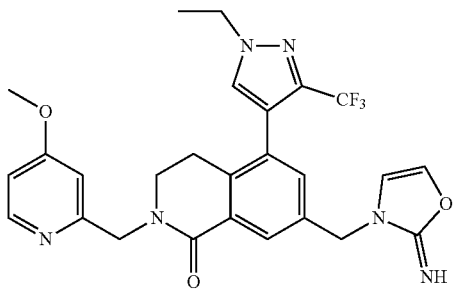 [SMILES: CCn1cc(-c2cc(Cn3ccoc3=N)cc3c2CCN(Cc2cc(OC)ccn2)C3=O)c(C(F)(F)F)n1]

Example 89

5-(1-Ethyl-3-(trifluoromethyl)-1H-pyrazol-4-yl)-7-((2-iminooxazol-3(2H)-yl)methyl)-2-((4-methoxypyridin-2-yl)methyl)-3,4-dihydroisoquinolin-1(2H)-one The title compound (31 mg, 0.059 mmol, 77%) was prepared following the procedures described in Example 8 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and oxazol-2-amine (26 mg, 0.31 mmol, 4 equiv). LC-MS: >95% (254 nm), RT=1.091 min, MS (ES) 527 [M+H]⁺.

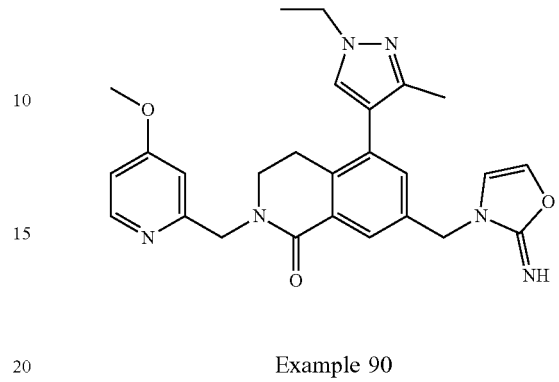

Example 90

5-(1-Ethyl-3-methyl-1H-pyrazol-4-yl)-7-((2-iminooxazol-3(2H)-yl)methyl)-2-((4-methoxypyridin-2-yl)methyl)-3,4-dihydroisoquinolin-1(2H)-one The title compound (11 mg, 0.023 mmol, 54%) was prepared following the procedures described in Example 8 using 7-(bromomethyl)-5-(1-ethyl-3-methyl-1H-pyrazol-4-yl)-2-methoxypyridin-2-yl)methyl)-3,4-dihydroisoquinolin-1(2H)-one (Intermediate 60) and oxazol-2-amine (24 mg, 0.17 mmol, 4 equiv). ¹H NMR (400 MHz, Methanol-d₄) δ 8.58 8.51 (m, 1H), 7.96 (d, J=2.0 Hz, 1H), 7.70 (d, J=1.7 Hz, 1H), 7.64 (s, 1H), 7.49 (d, J=2.1 Hz, 1H), 7.44-7.38 (m, 3H), 5.16 (s, 2H), 4.99 (s, 2H), 4.24-4.07 (m, 5H), 3.72 (t, J=6.6 Hz, 2H), 3.04 (t, J=6.6 Hz, 2H), 2.16 (s, 3H), 1.47 (t, J=7.3 Hz, 3H); LC-MS: >95% (254 nm), $R_T$=0.087 min, MS (ES) 473 [M+H]⁺.

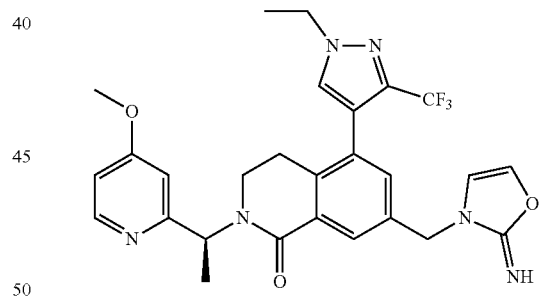

Example 91

(S)-5-(1-Ethyl-3-(trifluoromethyl)-1H-pyrazol-4-yl)-7-((2-iminooxazol-3(2H)-yl)methyl)-2-(1-(4-methoxypyridin-2-yl)ethyl)-3,4-dihydroisoquinolin-1(2H)-one The title compound (34 mg, 0.063 mmol, 68%) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and oxazol-2-amine (31 mg, 0.37 mmol, 4 equiv). ¹H NMR (400 MHz, Chloroform-d) δ 8.36 (d, J=5.7 Hz, 1H), 8.09 (d, J=2.0 Hz, 1H), 7.34 (d, J=1.0 Hz, 1H), 7.30 (d, J=1.9 Hz, 1H), 6.90

(d, J=2.5 Hz, 1H), 6.71 (dd, J=5.7, 2.5 Hz, 1H), 6.62 (d, J=1.9 Hz, 1H), 6.32 (d, J=1.9 Hz, 1H), 6.11 (q, J=7.0 Hz, 1H), 5.05 (s, 1H), 4.75 (s, 2H), 4.24 (q, J=7.3 Hz, 2H), 3.82 (s, 3H), 3.46 (ddd, J=12.6, 8.7, 5.2 Hz, 1H), 3.37-3.28 (m, 1H), 2.69-2.59 (m, 2H), 1.61 (d, J=7.1 Hz, 3H), 1.55 (t, J=7.3 Hz, 3H); LC-MS: >95% (254 nm), $R_T$=0.121 min, MS (ES) 541 [M+H]$^+$.

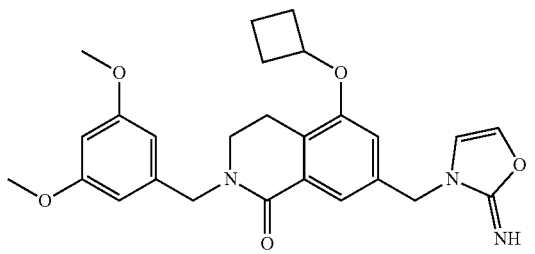 [SMILES: COc1cc(CN2CCc3c(OC4CCC4)cc(Cn4ccoc4=N)cc3C2=O)cc(OC)c1]

Example 92

5-Cyclobutoxy-2-(3,5-dimethoxybenzyl)-7-((2-iminooxazol-3(2H)-yl)methyl)-3,4-dihydroisoquinolin-1(2H)-one The title compound (7 mg, 0.015 mmol) was prepared following the procedures described in Example 8 using 7-(bromomethyl)-5-cyclobutoxy-2-(3,5-dimethoxybenzyl)-3,4-dihydroisoquinolin-1(2H)-one (Intermediate 64) and oxazol-2-amine. $^1$H NMR (CDCl$_3$) δ 7.64 (s, 1H), 6.86 (s, 1H), 6.61 (d, J=1.9 Hz, 1H), 6.47 (d, J=1.9 Hz, 2H), 6.37 (t, J=2.3 Hz, 1H), 6.32 (d, J=1.8 Hz, 1H), 4.71 (s, 2H), 4.69 (s, 2H), 4.66-4.59 (m, 1H), 3.76 (s, 6H), 3.45 (t, J=6.8 Hz, 2H), 2.89 (t, J=6.8 Hz, 2H), 2.48-2.40 (m, 2H), 2.16-2.06 (m, 2H), 1.88-1.80 (m, 1H), 1.74-1.63 (m, 1H); LCMS method 1: $R_T$=1.34 min, MS (ES) 464.0 [M+H]$^+$.

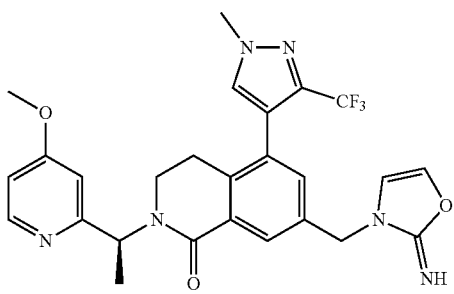 [SMILES: COc1ccnc([C@H](C)N2CCc3c(cc(Cn4ccoc4=N)cc3-c3cn(C)nc3C(F)(F)F)C2=O)c1]

Example 93

(S)-7-((2-Iminooxazol-3(2H)-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one The title compound (30 mg, 0.057 mmol, 57%) was prepared following the procedures described in Example 8 using (S)-7-(bromomethyl)-5-(1-methyl-3-(trifluoromethyl)-1H-pyrazol-4-yl)-2-(1-(4-methoxypyridin-2-yl)ethyl)-3,4-dihydroisoquinolin-1(2H)-one and oxazol-2-amine (32 mg, 0.38 mmol, 4 equiv). LC-MS: >95% (254 nm), $R_T$=0.193 min, MS (ES) 527 [M+H]$^+$.

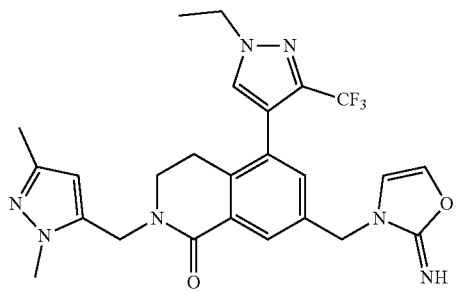 [SMILES: CCn1cc(-c2cc(Cn3ccoc3=N)cc3c2CCN(Cc2cc(C)nn2C)C3=O)c(C(F)(F)F)n1]

Example 94

2-((1,3-Dimethyl-1H-pyrazol-5-yl)methyl)-5-(1-ethyl-3-(trifluoromethyl)-1H-pyrazol-4-yl)-7-((2-iminooxazol-3(2H)-yl)methyl)-3,4-dihydroisoquinolin-1(2H)-one The title compound (21 mg, 0.041 mmol, 42%) was prepared following the procedures described in Example 8 using 7-(bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one (Intermediate 31) and oxazol-2-amine (33 mg, 0.39 mmol, 4 equiv). $^1$H NMR (400 MHz, Methanol-d$_4$) δ 8.02 (d, J=2.0 Hz, 1H), 7.84 (d, J=1.1 Hz, 1H), 7.70 (d, J=1.7 Hz, 1H), 7.43 (d, J=2.0 Hz, 1H), 7.37 (d, J=1.7 Hz, 1H), 6.12 (s, 1H), 5.16 (s, 2H), 4.82 (s, 2H), 4.28 (q, J=7.3 Hz, 2H), 3.81 (s, 3H), 3.53 (t, J=6.6 Hz, 2H), 2.84 (t, J=6.6 Hz, 2H), 2.19 (s, 3H), 1.52 (t, J=7.3 Hz, 3H); LC-MS: >95% (254 nm), $R_T$=0.148 min, MS (ES) 514 [M+H]$^+$.

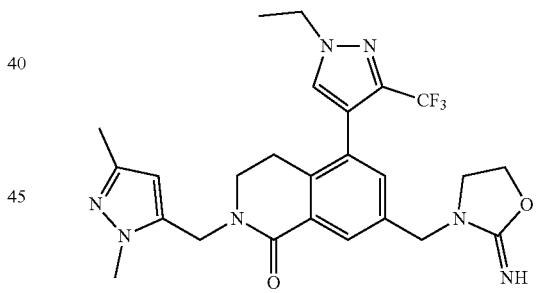

Example 95

2-((1,3-Dimethyl-1H-pyrazol-5-yl)methyl)-5-(1-ethyl-3-(trifluoromethyl)-1H-pyrazol-4-yl)-7-((2-iminooxazolidin-3-yl)methyl)-3,4-dihydroisoquinolin-1(2H)-one The title compound (28 mg, 0.054 mmol, 55%) was prepared following the procedures described in Example 8 using 7-(bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one (Intermediate 31) and 4,5-dihydrooxazol-2-amine (33 mg, 0.39 mmol, 4 equiv). LC-MS: >95% (254 nm), $R_T$=1.116 min, MS (ES) 516 [M+H]$^+$.

221

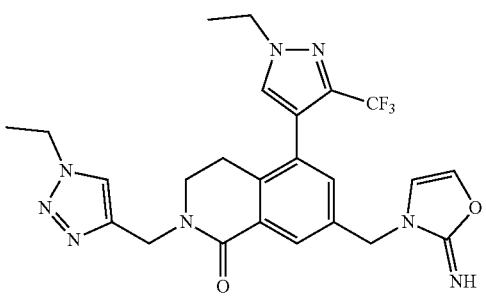 [SMILES: CCn1cc(CN2CCc3c(cc(Cn4ccoc4=N)cc3-c3cn(CC)nc3C(F)(F)F)C2=O)nn1]

Example 96

2-((1-Ethyl-1H-1,2,3-triazol-4-yl)methyl)-5-(1-ethyl-3-(trifluoromethyl)-1H-pyrazol-4-yl)-7-((2-iminooxazol-3(2H)-yl)methyl)-3,4-dihydroisoquinolin-1(2H)-one The title compound (34 mg, 0.066 mmol, 68%) was prepared following the procedures described in Example 8 using 7-(bromomethyl)-2-((1-ethyl-1H-1,2,3-triazol-4-yl)methyl)-5-(1-ethyl-3-(trifluoromethyl)-1H-pyrazol-4-yl)-3,4-dihydroisoquinolin-1(2H)-one (Intermediate 32) and oxazol-2-amine (33 mg, 0.39 mmol, 4 equiv). LC-MS: >95% (254 nm), $R_T$=1.207 min, MS (ES) 516 [M+H]$^+$.

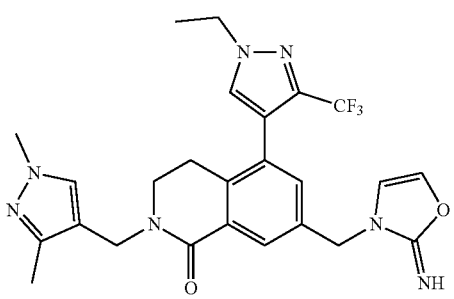

Example 97

2-((1,3-Dimethyl-1H-pyrazol-4-yl)methyl)-5-(1-ethyl-3-(trifluoromethyl)-1H-pyrazol-4-yl)-7-((2-iminooxazol-3(2H)-yl)methyl)-3,4-dihydroisoquinolin-1(2H)-one The title compound (31 mg, 0.060 mmol, 62%) was prepared following the procedures described in Example 8 using 7-(bromomethyl)-2-((1,3-dimethyl-1H-pyrazol-4-yl)methyl)-5-(1-ethyl-3-(trifluoromethyl)-1H-pyrazol-4-yl)-3,4-dihydroisoquinolin-1(2H)-one (Intermediate 37) and oxazol-2-amine (33 mg, 0.39 mmol, 4 equiv). LC-MS: >95% (254 nm), $R_T$=1.144 min, MS (ES) 514 [M+H]$^+$.

222

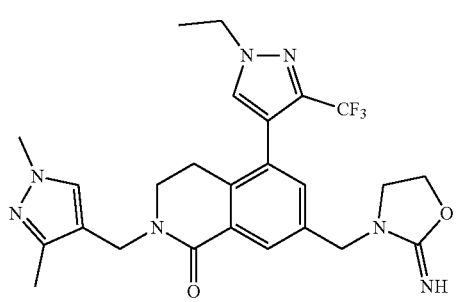 [SMILES: CCn1cc(-c2cc(CN3CCOC3=N)cc3c2CCN(Cc2cn(C)nc2C)C3=O)c(C(F)(F)F)n1]

Example 98

2-((1,3-Dimethyl-1H-pyrazol-4-yl)methyl)-5-(1-ethyl-3-(trifluoromethyl)-1H-pyrazol-4-yl)-7-((2-iminooxazolidin-3-yl)methyl)-3,4-dihydroisoquinolin-1(2H)-one The title compound (22 mg, 0.043 mmol, 44%) was prepared following the procedures described in Example 8 using 7-(bromomethyl)-2-((1,3-dimethyl-1H-pyrazol-4-yl)methyl)-5-(1-ethyl-3-(trifluoromethyl)-1H-pyrazol-4-yl)-3,4-dihydroisoquinolin-1(2H)-one (Intermediate 37) and 4,5-dihydrooxazol-2-amine (34 mg, 0.39 mmol, 4 equiv). LC-MS: >95% (254 nm), $R_T$=1.136 min, MS (ES) 516 [M+H]$^+$.

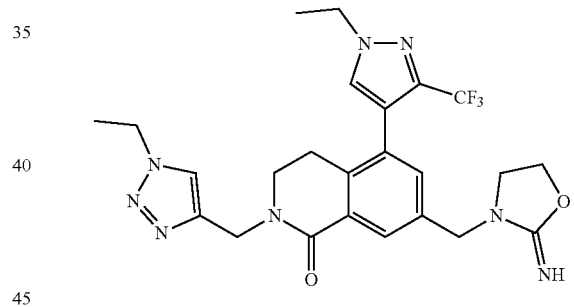

Example 99

2-((1-Ethyl-1H-1,2,3-triazol-4-yl)methyl)-5-(1-ethyl-3-(trifluoromethyl)-1H-pyrazol-4-yl)-7-((2-iminooxazolidin-3-yl)methyl)-3,4-dihydroisoquinolin-1(2H)-one The title compound (28 mg, 0.054 mmol, 55%) was prepared following the procedures described in Example 8 using 7-(bromomethyl)-2-((1-ethyl-1H-1,2,3-triazol-4-yl)methyl)-5-(1-ethyl-3-(trifluoromethyl)-1H-pyrazol-4-yl)-3,4-dihydroisoquinolin-1(2H)-one (Intermediate 32) and 4,5-dihydrooxazol-2-amine (34 mg, 0.39 mmol, 4 equiv). LC-MS: >95% (254 nm), $R_T$=1.228 min, MS (ES) 517.5 [M+H]$^+$.

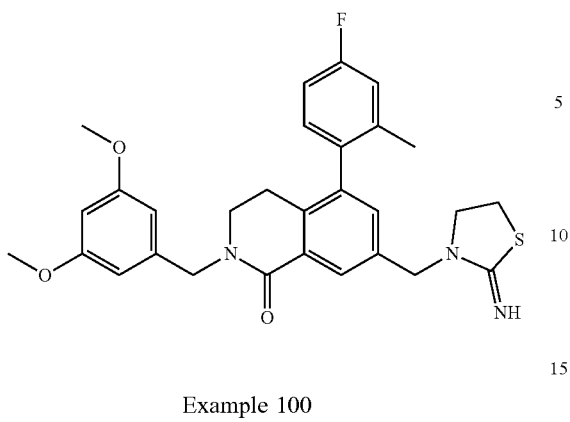

Example 100

2-(3,5-Dimethoxybenzyl)-5-(4-fluoro-2-methylphenyl)-7-((2-iminothiazolidin-3-yl)methyl)-3,4-dihydroisoquinolin-1(2H)-one To a solution of 7-(bromomethyl)-2-(3,5-dimethoxybenzyl)-5-(4-fluoro-2-methylphenyl)-3,4-dihydroisoquinolin-1(2H)-one (Intermediate 11, 22 mg, 0.044 mmol) in acetonitrile (3 mL) was added 2-amino-2-thiazoline (45 mg, 0.44 mmol), and N,N-diisopropylethylamine (76 μL, 0.44 mmol). The reaction mixture was stirred at 55° C. overnight. The solvent was removed under reduced pressure and the residue was purified by reverse phase HPLC (Phenomenex Gemini C18, H$_2$O/CH$_3$CN gradient from 15-95% CH$_3$CN, 0.1% TFA). The fractions containing the desired product were combined, concentrated, basified with NaHCO$_3$ (sat.), and extracted with CH$_2$Cl$_2$/EtOAc (2/1, V/V). The combined organic layers were dried (Na$_2$SO$_4$) and filtered. The filtrate was concentrated, dried under vacuum to provide the title compound (15.7 mg, 68%). $^1$H NMR (400 MHz, CDCl$_3$) δ 8.09 (d, J=1.6 Hz, 1H), 7.28 (s, 1H), 6.95 9m, 3H), 6.47 (d, J=2.0 Hz, 2H), 6.37 (m, 1H), 4.73 (m, 2H), 4.65 (s, 2H), 3.77 (s, 6H), 3.57 (t, J=6.8 Hz, 2H), 3.38 (t, J=6.8 Hz, 2H), 3.16 (t, J=6.8 Hz, 2H), 2.55 (m, 2H), 2.03 (s, 3H); LC-MS: >95% 254 nm, R$_T$=1.09 min, MS (ES) 520 [M+H]$^+$.

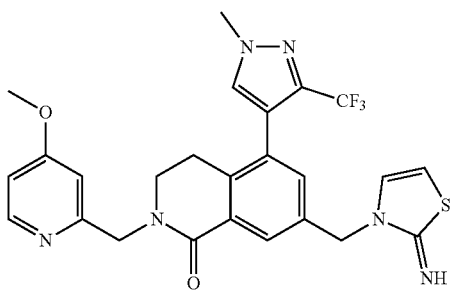 [SMILES: COc1ccnc(CN2CCc3c(cc(Cn4ccsc4=N)cc3-c3cn(C)nc3C(F)(F)F)C2=O)c1]

Example 101

7-((2-Iminothiazol-3(2H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (25 mg, 0.047 mmol, 80%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and thiazol-2-amine (12 mg, 0.12 mmol, 2 equiv). LC-MS: >95% (254 nm), R$_T$=0.099 min, MS (ES) 529 [M+H]$^+$.

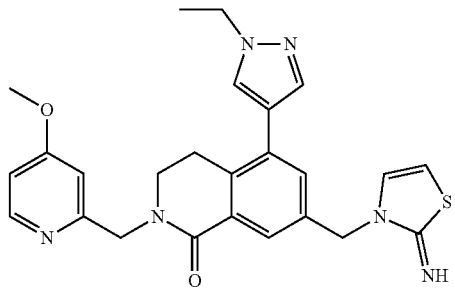 [SMILES: CCn1cc(-c2cc(Cn3ccsc3=N)cc3c2CCN(Cc2cc(OC)ccn2)C3=O)cn1]

Example 102

5-(1-ethyl-1H-pyrazol-4-yl)-7-((2-iminothiazol-3(2H)-yl)methyl)-2-((4-methoxypyridin-2-yl)methyl)-3,4-dihydroisoquinolin-1(2H)-one The title compound (43 mg, 0.091 mmol, 83%) was prepared following the procedures described in Example 8 using 7-(bromomethyl)-5-(1-ethyl-1H-pyrazol-4-yl)-2-((4-methoxypyridin-2-yl)methyl)-3,4-dihydroisoquinolin-1(2H)-one (Intermediate 53) and thiazol-2-amine (22 mg, 0.22 mmol, 2 equiv). $^1$H NMR (400 MHz, Methanol-d$_4$) δ 8.61-8.56 (m, 1H), 7.91 (d, J=0.8 Hz, 1H), 7.85 (d, J=2.0 Hz, 1H), 7.70 (d, J=0.8 Hz, 1H), 7.62 (d, J=2.0 Hz, 1H), 7.49-7.43 (m, 2H), 7.35 (d, J=4.6 Hz, 1H), 7.04 (d, J=4.5 Hz, 1H), 5.36 (s, 2H), 5.02 (s, 2H), 4.28 (q, J=7.3 Hz, 2H), 4.15 (s, 3H), 3.77 (t, J=6.6 Hz, 2H), 3.26 (t, J=6.6 Hz, 2H), 1.52 (t, J=7.3 Hz, 3H); LC-MS: >95% (254 nm), R$_T$=0.919 min, MS (ES) 475 [M+H]$^+$.

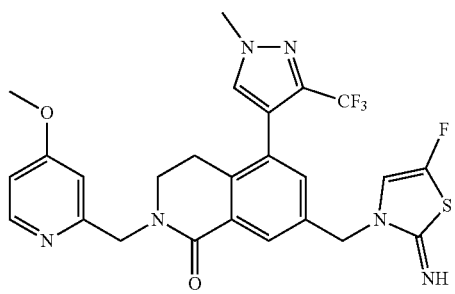 [SMILES: COc1ccnc(CN2CCc3c(cc(Cn4cc(F)sc4=N)cc3-c3cn(C)nc3C(F)(F)F)C2=O)c1]

Example 103

7-((5-Fluoro-2-iminothiazol-3(2H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (38 mg, 0.070 mmol, 71%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 5-fluorothiazol-2-amine (23 mg, 0.20 mmol, 2 equiv). LC-MS: >95% (254 nm), R$_T$=0.112 min, MS (ES) 547 [M+H]$^+$.

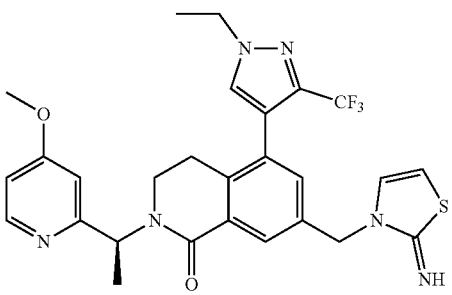 [SMILES: CCn1cc(-c2cc(Cn3ccsc3=N)cc3c2CCN([C@@H](C)c2cc(OC)ccn2)C3=O)c(C(F)(F)F)n1]

Example 104

(S)-5-(1-Ethyl-3-(trifluoromethyl)-1H-pyrazol-4-yl)-7-((2-iminothiazol-3(2H)-yl)methyl)-2-(1-(4-methoxypyridin-2-yl)ethyl)-3,4-dihydroisoquinolin-1(2H)-one The title compound (38 mg, 0.068 mmol, 73%) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and thiazol-2-amine (19 mg, 0.19 mmol, 2 equiv). LC-MS: >95% (254 nm), $R_T$=0.113 min, MS (ES) 557 [M+H]$^+$.

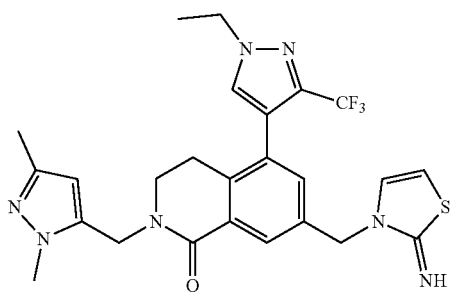

Example 106

2-((1,3-Dimethyl-1H-pyrazol-5-yl)methyl)-5-(1-ethyl-3-(trifluoromethyl)-1H-pyrazol-4-yl)-7-((2-iminothiazol-3(2H)-yl)methyl)-3,4-dihydroisoquinolin-1(2H)-one The title compound (40 mg, 0.076 mmol, 77%) was prepared following the procedures described in Example 8 using 7-(bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one (Intermediate 31) and thiazol-2-amine (20 mg, 0.2 mmol, 2 equiv). $^1$H NMR (400 MHz, Methanol-$d_4$) δ 7.99 (d, J=2.0 Hz, 1H), 7.86 (d, J=1.1 Hz, 1H), 7.34 (dd, J=4.9, 3.3 Hz, 2H), 7.05 (d, J=4.5 Hz, 1H), 6.14 (s, 1H), 5.38 (s, 2H), 4.83 (s, 2H), 4.30 (q, J=7.3 Hz, 2H), 3.83 (s, 3H), 3.55 (t, J=6.6 Hz, 2H), 2.86 (t, J=6.6 Hz, 2H), 2.21 (s, 3H), 1.54 (t, J=7.3 Hz, 3H); LC-MS: >95% (254 nm), $R_T$=1.139 min, MS (ES) 530 [M+H]$^+$.

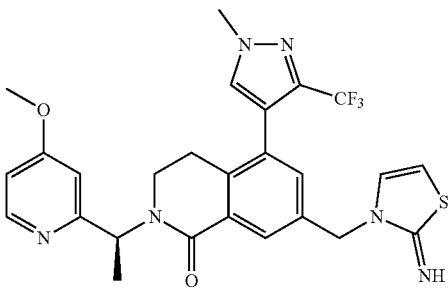 [SMILES: COc1ccnc([C@H](C)N2CCc3c(cc(Cn4ccsc4=N)cc3-c3cn(C)nc3C(F)(F)F)C2=O)c1]

Example 105

(S)-7-((2-iminothiazol-3(2H)-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one The title compound (38 mg, 0.070 mmol, 71%) was prepared following the procedures described in Example 8 using (S)-7-(bromomethyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one (Intermediate 66) and thiazol-2-amine (23 mg, 0.20 mmol, 2 equiv). LC-MS: >95% (254 nm), $R_T$=0.112 min, MS (ES) 547 [M+H]$^+$.

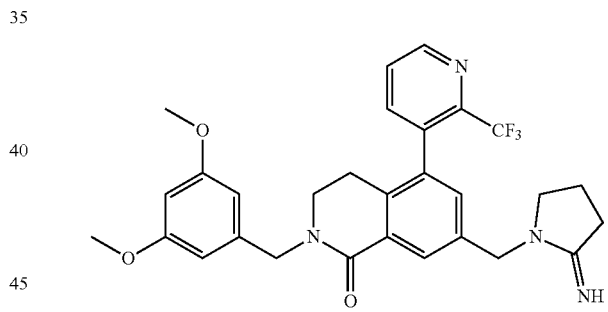

Example 107

2-(3,5-Dimethoxybenzyl)-7-((2-iminopyrrolidin-1-yl)methyl)-5-(2-(trifluoromethyl)pyridin-3-yl)-3,4-dihydroisoquinolin-1(2H)-one To a solution of 7-(bromomethyl)-2-(3,5-dimethoxybenzyl)-5-(2-(trifluoromethyl)pyridin-3-yl)-3,4-dihydroisoquinolin-1(2H)-one (Intermediate 50, 36 mg, 0.067 mmol) in acetonitrile (3 mL) was added pyrrolidin-2-imine hydrochloride (16.2 mg, 0.134 mmol), KI (56 mg, 0.335 mmol), and N,N-diisopropylethylamine (23 μL, 0.134 mmol). The reaction mixture was stirred at room temperature overnight. The solvent was removed under reduced pressure and the residue was purified by reverse phase HPLC (Phenomenex Gemini C18, H$_2$/OCH$_3$CN gradient from 15-95% CH$_3$CN, 0.1% TFA). The fractions containing the desired product were combined, concentrated, basified with K$_2$CO$_3$ (sat.), and extracted with CH$_2$Cl$_2$. The combined organic layers were dried (Na$_2$SO$_4$) and filtered. The filtrate was concentrated, dried under vacuum to provide the title compound (28 mg, 65%). $^1$H NMR (400 MHz, CDCl$_3$) δ 8.75 (m, 1H), 8.13 (d, J=1.6 Hz, 1H), 7.65 (d, J=6.4 Hz, 1H), 7.55 (m, 1H), 7.28 (s, 1H), 6.45 (d, J=2.4 Hz, 2H), 6.36 (m, 1H), 4.94 (d, J=15.2 Hz, 1H), 4.80 (d, J=14.4 Hz, 1H), 4.67 (d, J=15.2 Hz, 1H), 4.60 (d, J=14.4 Hz, 1H), 3.77 (s, 6H), 3.39 (m 4H), 2.84 (m, 2H), 2.56 (m, 2H), 2.02 (m, 2H); LC-MS: >95% 254 nm, R$_T$=0.92 min, MS (ES) 539 [M+H]$^+$.

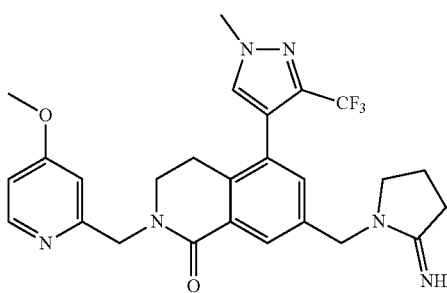 [SMILES: COc1ccnc(CN2CCc3c(cc(CN4CCCC4=N)cc3-c3cn(C)nc3C(F)(F)F)C2=O)c1]

Example 108

7-((2-Iminopyrrolidin-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (16 mg, 0.031 mmol, 53%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 3,4-dihydro-2H-pyrrol-5-amine (10 mg, 0.12 mmol, 2 equiv). LC-MS: >95% (254 nm), R$_T$=0.083 min, MS (ES) 513 [M+H]$^+$.

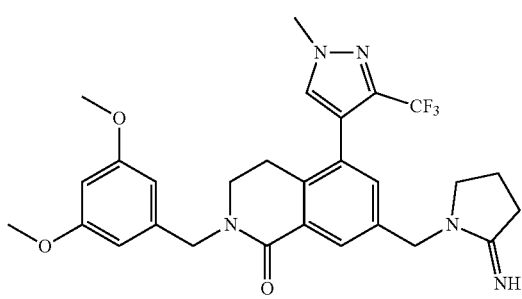 [SMILES: COc1cc(CN2CCc3c(cc(CN4CCCC4=N)cc3-c3cn(C)nc3C(F)(F)F)C2=O)cc(OC)c1]

Example 109

2-(3,5-Dimethoxybenzyl)-7-((2-iminopyrrolidin-1-yl)methyl)-5-(1-methyl-3-(trifluoromethyl)-1H-pyrazol-4-yl)-3,4-dihydroisoquinolin-1(2H)-one The title compound (27 mg, 91%) was prepared from the procedure described in Example 8 using 7-(bromomethyl)-2-(3,5-dimethoxybenzyl)-5-(1-methyl-3-(trifluoromethyl)-1H-pyrazol-4-yl)-3,4-dihydroisoquinolin-1(2H)-one (Intermediate 27) and 3,4-dihydro-2H-pyrrol-5-amine. $^1$H NMR (400 MHz, CDCl$_3$) δ 8.05 (d, J=1.6 Hz, 1H), 7.37 (s, 1H), 7.29 (s, 1H), 6.46 (d, J=2.4 Hz, 2H), 6.37 (m, 1H), 4.71 (s, 2H), 4.67 (s, 2H), 3.99 (s, 3H), 3.77 (s, 6H), 3.39 (m, 4H), 2.73 (m, 4H), 2.02 (p, J=7.6 Hz, 2H); LC-MS: >95% 254 nm, R$_T$=1.35 min, MS (ES) 542 [M+H]$^+$.

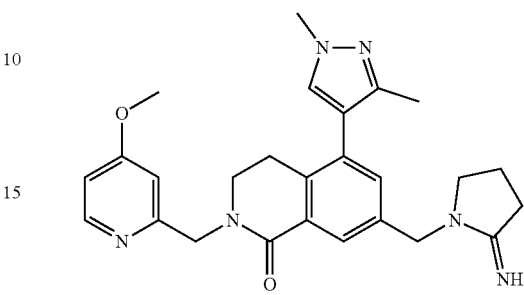

Example 110

5-(1,3-Dimethyl-1H-pyrazol-4-yl)-7-((2-iminopyrrolidin-1-yl)methyl)-2-((4-methoxypyridin-2-yl)methyl)-3,4-dihydroisoquinolin-1(2H)-one The title compound (23 mg, 0.05 mmol, 76%) was prepared following the procedures described in Example 8 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and 3,4-dihydro-2H-pyrrol-5-amine (10 mg, 0.12 mmol, 2 equiv). LC-MS: >95% (254 nm), R$_T$=0.085 min, MS (ES) 459 [M+H]$^+$.

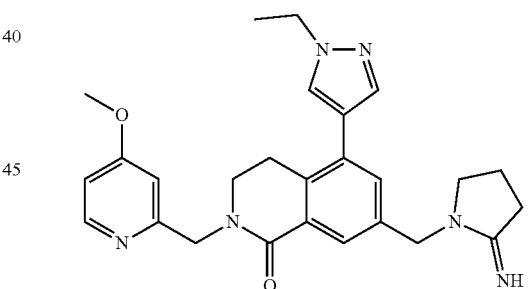

Example 111

5-(1-Ethyl-1H-pyrazol-4-yl)-7-((2-iminopyrrolidin-1-yl)methyl)-2-((4-methoxypyridin-2-yl)methyl)-3,4-dihydroisoquinolin-1(2H)-one The title compound (45 mg, 0.098 mmol, 89%) was prepared following the procedures described in Example 8 using 7-(bromomethyl)-5-(1-ethyl-1H-pyrazol-4-yl)-2-((4-methoxypyridin-2-yl)methyl)-3,4-dihydroisoquinolin-1 (2H)-one (Intermediate 53) and 3,4-dihydro-2H-pyrrol-5-amine (18 mg, 0.22 mmol, 2 equiv). LC-MS: >95% (254 nm), R$_T$=0.083 min, MS (ES) 459 [M+H]$^+$.

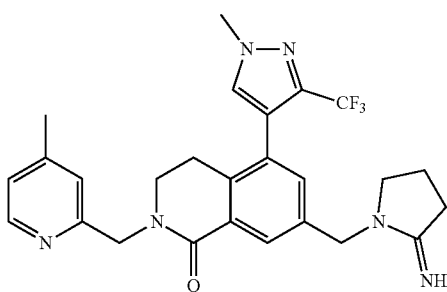 [SMILES: Cc1ccnc(CN2CCc3c(cc(CN4CCCC4=N)cc3-c3cn(C)nc3C(F)(F)F)C2=O)c1]

Example 112

7-((2-Iminopyrrolidin-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one The title compound (35 mg, 0.070 mmol, 87%) was prepared following the procedures described in Example 8 using 7-(bromomethyl)-5-(1-methyl-3-(trifluoromethyl)-1H-pyrazol-4-yl)-2-((4-methylpyridin-2-yl)methyl)-3,4-dihydroisoquinolin-1(2H)-one (Intermediate 54) and 3,4-dihydro-2H-pyrrol-5-amine (14 mg, 0.16 mmol, 2 equiv). $^1$H NMR (400 MHz, Methanol-$d_4$) δ 8.56 (d, J=5.8 Hz, 1H), 7.96 (d, J=2.0 Hz, 1H), 7.81 (d, J=1.1 Hz, 1H), 7.74 (d, J=1.7 Hz, 1H), 7.70-7.65 (m, 1H), 7.42 (d, J=2.0 Hz, 1H), 5.00 (s, 2H), 4.76 (s, 2H), 4.02 (s, 3H), 3.72 (t, J=6.6 Hz, 2H), 3.66 (t, J=7.2 Hz, 2H), 3.05-2.94 (m, 4H), 2.59 (d, J=0.8 Hz, 3H), 2.17 (p, J=7.7 Hz, 2H); LC-MS: >95% (254 nm), $R_T$=0.969 min, MS (ES) 497 [M+H]$^+$.

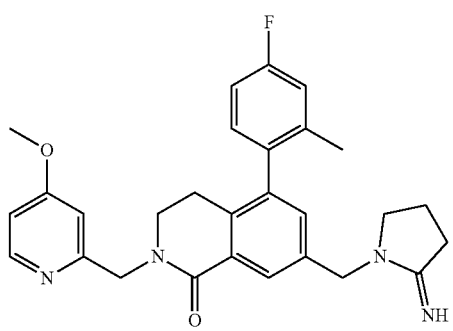

Example 114

5-(4-Fluoro-2-methylphenyl)-7-((2-iminopyrrolidin-1-yl)methyl)-2-((4-methoxypyridin-2-yl)methyl)-3,4-dihydroisoquinolin-1(2H)-one The title compound was prepared (4.2 mg, 0.0089 mmol) according to procedures described in Example 8 using 7-(bromomethyl)-5-(4-fluoro-2-methylphenyl)-2-((4-methoxypyridin-2-yl)methyl)-3,4-dihydroisoquinolin-1(2H)-one (Intermediate 55) and 3,4-dihydro-2H-pyrrol-5-amine (18 mg, 0.22 mmol, 2 equiv). $^1$H NMR (400 MHz, Chloroform-d) δ 8.36 (dd, J=5.6, 1.6 Hz, 1H), 8.05-8.03 (m, 1H), 7.36 (d, J=2.0 Hz, 1H), 7.06-6.90 (m, 4H), 6.75 (dd, J=5.6, 2.4 Hz, 1H), 5.15-5.03 (m, 1H), 4.89-4.77 (m, 3H), 3.85 (s, 3H), 3.62-3.55 (m, 4H), 3.42-3.37 (m, 1H), 3.18 (m, 1H), 2.73-2.55 (m, 2H), 2.15-2.03 (m, 2H), 2.01 (s, 3H); $^{19}$F NMR (376 MHz, Chloroform-d) δ -114.82; LC-MS: >95% 254 nm, $R_T$=1.078 min, MS (ES) 473.1 [M+H]$^+$.

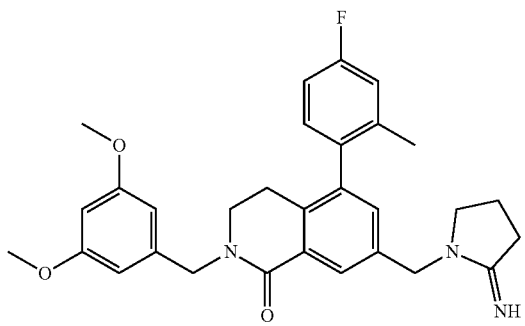 [SMILES: COc1cc(CN2CCc3c(cc(CN4CCCC4=N)cc3-c3ccc(F)cc3C)C2=O)cc(OC)c1]

Example 113

2-(3,5-Dimethoxybenzyl)-5-(4-fluoro-2-methylphenyl)-7-((2-iminopyrrolidin-1-yl)methyl)-3,4-dihydroisoquinolin-1(2H)-one The title compound (27 mg, 75%) was prepared from the procedure described in Example 8 using 7-(bromomethyl)-2-(3,5-dimethoxybenzyl)-5-(4-fluoro-2-methylphenyl)-3,4-dihydroisoquinolin-1(2H)-one (Intermediate 11) and 3,4-dihydro-2H-pyrrol-5-amine (14 mg, 0.16 mmol, 2 equiv). $^1$H NMR (400 MHz, CDCl$_3$) δ 8.05 (d, J=1.6 Hz, 1H), 7.20 (d, J=2.0 Hz, 1H), 7.03 (dd, J=6.0, 8.4 Hz, 1H), 6.95 (m, 2H), 6.47 (d, J=2.4 Hz, 2H), 6.37 (m, 1H), 4.72 (m, 2H), 4.60 (s, 2H), 3.77 (s, 6H), 3.35 (m, 4H), 2.58 (m, 4H), 2.05 (s, 3H), 1.96 (p, J=7.2 Hz, 2H); LC-MS: >95% 254 nm, $R_T$=1.08 min, MS (ES) 502 [M+H]$^+$.

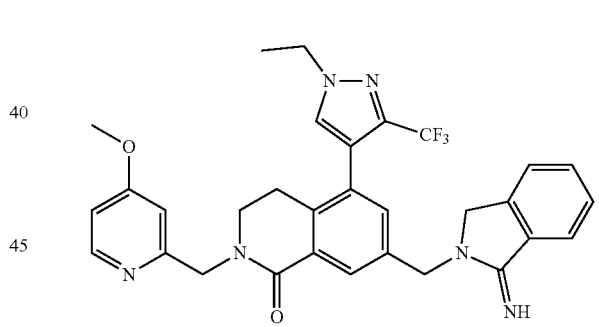

Example 115

5-(1-Ethyl-3-(trifluoromethyl)-1H-pyrazol-4-yl)-7-((1-iminoisoindolin-2-yl)methyl)-2-((4-methoxypyridin-2-yl)methyl)-3,4-dihydroisoquinolin-1(2H)-one The title compound (21 mg, 0.039 mmol, 51%) was prepared following the procedures described in Example 8 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and 1H-isoindol-3-amine (20 mg, 0.15 mmol, 2 equiv). $^1$H NMR (400 MHz, Methanol-$d_4$) δ 8.57-8.53 (m, 1H), 8.12 (dt, J=7.9, 1.0 Hz, 1H), 8.02 (d, J=2.0 Hz, 1H), 7.85 (d, J=1.0 Hz, 1H), 7.80 (dd, J=7.7, 1.1 Hz, 1H), 7.71-7.67 (m, 2H), 7.48 (d, J=2.0 Hz, 1H), 7.43 (dd, J=4.9, 2.7 Hz, 2H), 5.13 (s, 2H), 4.99 (s, 2H), 4.29 (q, J=7.3 Hz, 2H), 4.12 (s, 3H), 3.73 (t, J=6.6 Hz, 2H), 2.98 (t, J=6.6 Hz, 2H), 1.52 (t, J=7.3 Hz, 3H); LC-MS: >95% (254 nm), R$_T$=1.227 min, MS (ES) 575 [M+H]$^+$.

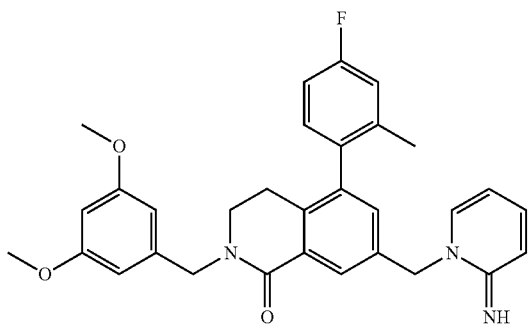 [SMILES: COc1cc(CN2CCc3c(cc(Cn4ccccc4=N)cc3-c3ccc(F)cc3C)C2=O)cc(OC)c1]

Example 116

2-(3,5-Dimethoxybenzyl)-5-(4-fluoro-2-methylphenyl)-7-((2-iminopyridin-1(2H)-yl)methyl)-3,4-dihydroisoquinolin-1(2H)-one Pyridin-2-amine (24 mg, 0.25 mmol) was added to a solution of 7-(bromomethyl)-2-(3,5-dimethoxybenzyl)-5-(4-fluoro-2-methylphenyl)-3,4-dihydroisoquinolin-1(2H)-one (Intermediate 11, 50 mg, 0.08 mmol) in CH$_3$CN (1.0 mL). The reaction mixture was stirred at 60° C. for 12 h. After cooling to ambient temperature, the crude reaction mixture was concentrated under reduced pressure. The residue was purified by reverse phase HPLC (Phenomenex Gemini C18, H$_2$O/CH$_3$CN gradient from 5-95% CH$_3$CN, 0.1% TFA) to yield the title compound (17.0 mg, 39% yield over 2 step). (To remove TFA, the organic layer has to be washed with sat. aq. K$_2$CO$_3$) LCMS: R$_T$=1.448 min, MS (ES) 512.6 [M+H]$^+$; $^1$H NMR (400 MHz, Chloroform-d) δ 8.04 (s, 1H), 7.32 (s, 1H), 7.09 (d, J=6.7 Hz, 1H), 7.01 (dd, J=8.2, 6.0 Hz, 1H), 6.98-6.91 (m, 2H), 6.88 (td, J=8.4, 2.4 Hz, 1H), 6.65 (d, J=8.7 Hz, 1H), 6.45 (d, J=1.9 Hz, 2H), 6.36 (d, J=2.0 Hz, 1H), 5.93 (t, J=6.5 Hz, 1H), 5.29 (s, 2H), 4.75-4.63 (m, 2H), 3.76 (s, 6H), 3.36 (t, J=6.6 Hz, 2H), 2.66-2.54 (m, 1H), 2.50 (m, 1H), 2.00 (s, 3H).

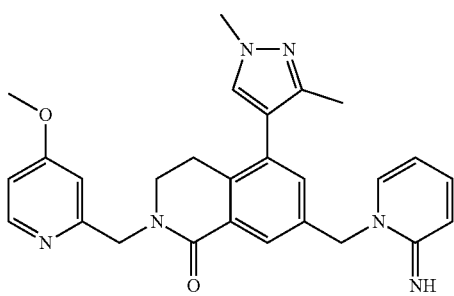 [SMILES: COc1ccnc(CN2CCc3c(cc(Cn4ccccc4=N)cc3-c3cn(C)nc3C)C2=O)c1]

Example 117

5-(1,3-Dimethyl-1H-pyrazol-4-yl)-7-((2-iminopyridin-1(2H)-yl)methyl)-2-((4-methoxypyridin-2-yl)methyl)-3,4-dihydroisoquinolin-1(2H)-one The title compound (18 mg, 35.7% yield) was prepared from the procedure described in Example 116 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20, 50 mg, 0.11 mmol) and pyridin-2-amine (31 mg, 0.33 mmol). LCMS: R$_T$=0.174 min, MS (ES) 469.6 [M+H]$^+$; $^1$H NMR (400 MHz, Chloroform-d) δ 8.33 (d, J=5.8 Hz, 1H), 7.98 (d, J=1.6 Hz, 1H), 7.34 (d, J=1.8 Hz, 1H), 7.22 (s, 1H), 7.03 (d, J=6.9 Hz, 1H), 6.89 (d, J=2.5 Hz, 2H), 6.71 (dd, J=5.8, 2.5 Hz, 1H), 6.50 (d, J=9.2 Hz, 1H), 5.85 (t, J=6.3 Hz, 1H), 5.20 (s, 2H), 4.82 (s, 2H), 3.85 (s, 3H), 3.81 (s, 3H), 3.54 (t, J=6.6 Hz, 2H), 2.83 (t, J=6.5 Hz, 2H), 2.11 (s, 3H).

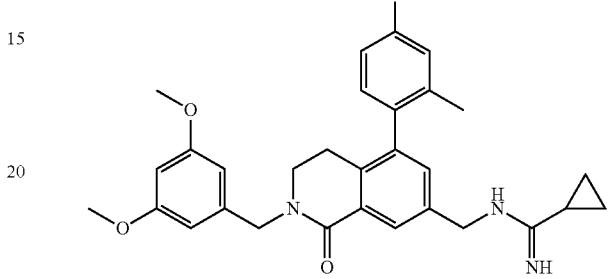

Example 118

N-((2-(3,5-Dimethoxybenzyl)-5-(4-fluoro-2-methylphenyl)-1-oxo-1,2,3,4-tetrahydroisoquinolin-7-yl)methyl)cyclopropanecarboximidamide To a solution of 7-(bromomethyl)-2-(3,5-dimethoxybenzyl)-5-(4-fluoro-2-methylphenyl)-3,4-dihydroisoquinolin-1(2H)-one (Intermediate 11, 30 mg, 0.06 mmol) in acetonitrile (3 mL) was added cyclopropylcarbamidine hydrochloride (14.5 mg, 0.12 mmol), KI (50 mg, 0.3 mmol), and N,N-diisopropylethylamine (23 μL, 0.13 mmol). The reaction mixture was stirred at room temperature overnight. The solvent was removed under reduced pressure and the residue was purified by reverse phase HPLC (Phenomenex Gemini C18, H$_2$/CH$_3$CN gradient from 15-95% CH$_3$CN, 0.1% TFA). The fractions containing the desired product were combined, concentrated, basified with K$_2$CO$_3$ (sat.), and extracted with CH$_2$Cl$_2$. The combined organic layers were dried (Na$_2$SO$_4$) and filtered. The filtrate was concentrated, dried under vacuum to provide the title compound (12.4 mg, 35%). $^1$H NMR (400 MHz, CDCl$_3$) δ 8.13 (d, J=2.0 Hz, 1H), 7.04 (m, 1H), 6.95 (m, 2H), 6.47 (d, J=2.4 Hz, 2H), 6.37 (m, 1H), 4.72 (m, 2H), 4.49 (brs, 2H), 3.77 (s, 6H), 3.37 (t, J=6.8 Hz, 2H), 2.55 (m, 2H), 2.04 (s, 3H), 1.45 (m, 1H), 0.80 (m, 4H); LC-MS: >95% 254 nm, R$_T$=1.10 min, MS (ES) 502 [M+H]$^+$.

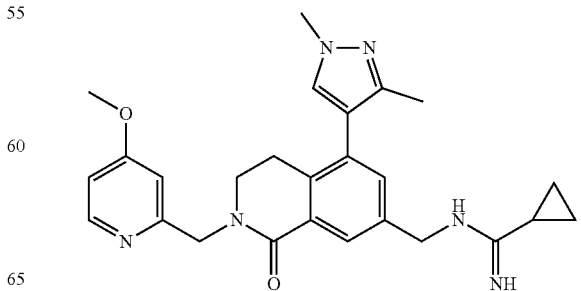

Example 119

N-((5-(1,3-Dimethyl-1H-pyrazol-4-yl)-2-((4-methoxypyridin-2-yl)methyl)-1-oxo-1,2,3,4-tetrahydroisoquinolin-7-yl)methyl)cyclopropanecarboximidamide The title compound was prepared following the procedures described in Example 118 using 7-(bromomethyl)-5-(1,3-dimethyl-1H-pyrazol-4-yl)-2-((4-methoxypyridin-2-yl)methyl)-3,4-dihydroisoquinolin-1(2H)-one (Intermediate 20) and cyclopropylcarbamidine hydrochloride. LC-MS: >95% (254 nm), $R_T$=0.24 min, MS (ES) 459.1 [M+H]$^+$.

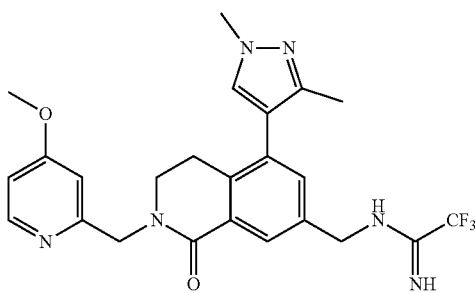 [SMILES: COc1ccnc(CN2CCc3c(cc(CNC(=N)C(F)(F)F)cc3-c3cn(C)nc3C)C2=O)c1]

Example 120

2,2,2-Trifluoro-N-((2-((4-methoxypyridin-2-yl)methyl)-5-(1-methyl-3-(trifluoromethyl)-1H-pyrazol-4-yl)-1-oxo-1,2,3,4-tetrahydroisoquinolin-7-yl)methyl)acetimidamide The title compound (45 mg, 0.083 mmol, 85%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 2,2,2-trifluoroacetimidamide (0.11 g, 0.98 mmol, 10 equiv). LC-MS: >95% (254 nm), $R_T$=0.095 min, MS (ES) 541 [M+H]$^+$.

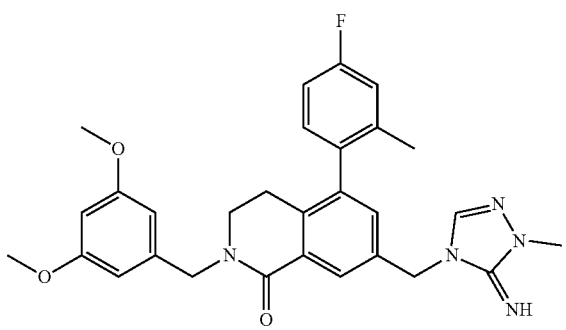

Example 121

2-(3,5-Dimethoxybenzyl)-5-(4-fluoro-2-methylphenyl)-7-((5-imino-1-methyl-1,5-dihydro-4H-1,2,4-triazol-4-yl)methyl)-3,4-dihydroisoquinolin-1(2H)-one The title compound (20 mg, 63% yield) was prepared from the procedure described in Example 116 using 7-(bromomethyl)-2-(3,5-dimethoxybenzyl)-5-(4-fluoro-2-methylphenyl)-3,4-dihydroisoquinolin-1(2H)-one (Intermediate 11, 25 mg, 0.06 mmol) and 1-methyl-1H-1,2,4-triazol-5-amine (12.9 mg, 0.12 mmol). LCMS: $R_T$=1.479 min, MS (ES) 516.6 [M+H]$^+$; $^1$H NMR (400 MHz, Chloroform-d) δ 8.10 (d, J=1.8 Hz, 1H), 7.20 (d, J=1.9 Hz, 1H), 7.19 (s, 1H), 7.03-6.87 (m, 3H), 6.45 (d, J=2.2 Hz, 2H), 6.36 (t, J=2.2 Hz, 1H), 4.84 (s, 2H), 4.76-4.64 (m, 2H), 3.76 (s, 6H), 3.41 (s, 3H), 3.37 (t, J=6.6 Hz, 2H), 2.66-2.47 (m, 2H), 2.00 (s, 3H).

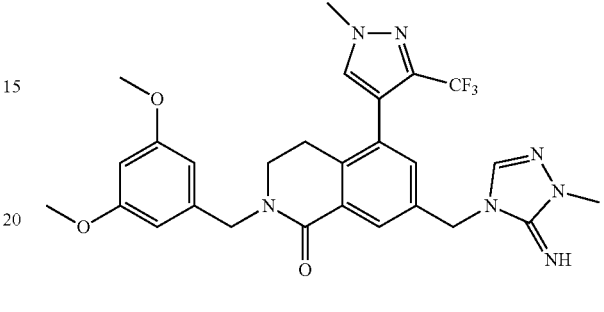

Example 122

2-(3,5-Dimethoxybenzyl)-7-((5-imino-1-methyl-1,5-dihydro-4H-1,2,4-triazol-4-yl)methyl)-5-(1-methyl-3-(trifluoromethyl)-1H-pyrazol-4-yl)-3,4-dihydroisoquinolin-1(2H)-one To a solution of 7-(bromomethyl)-2-(3,5-dimethoxybenzyl)-5-(1-methyl-3-(trifluoromethyl)-1H-pyrazol-4-yl)-3,4-dihydroisoquinolin-1(2H)-one (Intermediate 27, 30 mg, 0.056 mmol) in acetonitrile (3 mL) was added 1-methyl-1H-1,2,4-triazol-5-amine (28 mg, 0.28 mmol). The reaction mixture was stirred at 80° C. overnight. The solvent was removed under reduced pressure and the residue was purified by reverse phase HPLC (Phenomenex Gemini C18, H$_2$O/CH$_3$CN gradient from 15-95% CH$_3$CN, 0.1% TFA). The fractions containing the desired product were combined, concentrated, basified with 0.5 M NaOH, and extracted with CH$_2$Cl$_2$. The combined organic layers were dried (Na$_2$SO$_4$) and filtered. The filtrate was concentrated, dried under vacuum to provide the title compound (30 mg, 96%). $^1$H NMR (400 MHz, CDCl$_3$) δ 8.12 (d, J=1.6 Hz, 1H), 7.34 (s, 1H), 7.29 9s, 1H), 7.19 (s, 1H), 6.46 (d, J=2.0 Hz, 2H), 6.38 (m, 1H), 4.85 (s, 2H), 4.71 (s, 2H), 4.13 (s, 3H), 3.77 (s, 6H), 3.43 (s, 3H), 3.40 (t, J=6.8 Hz, 2H), 2.73 (t, J=6.8 Hz, 2H); LC-MS: >95% 254 nm, $R_T$=0.98 min, MS (ES) 556 [M+H]$^+$.

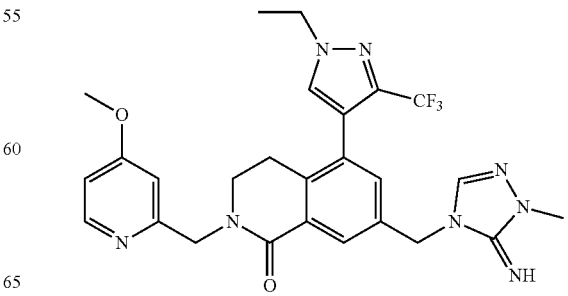

Example 123

5-(1-Ethyl-3-(trifluoromethyl)-1H-pyrazol-4-yl)-7-((5-imino-1-methyl-1,5-dihydro-4H-1,2,4-triazol-4-yl)methyl)-2-((4-methoxypyridin-2-yl)methyl)-3,4-dihydroisoquinolin-1(2H)-one The title compound (24 mg, 0.044 mmol, 58%) was prepared following the procedures described in Example 122 using 7-(bromomethyl)-5-(1-ethyl-3-(trifluoromethyl)-1H-pyrazol-4-yl)-2-((4-methoxypyridin-2-yl)methyl)-3,4-dihydroisoquinolin-1(2H)-one (Intermediate 57) and 4-methyl-4H-1,2,4-triazol-3-amine (30 mg, 0.31 mmol, 4 equiv). $^1$H NMR (400 MHz, Methanol-$d_4$) δ 8.57-8.53 (m, 1H), 8.22 (s, 1H), 8.00 (d, J=2.0 Hz, 1H), 7.85 (s, 1H), 7.46-7.39 (m, 3H), 5.26 (s, 2H), 4.99 (s, 2H), 4.30 (q, J=7.3 Hz, 2H), 4.11 (s, 3H), 3.73 (d, J=5.3 Hz, 5H), 2.96 (t, J=6.6 Hz, 2H), 1.53 (t, J=7.3 Hz, 3H); LC-MS: >95% (254 nm), $R_T$=0.087 min, MS (ES) 541 [M+H]$^+$.

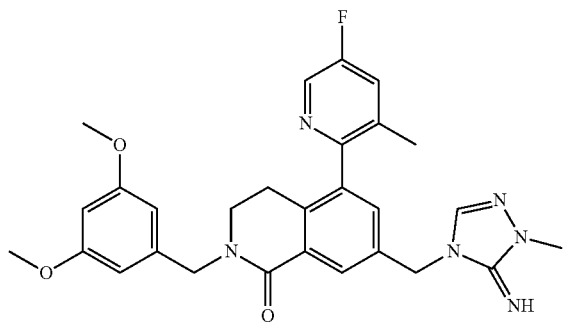

Example 124

2-(3,5-Dimethoxybenzyl)-5-(5-fluoro-3-methylpyridin-2-yl)-7-((5-imino-1-methyl-1,5-dihydro-4H-1,2,4-triazol-4-yl)methyl)-3,4-dihydroisoquinolin-1(2H)-one The title compound (20 mg, 63%) was prepared from the procedure described in Example 122 using 7-(bromomethyl)-2-(3,5-dimethoxybenzyl)-5-(5-fluoro-3-methylpyridin-2-yl)-3,4-dihydroisoquinolin-1(2H)-one (Intermediate 58) and 4-methyl-4H-1,2,4-triazol-3-amine. $^1$H NMR (400 MHz, CDCl$_3$) δ 8.35 (d, J=2.8 Hz, 1H), 8.17 (d, J=1.6 Hz, 1H), 7.35 (m, 2H), 7.20 (s, 1H), 6.46 (d, J=2.0 Hz, 2H), 6.37 (m, 1H), 4.88 (s, 2H), 4.72 (s, 2H), 3.77 (s, 6H), 3.40 (m, 5H), 2.62 (m, 2H), 2.15 (s, 3H); LC-MS: >95% 254 nm, $R_T$=0.95 min, MS 517 [M+H]$^+$.

Example 125

7-((3-Imino-[1,2,4]triazolo[4,3-a]pyridin-2(3H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (21 mg, 0.037 mmol, 38%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and [1,2,4]triazolo[4,3-a]pyridin-3-amine (26 mg, 0.2 mmol, 2 equiv). $^1$H NMR (400 MHz, Methanol-$d_4$) δ 8.57-8.53 (m, 1H), 8.50 (dt, J=7.0, 1.1 Hz, 1H), 8.12 8.05 (m, 2H), 8.00 (ddd, J=9.4, 6.8, 1.0 Hz, 1H), 7.77 (d, J=1.1 Hz, 1H), 7.54 (d, J=2.0 Hz, 1H), 7.46-7.41 (m, 3H), 5.70 (s, 2H), 4.12 (s, 3H), 4.00 (s, 3H), 3.71 (t, J=6.6 Hz, 2H), 2.95 (t, J=6.6 Hz, 2H); LC-MS: >95% (254 nm), $R_T$=0.095 min, MS (ES) 563 [M+H]$^+$.

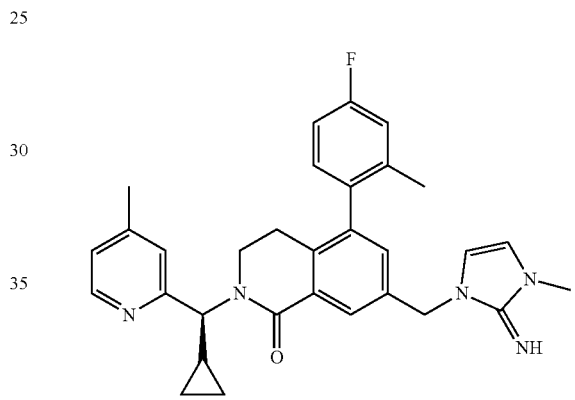

Example 126

(S)-2-(Cyclopropyl(4-methylpyridin-2-yl)methyl)-5-(4-fluoro-2-methylphenyl)-7-((5-imino-1-methyl-1,5-dihydro-4H-1,2,4-triazol-4-yl)methyl)-3,4-dihydroisoquinolin-1(2H)-one The title compound (15 mg, 46% yield) was prepared from the procedure described in Example 116 using (S)-7-(bromomethyl)-2-(cyclopropyl(4-methylpyridin-2-yl)methyl)-5-(4-fluoro-2-methylphenyl)-3,4-dihydroisoquinolin-1(2H)-one (34 mg, 0.06 mmol) (Intermediate 30) and 1-methyl-1H-1,2,4-triazol-5-amine (13 mg, 0.12 mmol). LCMS: $R_T$=1.226 min, MS (ES) 511.6 [M+H]$^+$; $^1$H NMR (400 MHz, Chloroform-d) δ 8.39 (t, J=4.8 Hz, 1H), 8.04 (s, 1H), 7.24 (d, J=6.3 Hz, 1H), 7.20 (m, 2H), 6.95 (m, 4H), 5.06 (dd, J=10.1, 3.3 Hz, 1H), 4.89 (s, 2H), 3.78-3.55 (m, 3H), 3.46 (s, 3H), 2.66-2.42 (m, 2H), 2.32* (d, J=3.4 Hz, 3H), 2.00* (d, J=32.6 Hz, 3H), 1.68-1.56 (m, 1H), 0.75 (m, 1H), 0.61 (m, 1H), 0.51 (m, 2H). (* Indicates two atropisomers (1:1))

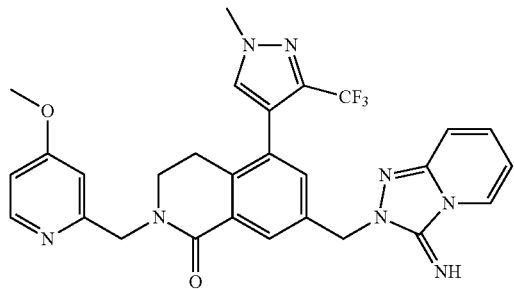 [SMILES: COc1ccnc(CN2CCc3c(cc(Cn4nc5ccccn5c4=N)cc3-c3cn(C)nc3C(F)(F)F)C2=O)c1]

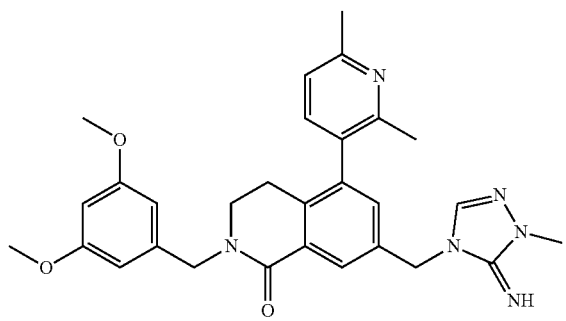

Example 127

2-(3,5-Dimethoxybenzyl)-5-(2,6-dimethylpyridin-3-yl)-7-((5-imino-1-methyl-1,5-dihydro-4H-1,2,4-triazol-4-yl)methyl)-3,4-dihydroisoquinolin-1(2H)-one The title compound (29.6 mg, 81%) was prepared from the procedure described in Example 122 using 7-(bromomethyl)-2-(3,5-dimethoxybenzyl)-5-(2,6-dimethylpyridin-3-yl)-3,4-dihydroisoquinolin-1(2H)-one (Intermediate 63) and 1-methyl-1H-1,2,4-triazol-5-amine (13 mg, 0.12 mmol). $^1$H NMR (400 MHz, CDCl$_3$) δ 8.12 (d, J=1.6 Hz, 1H), 7.27 (m, 1H), 7.22 (s, 1H), 7.20 (s, 1H), 7.03 (d, J=8.0 Hz, 1H), 6.46 (d, J=2.4 Hz, 2H), 6.37 (m, 1H), 4.86 (s, 2H), 4.76 (d, J=14.8 Hz, 1H), 4.66 (d, J=14.8 Hz, 1H), 3.77 (s, 6H), 3.39 (m, 5H), 2.59 (m, 5H), 2.24 (s, 3H); LC-MS: >95% 254 nm, R$_T$=0.75 min, MS (ES) 514 [M+H]$^+$.

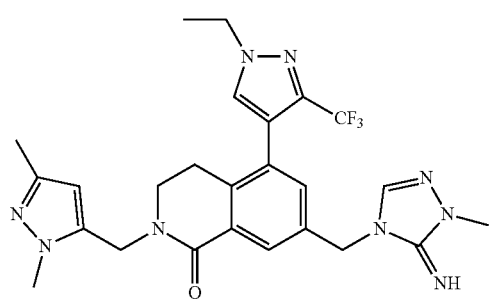 [SMILES: CCn1cc(-c2cc(Cn3cnn(C)c3=N)cc3c2CCN(Cc2cc(C)nn2C)C3=O)c(C(F)(F)F)n1]

Example 128

2-((1,3-Dimethyl-1H-pyrazol-5-yl)methyl)-7-((5-imino-1-methyl-1,5-dihydro-4H-1,2,4-triazol-4-yl)methyl)-5-(1-ethyl-3-(trifluoromethyl)-1H-pyrazol-4-yl)-3,4-dihydroisoquinolin-1(2H)-one The title compound (15 mg, 0.03 mmol) was prepared following the procedures described in Example 8 using 7-(bromomethyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one (Intermediate 31) and 1-methyl-1H-1,2,4-triazol-5-amine. $^1$H NMR (CDCl$_3$) δ 8.08 (d, J=1.8 Hz, 1H), 7.36 (s, 1H), 7.30 (s, 1H), 7.17 (s, 1H), 5.98 (s, 1H), 4.82 (s, 2H), 4.75 (S, 2H), 4.25 (q, J=7.3 Hz, 2H), 3.80 (s, 3H), 3.41 (t, J=6.8 Hz, 2H), 3.41 (s, 3H), 2.71 (t, J=6.8 Hz, 2H), 2.22 (s, 3H); 1.56 (t, J=7.3 Hz, 3H); LCMS method 1: R$_T$=1.15 min, MS (ES) 528.0 [M+H]$^+$.

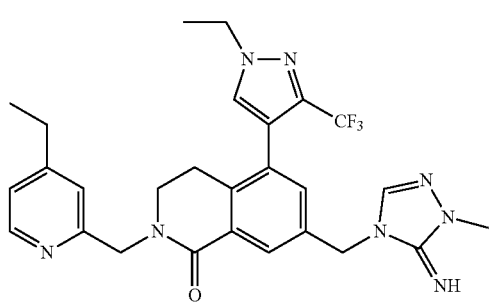 [SMILES: CCc1ccnc(CN2CCc3c(cc(Cn4cnn(C)c4=N)cc3-c3cn(CC)nc3C(F)(F)F)C2=O)c1]

Example 129

5-(1-Ethyl-3-(trifluoromethyl)-1H-pyrazol-4-yl)-2-((4-ethylpyridin-2-yl)methyl)-7-((5-imino-1-methyl-1,5-dihydro-4H-1,2,4-triazol-4-yl)methyl)-3,4-dihydroisoquinolin-1(2H)-one The title compound (12.3 mg, 52%) was prepared from the procedure described in Example 122 using 7-(bromomethyl)-5-(1-ethyl-3-(trifluoromethyl)-1H-pyrazol-4-yl)-2-((4-ethylpyridin-2-yl)methyl)-3,4-dihydroisoquinolin-1(2H)-one (Intermediate 38) and 1-methyl-1H-1,2,4-triazol-5-amine. $^1$H NMR (400 MHz, CDCl$_3$) δ 8.40 (d, J=4.8 Hz, 1H), 8.10 (s, 1H), 7.41 (s, 1H), 7.34 (s, 1H), 7.21 (s, 1H), 7.05 (m, 1H), 4.98 (s, 2H), 4.86 (s, 2H), 4.26 (q, J=7.2 Hz, 2H), 3.58 (t, J=6.4 Hz, 2H), 3.53 (s, 3H), 2.78 (t, J=6.4 Hz, 2H), 2.63 (q, J=7.6 Hz, 2H), 1.57 (t, J=7.2 Hz, 3H), 1.23 (t, J=7.2 Hz, 3H); LC-MS: >95% 254 nm, R$_T$=0.8 min, MS (ES) 539 [M+H]$^+$.

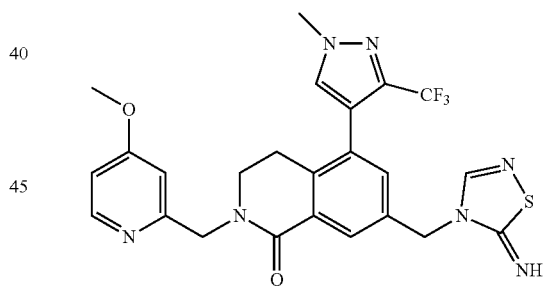

Example 130

7-((5-Imino-1,2,4-thiadiazol-4(5H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (30 mg, 0.057 mmol, 58%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and 1,2,4-thiadiazol-5-amine (0.2 g, 0.2 mmol, 2 equiv). LC-MS: >95% (254 nm), R$_T$=0.094 min, MS (ES) 530 [M+H]$^+$.

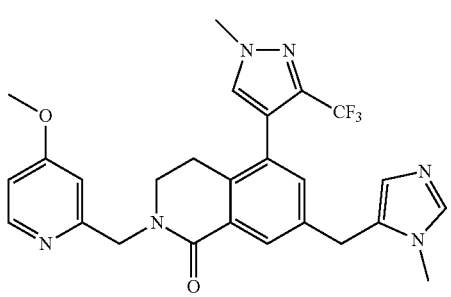 [SMILES: COc1ccnc(CN2CCc3c(cc(Cc4cncn4C)cc3-c3cn(C)nc3C(F)(F)F)C2=O)c1]

Example 131

2-((4-Methoxypyridin-2-yl)methyl)-7-((1-methyl-1H-imidazol-5-yl)methyl)-5-(1-methyl-3-(trifluoromethyl)-1H-pyrazol-4-yl)-3,4-dihydroisoquinolin-1(2H)-one Pd(PPh$_3$)$_4$ (5 mg, 0.004 mmol, 0.04 equiv) and potassium carbonate (34 mg, 0.25 mmol, 2.5 equiv) were added to a solution of 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18, 50 mg, 0.10 mmol, 1 equiv) and 1-methyl-5-(4,4,5,5-tetramethyl-1,3,2-dioxaborolan-2-yl)-1H-imidazole (31 mg, 0.15 mmol, 1.5 equiv) in dioxane/H$_2$O (2.3 mL, 0.04 M, 4:1) and degassed for 20 min. The reaction mixture was then placed in a preheated heating block and stirred for 14 h at 80° C. At 23° C., brine was added to the mixture and extracted with EtOAc (3×4 mL). The combined organic layers were dried over Na$_2$SO$_4$ and concentrated in vacuo. The residue was purified by reverse phase HPLC (Phenomenex Gemini C18, H$_2$O/CH$_3$CN gradient from 2-45% CH$_3$CN, 0.1% TFA) to yield the title compound (38 g, 0.074 mmol, 76%) as a white solid. $^1$H NMR (400 MHz, Methanol-d$_4$) δ 8.89-8.84 (m, 1H), 8.61 8.54 (m, 1H), 7.94 (d, J=2.0 Hz, 1H), 7.79 (d, J=1.1 Hz, 1H), 7.48-7.43 (m, 2H), 7.39 (d, J=2.0 Hz, 1H), 7.27 (q, J=1.1 Hz, 1H), 5.00 (s, 2H), 4.22 (s, 2H), 4.13 (s, 3H), 4.01 (s, 3H), 3.78-3.69 (m, 5H), 2.96 (t, J=6.6 Hz, 2H); LC-MS: >95% (254 nm), R$_T$=1.033 min, MS (ES) 511 [M+H]$^+$.

using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18, 50 mg, 0.10 mmol, 1 equiv) and 1-(tetrahydro-2H-pyran-2-yl)-5-(4,4,5,5-tetramethyl-1,3,2-dioxaborolan-2-yl)-1H-imidazole (41 mg, 0.15 mmol, 1.5 equiv). LC-MS: >95% (254 nm), R$_T$=0.10 min, MS (ES) 497 [M+H]$^+$.

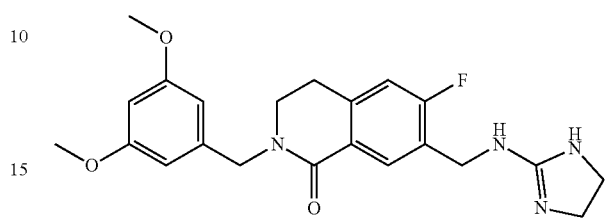

Example 133

7-(((4,5-Dihydro-1H-imidazol-2-yl)amino)methyl)-2-(3,5-dimethoxybenzyl)-6-fluoro-3,4-dihydroisoquinolin-1(2H)-one A mixture of 7-(aminomethyl)-2-(3,5-dimethoxybenzyl)-6-fluoro-3,4-dihydroisoquinolin-1(2H)-one (Intermediate 69, 11.4 mg, 0.033 mmol), 2-(methylthio)-4,5-dihydro-1H-imidazole hydroiodide (10.5 mg, 0.043 mmol) in acetonitrile (2.5 mL) was heated at 110° C. in a microwave reactor for 2 h. LC-MS analysis of the reaction mixture indicated that the reaction did not go completion. Then 2-(methylthio)-4,5-dihydro-1H-imidazole hydroiodide (12 mg, 0.049 mmol) was added and the reaction mixture was heated at 110° C. for another 2 h. The solvent was removed under reduced pressure. The residue was purified on Gilson (10-95% acetonitrile in water with 0.1% TFA). The fractions containing the desired product were combined, concentrated, basified with NaHCO$_3$ (sat.), and extracted with CH$_2$Cl$_2$/EtOAc (2/1, V/V). The combined organic layers were dried (Na$_2$SO$_4$) and filtered. The filtrate was concentrated, dried under vacuum to provide the desired product (6.7 mg, 48%): $^1$H NMR (400 MHz, CDCl$_3$) δ 7.69 (d, J=7.2 Hz, 1H), 6.72 (d, J=9.6 Hz, 1H), 6.40 (m, 3H), 4.66 (s, 2H), 4.41 (s, 2H), 3.77 (s, 6H), 3.41 (t, J=6.8 Hz, 2H), 2.78 (t, J=6.8 Hz, 2H); LC-MS, >90% (254 nm), R$_T$=0.90 min, m/z=413 [M+H]$^+$.

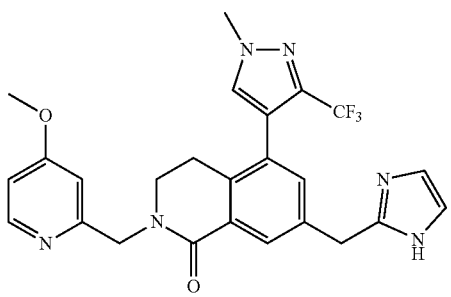 [SMILES: COc1ccnc(CN2CCc3c(cc(Cc4ncc[nH]4)cc3-c3cn(C)nc3C(F)(F)F)C2=O)c1]

Example 132

7-((1H-Imidazol-2-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (4 mg, 0.008 mmol, 8%) was prepared following the procedures described in Example 131

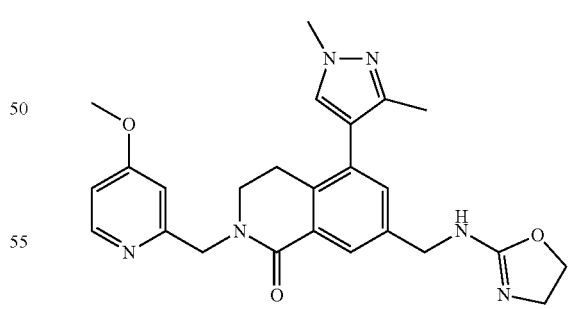

Example 134

7-(((4,5-Dihydrooxazol-2-yl)amino)methyl)-5-(1,3-dimethyl-1H-pyrazol-4-yl)-2-((4-methoxypyridin-2-yl)methyl)-3,4-dihydroisoquinolin-1(2H)-one 2-Chloroethyl isocyanate (13 µL, 0.15 mmol) was added to a solution of 7-(aminomethyl)-5-(1,3-dimethyl-1H-pyrazol-4-yl)-2-((4-methoxypyridin-2-yl)methyl)-3,4-dihydroisoquinolin-1(2H)-one (Intermediate 70, 50 mg, 0.13 mmol) in 3 mL of DCM. This was stirred at $R_T$ for 1 h when it was concentrated to dryness. The residue was diluted with 5 mL of acetonitrile and 1 mL of water. This solution was heated at 100° C. for 2 h. The reaction was concentrated, made basic with 1N $Na_2CO_3$ solution, and extracted with DCM. The DCM layer was concentrated to dryness and the crude product was purified by reverse phase HPLC (Phenomenex Gemini C18, $H_2O/CH_3CN$ gradient from 5-95% $CH_3CN$, 0.1% TFA) to yield the title compound (4 mg, 6% yield). $^1$H NMR (DMSO d6) δ 8.32 (d, J=6.1 Hz, 1H), 7.81 (d, J=1.7 Hz, 1H), 7.69 (s, 1H), 7.32 (d, J=1.8 Hz, 1H), 6.88-6.84 (m, 2H); 4.74 (s, 2H), 4.26 (s, 2H), 4.15 (t, J=8.7 Hz, 2H), 3.81 (s, 3H), 3.79 (s, 3H), 3.55 (t, J=8.7 Hz, 2H), 3.51 (t, J=6.4 Hz, 2H), 2.84 (t, J=6.4 Hz, 2H), 2.08 (s, 3H); LCMS method 1: $R_T$=0.20 min, MS (ES) 461.0 [M+H]$^+$.

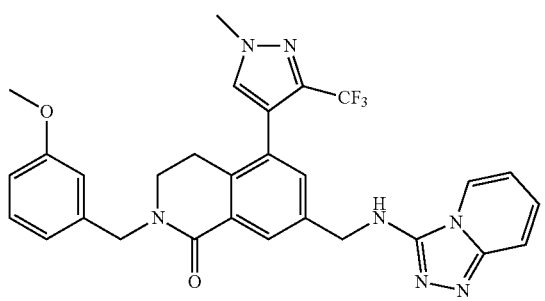 [SMILES: COc1cccc(CN2CCc3c(cc(CNc4nnc5ccccn45)cc3-c3cn(C)nc3C(F)(F)F)C2=O)c1]

Example 135

7-(([1,2,4]Triazolo[4,3-a]pyridin-3-ylamino)methyl)-2-((4-methoxypyridin-2-yl)methyl)-5-(1-methyl-3-(trifluoromethyl)-1H-pyrazol-4-yl)-3,4-dihydroisoquinolin-1(2H)-one The title compound (5 mg, 0.009 mmol, 9%) was prepared following the procedures described in Example 8 using 7-(bromomethyl)-2-((4-methoxypyridin-2-yl)methyl)-5-(1-methyl-3-(trifluoromethyl)-1H-pyrazol-4-yl)-3,4-dihydroisoquinolin-1(2H)-one (Intermediate 18) and [1,2,4]triazolo[4,3-a]pyridin-3-amine (26 mg, 0.2 mmol, 2 equiv). LC-MS: >95% (254 nm), $R_T$=0.093 min, MS (ES) 563 [M+H]$^+$.

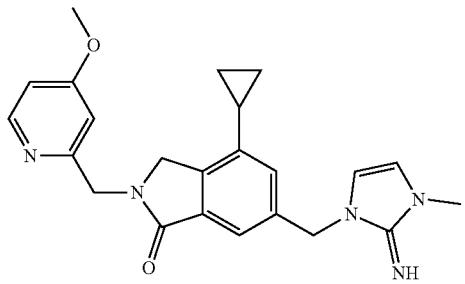 [SMILES: COc1ccnc(CN2Cc3c(cc(Cn4ccn(C)c4=N)cc3C3CC3)C2=O)c1]

Example 136

4-Cyclopropyl-6-((2-imino-3-methyl-2,3-dihydro-1H-imidazol-1-yl)methyl)-2-((4-methoxypyridin-2-yl)methyl)isoindolin-1-one The title compound (1.4 mg, 0.003 mmol) was prepared following the procedures described in Example 8 using 6-(bromomethyl)-4-cyclopropyl-2-((4-methoxypyridin-2-yl)methyl)isoindolin-1-one (Intermediate 72) and 1-methyl-1H-imidazol-2-amine. $^1$H NMR (DMSO d$_6$) δ 8.32 (d, J=5.8 Hz, 1H), 7.37 (s, 1H), 7.14 (s, 1H), 6.89-6.88 (m, 1H), 6.85 (d, J=2.4 Hz, 1H), 6.49 (d, J=2.7 Hz, 1H), 6.40 (d, J=2.7 Hz, 1H), 4.78 (s, 4H), 4.55 (s, 2H), 3.81 (s, 3H), 3.10 (s, 3H), 1.95-1.88 (m, 1H), 1.00-0.96 (m, 2H); 0.75-0.71 (m, 2H); LCMS method 1: $R_T$=0.74 min, MS (ES) 404.1 [M+H]$^+$.

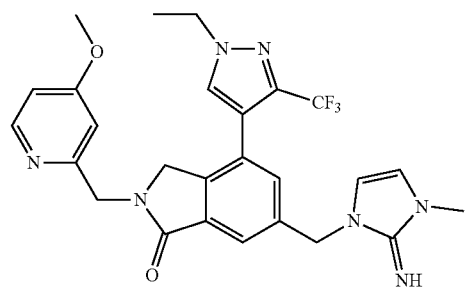 [SMILES: CCn1cc(-c2cc(Cn3ccn(C)c3=N)cc3c2CN(Cc2cc(OC)ccn2)C3=O)c(C(F)(F)F)n1]

Example 137

4-(1-Ethyl-3-(trifluoromethyl)-1H-pyrazol-4-yl)-6-((2-imino-3-methyl-2,3-dihydro-1H-imidazol-1-yl)methyl)-2-((4-methoxypyridin-2-yl)methyl)isoindolin-1-one The title compound (3 mg, 0.006 mmol) was prepared following the procedures described in Example 8 using 6-(bromomethyl)-4-(1-ethyl-3-(trifluoromethyl)-1H-pyrazol-4-yl)-2-((4-methoxypyridin-2-yl)methyl)isoindolin-1-one (Intermediate 73) and 1-methyl-1H-imidazol-2-amine. LC-MS: >95% (254 nm), $R_T$=1.097 min, MS (ES) 526 [M+H]$^+$.

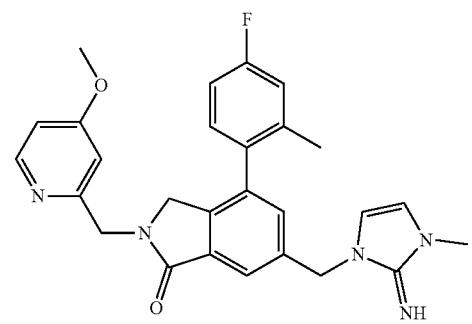 [SMILES: COc1ccnc(CN2Cc3c(cc(Cn4ccn(C)c4=N)cc3-c3ccc(F)cc3C)C2=O)c1]

Example 138

4-(4-Fluoro-2-methylphenyl)-6-((2-imino-3-methyl-2,3-dihydro-1H-imidazol-1-yl)methyl)-2-((4-methoxypyridin-2-yl)methyl)isoindolin-1-one The title compound (4.8 mg, 0.010 mmol) was prepared following the procedures described in Example 8 using 6-(bromomethyl)-4-(4-fluoro-2-methylphenyl)-2-((4-methoxypyridin-2-yl)methyl)isoindolin-1-one (Intermediate 74) and 1-methyl-1H-imidazol-2-amine. $^1$H NMR (DMSO d$_6$) δ 8.30 (d, J=5.8 Hz, 1H), 7.73 (s, 1H), 7.09-7.06 (m, 1H), 7.0-6.95 (m, 1H), 6.92-6.87 (m, 1H), 6.81 (d, J=2.6 Hz, 1H), 6.70-6.68 (m, 1H), 6.12 (d, J=2.6 Hz, 1H), 6.09 (d, J=2.6 Hz, 1H), 4.90 (s, 2H), 4.81 (s, 2H), 4.16 (s, 2H), 3.80 (s, 3H), 3.22 (s, 3H), 2.06 (s, 3H); LCMS method 1: R$_T$=1.14 min, MS (ES) 472.4 [M+H]$^+$.

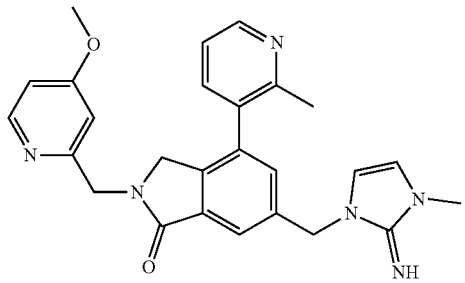 [SMILES: COc1ccnc(CN2Cc3c(cc(Cn4ccn(C)c4=N)cc3-c3cccnc3C)C2=O)c1]

Example 139

6-((2-Imino-3-methyl-2,3-dihydro-1H-imidazol-1-yl)methyl)-2-((4-methoxypyridin-2-yl)methyl)-4-(2-methylpyridin-3-yl)isoindolin-1-one The title compound (4.0 mg, 0.010 mmol) was prepared following the procedures described in Example 8 using 6-(bromomethyl)-2-((4-methoxypyridin-2-yl)methyl)-4-(2-methylpyridin-3-yl)isoindolin-1-one (Intermediate 75) and 1-methyl-1H-imidazol-2-amine. $^1$H NMR (CDCl$_3$) δ 8.53 (dd, J=4.9, 1.8 Hz, 1H), 8.30 (d, J=5.8 Hz, 1H), 7.76 (s, 1H), 7.44 (dd, J=7.6, 1.7 Hz, 1H), 7.30 (d, J=1.4 Hz, 1H), 7.18-7.15 (m, 1H), 6.82 (d, J=2.6 Hz, 1H), 6.69 (dd, J=5.5, 2.6 Hz, 1H), 6.12 (d 2.7 Hz, 1H), 6.10 (d 2.7 Hz, 1H), 4.91 (s, 2H), 4.81 (s, 2H), 4.18 (s, 2H), 3.80 (s, 3H), 3.21 (s, 3H), 2.32 (s, 3H); LCMS method 1: R$_T$=0.17 min, MS (ES) 455.0 [M+H]$^+$.

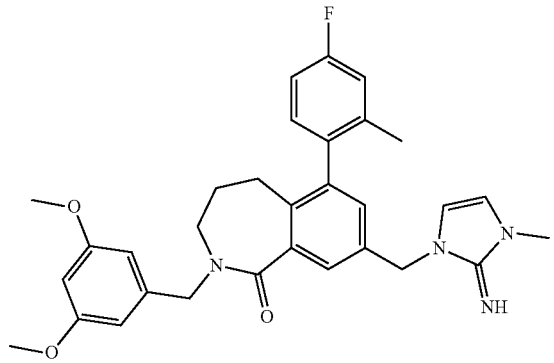

Example 140

2-(3,5-Dimethoxybenzyl)-6-(4-fluoro-2-methylphenyl)-8-((2-imino-3-methyl-2,3-dihydro-1H-imidazol-1-yl)methyl)-2,3,4,5-tetrahydro-1H-benzo[c]azepin-1-one The title compound (27 mg, 75%) was prepared from the procedure described in Example 68 using 8-(bromomethyl)-2-(3,5-dimethoxybenzyl)-6-(4-fluoro-2-methylphenyl)-2,3,4,5-tetrahydro-1H-benzo[c]azepin-1-one (Intermediate 76) and 1-methyl-1H-imidazol-2-amine. $^1$H NMR (400 MHz, CDCl$_3$) δ 7.59 (d, J=1.6 Hz, 1H), 7.13 (s, 1H), 6.92 (m, 3H), 6.50 (d, J=2.0 Hz, 2H), 6.37 (m, 1H), 6.22 (s, 2H), 4.99 (m, 2H), 4.70 (m, 2H), 3.77 (s, 6H), 3.40 (s, 3H), 3.21 (m, 2H), 2.48 (m, 2H), 1.98 (s, 3H), 1.55 (m, 2H); LC-MS, >95% (254 nm), R$_T$=1.10 min, m/z=530 [M+H]$^+$.

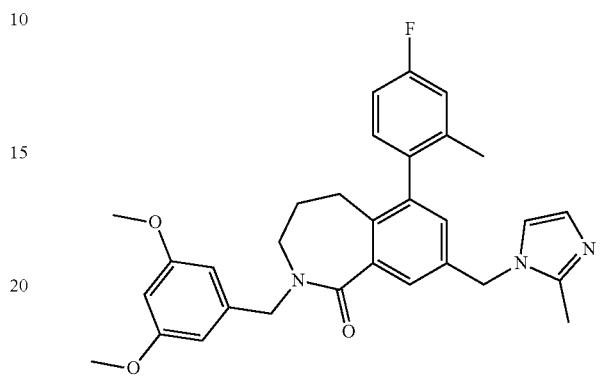

Example 141

2-(3,5-dimethoxybenzyl)-6-(4-fluoro-2-methylphenyl)-8-((2-methyl-1H-imidazol-1-yl)methyl)-2,3,4,5-tetrahydro-1H-benzo[c]azepin-1-one The title compound (18 mg, 51%) was prepared from the procedure described in Example 1 using 8-(bromomethyl)-2-(3,5-dimethoxybenzyl)-6-(4-fluoro-2-methylphenyl)-2,3,4,5-tetrahydro-1H-benzo[c]azepin-1-one (Intermediate 76) and 2-methyl-1H-imidazole. $^1$H NMR (400 MHz, CDCl$_3$) δ 7.565 (s, 1H), 6.89 (m, 6H), 6.51 9s, 2H), 6.38 (s, 1H), 5.08 (s, 2H), 4.69 (m, 2H), 3.77 (s, 6H), 3.21 (t, J=6.0 Hz, 2H), 2.44 (m, 2H), 2.37 (s, 3H), 1.94 (s, 3H), 1.53 (m, 2H); LC-MS: >95% (254 nm), R$_T$=1.09 min, MS (ES) 515 [M+H]$^+$.

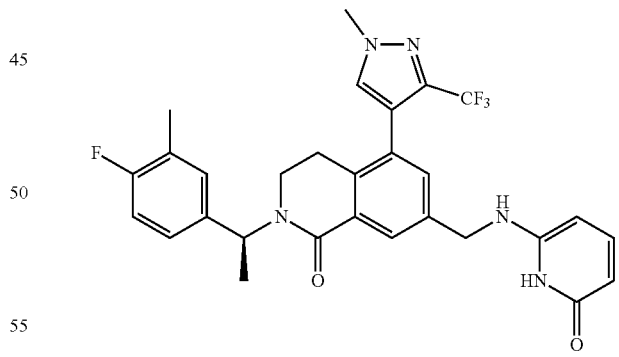

Example 142

(S)-2-(1-(4-Fluoro-3-methylphenyl)ethyl)-5-(1-methyl-3-(trifluoromethyl)-1H-pyrazol-4-yl)-7-(((6-oxo-1,6-dihydropyridin-2-yl)amino)methyl)-3,4-dihydroisoquinolin-1(2H)-one Step A. Preparation of (S)-7-(aminomethyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one. The title compound (77 mg, 0.17 mmol) was prepared following the procedures described in Intermediate 70 Step B and C utilizing (S)-7-(bromomethyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one (Intermediate 40).

Step B. Preparation of (S)-7-(((6-(benzyloxy)pyridin-2-yl)amino)methyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one. (S)-7-(aminomethyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-on e (77 mg, 0.17 mmol), 2-(benzyloxy)-6-bromopyridine (44 mg, 0.17 mmol), sodium t-butoxide (22 mg, 0.23 mmol), Pd$_2$(dba)$_3$ (1.5 mg, 1.7 μmol), and 2'-(dicyclohexylphosphaneyl)-N,N-dimethyl-[1,1'-biphenyl]-2-amine (0.6 mg, 1.7 μmol) were combined in 2 mL of toluene in a microwave vial. The reaction was degassed with Ar, capped, and heated in the microwave at 120° C. for 15 minutes. The reaction was diluted with 5 mL of EtOAc, filtered, and concentrated to dryness. The residue was purified by flash chromatography (Combi-flash Rf, Hex/EtOAc=0-50% gradient) to afford the title compound (39 mg, 36% yield). LCMS method 1: R$_T$=2.20 min, MS (ES) 643.9 [M+H]$^+$.

Step C. (S)-2-(1-(4-Fluoro-3-methylphenyl)ethyl)-5-(1-methyl-3-(trifluoromethyl)-1H-pyrazol-4-yl)-7-(((6-oxo-1,6-dihydropyridin-2-yl)amino)methyl)-3,4-dihydroisoquinolin-1(2H)-one. To a solution of (S)-7-(((6-(benzyloxy)pyridin-2-yl)amino)methyl)-2-(1-(4-fluoro-3-methylphenyl)ethyl)-5-(1-methyl-3-(trifluoromethyl)-1H-pyrazol-4-yl)-3,4-dihydroisoquinolin-1(2H)-one (39 mg, 0.06 mmol) in 2 mL of methanol was added 4 mg of 10% Pd/C. The reaction was degassed and placed under a H$_2$ balloon for 30 minutes. The catalyst was filtered off, the filtrate was concentrated to dryness, and the crude product was purified by flash chromatography (Combi-flash Rf, DCM/MeOH=0-10% gradient) to afford the title compound (18 mg, 54% yield). $^1$H NMR (CDCl$_3$) δ 8.15 (s, 1H), 7.31-7.28 (m, 2H), 7.22 (d, J=8.4 Hz, 1H), 7.17-7.11 (m, 2H), 6.94 (t, J=8.7 Hz, 1H), 6.15-6.06 (m, 2H), 5.73 (d, J=8.3 Hz, 1H), 5.31 (d, J=8.3 Hz, 1H), 4.38 (d, J=5.3 Hz, 2H), 3.95 (s, 3H), 3.30-3.24 (m, 1H), 3.04-2.98 (m, 1H), 2.65-2.50 (m, 2H), 2.24 (s, 3H), 1.53 (d, J=7.4 Hz, 3H); LCMS method 1: R$_T$=1.66 min, MS (ES) 553.9 [M+H]$^+$.

(S)-7-(bromomethyl)-5-(1,3-dimethyl-1H-pyrazol-4-yl)-2-(1-(4-fluoro-3-methylphenyl)ethyl)-3,4-dihydroisoquinolin-1(2H)-one (Intermediate 77) and 1-methyl-1H-imidazol-2-amine. LCMS method 1: R$_T$=1.31 min, MS (ES) 487.0 [M+H]$^+$.

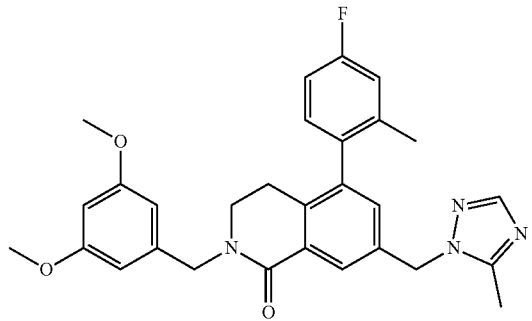

Example 144

2-(3,5-Dimethoxybenzyl)-5-(4-fluoro-2-methylphenyl)-7-((5-methyl-1H-1,2,4-triazol-1-yl)methyl)-3,4-dihydroisoquinolin-1(2H)-one The title compound (11 mg, 41%) was prepared as a mixture of two inseparable isomers (52/48, based on NMR spectrum) from the procedure described in Example 1 using 7-(bromomethyl)-2-(3,5-dimethoxybenzyl)-5-(4-fluoro-2-methyl phenyl)-3,4-dihydroisoquinolin-1(2H)-one (Intermediate 11) and 5-methyl-1H-1,2,4-triazole. Isomer 1 $^1$H NMR (400 MHz, CDCl$_3$) δ 8.12 (s, 1H), 7.99 (s, 1H), 7.16 (s, 1H), 6.95 (m, 3H), 6.46 (m, 2H), 6.37 (m, 1H), 5.32 (s, 2H), 4.72 (m, 2H), 3.77 (s, 6H), 3.38 (t, J=6.4 Hz, 2H), 2.59 (m, 2H), 2.39 (s, 3H), 2.00 (s, 3H); LC-MS: >52% (254 nm), R$_T$=1.16 min, MS (ES) 501.5 [M+H]. Isomer 2 $^1$H NMR (400 MHz, CDCl$_3$) δ 8.07 (s, 1H), 7.81 (s, 1H), 7.05 (s, 1H), 6.95 (m, 3H), 6.46 (m, 2H), 6.37 (m, 1H), 5.35 (s, 2H), 4.72 (m, 2H), 3.77 (s, 6H), 3.38 (t, J=6.4 Hz, 2H), 2.59 (m, 2H), 2.47 (s, 3H), 1.98 (s, 3H); LC-MS: >48% (254 nm), R$_T$=1.16 min, MS (ES) 501.5 [M+H]$^+$.

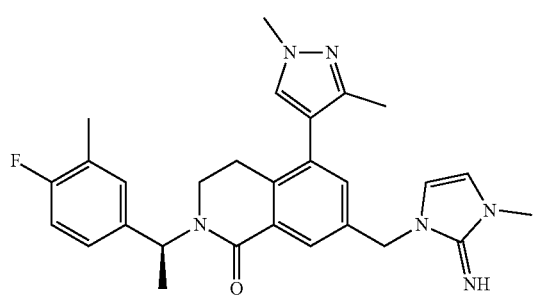 [SMILES: Cc1cc([C@H](C)N2CCc3c(cc(Cn4ccn(C)c4=N)cc3-c3cn(C)nc3C)C2=O)ccc1F]

Example 143

(S)-5-(1,3-Dimethyl-1H-pyrazol-4-yl)-2-(1-(4-fluoro-3-methylphenyl)ethyl)-7-((2-imino-3-methyl-2,3-dihydro-1H-imidazol-1-yl)methyl)-3,4-dihydroisoquinolin-1(2H)-one The title compound (6 mg, 0.01 mmol) was prepared following the procedures described in Example 8 using

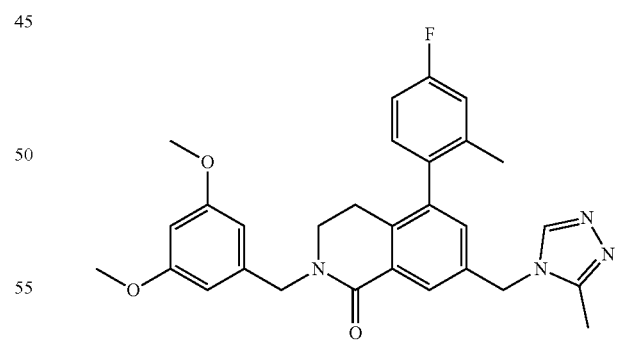

Example 145

2-(3,5-Dimethoxybenzyl)-5-(4-fluoro-2-methylphenyl)-7-((3-methyl-4H-1,2,4-triazol-4-yl)methyl)-3,4-dihydroisoquinolin-1(2H)-one The title compound (6.8 mg, 24%) was prepared from the procedure described in Example 1 using 7-(bromomethyl)-

2-(3,5-dimethoxybenzyl)-5-(4-fluoro-2-methylphenyl)-3,4-dihydroisoquinolin-1(2H)-one (Intermediate 11) and 5-methyl-1H-1,2,4-triazole. $^1$H NMR (400 MHz, CDCl$_3$) δ 8.17 (s, 1H), 8.10 (s, 1H), 6.93 (m, 4H), 6.46 (d, J=2.4 Hz, 2H), 6.37 (m, 1H), 5.16 (s, 2H), 4.71 (m, 2H), 3.77 (s, 6H), 3.40 (t, J=6.8 Hz, 2H), 2.55 (m, 2H), 2.39 (s, 3H), 1.97 (s, 3H); LC-MS: >95% (254 nm), R$_T$=1.09 min, MS (ES) 501.5 [M+H]$^+$.

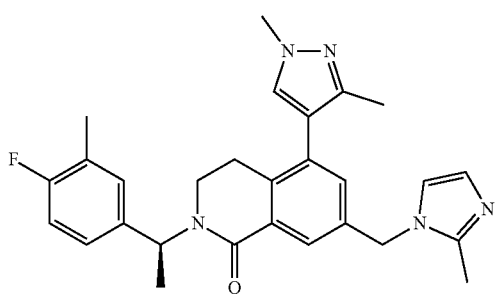 [SMILES: Cc1cc([C@H](C)N2CCc3c(cc(Cn4ccnc4C)cc3-c3cn(C)nc3C)C2=O)ccc1F]

Example 146

(S)-5-(1,3-Dimethyl-1H-pyrazol-4-yl)-2-(1-(4-fluoro-3-methylphenyl)ethyl)-7-((2-methyl-1H-imidazol-1-yl)methyl)-3,4-dihydroisoquinolin-1(2H)-one The title compound (14 mg, 0.03 mmol) was prepared following the procedures described in Example 8 using (S)-7-(bromomethyl)-5-(1,3-dimethyl-1H-pyrazol-4-yl)-2-(1-(4-fluoro-3-methylphenyl)ethyl)-3,4-dihydroisoquinolin-1(2H)-one (Intermediate 77) and 2-methyl-1H-imidazole. LCMS method 1: R$_T$=1.28 min, MS (ES) 472.0 [M+H]$^+$.

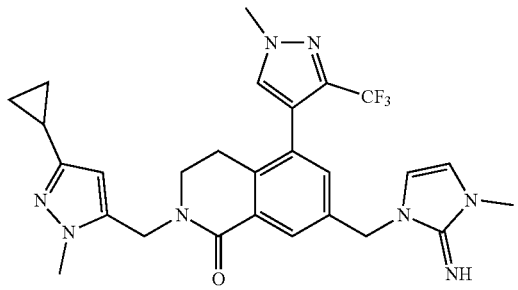 [SMILES: Cn1cc(-c2cc(Cn3ccn(C)c3=N)cc3c2CCN(Cc2cc(C4CC4)nn2C)C3=O)c(C(F)(F)F)n1]

Example 147

2-((3-Cyclopropyl-1-methyl-1H-pyrazol-5-yl)methyl)-7-((2-imino-3-methyl-2,3-dihydro-1H-imidazol-1-yl)methyl)-5-(1-methyl-3-(trifluoromethyl)-1H-pyrazol-4-yl)-3,4-dihydroisoquinolin-1(2H)-one The title compound (67 mg, 0.121 mmol, 84%) was prepared following the procedure described in Example 8 using 7-(bromomethyl)-2-((3-cyclopropyl-1-methyl-1H-pyrazol-5-yl)methyl)-5-(1-methyl-3-(trifluoromethyl)-1H-pyrazol-4-yl)-3,4-dihydroisoquinolin-1(2H)-one (Intermediate 78) and 1-methyl-1H-imidazol-2-amine (28 mg, 0.29 mmol, 2 equiv). LC-MS: >95% (254 nm), R$_T$=0.153 min, MS (ES) 539 [M+H]$^+$.

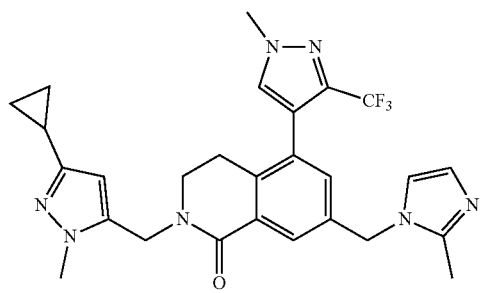 [SMILES: Cc1nccn1Cc1cc2c(c(-c3cn(C)nc3C(F)(F)F)c1)CCN(Cc1cc(C3CC3)nn1C)C2=O]

Example 148

2-((3-Cyclopropyl-1-methyl-1H-pyrazol-5-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (60 mg, 0.11 mmol, 75%) was prepared following the procedures described in Example 8 using 7-(bromomethyl)-2-((3-cyclopropyl-1-methyl-1H-pyrazol-5-yl)methyl)-5-(1-methyl-3-(trifluoromethyl)-1H-pyrazol-4-yl)-3,4-dihydroisoquinolin-1(2H)-one (Intermediate 78) and 2-methyl-1H-imidazole (24 mg, 0.29 mmol, 2 equiv). LC-MS: >95% (254 nm), R$_T$=0.82 min, MS (ES) 524 [M+H]$^+$.

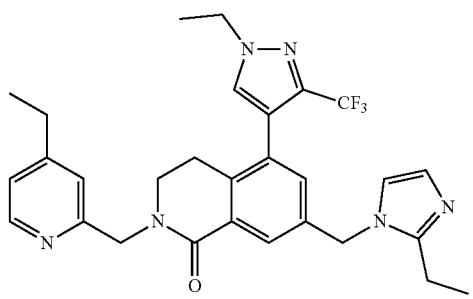 [SMILES: CCc1ccnc(CN2CCc3c(cc(Cn4ccnc4CC)cc3-c3cn(CC)nc3C(F)(F)F)C2=O)c1]

Example 149

7-((2-Ethyl-1H-imidazol-1-yl)methyl)-5-(1-ethyl-3-(trifluoromethyl)-1H-pyrazol-4-yl)-2-((4-ethylpyridin-2-yl)methyl)-3,4-dihydroisoquinolin-1(2H)-one The title compound (14.5 mg, 72%) was prepared from the procedure described in Example 8 using 7-(bromomethyl)-5-(1-ethyl-3-(trifluoromethyl)-1H-pyrazol-4-yl)-2-((4-ethylpyridin-2-yl)methyl)-3,4-dihydroisoquinolin-1(2H)-one (Intermediate 38) and 2-ethyl-1H-imidazole. $^1$H NMR (400 MHz, CDCl$_3$) δ 8.40 (d, J=5.2 Hz, 1H), 8.07 (s, 1H), 7.32 (s, 1H), 7.22 (s, 1H), 7.04 (m, 2H), 6.95 (s, 1H), 6.87 (s, 1H), 5.12 (s, 2H), 4.86 (s, 2H), 4.25 (q, J=7.6 Hz, 2H), 3.58 (t, J=6.4 Hz, 2H), 2.76 (t, J=6.4 Hz, 2H), 2.71 (q, J=7.6 Hz, 2H), 2.63 (q, J=7.6 Hz, 2H), 1.56 (t, J=7.6 Hz, 3H), 1.32 (t, J=7.6 Hz, 3H), 1.23 (t, J=7.6 Hz, 3H); LC-MS: >95% (254 nm), R$_T$=0.82 min, MS (ES) 537.6 [M+H]$^+$.

249

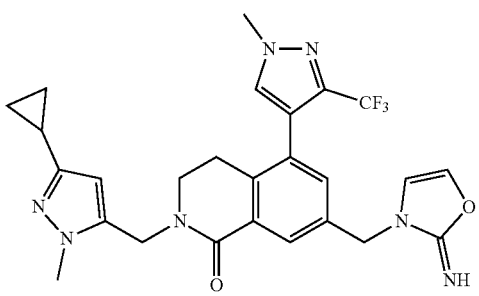 [SMILES: Cn1cc(-c2cc(Cn3ccoc3=N)cc3c2CCN(Cc2cc(C4CC4)nn2C)C3=O)c(C(F)(F)F)n1]

Example 150

2-((3-Cyclopropyl-1-methyl-1H-pyrazol-5-yl)methyl)-7-((2-iminooxazol-3(2H)-yl)methyl)-5-(1-methyl-3-(trifluoromethyl)-1H-pyrazol-4-yl)-3,4-dihydroisoquinolin-1(2H)-one The title compound (41 mg, 0.078 mmol, 54%) was prepared following the procedures described in Example 8 using 7-(bromomethyl)-2-((3-cyclopropyl-1-methyl-1H-pyrazol-5-yl)methyl)-5-(1-methyl-3-(trifluoromethyl)-1H-pyrazol-4-yl)-3,4-dihydroisoquinolin-1(2H)-one (Intermediate 78) and oxazol-2-amine (24 mg, 0.29 mmol, 2 equiv). $^1$H NMR (400 MHz, Methanol-$d_4$) δ 8.02 (d, J=2.0 Hz, 1H), 7.79 (d, J=1.1 Hz, 1H), 7.69 (d, J=1.7 Hz, 1H), 7.43 (d, J=2.0 Hz, 1H), 7.37 (d, J=1.7 Hz, 1H), 6.04 (s, 1H), 5.17 (s, 2H), 4.80 (s, 2H), 4.00 (s, 3H), 3.82 (s, 3H), 3.53 (t, J=6.6 Hz, 2H), 2.84 (t, J=6.6 Hz, 2H), 1.86 (tt, J=8.5, 5.0 Hz, 1H), 0.97-0.86 (m, 2H), 0.72-0.62 (m, 2H); LC-MS: >95% (254 nm), $R_T$=0.766 min, MS (ES) 526 [M+H]$^+$.

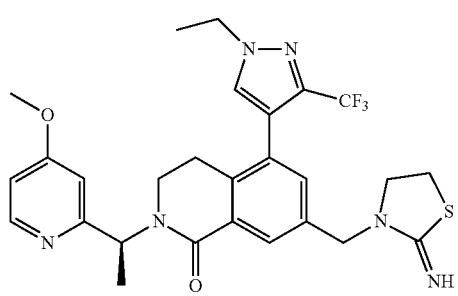 [SMILES: CCn1cc(-c2cc(CN3CCSC3=N)cc3c2CCN([C@@H](C)c2cc(OC)ccn2)C3=O)c(C(F)(F)F)n1]

Example 151

(S)-5-(1-Ethyl-3-(trifluoromethyl)-1H-pyrazol-4-yl)-7-((2-iminothiazolidin-3-yl)methyl)-2-(1-(4-methoxypyridin-2-yl)ethyl)-3,4-dihydroisoquinolin-1(2H)-one The title compound (61 mg, 0.13 mmol, 68%) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 4,5-dihydrothiazol-2-amine (38 mg, 0.37 mmol, 2 equiv). LC-MS: >95% (254 nm), $R_T$=1.084 min, MS (ES) 560 [M+H].

250

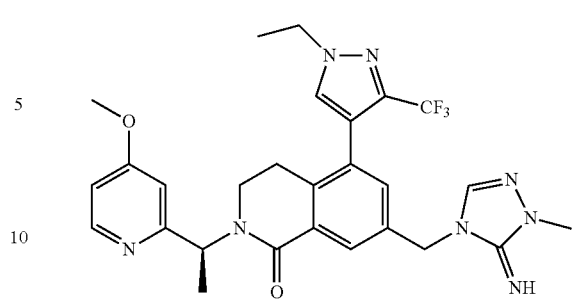

Example 152

(S)-5-(1-ethyl-3-(trifluoromethyl)-1H-pyrazol-4-yl)-7-((5-imino-1-methyl-1,5-dihydro-4H-1,2,4-triazol-4-yl)methyl)-2-(1-(4-methoxypyridin-2-yl)ethyl)-3,4-dihydroisoquinolin-1(2H)-one The title compound (14 mg, 0.02 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 1-methyl-1H-1,2,4-triazol-5-amine. LCMS method 1: $R_T$=1.02 min, MS (ES) 555.0 [M+H]$^+$.

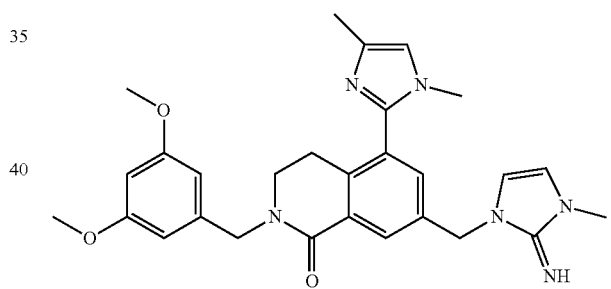

Example 153

2-(3,5-Dimethoxybenzyl)-5-(1,4-dimethyl-1H-imidazol-2-yl)-7-((2-imino-3-methyl-2,3-dihydro-1H-imidazol-1-yl)methyl)-3,4-dihydroisoquinolin-1(2H)-one The title compound (6.5 mg, 19%,) was prepared from the procedure described in Example 27 using 7-(bromomethyl)-2-(3,5-dimethoxybenzyl)-5-(1,4-dimethyl-1H-imidazol-2-yl)-3,4-dihydroisoquinolin-1(2H)-one (Intermediate 79) and 1-methyl-1H-imidazol-2-amine. $^1$H NMR (400 MHz, CDCl$_3$) δ 8.09 (s, 1H), 7.58 (s, 1H), 6.67 (s, 1H), 6.45 (d, J=2.0 Hz, 2H), 6.35 (m, 3H), 5.25 (s, 2H), 4.70 (s, 2H), 3.77 (s, 6H), 3.53 (s, 3H), 3.50 (s, 3H), 3.43 (t, J=6.4 Hz, 2H), 2.92 (t, J=6.4 Hz, 2H), 2.21 (s, 3H); LC-MS: >95% (254 nm), $R_T$=0.77 min, MS (ES) 501.6 [M+H]$^+$.

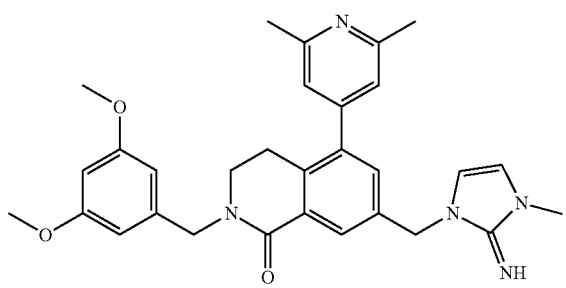

Example 154

2-(3,5-Dimethoxybenzyl)-5-(2,6-dimethylpyridin-4-yl)-7-((2-imino-3-methyl-2,3-dihydro-1H-imidazol-1-yl)methyl)-3,4-dihydroisoquinolin-1(2H)-one The title compound (9.8 mg, 38%) was prepared from the procedure described in Example 27 using 7-(bromomethyl)-2-(3,5-dimethoxybenzyl)-5-(2,6-dimethylpyridin-4-yl)-3,4-dihydroisoquinolin-1(2H)-one (Intermediate 80) and 1-methyl-1H-imidazol-2-amine. $^1$H NMR (400 MHz, CDCl$_3$) δ 8.06 (d, J=2.0 Hz, 1H), 7.48 (s, 1H), 6.89 (s, 2H), 6.46 (d, J=2.0 Hz, 2H), 6.38 (m, 3H), 5.29 (s, 2H), 4.69 (s, 2H), 3.77 (s, 6H), 3.58 (s, 3H), 3.39 (t, J=6.4 Hz, 2H), 2.84 (t, J=6.4 Hz, 2H), 2.54 (s, 6H); LC-MS: >95% (254 nm), R$_T$=0.80 min, MS (ES) 512.6 [M+H]$^+$.

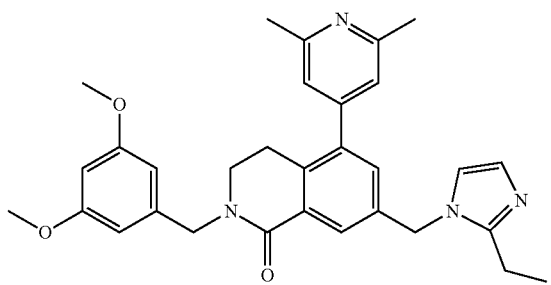 [SMILES: CCc1nccn1Cc1cc2c(c(-c3cc(C)nc(C)c3)c1)CCN(Cc1cc(OC)cc(OC)c1)C2=O]

Example 155

2-(3,5-Dimethoxybenzyl)-5-(2,6-dimethylpyridin-4-yl)-7-((2-ethyl-1H-imidazol-1-yl)methyl)-3,4-dihydroisoquinolin-1(2H)-one The title compound (10 mg, 38%) was prepared from the procedure described in Example 1 using 7-(bromomethyl)-2-(3,5-dimethoxybenzyl)-5-(2,6-dimethylpyridin-4-yl)-3,4-dihydroisoquinolin-1(2H)-one (Intermediate 80) and 2-ethyl-1H-imidazole. $^1$H NMR (400 MHz, CDCl$_3$) δ 8.09 (d, J=1.6 Hz, 1H), 7.07 (s, 1H), 7.00 (d, J=2.0 Hz, 1H), 6.90 (s, 1H), 6.80 (s, 2H), 6.47 (d, J=2.0 Hz, 2H), 6.38 (m, 1H), 5.15 (s, 2H), 4.72 (s, 2H), 3.78 (s, 6H), 3.41 (t, J=6.4 Hz, 2H), 2.81 (m, 4H), 2.56 (s, 6H), 1.35 (t, J=7.6 Hz, 3H); LC-MS: >95% (254 nm), R$_T$=0.81 min, MS (ES) 511.6 [M+H]$^+$.

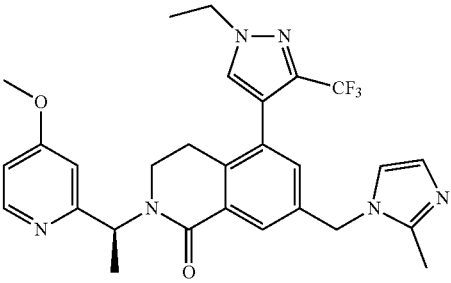 [SMILES: CCn1cc(-c2cc(Cn3ccnc3C)cc3c2CCN([C@@H](C)c2cc(OC)ccn2)C3=O)c(C(F)(F)F)n1]

Example 156

(S)-5-(1-Ethyl-3-(trifluoromethyl)-1H-pyrazol-4-yl)-2-(1-(4-methoxypyridin-2-yl)ethyl)-7-((2-methyl-1H-imidazol-1-yl)methyl)-3,4-dihydroisoquinolin-1(2H)-one The title compound (21 mg, 0.04 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 2-methyl-1H-imidazole. $^1$H NMR (CDCl$_3$) δ 8.39 (d, J=5.4 Hz, 1H), 8.06 (d, J=1.4 Hz, 1H), 7.31 (s, 1H), 6.97-6.96 (m, 2H), 6.93 (d, J=2.4 Hz, 1H), 6.88 (d, J=1.4 Hz, 1H), 6.74 (dd, J=5.4, 1.4 Hz, 1H), 6.12 (q, J=7.1 Hz, 1H), 5.11 (s, 2H), 4.25 (q, J=7.4 Hz, 2H), 3.85 (s, 3H), 3.53-3.46 (m, 1H), 3.40-3.33 (m, 1H), 2.73-2.60 (m, 2H), 2.38 (s, 3H), 1.64 (t, J=7.1 Hz, 3H), 1.57 (t, J=7.4 Hz, 3H); LCMS method 1: R$_T$=1.04 min, MS (ES) 538.9 [M+H]$^+$.

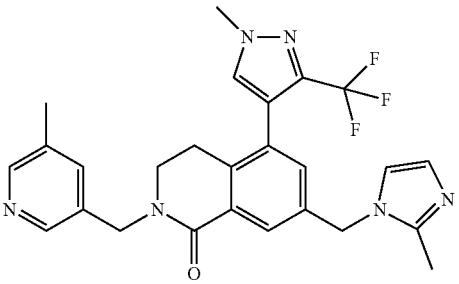 [SMILES: Cc1cncc(CN2CCc3c(cc(Cn4ccnc4C)cc3-c3cn(C)nc3C(F)(F)F)C2=O)c1]

Example 157

7-((2-Methyl-1H-imidazol-1-yl)methyl)-5-(1-methyl-3-(trifluoromethyl)-1H-pyrazol-4-yl)-2-((5-methylpyridin-3-yl)methyl)-3,4-dihydroisoquinolin-1(2H)-one The title compound (6.9 mg, 16% yield) was prepared from the procedure described in Example 12 using 7-(bromomethyl)-5-(1-methyl-3-(trifluoromethyl)-1H-pyrazol-4-yl)-2-((5-methylpyridin-3-yl)methyl)-3,4-dihydroisoquinolin-1(2H)-one (Intermediate 81, 42 mg, 0.09 mmol) and 2-methyl-1H-imidazole (21 mg, 0.26 mmol). LCMS: >95% 254 nm, R$_T$=0.958 min, MS (ES) 495.5 [M+H]$^+$; $^1$H NMR (400 MHz, Methanol-d$_4$) δ 8.33 (s, 1H), 8.30 (s, 1H), 7.89 (d, J=1.5 Hz, 1H), 7.73 (s, 1H), 7.65 (s, 1H), 7.13 (s, 1H), 7.07 (d, J=1.2 Hz, 1H), 6.85 (d, J=1.2 Hz, 1H), 5.25 (s, 2H), 4.77 (s, 2H), 3.96 (s, 3H), 3.50 (t, J=6.6 Hz, 2H), 3.34 (s, 2H), 2.79 (t, J=6.6 Hz, 2H), 2.34 (s, 3H), 2.29 (s, 3H).

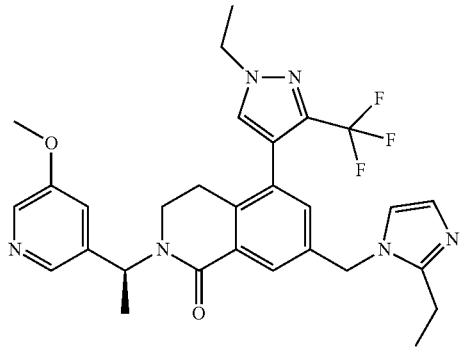 [SMILES: CCc1nccn1Cc1cc2c(c(-c3cn(CC)nc3C(F)(F)F)c1)CCN([C@@H](C)c1cncc(OC)c1)C2=O]

Example 158

(S)-7-((2-ethyl-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound (12 mg, 0.022 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 2-ethyl-1H-imidazole. LC-MS Method 2: >95% 254 nm, $R_T$=1.09 min, MS (ES) 553.0 [M+H]$^+$.

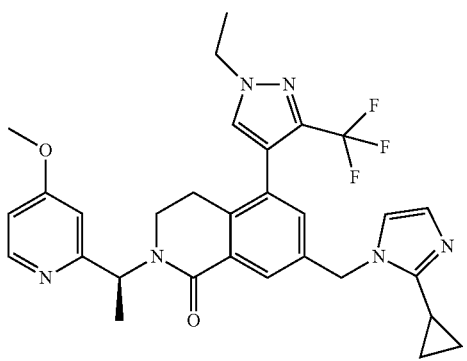 [SMILES: CCn1cc(-c2cc(Cn3ccnc3C3CC3)cc3c2CCN([C@@H](C)c2cc(OC)ccn2)C3=O)c(C(F)(F)F)n1]

Example 159

(S)-7-((2-Cyclopropyl-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound (10 mg, 0.019 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 2-cyclopropyl-1H-imidazole. LC-MS Method 2: >95% 254 nm, $R_T$=1.09 min, MS (ES) 565.0 [M+H]$^+$.

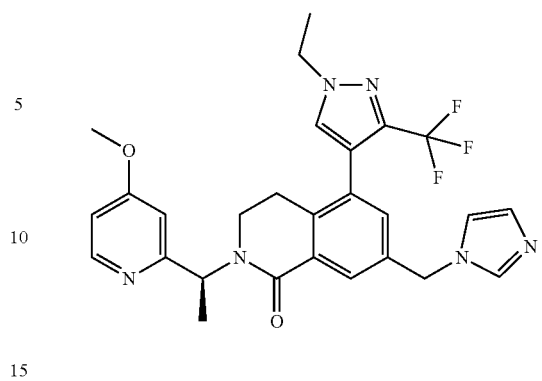

Example 160

(S)-7-((1H-Imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 1H-imidazole. LC-MS Method 2: >95% 254 nm, $R_T$=1.04 min, MS (ES) 525.0 [M+H]$^+$.

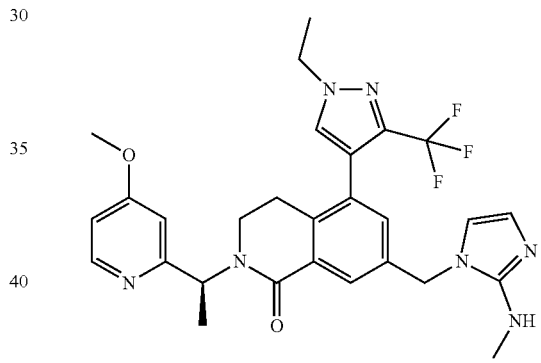

Example 161

(S)-5-(1-Ethyl-3-(trifluoromethyl)-1H-pyrazol-4-yl)-2-(1-(4-methoxypyridin-2-yl)ethyl)-7-((2-(methylamino)-1H-imidazol-1-yl)methyl)-3,4-dihydroisoquinolin-1(2H)-one Step A. Preparation of tert-butyl (S)-(1-((5-(1-ethyl-3-(trifluoromethyl)-1H-pyrazol-4-yl)-2-(1-(4-methoxypyridin-2-yl)ethyl)-1-oxo-1,2,3,4-tetrahydroisoquinolin-7-yl)methyl)-1H-imidazol-2-yl)(methyl)carbamate. The title compound was prepared from the procedure described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and tert-butyl (1H-imidazol-2-yl)(methyl)carbamate.

Step B. Preparation of (S)-5-(1-Ethyl-3-(trifluoromethyl)-1H-pyrazol-4-yl)-2-(1-(4-methoxypyridin-2-yl)ethyl)-7-((2-(methylamino)-1H-imidazol-1-yl)methyl)-3,4-dihydroisoquinolin-1(2H)-one. The title compound was prepared from tert-butyl (S)-(1-((5-(1-ethyl-3-(trifluoromethyl)-1H-pyrazol-4-yl)-2-(1-(4-methoxypyridin-2-yl)ethyl)-1-oxo-1,2,3, 4-tetrahydroisoquinolin-7-yl)methyl)-1H-imidazol-2-yl)(methyl)carbamate following the procedure described in Example 65, Step B. LC-MS Method 2: >95% 254 nm, R$_T$=1.05 min, MS (ES) 554.5 [M+H]$^+$.

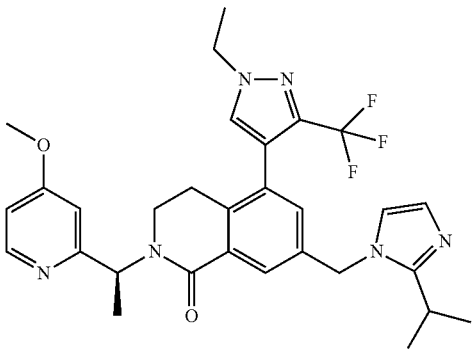 [SMILES: CCn1cc(-c2cc(Cn3ccnc3C(C)C)cc3c2CCN([C@@H](C)c2cc(OC)ccn2)C3=O)c(C(F)(F)F)n1]

Example 162

(S)-5-(1-Ethyl-3-(trifluoromethyl)-1H-pyrazol-4-yl)-7-((2-isopropyl-1H-imidazol-1-yl)methyl)-2-(1-(4-methoxypyridin-2-yl)ethyl)-3,4-dihydroisoquinolin-1(2H)-one The title compound (9 mg, 0.016 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 2-isopropyl-1H-imidazole. LC-MS Method 2: >95% 254 nm, R$_T$=1.11 min, MS (ES) 567.0 [M+H]$^+$.

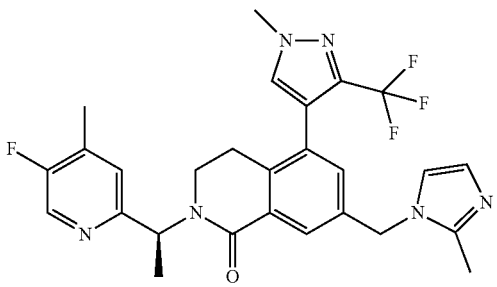 [SMILES: Cc1cc([C@H](C)N2CCc3c(cc(Cn4ccnc4C)cc3-c3cn(C)nc3C(F)(F)F)C2=O)ncc1F]

Example 163

(S)-2-(1-(5-fluoro-4-methylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one To a solution of (S)-7-(bromomethyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one (Intermediate 84, 45.2 mg, 0.09 mmol, 1.0 equiv.) in CH$_3$CN (1.0 mL), 2-methyl-1H-imidazole (21.2 mg, 0.26 mmol, 3.0 equiv.), and Hunig's base (70.0 µL, 0.43 mmol, 5.0 equiv.) were added and stirred at 90° C. for 1.0 h. Then, the reaction mixture was quenched with MeOH (0.5 mL) and concentrated under the reduced pressure. The crude reaction mixture was redissolved in DMSO (1.0 mL) and filtered. The DMSO solution was purified by reverse phase HPLC (Phenomenex Gemini C18, H$_2$O/CH$_3$CN gradient from 5-95% CH$_3$CN, 0.1% TFA) to yield the title compound (8.1 mg, 17%). *To remove TFA, the organic layer has to be washed with K$_2$CO$_3$ (sat.). LC-MS: >95% 254 nm, R$_T$=1.339, MS (ES) 526.5 [M+H]$^+$; $^1$H NMR (400 MHz, Chloroform-d) δ 8.28-8.23 (s, 1H), 8.03 (d, J=1.8 Hz, 1H), 7.27 (s, 1H), 7.24 (d, J=6.1 Hz, 1H), 6.94 (d, J=1.1 Hz, 1H), 6.92 (d, J=1.7 Hz, 1H), 6.85 (d, J=1.2 Hz, 1H), 6.10 (q, J=7.0 Hz, 1H), 5.08 (s, 2H), 3.97 (s, 3H), 3.46 (m, 1H), 3.32 (m, 1H), 2.71-2.54 (m, 2H), 2.34 (s, 3H), 2.29-2.24 (m, 3H), 1.59 (d, J=7.1 Hz, 3H).

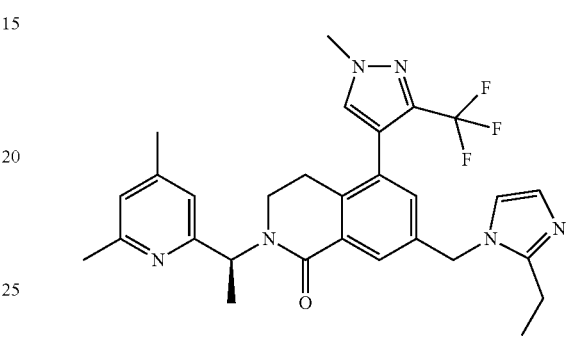

Example 164

(S)-2-(1-(4,6-Dimethylpyridin-2-yl)ethyl)-7-((2-ethyl-1H-imidazol-1-yl)methyl)-5-(1-methyl-3-(trifluoromethyl)-1H-pyrazol-4-yl)-3,4-dihydroisoquinolin-1(2H)-one The title compound (16.6 mg, 40% yield over 2 steps) was prepared following the procedures described in Example 163 using (S)-7-(bromomethyl)-2-(1-(4,6-dimethylpyridin-2-yl)ethyl)-5-(1-methyl-3-(trifluoromethyl)-1H-pyrazol-4-yl)-3,4-dihydroisoquinolin-1(2H)-one (Intermediate 85, 40.0 mg, 0.08 mmol, 1.0 equiv.) and 2-ethyl-1H-imidazole (22.1 mg, 0.23 mmol, 3.0 equiv.). $^1$H NMR (400 MHz, Chloroform-d) δ 8.04 (d, J=1.8 Hz, 1H), 7.26 (s, 1H), 6.96 (d, J=1.2 Hz, 2H), 6.89 (d, J=1.8 Hz, 1H), 6.83 (d, J=1.3 Hz, 2H), 6.05 (q, J=7.1 Hz, 1H), 5.08 (s, 2H), 3.96 (s, 3H), 3.43 (m, 2H), 2.63 (m, 4H), 2.45 (s, 3H), 2.25 (s, 3H), 1.59 (d, J=7.1 Hz, 3H), 1.28 (t, J=7.5 Hz, 3H); LC-MS: >95% 254 nm, R$_T$=1.085 min, MS (ES) 537.6 [M+H]$^+$.

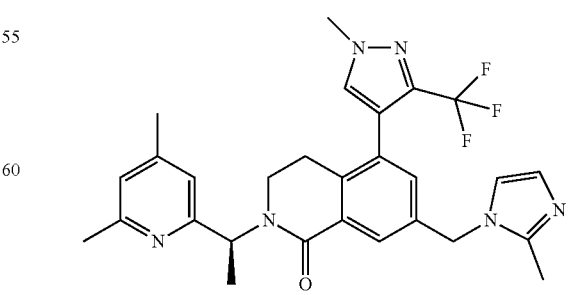

Example 165

(S)-2-(1-(4,6-Dimethylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (17.2 mg, 42% yield) was prepared from the procedure described in Example 163 using (S)-7-(bromomethyl)-2-(1-(4,6-dimethylpyridin-2-yl)ethyl)-5-(1-methyl-3-(trifluoromethyl)-1H-pyrazol-4-yl)-3,4-dihydroisoquinolin-1(2H)-one (Intermediate 85, 40.0 mg, 0.08 mmol, 1.0 equiv.) and 2-methyl-1H-imidazole (18.9 mg, 0.23 mmol, 3.0 equiv.) $^1$H NMR (400 MHz, Chloroform-d) δ 8.04 (d, J=1.6 Hz, 1H), 7.27 (s, 1H), 6.96 (s, 1H), 6.93 (d, J=1.0 Hz, 1H), 6.90 (d, J=1.6 Hz, 1H), 6.86-6.82 (m, 2H), 6.05 (q, J=7.0 Hz, 1H), 5.07 (s, 2H), 3.97 (s, 3H), 3.44 (ddq, J=18.7, 12.5, 6.7, 6.0 Hz, 2H), 2.64 (t, J=6.4 Hz, 2H), 2.45 (s, 3H), 2.34 (s, 3H), 2.25 (s, 3H), 1.59 (d, J=7.1 Hz, 3H); LC-MS: >95% 254 nm, $R_T$=1.069 min, MS (ES) 523.6 [M+H]$^+$.

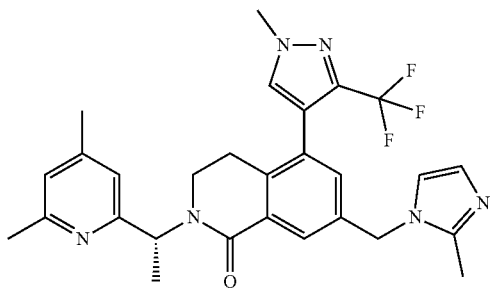 [SMILES: Cc1cc(C)nc([C@@H](C)N2CCc3c(cc(Cn4ccnc4C)cc3-c3cn(C)nc3C(F)(F)F)C2=O)c1]

Example 166

(R)-2-(1-(4,6-Dimethylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (15.5 mg, 47% yield) was prepared from the procedure described in Example 163 using (R)-7-(bromomethyl)-2-(1-(4,6-dimethylpyridin-2-yl)ethyl)-5-(1-methyl-3-(trifluoromethyl)-1H-pyrazol-4-yl)-3,4-dihydroisoquinolin-1(2H)-one (Intermediate 86, 32.3 mg, 0.06 mmol, 1.0 equiv.) and 2-methyl-1H-imidazole (15.3 mg, 0.19 mmol, 3.0 equiv.). $^1$H NMR (400 MHz, Chloroform-d) δ 8.03 (d, J=1.5 Hz, 1H), 7.27 (s, 1H), 6.96 (s, 1H), 6.93-6.91 (m, 1H), 6.91-6.88 (m, 1H), 6.84 (s, 2H), 6.05 (q, J=7.0 Hz, 1H), 5.07 (s, 2H), 3.96 (s, 3H), 3.43 (m, 2H), 2.64 (t, J=6.4 Hz, 2H), 2.45 (s, 3H), 2.33 (s, 3H), 2.25 (s, 3H), 1.58 (d, J=7.1 Hz, 3H); LC-MS: >95% 254 nm, $R_T$=1.064 min, MS (ES) 523.6 [M+H]$^+$.

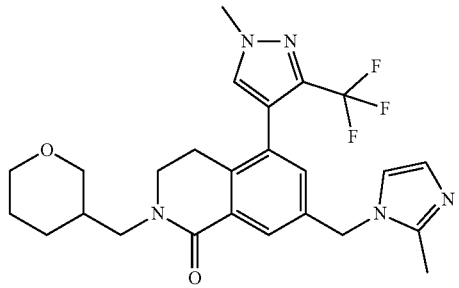 [SMILES: Cc1nccn1Cc1cc2c(c(-c3cn(C)nc3C(F)(F)F)c1)CCN(CC1CCCOC1)C2=O]

Example 167

7-((2-Methyl-1H-imidazol-1-yl)methyl)-5-(1-methyl-3-(trifluoromethyl)-1H-pyrazol-4-yl)-2-((tetrahydro-2H-pyran-3-yl)methyl)-3,4-dihydroisoquinolin-1(2H)-one 7-((2-Methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) was dissolved in DMF (0.2 mL) and then NaH (1.5 mg, 0.0617 mmol, 1.2 equiv.) was added. The reaction was stirred at room temperature for 15 minutes and then 3-(bromomethyl)-tetrahydro-2H-pyran (9.6 mg, 0.0539 mmol, 1.05 equiv.) was added. The reaction was stirred for 15 minutes at room temperature and then water (3 mL) was added and the aqueous layer was extracted with EtOAc (3×5 mL). The combined organic layers were washed with brine (3 mL), dried (MgSO$_4$), filtered and concentrated. The residue was purified by reverse phase HPLC (Phenomenex Gemini C18, H$_2$O/CH$_3$CN gradient from 20-95% CH$_3$CN, 0.1% TFA) to yield the title compound (10.8 mg, 43% yield). LCMS: >95% 254 nm, $R_T$=1.206 min, MS (ES) 488.0 [M+H]$^+$; $^1$H NMR (400 MHz, chloroform-d) δ 8.00 (d, J=2.0 Hz, 1H), 7.32 (s, 1H), 6.98 (d, J=1.2 Hz, 1H), 6.92 (d, J=2.0 Hz, 1H), 6.87 (d, J=1.2 Hz, 1H), 5.10 (s, 2H), 4.00 (s, 3H), 3.95-3.91 (m, 1H), 3.86-3.76 (m, 2H), 3.53-3.40 (m, 2H), 3.36-3.26 (m, 2H), 2.79-2.75 (m, 2H), 2.40 (s, 3H), 2.09-2.03 (m, 1H), 1.84-1.80 (m, 1H), 1.71-1.50 (m, 4H); $^{19}$F NMR (376 MHz, Chloroform-d) δ −60.15.

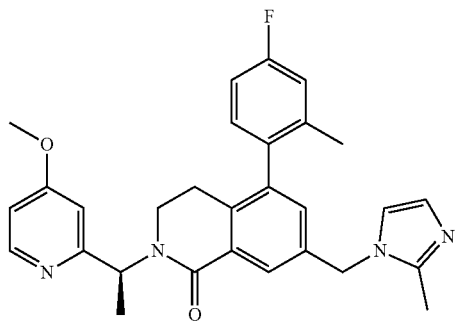 [SMILES: COc1ccnc([C@H](C)N2CCc3c(cc(Cn4ccnc4C)cc3-c3ccc(F)cc3C)C2=O)c1]

Example 168

(S)-5-(4-Fluoro-2-methylphenyl)-2-(1-(4-methoxypyridin-2-yl)ethyl)-7-((2-methyl-1H-imidazol-1-yl)methyl)-3,4-dihydroisoquinolin-1(2H)-one The title compound (10 mg, 0.015 mmol) was prepared following the procedures described in Example 8 using (S)-7-(bromomethyl)-5-(4-fluoro-2-methylphenyl)-2-(1-(4-methoxypyridin-2-yl)ethyl)-3,4-dihydroisoquinolin-1(2H)-one (Intermediate 82) and 2-methyl-1H-imidazole. LC-MS Method 2: >95% 254 nm, R$_T$=1.10 min, MS (ES) 485.0 [M+H]$^+$.

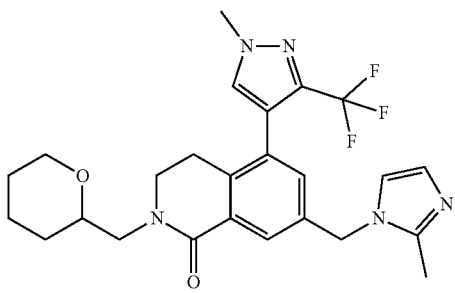 [SMILES: Cc1nccn1Cc1cc2c(c(-c3cn(C)nc3C(F)(F)F)c1)CCN(CC1CCCCO1)C2=O]

Example 169

7-((2-Methyl-1H-imidazol-1-yl)methyl)-5-(1-methyl-3-(trifluoromethyl)-1H-pyrazol-4-yl)-2-((tetrahydro-2H-pyran-2-yl)methyl)-3,4-dihydroisoquinolin-1(2H)-one The title compound (12.8 mg, 51% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(bromomethyl)-tetrahydro-2H-pyran (9.6 mg, 0.0539 mmol, 1.05 equiv.). LCMS: >95% 254 nm, R$_T$=1.268 min, MS (ES) 487.9 [M+H]$^+$; $^1$H NMR (400 MHz, chloroform-d) δ 8.00 (d, J=2.0 Hz, 1H), 7.30 (s, 1H), 6.95 (d, J=1.2 Hz, 1H), 6.91 (d, J=2.0 Hz, 1H), 6.85 (d, J=1.2 Hz, 1H), 5.07 (s, 2H), 3.99 (s, 3H), 3.95-3.92 (m, 1H), 3.88-3.81 (m, 1H), 3.69-3.59 (m, 2H), 3.56-3.49 (m, 1H), 3.41-3.35 (m, 1H), 3.29-3.23 (m, 1H), 2.76-2.72 (m, 2H), 2.35 (s, 3H), 1.88-1.83 (m, 1H), 1.69-1.65 (m, 1H), 1.57-1.45 (m, 4H).

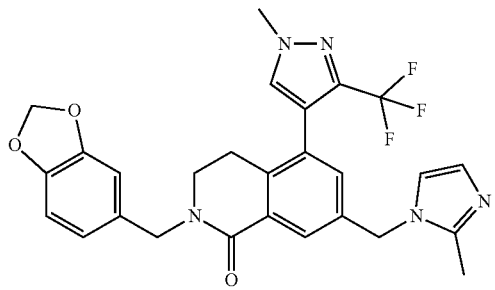 [SMILES: Cc1nccn1Cc1cc2c(c(-c3cn(C)nc3C(F)(F)F)c1)CCN(Cc1ccc3c(c1)OCO3)C2=O]

Example 170

2-(Benzo[d][1,3]dioxol-5-ylmethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (8.9 mg, 44% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 5-(bromomethyl)-1,3-benzodioxole (9.9 mg, 0.0463 mmol, 1.2 equiv.). LCMS: >95% 254 nm, R$_T$=1.325 min, MS (ES) 523.9 [M+H]$^+$; $^1$H NMR (400 MHz, MeOD) δ 7.97 (d, J=1.2 Hz, 1H), 7.79 (s, 1H), 7.57 (d, J=2.4 Hz, 1H), 7.52 (d, J=2.0 Hz, 1H), 7.38 (s, 1H), 6.85 (d, J=7.2 Hz, 2H), 6.80 (d, J=8.4 Hz, 1H), 5.94 (s, 2H), 5.50 (s, 2H), 4.70 (s, 2H), 4.00 (s, 3H), 3.47 (t, J=6.4 Hz, 2H), 2.81 (t, J=6.4 Hz, 2H), 2.65 (s, 3H); $^{19}$F NMR (376 MHz, MeOD) δ −61.07.

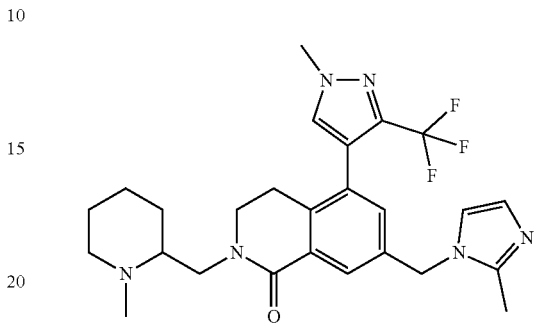

Example 171

7-((2-Methyl-1H-imidazol-1-yl)methyl)-5-(1-methyl-3-(trifluoromethyl)-1H-pyrazol-4-yl)-2-((1-methylpiperidin-2-yl)methyl)-3,4-dihydroisoquinolin-1(2H)-one The title compound (8.1 mg, 42% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(bromomethyl)-1-methylpiperidine (8.8 mg, 0.0463 mmol, 1.2 equiv.). LCMS: >95% 254 nm, R$_T$=0.947 min, MS (ES) 501.0 [M+H]$^+$; $^1$H NMR (400 MHz, MeOD) δ 7.97 (s, 1H), 7.82 (s, 1H), 7.55 (d, J=2.0 Hz, 1H), 7.52 (s, 1H), 7.41 (d, J=7.2 Hz, 1H), 5.50 (s, 2H), 4.06 (s, 3H), 3.96-3.94 (m, 1H), 3.66-3.60 (m, 3H), 3.56-3.50 (m, 1H), 3.14 (s, 3H), 3.10-3.06 (m, 1H), 2.92-2.88 (m, 2H), 2.64 (s, 3H), 2.13-2.10 (m, 1H), 2.01-1.93 (m, 3H), 1.80-1.70 (m, 1H), 1.66-1.59 (m, 2H); $^{19}$F NMR (376 MHz, MeOD) δ −61.07.

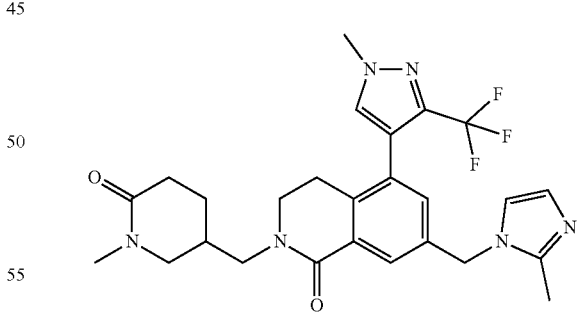

Example 172

7-((2-Methyl-1H-imidazol-1-yl)methyl)-5-(1-methyl-3-(trifluoromethyl)-1H-pyrazol-4-yl)-2-((1-methyl-6-oxopiperidin-3-yl)methyl)-3,4-dihydroisoquinolin-1(2H)-one The title compound (9.3 mg, 47% yield) was prepared from the procedure described in Example 167 using 7-((2- methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 5-(bromomethyl)-1-methyl-2-piperidinone (9.5 mg, 0.0463 mmol, 1.2 equiv.). LCMS: >95% 254 nm, R$_T$=1.092 min, MS (ES) 515.0 [M+H]$^+$; $^1$H NMR (400 MHz, MeOD) δ 7.93 (s, 1H), 7.82 (s, 1H), 7.56 (d, J=2.0 Hz, 1H), 7.52 (d, J=2.0 Hz, 1H), 7.39 (s, 1H), 5.51 (s, 3H), 5.49 (s, 2H), 4.03 (s, 3H), 3.69-3.55 (m, 4H), 3.25-3.15 (m, 1H), 2.94 (s, 3H), 2.93-2.88 (m, 1H), 2.72 (s, 3H), 2.68-2.65 (m, 1H), 2.52-2.32 (m, 1H), 1.95-1.91 (m, 1H), 1.68-1.58 (m, 1H); $^{19}$F NMR (376 MHz, MeOD) δ −61.04.

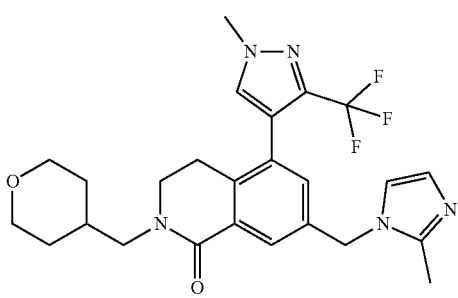 [SMILES: Cc1nccn1Cc1cc2c(c(-c3cn(C)nc3C(F)(F)F)c1)CCN(CC1CCOCC1)C2=O]

Example 173

7-((2-Methyl-1H-imidazol-1-yl)methyl)-5-(1-methyl-3-(trifluoromethyl)-1H-pyrazol-4-yl)-2-((tetrahydro-2H-pyran-4-yl)methyl)-3,4-dihydroisoquinolin-1(2H)-one The title compound (13.2 mg, 53% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 4-(bromomethyl)-tetrahydro-2H-pyran (9.6 mg, 0.0539 mmol, 1.05 equiv.). LCMS: >95% 254 nm, R$_T$=1.180 min, MS (ES) 488.0 [M+H]$^+$; $^1$H NMR (400 MHz, MeOD) δ 7.91 (d, J=1.2 Hz, 1H), 7.82 (s, 1H), 7.56 (d, J=2.0 Hz, 1H), 7.51 (d, J=2.0 Hz, 1H), 7.38 (s, 1H), 5.49 (s, 2H), 4.03 (s, 3H), 3.98-3.94 (m, 2H), 3.59-3.56 (m, 2H), 3.51-3.39 (m, 4H), 2.86 (t, J=6.4 Hz, 2H), 2.64 (s, 3H), 2.08-2.02 (m, 1H), 1.66-1.62 (m, 2H), 1.44-1.34 (m, 2H); $^{19}$F NMR (376 MHz, MeOD) δ −61.07.

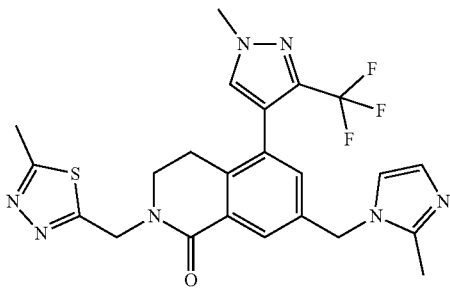 [SMILES: Cc1nnc(CN2CCc3c(cc(Cn4ccnc4C)cc3-c3cn(C)nc3C(F)(F)F)C2=O)s1]

Example 174

2-((5-Methyl-1,3,4-thiadiazol-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (7.7 mg, 30% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-5-methyl-1,3,4-thiadiazole (9.2 mg, 0.062 mmol, 1.2 equiv.). $^1$H NMR (400 MHz, Chloroform-d) δ 8.01 (d, J=1.2 Hz, 1H), 7.29 (s, 1H), 6.95-6.94 (m, 2H), 6.84 (s, 1H), 5.08 (s, 2H), 5.06 (s, 2H), 3.99 (s, 3H), 3.61 (t, J=6.6 Hz, 2H), 2.79 (t, J=6.6 Hz, 2H), 2.75 (s, 3H), 2.33 (s, 3H).

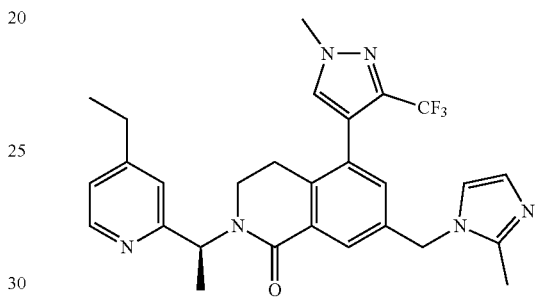

Example 175

(S)-2-(1-(4-Ethylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (25 mg, 0.048 mmol, 77% yield) was prepared following the procedure described in Example 8 using (S)-7-(bromomethyl)-2-(1-(4-ethylpyridin-2-yl)ethyl)-5-(1-methyl-3-(trifluoromethyl)-1H-pyrazol-4-yl)-3,4-dihydroisoquinolin-1(2H)-one (Intermediate 88) and 2-methyl-1H-imidazole. $^1$H NMR (400 MHz, Chloroform-d) δ 8.43 (d, J=5.0 Hz, 1H), 8.05 (d, J=1.2 Hz, 1H), 7.21 (s, 1H), 7.03 (d, J=4.3 Hz, 1H), 6.94 (s, 1H), 6.91 (s, 1H), 6.86 (s, 1H), 6.15 (q, J=7.0 Hz, 1H), 5.08 (s, 2H), 3.97 (s, 3H), 3.50-3.34 (m, 2H), 3.36-3.30 (m, 2H), 2.62 (q, J=7.5 Hz, 2H), 2.35 (s, 3H), 1.62 (d, J=6.9 Hz, 3H), 1.22 (t, J=7.6 Hz, 1H); LCMS: >95% 254 nm, R$_T$=1.162 min, MS (ES) 522.9 [M+H]$^+$.

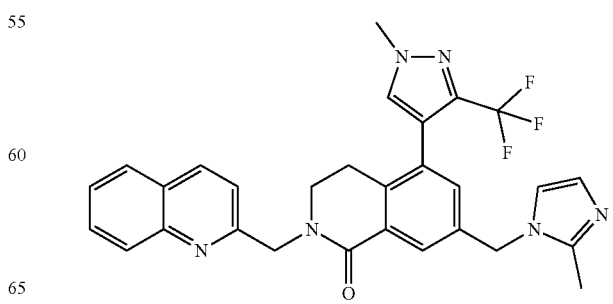

Example 176

7-((2-Methyl-1H-imidazol-1-yl)methyl)-5-(1-methyl-3-(trifluoromethyl)-1H-pyrazol-4-yl)-2-(quinolin-2-ylmethyl)-3,4-dihydroisoquinolin-1(2H)-one The title compound (8.9 mg, 44% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(bromomethyl)quinoline (10.2 mg, 0.0463 mmol, 1.2 equiv.). LCMS: >95% 254 nm, $R_T$=1.274 min, MS (ES) 531.0 [M+H]$^+$; $^1$H NMR (400 MHz, chloroform-d) δ 8.52 (d, J=8.8 Hz, 1H), 8.16-7.96 (m, 3H), 7.89-7.83 (m, 2H), 7.71-7.56 (m, 2H), 7.53-7.51 (m, 2H), 7.42 (d, J=1.6 Hz, 1H), 5.51 (s, 2H), 5.14 (s, 2H), 4.02 (s, 3H), 3.74 (t, J=6.8 Hz, 2H), 2.97 (t, J=6.8 Hz, 2H), 2.65 (s, 3H).

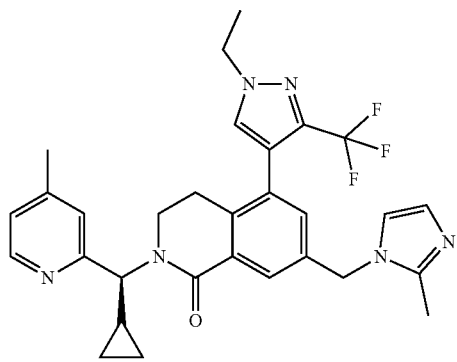 [SMILES: CCn1cc(-c2cc(Cn3ccnc3C)cc3c2CCN([C@H](c2cc(C)ccn2)C2CC2)C3=O)c(C(F)(F)F)n1]

Example 177

(S)-2-(Cyclopropyl(4-methylpyridin-2-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one The title compound (67.0 mg, 65% yield) was prepared from the procedure described in Example 8 using (S)-7-(bromomethyl)-2-(cyclopropyl(4-methylpyridin-2-yl)methyl)-5-(1-ethyl-3-(trifluoromethyl)-1H-pyrazol-4-yl)-3,4-dihydroisoquinolin-1(2H)-one (Intermediate 89) and 2-methyl-1H-imidazole. LCMS: >95% 254 nm, $R_T$=1.197 min, MS (ES) 549.0 [M+H]$^+$; $^1$H NMR (400 MHz, MeOD) δ 8.58 (d, J=6.0 Hz, 1H), 8.03 (s, 1H), 7.93 (d, J=2.0 Hz, 1H), 7.87 (s, 1H), 7.74 (d, J=5.6 Hz, 1H), 7.54 (d, J=2.0 Hz, 1H), 7.51 (d, J=2.0 Hz, 1H), 7.42 (d, J=1.2 Hz, 1H), 5.49 (s, 2H), 4.90 (s, 1H), 4.32 (q, J=7.2 Hz, 2H), 3.86-3.80 (m, 1H), 3.75-3.68 (m, 1H), 2.96 (t, J=6.4 Hz, 2H), 2.66 (s, 3H), 2.63 (s, 3H), 1.71-1.62 (m, 1H), 1.55 (t, J=7.2 Hz, 3H), 0.99-0.95 (m, 1H), 0.87-0.82 (m, 1H), 0.70-0.63 (m, 2H).

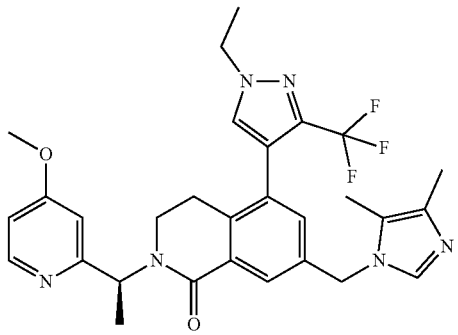 [SMILES: CCn1cc(-c2cc(Cn3cnc(C)c3C)cc3c2CCN([C@@H](C)c2cc(OC)ccn2)C3=O)c(C(F)(F)F)n1]

Example 178

(S)-7-((4,5-Dimethyl-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound (8 mg, 0.014 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 4,5-dimethyl-1H-imidazole. LC-MS Method 2: >95% 254 nm, $R_T$=1.04 min, MS (ES) 553.0 [M+H]$^+$.

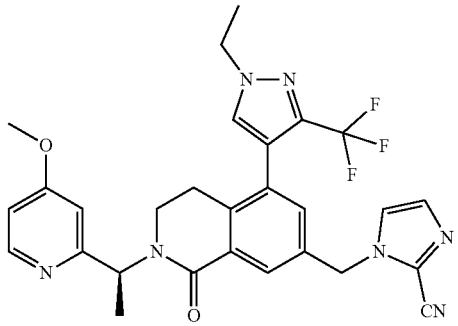 [SMILES: CCn1cc(-c2cc(Cn3ccnc3C#N)cc3c2CCN([C@@H](C)c2cc(OC)ccn2)C3=O)c(C(F)(F)F)n1]

Example 179

7-((2-Methyl-1H-imidazol-1-yl)methyl)-5-(1-methyl-3-(trifluoromethyl)-1H-pyrazol-4-yl)-2-((5-methylpyridin-3-yl)methyl)-3,4-dihydroisoquinolin-1(2H)-one The title compound (3 mg, 0.006 mmol) was prepared following the procedures described in Example 8 using (S)-7-(bromomethyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one (Intermediate 62) and 2-cyano-1H-imidazole. LC-MS Method 2: >95% 254 nm, $R_T$=1.27 min, MS (ES) 550.0 [M+H]$^+$.

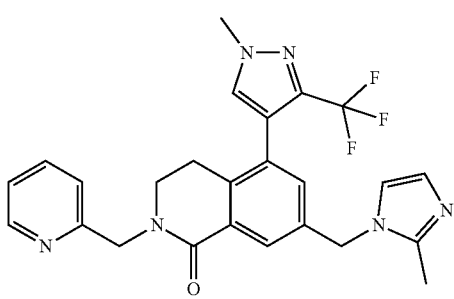 [SMILES: Cc1nccn1Cc1cc2c(c(-c3cn(C)nc3C(F)(F)F)c1)CCN(Cc1ccccn1)C2=O]

Example 180

7-((2-Methyl-1H-imidazol-1-yl)methyl)-5-(1-methyl-3-(trifluoromethyl)-1H-pyrazol-4-yl)-2-(pyridin-2-ylmethyl)-3,4-dihydroisoquinolin-1(2H)-one The title compound (10.1 mg, 55% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(bromomethyl)pyridine (7.9 mg, 0.0463 mmol, 1.2 equiv.). LCMS: >95% 254 nm, $R_T$=1.109 min, MS (ES) 481.0 [M+H]$^+$; $^1$H NMR (400 MHz, MeOD) δ 8.71 (d, J=5.2 Hz, 1H), 8.28 (td, J=8.0, 1.6 Hz, 1H), 7.97 (d, J=2.0 Hz, 1H), 7.83 (s, 1H), 7.81 (s, 1H), 7.74 (t, J=6.4 Hz, 1H), 7.56 (d, J=2.0 Hz, 1H), 7.51 (d, J=2.0 Hz, 1H), 7.42 (d, J=1.6 Hz, 1H), 5.50 (s, 2H), 5.03 (s, 2H), 4.03 (s, 3H), 3.72 (t, J=6.8 Hz, 2H), 2.97 (t, J=6.4 Hz, 2H), 2.64 (s, 3H).

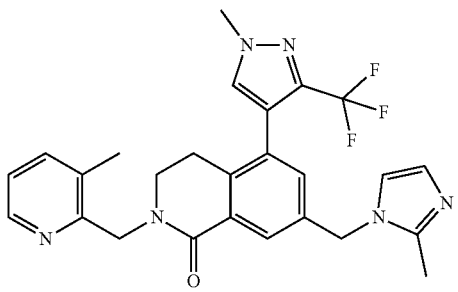 [SMILES: Cc1cccnc1CN1CCc2c(cc(Cn3ccnc3C)cc2-c2cn(C)nc2C(F)(F)F)C1=O]

Example 181

7-((2-Methyl-1H-imidazol-1-yl)methyl)-5-(1-methyl-3-(trifluoromethyl)-1H-pyrazol-4-yl)-2-((3-methylpyridin-2-yl)methyl)-3,4-dihydroisoquinolin-1(2H)-one The title compound (13 mg, 51% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-3-methylpyridine (8.0 mg, 0.0565 mmol, 1.1 equiv.). LCMS: >95% 254 nm, $R_T$=1.302 min, MS (ES) 495.0 [M+H]$^+$; $^1$H NMR (400 MHz, MeOD) δ 8.52 (d, J=5.6 Hz, 1H), 8.20-8.13 (m, 1H), 7.96 (d, J=2.4 Hz, 1H), 7.82 (s, 1H), 7.71-7.66 (m, 1H), 7.55 (d, J=2.0 Hz, 1H), 7.51 (d, J=2.0 Hz, 1H), 7.42 (s, 1H), 5.50 (s, 2H), 5.03 (d, J=4.4 Hz, 2H), 4.02 (s, 3H), 3.70 (t, J=6.4 Hz, 2H), 2.97 (t, J=4.4 Hz, 2H), 2.64 (s, 3H), 2.55 (s, 3H).

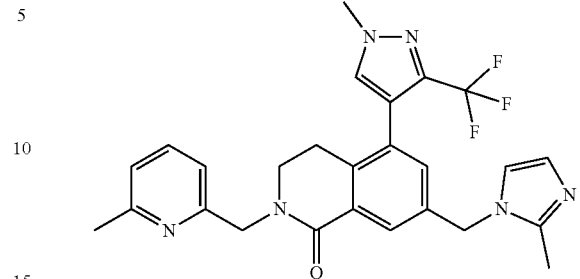

Example 182

7-((2-Methyl-1H-imidazol-1-yl)methyl)-5-(1-methyl-3-(trifluoromethyl)-1H-pyrazol-4-yl)-2-((6-methylpyridin-3-yl)methyl)-3,4-dihydroisoquinolin-1(2H)-one The title compound (14 mg, 55% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-6-methylpyridine (8.0 mg, 0.0565 mmol, 1.1 equiv.). LCMS: >95% 254 nm, $R_T$=1.282 min, MS (ES) 495.0 [M+H]$^+$; $^1$H NMR (400 MHz, chloroform-d) δ 8.06 (d, J=1.6 Hz, 1H), 7.56-7.52 (m, 1H), 7.30 (s, 1H), 7.17 (d, J=7.6 Hz, 1H), 7.06 (d, J=7.6 Hz, 1H), 6.95-6.92 (m, 2H), 6.86 (s, 1H), 5.09 (s, 2H), 4.86 (s, 2H), 3.98 (s, 3H), 3.56 (t, J=6.8 Hz, 2H), 2.77 (t, J=6.8 Hz, 2H), 2.53 (s, 3H), 2.35 (s, 3H); $^{19}$F NMR (376 MHz, Chloroform-d) δ −60.15.

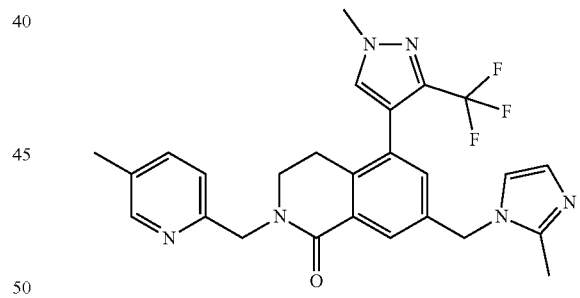

Example 183

7-((2-Methyl-1H-imidazol-1-yl)methyl)-5-(1-methyl-3-(trifluoromethyl)-1H-pyrazol-4-yl)-2-((5-methylpyridin-3-yl)methyl)-3,4-dihydroisoquinolin-1(2H)-one The title compound (12 mg, 47% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-5-methylpyridine (8.0 mg, 0.0565 mmol, 1.1 equiv.). LCMS: >95% 254 nm, $R_T$=1.154 min, MS (ES) 495.0 [M+H]$^+$; $^1$H NMR (400 MHz, MeOD) δ 8.50 (s, 1H), 8.02 (d, J=8.0 Hz, 1H), 7.97 (d, J=1.6 Hz, 1H), 7.82 (s, 1H), 7.63 (d, J=8.0 Hz, 1H), 7.56 (d, J=2.4 Hz, 1H), 7.52 (d, J=2.4 Hz, 1H), 7.41 (d, J=1.6 Hz, 1H), 5.50 (s, 2H), 4.96 (s, 2H), 4.02 (s, 3H), 3.67 (t, J=6.4 Hz, 2H), 2.93 (d, J=6.4 Hz, 2H), 2.64 (s, 3H), 2.46 (s, 3H).

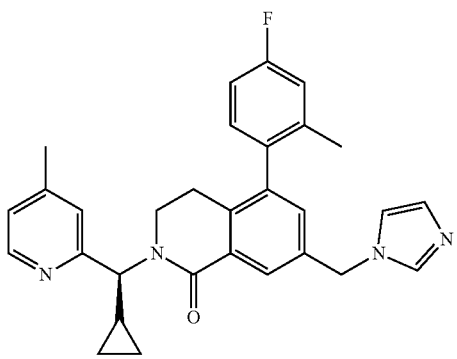 [SMILES: Cc1ccnc([C@H](C2CC2)N2CCc3c(cc(Cn4ccnc4)cc3-c3ccc(F)cc3C)C2=O)c1]

Example 184

(S)-7-((1H-Imidazol-1-yl)methyl)-2-(cyclopropyl(4-methylpyridin-2-yl)methyl)-5-(4-fluoro-2-methylphenyl)-3,4-dihydroisoquinolin-1(2H)-one The title compound (26.9 mg, 80% yield) was prepared from the procedure described in Example 163 using (S)-7-(bromomethyl)-2-(cyclopropyl(4-methylpyridin-2-yl)methyl)-5-(4-fluoro-2-methylphenyl)-3,4-dihydroisoquinolin-1(2H)-one (Intermediate 30, 34.4 mg, 0.07 mmol, 1.0 equiv.) and imidazole (14.2 mg, 0.21 mmol, 3.0 equiv.). LCMS: >95% 254 nm, $R_T$=1.487 min, MS (ES) 481.6 [M+H]$^+$; $^1$H NMR (400 MHz, Chloroform-d) δ 8.38 (t, J=4.8 Hz, 1H), 8.03 (s, 1H), 7.53 (s, 1H), 7.24 (d, J=6.4 Hz, 1H), 7.05 (s, 1H), 7.00-6.93 (m, 3H), 6.93-6.84 (m, 3H), 5.13 (s, 2H), 5.06 (dd, J=10.1, 3.5 Hz, 1H), 3.67 (m, 2H), 2.54 (m, 2H), 2.32 (d, J=3.4 Hz, 3H), 1.97* (d, J=32.2 Hz, 3H), 1.69-1.55 (m, 1H), 0.75 (td, J=7.7, 3.5 Hz, 1H), 0.61 (dt, J=7.7, 3.7 Hz, 1H), 0.55-0.45 (m, 2H).

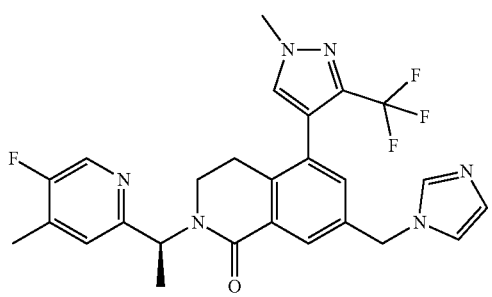 [SMILES: Cc1cc([C@H](C)N2CCc3c(cc(Cn4ccnc4)cc3-c3cn(C)nc3C(F)(F)F)C2=O)ncc1F]

Example 185

(S)-7-((1H-Imidazol-1-yl)methyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one The title compound (12.2 mg, 48%) was prepared from the procedure described in Example 163 using (S)-7-(bromomethyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one (Intermediate 84, 26.0 mg, 0.05 mmol, 1.0 equiv.) and imidazole (10.1 mg, 0.15 mmol, 3.0 equiv.). LCMS: >95% 254 nm, $R_T$=1.351 min, MS (ES) 513.5 [M+H]$^+$; $^1$H NMR (400 MHz, Chloroform-d) δ 8.25 (s, 1H), 8.07 (d, J=1.5 Hz, 1H), 7.59 (s, 1H), 7.28 (s, 1H), 7.23 (d, J=6.1 Hz, 1H), 7.07 (m, 2H), 6.91 (s, 1H), 6.10 (q, J=7.0 Hz, 1H), 5.15 (s, 2H), 3.97 (s, 3H), 3.46 (m, 1H), 3.31 (m, 1H), 2.72-2.54 (m, 2H), 2.27 (s, 3H), 1.59 (d, J=7.1 Hz, 3H).

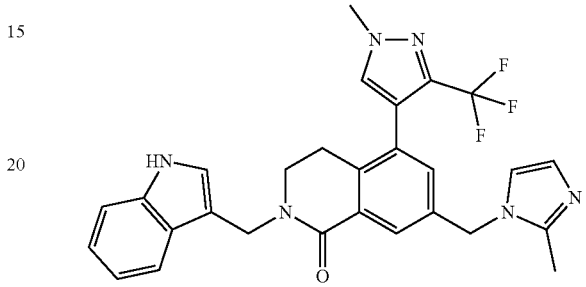

Example 186

2-((1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one Step A. Preparation of tert-butyl 3-((7-((2-methyl-1H-imidazol-1-yl)methyl)-5-(1-methyl-3-(trifluoromethyl)-1H-pyrazol-4-yl)-1-oxo-3,4-dihydroisoquinolin-2(1H)-yl)methyl)-1H-indole-1-carboxylate. 7-((2-Methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 100 mg, 0.257 mmol, 1.0 equiv.) was dissolved in DMF (1.3 mL) and then NaH (15.4 mg, 0.642 mmol, 2.5 equiv.) was added. The reaction was stirred at room temperature for 15 minutes and then tert-butyl 3-(bromomethyl)-1H-indole-1-carboxylate (87.4 mg, 0.283 mmol, 1.1 equiv.) was added. The reaction was stirred for 15 minutes at room temperature and then water (5 mL) was added and the aqueous layer was extracted with EtOAc (3×5 mL). The combined organic layers were washed with brine (5 mL), dried (MgSO$_4$), filtered and concentrated. The residue was purified by flash chromatography (Combi-flash Rf, DCM/MeOH=0-10% gradient) to afford the title compound (103 mg, 65% yield). LCMS: $R_T$=1.623 min, MS (ES) 619.0 [M+H]$^+$.

Step B. Preparation of 24(1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one. tert-Butyl 3-((7-((2-methyl-1H-imidazol-1-yl)methyl)-5-(1-methyl-3-(trifluoromethyl)-1H-pyrazol-4-yl)-1-oxo-3, 4-dihydroisoquinolin-2(11/)-yl)methyl)-1H-indole-1-carboxylate (101 mg, 0.162 mmol, 1.0 equiv.) was dissolved in DCM (0.2 mL) and then TFA (0.2 mL) was added. After stirring at room temperature overnight the reaction was concentrated and the residue was taken up in EtOAc (5 mL), and washed with saturated NaHCO$_3$ (5 mL), brine (5 mL), dried (MgSO$_4$), filtered and concentrated. The residue was purified by flash chromatography (Combi-flash Rf, DCM/

MeOH=0-10% gradient) to afford the title compound (65.2 mg, 78% yield). LCMS: >95% 254 nm, $R_T$=1.275 min, MS (ES) 519.0 [M+H]$^+$.

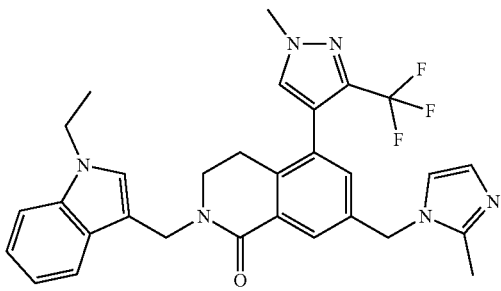 [SMILES: CCn1cc(CN2CCc3c(cc(Cn4ccnc4C)cc3-c3cn(C)nc3C(F)(F)F)C2=O)c2ccccc21]

Example 187

2-((1-Ethyl-1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one 2-((1H-Indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 186, 20 mg, 0.0386 mmol, 1.0 equiv.) was dissolved in DMF (0.2 mL) and then NaH (2.3 mg, 0.0965 mmol, 2.5 equiv.) was added. The reaction was stirred at room temperature for 15 minutes and then ethyl bromide (3.1 µL, 0.0425 mmol, 1.1 equiv.) was added. The reaction was stirred for 15 minutes at room temperature and then water (5 mL) was added and the aqueous layer was extracted with EtOAc (3×5 mL). The combined organic layers were washed with brine (5 mL), dried (MgSO$_4$), filtered and concentrated. The residue was purified by reverse phase HPLC (Phenomenex Gemini C18, H$_2$O/CH$_3$CN gradient from 20-95% CH$_3$CN, 0.1% TFA) to yield the title compound (9.8 mg, 46% yield). LCMS: >95% 254 nm, $R_T$=1.512 min, MS (ES) 547.0 [M+H]$^+$; $^1$H NMR (400 MHz, chloroform-d) δ 8.14 (s, 1H), 7.69 (d, J=8.0 Hz, 1H), 7.32-7.29 (m, 3H), 7.16 (s, 1H), 7.10 (s, 1H), 7.06-6.99 (m, 3H), 5.20 (s, 2H), 4.94 (s, 2H), 4.14 (q, J=7.2 Hz, 2H), 3.97 (s, 3H), 3.44 (t, J=6.8 Hz, 2H), 2.84 (t, J=6.8 Hz, 2H), 2.71 (s, 3H), 1.46 (t, J=7.2 Hz, 3H).

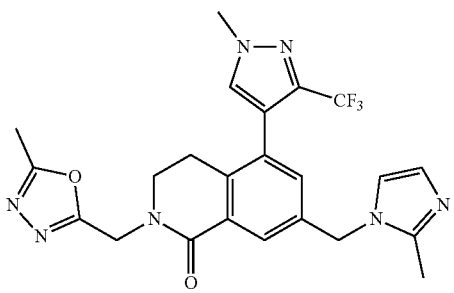 [SMILES: Cc1nnc(CN2CCc3c(cc(Cn4ccnc4C)cc3-c3cn(C)nc3C(F)(F)F)C2=O)o1]

Example 188

2-((5-Methyl-1,3,4-oxadiazol-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (17 mg, 0.035 mmol, 68% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-5-methyl-1,3,4-oxadiazole. $^1$H NMR (400 MHz, Chloroform-d) δ 8.01 (d, J=1.7 Hz, 1H), 7.31 (s, 1H), 6.95 (d, J=1.7 Hz, 1H), 6.93 (s, 1H), 6.84 (s, 1H), 5.08 (s, 2H), 4.95 (s, 2H), 3.99 (s, 3H), 3.61 (t, J=6.6 Hz, 2H), 2.83 (t, J=6.5 Hz, 2H), 2.52 (s, 3H), 2.33 (s, 3H).

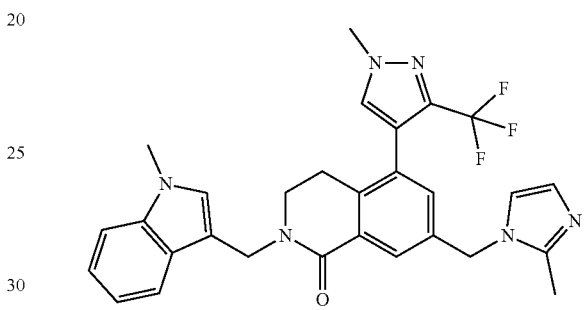

Example 189

7-((2-Methyl-1H-imidazol-1-yl)methyl)-2-((1-methyl-1H-indol-3-yl)methyl)-5-(1-methyl-3-(trifluoromethyl)-1H-pyrazol-4-yl)-3,4-dihydroisoquinolin-1(2H)-one The title compound (8.2 mg, 40% yield) was prepared from the procedure described in Example 187 using 2-((1H-Indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 186, 20 mg, 0.0386 mmol, 1.0 equiv.) and methyl iodide (2.6 µL, 0.0425 mmol, 1.1 equiv.). LCMS: >95% 254 nm, $R_T$=1.583 min, MS (ES) 532.9 [M+H]$^+$; $^1$H NMR (400 MHz, chloroform-d) δ 8.14 (s, 1H), 7.69 (d, J=7.6 Hz, 1H), 7.31-7.29 (m, 3H), 7.13-7.09 (m, 2H), 7.02-6.99 (m, 3H), 5.20 (s, 2H), 4.93 (s, 2H), 3.97 (s, 3H), 3.77 (s, 3H), 3.45 (t, J=6.8 Hz, 2H), 2.71 (s, 3H), 2.65 (t, J=6.8 Hz, 2H).

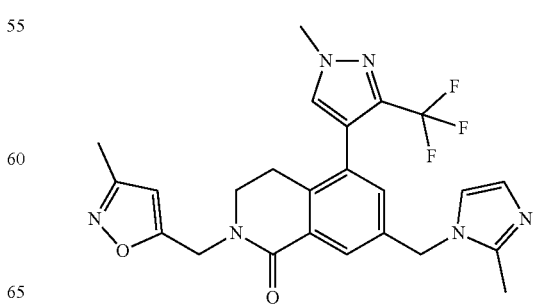

Example 190

7-((2-Methyl-1H-imidazol-1-yl)methyl)-5-(1-methyl-3-(trifluoromethyl)-1H-pyrazol-4-yl)-2-((3-methylisoxazol-5-yl)methyl)-3,4-dihydroisoquinolin-1(2H)-one The title compound (1 mg, 0.003 mmol, 4% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 5-(chloromethyl)-3-methylisoxazole. $^1$H NMR (400 MHz, Chloroform-d) δ 8.00 (d, J=1.4 Hz, 1H), 7.30 (s, 1H), 6.95 (s, 1H), 6.94 (d, J=1.4 Hz, 1H), 6.85 (s, 1H), 6.10 (s, 1H), 5.08 (s, 2H), 4.81 (s, 2H), 3.99 (s, 3H), 3.60 (t, J=6.6 Hz, 2H), 2.81 (t, J=6.5 Hz, 2H), 2.35 (s, 3H), 2.27 (s, 3H).

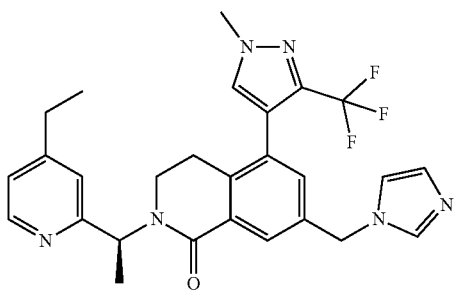 [SMILES: CCc1ccnc([C@H](C)N2CCc3c(cc(Cn4ccnc4)cc3-c3cn(C)nc3C(F)(F)F)C2=O)c1]

Example 191

(S)-7-((1H-Imidazol-1-yl)methyl)-2-(1-(4-ethylpyridin-2-yl)ethyl)-5-(1-methyl-3-(trifluoromethyl)-1H-pyrazol-4-yl)-3,4-dihydroisoquinolin-1(2H)-one The title compound (20 mg, 0.039 mmol, 64% yield) was prepared from the procedure described in Example 8 using (S)-7-(bromomethyl)-2-(1-(4-ethylpyridin-2-yl)ethyl)-5-(1-methyl-3-(trifluoromethyl)-1H-pyrazol-4-yl)-3,4-dihydroisoquinolin-1(2H)-one (Intermediate 88) and 1H-imidazole. $^1$H NMR (400 MHz, Chloroform-d) δ 8.42 (d, J=5.1 Hz, 1H), 8.09 (d, J=1.6 Hz, 1H), 7.55 (s, 1H), 7.27 (s, 1H), 7.21 (s, 1H), 7.08 (s, 1H), 7.06 (d, J=1.6 Hz, 1H), 7.02 (d, J=5.0 Hz, 1H), 6.92 (s, 1H), 6.14 (q, J=7.1 Hz, 1H), 5.15 (s, 2H), 3.97 (s, 3H), 3.50-3.43 (m, 1H), 3.35-3.29 (m, 1H), 2.68-2.56 (m, 4H), 1.62 (d, J=7.1 Hz, 3H), 1.21 (t, J=7.6 Hz, 1H).

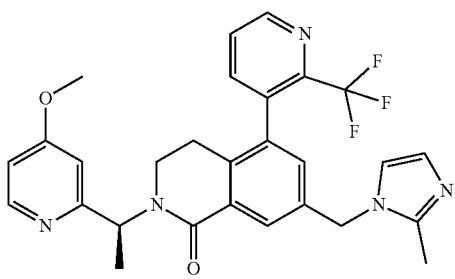 [SMILES: COc1ccnc([C@H](C)N2CCc3c(cc(Cn4ccnc4C)cc3-c3cccnc3C(F)(F)F)C2=O)c1]

Example 192

(S)-2-(1-(4-Methoxypyridin-2-yl)ethyl)-7-((2-methyl-1H-imidazol-1-yl)methyl)-5-(2-(trifluoromethyl)pyridin-3-yl)-3,4-dihydroisoquinolin-1(2H)-one The title compound (16 mg, 0.016 mmol) was prepared following the procedures described in Example 8 using (S)-7-(bromomethyl)-2-(1-(4-methoxypyridin-2-yl)ethyl)-5-(2-(trifluoromethyl)pyridin-3-yl)-3,4-dihydroisoquinolin-1(2H)-one (Intermediate 83) and 2-methyl-1H-imidazole. LC-MS Method 2: >95% 254 nm, $R_T$=1.03 min, MS (ES) 522.0 [M+H]$^+$.

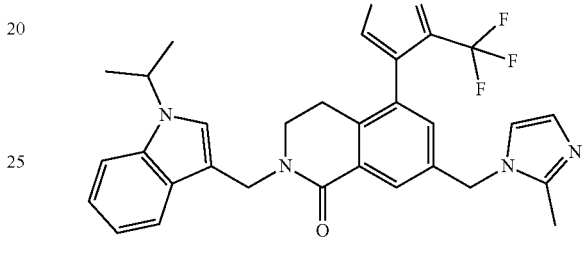

Example 193

2-((1-Isopropyl-1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (9.2 mg, 43% yield) was prepared from the procedure described in Example 187 using 2-((1H-Indol-3-yl)methyl)-7-methyl-1H-imidazol-1-yl)methyl)-5-(1-methyl-3-(trifluoromethyl)-1H-pyrazol-4-yl)-3,4-dihydroisoquinolin-1(2H)-one (Example 186, 20 mg, 0.0386 mmol, 1.0 equiv.) and isopropyl bromide (4.0 μL, 0.0425 mmol, 1.1 equiv.). LCMS: >95% 254 nm, $R_T$=1.682 min, MS (ES) 561.0 [M+H]$^+$. $^1$H NMR (400 MHz, chloroform-d) δ 8.16 (d, J=2.0 Hz, 1H), 8.04 (s, 1H), 7.68 (d, J=7.6 Hz, 1H), 7.41 (s, 1H), 7.36 (s, 1H), 7.34-7.30 (m, 1H), 7.11-7.08 (m, 1H), 7.05-7.02 (m, 2H), 6.90 (s, 1H), 5.22 (d, J=2.0 Hz, 2H), 4.95 (s, 2H), 4.67-4.64 (m, 1H), 3.96 (s, 3H), 3.44 (t, J=6.4 Hz, 2H), 2.85 (t, J=6.4 Hz, 2H), 2.70 (s, 3H), 2.68 (s, 6H).

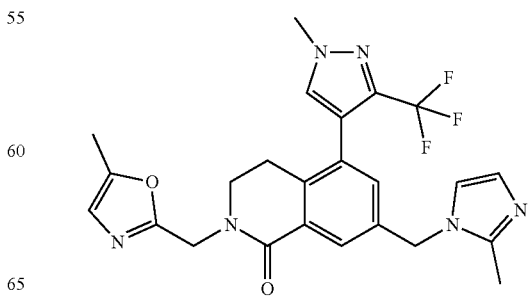

Example 194

7-((2-Methyl-1H-imidazol-1-yl)methyl)-5-(1-methyl-3-(trifluoromethyl)-1H-pyrazol-4-yl)-2-((5-methyloxazol-2-yl)methyl)-3,4-dihydroisoquinolin-1(2H)-one The title compound (1 mg, 0.002 mmol, 2% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-5-methyloxazole. $^1$H NMR (400 MHz, Chloroform-d) δ 8.05 (d, J=1.7 Hz, 1H), 7.29 (s, 1H), 6.94 (s, 1H), 6.92 (d, J=1.7 Hz, 1H), 6.84 (s, 1H), 6.65 (d, J=1.0 Hz, 1H), 5.08 (s, 2H), 4.84 (s, 2H), 3.98 (s, 3H), 3.57 (t, J=6.6 Hz, 2H), 2.80 (t, J=6.5 Hz, 2H), 2.34 (s, 3H), 2.28 (s, 3H).

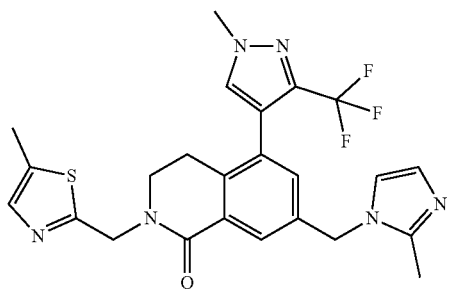 [SMILES: Cc1cnc(CN2CCc3c(cc(Cn4ccnc4C)cc3-c3cn(C)nc3C(F)(F)F)C2=O)o1]

Example 195

7-((2-Methyl-1H-imidazol-1-yl)methyl)-5-(1-methyl-3-(trifluoromethyl)-1H-pyrazol-4-yl)-2-((5-methylthiazol-2-yl)methyl)-3,4-dihydroisoquinolin-1(2H)-one The title compound (3 mg, 0.006 mmol, 12% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 2-(chloromethyl)-5-methylthiazole. $^1$H NMR (400 MHz, Chloroform-d) δ 8.06 (d, J=1.2 Hz, 1H), 7.33 (s, 1H), 7.29 (s, 1H), 6.95 (s, 1H), 6.93 (d, J=1.2 Hz, 1H), 6.85 (s, 1H), 5.09 (s, 2H), 4.96 (s, 2H), 3.98 (s, 3H), 3.59 (t, J=6.6 Hz, 2H), 2.78 (t, J=6.5 Hz, 2H), 2.43 (s, 3H), 2.35 (s, 3H).

Example 196

(S)-2-(1-(4-Methoxypyridin-2-yl)ethyl)-7-((2-methyl-1H-imidazol-1-yl)methyl)-5-(4-methylpyridin-3-yl)-3,4-dihydroisoquinolin-1(2H)-one The title compound (17.5 mg, 0.037 mmol, 26% yield) was prepared from the procedure described in Example 1 using (S)-7-(bromomethyl)-2-(1-(4-methoxypyridin-2-yl)ethyl)-5-(4-methylpyridin-3-yl)-3,4-dihydroisoquinolin-1(2H)-one (Intermediate 90, 69 mg, 0.14 mmol, 1 equiv) and 2-methyl-1H-imidazole (34.4 mg, 0.42 mmol, 3 equiv). $^1$H NMR (400 MHz, Chloroform-d) δ 8.49 (m, 1H), 8.36 (m, 1H), 8.27 (s, 0.5H), 8.21 (s, 0.5H), 8.08 (m, 1H), 7.19 (m, 1H), 6.99 (s, 1H), 6.91 (m, 3H), 6.72 (m, 1H), 6.11 (m, 1H), 5.13 (s, 2H), 3.83 (s, 3H), 3.49 (m, 1H), 3.38 (m, 1H), 2.59 (m, 1H), 2.46 (m, 1H), 2.43 (s, 3H), 2.07 (s, 1.5H), 1.98 (s, 1.5H), 1.62 (m, 3H); LC-MS (ES): >95%, 468.5 [M+H]$^+$.

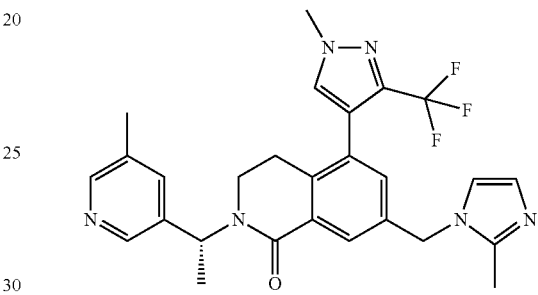

Example 197

(R)-7-((2-Methyl-1H-imidazol-1-yl)methyl)-5-(1-methyl-3-(trifluoromethyl)-1H-pyrazol-4-yl)-2-(1-(5-methylpyridin-3-yl)ethyl)-3,4-dihydroisoquinolin-1(2H)-one The title compound (12.7 mg, 30% yield) was prepared from the procedure described in Example 163 using (R)-7-(bromomethyl)-5-(1-methyl-3-(trifluoromethyl)-1H-pyrazol-4-yl)-2-(1-(5-methylpyridin-3-yl)ethyl)-3,4-dihydroisoquinolin-1(2H)-one (Intermediate 91, 41.4 mg, 0.08 mmol, 1.0 equiv.) and 2-methyl-1H-imidazole (20.1 mg, 0.25 mmol, 3.0 equiv.). LC-MS: >95% 254 nm, R$_T$=1.10 min, MS (ES) 509.6 [M+H]$^+$; $^1$H NMR (400 MHz, Chloroform-d) δ 8.43 (d, J=2.0 Hz, 1H), 8.36 (d, J=1.7 Hz, 1H), 8.06 (d, J=1.9 Hz, 1H), 7.47 (s, 1H), 7.26 (s, 1H), 6.94 (d, J=1.3 Hz, 1H), 6.93 (d, J=1.8 Hz, 1H), 6.86 (d, J=1.3 Hz, 1H), 6.20 (q, J=7.1 Hz, 1H), 5.09 (s, 2H), 3.96 (s, 3H), 3.33 (ddd, J=12.5, 9.3, 5.0 Hz, 1H), 3.04 (dt, J=12.2, 5.8 Hz, 1H), 2.72-2.53 (m, 2H), 2.34 (s, 3H), 2.32 (s, 3H), 1.60 (d, J=7.1 Hz, 3H).

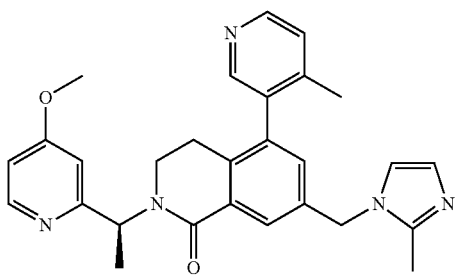 [SMILES: COc1ccnc([C@H](C)N2CCc3c(cc(Cn4ccnc4C)cc3-c3cnccc3C)C2=O)c1]

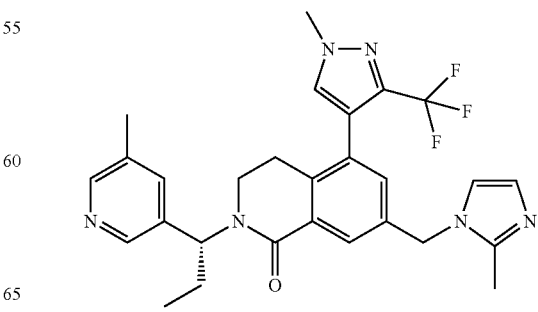

Example 198

(R)-7-((2-Methyl-1H-imidazol-1-yl)methyl)-5-(1-methyl-3-(trifluoromethyl)-1H-pyrazol-4-yl)-2-(1-(5-methylpyridin-3-yl)propyl)-3,4-dihydroisoquinolin-1(2H)-one The title compound (35.6 mg, 33% yield) was prepared from the procedure described in Example 163 using (R)-7-(bromomethyl)-5-(1-methyl-3-(trifluoromethyl)-1H-pyrazol-4-yl)-2-(1-(5-methylpyridin-3-yl)propyl)-3,4-dihydroisoquinolin-1(2H)-one (Intermediate 92, 87.7 mg, 0.17 mmol, 1.0 equiv.) and 2-methyl-1H-imidazole (41.4 mg, 0.50 mmol, 3.0 equiv.). LC-MS: >95% 254 nm, $R_T$=1.124 min, MS (ES) 523.6 [M+H]$^+$; $^1$H NMR (400 MHz, Chloroform-d) δ 8.42 (d, J=1.9 Hz, 1H), 8.34 (d, J=1.6 Hz, 1H), 8.04 (d, J=1.8 Hz, 1H), 7.47 (s, 1H), 7.25 (s, 1H), 6.91 (dd, J=2.9, 1.7 Hz, 2H), 6.84 (d, J=1.3 Hz, 1H), 5.94 (dd, J=10.0, 5.9 Hz, 1H), 5.07 (s, 2H), 3.94 (s, 3H), 3.30 (ddd, J=13.3, 8.9, 4.7 Hz, 1H), 3.04 (ddd, J=12.4, 7.3, 5.0 Hz, 1H), 2.66 (ddd, J=16.0, 7.2, 4.8 Hz, 1H), 2.54 (dq, J=16.0, 5.0 Hz, 1H), 2.32 (s, 3H), 2.30 (s, 3H), 2.12-2.02 (m, 1H), 1.95 (ddd, J=14.0, 10.0, 7.2 Hz, 1H), 1.02 (t, J=7.3 Hz, 3H).

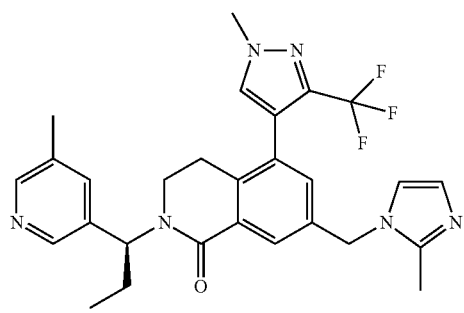 [SMILES: CC[C@@H](c1cncc(C)c1)N1CCc2c(cc(Cn3ccnc3C)cc2-c2cn(C)nc2C(F)(F)F)C1=O]

Example 199

(S)-7-((2-Methyl-1H-imidazol-1-yl)methyl)-5-(1-methyl-3-(trifluoromethyl)-1H-pyrazol-4-yl)-2-(1-(5-methylpyridin-3-yl)propyl)-3,4-dihydroisoquinolin-1(2H)-one The title compound (30.2 mg, 34% yield) was prepared from the procedure described in Example 163 using (S)-7-(bromomethyl)-5-(1-methyl-3-(trifluoromethyl)-1H-pyrazol-4-yl)-2-(1-(5-methylpyridin-3-yl)propyl)-3,4-dihydroisoquinolin-1(2H)-one (Intermediate 93, 87.7 mg, 0.17 mmol, 1.0 equiv.) and 2-methyl-1H-imidazole (41.4 mg, 0.50 mmol, 3.0 equiv.). LC-MS: >95% 254 nm, $R_T$=1.237 min, MS (ES) [523.6 M+H]$^+$; $^1$H NMR (400 MHz, Chloroform-d) δ 8.44-8.41 (m, 1H), 8.35-8.33 (m, 1H), 8.05 (d, J=1.6 Hz, 1H), 7.48 (s, 1H), 7.25 (s, 1H), 6.93-6.92 (m, 1H), 6.91 (d, J=1.5 Hz, 1H), 6.85 (d, J=1.1 Hz, 1H), 5.94 (dd, J=9.9, 5.9 Hz, 1H), 5.08 (s, 2H), 3.95 (s, 3H), 3.30 (m, 1H), 3.05 (m, 1H), 2.66 (m, 1H), 2.55 (m, 1H), 2.33 (s, 3H), 2.31 (s, 3H), 2.09 (m, 1H), 1.95 (m, 1H), 1.02 (t, J=7.3 Hz, 3H).

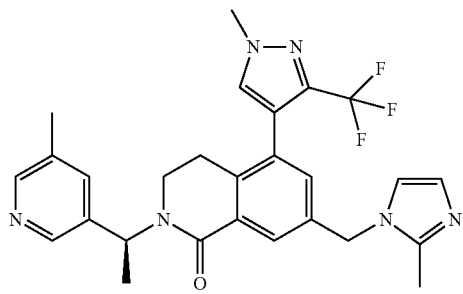 [SMILES: Cc1cncc([C@H](C)N2CCc3c(cc(Cn4ccnc4C)cc3-c3cn(C)nc3C(F)(F)F)C2=O)c1]

Example 200

(S)-7-((2-Methyl-1H-imidazol-1-yl)methyl)-5-(1-methyl-3-(trifluoromethyl)-1H-pyrazol-4-yl)-2-(1-(5-methylpyridin-3-yl)ethyl)-3,4-dihydroisoquinolin-1(2H)-one The title compound (21.4 mg, 25% yield) was prepared from the procedure described in Example 163 using (S)-7-(bromomethyl)-5-(1-methyl-3-(trifluoromethyl)-1H-pyrazol-4-yl)-2-(1-(5-methylpyridin-3-yl)ethyl)-3,4-dihydroisoquinolin-1(2H)-one (Intermediate 94, 84.1 mg, 0.17 mmol, 1.0 equiv.) and 2-methyl-1H-imidazole (41.0 mg, 0.50 mmol, 3.0 equiv.). LC-MS: >95% 254 nm, $R_T$=1.037 min, MS (ES) 509.6 [M+H]$^+$; $^1$H NMR (400 MHz, Chloroform-d) δ 8.42 (d, J=2.0 Hz, 1H), 8.35 (d, J=1.7 Hz, 1H), 8.05 (d, J=1.9 Hz, 1H), 7.47 (s, 1H), 7.26 (s, 1H), 6.93 (d, J=1.1 Hz, 2H), 6.85 (d, J=1.3 Hz, 1H), 6.19 (q, J=7.1 Hz, 1H), 5.08 (s, 2H), 3.95 (s, 3H), 3.33 (ddd, J=12.5, 9.3, 5.0 Hz, 1H), 3.04 (dt, J=12.2, 5.8 Hz, 1H), 2.68 2.53 (m, 2H), 2.33 (s, 3H), 2.32 (s, 3H), 1.59 (d, J=7.1 Hz, 3H).

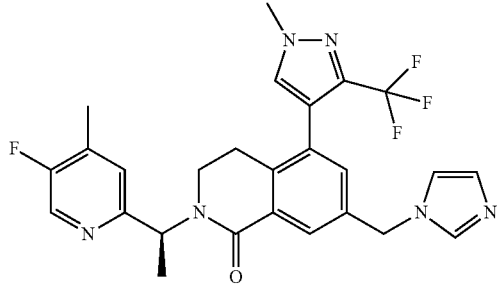 [SMILES: Cc1cc([C@H](C)N2CCc3c(cc(Cn4ccnc4)cc3-c3cn(C)nc3C(F)(F)F)C2=O)ncc1F]

Example 201

(S)-7-((1H-imidazol-1-yl)methyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one The title compound (56 mg, 0.11 mmol) was prepared following the procedures described in Example 8 using (S)-7-(bromomethyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one (Intermediate 84) and imidazole. LC-MS Method 1: >95% 254 nm, $R_T$=0.97 min, MS (ES) 512.4 [M+H]$^+$.

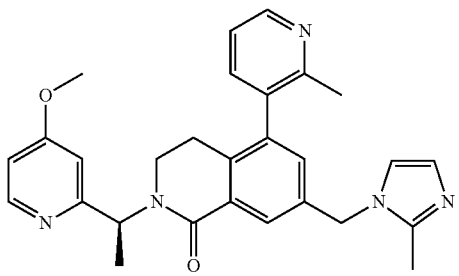 [SMILES: COc1ccnc([C@H](C)N2CCc3c(cc(Cn4ccnc4C)cc3-c3cccnc3C)C2=O)c1]

Example 202

(S)-2-(1-(4-Methoxypyridin-2-yl)ethyl)-7-((2-methyl-1H-imidazol-1-yl)methyl)-5-(2-methylpyridin-3-yl)-3,4-dihydroisoquinolin-1(2H)-one The title compound (27 mg, 0.057 mmol, 31% yield) was prepared from the procedure described in Example 1 using (S)-7-(bromomethyl)-2-(1-(4-methoxypyridin-2-yl)ethyl)-5-(2-methylpyridin-3-yl)-3,4-dihydroisoquinolin-1(2H)-one (Intermediate 95, 0.18 mmol, 1 equiv) and 2-methyl-1H-imidazole (44.3 mg, 0.54 mmol, 3 equiv). $^1$H NMR (400 MHz, Chloroform-d) δ 8.54 (m, 1H), 8.36 (t, J=5.2 Hz, 1H), 8.07 (s, 1H), 7.32 (m, 1H), 7.17 (m, 1H), 7.02 (s, 1H), 6.91 (m, 3H), 6.72 (m, 1H), 6.10 (m, 1H), 5.14 (s, 2H), 3.83 (s, 3H), 3.49 (m, 1H), 3.38 (m, 1H), 2.53 (m, 2H), 2.46 (s, 3H), 2.27 (s, 1.5H), 2.21 (s, 1.5H), 1.62 (m, 3H); LCMS (ES): >95% 254 nm, MS (ES) 468.5 [M+H]$^+$.

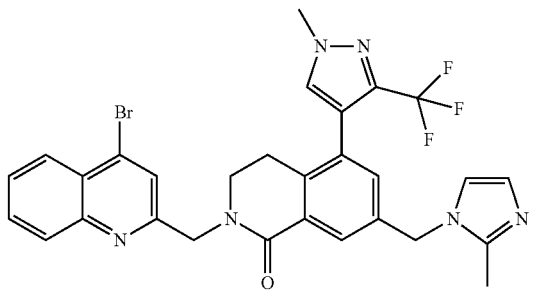

Example 204

2-((4-Bromoquinolin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (8.3 mg, 53% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.0514 mmol, 1.0 equiv.) and 4-bromo-2-(bromomethyl)quinoline (7.0 mg, 0.0283 mmol, 1.1 equiv.). LCMS: >95% 254 nm, R$_T$=1.536 min, MS (ES) 608.8 [M+H]$^+$; $^1$H NMR (400 MHz, chloroform-d) δ 8.18 (d, J=7.6 Hz, 1H), 8.09 (d, J=1.6 Hz, 1H), 8.03 (d, J=8.4 Hz, 1H), 7.81 (s, 1H), 7.75 (t, J=7.2 Hz, 1H), 7.63 (t, J=7.2 Hz, 1H), 7.30 (s, 1H), 6.95-6.93 (m, 2H), 6.87 (s, 1H), 5.11 (s, 2H), 5.04 (s, 2H), 3.98 (s, 3H), 3.61 (t, J=6.4 Hz, 2H), 2.79 (t, J=6.4 Hz, 2H), 2.36 (s, 3H).

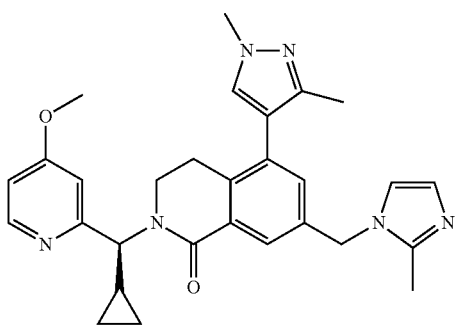 [SMILES: COc1ccnc([C@H](C2CC2)N2CCc3c(cc(Cn4ccnc4C)cc3-c3cn(C)nc3C)C2=O)c1]

Example 203

(S)-2-(Cyclopropyl(4-methoxypyridin-2-yl)methyl)-5-(1,3-dimethyl-1H-pyrazol-4-yl)-7-((2-methyl-1H-imidazol-1-yl)methyl)-3,4-dihydroisoquinolin-1(2H)-one The title compound (19 mg, 0.04 mmol) was prepared from the procedure described in Example 8 using (S)-7-(bromomethyl)-2-(cyclopropyl(4-methoxypyridin-2-yl)methyl)-5-(1,3-dimethyl-1H-pyrazol-4-yl)-3,4-dihydroisoquinolin-1(2H)-one (Intermediate 96) and 2-methyl-1H-imidazole. LC-MS: >95% 254 nm, MS (ES) 497.5 [M+H]$^+$.

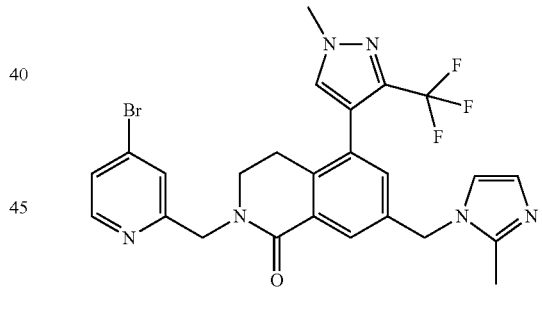

Example 205

2-((4-Bromopyridin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (5.9 mg, 51% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 4-bromo-2-(bromomethyl)pyridine (5.6 mg, 0.0226 mmol, 1.1 equiv.). LCMS: >95% 254 nm, R$_T$=1.887 min, MS (ES) 558.8 [M+H]$^+$; $^1$H NMR (400 MHz, chloroform-d) δ 8.35 (d, J=5.2 Hz, 1H), 8.05 (d, J=1.6 Hz, 1H), 7.57 (d, J=1.6 Hz, 1H), 7.38 (dd, J=5.6, 2.0 Hz, 1H), 7.30 (s, 1H), 6.94-6.92 (m, 2H), 6.85 (d, J=1.2 Hz, 1H), 5.09 (s, 2H), 4.85 (s, 2H), 3.99 (s, 3H), 3.59 (t, J=6.4 Hz, 2H), 2.79 (t, J=6.4 Hz, 2H), 2.34 (s, 3H).

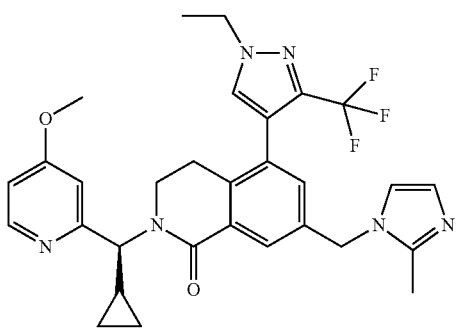 [SMILES: CCn1cc(-c2cc(Cn3ccnc3C)cc3c2CCN([C@H](c2cc(OC)ccn2)C2CC2)C3=O)c(C(F)(F)F)n1]

Example 206

(S)-2-(cyclopropyl(4-methoxypyridin-2-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one The title compound (23 mg, 0.04 mmol) was prepared from the procedure described in Example 8 using (S)-7-(bromomethyl)-2-(cyclopropyl(4-methoxypyridin-2-yl) methyl)-5-(1-ethyl-3-(trifluoromethyl)-1H-pyrazol-4-yl)-3, 4-dihydroisoquinolin-1(2H)-one (Intermediate 97) and 2-methyl-1H-imidazole. LC-MS: >95% 254 nm, $R_T$=0.78 min, MS (ES) 565.0 [M+H]$^+$.

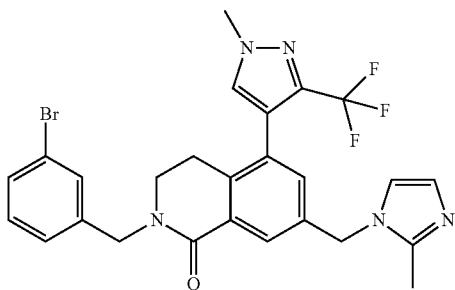 [SMILES: Cc1nccn1Cc1cc2c(c(-c3cn(C)nc3C(F)(F)F)c1)CCN(Cc1cccc(Br)c1)C2=O]

Example 207

2-(3-Bromobenzyl)-7-((2-methyl-1H-imidazol-1-yl) methyl)-5-(1-methyl-3-(trifluoromethyl)-1H-pyrazol-4-yl)-3,4-dihydroisoquinolin-1(2H)-one The title compound (55 mg, 64% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 3-bromobenzyl bromide (42.0 mg, 0.169 mmol, 1.1 equiv.). LCMS: >95% 254 nm, $R_T$=1.569 min, MS (ES) 557.8 [M+H]$^+$; $^1$H NMR (400 MHz, chloroform-d) δ 8.07 (s, 1H), 7.47 (s, 1H), 7.42 (d, J=7.6 Hz, 1H), 7.29-7.18 (m, 3H), 6.94-6.92 (m, 2H), 6.86 (d, J=0.8 Hz, 1H), 5.10 (s, 2H), 4.74 (s, 2H), 3.98 (s, 3H), 3.40 (t, J=6.8 Hz, 2H), 2.73 (t, J=6.8 Hz, 2H), 2.34 (s, 3H); $^{19}$F NMR (376 MHz, Chloroform-d) δ-60.16.

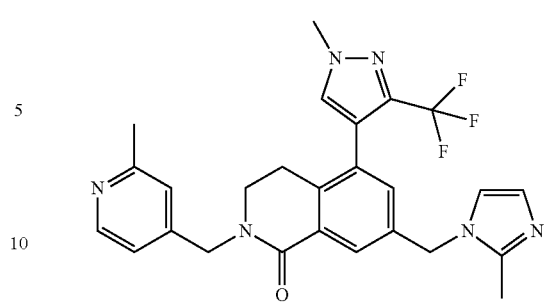

Example 208

7-((2-Methyl-1H-imidazol-1-yl)methyl)-5-(1-methyl-3-(trifluoromethyl)-1H-pyrazol-4-yl)-2-((2-methylpyridin-4-yl)methyl)-3,4-dihydroisoquinolin-1(2H)-one The title compound (8.3 mg, 65% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 4-(bromomethyl-2-methylpyridine (5.2 mg, 0.0283 mmol, 1.1 equiv.). LCMS: >95% 254 nm, $R_T$=1.136 min, MS (ES) 495.0 [M+H]$^+$; $^1$H NMR (400 MHz, chloroform-d) δ 8.45 (d, J=5.2 Hz, 1H), 8.07 (d, J=2.0 Hz, 1H), 7.30 (s, 1H), 7.09 (s, 1H), 7.04 (d, J=4.8 Hz, 1H), 6.95-6.94 (m, 2H), 6.86 (d, J=1.2 Hz, 1H), 5.10 (s, 2H), 4.73 (s, 2H), 3.98 (s, 3H), 3.42 (t, J=6.8 Hz, 2H), 2.76 (t, J=6.8 Hz, 2H), 2.54 (s, 3H), 2.35 (s, 3H); $^{19}$F NMR (376 MHz, Chloroform-d) δ-60.17.

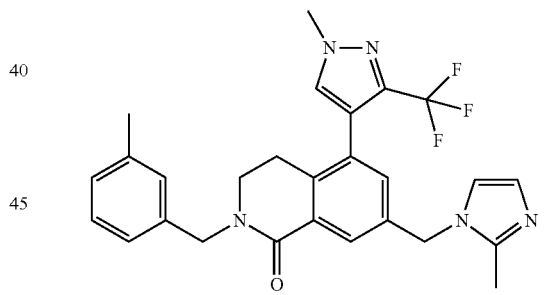

Example 209

7-((2-Methyl-1H-imidazol-1-yl)methyl)-5-(1-methyl-3-(trifluoromethyl)-1H-pyrazol-4-yl)-2-(3-methylbenzyl)-3,4-dihydroisoquinolin-1(2H)-one The title compound (7.7 mg, 61% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 3-methylbenzylbromide (5.2 mg, 0.0283 mmol, 1.1 equiv.). LCMS: >95% 254 nm, $R_T$=1.606 min, MS (ES) 493.9 [M+H]$^+$; $^1$H NMR (400 MHz, MeOD) δ 7.99 (d, J=1.6 Hz, 1H), 7.80 (s, 1H), 7.57 (d, J=2.4 Hz, 1H), 7.52 (d, J=2.4 Hz, 1H), 7.39 (d, J=1.6 Hz, 1H), 7.26-7.22 (m, 1H), 7.17-7.12 (m, 3H), 5.51 (s, 2H), 4.76 (s, 2H), 4.00 (s, 3H), 3.48 (t, J=6.4 Hz, 2H), 2.81 (t, J=6.4 Hz, 2H), 2.66 (s, 3H), 2.34 (s, 3H); $^{19}$F NMR (376 MHz, MeOD) δ −61.08.

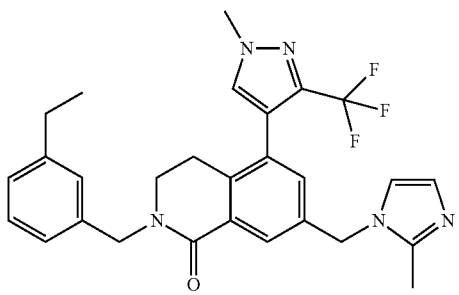 [SMILES: CCc1cccc(CN2CCc3c(cc(Cn4ccnc4C)cc3-c3cn(C)nc3C(F)(F)F)C2=O)c1]

Example 210

2-(3-Ethylbenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (7.7 mg, 59% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 1-(bromomethyl)-3-ethylbenzene (5.6 mg, 0.0283 mmol, 1.1 equiv.). LCMS: >95% 254 nm, $R_T$=1.713 min, MS (ES) 508.0 [M+H]$^+$; $^1$H NMR (400 MHz, chloroform-d) δ 8.09 (s, 1H), 7.38-7.34 (m, 2H), 7.28 (s, 1H), 7.14-7.11 (m, 2H), 6.94 (s, 1H), 6.91 (s, 1H), 6.86 (d, J=0.8 Hz, 1H), 5.09 (s, 2H), 4.76 (s, 2H), 3.97 (s, 3H), 3.39 (t, J=6.8 Hz, 2H), 2.72-2.60 (m, 4H), 2.34 (s, 3H), 1.23 (t, J=7.6 Hz, 3H).

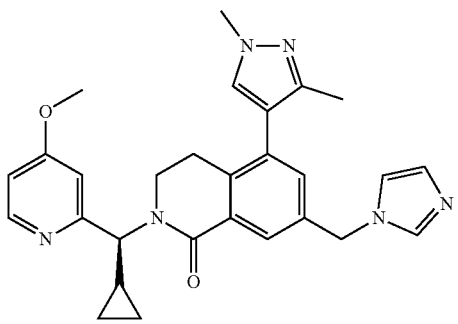 [SMILES: COc1ccnc([C@H](C2CC2)N2CCc3c(cc(Cn4ccnc4)cc3-c3cn(C)nc3C)C2=O)c1]

Example 211

(S)-7-((1H-Imidazol-1-yl)methyl)-2-(cyclopropyl(4-methoxypyridin-2-yl)methyl)-5-(1,3-dimethyl-1H-pyrazol-4-yl)-3,4-dihydroisoquinolin-1(2H)-one The title compound (21 mg, 0.044 mmol) was prepared from the procedure described in Example 8 using (S)-7-(bromomethyl)-2-(cyclopropyl(4-methoxypyridin-2-yl)methyl)-5-(1,3-dimethyl-1H-pyrazol-4-yl)-3,4-dihydroisoquinolin-1(2H)-one (Intermediate 96) and imidazole. LC-MS Method 1: >95% 254 nm, $R_T$=0.65 min, MS (ES) 483.5 [M+H]$^+$.

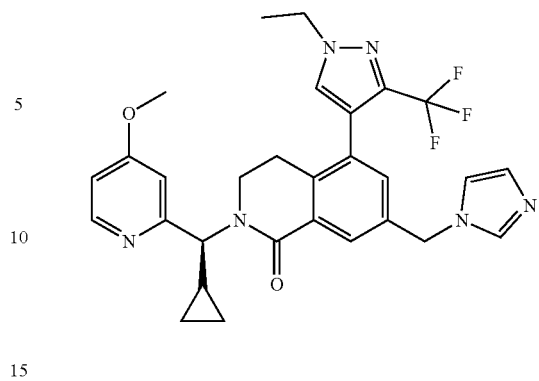

Example 212

(S)-7-((1H-Imidazol-1-yl)methyl)-2-(cyclopropyl(4-methoxypyridin-2-yl)methyl)-5-(1-ethyl-3-(trifluoromethyl)-1H-pyrazol-4-yl)-3,4-dihydroisoquinolin-1(2H)-one The title compound (24 mg, 0.04 mmol) was prepared from the procedure described in Example 8 using (S)-7-(bromomethyl)-2-(cyclopropyl(4-methoxypyridin-2-yl)methyl)-5-(1-ethyl-3-(trifluoromethyl)-1H-pyrazol-4-yl)-3,4-dihydroisoquinolin-1(2H)-one (Intermediate 97) and imidazole. LC-MS Method 2: >95% 254 nm, $R_T$=1.20 min, MS (ES) 551.5 [M+H]$^+$.

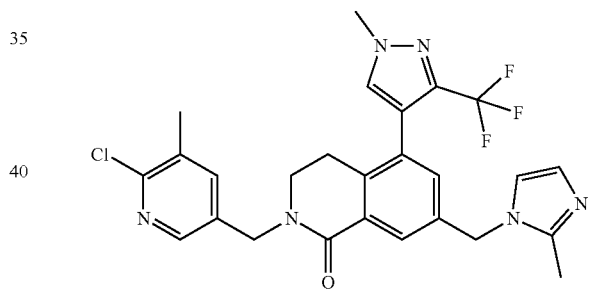

Example 213

2-((6-Chloro-5-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (7.7 mg, 59% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.05 mmol, 1.0 equiv.) and 5-(bromomethyl)-2-chloro-3-methylpyridine (12.0 mg, 0.05 mmol, 1.1 equiv.). LCMS: >95% 254 nm, $R_T$=1.304 min, MS (ES) 530.0 [M+H]$^+$; $^1$H NMR (400 MHz, Chloroform-d) δ 8.17 (d, J=1.8 Hz, 1H), 8.03 (s, 1H), 7.61-7.55 (m, 1H), 7.28 (s, 1H), 6.93 (s, 2H), 6.86-6.83 (m, 1H), 5.08 (s, 2H), 4.70 (s, 2H), 3.97 (s, 3H), 3.41 (t, J=6.6 Hz, 2H), 2.73 (t, J=6.5 Hz, 2H), 2.35 (s, 3H), 2.33 (s, 3H).

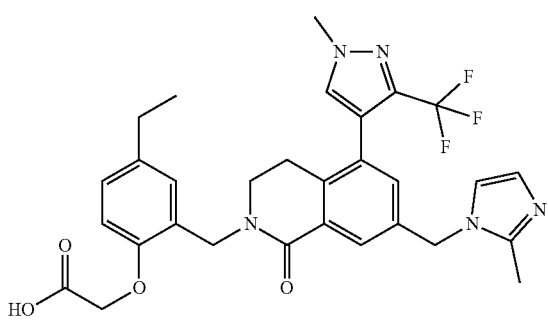 [SMILES: CCc1ccc(OCC(=O)O)c(CN2CCc3c(cc(Cn4ccnc4C)cc3-c3cn(C)nc3C(F)(F)F)C2=O)c1]

Example 214

2-(4-Ethyl-2-((7-((2-methyl-1H-imidazol-1-yl)methyl)-5-(1-methyl-3-(trifluoromethyl)-1H-pyrazol-4-yl)-1-oxo-3,4-dihydroisoquinolin-2(1H)-yl)methyl)phenoxy)acetic acid The title compound (109 mg, 81% yield)) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 91.0 mg, 0.231 mmol, 1.0 equiv.) and methyl 2-(2-(bromomethyl)-4-ethylphenoxy)acetate (72.7 mg, 0.254 mmol, 1.1 equiv.). LCMS: >95% 254 nm, $R_T$=1.906 min, MS (ES) 582.0 [M+H]$^+$; $^1$H NMR (400 MHz, MeOD) δ 7.95 (d, J=2.0 Hz, 1H), 7.79 (s, 1H), 7.56 (d, J=2.4 Hz, 1H), 7.50 (d, J=2.0 Hz, 1H), 7.37 (d, J=1.6 Hz, 1H), 7.18 (d, J=2.0 Hz, 1H), 7.10 (dd, J=8.4, 2.4 Hz, 1H), 6.84 (d, J=8.4 Hz, 1H), 5.50 (s, 2H), 4.84 (s, 2H), 4.71 (s, 2H), 4.00 (s, 3H), 3.61 (t, J=6.4 Hz, 2H), 2.81 (t, J=6.4 Hz, 2H), 2.65 (s, 3H), 2.57 (q, J=7.6 Hz, 2H), 1.19 (t, J=7.6 Hz, 3H); $^{19}$F NMR (376 MHz, MeOD) δ −61.08.

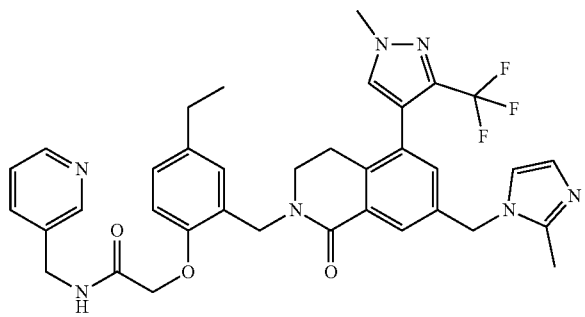 [SMILES: CCc1ccc(OCC(=O)NCc2cccnc2)c(CN2CCc3c(cc(Cn4ccnc4C)cc3-c3cn(C)nc3C(F)(F)F)C2=O)c1]

Example 215

2-(4-Ethyl-2-((7-((2-methyl-1H-imidazol-1-yl)methyl)-5-(1-methyl-3-(trifluoromethyl)-1H-pyrazol-4-yl)-1-oxo-3,4-dihydroisoquinolin-2(19)-yl)methyl)phenoxy)-N-(pyridin-3-ylmethyl)acetamide 2-(4-Ethyl-2-((7-((2-methyl-1H-imidazol-1-yl)methyl)-5-(1-methyl-3-(trifluoromethyl)-1H-pyrazol-4-yl)-1-oxo-3,4-dihydroisoquinolin-2(1H)-yl)methyl)phenoxy)acetic acid (Example 214, 10.0 mg, 0.0257 mmol, 1.0 equiv.) was dissolved in DMF (0.25 mL) and then TBTU (8.3 mg, 0.0257 mmol, 1.0 equiv.) and diisopropylethylamine (9 μL, 0.0514 mmol, 2.0 equiv.) were added. After stirring at room temperature for 10 min 3-picolylamine (5.9 mg, 0.0257 mmol, 1.0 equiv.) was added and the reaction was stirred overnight. The reaction was then diluted with water (5 mL) and extracted with EtOAc (3×5 mL). The combined organic layers were washed with water brine (5 mL), dried (MgSO$_4$), filtered and concentrated. The residue was purified by reverse phase HPLC (Phenomenex Gemini C18, H$_2$O/CH$_3$CN gradient from 20-95% CH$_3$CN, 0.1% TFA) to yield the title compound (6.7 mg, 58% yield). LC-MS: >95% 254 nm, $R_T$=1.516 min, MS (ES) 672.0 [M+H]$^+$; $^1$H NMR (400 MHz, chloroform-d) δ 9.09 (t, J=6.0 Hz, 1H), 8.72 (d, J=1.6 Hz, 1H), 8.49 (dd, J=4.8, 1.6 Hz, 1H), 7.77-7.72 (m, 2H), 7.24-7.19 (m, 2H), 7.15 (dd, J=8.0, 2.0 Hz, 1H), 7.07 (d, J=2.0 Hz, 1H), 6.92 (d, J=1.2 Hz, 1H), 6.85 (d, J=1.6 Hz, 1H), 6.82 (d, J=1.2 Hz, 1H), 6.77 (d, J=8.4 Hz, 1H), 5.03 (s, 2H), 4.81 (s, 2H), 4.62 (d, J=6.0 Hz, 2H), 4.48 (s, 2H), 3.95 (s, 3H), 3.35 (t, J=6.4 Hz, 2H), 2.63-2.57 (m, 4H), 2.31 (s, 3H), 1.21 (t, J=7.6 Hz, 3H).

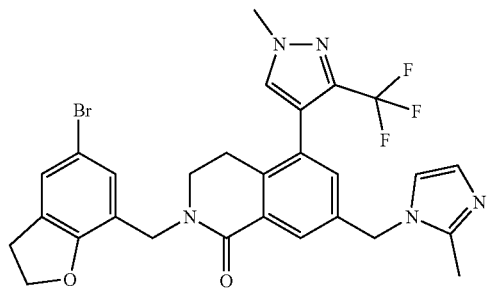

Example 216

2-((5-Bromo-2,3-dihydrobenzofuran-7-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (89.3 mg, 83% yield)) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 5-bromo-7-(bromomethyl)-2,3-dihydrobenzofuran (44.7 mg, 0.198 mmol, 1.1 equiv.). LCMS: >95% 254 nm, $R_T$=1.476 min, MS (ES) 599.8 [M+H]$^+$; $^1$H NMR (400 MHz, chloroform-d) δ 8.06 (d, J=2.0 Hz, 1H), 7.29 (s, 1H), 7.25 (d, J=1.6 Hz, 1H), 7.21 (s, 1H), 6.93 (d, J=1.2 Hz, 1H), 6.90 (d, J=2.0 Hz, 1H), 6.85 (d, J=1.6 Hz, 1H), 5.08 (s, 2H), 4.68 (s, 2H), 4.57 (t, J=8.8 Hz, 2H), 3.98 (s, 3H), 3.47 (t, J=6.8 Hz, 2H), 3.20 (t, J=8.8 Hz, 2H), 2.73 (t, J=6.8 Hz, 2H), 2.34 (s, 3H); $^{19}$F NMR (376 MHz, Chloroform-d) δ −60.16.

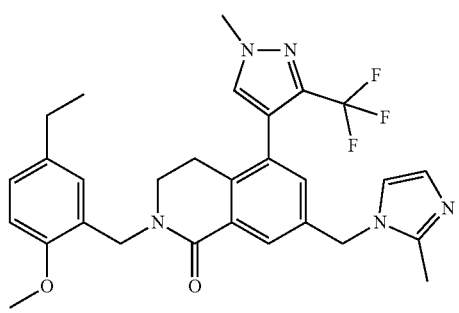 [SMILES: CCc1ccc(OC)c(CN2CCc3c(cc(Cn4ccnc4C)cc3-c3cn(C)nc3C(F)(F)F)C2=O)c1]

Example 217

2-(5-Ethyl-2-methoxybenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (8.8 mg, 64% yield)) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 2-(bromomethyl)-4-ethyl-1-methoxybenzene (6.4 mg, 0.0282 mmol, 1.1 equiv.). LCMS: >95% 254 nm, $R_T$=1.644 min, MS (ES) 538.0 [M+H]$^+$; $^1$H NMR (400 MHz, chloroform-d) δ 8.07 (d, J=2.0 Hz, 1H), 7.28 (s, 1H), 7.17 (d, J=2.4 Hz, 1H), 7.07 (dd, J=8.0, 2.0 Hz, 1H), 6.94 (d, J=1.2 Hz, 1H), 6.90 (d, J=2.0 Hz, 1H), 6.85 (d, J=1.2 Hz, 1H), 6.81 (d, J=8.4 Hz, 1H), 5.08 (s, 2H), 4.77 (s, 2H), 3.97 (s, 3H), 3.80 (s, 3H), 3.46 (t, J=6.8 Hz, 2H), 2.70 (t, J=6.4 Hz, 2H), 2.59-2.53 (m, 2H), 2.34 (s, 3H), 1.18 (t, J=7.6 Hz, 3H).

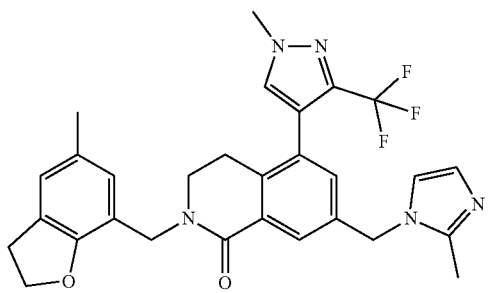

Example 218

7-((2-Methyl-1H-imidazol-1-yl)methyl)-2-((5-methyl-2,3-dihydrobenzofuran-7-yl)methyl)-5-(1-methyl-3-(trifluoromethyl)-1H-pyrazol-4-yl)-3,4-dihydroisoquinolin-1(2H)-one 2-((5-Bromo-2,3-dihydrobenzofuran-7-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (10.0 mg, 0.0167 mmol, 1.0 equiv.), $K_2CO_3$ (6.9 mg, 0.0501 mmol, 3.0 equiv.) and methylboronic acid (4.0 mg, 0.0668 mmol, 4.0 equiv.) were dissolved in 1,4-dioxane:$H_2O$ (0.2 mL, 3:1). The resulting mixture was degassed for 10 minutes and then Pd(dppf)Cl$_2$ (0.6 mg, 0.000835 mmol, 0.05 equiv.) was added. The reaction was heated to 95° C. for 2 hours and then cooled to room temperature. The reaction was diluted with water (5 mL) and extracted with EtOAc (3×5 mL). The combined organic layers were washed with brine (5 mL), dried (MgSO$_4$), filtered and concentrated. The crude residue was purified by reverse phase HPLC eluting with 20% to 95% MeCN in H$_2$O containing 0.1% TFA to yield the title compound (3.1 mg, 35% yield). LC-MS: >95% 254 nm, $R_T$=1.572 min, MS (ES) 535.9 [M+H]$^+$; $^1$H NMR (400 MHz, chloroform-d) δ 8.07 (s, 1H), 7.27 (s, 1H), 6.95-6.93 (m, 3H), 6.89 (s, 1H), 6.85 (s, 1H), 5.08 (s, 2H), 4.70 (s, 2H), 4.52 (t, J=8.4 Hz, 2H), 4.00 (s, 3H), 3.48 (t, J=6.4 Hz, 2H), 3.16 (t, J=8.4 Hz, 2H), 2.71 (t, J=6.4 Hz, 2H), 2.34 (s, 3H), 2.24 (s, 3H).

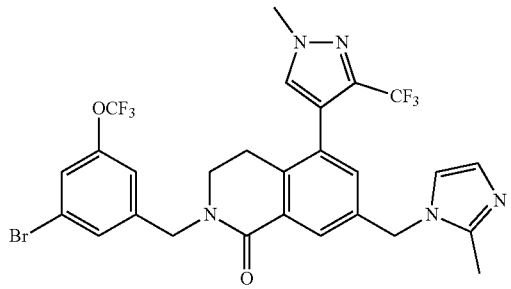 [SMILES: Cc1nccn1Cc1cc2c(c(-c3cn(C)nc3C(F)(F)F)c1)CCN(Cc1cc(Br)cc(OC(F)(F)F)c1)C2=O]

Example 219

2-(3-Bromo-5-(trifluoromethoxy)benzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one 7-((2-Methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20 mg, 0.051 mmol, 1 equiv) was dissolved DMF (0.3 mL) and cooled to 0° C. Then sodium hydride (2.7 mg, 0.10 mmol, 2 equiv) was added and the reaction mixture was stirred at 0° C. for 20 min. 1-bromo-3-(bromomethyl)-5-(trifluoromethoxy)benzene (26 mg, 77 μmol, 1.5 equiv) was dissolved in DMF (0.3 mL) and added dropwise to the reaction mixture. The reaction mixture was warmed slowly to room temperature. After completion, the reaction mixture was diluted in water, extracted with DCM, dried over MgSO$_4$, and concentrated. The residue was purified by flash chromatography (Combiflash Rf, Hex/EtOAc=0-100% gradient) to afford the title compound (33 mg, 0.051 mmol, quant.). LC-MS: >95% 254 nm, $R_T$=1.821 min, MS (ES) 641.8 [M+H]$^+$.

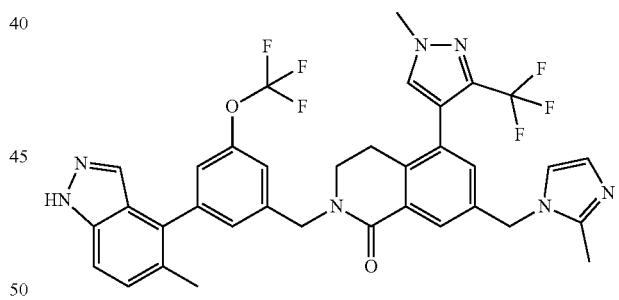

Example 220

7-((2-Methyl-1H-imidazol-1-yl)methyl)-2-(3-(5-methyl-1H-indazol-4-yl)-5-(trifluoromethoxy)benzyl)-5-(1-methyl-3-(trifluoromethyl)-1H-pyrazol-4-yl)-3,4-dihydroisoquinolin-1(2H)-one In a sealed tube, 2-(3-bromo-5-(trifluoromethoxy)benzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 219, 15 mg, 0.023 mmol, 1 equiv), (5-methyl-1H-indazol-4-yl)boronic acid (12 mg, 0.070 mmol, 3 equiv), potassium carbonate (8.1 mg, 0.058 mmol, 2.5 equiv), and Pd(dppf)Cl$_2$ (0.85 mg, 1.2 μmol, 0.05 equiv) were dissolved in 1,4-dioxane:water (0.5 mL, 4:1) and placed under an argon atmosphere. The reaction mixture was then placed in a preheated heating block and stirred for 14 h at 95° C. At 23° C., brine was added to the mixture and extracted with EtOAc. The combined organic layers were dried over MgSO$_4$ and concentrated under reduced pressure. The residue was purified by reverse phase HPLC (Phenomenex Gemini C18, H$_2$O/CH$_3$CN gradient from 10-95% CH$_3$CN, 0.1% TFA) to yield the title compound (5.0 mg, 7.2 μmol, 31% yield). $^1$H NMR (400 MHz, Chloroform-d) δ 8.06 (s, 1H), 7.56 (s, 1H), 7.47 (s, 1H), 7.45 (s, 1H), 7.41 (s, 1H), 7.34 (s, 1H), 7.31 (d, J=10 Hz, 1H), 7.23 (s, 2H), 7.18 (d, J=5.0 Hz, 2H), 7.05 (s, 1H), 5.19 (s, 2H), 4.88 (s, 2H), 4.01 (s, 3H), 3.53 (t, J=6.2 Hz, 2H), 2.86 (t, J=6.2 Hz, 2H), 2.68 (s, 3H), 2.35 (s, 3H); LC-MS: >95% 254 nm, R$_T$=1.618 min, MS (ES) 693.9 [M+H]$^+$.

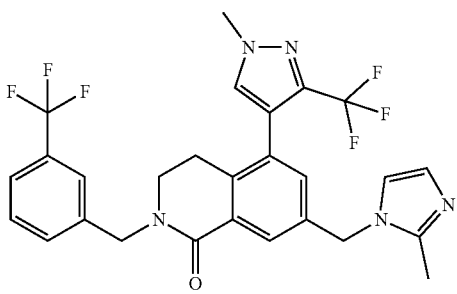 [SMILES: Cc1nccn1Cc1cc2c(c(-c3cn(C)nc3C(F)(F)F)c1)CCN(Cc1cccc(C(F)(F)F)c1)C2=O]

Example 221

7-((2-Methyl-1H-imidazol-1-yl)methyl)-5-(1-methyl-3-(trifluoromethyl)-1H-pyrazol-4-yl)-2-(3-(trifluoromethyl)benzyl)-3,4-dihydroisoquinolin-1(2H)-one The title compound (7.8 mg, 55% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 3-trifluoromethylbenzyl bromide (6.7 mg, 0.0282 mmol, 1.1 equiv.). LCMS: >95% 254 nm, R$_T$=2.055 min, MS (ES) 547.9 [M+H]$^+$; $^1$H NMR (400 MHz, chloroform-d) δ 8.08 (d, J=1.6 Hz, 1H), 7.56-7.53 (m, 3H), 7.46 (t, J=7.6 Hz, 1H), 7.29 (s, 1H), 6.95-6.93 (m, 2H), 6.86 (d, J=1.2 Hz, 1H), 5.10 (s, 2H), 4.83 (s, 2H), 3.98 (s, 3H), 3.42 (t, J=6.8 Hz, 2H), 2.74 (t, J=6.8 Hz, 2H), 2.34 (s, 3H).

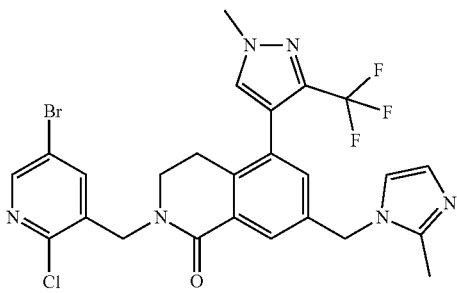 [SMILES: Cc1nccn1Cc1cc2c(c(-c3cn(C)nc3C(F)(F)F)c1)CCN(Cc1cc(Br)cnc1Cl)C2=O]

Example 222

2-((5-Bromo-2-chloropyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (54.6 mg, 72% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 50.0 mg, 0.13 mmol, 1.0 equiv.) and 5-bromo-3-(bromomethyl)-2-chloropyridine (37.0 mg, 0.13 mmol, 1.0 equiv.) LCMS: >95% 254 nm, R$_T$=1.297 min, MS (ES) 593.0 [M+H]$^+$;

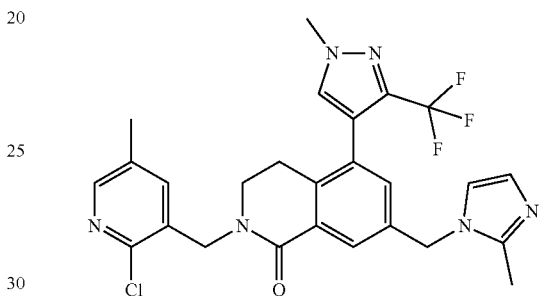

Example 223

2-((2-Chloro-5-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one To a solution of 2-((5-bromo-2-chloropyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (54.6 mg, 0.09 mmol, 1.0 equiv.) in 1,4-dioxane (0.5 mL) and H$_2$O (0.13 mL), methylboronic acid (27.5 mg, 0.46 mmol, 5.0 equiv.), K$_2$CO$_3$ (5.3 mg, 0.05 mmol, 0.05 equiv.) was added followed by Pd(PPh$_3$)$_4$ (5.3 mg, 0.05 mmol, 0.05 equiv.). The reaction mixture was purged with Ar. The resulting mixture was heated at 80° C. for 6.5 h. The reaction mixture was partitioned between CH$_2$Cl$_2$ (5.0 mL) and H$_2$O (1.0 mL), and extracted with CH$_2$Cl$_2$ (3×10.0 mL). The combined organics were dried over Na$_2$SO$_4$, filtered and concentrated. The residue was purified by flash chromatography (Combi-flash Rf, DCM/MeOH=0-10% gradient) to afford the title compound (11.8 mg, 24% yield). LCMS: >95% 254 nm, R$_T$=0.879 min, MS (ES) 529.2 [M+H]$^+$; $^1$H NMR (400 MHz, Chloroform-d) δ 8.13 (d, J=1.9 Hz, 1H), 8.03 (d, J=1.7 Hz, 1H), 7.58 (d, J=1.9 Hz, 1H), 7.31 (s, 1H), 6.95 (d, J=1.6 Hz, 1H), 6.93 (s, 1H), 6.86-6.84 (m, 1H), 5.09 (s, 2H), 4.82 (s, 2H), 3.98 (s, 3H), 3.54 (t, J=6.6 Hz, 2H), 2.79 (t, J=6.5 Hz, 2H), 2.34 (s, 3H), 2.30 (s, 3H).

289

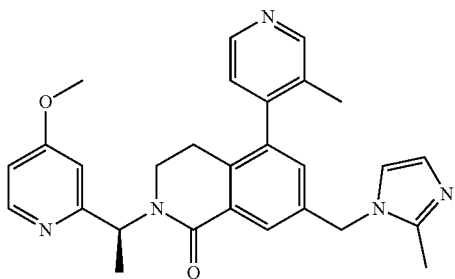 [SMILES: COc1ccnc([C@H](C)N2CCc3c(cc(Cn4ccnc4C)cc3-c3ccncc3C)C2=O)c1]

Example 224

(S)-2-(1-(4-Methoxypyridin-2-yl)ethyl)-7-((2-methyl-1H-imidazol-1-yl)methyl)-5-(3-methylpyridin-4-yl)-3,4-dihydroisoquinolin-1(2H)-one The title compound ((27 mg, 0.057 mmol, 31% yield) was prepared from the procedure described in Example 1 using (S)-7-(bromomethyl)-2-(1-(4-methoxypyridin-2-yl)ethyl)-5-(3-methylpyridin-4-yl)-3,4-dihydroisoquinolin-1(2H)-one (Intermediate 98, 40 mg, 0.085 mmol, 1 equiv) and 2-methyl-1H-imidazole (26 mg, 0.33 mmol, 4 equiv). $^1$H NMR (400 MHz, Chloroform-d) δ 8.51 (m, 1H), 8.46 (m, 1H), 8.37 (m, 1H), 8.08 (s, 1H), 7.00 (s, 1H), 6.89 (m, 3H), 6.73 (m, 1H), 6.11 (m, 1H), 5.12 (s, 2H), 3.83 (s, 3H), 3.46 (m, 1H), 3.38 (m, 1H), 2.55 (m, 1H), 1.96 (m, 1H), 2.41 (s, 3H), 2.05 (s, 1.5H), 1.96 (s, 1.5H), 1.61 (m, 3H); LCMS (ES): >95% 254 nm, MS (ES) 468.5 [M+H]$^+$.

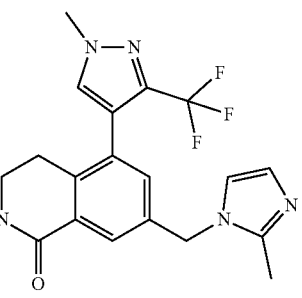

Example 225

2-((3-Chloronaphthalen-1-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (7.4 mg, 51% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 1-(bromomethyl)-3-chloronaphthalene (7.2 mg, 0.0282 mmol, 1.1 equiv.). LCMS: >95% 254 nm, R$_T$=0.451 min, MS (ES) 563.9 [M+H]$^+$; $^1$H NMR (400 MHz, chloroform-d) δ 8.08 (d, J=2.0 Hz, 1H), 7.31-7.20 (m, 7H), 6.95-6.92 (m, 2H), 6.86 (d, J=1.2 Hz, 1H), 5.10 (s, 2H), 4.75 (s, 2H), 3.98 (s, 3H), 3.41 (t, J=6.8 Hz, 2H), 2.74 (t, J=6.8 Hz, 2H), 2.35 (s, 3H); $^{19}$F NMR (376 MHz, Chloroform-d) δ −60.16.

290

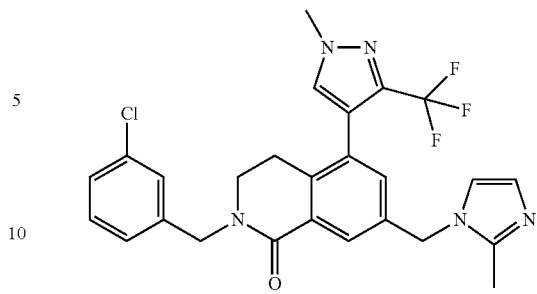

Example 226

2-(3-Chlorobenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (6.1 mg, 46% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 3-chlorobenzyl bromide (5.8 mg, 0.0282 mmol, 1.1 equiv.). LCMS: >95% 254 nm, R$_T$=0.221 min, MS (ES) 513.9 [M+H]$^+$; $^1$H NMR (400 MHz, chloroform-d) δ 8.16-8.12 (m, 2H), 7.81 (s, 1H), 7.55-7.51 (m, 1H), 7.38 (d, J=2.0 Hz, 1H), 7.24 (s, 1H), 6.95 (d, J=1.2 Hz, 1H), 6.92 (d, J=1.6 Hz, 1H), 6.86 (d, J=1.2 Hz, 1H), 5.21 (s, 2H), 5.11 (s, 2H), 3.94 (s, 3H), 3.37 (t, J=6.8 Hz, 2H), 2.63 (t, J=6.8 Hz, 2H), 2.36 (s, 3H); $^{19}$F NMR (376 MHz, Chloroform-d) δ-60.15.

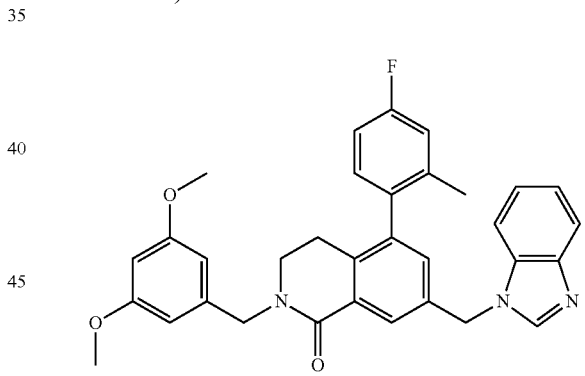

Example 227

(S)-2-(Cyclopropyl(4-methoxypyridin-2-yl)methyl)-5-(1,3-dimethyl-1H-pyrazol-4-yl)-7-((2-methyl-1H-imidazol-1-yl)methyl)-3,4-dihydroisoquinolin-1(2H)-one The title compound (19 mg, 0.04 mmol) was prepared from the procedure described in Example 1 using 7-(bromomethyl)-2-(3,5-dimethoxybenzyl)-5-(4-fluoro-2-methylphenyl)-3,4-dihydroisoquinolin-1(2H)-one (Intermediate 11) and 1H-benzo[d]imidazole (30 mg, 0.25 mmol, 5 equiv). $^1$H NMR (400 MHz, Chloroform-d) δ 8.20 (d, J=1.6 Hz, 1H), 7.98 (s, 1H), 7.82 (m, 1H), 7.33 (m, 1H), 7.27 (m, 2H), 7.00 (d, J=2.0 Hz, 1H), 6.89 (m, 3H), 6.47 (m 2H), 6.37 (m, 1H), 5.42 (s, 2H), 4.71 (m, 2H), 3.78 (s, 6H), 3.38 (t, J=6.4

Hz, 2H), 2.62 (m, 1H), 2.49 (m, 1H), 1.89 (s, 3H); LCMS: >95% 254 nm, MS (ES) 536.6 [M+H]+.

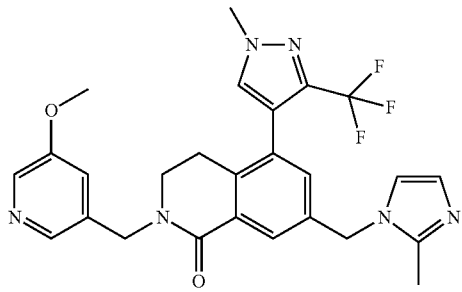 [SMILES: COc1cncc(CN2CCc3c(cc(Cn4ccnc4C)cc3-c3cn(C)nc3C(F)(F)F)C2=O)c1]

Example 228

2-((5-Methoxypyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (6.1 mg, 46% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 12.0 mg, 0.06 mmol, 1.5 equiv.) and 3-(bromomethyl)-5-methoxypyridine (12.0 mg, 0.06 mmol, 1.5 equiv.). LCMS: >95% 254 nm, $R_T$=1.043 min, MS (ES) 511.5 [M+H]+; 1H NMR (400 MHz, Chloroform-d) δ 8.23 (d, J=2.8 Hz, 1H), 8.16 (d, J=1.6 Hz, 1H), 8.03 (d, J=1.8 Hz, 1H), 7.28 (d, J=1.0 Hz, 1H), 7.22-7.19 (m, 1H), 6.94-6.91 (m, 2H), 6.84 (d, J=1.3 Hz, 1H), 5.08 (s, 2H), 4.75 (s, 2H), 3.96 (s, 3H), 3.83 (s, 3H), 3.41 (t, J=6.6 Hz, 2H), 2.72 (t, J=6.5 Hz, 2H), 2.33 (s, 3H).

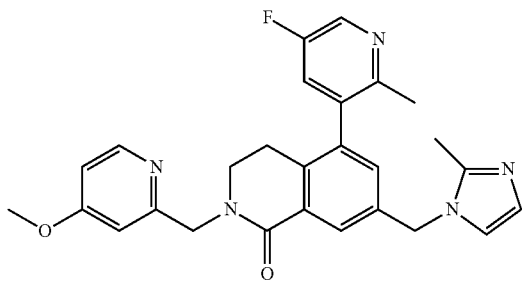 [SMILES: COc1ccnc(CN2CCc3c(cc(Cn4ccnc4C)cc3-c3cc(F)cnc3C)C2=O)c1]

Example 229

5-(5-Fluoro-2-methylpyridin-3-yl)-2-((4-methoxypyridin-2-yl)methyl)-7-((2-methyl-1H-imidazol-1-yl)methyl)-3,4-dihydroisoquinolin-1(2H)-one Step A. Preparation of methyl 5-(benzyloxy)-2-((4-methoxypyridin-2-yl)methyl)-1-oxo-1,2,3,4-tetrahydroisoquinoline-7-carboxylate. To a solution of methyl 5-hydroxy-2-((4-methoxypyridin-2-yl)methyl)-1-oxo-1,2,3,4-tetrahydroisoquinoline-7-carboxylate (Intermediate 15, 0.73 g, 2.1 mmol, 1 equiv) in acetone (60 mL) was added $K_2CO_3$ (871 mg, 6.3 mmol, 3 equiv) and benzylbromide (324 µL, 2.73 mmol, 1.3 equiv). The resulting mixture was stirred at room temperature for 48 h then concentrated. The residue was partitioned between EtOAc and water. The organic layer was dried ($Na_2SO_4$) and concentrated. The residue was purified by flash chromatography (Combi-flash Rf, Hex/EtOAc=0-90% gradient) to afford the title compound (0.83 g, 1.9 mmol, 90% yield): LCMS (ES): m/z=433.4 [M+H]+.

Step B. Preparation of 5-(benzyloxy)-7-(hydroxymethyl)-2-((4-methoxypyridin-2-yl)methyl)-3,4-dihydroisoquinolin-1(2H)-one. To a solution of methyl 5-(benzyloxy)-2-((4-methoxypyridin-2-yl)methyl)-1-oxo-1,2,3,4-tetrahydroisoquinoline-7-carboxylate (0.95 g, 2.19 mmol, 1 equiv) in EtOH (44 mL) was added $NaBH_4$ (836 mg, 22 mmol, 10 equiv). The mixture was heated under reflux for 6 h, then concentrated. The residue was taken up in EtOAc and washed with brine. The organic layer was dried ($Na_2SO_4$) and concentrated. The residue was purified by flash chromatography (Combi-flash Rf, Hex/EtOAc=0-80% gradient) to afford the title compound (0.48 g, 1.18 mmol, 53% yield): 1H NMR (400 MHz, Chloroform-d) δ 8.37 (d, J=6.0 Hz, 1H), 7.71 (s, 1H), 7.36 (m, 5H), 7.17 (s, 1H), 7.00 (d, J=2.0 Hz, 1H), 6.79 (m, 1H), 5.12 (s, 2H), 4.91 (s, 2H), 4.72 (d, J=2.8 Hz, 2H), 3.85 (s, 3H), 3.67 (t, J=6.8 Hz, 2H), 3.02 (t, J=6.8 Hz, 2H); LCMS (ES): m/z=405.4 [M+H]+.

Step C. Preparation of 5-(benzyloxy)-7-(bromomethyl)-2-((4-methoxypyridin-2-yl)methyl)-3,4-dihydroisoquinolin-1(2H)-one. The title compound was prepared as a crude product following the procedure described in Intermediate 18 using 5-(benzyloxy)-7-(hydroxymethyl)-2-((4-methoxypyridin-2-yl)methyl)-3,4-dihydroisoquinolin-1(2H)-one (0.38 g, 0.94 mmol, 1 equiv). LCMS: >95% 254 nm, MS (ES) 467.4 [M+H]+.

Step D. Preparation of 5-(benzyloxy)-2-((4-methoxypyridin-2-yl)methyl)-7-((2-methyl-1H-imidazol-1-yl)methyl)-3,4-dihydroisoquinolin-1(2H)-one. The title compound was prepared (250 mg, 0.53 mmol, 56% yield over two steps) following the procedure described in Example 1 using 5-(benzyloxy)-7-(bromomethyl)-2-((4-methoxypyridin-2-yl)methyl)-3,4-dihydroisoquinolin-1(2H)-one (0.38 g, 0.94 mmol, 1 equiv) and 2-methyl-1H-imidazole. 1H NMR (400 MHz, Chloroform-d) δ 8.28 (d, J=6.0 Hz, 1H), 7.56 (s, 1H), 7.29 (m, 5H), 6.89 (s, 1H), 6.83 (d, J=2.4 Hz, 1H), 6.76 (s, 1H), 6.65 (m, 1H), 6.51 (s, 1H), 4.95 (s, 2H), 4.91 (s, 2H), 4.77 (s, 2H), 3.73 (s, 3H), 3.56 (t, J=6.8 Hz, 2H), 2.93 (t, J=6.8 Hz, 2H), 2.22 (s, 3H); LCMS (ES): m/z=469.4 [M+H]+.

Step E. Preparation of 5-hydroxy-2-((4-methoxypyridin-2-yl)methyl)-7-((2-methyl-1H-imidazol-1-yl)methyl)-3,4-dihydroisoquinolin-1(2H)-one. To a solution of 5-(benzyloxy)-2-((4-methoxypyridin-2-yl)methyl)-7-((2-methyl-1H-imidazol-1-yl)methyl)-3,4-dihydroisoquinolin-1(2H)-one (290 mg, 0.62 mmol, 1 equiv) in MeOH (10 mL) was added Pd/C (10 wt. %, 66 mg, 0.062 mmol, 0.1 equiv) and 4M HCl in dioxane (0.62 mL, 2.48 mmol). The mixture was shaked under 50 PSI of hydrogen gas on a Parr shaker for 16 h. Then the mixture was filtered and the filtrated was concentrated to provide the crude title compound as a HCl salt, which was used without purification: LCMS (ES): m/z=379.4 [M+H]+.

Step F. Preparation of 2-((4-methoxypyridin-2-yl)methyl)-7-((2-methyl-1H-imidazol-1-yl)methyl)-1-oxo-1,2,3,4-tetrahydroisoquinolin-5-yl trifluoromethanesulfonate. To a suspension of 5-hydroxy-2-((4-methoxypyridin-2-yl)methyl)-7-((2-methyl-1H-imidazol-1-yl)methyl)-3,4-dihydroisoquinolin-1(2H)-one (0.62 mmol, 1 equiv) in dichloromethane (12 mL) was added phenyl triflimide (0.8 g, 2.23 mmol, 3.6 equiv) and $Et_3N$ (520 µL, 3.72 mmol, 6 equiv). The mixture was stirred at room temperature for 24 h, then diluted with EtOAc and washed with saturated aqueous $NaHCO_3$. The organic layer was dried ($Na_2SO_4$) and concentrated. The residue was purified by flash chromatography (Combi-flash Rf, DCM/MeOH=0-10% gradient) to afford the title compound (183 mg, 0.35 mmol, 56% yield over two steps): $^1$H NMR (400 MHz, Chloroform-d) δ 8.37 (d, J=6.0 Hz, 1H), 8.02 (s, 1H), 7.10 (s, 1H), 7.07 (s, 1H), 6.95 (s, 1H), 6.89 (d, J=2.4 Hz, 1H), 6.76 (m, 1H), 5.18 (s, 2H), 4.83 9s, 2H), 3.84 (s, 3H), 3.73 9t, J=6.8 Hz, 2H), 3.07 (t, J=6.8 Hz, 2H), 2.48 (s, 3H); LCMS (ESI): m/z=511.4 [M+H]$^+$.

Step G. Preparation of 5-(5-fluoro-2-methylpyridin-3-yl)-2-((4-methoxypyridin-2-yl)methyl)-7-((2-methyl-1H-imidazol-1-yl)methyl)-3,4-dihydroisoquinolin-1(2H)-one. To a solution of 3-bromo-5-fluoro-2-methylpyridine (80 mg, 0.42 mmol, 1 equiv) in 1,4-dioxane (4 mL) was added bis(pinacolato)diboron (117.3 mg, 0.46 mmol, 1.1 equiv), KOAc (124 mg, 1.26 mmol, 3 equiv), and PdCl$_2$(dppf) (31 mg, 0.042 mmol, 0.1 equiv). The resulting mixture was heated at 85° C. for 16 h, then cooled to room temperature. To this mixture was added 2-((4-methoxypyridin-2-yl)methyl)-7-((2-methyl-1H-imidazol-1-yl)methyl)-1-oxo-1,2,3,4-tetrahydroisoquinolin-5-yl trifluoromethanesulfonate (183 mg, 0.36 mmol, 0.85 equiv), Na$_2$CO$_3$ (96 mg, 0.85 mmol, 2.14 equiv), Pd(PPh$_3$)$_4$ (26 mg, 0.022 mmol, 0.05 equiv), and water (0.6 mL). The mixture was heated at 80° C. for another 16 h, then cooled to room temperature. EtOAc and water were added, and the aqueous layer was extracted with EtOAc. The combined organic layers were dried over Na$_2$SO$_4$ and concentrated. The residue was purified by flash chromatography (Combi-flash Rf, DCM/MeOH=0-10% gradient) then concentrated. The residue was purified by reverse phase HPLC (Phenomenex Gemini C18, H$_2$O/CH$_3$CN gradient from 5-25% CH$_3$CN, 0.1% TFA) to yield the title compound (4 mg, 0.008 mmol, 2% yield over two steps). $^1$H NMR (400 MHz, Chloroform-d) δ 8.42 (d, J=2.8 Hz, 1H), 8.35 (d, J=6.4 Hz, 1H), 8.10 (d, J=2.0 Hz, 1H), 7.11 (dd, J=2.8, 8.4 Hz, 1H), 6.99 (s, 1H), 6.90 (m, 3H), 6.74 (dd, J=2.4, 5.6 Hz, 1H), 5.14 (s, 2H), 4.84 (m 2H), 3.84 (s, 3H), 3.61 (t, J=6.8 Hz, 2H), 2.64 (m, 2H), 2.42 (s, 3H), 2.22 (s, 3H); LCMS: >95% 254 nm, MS (ES) 472.5 [M+H]$^+$.

mg, 1.1 eq.). The reaction was stirred at R$_T$ for 20 h then concentrated. The residue was purified by flash chromatography (Combi-flash Rf, DCM/MeOH=0-5% gradient) to afford the title compound: LCMS Method 1: >95% 254 nm, R$_T$=1.28 min, MS (ES) 472.9 [M+H]$^+$.

Step B. Preparation of 5-(1-ethyl-3-(trifluoromethyl)-1H-pyrazol-4-yl)-7-(hydroxy(1-trityl-1H-imidazol-2-yl)methyl)-2-((S)-1-(4-methoxypyridin-2-yl)ethyl)-3,4-dihydroisoquinolin-1(2H)-one. To a solution of 2-iodo-1-trityl-1H-imidazole (2.0 eq) in DCM was added 3.0 M ethyl magnesium bromide solution (2.0 eq). The reaction mixture was stirred at R$_T$ for 20 h, and a solution of (S)-5-(1-ethyl-3-(trifluoromethyl)-1H-pyrazol-4-yl)-2-(1-(4-methoxypyridin-2-yl)ethyl)-1-oxo-1,2,3,4-tetrahydroisoquinoline-7-carbaldehyde (1.0 eq) in DCM was added. The resulting mixture was stirred at R$_T$ for 1 h then quenched with sat. aq. NH$_4$Cl solution. The layers were separated, and the organic layer was concentrated. The residue was purified by flash chromatography (Combi-flash Rf, DCM/MeOH=0-10% gradient) to afford the title compound.

Step C. Preparation of (S)-7-((1H-imidazol-2-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one. To a sealable pressure flask was added (S)-5-(1-ethyl-3-(trifluoromethyl)-1H-pyrazol-4-yl)-2-(1-(4-methoxypyridin-2-yl)ethyl)-7-((1-trityl-1H-imidazol-2-yl)methyl)-3,4-dihydroisoquinolin-1(2H)-one (285 mg, 0.36 mmol), 1,2-dichloroethane (2 mL), TFA (20.0 eq), and triethylsilane (10.0 eq). The flask was sealed and heated at 110° C. for 48 h. The reaction was cooled to ambient temperature and concentrated. This was dissolved in EtOAc and washed with 1N NaOH, and the organic layer was concentrated. The residue was purified by reverse phase HPLC (Phenomenex Gemini C18, H$_2$O/CH$_3$CN gradient from 5-95% CH$_3$CN, 0.1% TFA) to yield the title compound (0.12 g, 65% yield). $^1$H NMR (400 MHz, CDCl$_3$) δ 8.36 (d, J=5.0 Hz, 1H), 8.04 (d, J=1.8 Hz, 1H), 7.30 (s, 1H), 7.23 (d, J=1.8 Hz, 1H), 6.95 (s, 2H), 6.90 (d, J=2.4 Hz, 1H), 6.73-6.71 (m, 1H), 6.12 (q, J=7.4 Hz, 1H), 4.23 (q, J=7.3 Hz, 2H), 4.12 (s, 2H), 3.82 (s, 3H), 3.48-3.41 (m, 1H), 3.34-3.28 (m, 1H), 2.70-2.58 (m, 2H), 1.61 (d, J=7.4 Hz, 3H), 1.53 (d, J=7.3 Hz, 3H); LCMS Method 1: >95% 254 nm, R$_T$=1.06 min, MS (ES) 525.0 [M+H]$^+$.

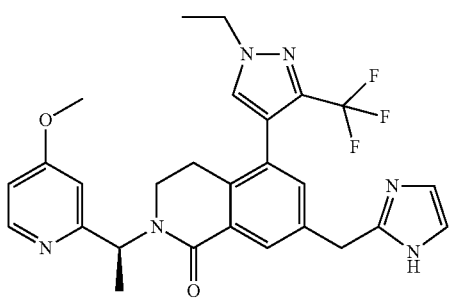 [SMILES: CCn1cc(-c2cc(Cc3ncc[nH]3)cc3c2CCN([C@@H](C)c2cc(OC)ccn2)C3=O)c(C(F)(F)F)n1]

Example 230

(S)-7-((1H-Imidazol-2-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one Step A. Preparation of (S)-5-(1-ethyl-3-(trifluoromethyl)-1H-pyrazol-4-yl)-2-(1-(4-methoxypyridin-2-yl)ethyl)-1-oxo-1,2,3,4-tetrahydroisoquinolin-7-carbaldehyde. To a solution of (5)-5-(1-ethyl-3-(trifluoromethyl)-1H-pyrazol-4-yl)-7-(hydroxymethyl)-2-(1-(4-methoxypyridin-2-yl)ethyl)-3,4-dihydroisoquinolin-1(2H)-one (300 mg, 0.63 mmol) in 10 mL of DCM was added Dess-Martin periodinane (294

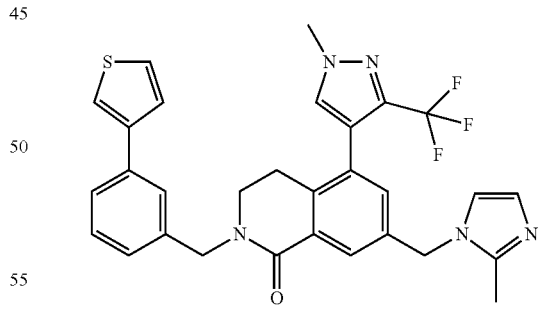

Example 231

7-((2-Methyl-1H-imidazol-1-yl)methyl)-5-(1-methyl-3-(trifluoromethyl)-1H-pyrazol-4-yl)-2-(3-(thiophen-3-yl)benzyl)-3,4-dihydroisoquinolin-1(2H)-one 2-(3-Bromobenzyl)-7-((2-methyl-1H-imidazol-1-yl)methyl)-5-(1-methyl-3-(trifluoromethyl)-1H-pyrazol-4-yl)-

3,4-dihydroisoquinolin-1(2H)-one (Example 207, 15.0 mg, 0.0269 mmol, 1.0 equiv.), K₂CO₃ (11.2 mg, 0.0808 mmol, 3.0 equiv.) and thiophene-3-boronic acid (6.9 mg, 0.0539 mmol, 2.0 equiv.) were dissolved in DMF (0.3 mL). The resulting mixture was degassed for 10 minutes and then Pd(dppf)Cl₂ (1.0 mg, 0.00135 mmol, 0.05 equiv.) was added. The reaction was heated to 95° C. for 2 h then cooled to room temperature. The reaction was quenched with water (5 mL) and extracted with EtOAc (3×5 mL). The combined organic layers were washed with brine (5 mL), dried (MgSO₄), filtered and concentrated. The residue was purified by reverse phase HPLC (Phenomenex Gemini C18, H₂O/CH₃CN gradient from 20-95% CH₃CN, 0.1% TFA) to yield the title compound (6.4 mg, 42% yield). LCMS: >95% 254 nm, R$_T$=1.523 min, MS (ES) 561.9 [M+H]⁺; ¹H NMR (400 MHz, chloroform-d) δ 8.09 (s, 1H), 7.54-7.51 (m, 2H), 7.45 (t, J=2.4 Hz, 1H), 7.39-7.34 (m, 3H), 7.27 (s, 1H), 7.24 (s, 1H), 6.94-6.91 (m, 2H), 6.85 (s, 1H), 5.10 (s, 2H), 4.82 (s, 2H), 3.96 (s, 3H), 3.43 (t, J=6.8 Hz, 2H), 2.72 (t, J=6.8 Hz, 2H), 2.35 (s, 3H).

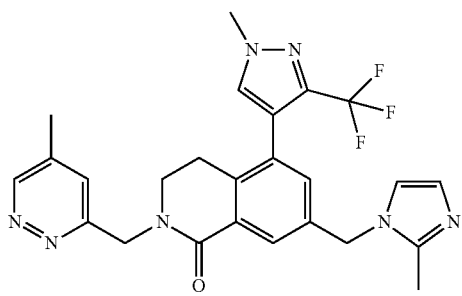 [SMILES: Cc1cnnc(CN2CCc3c(cc(Cn4ccnc4C)cc3-c3cn(C)nc3C(F)(F)F)C2=O)c1]

Example 232

7-((2-Methyl-1H-imidazol-1-yl)methyl)-5-(1-methyl-3-(trifluoromethyl)-1H-pyrazol-4-yl)-2-((5-methylpyridazin-3-yl)methyl)-3,4-dihydroisoquinolin-1(2H)-one The title compound (2.0 mg, 40% yield) was prepared following the procedures described in Example 8 using 7-(bromomethyl)-5-(1-methyl-3-(trifluoromethyl)-1H-pyrazol-4-yl)-2-((5-methylpyridazin-3-yl)methyl)-3,4-dihydroisoquinolin-1(2H)-one (Intermediate 99, 6.0 mg, 0.01 mmol, 1.0 equiv.) and 2-methyl-1H-imidazole (3.0 mg, 0.04 mmol, 3.0 equiv.). LC-MS: >95% 254 nm, R$_T$=1.167 min, MS (ES) 496.5 [M+H]⁺; ¹H NMR (400 MHz, Chloroform-d) δ 8.97 (d, J=2.0 Hz, 1H), 8.10 (d, J=1.8 Hz, 1H), 7.47-7.43 (m, 1H), 7.00 (d, J=1.8 Hz, 1H), 6.97 (d, J=1.2 Hz, 1H), 6.86 (d, J=1.3 Hz, 1H), 6.44 (s, 1H), 5.12 (s, 2H), 5.00 (s, 2H), 3.74 (t, J=6.6 Hz, 2H), 3.64 (s, 3H), 2.78 (t, J=6.6 Hz, 2H), 2.37 (s, 3H), 2.36 (s, 3H).

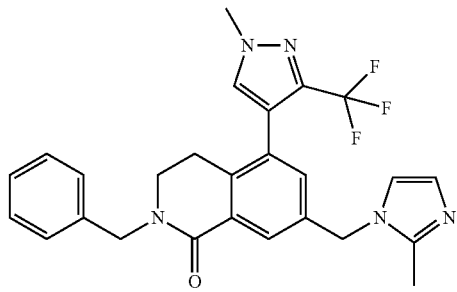 [SMILES: Cc1nccn1Cc1cc2c(c(-c3cn(C)nc3C(F)(F)F)c1)CCN(Cc1ccccc1)C2=O]

Example 233

2-Benzyl-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (5.3 mg, 38% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 12.0 mg, 0.06 mmol) and benzyl bromide. LC-MS: >95% 254 nm, R$_T$=1.337 min, MS (ES) 480.0 [M+H]⁺; ¹H NMR (400 MHz, chloroform-d) δ 8.08 (s, 1H), 7.33-7.27 (m, 6H), 6.94-6.91 (m, 2H), 6.86 (s, 1H), 5.09 (s, 2H), 4.78 (s, 2H), 3.97 (s, 3H), 3.40 (t, J=6.4 Hz, 2H), 2.71 (t, J=6.4 Hz, 2H), 2.34 (s, 3H).

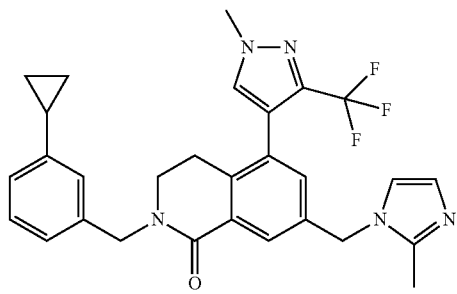 [SMILES: Cc1nccn1Cc1cc2c(c(-c3cn(C)nc3C(F)(F)F)c1)CCN(Cc1cccc(C3CC3)c1)C2=O]

Example 234

2-(3-Cyclopropylbenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (5.3 mg, 38% yield) was prepared from the procedure described in Example 231 using 2-(3-Bromobenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 207, 15.0 mg, 0.0269 mmol, 1.0 equiv.) and cyclopropylboronic acid (4.6 mg, 0.0536 mmol, 2.0 equiv.). LC-MS: >95% 254 nm, R$_T$=1.480 min, MS (ES) 520.0 [M+H]⁺; ¹H NMR (400 MHz, chloroform-d) δ 8.08 (s, 1H), 7.27 (d, J=5.6 Hz, 1H), 7.21 (t, J=7.6 Hz, 1H), 7.09 (d, J=7.6 Hz, 1H), 7.04 (s, 1H), 6.96-6.94 (m, 2H), 6.91 (s, 1H), 6.86 (d, J=0.8 Hz, 1H), 5.09 (s, 2H), 4.74 (s, 2H), 3.97 (s, 3H), 3.83 (t, J=6.4 Hz, 2H), 2.70 (t, J=6.4 Hz, 2H), 2.35 (s, 3H), 1.91-1.84 (m, 1H), 0.97-0.92 (m, 2H), 0.69-0.65 (m, 2H).

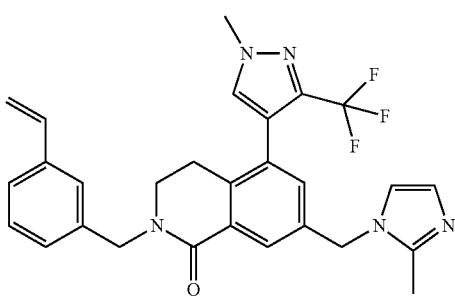 [SMILES: C=Cc1cccc(CN2CCc3c(cc(Cn4ccnc4C)cc3-c3cn(C)nc3C(F)(F)F)C2=O)c1]

Example 235

7-((2-Methyl-1H-imidazol-1-yl)methyl)-5-(1-methyl-3-(trifluoromethyl)-1H-pyrazol-4-yl)-2-(3-vinylbenzyl)-3,4-dihydroisoquinolin-1(2H)-one The title compound (5.5 mg, 40% yield) was prepared from the procedure described in Example 231 using 2-(3-Bromobenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (Example 207, 15.0 mg, 0.0269 mmol, 1.0 equiv.) and potassium vinyl trifluoroborate (7.2 mg, 0.0536 mmol, 2.0 equiv.). LC-MS: >95% 254 nm, $R_T$=1.434 min, MS (ES) 506.0 [M+H]$^+$; $^1$H NMR (400 MHz, chloroform-d) δ 8.08 (s, 1H), 7.52 (s, 1H), 7.33-7.26 (m, 3H), 7.22 (d, J=7.2 Hz, 1H), 6.94-6.92 (m, 2H), 6.86 (s, 1H), 6.73-6.66 (m, 1H), 5.76 (d, J=17.6 Hz, 1H), 5.30-5.24 (m, 1H), 5.09 (s, 2H), 4.77 (s, 2H), 3.97 (s, 3H), 3.40 (t, J=6.4 Hz, 2H), 2.71 (t, J=6.4 Hz, 2H), 2.35 (s, 3H).

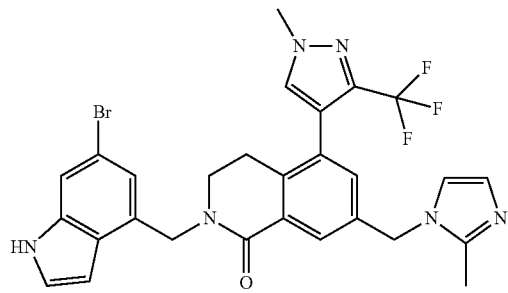 [SMILES: Cc1nccn1Cc1cc2c(c(-c3cn(C)nc3C(F)(F)F)c1)CCN(Cc1cc(Br)cc3[nH]ccc13)C2=O]

Example 236

2-((6-Bromo-1H-indol-4-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one Step A. Preparation of tert-butyl 6-bromo-44(7-((2-methyl-1H-imidazol-1-yl)methyl)-5-(1-methyl-3-(trifluoromethyl)-1H-pyrazol-4-yl)-1-oxo-3,4-dihydroisoquinolin-2(19)-yl)methyl)-1H-indole-1-carboxylate. The title compound (6.8 mg, 38% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 10.0 mg, 0.0257 mmol, 1.0 equiv.) and tert-butyl 6-bromo-4-(bromomethyl)-1H-indole-1-carboxylate (10.9 mg, 0.0283 mmol, 1.1 equiv.). LC-MS: >95% 254 nm, 1.774 min, MS (ES) 696.8 [M+H]$^+$.

Preparation of 2-((6-bromo-1H-indol-4-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one. tert-Butyl 6-bromo-4-((7-((2-methyl-1H-imidazol-1-yl)methyl)-5-(1-methyl-3-(trifluoromethyl)-1H-pyrazol-4-yl)-1-oxo-3,4-dihydroisoquinolin-2(1/)-yl)methyl)-1H-indole-1-carboxylate (6.8 mg, 0.00862 mmol, 1.0 equiv.) was dissolved in DCM (0.1 mL) and then TFA (0.1 mL) was added. The reaction was stirred for 1 h at room temperature and then concentrated. The residue was purified by reverse phase HPLC (Phenomenex Gemini C18, H$_2$O/CH$_3$CN gradient from 20-95% CH$_3$CN, 0.1% TFA) to yield the title compound (2.1 mg, 39% yield). LC-MS: >95% 254 nm, $R_T$=1.409 min, MS (ES) 596.8 [M+H]$^+$; $^1$H NMR (400 MHz, chloroform-d) δ 8.41 (s, 1H), 8.12 (s, 1H), 7.51 (s, 1H), 7.25 (s, 1H), 7.19-7.16 (m, 2H), 6.95 (s, 1H), 6.91 (s, 1H), 6.86 (s, 1H), 6.67 (s, 1H), 5.10 (s, 2H), 5.04 (s, 2H), 3.95 (s, 3H), 3.37 (t, J=6.4 Hz, 2H), 2.64 (t, J=6.4 Hz, 2H), 2.35 (s, 3H).

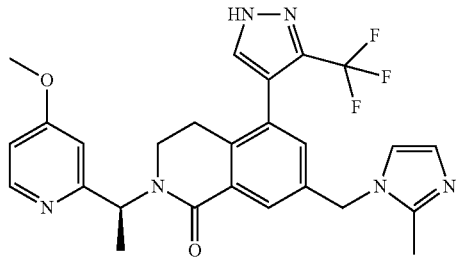 [SMILES: COc1ccnc([C@H](C)N2CCc3c(cc(Cn4ccnc4C)cc3-c3c[nH]nc3C(F)(F)F)C2=O)c1]

Example 237

(S)-2-(1-(4-methoxypyridin-2-yl)ethyl)-7-((2-methyl-1H-imidazol-1-yl)methyl)-5-(3-(trifluoromethyl)-1H-pyrazol-4-yl)-3,4-dihydroisoquinolin-1(2H)-one The title compound was prepared from the synthetic sequence described in Intermediate 16 substituting (5)-5-hydroxy-2-(1-(4-methoxypyridin-2-yl)ethyl)-7-((2-methyl-1H-imidazol-1-yl)methyl)-3,4-dihydroisoquinolin-1(2H)-one (Intermediate 100) and 4-(4,4,5,5-tetramethyl-1,3,2-dioxaborolan-2-yl)-3-(trifluoromethyl)-1H-pyrazole in Step A and B, respectively. $^1$H NMR (400 MHz, CDCl$_3$) δ 8.37 (d, J=5.8 Hz, 1H), 8.06 (d, J=1.8 Hz, 1H), 7.47 (s, 1H), 6.7 (d, J=1.1 Hz, 1H), 6.91-6.88 (m, 2H), 6.87 (d, J=1.1 Hz, 1H), 6.71-6.89 (m, 1H), 6.12 (q, J=7.4 Hz, 1H), 5.10 (s, 2H), 3.82 (s, 3H), 3.50-3.42 (m, 1H), 3.38-3.32 (m, 1H), 2.70-2.58 (m, 2H), 1.61 (d, J=7.4 Hz, 3H). LCMS Method 2: >95% 254 nm, $R_T$=0.92 min, MS (ES) 511.0 [M+H]$^+$.

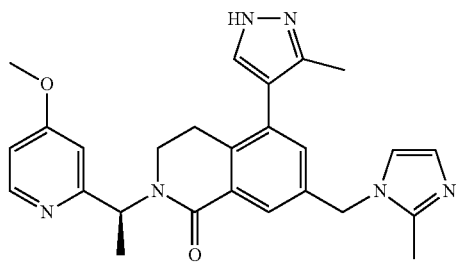 [SMILES: COc1ccnc([C@H](C)N2CCc3c(cc(Cn4ccnc4C)cc3-c3c[nH]nc3C)C2=O)c1]

Example 238

(S)-2-(1-(4-methoxypyridin-2-yl)ethyl)-7-((2-methyl-1H-imidazol-1-yl)methyl)-5-(3-methyl-1H-pyrazol-4-yl)-3,4-dihydroisoquinolin-1(2H)-one The title compound was prepared from the synthetic sequence described in Intermediate 16 substituting (S)-5-hydroxy-2-(1-(4-methoxypyridin-2-yl)ethyl)-7-((2-methyl-1H-imidazol-1-yl)methyl)-3,4-dihydroisoquinolin-1(2H)-one (Intermediate 100) and substituting 4-(4,4,5,5-tetramethyl-1,3,2-dioxaborolan-2-yl)-3-(methyl)-1H-pyrazole in Step A and B, respectively. LCMS Method 2: >95% 254 nm, $R_T$=1.800 min, MS (ES) 457.0 [M+H]$^+$.

Example 239

(S)-2-(1-(3-Cyclopropyl-1-methyl-1H-pyrazol-5-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (143 mg, 59% yield) was prepared from the procedure described in Example 8 using (S)-7-(bromomethyl)-2-(1-(3-cyclopropyl-1-methyl-1H-pyrazol-5-yl)ethyl)-5-(1-methyl-3-(trifluoromethyl)-1H-pyrazol-4-yl)-3,4-dihydroisoquinolin-1(2H)-one (Intermediate 101) and 2-methyl-1H-imidazole. LC-MS: >95% 254 nm, $R_T$=1.273 min, MS (ES) 538.0 [M+H]$^+$; $^1$H NMR (400 MHz, chloroform-d) δ 8.03 (d, J=2.0 Hz, 1H), 6.94 (d, J=2.0 Hz, 2H), 6.86 (d, J=1.2 Hz, 1H), 6.10 (q, J=7.2 Hz, 1H), 5.92 (s, 1H), 5.29 (s, 1H), 5.09 (d, J=1.2 Hz, 2H), 3.97 (s, 3H), 3.68 (s, 3H), 3.32-3.26 (m, 1H), 3.08-3.02 (m, 1H), 2.65-2.61 (m, 2H), 2.34 (s, 3H), 1.91-1.84 (m, 1H), 1.51 (d, J=7.2 Hz, 3H), 0.91-0.86 (m, 2H), 0.73-0.67 (m, 2H); $^{19}$F NMR (376 MHz, Chloroform-d) δ -60.14.

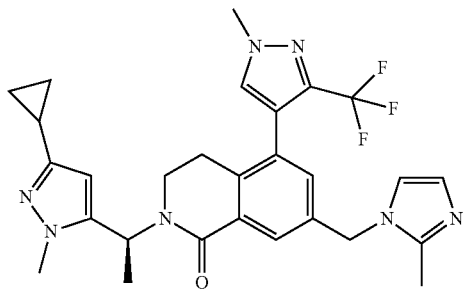 [SMILES: Cc1nccn1Cc1cc2c(c(-c3cn(C)nc3C(F)(F)F)c1)CCN([C@@H](C)c1cc(C3CC3)nn1C)C2=O]

Example 240

2-((5-Bromo-6-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (18.9 mg, 43% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 30.0 mg, 0.08 mmol, 1.0 equiv.) and 3-bromo-5-(bromomethyl)-2-methylpyridine (20.0 mg, 0.08 mmol, 1.0 equiv.). LC-MS: >95% 254 nm, $R_T$=1.281 min, MS (ES) 574.4 [M+H]$^+$.

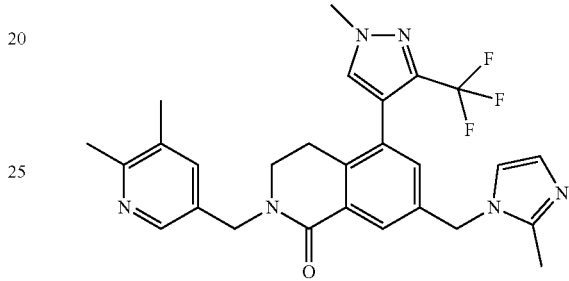

Example 241

2-((5,6-Dimethylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (8.5 mg, 51% yield) was prepared from the procedure described in Example 223 using 2-((5-bromo-6-methylpyridin-3-yl)methyl)-7-(2-methyl-1H-imidazol-1-yl)methyl)-5-(1-methyl-3-(trifluoromethyl)-1H-pyrazol-4-yl)-3,4-dihydroisoquinolin-1(2H)-one (Example 240, 18.9 mg, 0.03 mmol, 1.0 equiv.) and methylboronic acid (9.9 mg, 0.17 mmol, 5.0 equiv.). The reaction mixture was stirred at 80° C. for 12 h. $^1$H NMR (400 MHz, Chloroform-d) δ 8.25 (s, 1H), 8.05 (s, 1H), 7.43 (s, 1H), 7.27 (s, 1H), 6.93 (s, 1H), 6.92 (s, 1H), 6.85 (s, 1H), 5.09 (s, 2H), 4.70 (s, 2H), 3.97 (s, 3H), 3.39 (t, J=6.5 Hz, 2H), 2.70 (t, J=6.5 Hz, 2H), 2.47 (s, 3H), 2.34 (s, 3H), 2.25 (s, 3H); LC-MS: >95% 254 nm, $R_T$=0.962, MS (ES) 509.2 [M+H]$^+$.

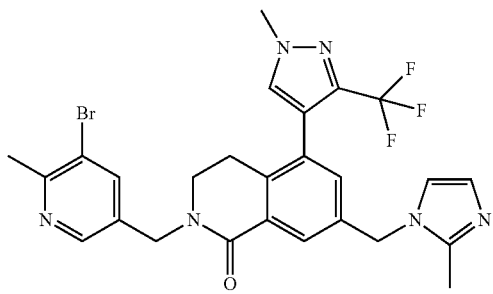 [SMILES: Cc1ncc(CN2CCc3c(cc(Cn4ccnc4C)cc3-c3cn(C)nc3C(F)(F)F)C2=O)cc1Br]

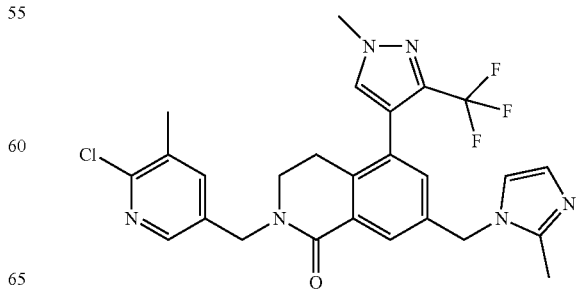

Example 242

2-((6-Chloro-5-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (26.0 mg, 96% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20.0 mg, 0.05 mmol, 1.0 equiv.) and 5-(bromomethyl)-2-chloro-3-methylpyridine (12.0 mg, 0.05 mmol, 1.1 equiv.). LC-MS: >95% 254 nm, $R_T$=1.304 min, MS (ES) 530.0 [M+H]$^+$; $^1$H NMR (400 MHz, Chloroform-d) δ 8.17 (d, J=1.8 Hz, 1H), 8.03 (s, 1H), 7.61-7.55 (m, 1H), 7.28 (s, 1H), 6.93 (s, 2H), 6.86-6.83 (m, 1H), 5.08 (s, 2H), 4.70 (s, 2H), 3.97 (s, 3H), 3.41 (t, J=6.6 Hz, 2H), 2.73 (t, J=6.5 Hz, 2H), 2.35 (s, 3H), 2.33 (s, 3H).

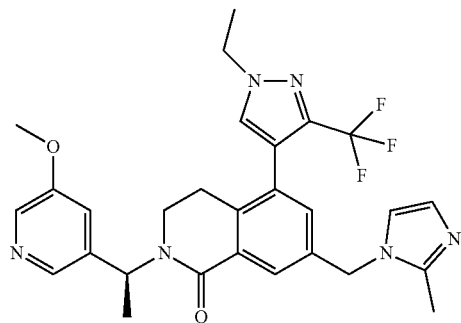 [SMILES: CCn1cc(-c2cc(Cn3ccnc3C)cc3c2CCN([C@@H](C)c2cncc(OC)c2)C3=O)c(C(F)(F)F)n1]

Example 243

(S)-5-(1-Ethyl-3-(trifluoromethyl)-1H-pyrazol-4-yl)-2-(1-(5-methoxypyridin-3-yl)ethyl)-7-((2-methyl-1H-imidazol-1-yl)methyl)-3,4-dihydroisoquinolin-1(2H)-one The title compound (13.4 mg, 28% yield) was prepared from the procedure described in Example 8 using (S)-7-(bromomethyl)-5-(1-ethyl-3-(trifluoromethyl)-1H-pyrazol-4-yl)-2-(1-(5-methoxypyridin-3-yl)ethyl)-3,4-dihydroisoquinolin-1(2H)-one (Intermediate 102, 47.8 mg, 0.09 mmol, 1.0 equiv.) and 2-methyl-1H-imidazole (21.9 mg, 0.27 mmol, 3.0 equiv.). LC-MS: >95% 254 nm, $R_T$=1.180 min, MS (ES) 539.6 [M+H]$^+$; $^1$H NMR (400 MHz, Chloroform-d) δ 8.25 (d, J=1.5 Hz, 1H), 8.23 (d, J=2.7 Hz, 1H), 8.05 (d, J=1.8 Hz, 1H), 7.29 (s, 1H), 7.17 (t, J=1.9 Hz, 1H), 6.95 (d, J=1.7 Hz, 1H), 6.94 (d, J=1.2 Hz, 1H), 6.86 (d, J=1.3 Hz, 1H), 6.21 (q, J=7.0 Hz, 1H), 5.09 (s, 2H), 4.22 (q, J=7.3 Hz, 2H), 3.84 (s, 3H), 3.34 (m, 1H), 3.06 (m, 1H), 2.63 (m, 2H), 2.34 (s, 3H), 1.60 (d, J=7.1 Hz, 3H), 1.53 (t, J=7.3 Hz, 3H).

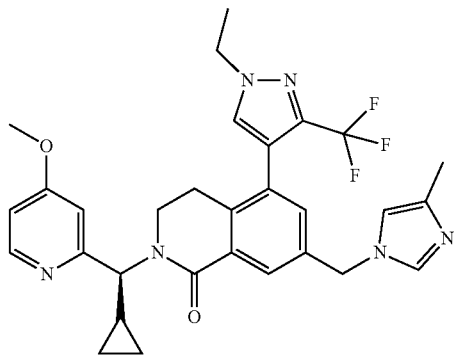 [SMILES: CCn1cc(-c2cc(Cn3cnc(C)c3)cc3c2CCN([C@H](c2cc(OC)ccn2)C2CC2)C3=O)c(C(F)(F)F)n1]

Example 244

(S)-2-(cyclopropyl(4-methoxypyridin-2-yl)methyl)-5-(1-ethyl-3-(trifluoromethyl)-1H-pyrazol-4-yl)-7-((4-methyl-1H-imidazol-1-yl)methyl)-3,4-dihydroisoquinolin-1(2H)-one The title compound (24 mg, 0.042 mmol) was prepared following the procedures described in Example 8 using (S)-7-(bromomethyl)-2-(cyclopropyl(4-methoxypyridin-2-yl)methyl)-5-(1-ethyl-3-(trifluoromethyl)-1H-pyrazol-4-yl)-3,4-dihydroisoquinolin-1(2H)-one (Intermediate 97) and 4-methyl-1H-imidazole. LC-MS Method 1: >95% 254 nm, Rt=1.19 min, MS (ES) 565.05 [M+H]$^+$.

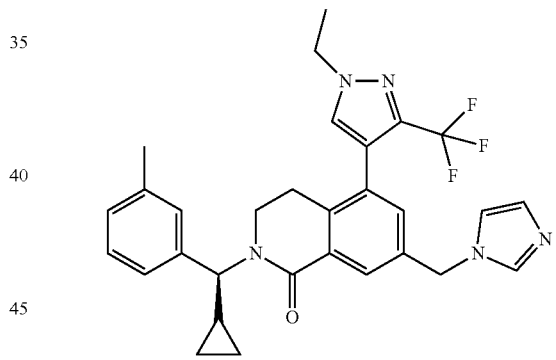

Example 245

(S)-7-((1H-imidazol-1-yl)methyl)-2-(cyclopropyl(4-methylpyridin-2-yl)methyl)-5-(1-ethyl-3-(trifluoromethyl)-1H-pyrazol-4-yl)-3,4-dihydroisoquinolin-1(2H)-one The title compound (7.8 mg, 27% yield) was prepared following the procedures described in Example 8 using (S)-7-(bromomethyl)-2-(cyclopropyl(4-methylpyridin-2-yl)methyl)-5-(1-ethyl-3-(trifluoromethyl)-1H-pyrazol-4-yl)-3,4-dihydroisoquinolin-1(2H)-one (Intermediate 89) and imidazole. LC-MS: >95% 254 nm, $R_T$=1.306 min, MS (ES) 535.0 [M+H]$^+$. $^1$H NMR (400 MHz, chloroform-d) δ 8.41 (d, J=5.2 Hz, 1H), 8.06 (d, J=2.0 Hz, 1H), 7.53 (s, 1H), 7.31 (s, 1H), 7.24 (s, 1H), 7.08 (d, J=2.4 Hz, 2H), 7.01 (d, J=4.4 Hz, 1H), 6.91 (s, 1H), 5.13 (s, 2H), 5.07 (d, J=10.0 Hz, 1H), 4.25 (q, J=7.2 Hz, 2H), 3.76-3.63 (m, 2H), 2.76-2.65 (m, 2H), 2.33 (s, 3H), 1.66-1.62 (m, 1H), 1.55 (t, J=7.2 Hz, 3H), 0.80-0.75 (m, 1H), 0.63-0.59 (m, 1H), 0.54-0.51 (m, 2H).

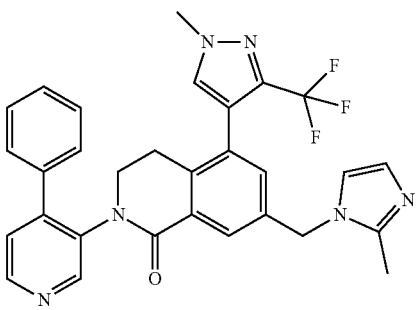 [SMILES: Cc1nccn1Cc1cc2c(c(-c3cn(C)nc3C(F)(F)F)c1)CCN(c1cnccc1-c1ccccc1)C2=O]

Example 246

7-((2-Methyl-1H-imidazol-1-yl)methyl)-5-(1-methyl-3-(trifluoromethyl)-1H-pyrazol-4-yl)-2-(4-phenylpyridin-3-yl)-3,4-dihydroisoquinolin-1(2H)-one To a solution of 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 15.0 mg, 38.5 μmol, 1 equiv) in DMF (0.5 mL) was added 3-bromo-4-phenylpyridine (18.0 mg, 77.0 μmol, 2 equiv), CuI (9.4 mg, 49.4 μmol, 1.3 equiv), and K$_2$CO$_3$ (10.6 mg, 77.0 μmol, 2 equiv). The mixture was stirred at 150° C. for 16 h. The mixture was cooled to ambient temperature, diluted with EtOAc and washed with saturated aqueous NH$_4$Cl. The organic layer dried (Na$_2$SO$_4$) and concentrated. The residue was purified by flash chromatography (Combi-flash Rf, DCM/MeOH=0-10% gradient) to afford the title compound (8.0 mg, 0.039 mmol, 38% yield). $^1$H NMR (400 MHz, Chloroform-d) δ 8.64 (s, 1H), 8.63 (s, 1H), 8.08 (d, J=1.6 Hz, 1H), 7.40 (m, 6H), 6.93 (m, 3H), 5.12 (s, 2H), 3.99 (s, 3H), 3.60 (m, 1H), 3.19 (m, 1H), 2.54 (m, 1H), 2.37 (s, 3H), 2.34 (m, 1H); LCMS: >95% 254 nm, MS (ES) 543.5 [M+H]$^+$.

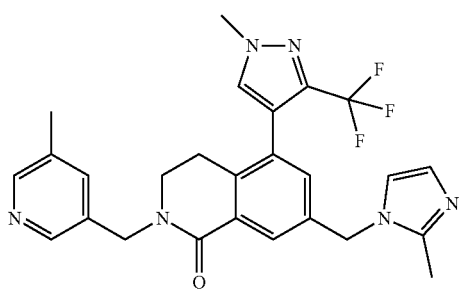 [SMILES: Cc1cncc(CN2CCc3c(cc(Cn4ccnc4C)cc3-c3cn(C)nc3C(F)(F)F)C2=O)c1]

Example 247

7-((2-Methyl-1H-imidazol-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one The title compound (3.7 mg, 29% yield) was prepared from the procedure described in Example 167 using 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87) and 2-(bromomethyl)-4-methylpyridine (5.2 mg, 0.0282 mmol, 1.1 equiv.). $^1$H NMR (400 MHz, chloroform-d) δ 8.38 (d, J=5.2 Hz, 1H), 8.07 (d, J=1.6 Hz, 1H), 7.33 (s, 1H), 7.20 (s, 1H), 7.08 (s, 1H), 7.02 (d, J=4.8 Hz, 1H), 6.96 (d, J=1.6 Hz, 1H), 6.93 (d, J=1.6 Hz, 1H), 5.14 (s, 2H), 4.84 (s, 2H), 4.00 (s, 3H), 3.59 (t, J=6.4 Hz, 2H), 2.78 (t, J=6.4 Hz, 2H), 2.52 (s, 3H), 2.33 (s, 3H); LCMS: >95% 254 nm, R$_T$=1.091 min, MS (ES) 495.0 [M+H]$^+$.

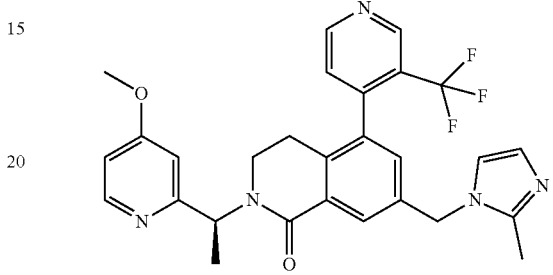

Example 248

(S)-2-(1-(4-Methoxypyridin-2-yl)ethyl)-7-((2-methyl-1H-imidazol-1-yl)methyl)-5-(3-(trifluoromethyl)pyridin-4-yl)-3,4-dihydroisoquinolin-1(2H)-one The title compound was prepared from the synthetic sequence described in Intermediate 16 substituting (5)-5-hydroxy-2-(1-(4-methoxypyridin-2-yl)ethyl)-7-((2-methyl-1H-imidazol-1-yl)methyl)-3,4-dihydroisoquinolin-1(2H)-one (Intermediate 100) and (3-(trifluoromethyl)pyridin-4-yl)boronic acid in Steps A and B, respectively. LCMS Method 2: >95% 254 nm, R$_T$=1.07 min, MS (ES) 522.1 [M+H]$^+$.

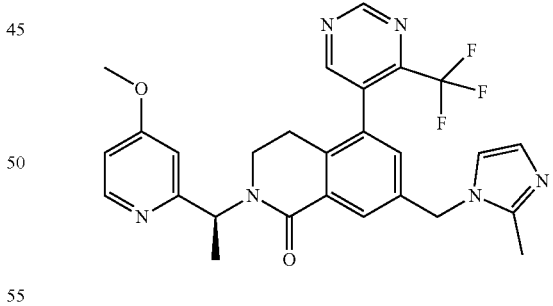

Example 249

(S)-2-(1-(4-Methoxypyridin-2-yl)ethyl)-7-((2-methyl-1H-imidazol-1-yl)methyl)-5-(4-(trifluoromethyl)pyrimidin-5-yl)-3,4-dihydroisoquinolin-1(2H)-one The title compound was prepared from the synthetic sequence described in Intermediate 16 substituting (S)-5-hydroxy-2-(1-(4-methoxypyridin-2-yl)ethyl)-7-((2-methyl-1H-imidazol-1-yl)methyl)-3,4-dihydroisoquinolin-1(2H)- one (Intermediate 100) and 5-(4,4,5,5-tetramethyl-1,3,2-dioxaborolan-2-yl)-4-(trifluoromethyl)pyrimidine in Steps A and B, respectively. LCMS Method 2: >95% 254 nm, $R_T$=1.03 min, MS (ES) 523.0 [M+H]$^+$.

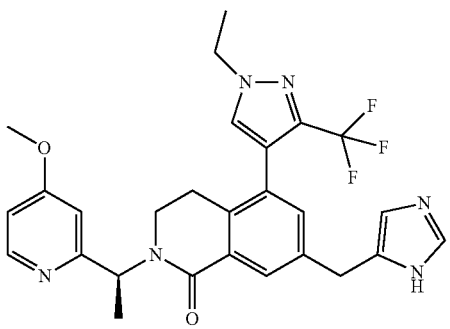 [SMILES: CCn1cc(-c2cc(Cc3cnc[nH]3)cc3c2CCN([C@@H](C)c2cc(OC)ccn2)C3=O)c(C(F)(F)F)n1]

Example 250

(S)-7-((1H-Imidazol-5-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one The title compound was prepared following the procedures described in Example 230 substituting 5-iodo-1-trityl-1H-imidazole for 2-iodo-1-trityl-1H-imidazole in Step B. LC-MS Method 2: >95% 254 nm, $R_T$=1.17 min, MS (ES) 525.0 [M+H]$^+$.

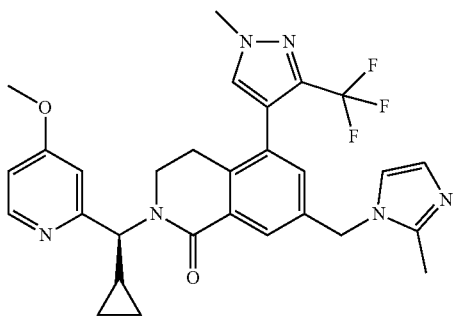 [SMILES: COc1ccnc([C@H](C2CC2)N2CCc3c(cc(Cn4ccnc4C)cc3-c3cn(C)nc3C(F)(F)F)C2=O)c1]

Example 251

(S)-2-(Cyclopropyl(4-methoxypyridin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound was prepared from the procedure described in Example 8 using (S)-7-(bromomethyl)-2-(cyclopropyl (4-methoxypyridin-2-yl)methyl)-5-(1-methyl-3-(trifluoromethyl)-1H-pyrazol-4-yl)-3,4-dihydroisoquinolin-1(2H)-one (Intermediate 103) and 2-methyl-1H-imidazole. LC-MS Method 1: >95% 254 nm, $R_T$=0.83 min, MS (ES) 551.5 [M+H]$^+$.

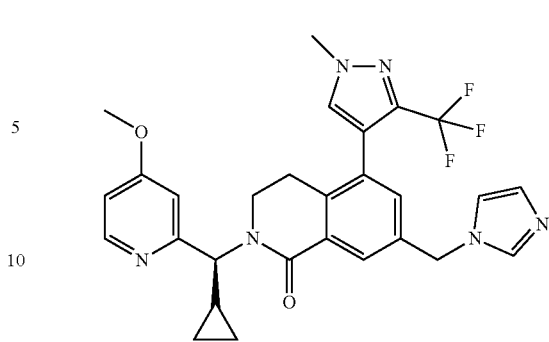

Example 252

(S)-7-((1H-Imidazol-1-yl)methyl)-2-(cyclopropyl(4-methoxypyridin-2-yl)methyl)-5-(1-methyl-3-(trifluoromethyl)-1H-pyrazol-4-yl)-3,4-dihydroisoquinolin-1(2H)-one The title compound was prepared from the procedure described in Example 8 using (S)-7-(bromomethyl)-2-(cyclopropyl (4-methoxypyridin-2-yl)methyl)-5-(1-methyl-3-(trifluoromethyl)-1H-pyrazol-4-yl)-3,4-dihydroisoquinolin-1(2H)-one (Intermediate 103) and imidazole. LC-MS Method 1: >95% 254 nm, $R_T$=0.85 min, MS (ES) 537.6 [M+H]$^+$.

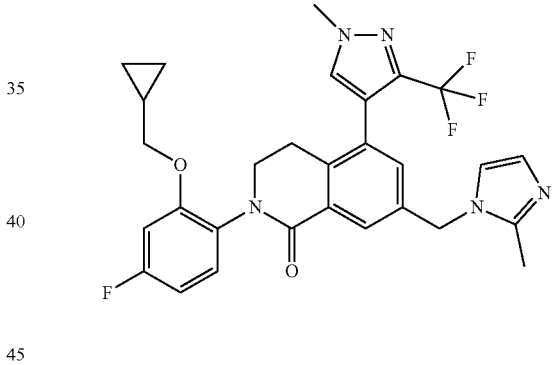

Example 253

2-(2-(Cyclopropylmethoxy)-4-fluorophenyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one To a solution of 7-((2-methyl-1H-imidazol-1-yl)methyl)-5-(1-methyl-3-(trifluoromethyl)-1H-pyrazol-4-yl)-3,4-dihydroisoquinolin-1(2H)-one (Intermediate 87, 20 mg, 0.051 mmol, 1 equiv) in 1,4-dioxane (0.5 mL) was added 2-(cyclopropylmethoxy)-4-fluoro-1-iodobenzene (45 mg, 0.15 mmol, 3 equiv), CuI (1.0 mg, 0.005 mmol, 0.1 equiv), and N,N'-dimethyl-1,2-cyclohexanediamine (0.73 mg, 0.005 mmol, 0.1 equiv). The mixture was stirred at 110° C. for 24 h. The mixture was cooled to ambient temperature, diluted with DCM and washed with saturated aqueous NH$_4$Cl. The organic layer was dried (MgSO$_4$) and concentrated. The residue was purified by reverse phase HPLC (Phenomenex Gemini C18, H$_2$O/CH$_3$CN gradient from 20-95% CH$_3$CN, 0.1% TFA) to yield the title compound (1.9 mg, 6.7% yield). LCMS: >95% 254 nm, MS (ES) 554.3 [M+H]$^+$.

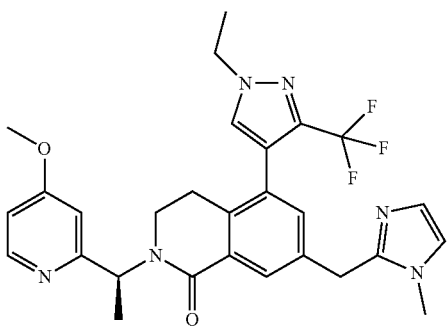 [SMILES: CCn1cc(-c2cc(Cc3nccn3C)cc3c2CCN([C@@H](C)c2cc(OC)ccn2)C3=O)c(C(F)(F)F)n1]

Example 254

(S)-5-(1-Ethyl-3-(trifluoromethyl)-1H-pyrazol-4-yl)-2-(1-(4-methoxypyridin-2-yl)ethyl)-7-((1-methyl-1H-imidazol-2-yl)methyl)-3,4-dihydroisoquinolin-1(2H)-one The title compound was prepared following the procedures described in Example 230 substituting 2-iodo-1-methyl-imidazole for 2-iodo-1-trityl-1H-imidazole in Step B. LCMS Method 2>95% 254 nm, $R_T$=1.17 min, MS (ES) 539.0 [M+H]$^+$.

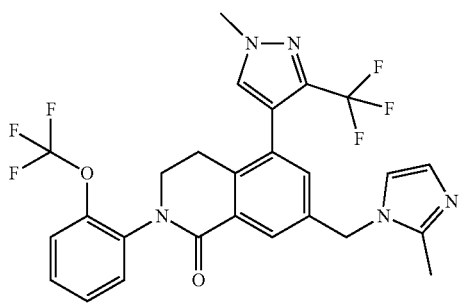 [SMILES: Cc1nccn1Cc1cc2c(c(-c3cn(C)nc3C(F)(F)F)c1)CCN(c1ccccc1OC(F)(F)F)C2=O]

Example 255

7-((2-Methyl-1H-imidazol-1-yl)methyl)-5-(1-methyl-3-(trifluoromethyl)-1H-pyrazol-4-yl)-2-(2-(trifluoromethoxy)phenyl)-3,4-dihydroisoquinolin-1(2H)-one The title compound (2.7 mg, 9.6% yield) was prepared from the procedure described in Example 253 substituting 1-iodo-2-(trifluoromethoxy)benzene (44 mg, 0.15 mmol, 3 equiv) for 2-(cyclopropylmethoxy)-4-fluoro-1-iodobenzene. LCMS: >95% 254 nm, MS (ES) 550.3 [M+H]$^+$.

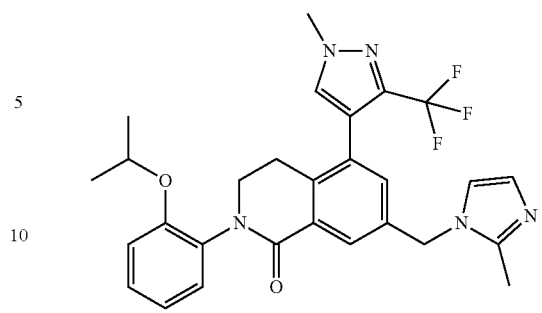

Example 256

2-(2-Isopropoxyphenyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one The title compound (1.8 mg, 6.7% yield) was prepared from the procedure described in Example 253 substituting 1-iodo-2-(isopropoxy)benzene (40 mg, 0.15 mmol, 3 equiv) for 2-(cyclopropylmethoxy)-4-fluoro-1-iodobenzene. LCMS: >95% 254 nm, MS (ES) 524.3 [M+H]$^+$.

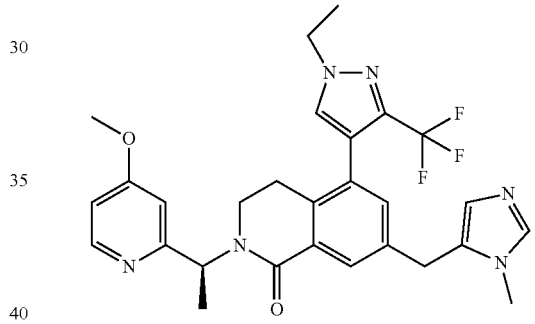

Example 257

(S)-5-(1-Ethyl-3-(trifluoromethyl)-1H-pyrazol-4-yl)-2-(1-(4-methoxypyridin-2-yl)ethyl)-7-((1-methyl-1H-imidazol-5-yl)methyl)-3,4-dihydroisoquinolin-1(2H)-one The title compound was prepared following the procedures described in Example 230 substituting 5-iodo-1-methyl-imidazole for 2-iodo-1-trityl-1H-imidazole in Step B. LC-MS Method 2: >95% 254 nm, $R_T$=1.19 min, MS (ES) 539.0 [M+H]+.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The routes by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizawa, 2007) and 10% of all acute leukemia cases (Marschalek, 2011). MLL leukemia patients have a poor prognosis with overall 5-year survival ratio around 35% (Dimartino, 1999; Pui, 2003; Tomizawa, 2007).

MLL is composited of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of Drosophila trithorax (Trx) (Thachuk, 1992). Wild type MLL binds to regulatory regions of homeox (HOX) genes (Milne, 2005) through the amino terminal fragment while the catalytic C-terminal domain catalyzes the Histone 3 lysine 4 (H3K4) methylation via interaction with WDR5 and up regulates target genes transcription (Nakamura, 2002; Yokoyama, 2004; Milne, 2002). Wild type MLL in conjunction with WDR5 is required for maintenance HOX genes expression and is widely expressed not only during embryo development but also in adult tissues including myeloid and lymphoid cells (Butler, 1997; Yu, 1998). Reciprocal translocations of MLL gene result inframe fusion of 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005). The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct dysregulated target gene expression patterns and downstream events (Slany, 2009). Clinical studies reveal that MLL of different chromosomal translocations are associated with different prognosis and are treated differently under current protocols (Tamai, 2010; Balgobind, 2011; Pigazzi, 2011).

Intrinsic HMT activity of MLL1 is extremely low and requires a complex assembly of WDR5, RbBP5, ASH2L, and DPY30 protein partners for effective H3K4 trimethylation, so called WRAD complex. The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, et al. Molecular Cell, 2014, 53, 247-261.) In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. The molecules described herein will target this interaction and could provide an attractive therapeutic approach to develop novel drugs for leukemias with translocations of MLL gene and other leukemias with upregulation of target genes. It also appreciated that WDR5 has been implicated in other cancer types and may utilize the WIN-site for other chromatin regulatory complexes outside and/or overlapping with WRAD complex. As such the WIN-site inhibitors described herein may have utility in multiple cancer types through mechanisms of action involving both direct competitive WIN-site antagonism, or through allosteric inhibition of higher complexes wherein WDR5 is dependent for their proliferative activity and tumor formation. Examples include breast cancer (Dai, X. et al. PLoS One, 2015), MYC-driven tumor types (Thomas, et al. Molecular Cell, 2015), bladder cancer (Chen, X. et al. Nature, Scientific Reports, 2015), neuroblastoma (Sun, Y. et al. Cancer Research, 2015), and pancreatic cancer (Carugo, A. et al. Cell Reports, 2016).

The disclosed compounds and compositions may be used in methods for treatment of MLL related cancers. The methods of treatment may comprise administering to a subject in need of such treatment a composition comprising a therapeutically effective amount of the compound of formula (I).

In one aspect, disclosed is a method of treating cancer, the method comprising administration of a therapeutically effective amount of a compound of formula (I), or a pharmaceutically acceptable salt thereof to a subject in need thereof.

In certain embodiments, the cancer being treated is associated with dysfunction of MLL.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MLL1, the method comprising administration of a therapeutically effective amount of a compound of formula (I), or a pharmaceutically acceptable salt thereof to a subject in need thereof.

The compositions can be administered to a subject in need thereof to bind WDR5 and modulate MLL, to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL1.

The compositions may be useful for treating certain cancers in humans and animals related to MLL dysfunction. Treatment of such cancers can be effected by modulating MLL1 in a subject, by administering a compound or composition of the invention, either alone or in combination with another active agent as part of a therapeutic regimen to a subject in need thereof.

Disruption of the interaction between WDR5 and its binding partners (such as MLL1) can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof can mediate reduction, clearance or prevention of additional growth of tumor cells by disrupting the ability of MLL1, another transcription factor, or chromatin to associate with WDR5, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of different anti-cancer drugs such as chemotherapeutics, anti-tumor agents, and anti-proliferative agents.

Further, the compound of formula (I) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, Ca²⁺ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, vitamin D3 analogs, □-radiation, DOT1L inhibitors, agents targeting epigenetic mechanisms, or an additional chemotherapeutic agent such as N—Ac-Sar-Gly-Val-D-alloIle-Thr-Nva-Ile-Arg-Pro-NHCH2CH3 or a salt thereof, actinomycin D, AG13736, 17-allylamino-17-demethoxygeldanamycin, 9-aminocamptothecin, N-(4-(3-amino-1H-indazol-4-yl)phenyl}-N-(2-fluoro-5-methylphenyl)urea or a salt thereof, N-(4-(4-aminothieno[2,3-d]pyrimidin-5-yl)phenyl-N-(2-fluoro-5-(trifluoromethyl)phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN518, MLN4924, MS-275, mycophenolic acid, mitomycin C, nitrosoureas, oprelvekin, oxaliplatin, paclitaxel, PARP inhibitors (e.g., rucaparib, niraparib, olaparib, iniparib, talazoparib, and veliparib), PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

The in vitro modulation of WDR5 protein was determined as follows.
MLL Peptide Binding Assay
General
Provided compounds of the present invention can be demonstrated to compete for binding with fluorescently labeled peptides derived from relevant MLL protein.
Time Resolved-Fluorescence Energy Transfer Competition Assay
A Time-Resolved Fluorescence Resonance Energy Transfer (TR-FRET) assay that measures the displacement of the 1 Omer-Thr-FAM probe in response to compound treatment was performed for compounds wherein the $IC_{50}$ from FPA assay using 10 mer-Thr-FAM was below the lower assay $IC_{50}$ limit ~1 nM. Excess 10 mer-Thr-FAM probe was utilized with His-tagged WDR5 in conjunction with a commercial anti-His antibody containing a Terbium label. The LanthaScreen™ Elite Tb-anti-HIS Antibody from ThermoFisher Scientific was used for this purpose. This Tb-anti-HIS has an excitation/emission of 340 nm and 490 nm, respectively. The 10mer-Thr-FAM probe when bound to WDR5 will undergo a FRET interaction with the Tb-anti-HIS and emit at 520 nm. The ratio of the 520 and 495 signals are then utilized to generate a dose-response curve to calculate an $IC_{50}$ value. By virtue of FRET there is little to no background fluorescence interference from 10 mer-Thr-FAM probe allowing an excess of the probe to be used permitting an increase in the lower limit of the calculated $K_i$ when testing against highly potent inhibitors with $K_i \ll 1$ nM. WDR5-His Tag (Δ23, residues 24-334) is expressed and purified in our lab in sufficient quantities for screening. 10 mer-Thr-FAM peptide is used at 150 nM. WDR5-His tag protein is used at 2 nM. A source plate is prepared using an Echo Liquid Handler, which distributes the compounds to the assay plate (white, flat-bottom; OptiPlate) in a 10-point, 5-fold dilution schemes with a top concentration of 5 μM, in a final volume of 20 μL. A final target (WDR5)/Tb-Ab concentration of 2 nM/1 nM is dispensed from appropriate stock solutions, respectively. The final DMSO concentration in each well of the assay plate is 1% or lower. The plate is covered, shielded from light, and incubated for 60 minutes at room temperature with rocking. 10 mer-Thr-FAM and Anti-His terbium antibody fluorescence is then measured on a Biotek Cytation 3 at excitation wavelength of 340 nm, and emission wavelengths of 495 nm and 520 nm. Working buffer conditions contain 1× Phosphate Buffered Saline, 300 mM NaCl, 0.5 mM TCEP, 0.1% CHAPS, at pH 7.2. TR-FRET signal is plotted and $IC_{50}$ and $K_i$ values are calculated according to the formula of Wang Z. FEBS Lett (1996) 3, 245.

$$K_i = [I]_{50}/([L]_{50}/K_d + [P]_0/K_d + 1)$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, K$_d$ represents the dissociation constant of the FITC-MLL or 10 mer-Thr-FAM probe for WDR5. Total fluorescence is also measured, to rule out compounds that are inherently fluorescent or able to act as quenchers in the assay.

TR-FRET Binding Assay

TABLE 2

K$_i$ for Exemplified Compounds for Inhibition of WDR5 by TR-FRET assay

| Example | K$_i$ (nM) |
|---|---|
| 1 | 7.3 |
| 2 | 14 |
| 3 | 28 |
| 4 | 49 |
| 5 | 5.9 |
| 6 | <0.05 |
| 7 | 0.19 |
| 8 | <0.05 |
| 9 | 0.19 |
| 10 | 5.0 |
| 11 | <0.05 |
| 12 | <0.05 |
| 13 | <0.05 |
| 14 | 0.29 |
| 15 | <0.05 |
| 16 | 0.086 |
| 17 | <0.05 |
| 18 | 0.41 |
| 19 | 9.7 |
| 20 | 0.089 |
| 21 | 0.034 |
| 22 | 0.061 |
| 23 | 4.1 |
| 24 | 0.056 |
| 25 | 6.1 |
| 26 | 22 |
| 27 | <0.05 |
| 28 | 0.02 |
| 29 | <0.05 |
| 30 | <0.05 |
| 31 | <0.05 |
| 32 | 0.060 |
| 33 | 0.065 |
| 34 | <0.05 |
| 35 | <0.05 |
| 36 | <0.05 |
| 37 | <0.05 |
| 38 | <0.05 |
| 39 | <0.05 |
| 40 | <0.05 |
| 41 | <0.05 |
| 42 | <0.05 |
| 43 | <0.05 |
| 44 | <0.05 |
| 45 | <0.05 |
| 46 | <0.05 |
| 47 | <0.05 |
| 48 | <0.05 |
| 49 | 1.1 |
| 50 | 1.0 |
| 51 | <0.05 |
| 52 | <0.05 |
| 53 | <0.05 |
| 54 | 0.57 |
| 55 | <0.05 |
| 56 | 0.050 |
| 57 | <0.05 |
| 58 | <0.05 |
| 59 | 0.14 |
| 60 | 0.03 |
| 61 | <0.05 |
| 62 | <0.05 |
| 63 | <0.05 |
| 64 | 2.0 |
| 65 | <0.05 |
| 66 | <0.05 |
| 67 | <0.05 |
| 68 | 0.056 |
| 69 | 0.55 |
| 70 | <0.05 |
| 71 | <0.05 |
| 72 | <0.05 |
| 73 | 0.37 |
| 74 | <0.05 |
| 75 | 0.63 |
| 76 | 0.16 |
| 77 | <0.05 |
| 78 | 0.21 |
| 79 | 0.04 |
| 80 | <0.05 |
| 81 | <0.05 |
| 82 | <0.05 |
| 83 | <0.05 |
| 84 | <0.05 |
| 85 | 0.065 |
| 86 | 1.8 |
| 87 | 0.77 |
| 88 | <0.05 |
| 89 | <0.05 |
| 90 | <0.05 |
| 91 | <0.05 |
| 92 | 1.1 |
| 93 | <0.05 |
| 94 | <0.05 |
| 95 | <0.05 |
| 96 | <0.05 |
| 97 | 0.086 |
| 98 | <0.05 |
| 99 | <0.05 |
| 100 | <0.05 |
| 101 | <0.05 |
| 102 | 2.6 |
| 103 | 17 |
| 104 | <0.05 |
| 105 | <0.05 |
| 106 | <0.05 |
| 107 | 0.11 |
| 108 | <0.05 |
| 109 | <0.05 |
| 110 | 0.55 |
| 111 | 1.7 |
| 112 | <0.020 |
| 113 | 0.45 |
| 114 | 0.28 |
| 115 | 13 |
| 116 | 0.25 |
| 117 | 3.1 |
| 118 | 0.064 |
| 119 | 0.79 |
| 120 | 0.22 |
| 121 | 0.14 |
| 122 | <0.05 |
| 123 | <0.05 |
| 124 | 0.13 |
| 125 | 5.4 |
| 126 | <0.05 |
| 127 | 0.098 |
| 128 | <0.05 |
| 129 | <0.05 |
| 130 | 0.33 |
| 131 | 0.30 |
| 132 | <0.05 |
| 133 | 7.4 |
| 134 | 0.94 |
| 135 | 20 |
| 136 | 12 |
| 137 | 0.11 |
| 138 | 0.62 |

TABLE 2-continued $K_i$ for Exemplified Compounds for Inhibition of WDR5 by TR-FRET assay

| Example | $K_i$ (nM) |
|---|---|
| 139 | 2.3 |
| 140 | 0.054 |
| 141 | 0.17 |
| 142 | 25 |
| 143 | <0.05 |
| 144 | 33 |
| 145 | 7.9 |
| 146 | <0.05 |
| 147 | <0.05 |
| 148 | <0.05 |
| 149 | <0.05 |
| 150 | <0.05 |
| 151 | <0.05 |
| 152 | <0.05 |
| 153 | 0.37 |
| 154 | 0.050 |
| 155 | 0.13 |
| 156 | <0.05 |
| 157 | <0.05 |
| 158 | <0.05 |
| 159 | <0.05 |
| 160 | <0.05 |
| 161 | <0.05 |
| 162 | 2.5 |
| 163 | <0.05 |
| 164 | <0.05 |
| 165 | <0.05 |
| 166 | <0.05 |
| 167 | 0.53 |
| 168 | <0.05 |
| 169 | 1.1 |
| 170 | 0.15 |
| 171 | 1.2 |
| 172 | <0.05 |
| 173 | 0.63 |
| 174 | 0.075 |
| 175 | <0.05 |
| 176 | <0.05 |
| 177 | <0.05 |
| 178 | <0.05 |
| 179 | 2.4 |
| 180 | 0.22 |
| 181 | 0.75 |
| 182 | 0.11 |
| 183 | 0.17 |
| 184 | <0.05 |
| 185 | 0.55 |
| 187 | 0.14 |
| 188 | 0.18 |
| 189 | 0.22 |
| 190 | 0.14 |
| 191 | 0.098 |
| 192 | 0.096 |
| 193 | 0.30 |
| 194 | 0.14 |
| 195 | 0.15 |
| 196 | 0.27 |
| 197 | 0.075 |
| 198 | 0.056 |
| 199 | <0.05 |
| 200 | <0.05 |
| 201 | <0.05 |
| 202 | 0.052 |
| 203 | <0.05 |
| 204 | <0.05 |
| 205 | <0.05 |
| 206 | <0.05 |
| 207 | <0.05 |
| 208 | 0.059 |
| 209 | <0.05 |
| 210 | <0.05 |
| 211 | <0.05 |
| 212 | <0.05 |
| 213 | <0.05 |
| 215 | <0.05 |
| 216 | <0.05 |
| 217 | <0.05 |
| 218 | <0.05 |
| 220 | 0.13 |
| 221 | 0.053 |
| 223 | <0.05 |
| 224 | <0.05 |
| 225 | <0.05 |
| 226 | <0.05 |
| 227 | >33 |
| 228 | <0.05 |
| 229 | 0.19 |
| 230 | <0.05 |
| 231 | 0.052 |
| 232 | 0.056 |
| 233 | 0.20 |
| 234 | <0.05 |
| 236 | <0.05 |
| 237 | <0.05 |
| 238 | <0.05 |
| 241 | <0.05 |
| 242 | <0.05 |
| 243 | <0.05 |
| 244 | <0.05 |
| 245 | <0.05 |
| 246 | 0.44 |
| 247 | <0.05 |
| 248 | <0.05 |
| 249 | 0.22 |
| 250 | <0.05 |
| 251 | <0.05 |
| 252 | <0.05 |
| 253 | 0.21 |
| 254 | 0.095 |
| 255 | 0.58 |
| 256 | 2.4 |
| 257 | <0.05 |

Among other things, these data demonstrate the utility of representative compounds as selective inhibitors of the activity of WDR5 protein to bind peptides from relevant MLL domain.

Cellular Viability of Human Tumor Cell Lines

Anti proliferative activity using MLL-harboring cell lines. MV-4-11 and K562 cells are grown in IMDM media supplemented with 10% FBS and 1% penicillin/streptomycin, Molm-13 cells are cultured in RPMI-1640 media supplemented with 10% FBS and 1% penicillin/streptomycin. Viability assays are performed by dispensing 200 cells at 7200 cells/mL into each well of an opaque 384-well plate and adding compounds at the indicated concentrations in a final volume of 32 μL and a final concentration of DMSO of 0.3% for all samples. A certain range of compound concentrations is made through a series of 2-fold dilutions starting 30 μM at the highest, total 22 dilutions. After a set incubation period, 5 day protocol, the viability of cells in each well is assessed using the CellTiter-Glo assay (Promega), read on a 96 Microplane Luminometer (Cytation 3, BioTek). Serial dilutions of each cell type are performed in all assays to generate standard curves and the final densities of cells are determined within the dynamic range of the instrument. $GI_{50}$ values are calculated based on XLfit software (IDBS, Guildford, UK) with Sigmoidal Dose-Response Model. Each compound is tested in minimum of two replicates. Data are expressed as mean.

TABLE 3

GI$_{50}$ (in μM) for representative compounds on cellular proliferation of MV4:11 human cancer cell lines

| Example | GI$_{50}$ (nM) |
|---|---|
| 1 | 239 |
| 2 | >938 |
| 5 | >938 |
| 6 | 301 |
| 7 | 572 |
| 8 | <50 |
| 9 | 553 |
| 10 | <50 |
| 11 | 54 |
| 12 | 69 |
| 13 | 105 |
| 14 | >938 |
| 15 | 76 |
| 16 | >938 |
| 17 | 360 |
| 18 | >938 |
| 19 | >938 |
| 20 | 508 |
| 21 | <50 |
| 22 | 145 |
| 23 | >938 |
| 24 | <50 |
| 25 | >938 |
| 26 | >938 |
| 27 | >938 |
| 28 | >938 |
| 29 | 63 |
| 30 | 95 |
| 31 | <50 |
| 32 | 64 |
| 33 | 553 |
| 34 | 215 |
| 35 | 143 |
| 36 | 201 |
| 37 | <50 |
| 38 | 95 |
| 39 | <50 |
| 40 | <50 |
| 41 | 64 |
| 42 | 291 |
| 43 | <50 |
| 44 | <50 |
| 45 | 113 |
| 46 | 449 |
| 47 | 165 |
| 48 | 423 |
| 49 | 906 |
| 50 | >938 |
| 51 | <50 |
| 52 | <50 |
| 53 | <50 |
| 54 | 880 |
| 55 | <50 |
| 56 | 870 |
| 57 | 50 |
| 58 | 54 |
| 59 | 274 |
| 60 | >938 |
| 61 | <50 |
| 62 | 572 |
| 63 | 274 |
| 64 | >938 |
| 65 | <50 |
| 66 | <50 |
| 67 | <50 |
| 68 | 333 |
| 69 | 502 |
| 70 | 77 |
| 71 | <50 |
| 72 | <50 |
| 73 | >938 |
| 74 | >938 |
| 75 | >938 |
| 76 | >938 |
| 77 | >938 |
| 78 | >938 |
| 79 | <50 |
| 80 | <50 |
| 81 | 155 |
| 82 | 55 |
| 83 | <50 |
| 84 | <50 |
| 85 | 57 |
| 86 | 740 |
| 87 | 837 |
| 88 | <50 |
| 89 | <50 |
| 90 | 209 |
| 91 | <50 |
| 92 | >938 |
| 93 | <50 |
| 94 | 159 |
| 95 | 197 |
| 96 | <50 |
| 97 | 212 |
| 98 | 207 |
| 99 | 77 |
| 100 | 269 |
| 101 | <50 |
| 102 | >938 |
| 103 | >938 |
| 104 | <50 |
| 105 | <50 |
| 106 | 182 |
| 108 | 181 |
| 109 | 104 |
| 110 | >938 |
| 111 | >938 |
| 112 | 160 |
| 113 | 462 |
| 114 | 129 |
| 115 | >938 |
| 116 | 268 |
| 117 | >938 |
| 118 | 159 |
| 119 | >938 |
| 120 | >938 |
| 121 | 134 |
| 122 | <50 |
| 123 | <50 |
| 124 | 935 |
| 125 | >938 |
| 126 | <50 |
| 127 | 345 |
| 128 | >938 |
| 129 | <50 |
| 130 | 845 |
| 131 | >938 |
| 132 | <50 |
| 133 | 173 |
| 134 | >938 |
| 135 | >938 |
| 136 | >938 |
| 137 | 944 |
| 138 | 2280 |
| 139 | >938 |
| 140 | 200 |
| 141 | >938 |
| 142 | >938 |
| 143 | <50 |
| 144 | >938 |
| 145 | >938 |
| 146 | <50 |
| 147 | 73, 81 |
| 148 | <50 |
| 149 | <50 |
| 150 | <50 |
| 151 | <50 |
| 152 | <50 |
| 153 | >938 |

TABLE 3-continued

GI$_{50}$ (in µM) for representative compounds on cellular proliferation of MV4:11 human cancer cell lines

| Example | GI$_{50}$ (nM) |
|---|---|
| 154 | 559 |
| 155 | 407 |
| 156 | <50 |
| 157 | <50 |
| 158 | <50 |
| 159 | <50 |
| 160 | <50 |
| 161 | <50 |
| 162 | 13400 |
| 163 | <50 |
| 164 | 57 |
| 165 | <50 |
| 166 | 89 |
| 167 | 3023 |
| 168 | <50 |
| 169 | 1999 |
| 170 | 835 |
| 171 | 6897 |
| 172 | 221 |
| 173 | 3908 |
| 174 | 329 |
| 175 | <50 |
| 176 | 293 |
| 177 | <50 |
| 178 | 152 |
| 179 | 9639 |
| 180 | 1592 |
| 181 | 3459 |
| 182 | 319 |
| 183 | 504 |
| 184 | 125 |
| 185 | <50 |
| 187 | 591 |
| 188 | 730 |
| 189 | 1000 |
| 190 | 349 |
| 191 | <50 |
| 192 | 77 |
| 193 | 2332 |
| 194 | 252 |
| 195 | 217 |
| 196 | 936 |
| 197 | <50 |
| 198 | 62 |
| 199 | <50 |
| 200 | <50 |
| 201 | <50 |
| 202 | 230 |
| 203 | 52 |
| 204 | 58 |
| 205 | <50 |
| 206 | <50 |
| 207 | 75 |
| 208 | 251 |
| 209 | 85 |
| 210 | 148 |
| 211 | 84 |
| 212 | <50 |
| 213 | <50 |
| 215 | 168 |
| 216 | 56 |
| 217 | 149 |
| 218 | <50 |
| 220 | 1939 |
| 221 | 421 |
| 223 | <50 |
| 224 | 72 |
| 225 | 195 |
| 226 | 950 |
| 227 | 7450 |
| 228 | <50 |
| 229 | 1048 |
| 230 | <50 |
| 231 | 550 |
| 232 | 199 |
| 233 | 748 |
| 234 | 283 |
| 235 | 199 |
| 236 | 121 |
| 237 | <50 |
| 238 | 227 |
| 239 | 573 |
| 241 | <50 |
| 242 | 50 |
| 243 | <50 |
| 244 | 119 |
| 245 | <50 |
| 246 | 1873 |
| 247 | 67 |
| 248 | 55 |
| 249 | 1970 |
| 250 | <50 |
| 251 | <50 |
| 252 | <50 |
| 253 | 2091 |
| 254 | 1342 |
| 255 | 2787 |
| 256 | 3862 |
| 257 | <50 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A compound of formula (I)

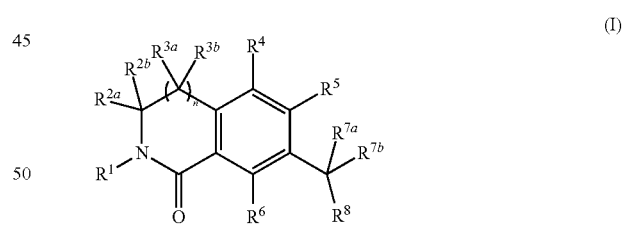

(I)

or a pharmaceutically acceptable salt thereof, wherein:
n is 0, 1, or 2;
$R^1$ is $G^1$ or $-(CR^aR^b)_p-G^1$;
p is 1, 2, or 3;
$G^1$ is a 6- to 12-membered aryl, a 5- to 12-membered heteroaryl, a 4- to 12-membered heterocyclyl, or a $C_{3-10}$carbocyclyl attached to the parent molecular moiety and optionally fused to a 6-membered arene or to a 5- to 6-membered heteroarene, wherein $G^1$ is optionally substituted with 1-5 substituents independently selected from the group consisting of halogen, $C_{1-6}$alkyl, $C_{1-6}$haloalkyl, $C_{2-6}$alkenyl, $C_{2-6}$alkynyl, oxo, $-OR^{1a}$, $-N(R^{1a})_2$, $-SR^{1a}$, cyano, $-C(O)OR^{1a}$, $-C(O)N(R^{1a})_2$, $-C(O)R^{1a}$, $-SOR^{1b}$, $-SO_2R^{1b}$, —SO$_2$N(R$^{1a}$)$_2$, —NR$^{1a}$C(O)R$^{1a}$, —NRC(O)OR$^{1a}$, —NR$^{1a}$C(O)N(R$^{1a}$)$_2$, —NR$^{1a}$S(O)$_2$R$^{1b}$, —NR$^{1a}$S(O)$_2$N(R$^{1a}$)$_2$, —OC$_{1-3}$alkylene-Y—R$^{1a}$, and -L$^1$-G$^{1a}$;

R$^{1a}$, at each occurrence, is independently hydrogen, C$_{1-6}$alkyl, C$_{1-6}$haloalkyl, G$^{1a}$, or —C$_{1-6}$alkylene-G$^{1a}$, wherein alternatively two R$^{1a}$, together with a common nitrogen atom to which the R$^{1a}$ attach form a 4- to 8-membered saturated or partially unsaturated heterocyclic ring, optionally substituted with 1-4 substituents independently selected from the group consisting of C$_{1-4}$alkyl, C$_{1-4}$haloalkyl, oxo, —OH, and —OC$_{1-4}$alkyl;

R$^{1b}$, at each occurrence, is independently C$_{1-6}$alkyl, C$_{1-6}$haloalkyl, G$^{1a}$, or —C$_{1-6}$alkylene-G$^{1a}$;

Y is —C(O)O—, —C(O)N(R$^{1a}$)—, —C(O)—, —SO$_2$—, or —SO$_2$N(R$^{1a}$)—;

L$^1$ is a bond or C$_{1-3}$alkylene;

G$^{1a}$, at each occurrence, is independently C$_{3-8}$cycloalkyl, 6- to 10-membered aryl, 5- to 10-membered heteroaryl, or 4- to 10-membered heterocyclyl, wherein G$^{1a}$ is optionally substituted with 1-4 substituents independently selected from the group consisting of halogen, C$_{1-4}$alkyl, C$_{1-4}$haloalkyl, oxo, —OR$^{1c}$, —N(R$^{1c}$)$_2$, cyano, —C(O)OR$^{1c}$, —C(O)N(R$^{1c}$)$_2$, —C(O)R$^{1c}$, —SOR$^{1d}$, —SO$_2$R$^{1d}$, —SO$_2$N(R$^{1c}$)$_2$, —NR$^{1e}$C(O)R$^{1e}$, —NR$^{1e}$C(O)OR$^{1e}$, —NR$^{1c}$C(O)N(R$^{1c}$)$_2$, —NR$^{1c}$S(O)$_2$R$^{1d}$, and —NR$^{1c}$S(O)$_2$N(R$^{1d}$)$_2$;

R$^a$, at each occurrence, is independently hydrogen, C$_{1-4}$alkyl, C$_{1-4}$haloalkyl, —C$_{1-6}$alkylene-R$^{aa}$, G$^{1b}$, or —C$_{1-6}$alkylene-G$^{1b}$, wherein each C$_{1-6}$alkylene is optionally substituted with 1-4 halogen;

R$^{aa}$, at each occurrence, is independently —OR$^{1e}$, —N(R$^{1e}$)$_2$, —SR$^{1e}$, cyano, —C(O)OR$^{1e}$, —C(O)N(R$^{1e}$)$_2$, —C(O)R$^{1e}$, —SOR$^{1f}$, —SO$_2$R$^{1f}$, —SO$_2$N(R$^{1e}$)$_2$, —NR$^{1e}$C(O)R$^{1e}$, —NR$^{1e}$C(O)OR$^{1e}$, —NR$^{1e}$C(O)N(R$^{1e}$)$_2$, —NR$^{1e}$S(O)$_2$R$^{1f}$, or —NR$^{1e}$S(O)$_2$N(R$^{1e}$)$_2$;

G$^{1b}$, at each occurrence, is independently a C$_{3-6}$carbocyclyl or a 4- to 10-membered heterocyclyl, wherein the C$_{3-6}$carbocyclyl and 4- to 10-membered heterocyclyl are optionally substituted with 1-4 substituents independently selected from the group consisting of halogen, C$_{1-4}$alkyl, C$_{1-4}$haloalkyl, oxo, —OR$^{1e}$, —N(R$^{1e}$)$_2$, —SR$^{1e}$, cyano, —C(O)OR$^{1e}$, —C(O)N(R$^{1e}$)$_2$, —C(O)R$^{1e}$, —SOR$^{1f}$, —SO$_2$R$^{1f}$, —SO$_2$N(R$^{1e}$)$_2$, —NR$^{1e}$C(O)R$^{1e}$, —NR$^{1e}$C(O)OR$^{1e}$, —NR$^{1e}$C(O)N(R$^{1e}$)$_2$, —NR$^{1e}$S(O)$_2$R$^{1f}$, and —NR$^{1e}$S(O)$_2$N(R$^{1e}$)$_2$;

R$^b$ is hydrogen or C$_{1-4}$alkyl;

or alternatively one R$^a$ and one R$^b$ together with the carbon atom to which they are attached form a 3-8 membered saturated or partially unsaturated carbocyclic or heterocyclic ring;

or alternatively one R$^a$ and one R$^b$ are taken together to form an oxo group;

R$^{2a}$, R$^{2b}$, R$^{3a}$, and R$^{3b}$ are independently hydrogen, halogen, C$_{1-4}$alkyl, C$_{1-4}$haloalkyl, or —OC$_{1-4}$alkyl; or alternatively any two of R$^{2a}$, R$^{2b}$, R$^{3a}$, and R$^b$ are taken together with the atom or atoms to which they attach to form a 3-8 membered saturated or partially unsaturated carbocyclic or heterocyclic ring that is optionally substituted with 1-4 substituents independently selected from the group consisting of halogen, C$_{1-4}$alkyl, C$_{1-4}$haloalkyl, and —OC$_{1-4}$alkyl;

or alternatively one R$^{1a}$ and one R$^{1b}$ are taken together to form an oxo group;

R$^4$ is hydrogen, halogen, C$_{1-6}$alkyl, C$_{1-6}$haloalkyl, C$_{1-6}$haloalkenyl, —OR$^{4a}$, —SR$^{4a}$, —N(R$^{4a}$)$_2$, —S(O)R$^{4b}$, —S(O)$_2$R$^{4b}$, —S(O)$_2$N(R$^{4a}$)$_2$, —C(O)N(R$^{4a}$)$_2$, —C(O)R$^{4a}$, —NR$^{4a}$C(O)R$^{4a}$, —NR$^{4a}$C(O)OR$^{4a}$, —NR$^{4a}$C(O)N(R$^{4a}$)$_2$, —NR$^{4a}$S(O)$_2$R$^{4b}$, —NR$^{4a}$S(O)$_2$N(R$^{4a}$)$_2$, or G$^2$;

R$^{4a}$ at each occurrence, is independently hydrogen, C$_{1-6}$alkyl, C$_{1-6}$haloalkyl, G$^2$, or —C$_{1-3}$alkylene-G$^2$;

R$^{4b}$ is C$_{1-6}$alkyl, C$_{1-6}$haloalkyl, G$^2$, or —C$_{1-3}$alkylene-G$^2$;

G$^2$, at each occurrence, is independently a C$_{3-10}$carbocyclyl, a 6- to 12-membered aryl, a 5- to 12-membered heteroaryl, or a 4- to 12-membered heterocyclyl, wherein G$^2$ is optionally substituted with 1-5 substituents independently selected from the group consisting of halogen, C$_{1-6}$alkyl, C$_{1-6}$haloalkyl, oxo, —OR$^{4c}$, —N(R$^{4c}$)$_2$, —SR$^{4c}$, cyano, —C(O)OR$^{4c}$, —C(O)N(R$^{4c}$)$_2$, —C(O)R$^{4c}$, —SOR$^{4d}$, —SO$_2$R$^{4d}$, —SO$_2$N(R$^{4c}$)$_2$, —NR$^{40}$C(O)R$^{4c}$, —NR$^{4c}$C(O)OR$^{4c}$, —NR$^{4c}$C(O)N(R$^{4c}$)$_2$, —NR$^{4c}$S(O)$_2$R$^{4d}$, —NR$^{4c}$S(O)$_2$N(R$^{4c}$)$_2$, C$_{3-8}$cycloalkyl, and —C$_{1-3}$alkylene-C$_{3-8}$cycloalkyl, wherein each C$_{3-8}$cycloalkyl is optionally substituted with 1-4 substituents independently selected from the group consisting of C$_{1-4}$alkyl and halogen;

R$^{1c}$, R$^{1e}$, and R$^{4c}$, at each occurrence, are independently hydrogen, C$_{1-6}$alkyl, C$_{1-6}$haloalkyl, C$_{3-8}$cycloalkyl, or —C$_{1-6}$alkylene-C$_{3-8}$cycloalkyl, wherein each C$_{3-8}$cycloalkyl is optionally substituted with 1-4 substituents independently selected from the group consisting of C$_{1-4}$alkyl and halogen, wherein alternatively two R$^{1c}$, two R$^{1e}$, and/or two R$^{4c}$, together with a common nitrogen atom to which the R$^{1c}$, R$^{1e}$, and/or R$^{4c}$ attach form a 4- to 8-membered saturated or partially unsaturated heterocyclic ring, optionally substituted with 1-4 substituents independently selected from the group consisting of C$_{1-4}$alkyl, C$_{1-4}$haloalkyl, oxo, —OH, and —OC$_{1-4}$alkyl;

R$^{1d}$, R$^{1f}$, and R$^{4d}$, at each occurrence, are independently C$_{1-6}$alkyl, C$_{1-6}$haloalkyl, C$_{3-8}$cycloalkyl, or —C$_{1-6}$alkylene-C$_{3-8}$cycloalkyl, wherein each C$_{3-8}$cycloalkyl is optionally substituted with 1-4 substituents independently selected from the group consisting of C$_{1-4}$alkyl and halogen;

R$^5$ and R$^6$ are each independently hydrogen, halogen, C$_{1-4}$alkyl, C$_{1-4}$haloalkyl, or —OC$_{1-4}$alkyl;

R$^{7a}$ and R$^{7b}$ are independently selected from the group consisting of hydrogen, halogen, C$_{1-4}$alkyl, and C$_{1-4}$haloalkyl, or R$^{7a}$ and R$^{7b}$ are taken together to form an oxo group;

R$^8$ is

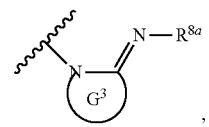

imidazolyl, triazolyl,

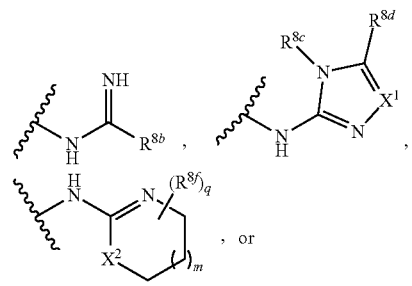

, or

-continued

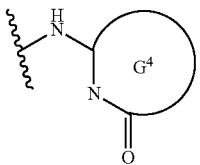

wherein the imidazolyl and triazolyl are optionally fused to a 6-membered arene and the optionally fused imidazolyl and triazolyl are optionally substituted with 1-3 substituents independently selected from the group consisting of halogen, cyano, $C_{1-4}$alkyl, $C_{1-4}$haloalkyl, $NH_2$, —NH($C_{1-4}$alkyl), —N($C_{1-4}$alkyl)$_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl;

$X^1$ is N or $CR^{8e}$;
$X^2$ is $C(R^{8f})_2$, O, or $NR^{8f}$;
m is 0, 1, or 2;
q is 0, 1, 2, 3, or 4;
$G^3$ is a 5- to 12-membered heterocyclic ring system containing a first nitrogen at the point of attachment and optionally 1-4 additional heteroatoms selected from the group consisting of oxygen, nitrogen, and sulfur, $G^3$ having the imine substituent =$NR^{8a}$ adjacent to the first nitrogen and being optionally substituted with 1-4 substituents independently selected from the group consisting of halogen, oxo, $C_{1-6}$alkyl, $C_{1-6}$haloalkyl, $G^{1a}$, and —$C_{1-3}$alkylene-$G^{3a}$;
$G^4$ is a 5- to 12-membered heterocyclic ring system attached at a first carbon atom and containing a first nitrogen bonded to the first carbon atom, $G^4$ having a first oxo substituent adjacent to the first nitrogen and being optionally substituted with 1-4 substituents independently selected from the group consisting of halogen, oxo, $C_{1-6}$alkyl, and $C_{1-6}$haloalkyl;
$R^{8a}$ is hydrogen, $C_{1-4}$alkyl, $C_{3-6}$cycloalkyl, $C(O)C_{1-4}$alkyl, or $C(O)OC_{1-4}$alkyl;
$R^{8b}$ is —$N(R^{8g})_2$, $C_{1-6}$alkyl, $C_{1-6}$haloalkyl, $G^{1a}$, or —$C_{1-3}$alkylene-$G^{3a}$;
$R^{8c}$, $R^{8d}$, and $R^{8e}$, are each independently hydrogen, halogen, $C_{1-4}$alkyl, $C_{1-4}$haloalkyl, $C_{3-8}$cycloalkyl, or —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl, wherein alternatively, $R^{8d}$ and $R^{8c}$, together with the atoms to which each attaches form a 5- to 6-membered ring containing 0-2 double bonds, or $R^{8d}$ and $R^{8e}$, together with the atoms to which each attaches form a 5- to 6-membered ring containing 1-3 double bonds;
$R^f$, at each occurrence, is independently hydrogen, $C_{1-4}$alkyl, $C_{1-4}$haloalkyl, $G^{3a}$, or —$C_{1-3}$alkylene-$G^{3a}$, wherein optionally two $R^{8f}$ are taken together to form an oxo group, a 3-8 membered saturated or partially unsaturated carbocyclic ring, or a 3-8 membered saturated or partially unsaturated heterocyclic ring having 1-4 heteroatoms independently selected from the group consisting of nitrogen, oxygen, or sulfur;
$R^{8g}$, at each occurrence, is independently hydrogen, $C_{1-6}$alkyl, $C_{1-6}$haloalkyl, $G^{1a}$, or $C_{1-3}$alkylene-$G^{3a}$; and
$G^{3a}$ is $C_{3-10}$carbocyclyl or a 6- to 12 membered aryl, wherein $G^{3a}$ is optionally substituted with 1-4 substituents independently selected from the group consisting of halogen, $C_{1-4}$alkyl, $C_{1-4}$haloalkyl, OH, and —$OC_{1-4}$alkyl.

Clause 2. A compound of formula (I)

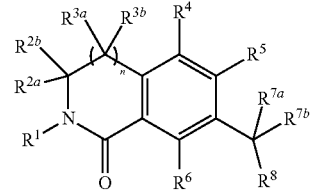

(I)

or a pharmaceutically acceptable salt thereof, wherein:
n is 0, 1, or 2;
$R^1$ is $G^1$ or —$(CR^aR^b)_p$-$G^1$;
p is 1, 2, or 3;
$G^1$ is a 6- to 12-membered aryl, a 5- to 12-membered heteroaryl, a 4- to 12-membered heterocyclyl, or a $C_{3-10}$carbocycle optionally fused to a phenyl or to a 5- to 6-membered heteroaryl, wherein $G^1$ is optionally substituted with 1-5 substituents independently selected from the group consisting of halogen, $C_{1-6}$alkyl, $C_{1-6}$haloalkyl, oxo, —$N(R^{1a})_2$, —$SR^{1a}$, cyano, —$C(O)OR^{1a}$, —$C(O)N(R^{1a})_2$, —$C(O)R^{1a}$, —$SOR^{1b}$, —$SO_2R^{1b}$, —$SO_2N(R^{1a})_2$, —$NR^{1a}C(O)R^{1a}$, —$NR^{1a}C(O)OR^{1a}$, —$NR^{1a}C(O)N(R^{1a})_2$; —$NR^{1a}S(O)_2R^{1b}$, —$NR^{1a}S(O)_2N(R^{1a})_2$, and -$L^1$-$G^{1a}$;
$R^{1a}$, at each occurrence, is independently hydrogen, $C_{1-6}$alkyl, $C_{1-6}$haloalkyl, $G^{1a}$, or —$C_{1-6}$alkylene-$G^{1a}$, wherein alternatively two $R^{1a}$, together with a common nitrogen atom to which the $R^{1a}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;
$R^{1b}$, at each occurrence, is independently $C_{1-6}$alkyl, $C_{1-6}$haloalkyl, $G^{1a}$, or —$C_{1-6}$alkylene-$G^{1a}$;
$L^1$ is a bond or $C_{1-3}$alkylene;
$G^{1a}$, at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, —$N(R^{1c})_2$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}C(O)R^{1c}$, —$NR^{1c}C(O)OR^{1c}$, —$NR^{1c}C(O)N(R^{1c})_2$, —$NR^{1c}S(O)_2R^{1d}$, and —$NR^{1c}S(O)_2N(R^{1d})_2$;
$R^a$, at each occurrence, is independently hydrogen, $C_{1-4}$alkyl, $C_{1-4}$haloalkyl, —$C_{1-6}$alkylene-$R^{aa}$, $G^{1b}$, or —$C_{1-6}$alkylene-$G^{1b}$, wherein each $C_{1-6}$alkylene is optionally substituted with 1-4 halogen;
$R^{aa}$, at each occurrence, is independently —$OR^{1e}$, —$N(R^{1e})_2$, —$SR^{1e}$, cyano, —$C(O)OR^{1e}$, —$C(O)N(R^{1e})_2$, —$C(O)R^{1e}$, —$SOR^{1f}$, —$SO_2R^{1f}$, —$SO_2N(R^{1e})_2$, —$NR^{1e}C(O)R^{1e}$, —$NR^{1e}C(O)OR^{1e}$, —$NR^{1e}C(O)N(R^{1e})_2$, —$NR^{1e}S(O)_2R^{1f}$, or —$NR^{1e}S(O)_2N(R^{1e})_2$;
$G^{1b}$, at each occurrence, is independently a $C_{3-6}$carbocycle or a 4- to 10-membered heterocyclyl, wherein the $C_{3-6}$carbocycle and 4- to 10-membered heterocyclyl are optionally substituted with 1-4 substituents independently selected from the group consisting of halogen, $C_{1-4}$alkyl, $C_{1-4}$haloalkyl, oxo, —$OR^{1e}$, —$N(R^{1e})_2$, —$SR^{1e}$, cyano, —$C(O)OR^{1e}$, —$C(O)N(R^{1e})_2$, —$C(O)R^{1e}$, —$SOR^{1f}$, —$SO_2R^{1f}$, —$SO_2N(R^{1e})_2$, —$NR^{1e}C(O)R^{1e}$, —$NR^{1e}C(O)OR^{1e}$, —$NR^{1e}C(O)N(R^{1e})_2$, —$NR^{1e}S(O)_2R^{1f}$, and —$NR^{1e}S(O)_2N(R^{1e})_2$;

$R^b$ is hydrogen or $C_{1-4}$alkyl;

or alternatively one $R^a$ and one $R^b$ together with the carbon atom to which they are attached form a 3-8 membered saturated or partially unsaturated carbocyclic or heterocyclic ring;

or alternatively one $R^a$ and one $R^b$ are taken together to form an oxo group;

$R^{2a}$, $R^{2b}$, $R^{3a}$, and $R^{3b}$ are independently hydrogen, halogen, $C_{1-4}$alkyl, $C_{1-4}$haloalkyl, or —$OC_{1-4}$alkyl; or alternatively any two of $R^{2a}$, $R^{2b}$, $R^{3a}$, and $R^{3b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$haloalkyl, and —$OC_{1-4}$alkyl;

or alternatively one $R^{1a}$ and one $R^{3b}$ are taken together to form an oxo group;

$R^4$ is hydrogen, halogen, $C_{1-6}$alkyl, $C_{1-6}$haloalkyl, $C_{1-6}$haloalkenyl, —$OR^{4a}$, —$SR^{4a}$, —$N(R^{4a})_2$, —$S(O)R^{4b}$, —$S(O)_2R^{4b}$, —$S(O)_2N(R^{4a})_2$, —$C(O)N(R^{4a})_2$, —$C(O)R^{4a}$, —$NR^{4a}C(O)R^{4a}$, —$NR^{4a}C(O)OR^{4a}$, —$NR^{4a}C(O)N(R^{4a})_2$, —$NR^{4a}S(O)_2R^{4b}$, —$NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or —$C_{1-3}$alkylene-$G^2$;

$R^{4b}$ is $C_{1-6}$alkyl, $C_{1-6}$haloalkyl, $G^2$, or —$C_{1-3}$alkylene-$G^2$;

$G^2$, at each occurrence, is independently a $C_{3-10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of halogen, $C_{1-6}$alkyl, $C_{1-6}$haloalkyl, oxo, —$OR^{4c}$, —$N(R^{4c})_2$, cyano, —$C(O)OR^{4c}$, —$C(O)N(R^{4c})_2$, —$C(O)R^{4c}$, —$SOR^{4d}$, —$SO_2R^{4d}$, —$SO_2N(R^{4c})_2$, —$NR^{4c}C(O)R^{4c}$, —$NR^{4c}C(O)OR^{4c}$, —$NR^{4c}C(O)N(R^{4c})_2$, —$NR^{4c}S(O)_2R^{4d}$, —$NR^{4c}S(O)_2N(R^{4c})_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^{1c}$, $R^{1e}$, and $R^{4c}$, at each occurrence, are independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{1c}$, two $R^{1e}$, and/or two $R^{4c}$, together with a common nitrogen atom to which the $R^{1c}$, $R^{1e}$, and/or $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, OH, and —$OC_{1-4}$alkyl;

$R^{1d}$, $R^{1f}$, and $R^{4d}$, at each occurrence, are independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or —$OC_{1-4}$alkyl;

$R^{7a}$ and $R^{7b}$ are independently selected from the group consisting of hydrogen, halogen, $C_{1-4}$alkyl, and $C_{1-4}$haloalkyl, or $R^{7a}$ and $R^{7b}$ are taken together to form an oxo group;

$R^8$ is

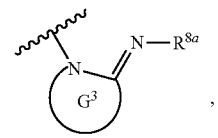

imidazolyl, triazolyl,

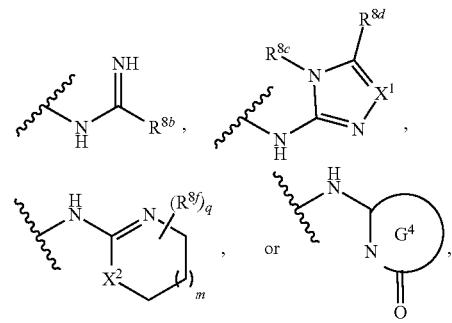

wherein the imidazolyl and triazolyl are optionally substituted with 1-3 substituents independently selected from the group consisting of halogen, $C_{1-4}$alkyl, $C_{1-4}$haloalkyl, $NH_2$, $NH(C_{1-4}$alkyl), $N(C_{1-4}$alkyl$)_2$, $C_{3-8}$cycloalkyl, and $C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl;

$X^1$ is N or $CR^{8e}$;

$X^2$ is $C(R^{8f})_2$, O, or $NR^{8f}$;

m is 0, 1, or 2;

q is 0, 1, 2, 3, or 4;

$G^3$ is a 5- to 12-membered heterocyclic ring system containing a first nitrogen at the point of attachment and optionally 1-4 additional heteroatoms selected from the group consisting of oxygen, nitrogen, and sulfur, $G^3$ having the imine substituent =$NR^{8a}$ adjacent to the first nitrogen and being optionally substituted with 1-4 substituents independently selected from the group consisting of halogen, oxo, $C_{1-6}$alkyl, $C_{1-6}$haloalkyl, $G^{1a}$, and $C_{1-3}$alkylene-$G^{3a}$;

$G^4$ is a 5- to 12-membered heterocyclic ring system attached at a first carbon atom and containing a first nitrogen bonded to the first carbon atom, $G^4$ having the oxo substituent adjacent to the first nitrogen and being optionally substituted with 1-4 substituents independently selected from the group consisting of halogen, oxo, $C_{1-6}$alkyl, and $C_{1-6}$haloalkyl;

$R^{8a}$ is hydrogen, $C_{1-4}$alkyl, $C_{3-6}$cycloalkyl, $C(O)C_{1-4}$alkyl, or $C(O)OC_{1-4}$alkyl;

$R_{8b}$ is —$N(R^{8g})_2$, $C_{1-6}$alkyl, $C_{1-6}$haloalkyl, $G^{1a}$, or $C_{1-3}$alkylene-$G^{3a}$;

$R^{8c}$, $R^{8d}$, and $R^{8e}$, are each independently hydrogen, halogen, $C_{1-4}$alkyl, $C_{1-4}$haloalkyl, $C_{3-8}$cycloalkyl, or $C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl, wherein alternatively, $R^{8d}$ and $R^{8c}$, together with the atoms to which each attaches form a 5- to 6-membered ring containing 0-2 double bonds, or $R^{8d}$ and lee, together with the atoms to which each attaches form a 5- to 6-membered ring containing 1-3 double bonds;

$R^{8f}$, at each occurrence, is independently hydrogen, $C_{1-4}$alkyl, $C_{1-4}$haloalkyl, $G^{1a}$, or $C_{1-3}$alkylene-$G^{3a}$, wherein optionally two $R^{8f}$ are taken together to form an oxo group, a 3-8 membered saturated or partially unsaturated carbocyclic ring, or a 3-8 membered saturated or partially unsaturated heterocyclic ring having 1-4 heteroatoms independently selected from the group consisting of nitrogen, oxygen, or sulfur;

$R^{8g}$, at each occurrence, is independently hydrogen, $C_{1-6}$alkyl, $C_{1-6}$haloalkyl, $G^{3a}$, or $C_{1-3}$alkylene-$G^{3a}$; and $G^{3a}$ is $C_{3-10}$carbocycle or a 6- to 12 membered aryl, wherein $G^{3a}$ is optionally substituted with 1-4 substituents independently selected from the group consisting of halogen, $C_{1-4}$alkyl, $C_{1-4}$haloalkyl, OH, and —$OC_{1-4}$alkyl.

Clause 3. The compound of clause 1 or 2, or a pharmaceutically acceptable salt thereof, wherein $R^{8e}$ is

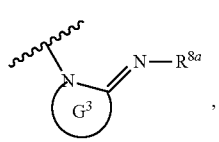

which is selected from the group consisting of

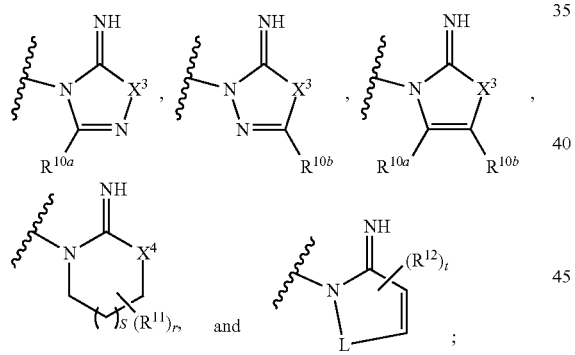

$X^3$ is $NR^{13}$, O, or S;
$X^4$ is $C(R^{14a})(R^{14b})$, $NR^{13}$, O, or S;
$R^{10a}$ and $R^{10b}$ are independently hydrogen, halogen, $C_{1-4}$alkyl, or $C_{1-4}$haloalkyl;
$R^{11}$, at each occurrence, is independently halogen, $C_{1-4}$alkyl, $C_{1-4}$haloalkyl, or two $R^{11}$ optionally form an oxo;
L is a $C_{1-2}$alkylene or a $C_2$alkenylene;
$R^{12}$, at each occurrence, is independently halogen, $C_{1-4}$alkyl, or $C_{1-4}$haloalkyl, wherein alternatively, two $R^{12}$ on adjacent carbon atoms together are a $C_{3-4}$alkylene or a $C_4$alkenylene group that forms a fused ring with the atoms to which the two $R^{12}$ attach;
$R^{13}$ is hydrogen, $C_{1-4}$alkyl, $C_{1-4}$haloalkyl, $C_{3-8}$cycloalkyl, —$C_{1-3}$alkylene-$C_{3-8}$cycloalkyl, or phenyl, each phenyl and cycloalkyl being further optionally substituted with 1-4 substituents independently selected from the group consisting of halogen, $C_{1-4}$alkyl, $C_{1-4}$haloalkyl, OH, and —$OC_{1-4}$alkyl;

wherein alternatively, $R^{10b}$ and $R^{13}$ together are a $C_{3-4}$alkylene or a $C_4$alkenylene group that forms a fused ring with the atoms to which the $R^{10b}$ and $R^{13}$ attach;
$R^{14a}$ and $R^{14b}$ are independently hydrogen or $C_{1-4}$alkyl;
s is 0, 1, or 2; and
r and t are each independently 0, 1, 2, 3, or 4.

Clause 4. The compound of clause 3, or a pharmaceutically acceptable salt thereof, wherein $R^8$ is

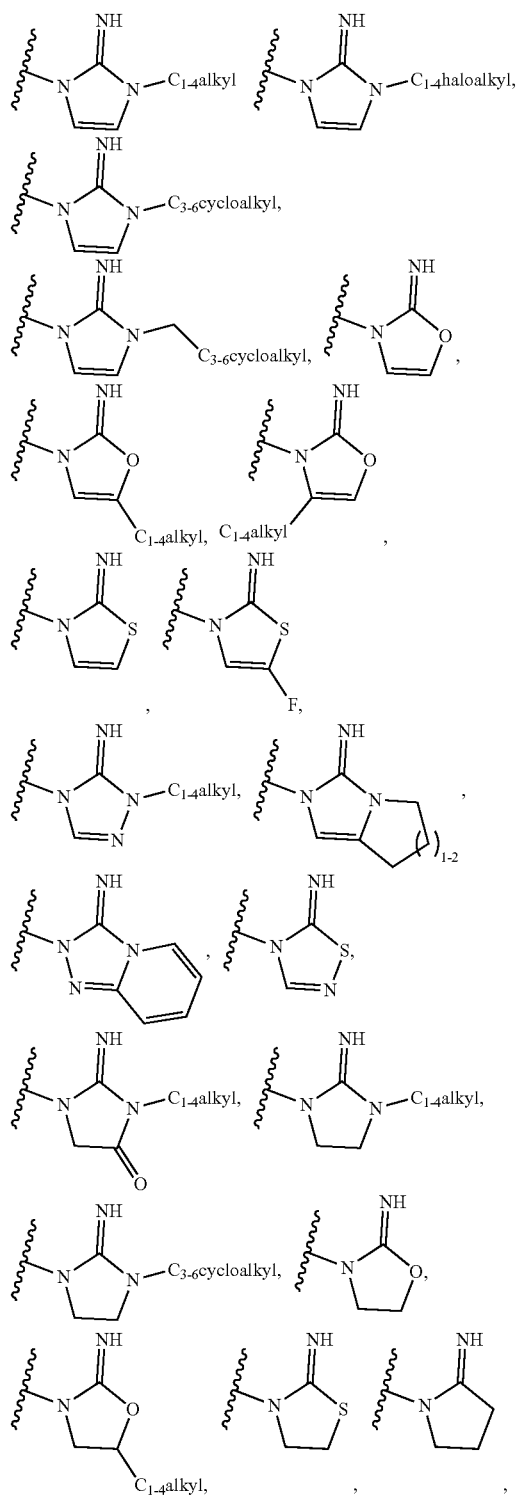

-continued

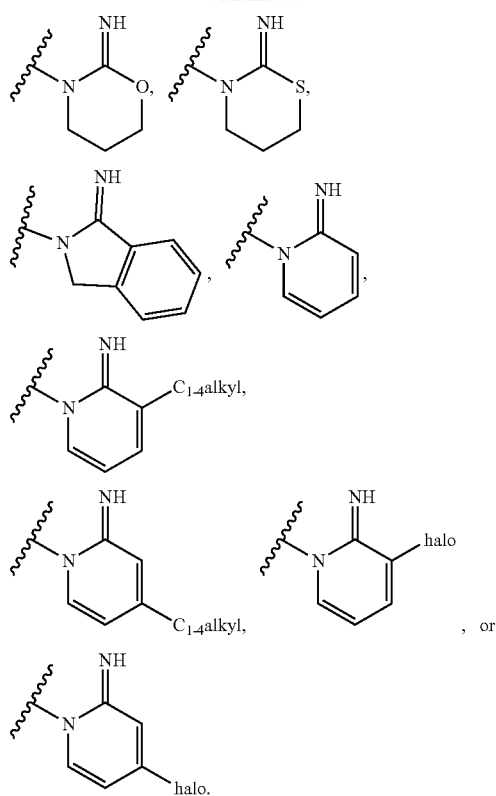

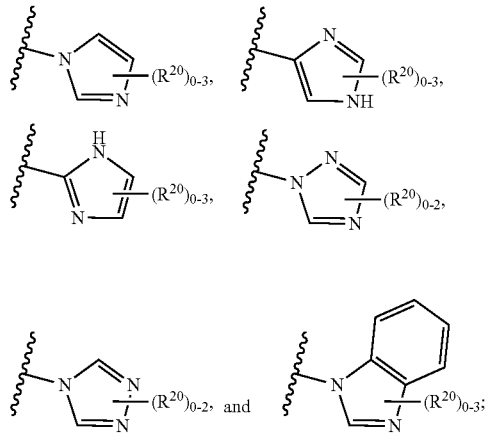

Clause 5. The compound of clause 1, or a pharmaceutically acceptable salt thereof, wherein $R^8$ is the optionally fused imidazolyl or triazolyl, which are selected from the group consisting of and $R^{20}$, at each occurrence, is independently halogen, cyano, $C_{1-4}$alkyl, $C_{1-4}$haloalkyl, $NH_2$, $NH(C_{1-4}$alkyl), $N(C_{1-4}$ alkyl)$_2$, $C_{3-8}$cycloalkyl, or $C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

Clause 6. The compound of clause 5, or a pharmaceutically acceptable salt thereof, wherein $R^8$ is

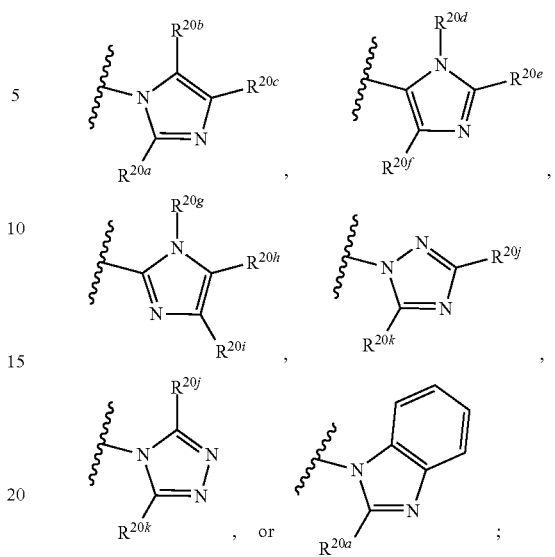

$R^{20a}$ is hydrogen, cyano, $C_{1-4}$alkyl, $NH_2$, —$NH(C_{1-4}$alkyl), —$N(C_{1-4}$alkyl)$_2$, or $C_{3-8}$cycloalkyl; and $R^{20b}$, $R^{20c}$, $R^{20d}$, $R^{20e}$, $R^{20f}$, $R^{20g}$, $R^{20h}$, $R^{20i}$, $R^{20j}$, and $R^{20k}$, are each independently hydrogen, $C_{1-4}$alkyl, or $C_{3-8}$cycloalkyl.

Clause 7. The compound of clause 6, or a pharmaceutically acceptable salt thereof, wherein $R^8$ is

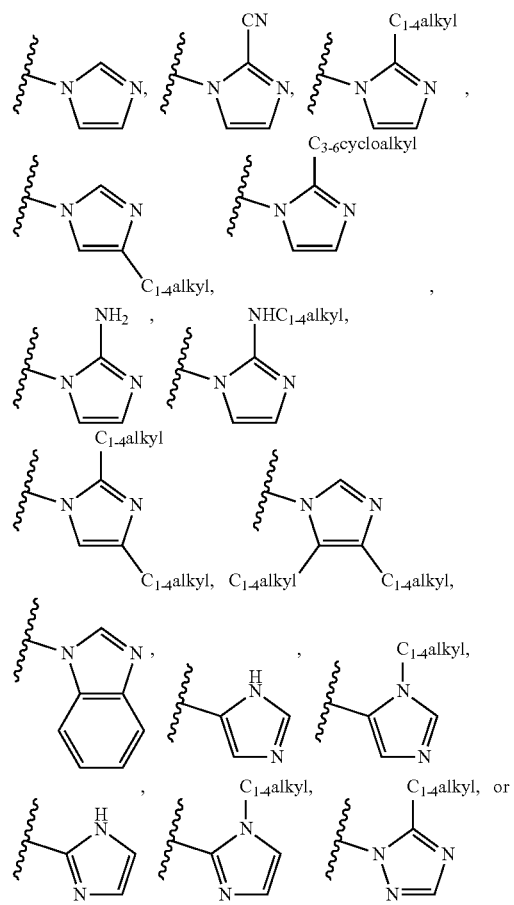

-continued

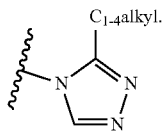

Clause 8. The compound of clause 2, or a pharmaceutically acceptable salt thereof, wherein $R^8$ is the imidazolyl or triazolyl, which are selected from the group consisting of

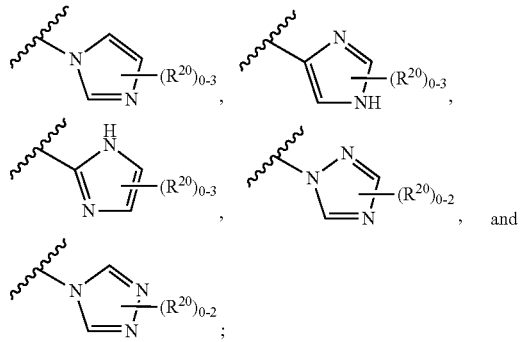

and $R^{20}$, at each occurrence, is independently halogen, $C_{1-4}$alkyl, $C_{1-4}$haloalkyl, $NH_2$, —$NH(C_{1-4}$alkyl), $N(C_{1-4}$alkyl)$_2$, $C_{3-8}$cycloalkyl, or $C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

Clause 9. The compound of clause 8, or a pharmaceutically acceptable salt thereof, wherein $R^8$ is

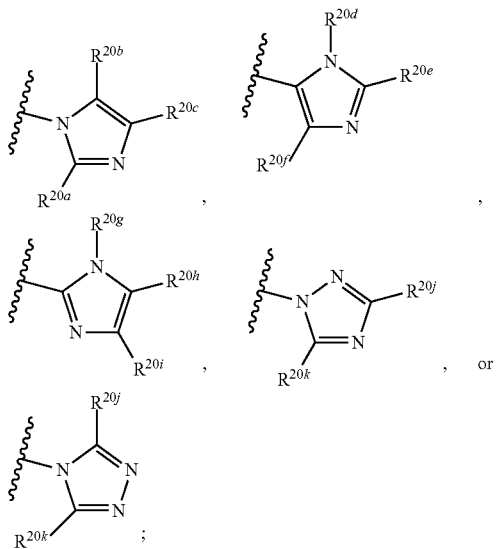

$R^{20a}$ is hydrogen, $C_{1-4}$alkyl, $NH_2$, —$NH(C_{1-4}$alkyl), —$N(C_{1-4}$alkyl)$_2$, or $C_{3-8}$cycloalkyl; and $R^{20b}$, $R^{20c}$, $R^{20d}$, $R^{20f}$, $R^{20g}$, $R^{20h}$, $R^{20i}$, $R^{20j}$, and $R^{20k}$, are each independently hydrogen, $C_{1-4}$alkyl, or $C_{3-8}$cycloalkyl.

Clause 10. The compound of clause 9, or a pharmaceutically acceptable salt thereof, wherein $R^8$ is

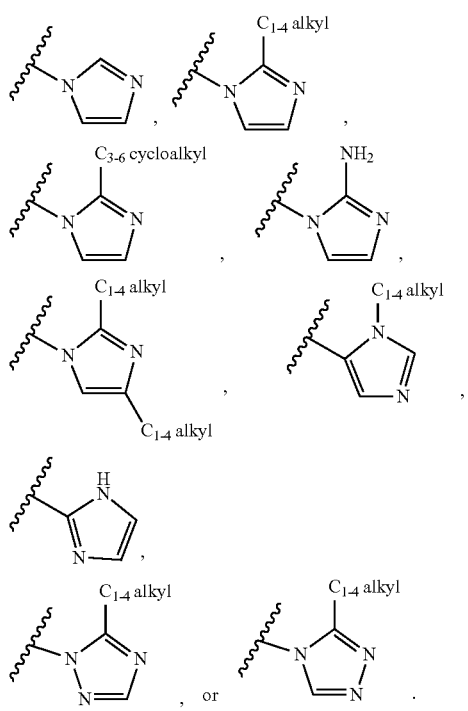

Clause 11. The compound of clause 1 or 2, or a pharmaceutically acceptable salt thereof, wherein
$R^8$ is

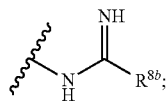

$R^{8b}$ is $C_{1-6}$alkyl, $C_{1-6}$haloalkyl, $G^{3a}$, or $C_{1-3}$alkylene-$G^{3a}$; and $G^{3a}$ is $C_{3-6}$cycloalkyl optionally substituted with 1-4 substituents independently selected from the group consisting of halogen and $C_{1-4}$alkyl.

Clause 12. The compound of clause 1 or 2, or a pharmaceutically acceptable salt thereof, wherein
$R^8$ is

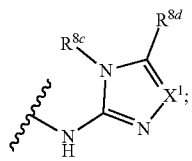

and $R^{8d}$ and $R^{8c}$, together are a $C_{3-4}$alkylene or a $C_4$alkenylene group that, with the atoms to which $R^{8d}$ and $R^{8c}$ attach, form a 5- to 6-membered ring containing 0-2 double bonds.

Clause 13. The compound of clause 1 or 2, or a pharmaceutically acceptable salt thereof, wherein R$^e$ is

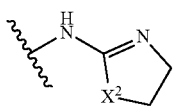

and

X$^2$ is CH$_2$, O, or NH.

Clause 14. The compound of clause 1 or 2, or a pharmaceutically acceptable salt thereof, wherein R$^8$ is

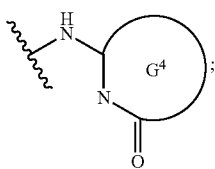

and

G$^4$ together with the oxo substituent is a pyridone.

Clause 15. The compound of any of clauses 1-14, or a pharmaceutically acceptable salt thereof, wherein R$^1$ is —(CR$^a$R$^b$)$_p$-G$^1$; and p is 1.

Clause 16. The compound of clause 15, or a pharmaceutically acceptable salt thereof, wherein G$^1$ is (a) phenyl,
(b) naphthyl,
(c) phenyl attached to the parent molecular moiety and fused to a 5- to 7-membered heterocycle containing 1-2 heteroatoms independently selected from oxygen, nitrogen, and sulfur,
(d) a 5- to 6-membered heteroaryl,
(e) a 8- to 12-membered fused bicyclic heteroaryl, or
(f) a 4- to 8-membered heterocyclyl, wherein G$^1$ is optionally substituted as defined in clause 1.

Clause 17. The compound of clause 16, or a pharmaceutically acceptable salt thereof, wherein G$^1$ is a phenyl, naphthyl, benzo[d][1,3]dioxol-5-yl, dihydrobenzofuran-7-yl, pyridinyl, pyridazinyl, pyrazolyl, triazolyl, oxazolyl, thiazolyl, isoxazolyl, thiadiazolyl, oxadiazolyl, indolyl, quinolinyl, tetrahydropyranyl, or piperidinyl, and G$^1$ is optionally substituted as defined in clause 1.

Clause 18. The compound of any of clauses 1 or 3-17, wherein G$^1$ is optionally substituted with 1-3 substituents independently selected from the group consisting of halogen, C$_{1-6}$alkyl, C$_{1-6}$haloalkyl, C$_{2-6}$alkenyl, oxo, —OR$^{1a}$, —N(R$^{1a}$)$_2$, cyano, —C(O)OR$^{1a}$, —C(O)N(R$^{1a}$)$_2$, —C(O)R$^{1a}$, —SO$_2$R$^{1b}$, —NR$^{1a}$C(O)R$^{1a}$, -L$^1$-G$^{1a}$, and —OC$_{1-3}$alkylene-Y—R$^{1a}$, wherein G$^{1a}$ is optionally substituted with 1-4 substituents independently selected from the group consisting of C$_{1-4}$alkyl and halogen; and Y is —C(O)O— or —C(O)N(R$^{1a}$).

Clause 19. The compound of clause 15, or a pharmaceutically acceptable salt thereof, wherein G$^1$ is

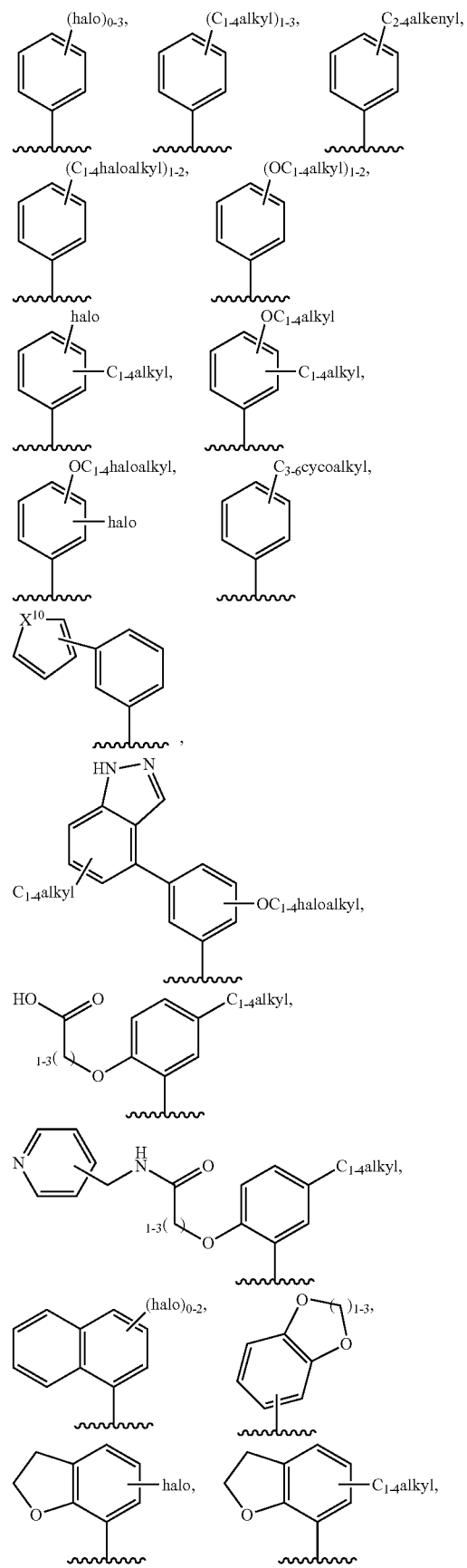

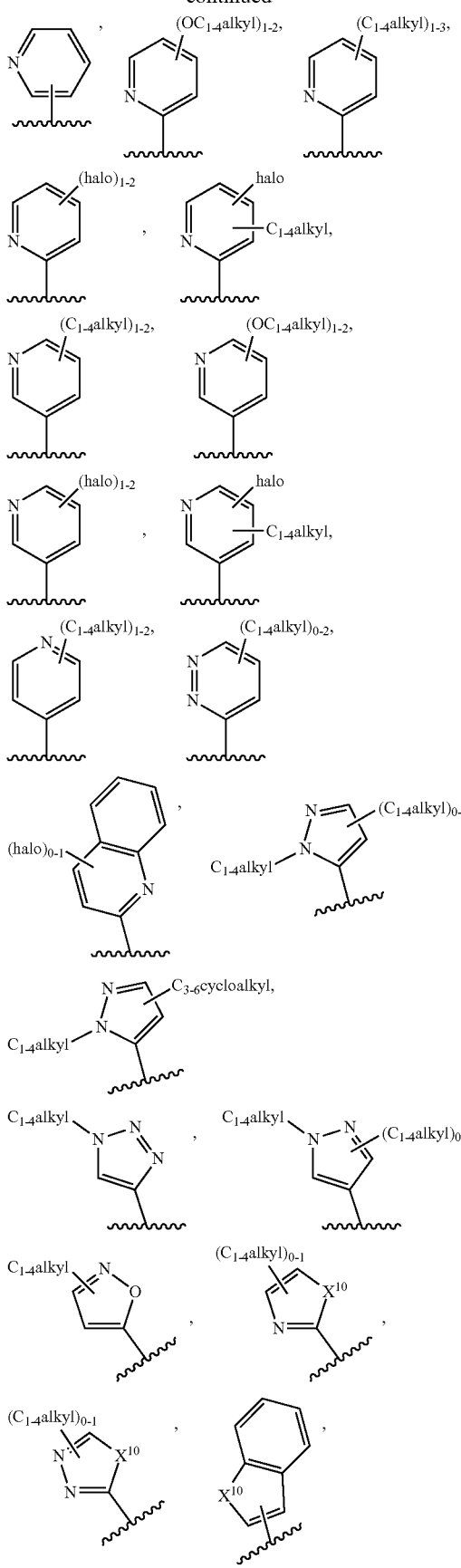
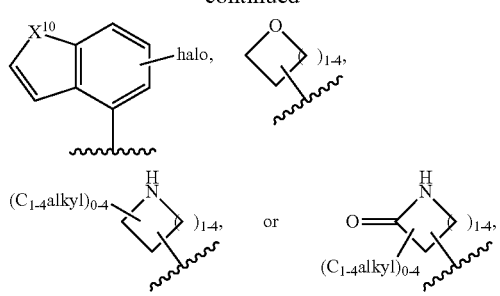
wherein $X^{10}$ is O, S, NH, or $NC_{1-4}$alkyl.
Clause 20. The compound of clause 15, or a pharmaceutically acceptable salt thereof, wherein $G^1$ is
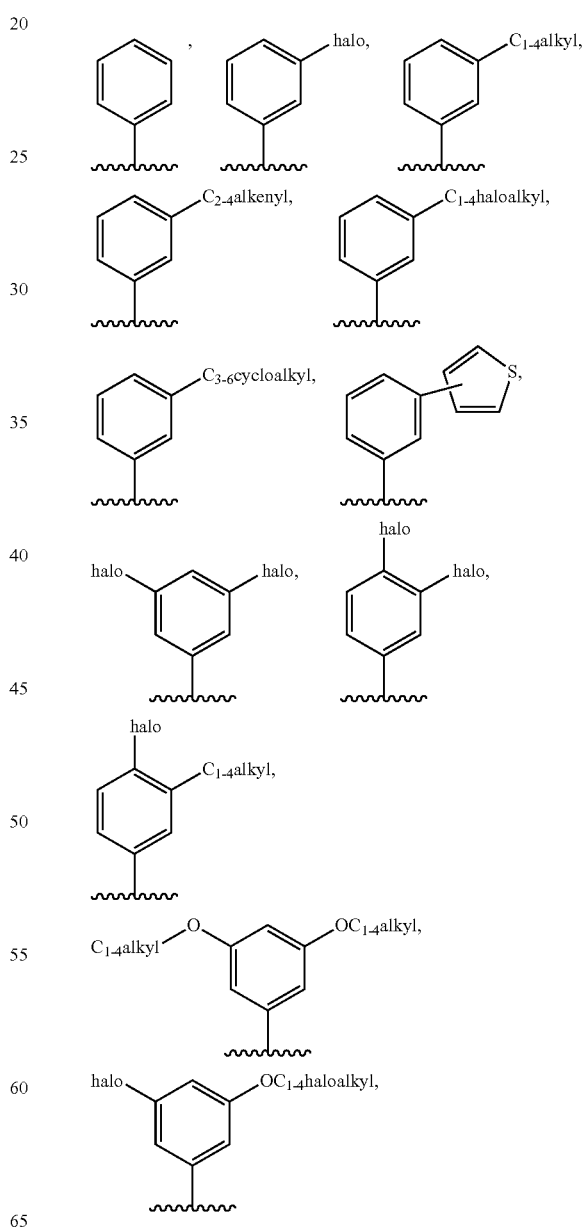

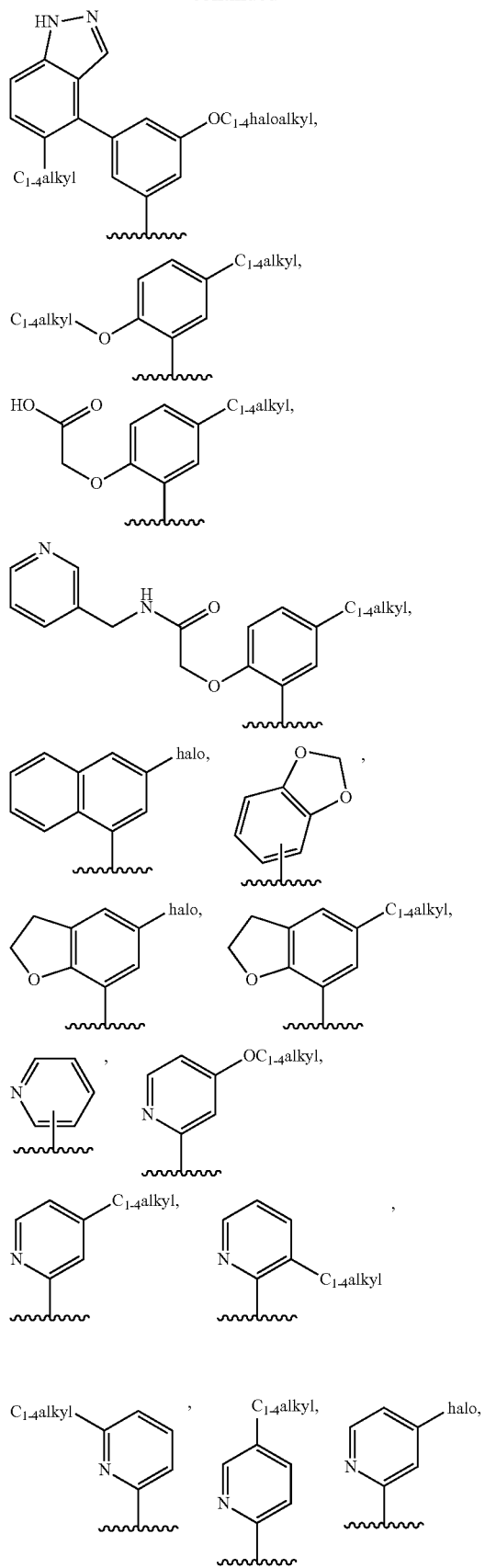
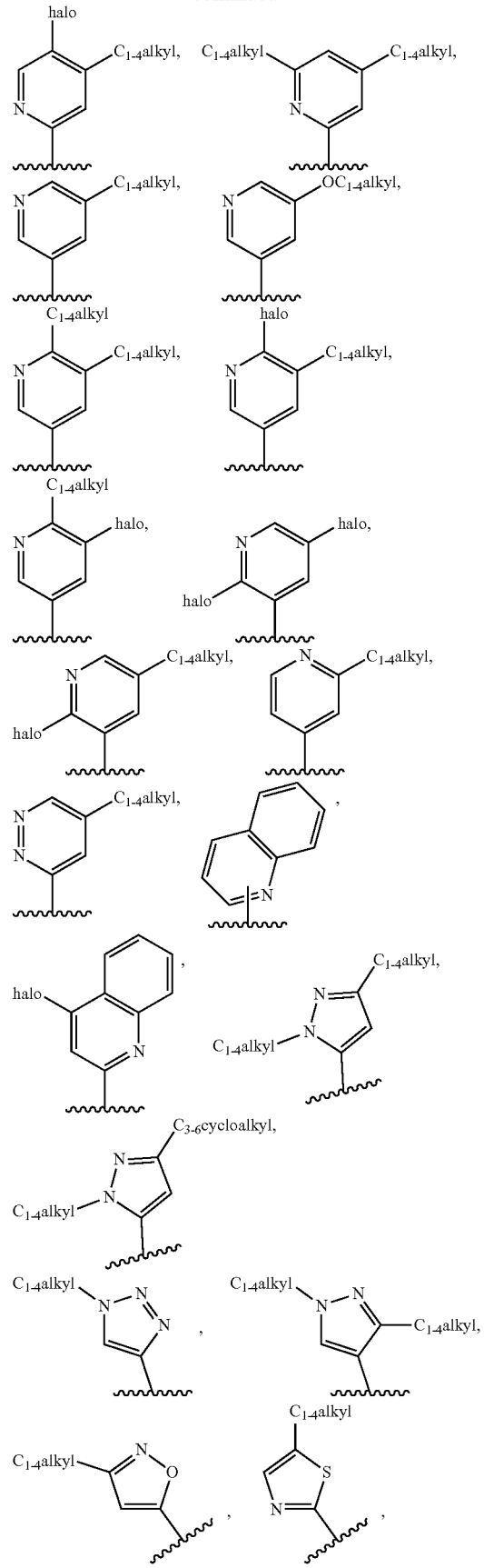

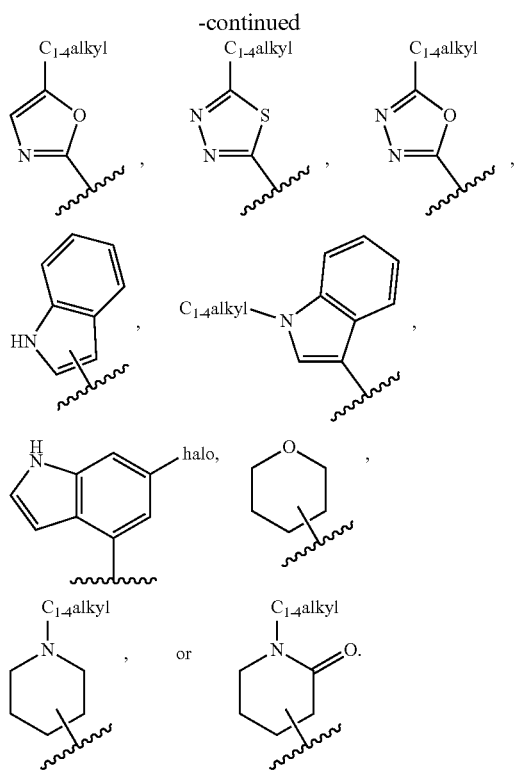
Clause 21. The compound of clause 15, or a pharmaceutically acceptable salt thereof, wherein
G¹ is
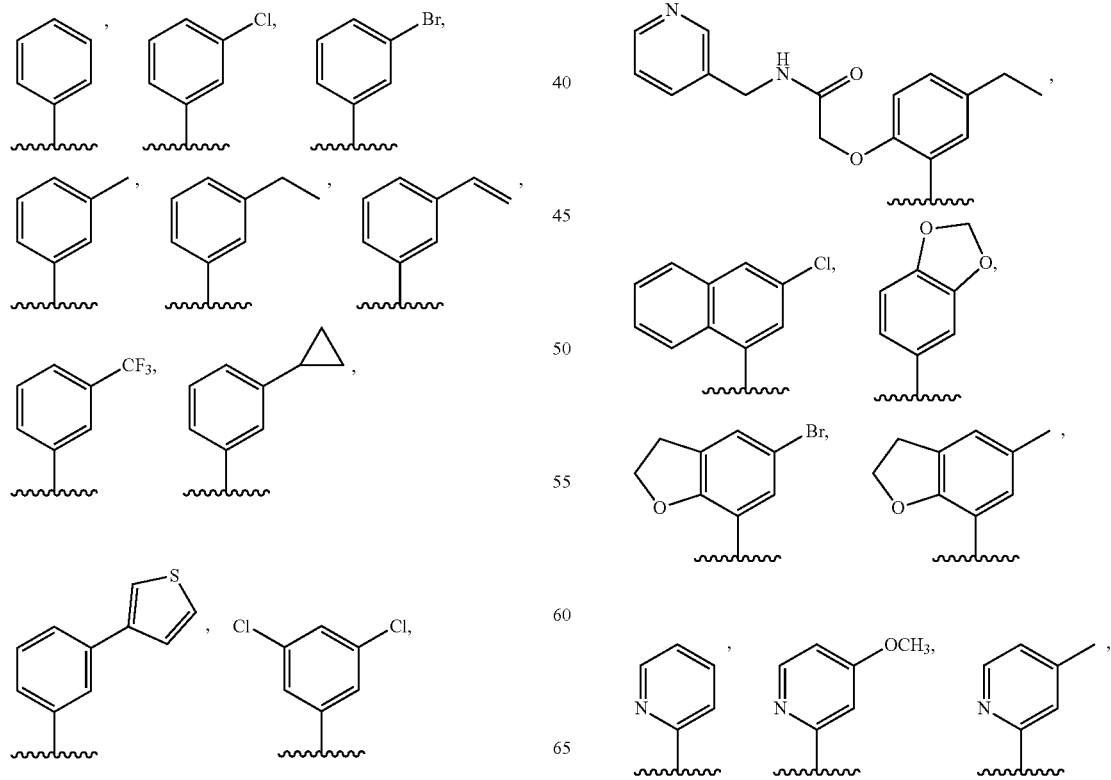
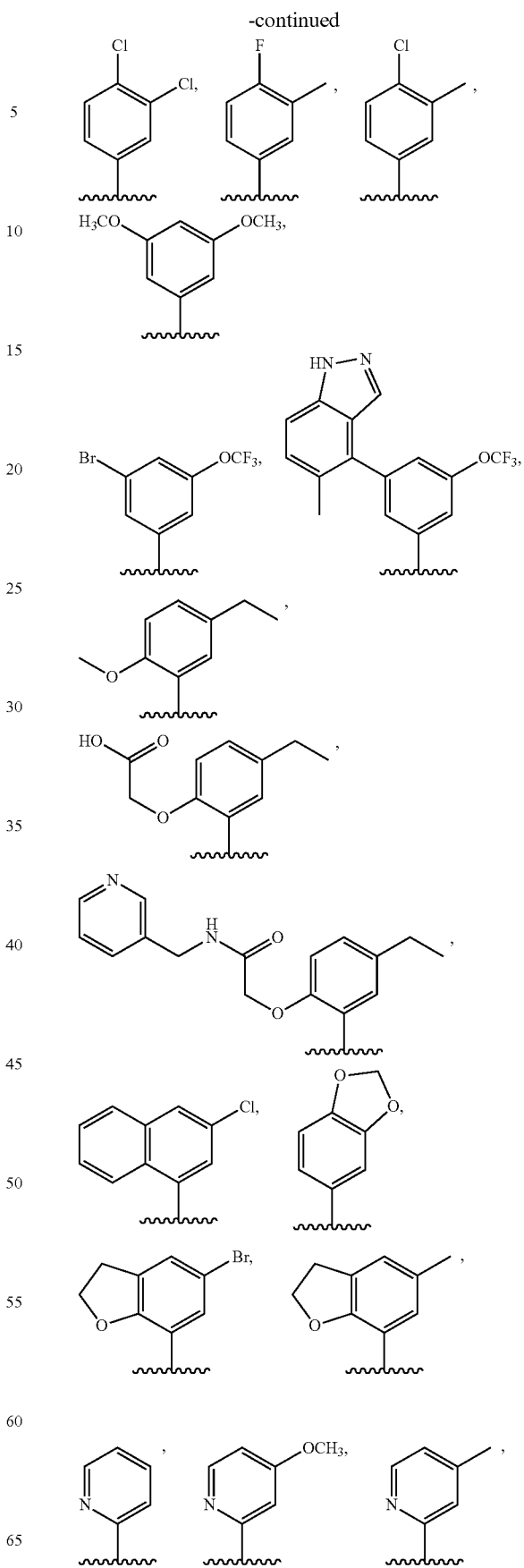

347
-continued

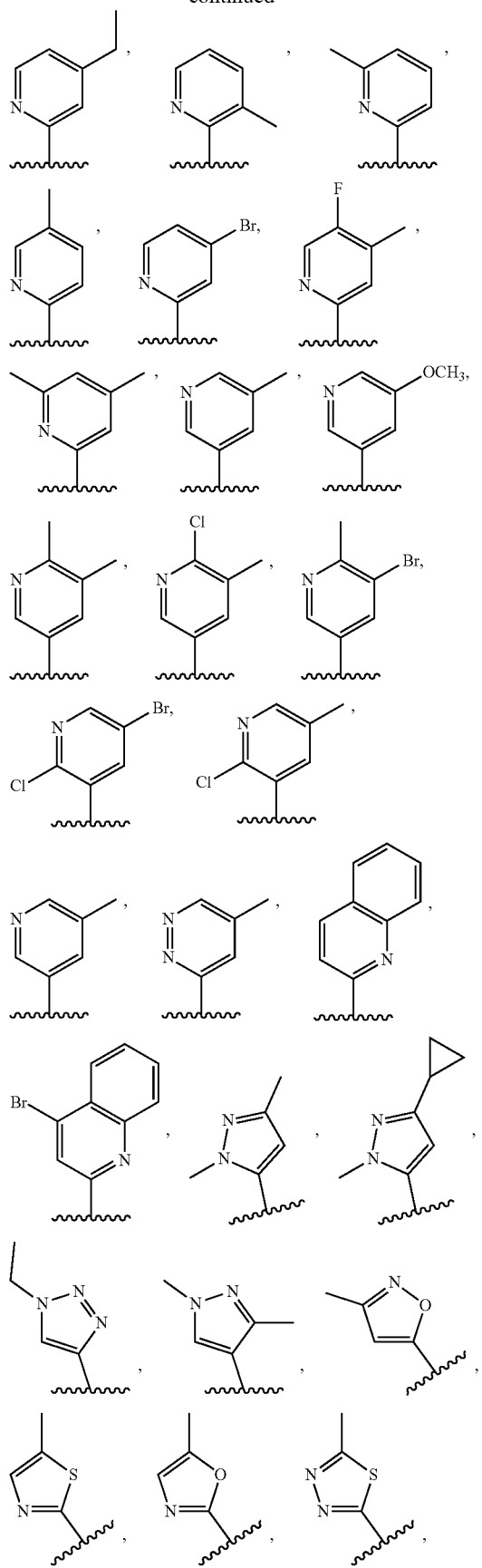

348
-continued

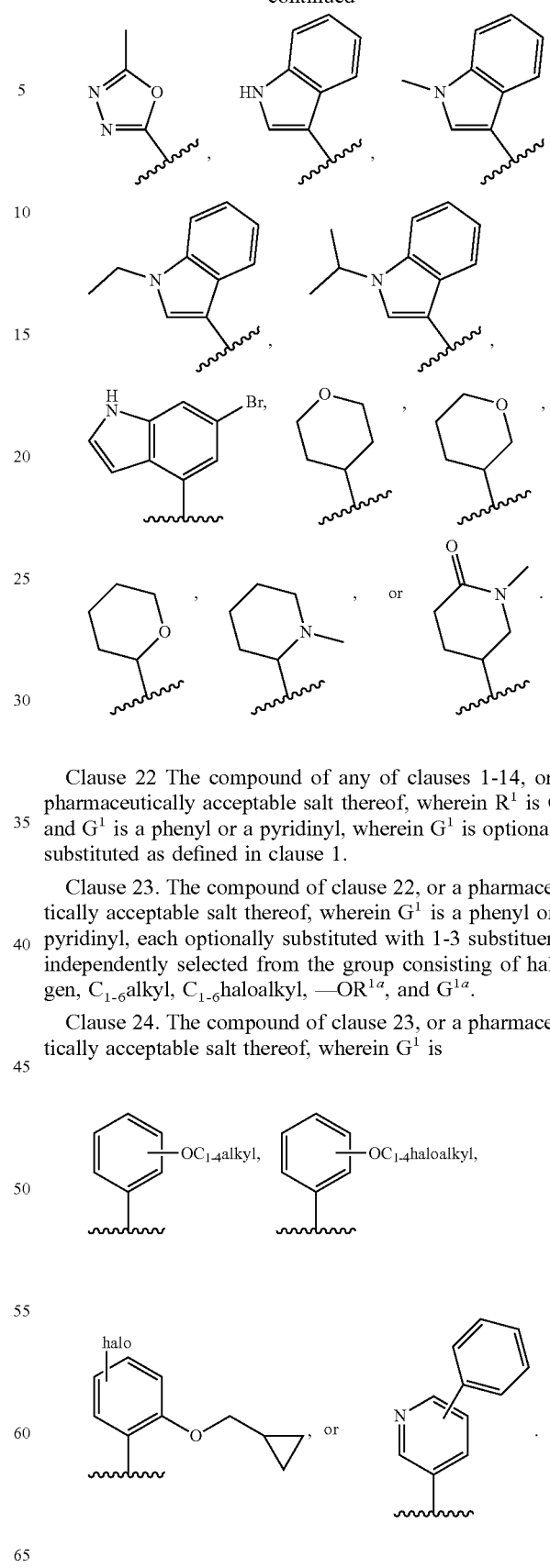

Clause 22 The compound of any of clauses 1-14, or a pharmaceutically acceptable salt thereof, wherein $R^1$ is $G^1$ and $G^1$ is a phenyl or a pyridinyl, wherein $G^1$ is optionally substituted as defined in clause 1.

Clause 23. The compound of clause 22, or a pharmaceutically acceptable salt thereof, wherein $G^1$ is a phenyl or a pyridinyl, each optionally substituted with 1-3 substituents independently selected from the group consisting of halogen, $C_{1-6}$alkyl, $C_{1-6}$haloalkyl, —$OR^{1a}$, and $G^{1a}$.

Clause 24. The compound of clause 23, or a pharmaceutically acceptable salt thereof, wherein $G^1$ is Clause 25. The compound of clause 23, or a pharmaceutically acceptable salt thereof, wherein $G^1$ is

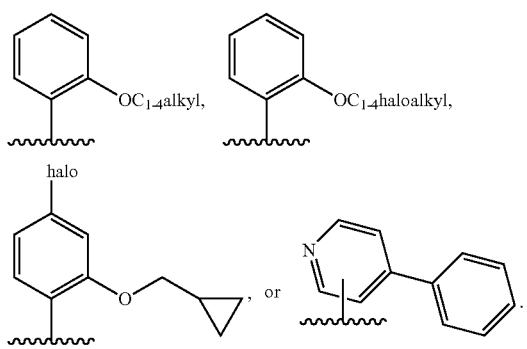

Clause 26. The compound of clause 23, or a pharmaceutically acceptable salt thereof, wherein G¹ is

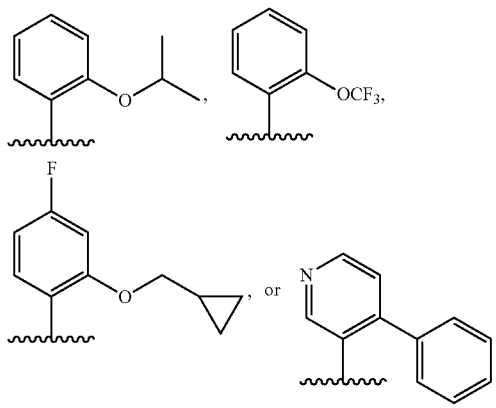

Clause 27. The compound of clause 15, or a pharmaceutically acceptable salt thereof, wherein G¹ is a phenyl or a 5- to 6-membered heteroaryl, wherein G¹ is optionally substituted as defined in clause 2.

Clause 28. The compound of clause 27, or a pharmaceutically acceptable salt thereof, wherein the 5- to 6-membered heteroaryl of G¹ contains 1-3 nitrogen atoms.

Clause 29. The compound of clause 28, or a pharmaceutically acceptable salt thereof, wherein G¹ is a phenyl, pyridinyl, pyrazolyl, or triazolyl, and G¹ is optionally substituted as defined in clause 2.

Clause 30. The compound of any of clauses 1-15, or a pharmaceutically acceptable salt thereof, wherein G¹ is

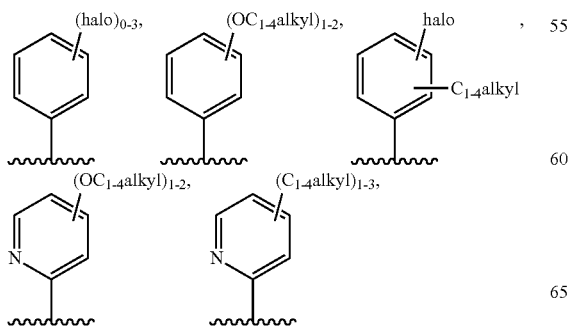

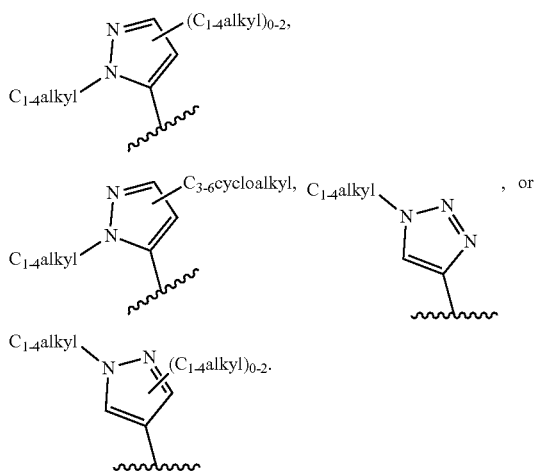

Clause 31. The compound of any of clauses 1-15, or a pharmaceutically acceptable salt thereof, wherein G¹ is

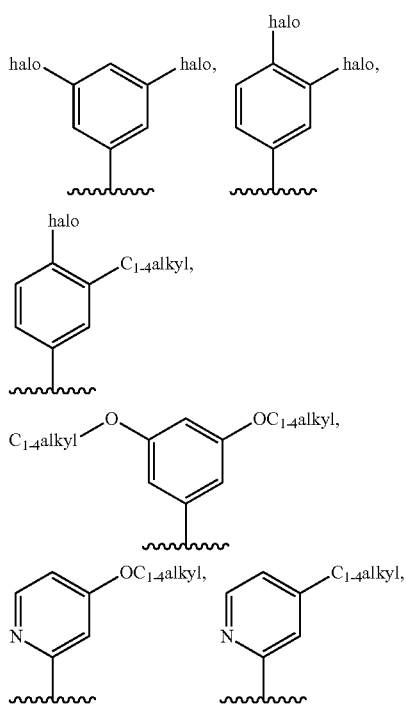

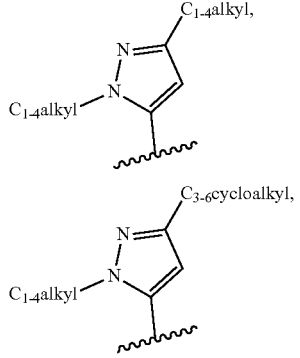

-continued

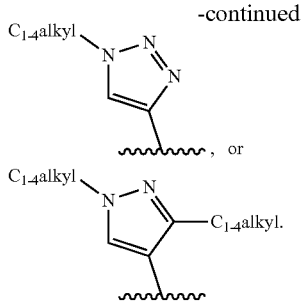

Clause 32. The compound of any of clauses 1-15, or a pharmaceutically acceptable salt thereof, wherein G$^1$ is

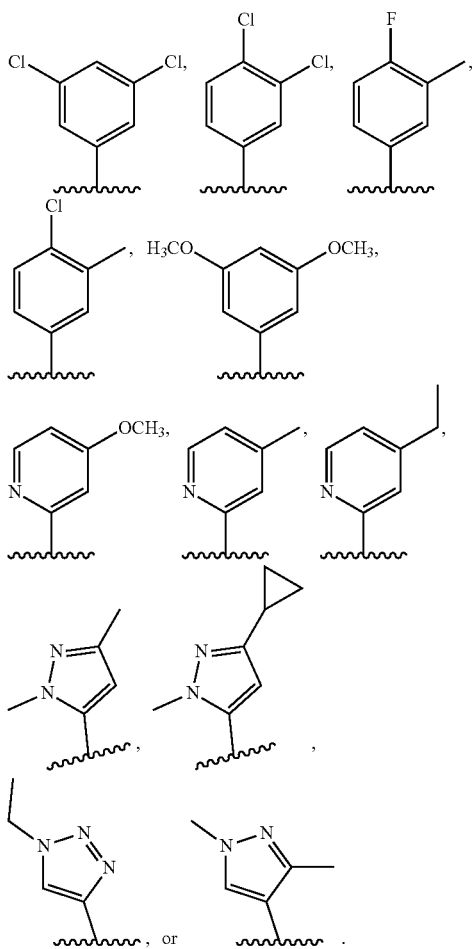

Clause 33. The compound of any of clauses 1-32, or a pharmaceutically acceptable salt thereof, wherein R$^b$ is hydrogen.

Clause 34. The compound of any of clauses 1-33, or a pharmaceutically acceptable salt thereof, wherein R$^4$ is hydrogen, —OR$^{4a}$, or G$^2$.

Clause 35. The compound of clause 34, or a pharmaceutically acceptable salt thereof, wherein R$^4$ is hydrogen.

Clause 36. The compound of clause 34, or a pharmaceutically acceptable salt thereof, wherein R$^4$ is —OR$^{4a}$.

Clause 37. The compound of clause 36, or a pharmaceutically acceptable salt thereof, wherein R$^{4a}$ is C$_{1-6}$haloalkyl, G$^2$, or C$_{1-3}$alkylene-G$^2$.

Clause 38. The compound of clause 37, or a pharmaceutically acceptable salt thereof, wherein G$^2$ is a C$_{3-10}$carbocyclyl optionally substituted with 1-4 substituents independently selected from the group consisting of C$_{1-4}$alkyl and halogen.

Clause 39. The compound of clause 38, or a pharmaceutically acceptable salt thereof, wherein G$^2$ is a C$_{3-8}$cycloalkyl optionally substituted with 1-4 substituents independently selected from the group consisting of C$_{1-4}$alkyl and halogen.

Clause 40. The compound of clause 34, or a pharmaceutically acceptable salt thereof, wherein
R$^4$ is G$^2$; and
G$^2$ is a C$_{3-10}$carbocyclyl, a 6- to 12-membered aryl, or a 5- to 12-membered heteroaryl, and optionally substituted as defined in clause 1 or 2.

Clause 41. The compound of clause 40, or a pharmaceutically acceptable salt thereof, wherein G$^2$ is a C$_{3-8}$cycloalkyl, a phenyl, or a 5- to 6-membered heteroaryl, and optionally substituted as defined in clause 1 or 2.

Clause 42. The compound of clause 41, or a pharmaceutically acceptable salt thereof, wherein the 5- to 6-membered heteroaryl of G$^2$ contains 1-3 heteroatoms independently selected from the group consisting of oxygen and nitrogen.

Clause 43. The compound of clause 42, or a pharmaceutically acceptable salt thereof, wherein G$^2$ is cyclopropyl, phenyl, pyridinyl, pyrimidinyl, pyrazolyl, imidazolyl, or isoxazoyl, and G$^2$ is optionally substituted as defined in clause 1.

Clause 44. The compound of clause 42, or a pharmaceutically acceptable salt thereof, wherein G$^2$ is cyclopropyl, phenyl, pyridinyl, pyrazolyl, imidazolyl, or isoxazoyl, and G$^2$ is optionally substituted as defined in clause 2.

Clause 45. The compound of any of clauses 1-44, or a pharmaceutically acceptable salt thereof, wherein G$^2$ is optionally substituted with 1-4 substituents independently selected from the group consisting of halogen, C$_{1-6}$alkyl, and C$_{1-6}$haloalkyl.

Clause 46. The compound of clause 34, or a pharmaceutically acceptable salt thereof, wherein R$^4$ is hydrogen, —OC$_{1-6}$haloalkyl, —OC$_{3-6}$cycloalkyl, —OC$_{1-3}$alkylene-C$_{3-6}$cycloalkyl, C$_{3-6}$cycloalkyl, phenyl,

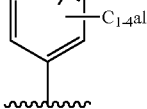

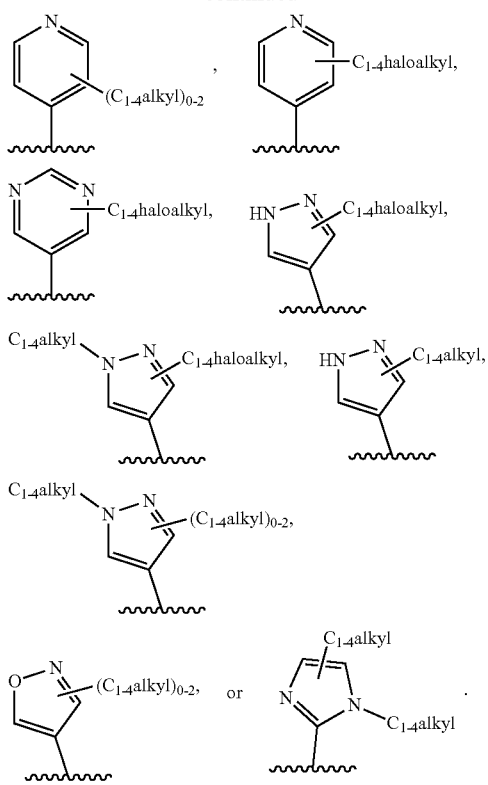
Clause 47. The compound of clause 34, or a pharmaceutically acceptable salt thereof, wherein, $R^4$ is hydrogen, —$OC_{1-2}$haloalkyl, —$OC_{3-4}$cycloalkyl, —$OC_{1-3}$alkylene-$C_{3-4}$cycloalkyl, $C_{3-4}$cycloalkyl, phenyl,
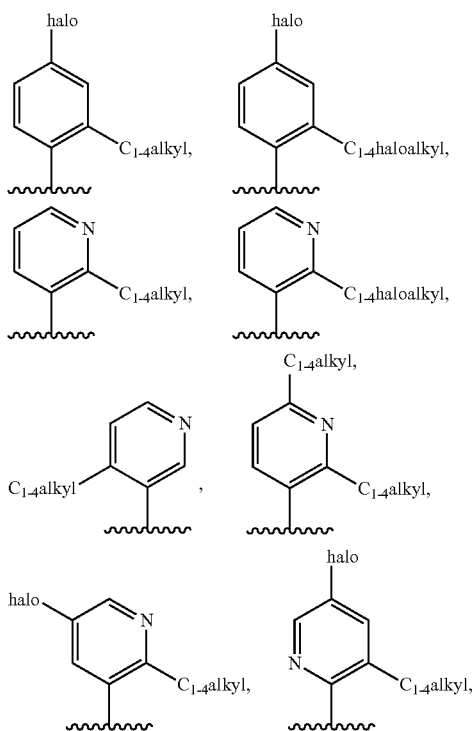
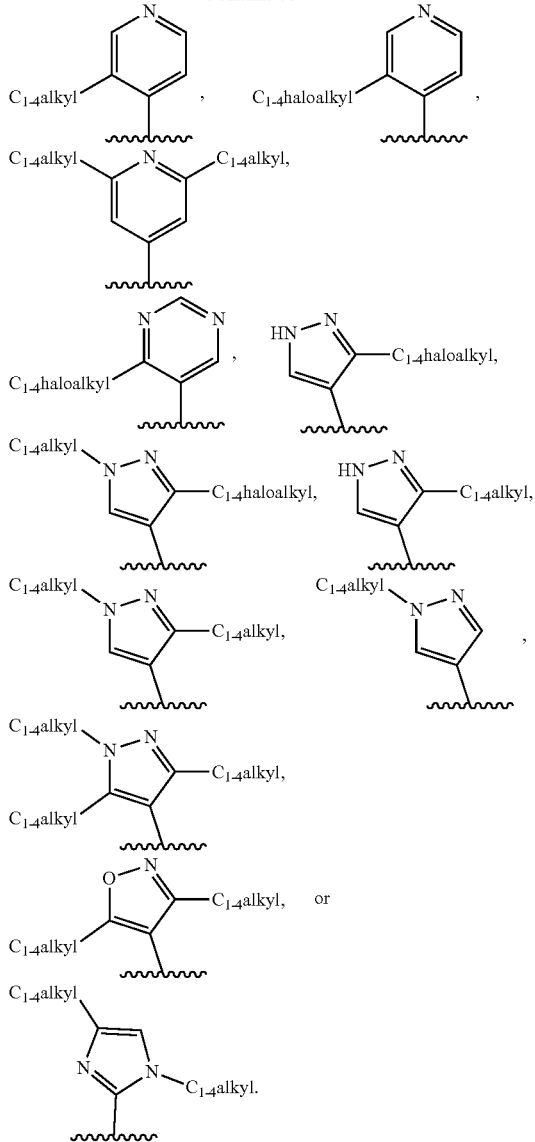
Clause 48. The compound of clause 34, or a pharmaceutically acceptable salt thereof, wherein, $R^4$ is hydrogen, —$OCH_2CF_3$, —O-cyclobutyl, —$OCH_2$-cyclopropyl, cyclopropyl, phenyl,
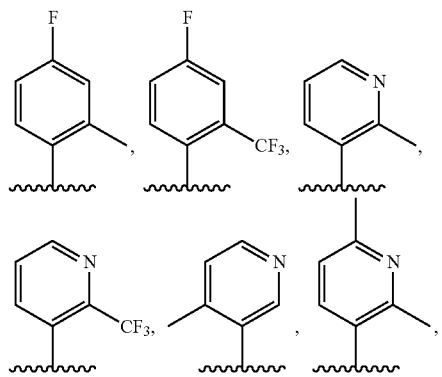

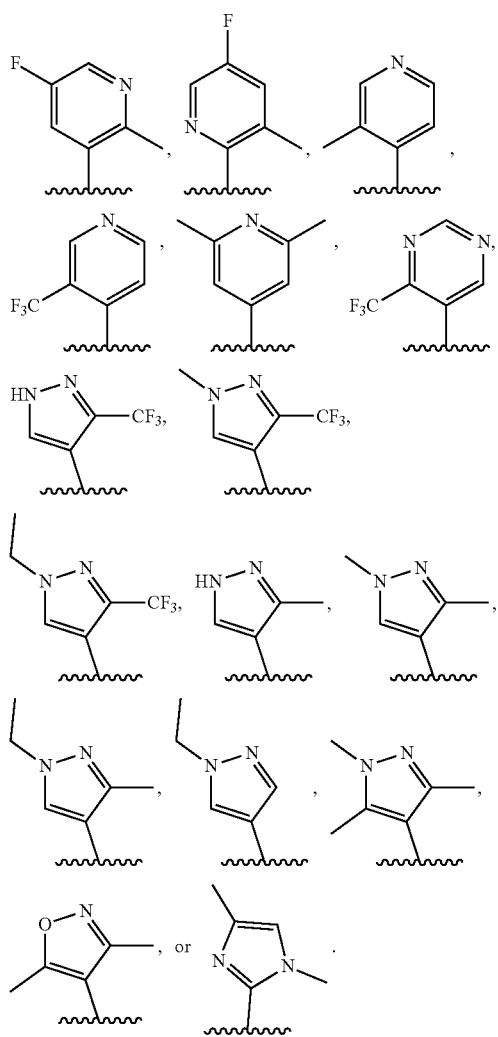

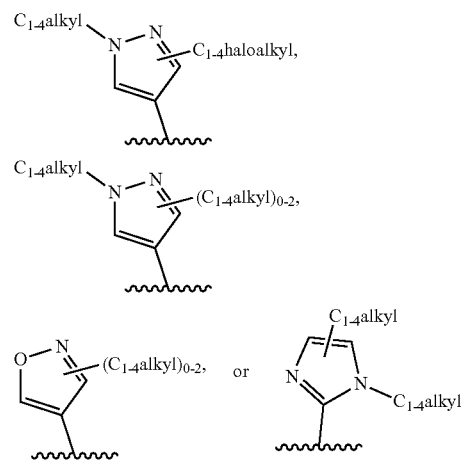

Clause 50. The compound of clause 34, or a pharmaceutically acceptable salt thereof, wherein, $R^4$ is hydrogen, $-OC_{1-2}$haloalkyl, $-OC_{3-4}$cycloalkyl, $-OC_{1-3}$alkylene-$C_{3-4}$cycloalkyl, $C_{3-4}$cycloalkyl, phenyl,

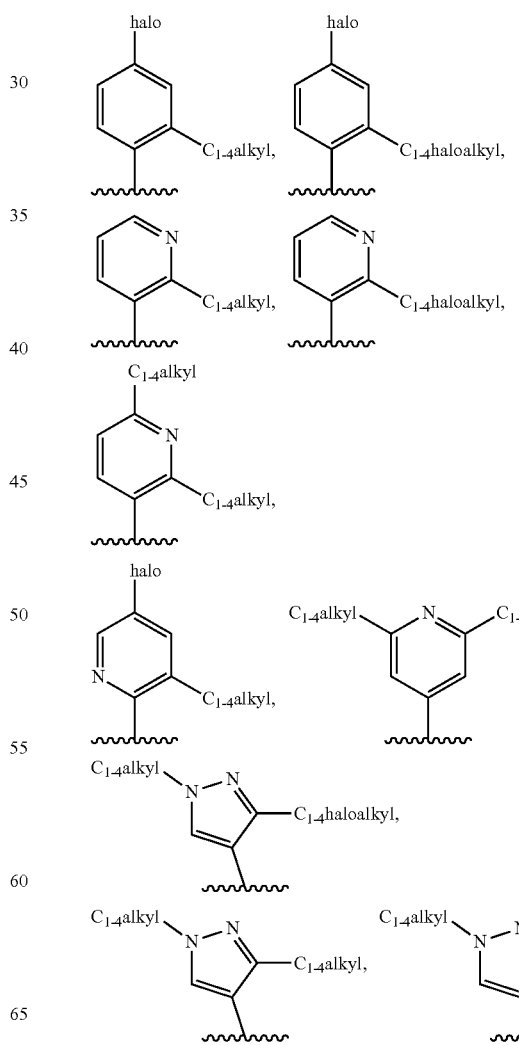

Clause 49. The compound of clause 34, or a pharmaceutically acceptable salt thereof, wherein, $R^4$ is hydrogen, $-OC_{1-6}$haloalkyl, $-OC_{3-6}$cycloalkyl, $-OC_{1-3}$alkylene-$C_{3-6}$cycloalkyl, $C_{3-6}$cycloalkyl, phenyl,

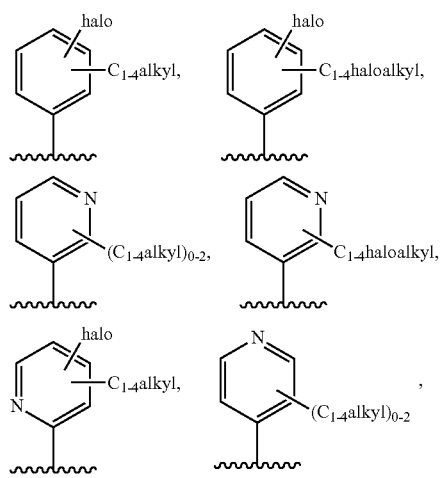

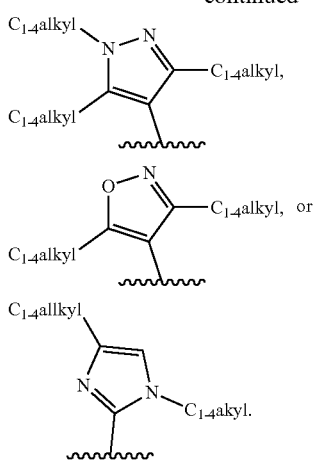

Clause 51. The compound of clause 34, or a pharmaceutically acceptable salt thereof, wherein, $R^4$ is hydrogen, —OCH$_2$CF$_3$, —O-cyclobutyl, —OCH$_2$-cyclopropyl, cyclopropyl, phenyl,

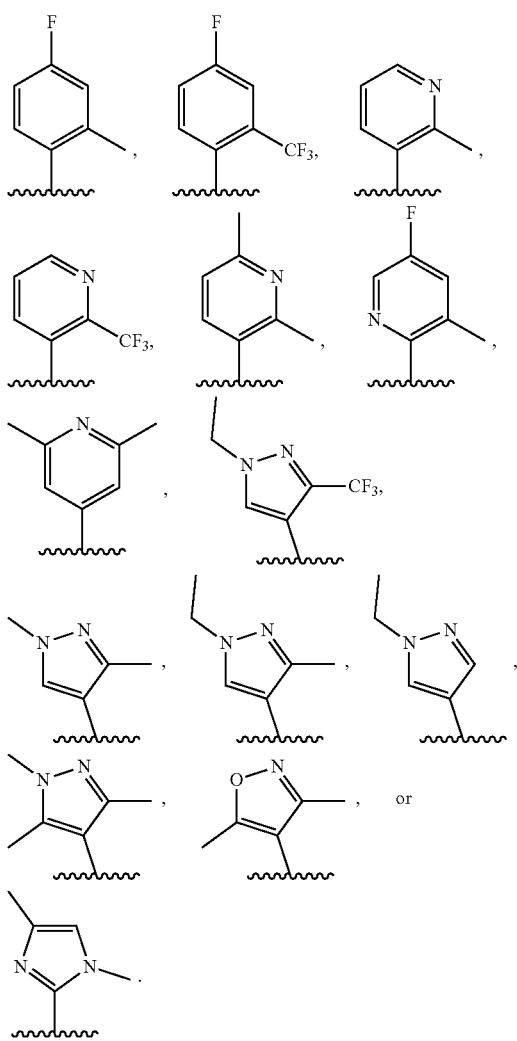

Clause 52. The compound of any of clauses 1-51, or a pharmaceutically acceptable salt thereof, wherein $R^a$ is hydrogen, C$_{1-4}$alkyl (e.g., methyl), or C$_{3-6}$cycloalkyl (e.g., cyclopropyl).

Clause 53. The compound of any of clauses 1-52, or a pharmaceutically acceptable salt thereof, wherein $R^b$ is hydrogen.

Clause 54. The compound of any of clauses 1-53, or a pharmaceutically acceptable salt thereof, wherein $R^{2a}$, $R^{2b}$, $R^{1a}$, $R^{3a}$, and $R^{3b}$ are each hydrogen.

Clause 55. The compound of any of clauses 1-54, or a pharmaceutically acceptable salt thereof, wherein n is 0.

Clause 56. The compound of any of clauses 1-54, or a pharmaceutically acceptable salt thereof, wherein n is 1.

Clause 57. The compound of any of clauses 1-54, or a pharmaceutically acceptable salt thereof, wherein n is 2.

Clause 58. The compound of any of clauses 1-57, or a pharmaceutically acceptable salt thereof, wherein $R^5$ is hydrogen or halogen.

Clause 59. The compound of any of clauses 1-58, or a pharmaceutically acceptable salt thereof, wherein $R^6$ is hydrogen.

Clause 60. The compound of any of clauses 1-59, or a pharmaceutically acceptable salt thereof, wherein $R^{7a}$ and $R^{7b}$ are each hydrogen.

Clause 61. The compound of clause 1 selected from the group consisting of
7-((1H-imidazol-1-yl)methyl)-2-(3,5-dichlorobenzyl)-3,4-dihydroisoquinolin-1(2H)-one;
2-(3,5-dichlorobenzyl)-7-((2-methyl-1H-imidazol-1-yl)methyl)-3,4-dihydroisoquinolin-1(2H)-one;
2-(3,4-dichlorobenzyl)-6-fluoro-7-((2-methyl-1H-imidazol-1-yl)methyl)-3,4-dihydroisoquinolin-1(2H)-one;
2-(3,5-dimethoxybenzyl)-6-fluoro-7-((2-methyl-1H-imidazol-1-yl)methyl)-3,4-dihydroisoquinolin-1(2H)-one;
2-(4-chloro-3-methylbenzyl)-7-((2-methyl-1H-imidazol-1-yl)methyl)-5-phenyl-3,4-dihydroisoquinolin-1(2H)-one;
2-(3,5-dimethoxybenzyl)-5-(4-fluoro-2-methylphenyl)-7-((2-methyl-1H-imidazol-1-yl)methyl)-3,4-dihydroisoquinolin-1(2H)-one;
2-(4-chloro-3-methylbenzyl)-7-((2-methyl-1H-imidazol-1-yl)methyl)-5-(2-methylpyridin-3-yl)-3,4-dihydroisoquinolin-1(2H)-one;
7-((2-cyclopropyl-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;
7-((2-cyclopropyl-1H-imidazol-1-yl)methyl)-5-(1,3-dimethyl-1H-pyrazol-4-yl)-2-((4-methoxypyridin-2-yl)methyl)-3,4-dihydroisoquinolin-1(2H)-one;
2-(3,5-dimethoxybenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;
2-((4-methoxypyridin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;
(S)-2-(cyclopropyl(4-methylpyridin-2-yl)methyl)-5-(4-fluoro-2-methylphenyl)-7-((2-methyl-1H-imidazol-1-yl)methyl)-3,4-dihydroisoquinolin-1(2H)-one;
(S)-2-(cyclopropyl(4-methylpyridin-2-yl)methyl)-7-((2-ethyl-1H-imidazol-1-yl)methyl)-5-(4-fluoro-2-methylphenyl)-3,4-dihydroisoquinolin-1(2H)-one;
7-((2-cyclopropyl-1H-imidazol-1-yl)methyl)-2-((1,3-dimethyl-1H-pyrazol-5-yl)methyl)-5-(1-ethyl-3-(trifluoromethyl)-1H-pyrazol-4-yl)-3,4-dihydroisoquinolin-1(2H)-one;

2-((1-ethyl-1H-1,2,3-triazol-4-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one;

7-((2-cyclopropyl-1H-imidazol-1-yl)methyl)-2-(3,5-dimethoxybenzyl)-5-(4-fluoro-2-methylphenyl)-3,4-dihydroisoquinolin-1(2H)-one;

2-(3,5-dimethoxybenzyl)-7-((2,4-dimethyl-1H-imidazol-1-yl)methyl)-5-(1-methyl-3-(trifluoromethyl)-1H-pyrazol-4-yl)-3,4-dihydroisoquinolin-1(2H)-one;

2-(3,5-dimethoxybenzyl)-7-((2,4-dimethyl-1H-imidazol-1-yl)methyl)-5-(4-fluoro-2-methylphenyl)-3,4-dihydroisoquinolin-1(2H)-one;

7-((2-cyclopropyl-1H-imidazol-1-yl)methyl)-5-(cyclopropylmethoxy)-2-(3,5-dimethoxybenzyl)-3,4-dihydroisoquinolin-1(2H)-one;

2-((1,3-dimethyl-1H-pyrazol-5-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one;

5-(1-ethyl-3-(trifluoromethyl)-1H-pyrazol-4-yl)-2-((4-ethylpyridin-2-yl)methyl)-7-((2-methyl-1H-imidazol-1-yl)methyl)-3,4-dihydroisoquinolin-1(2H)-one;

7-((2,4-dimethyl-1H-imidazol-1-yl)methyl)-5-(1-ethyl-3-(trifluoromethyl)-1H-pyrazol-4-yl)-2-((4-ethylpyridin-2-yl)methyl)-3,4-dihydroisoquinolin-1(2H)-one;

(S)-7-((2-cyclopropyl-1H-imidazol-1-yl)methyl)-5-(cyclopropylmethoxy)-2-(1-(4-fluoro-3-methylphenyl)ethyl)-3,4-dihydroisoquinolin-1(2H)-one;

(S)-2-(1-(4-fluoro-3-methylphenyl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(3,5-dimethoxybenzyl)-6-fluoro-7-((2-imino-3-methyl-2,3-dihydro-1H-imidazol-1-yl)methyl)-3,4-dihydroisoquinolin-1(2H)-one;

2-(3,4-dichlorobenzyl)-6-fluoro-7-((2-imino-3-methyl-2,3-dihydro-1H-imidazol-1-yl)methyl)-3,4-dihydroisoquinolin-1(2H)-one;

2-(4-chloro-3-methylbenzyl)-7-((2-imino-3-methyl-2,3-dihydro-1H-imidazol-1-yl)methyl)-5-(2-methylpyridin-3-yl)-3,4-dihydroisoquinolin-1(2H)-one;

2-(4-chloro-3-methylbenzyl)-5-(4-fluoro-2-methylphenyl)-7-((2-imino-3-methyl-2,3-dihydro-1H-imidazol-1-yl)methyl)-3,4-dihydroisoquinolin-1(2H)-one;

2-(3,5-dimethoxybenzyl)-5-(4-fluoro-2-methylphenyl)-7-((2-imino-3-methyl-2,3-dihydro-1H-imidazol-1-yl)methyl)-3,4-dihydroisoquinolin-1(2H)-one;

2-(cyclopropyl(4-methylpyridin-2-yl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one;

5-(4-fluoro-2-methylphenyl)-2-(4-fluoro-3-methylbenzyl)-7-((2-imino-3-methyl-2,3-dihydro-1H-imidazol-1-yl)methyl)-3,4-dihydroisoquinolin-1(2H)-one;

(S)-2-(cyclopropyl(4-fluoro-3-methylphenyl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one;

(R)-2-(cyclopropyl(4-methylpyridin-2-yl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one;

(S)-2-(cyclopropyl(4-fluoro-3-methylphenyl)methyl)-7-((2-imino-3-methyl-2,3-dihydro-1H-imidazol-1-yl)methyl)-5-(2-(trifluoromethyl)pyridin-3-yl)-3,4-dihydroisoquinolin-1(2H)-one;

2-(3,5-dimethoxybenzyl)-7-((2-imino-3-methyl-2,3-dihydro-1H-imidazol-1-yl)methyl)-5-(2-(trifluoromethyl)pyridin-3-yl)-3,4-dihydroisoquinolin-1(2H)-one;

(S)-2-(cyclopropyl(4-methylpyridin-2-yl)methyl)-7-((2-imino-3-methyl-2,3-dihydro-1H-imidazol-1-yl)methyl)-5-(2-(trifluoromethyl)pyridin-3-yl)-3,4-dihydroisoquinolin-1(2H)-one;

(S)-2-(cyclopropyl(4-methylpyridin-2-yl)methyl)-5-(4-fluoro-2-methylphenyl)-7-((2-imino-3-methyl-2,3-dihydro-1H-imidazol-1-yl)methyl)-3,4-dihydroisoquinolin-1(2H)-one;

7-((3-cyclopropyl-2-imino-2,3-dihydro-1H-imidazol-1-yl)methyl)-2-(3,5-dimethoxybenzyl)-5-(4-fluoro-2-methylphenyl)-3,4-dihydroisoquinolin-1(2H)-one;

2-(3,5-dimethoxybenzyl)-7-((2-imino-3-methyl-2,3-dihydro-1H-imidazol-1-yl)methyl)-5-(1-methyl-3-(trifluoromethyl)-1H-pyrazol-4-yl)-3,4-dihydroisoquinolin-1(2H)-one;

(S)-5-(4-fluoro-2-methylphenyl)-2-(1-(4-fluoro-3-methylphenyl)ethyl)-7-((2-imino-3-methyl-2,3-dihydro-1H-imidazol-1-yl)methyl)-3,4-dihydroisoquinolin-1(2H)-one;

7-((2-imino-3-methyl-2,3-dihydro-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

5-(1,3-dimethyl-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one;

7-((2-imino-3-methylimidazolidin-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

7-((3-cyclopropyl-2-iminoimidazolidin-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

7-((3-cyclopropyl-2-imino-2,3-dihydro-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

7-((3-cyclopropyl-2-iminoimidazolidin-1-yl)methyl)-5-(1,3-dimethyl-1H-pyrazol-4-yl)-2-((4-methoxypyridin-2-yl)methyl)-3,4-dihydroisoquinolin-1(2H)-one;

5-(1,3-dimethyl-1H-pyrazol-4-yl)-7-((2-imino-3-methylimidazolidin-1-yl)methyl)-2-((4-methoxypyridin-2-yl)methyl)-3,4-dihydroisoquinolin-1(2H)-one;

7-(3-cyclopropyl-2-imino-2,3-dihydro-1H-imidazol-1-yl)methyl)-5-(1,3-dimethyl-1H-pyrazol-4-yl)-2(4-methoxypyridin-2-yl)methyl)-3,4-dihydroisoquinolin-1(2H)-one;

5-(1-ethyl-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one;

7-(3-cyclopropyl-2-imino-2,3-dihydro-1H-imidazol-1-yl)methyl)-5-(1-ethyl-1H-pyrazol-4-yl)-2-(4-methoxypyridin-2-yl)methyl)-3,4-dihydroisoquinolin-1(2H)-one;

7-(3-cyclopropyl-2-imino-2,3-dihydro-1H-imidazol-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one;

5-(4-fluoro-2-methylphenyl)-7-((2-imino-3-methyl-2,3-dihydro-1H-imidazol-1-yl)methyl)-2-((4-methoxypyridin-2-yl)methyl)-3,4-dihydroisoquinolin-1(2H)-one;

7-((2-imino-3-methyl-2,3-dihydro-1H-imidazol-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one;

5-cyclopropyl-7-((2-imino-3-methyl-2,3-dihydro-1H-imidazol-1-yl)methyl)-2-((4-methoxypyridin-2-yl)methyl)-3,4-dihydroisoquinolin-1(2H)-one;

5-(1-ethyl-3-(trifluoromethyl)-1H-pyrazol-4-yl)-7-((2-imino-3-methylimidazolidin-1-yl)methyl)-2-((4-methoxypyridin-2-yl)methyl)-3,4-dihydroisoquinolin-1(2H)-one;

5-(1-ethyl-3-(trifluoromethyl)-1H-pyrazol-4-yl)-7-((3-imino-6,7-dihydro-3H-pyrrolo[1,2-c]imidazol-2(5H)-yl)methyl)-2-((4-methoxypyridin-2-yl)methyl)-3,4-dihydroisoquinolin-1(2H)-one;

5-(1-ethyl-3-(trifluoromethyl)-1H-pyrazol-4-yl)-7-((2-imino-3-methyl-2,3-dihydro-1H-imidazol-1-yl)methyl)-2-((4-methoxypyridin-2-yl)methyl)-3,4-dihydroisoquinolin-1(2H)-one;

7-(3-cyclopropyl-2-imino-2,3-dihydro-1H-imidazol-1-yl)methyl)-5-(1-ethyl-3-(trifluoromethyl)-1H-pyrazol-4-yl)-2-((4-methoxypyridin-2-yl)methyl)-3,4-dihydroisoquinolin-1(2H)-one;

2-(3,5-dimethoxybenzyl)-5-(5-fluoro-3-methylpyridin-2-yl)-7-((2-imino-3-methyl-2,3-dihydro-1H-imidazol-1-yl)methyl)-3,4-dihydroisoquinolin-1(2H)-one;

7-(2-imino-3-methyl-2,3-dihydro-1H-imidazol-1-yl)methyl)-2-((4-methoxypyridin-2-yl)methyl)-5-(2-methylpyridin-3-yl)-3,4-dihydroisoquinolin-1(2H)-one;

7-(3-(difluoromethyl)-2-imino-2,3-dihydro-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

7-(3-imino-6,7-dihydro-3H-pyrrolo[1,2-c]imidazol-2(5H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

5-(1-ethyl-3-methyl-1H-pyrazol-4-yl)-7-((2-imino-3-methyl-2,3-dihydro-1H-imidazol-1-yl)methyl)-2-(4-methoxypyridin-2-yl)methyl)-3,4-dihydroisoquinolin-1(2H)-one;

2-(3,5-dimethoxybenzyl)-7-((2-imino-3-methyl-2,3-dihydro-1H-imidazol-1-yl)methyl)-5-(1,3,5-trimethyl-1H-pyrazol-4-yl)-3,4-dihydroisoquinolin-1(2H)-one;

7-(2-amino-1H-imidazol-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

(S)-5-(1-ethyl-3-(trifluoromethyl)-1H-pyrazol-4-yl)-7-((2-imino-3-methyl-2,3-dihydro-1H-imidazol-1-yl)methyl)-2-(1-(4-methoxypyridin-2-yl)ethyl)-3,4-dihydroisoquinolin-1(2H)-one;

(S)-7-(3-(difluoromethyl)-2-imino-2,3-dihydro-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

2-(3,5-dimethoxybenzyl)-5-(2,6-dimethylpyridin-3-yl)-7-((2-imino-3-methyl-2,3-dihydro-1H-imidazol-1-yl)methyl)-3,4-dihydroisoquinolin-1(2H)-one;

5-cyclobutoxy-2-(3,5-dimethoxybenzyl)-7-((2-imino-3-methyl-2,3-dihydro-1H-imidazol-1-yl)methyl)-3,4-dihydroisoquinolin-1(2H)-one;

2-(3,5-dimethoxybenzyl)-5-(1,3-dimethyl-1H-pyrazol-4-yl)-7-((2-imino-3-methyl-2,3-dihydro-1H-imidazol-1-yl)methyl)-3,4-dihydroisoquinolin-1(2H)-one;

(S)-7-((2-imino-3-methyl-2,3-dihydro-1H-imidazol-1-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one;

(S)-7-(3-(difluoromethyl)-2-imino-2,3-dihydro-1H-imidazol-1-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one;

2-(3,5-dimethoxybenzyl)-7-((2-imino-3-methyl-2,3-dihydro-1H-imidazol-1-yl)methyl)-5-(2,2,2-trifluoroethoxy)-3,4-dihydroisoquinolin-1(2H)-one;

2-((1,3-dimethyl-1H-pyrazol-5-yl)methyl)-5-(1-ethyl-3-(trifluoromethyl)-1H-pyrazol-4-yl)-7-((2-imino-3-methyl-2,3-dihydro-1H-imidazol-1-yl)methyl)-3,4-dihydroisoquinolin-1(2H)-one;

5-(cyclopropylmethoxy)-2-(3,5-dimethoxybenzyl)-7-((2-imino-3-methyl-2,3-dihydro-1H-imidazol-1-yl)methyl)-3,4-dihydroisoquinolin-1(2H)-one;

2-(3,5-dimethoxybenzyl)-5-(3,5-dimethylisoxazol-4-yl)-7-((2-imino-3-methyl-2,3-dihydro-1H-imidazol-1-yl)methyl)-3,4-dihydroisoquinolin-1(2H)-one;

2-((1,3-dimethyl-1H-pyrazol-4-yl)methyl)-5-(1-ethyl-3-(trifluoromethyl)-1H-pyrazol-4-yl)-7-((2-imino-3-methyl-2,3-dihydro-1H-imidazol-1-yl)methyl)-3,4-dihydroisoquinolin-1(2H)-one;

(S)-5-(cyclopropylmethoxy)-2-(1-(4-fluoro-3-methylphenyl)ethyl)-7-((2-imino-3-methyl-2,3-dihydro-1H-imidazol-1-yl)methyl)-3,4-dihydroisoquinolin-1(2H)-one;

(S)-2-(1-(4-fluoro-3-methylphenyl)ethyl)-7-((2-imino-3-methyl-2,3-dihydro-1H-imidazol-1-yl)methyl)-5-(1-methyl-3-(trifluoromethyl)-1H-pyrazol-4-yl)-3,4-dihydroisoquinolin-1(2H)-one;

2-(3,5-dimethoxybenzyl)-7-((2-iminooxazol-3(2H)-yl)methyl)-5-(2-(trifluoromethyl)pyridin-3-yl)-3,4-dihydroisoquinolin-1(2H)-one;

2-(3,5-dimethoxybenzyl)-5-(4-fluoro-2-methylphenyl)-7-((2-iminooxazol-3(2H)-yl)methyl)-3,4-dihydroisoquinolin-1(2H)-one;

2-(3,5-dimethoxybenzyl)-7-((2-iminooxazolidin-3-yl)methyl)-5-(2-(trifluoromethyl)pyridin-3-yl)-3,4-dihydroisoquinolin-1(2H)-one;

7-(2-iminooxazolidin-3-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

7-((2-iminooxazol-3(2H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

5-(1,3-dimethyl-1H-pyrazol-4-yl)-7-((2-iminooxazol-3(2H)-yl)methyl)-2-((4-methoxypyridin-2-yl)methyl)-3,4-dihydroisoquinolin-1(2H)-one;

5-(1-ethyl-1H-pyrazol-4-yl)-7-((2-iminooxazolidin-3-yl)methyl)-2-((4-methoxypyridin-2-yl)methyl)-3,4-dihydroisoquinolin-1(2H)-one;

5-(1-ethyl-1H-pyrazol-4-yl)-7-((2-iminooxazol-3(2H)-yl)methyl)-2-((4-methoxypyridin-2-yl)methyl)-3,4-dihydroisoquinolin-1(2H)-one;

7-((2-iminooxazol-3(2H)-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one;

5-(1-ethyl-3-(trifluoromethyl)-1H-pyrazol-4-yl)-7-((2-iminooxazol-3(2H)-yl)methyl)-2-((4-methoxypyridin-2-yl)methyl)-3,4-dihydroisoquinolin-1(2H)-one;

5-(1-ethyl-3-methyl-1H-pyrazol-4-yl)-7-((2-iminooxazol-3(2H)-yl)methyl)-2-(4-methoxypyridin-2-yl)methyl)-3,4-dihydroisoquinolin-1(2H)-one;

(S)-5-(1-ethyl-3-(trifluoromethyl)-1H-pyrazol-4-yl)-7-((2-iminooxazol-3(2H)-yl)methyl)-2-(1-(4-methoxypyridin-2-yl)ethyl)-3,4-dihydroisoquinolin-1(2H)-one;

5-cyclobutoxy-2-(3,5-dimethoxybenzyl)-7-((2-iminooxazol-3(2H)-yl)methyl)-3,4-dihydroisoquinolin-1(2H)-one;

(S)-7-((2-iminooxazol-3(2H)-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one;

2-((1,3-dimethyl-1H-pyrazol-5-yl)methyl)-5-(1-ethyl-3-(trifluoromethyl)-1H-pyrazol-4-yl)-7-((2-iminoooxazol-3(2H)-yl)methyl)-3,4-dihydroisoquinolin-1(2H)-one;

2-((1,3-dimethyl-1H-pyrazol-5-yl)methyl)-5-(1-ethyl-3-(trifluoromethyl)-1H-pyrazol-4-yl)-7-((2-iminoooxazolidin-3-yl)methyl)-3,4-dihydroisoquinolin-1(2H)-one;

2-((1-ethyl-1H-1,2,3-triazol-4-yl)methyl)-5-(1-ethyl-3-(trifluoromethyl)-1H-pyrazol-4-yl)-7-((2-iminoooxazol-3(2H)-yl)methyl)-3,4-dihydroisoquinolin-1(2H)-one;

2-((1,3-dimethyl-1H-pyrazol-4-yl)methyl)-5-(1-ethyl-3-(trifluoromethyl)-1H-pyrazol-4-yl)-7-((2-iminoooxazol-3(2H)-yl)methyl)-3,4-dihydroisoquinolin-1(2H)-one;

2-((1,3-dimethyl-1H-pyrazol-4-yl)methyl)-5-(1-ethyl-3-(trifluoromethyl)-1H-pyrazol-4-yl)-7-((2-iminoooxazolidin-3-yl)methyl)-3,4-dihydroisoquinolin-1(2H)-one;

2-((1-ethyl-1H-1,2,3-triazol-4-yl)methyl)-5-(1-ethyl-3-(trifluoromethyl)-1H-pyrazol-4-yl)-7-((2-iminoooxazolidin-3-yl)methyl)-3,4-dihydroisoquinolin-1(2H)-one;

2-(3,5-dimethoxybenzyl)-5-(4-fluoro-2-methylphenyl)-7-((2-iminothiazolidin-3-yl)methyl)-3,4-dihydroisoquinolin-1(2H)-one;

7-((2-iminothiazol-3(2H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

5-(1-ethyl-1H-pyrazol-4-yl)-7-((2-iminothiazol-3(2H)-yl)methyl)-2-((4-methoxypyridin-2-yl)methyl)-3,4-dihydroisoquinolin-1(2H)-one;

7-((5-fluoro-2-iminothiazol-3(2H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

(S)-5-(1-ethyl-3-(trifluoromethyl)-1H-pyrazol-4-yl)-7-((2-iminothiazol-3(2H)-yl)methyl)-2-(1-(4-methoxypyridin-2-yl)ethyl)-3,4-dihydroisoquinolin-1(2H)-one;

(S)-7-((2-iminothiazol-3(2H)-yl)methyl)-2-(1-(4-methoxypyridin-2-yl)ethyl)-5-(1-methyl-3-(trifluoromethyl)-1H-pyrazol-4-yl)-3,4-dihydroisoquinolin-1(2H)-one;

2-((1,3-dimethyl-1H-pyrazol-5-yl)methyl)-5-(1-ethyl-3-(trifluoromethyl)-1H-pyrazol-4-yl)-7-((2-iminothiazol-3(2H)-yl)methyl)-3,4-dihydroisoquinolin-1(2H)-one;

2-(3,5-dimethoxybenzyl)-7-((2-iminopyrrolidin-1-yl)methyl)-5-(2-(trifluoromethyl)pyridin-3-yl)-3,4-dihydroisoquinolin-1(2H)-one;

7-(2-iminopyrrolidin-1-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

2-(3,5-dimethoxybenzyl)-7-((2-iminopyrrolidin-1-yl)methyl)-5-(1-methyl-3-(trifluoromethyl)-1H-pyrazol-4-yl)-3,4-dihydroisoquinolin-1(2H)-one;

5-(1,3-dimethyl-1H-pyrazol-4-yl)-7-((2-iminopyrrolidin-1-yl)methyl)-2-((4-methoxypyridin-2-yl)methyl)-3,4-dihydroisoquinolin-1(2H)-one;

5-(1-ethyl-1H-pyrazol-4-yl)-7-((2-iminopyrrolidin-1-yl)methyl)-2-((4-methoxypyridin-2-yl)methyl)-3,4-dihydroisoquinolin-1(2H)-one;

7-((2-iminopyrrolidin-1-yl)methyl)-5-(1-methyl-3-(trifluoromethyl)-1H-pyrazol-4-yl)-2-(4-methylpyridin-2-yl)methyl)-3,4-dihydroisoquinolin-1(2H)-one;

2-(3,5-dimethoxybenzyl)-5-(4-fluoro-2-methylphenyl)-7-((2-iminopyrrolidin-1-yl)methyl)-3,4-dihydroisoquinolin-1(2H)-one;

5-(4-fluoro-2-methylphenyl)-7-((2-iminopyrrolidin-1-yl)methyl)-2-(4-methoxypyridin-2-yl)methyl)-3,4-dihydroisoquinolin-1(2H)-one;

5-(1-ethyl-3-(trifluoromethyl)-1H-pyrazol-4-yl)-7-((1-iminoisoindolin-2-yl)methyl)-2-((4-methoxypyridin-2-yl)methyl)-3,4-dihydroisoquinolin-1(2H)-one;

2-(3,5-dimethoxybenzyl)-5-(4-fluoro-2-methylphenyl)-7-((2-iminopyridin-1(2H)-yl)methyl)-3,4-dihydroisoquinolin-1(2H)-one;

5-(1,3-dimethyl-1H-pyrazol-4-yl)-7-((2-iminopyridin-1(2H)-yl)methyl)-2-((4-methoxypyridin-2-yl)methyl)-3,4-dihydroisoquinolin-1(2H)-one;

N-((2-(3,5-dimethoxybenzyl)-5-(4-fluoro-2-methylphenyl)-1-oxo-1,2,3,4-tetrahydroisoquinolin-7-yl)methyl)cyclopropanecarboximidamide;

N-((5-(1,3-dimethyl-1H-pyrazol-4-yl)-2-((4-methoxypyridin-2-yl)methyl)-1-oxo-1,2,3,4-tetrahydroisoquinolin-7-yl)methyl)cyclopropanecarboximidamide;

2,2,2-trifluoro-N-((2-((4-methoxypyridin-2-yl)methyl)-5-(1-methyl-3-(trifluoromethyl)-1H-pyrazol-4-yl)-1-oxo-1,2,3,4-tetrahydroisoquinolin-7-yl)methyl)acetimidamide;

2-(3,5-dimethoxybenzyl)-5-(4-fluoro-2-methylphenyl)-7-((5-imino-1-methyl-1,5-dihydro-4H-1,2,4-triazol-4-yl)methyl)-3,4-dihydroisoquinolin-1(2H)-one;

2-(3,5-dimethoxybenzyl)-7-((5-imino-1-methyl-1,5-dihydro-4H-1,2,4-triazol-4-yl)methyl)-5-(1-methyl-3-(trifluoromethyl)-1H-pyrazol-4-yl)-3,4-dihydroisoquinolin-1(2H)-one;

5-(1-ethyl-3-(trifluoromethyl)-1H-pyrazol-4-yl)-7-((5-imino-1-methyl-1,5-dihydro-4H-1,2,4-triazol-4-yl)methyl)-2-((4-methoxypyridin-2-yl)methyl)-3,4-dihydroisoquinolin-1(2H)-one;

2-(3,5-dimethoxybenzyl)-5-(5-fluoro-3-methylpyridin-2-yl)-7-((5-imino-1-methyl-1,5-dihydro-4H-1,2,4-triazol-4-yl)methyl)-3,4-dihydroisoquinolin-1(2H)-one;

7-((3-imino-[1,2,4]triazolo[4,3-a]pyridin-2(3H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

(S)-2-(cyclopropyl(4-methylpyridin-2-yl)methyl)-5-(4-fluoro-2-methylphenyl)-7-(5-imino-1-methyl-1,5-dihydro-4H-1,2,4-triazol-4-yl)methyl)-3,4-dihydroisoquinolin-1(2H)-one;

2-(3,5-dimethoxybenzyl)-5-(2,6-dimethylpyridin-3-yl)-7-((5-imino-1-methyl-1,5-dihydro-4H-1,2,4-triazol-4-yl)methyl)-3,4-dihydroisoquinolin-1(2H)-one;

2-((1,3-dimethyl-1H-pyrazol-5-yl)methyl)-7-((5-imino-1-methyl-1,5-dihydro-4H-1,2,4-triazol-4-yl)methyl)-5-(1-methyl-3-(trifluoromethyl)-1H-pyrazol-4-yl)-3,4-dihydroisoquinolin-1(2H)-one;

5-(1-ethyl-3-(trifluoromethyl)-1H-pyrazol-4-yl)-2-((4-ethylpyridin-2-yl)methyl)-7-(5-imino-1-methyl-1,5-dihydro-4H-1,2,4-triazol-4-yl)methyl)-3,4-dihydroisoquinolin-1(2H)-one;

7-(5-imino-1,2,4-thiadiazol-4(5H)-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

2-((4-methoxypyridin-2-yl)methyl)-7-((1-methyl-1H-imidazol-5-yl)methyl)-5-(1-methyl-3-(trifluoromethyl)-1H-pyrazol-4-yl)-3,4-dihydroisoquinolin-1(2H)-one;

7-(1H-imidazol-2-yl)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

7-(((4,5-dihydro-1H-imidazol-2-yl)amino)methyl)-2-(3,5-dimethoxybenzyl)-6-fluoro-3,4-dihydroisoquinolin-1(2H)-one;

7-((4,5-dihydrooxazol-2-yl)amino)methyl)-5-(1,3-dimethyl-1H-pyrazol-4-yl)-2-(4-methoxypyridin-2-yl)methyl)-3,4-dihydroisoquinolin-1(2H)-one;

7-(([1,2,4]triazolo[4,3-a]pyridin-3-ylamino)methyl)-2-((4-methoxypyridin-2-yl)methyl)-5-(1-methyl-3-(trifluoromethyl)-1H-pyrazol-4-yl)-3,4-dihydroisoquinolin-1(2H)-one;

4-cyclopropyl-6-((2-imino-3-methyl-2,3-dihydro-1H-imidazol-1-yl)methyl)-2-(4-methoxypyridin-2-yl)methyl)isoindolin-1-one;

4-(1-ethyl-3-(trifluoromethyl)-1H-pyrazol-4-yl)-6-((2-imino-3-methyl-2,3-dihydro-1H-imidazol-1-yl)methyl)-2-((4-methoxypyridin-2-yl)methyl)isoindolin-1-one;

4-(4-fluoro-2-methylphenyl)-6-((2-imino-3-methyl-2,3-dihydro-1H-imidazol-1-yl)methyl)-2-((4-methoxypyridin-2-yl)methyl)isoindolin-1-one;

6-(2-imino-3-methyl-2,3-dihydro-1H-imidazol-1-yl)methyl)-2-((4-methoxypyridin-2-yl)methyl)-4-(2-methylpyridin-3-yl)isoindolin-1-one;

2-(3,5-dimethoxybenzyl)-6-(4-fluoro-2-methylphenyl)-8-((2-imino-3-methyl-2,3-dihydro-1H-imidazol-1-yl)methyl)-2,3,4,5-tetrahydro-1H-benzo[c]azepin-1-one;

2-(3,5-dimethoxybenzyl)-6-(4-fluoro-2-methylphenyl)-8-((2-methyl-1H-imidazol-1-yl)methyl)-2,3,4,5-tetrahydro-1H-benzo[c]azepin-1-one;

2-((1,3-dimethyl-1H-pyrazol-5-yl)methyl)-5-(1-ethyl-3-(trifluoromethyl)-1H-pyrazol-4-yl)-7-((5-imino-1-methyl-1,5-dihydro-4H-1,2,4-triazol-4-yl)methyl)-3,4-dihydroisoquinolin-1(2H)-one;

2-((1,3-dimethyl-1H-pyrazol-4-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one;

(S)-2-(1-(4-fluoro-3-methylphenyl)ethyl)-5-(1-methyl-3-(trifluoromethyl)-1H-pyrazol-4-yl)-7-(((6-oxo-1,6-dihydropyridin-2-yl)amino)methyl)-3,4-dihydroisoquinolin-1(2H)-one;

(S)-5-(1,3-dimethyl-1H-pyrazol-4-yl)-2-(1-(4-fluoro-3-methylphenyl)ethyl)-7-((2-imino-3-methyl-2,3-dihydro-1H-imidazol-1-yl)methyl)-3,4-dihydroisoquinolin-1(2H)-one;

2-(3,5-dimethoxybenzyl)-5-(4-fluoro-2-methylphenyl)-7-((5-methyl-1H-1,2,4-triazol-1-yl)methyl)-3,4-dihydroisoquinolin-1(2H)-one;

2-(3,5-dimethoxybenzyl)-5-(4-fluoro-2-methylphenyl)-7-((3-methyl-4H-1,2,4-triazol-4-yl)methyl)-3,4-dihydroisoquinolin-1(2H)-one;

(S)-5-(1,3-dimethyl-1H-pyrazol-4-yl)-2-(1-(4-fluoro-3-methylphenyl)ethyl)-7-((2-methyl-1H-imidazol-1-yl)methyl)-3,4-dihydroisoquinolin-1(2H)-one;

2-((3-cyclopropyl-1-methyl-1H-pyrazol-5-yl)methyl)-7-((2-imino-3-methyl-2,3-dihydro-1H-imidazol-1-yl)methyl)-5-(1-methyl-3-(trifluoromethyl)-1H-pyrazol-4-yl)-3,4-dihydroisoquinolin-1(2H)-one;

2-((3-cyclopropyl-1-methyl-1H-pyrazol-5-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((2-ethyl-1H-imidazol-1-yl)methyl)-5-(1-ethyl-3-(trifluoromethyl)-1H-pyrazol-4-yl)-2-(4-ethylpyridin-2-yl)methyl)-3,4-dihydroisoquinolin-1(2H)-one;

2-((3-cyclopropyl-1-methyl-1H-pyrazol-5-yl)methyl)-7-((2-iminooxazol-3(2H)-yl)methyl)-5-(1-methyl-3-(trifluoromethyl)-1H-pyrazol-4-yl)-3,4-dihydroisoquinolin-1(2H)-one;

(S)-5-(1-ethyl-3-(trifluoromethyl)-1H-pyrazol-4-yl)-7-((2-iminothiazolidin-3-yl)methyl)-2-(1-(4-methoxypyridin-2-yl)ethyl)-3,4-dihydroisoquinolin-1(2H)-one;

(S)-5-(1-ethyl-3-(trifluoromethyl)-1H-pyrazol-4-yl)-7-((5-imino-1-methyl-1,5-dihydro-4H-1,2,4-triazol-4-yl)methyl)-2-(1-(4-methoxypyridin-2-yl)ethyl)-3,4-dihydroisoquinolin-1(2H)-one;

2-(3,5-dimethoxybenzyl)-5-(1,4-dimethyl-1H-imidazol-2-yl)-7-((2-imino-3-methyl-2,3-dihydro-1H-imidazol-1-yl)methyl)-3,4-dihydroisoquinolin-1(2H)-one;

2-(3,5-dimethoxybenzyl)-5-(2,6-dimethylpyridin-4-yl)-7-((2-imino-3-methyl-2,3-dihydro-1H-imidazol-1-yl)methyl)-3,4-dihydroisoquinolin-1(2H)-one;

2-(3,5-dimethoxybenzyl)-5-(2,6-dimethylpyridin-4-yl)-7-((2-ethyl-1H-imidazol-1-yl)methyl)-3,4-dihydroisoquinolin-1(2H)-one;

(S)-5-(1-ethyl-3-(trifluoromethyl)-1H-pyrazol-4-yl)-2-(1-(4-methoxypyridin-2-yl)ethyl)-7-((2-methyl-1H-imidazol-1-yl)methyl)-3,4-dihydroisoquinolin-1(2H)-one;

7-((2-Methyl-1H-imidazol-1-yl)methyl)-5-(1-methyl-3-(trifluoromethyl)-1H-pyrazol-4-yl)-2-((5-methylpyridin-3-yl)methyl)-3,4-dihydroisoquinolin-1(2H)-one;

(S)-7-((2-ethyl-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

(S)-7-((2-cyclopropyl-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

(S)-7-((1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

(S)-5-(1-ethyl-3-(trifluoromethyl)-1H-pyrazol-4-yl)-2-(1-(4-methoxypyridin-2-yl)ethyl)-7-((2-(methylamino)-1H-imidazol-1-yl)methyl)-3,4-dihydroisoquinolin-1(2H)-one;

(S)-5-(1-ethyl-3-(trifluoromethyl)-1H-pyrazol-4-yl)-7-((2-isopropyl-1H-imidazol-1-yl)methyl)-2-(1-(4-methoxypyridin-2-yl)ethyl)-3,4-dihydroisoquinolin-1(2H)-one;

(S)-2-(1-(5-fluoro-4-methylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-2-(1-(4,6-dimethylpyridin-2-yl)ethyl)-7-((2-ethyl-1H-imidazol-1-yl)methyl)-5-(1-methyl-3-(trifluoromethyl)-1H-pyrazol-4-yl)-3,4-dihydroisoquinolin-1(2H)-one;

(S)-2-(1-(4,6-dimethylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(R)-2-(1-(4,6-dimethylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((tetrahydro-2H-pyran-3-yl)methyl)-3,4-dihydroisoquinolin-1(2H)-one;

(S)-5-(4-fluoro-2-methylphenyl)-2-(1-(4-methoxypyridin-2-yl)ethyl)-7-((2-methyl-1H-imidazol-1-yl)methyl)-3,4-dihydroisoquinolin-1(2H)-one;

7-((2-methyl-1H-imidazol-1-yl)methyl)-5-(1-methyl-3-(trifluoromethyl)-1H-pyrazol-4-yl)-2-((tetrahydro-2H-pyran-2-yl)methyl)-3,4-dihydroisoquinolin-1(2H)-one;

2-(benzo[d][1,3]dioxol-5-ylmethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7(2-methyl-1H-imidazol-1-yl)methyl)-5-(1-methyl-3-(trifluoromethyl)-1H-pyrazol-4-yl)-2-((1-methylpiperidin-2-yl)methyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((1-methyl-6-oxopiperidin-3-yl)methyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((tetrahydro-2H-pyran-4-yl)methyl)-3,4-dihydroisoquinolin-1(2H)-one;

2-(5-methyl-1,3,4-thiadiazol-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one (S)-2-(1-(4-ethylpyridin-2-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-(quinolin-2-ylmethyl)-3,4-dihydroisoquinolin-1(2H)-one;

(S)-2-(cyclopropyl(4-methylpyridin-2-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one;

(S)-7-((4,5-dimethyl-1H-imidazol-1-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

(S)-1-((5-(1-ethyl-3-(trifluoromethyl)-1H-pyrazol-4-yl)-2-(1-(4-methoxypyridin-2-yl)ethyl)-1-oxo-1,2,3,4-tetrahydroisoquinolin-7-yl)methyl)-1H-imidazole-2-carbonitrile;

7-(2-methyl-1H-imidazol-1-yl)methyl)-5-(1-methyl-3-(trifluoromethyl)-1H-pyrazol-4-yl)-2-(pyridin-2-ylmethyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((3-methylpyridin-2-yl)methyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((6-methylpyridin-2-yl)methyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((5-methylpyridin-2-yl)methyl)-3,4-dihydroisoquinolin-1(2H)-one;

(S)-7-((1H-imidazol-1-yl)methyl)-2-(cyclopropyl(4-methylpyridin-2-yl)methyl)-5-(4-fluoro-2-methylphenyl)-3,4-dihydroisoquinolin-1(2H)-one;

(S)-7-(1H-imidazol-1-yl)methyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one;

2-(1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(1-ethyl-1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-methyl-1,3,4-oxadiazol-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-2-((1-methyl-1H-indol-3-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((3-methylisoxazol-5-yl)methyl)-3,4-dihydroisoquinolin-1(2H)-one;

(S)-7-(1H-imidazol-1-yl)methyl)-2-(1-(4-ethylpyridin-2-yl)ethyl)-5-(1-methyl-3-(trifluoromethyl)-1H-pyrazol-4-yl)-3,4-dihydroisoquinolin-1(2H)-one;

(S)-2-(1-(4-methoxypyridin-2-yl)ethyl)-7-((2-methyl-1H-imidazol-1-yl)methyl)-5-(2-(trifluoromethyl)pyridin-3-yl)-3,4-dihydroisoquinolin-1(2H)-one;

2-(1-isopropyl-1H-indol-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((5-methyloxazol-2-yl)methyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((5-methylthiazol-2-yl)methyl)-3,4-dihydroisoquinolin-1(2H)-one;

(S)-2-(1-(4-methoxypyridin-2-yl)ethyl)-7-((2-methyl-1H-imidazol-1-yl)methyl)-5-(4-methylpyridin-3-yl)-3,4-dihydroisoquinolin-1(2H)-one;

(R)-7-((2-methyl-1H-imidazol-1-yl)methyl)-5-(1-methyl-3-(trifluoromethyl)-1H-pyrazol-4-yl)-2-(1-(5-methylpyridin-3-yl)ethyl)-3,4-dihydroisoquinolin-1(2H)-one;

(R)-7-((2-methyl-1H-imidazol-1-yl)methyl)-5-(1-methyl-3-(trifluoromethyl)-1H-pyrazol-4-yl)-2-(1-(5-methylpyridin-3-yl)propyl)-3,4-dihydroisoquinolin-1(2H)-one;

(S)-7-((2-methyl-1H-imidazol-1-yl)methyl)-5-(1-methyl-3-(trifluoromethyl)-1H-pyrazol-4-yl)-2-(1-(5-methylpyridin-3-yl)propyl)-3,4-dihydroisoquinolin-1(2H)-one;

(S)-7-((2-methyl-1H-imidazol-1-yl)methyl)-5-(1-methyl-3-(trifluoromethyl)-1H-pyrazol-4-yl)-2-(1-(5-methylpyridin-3-yl)ethyl)-3,4-dihydroisoquinolin-1(2H)-one;

(S)-7-((1H-imidazol-1-yl)methyl)-2-(1-(5-fluoro-4-methylpyridin-2-yl)ethyl)-5-(1-methyl-3-(trifluoromethyl)-1H-pyrazol-4-yl)-3,4-dihydroisoquinolin-1(2H)-one;

(S)-2-(1-(4-methoxypyridin-2-yl)ethyl)-7-((2-methyl-1H-imidazol-1-yl)methyl)-5-(2-methylpyridin-3-yl)-3,4-dihydroisoquinolin-1(2H)-one;

(S)-2-(cyclopropyl(4-methoxypyridin-2-yl)methyl)-5-(1,3-dimethyl-1H-pyrazol-4-yl)-7-((2-methyl-1H-imidazol-1-yl)methyl)-3,4-dihydroisoquinolin-1(2H)-one;

2-((4-bromoquinolin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(4-bromopyridin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-2-(cyclopropyl(4-methoxypyridin-2-yl)methyl)-5-(1-ethyl-3-(trifluoromethyl)-1H-pyrazol-4-yl)-7-((2-methyl-1H-imidazol-1-yl)methyl)-3,4-dihydroisoquinolin-1(2H)-one;

2-(3-bromobenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((2-methylpyridin-4-yl)methyl)-3,4-dihydroisoquinolin-1(2H)-one;

7-((2-methyl-1H-imidazol-1-yl)methyl)-5-(1-methyl-3-(trifluoromethyl)-1H-pyrazol-4-yl)-2-(3-methylbenzyl)-3,4-dihydroisoquinolin-1(2H)-one;

2-(3-ethylbenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-7-((1H-imidazol-1-yl)methyl)-2-(cyclopropyl(4-methoxypyridin-2-yl)methyl)-5-(1,3-dimethyl-1H-pyrazol-4-yl)-3,4-dihydroisoquinolin-1(2H)-one;

(S)-7-((1H-imidazol-1-yl)methyl)-2-(cyclopropyl(4-methoxypyridin-2-yl)methyl)-5-(1-ethyl-3-(trifluoromethyl)-1H-pyrazol-4-yl)-3,4-dihydroisoquinolin-1(2H)-one;

2-(6-chloro-5-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(4-ethyl-2-((7-((2-methyl-1H-imidazol-1-yl)methyl)-5-(1-methyl-3-(trifluoromethyl)-1H-pyrazol-4-yl)-1-oxo-3,4-dihydroisoquinolin-2(1H)-yl)methyl)phenoxy)acetic acid;

2-(4-ethyl-2-((7-((2-methyl-1H-imidazol-1-yl)methyl)-5-(1-methyl-3-(trifluoromethyl)-1H-pyrazol-4-yl)-1-oxo-3,4-dihydroisoquinolin-2(1H)-yl)methyl)phenoxy)-N-(pyridin-3-ylmethyl)acetamide;

2-((5-bromo-2,3-dihydrobenzofuran-7-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-ethyl-2-methoxybenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((2-methyl-1H-imidazol-1-yl)methyl)-2-((5-methyl-2,3-dihydrobenzofuran-7-yl)methyl)-5-(1-methyl-3-(trifluoromethyl)-1H-pyrazol-4-yl)-3,4-dihydroisoquinolin-1(2H)-one;

2-(3-Bromo-5-(trifluoromethoxy)benzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(2-methyl-1H-imidazol-1-yl)methyl)-2-(3-(5-methyl-1H-indazol-4-yl)-5-(trifluoromethoxy)benzyl)-5-(1-methyl-3-(trifluoromethyl)-1H-pyrazol-4-yl)-3,4-dihydroisoquinolin-1(2H)-one;

7-((2-methyl-1H-imidazol-1-yl)methyl)-5-(1-methyl-3-(trifluoromethyl)-1H-pyrazol-4-yl)-2-(3-(trifluoromethyl)benzyl)-3,4-dihydroisoquinolin-1(2H)-one;

2-((5-bromo-2-chloropyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(2-chloro-5-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-2-(1-(4-methoxypyridin-2-yl)ethyl)-7-((2-methyl-1H-imidazol-1-yl)methyl)-5-(3-methylpyridin-4-yl)-3,4-dihydroisoquinolin-1(2H)-one;

2-(3-chlorobenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(3-chlorobenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-(1H-benzo[d]imidazol-1-yl)methyl)-2-(3,5-dimethoxybenzyl)-5-(4-fluoro-2-methylphenyl)-3,4-dihydroisoquinolin-1(2H)-one;

2-((5-methoxypyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

5-(5-Fluoro-2-methylpyridin-3-yl)-2-(4-methoxypyridin-2-yl)methyl)-7-((2-methyl-1H-imidazol-1-yl)methyl)-3,4-dihydroisoquinolin-1(2H)-one;

(S)-7-((1H-imidazol-2-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

7-((2-methyl-1H-imidazol-1-yl)methyl)-5-(1-methyl-3-(trifluoromethyl)-1H-pyrazol-4-yl)-2-(3-(thiophen-3-yl)benzyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((5-methylpyridazin-3-yl)methyl)-3,4-dihydroisoquinolin-1(2H)-one;

2-benzyl-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(3-cyclopropylbenzyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

7-((2-methyl-1H-imidazol-1-yl)methyl)-5-(1-methyl-3-(trifluoromethyl)-1H-pyrazol-4-yl)-2-(3-vinylbenzyl)-3,4-dihydroisoquinolin-1(2H)-one;

2-(6-bromo-1H-indol-4-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-2-(1-(4-methoxypyridin-2-yl)ethyl)-7-((2-methyl-1H-imidazol-1-yl)methyl)-5-(3-(trifluoromethyl)-1H-pyrazol-4-yl)-3,4-dihydroisoquinolin-1(2H)-one;

(S)-2-(1-(4-methoxypyridin-2-yl)ethyl)-7-((2-methyl-1H-imidazol-1-yl)methyl)-5-(3-methyl-1H-pyrazol-4-yl)-3,4-dihydroisoquinolin-1(2H)-one;

(S)-2-(1-(3-cyclopropyl-1-methyl-1H-pyrazol-5-yl)ethyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5-Bromo-6-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(5,6-dimethylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

2-(6-chloro-5-methylpyridin-3-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-5-(1-ethyl-3-(trifluoromethyl)-1H-pyrazol-4-yl)-2-(1-(5-methoxypyridin-3-yl)ethyl)-7-((2-methyl-1H-imidazol-1-yl)methyl)-3,4-dihydroisoquinolin-1(2H)-one;

(S)-2-(cyclopropyl(4-methoxypyridin-2-yl)methyl)-5-(1-ethyl-3-(trifluoromethyl)-1H-pyrazol-4-yl)-7-((4-methyl-1H-imidazol-1-yl)methyl)-3,4-dihydroisoquinolin-1(2H)-one;

(S)-7-((1H-imidazol-1-yl)methyl)-2-(cyclopropyl(4-methylpyridin-2-yl)methyl)-5-(1-ethyl-3-(trifluoromethyl)-1H-pyrazol-4-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-(4-phenylpyridin-3-yl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-((4-methylpyridin-2-yl)methyl)-3,4-dihydroisoquinolin-1(2H)-one;

(S)-2-(1-(4-methoxypyridin-2-yl)ethyl)-7-((2-methyl-1H-imidazol-1-yl)methyl)-5-(3-(trifluoromethyl)pyridin-4-yl)-3,4-dihydroisoquinolin-1(2H)-one;

(S)-2-(1-(4-methoxypyridin-2-yl)ethyl)-7-((2-methyl-1H-imidazol-1-yl)methyl)-5-(4-(trifluoromethyl)pyrimidin-5-yl)-3,4-dihydroisoquinolin-1(2H)-one;

(S)-7-((1H-imidazol-5-yl)methyl)-5-(1-ethyl-3-(trifluoromethyl)-1H-pyrazol-4-yl)-2-(1-(4-methoxypyridin-2-yl)ethyl)-3,4-dihydroisoquinolin-1(2H)-one;

(S)-2-(cyclopropyl(4-methoxypyridin-2-yl)methyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-7-((1H-imidazol-1-yl)methyl)-2-(cyclopropyl(4-methoxypyridin-2-yl)methyl)-5-(1-methyl-3-(trifluoromethyl)-1H-pyrazol-4-yl)-3,4-dihydroisoquinolin-1(2H)-one;

2-(2-(cyclopropylmethoxy)-4-fluorophenyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one;

(S)-5-(1-ethyl-3-(trifluoromethyl)-1H-pyrazol-4-yl)-2-(1-(4-methoxypyridin-2-yl)ethyl)-7-(1-methyl-1H-imidazol-2-yl)methyl)-3,4-dihydroisoquinolin-1(2H)-one;

7-(2-methyl-1H-imidazol-1-yl)methyl)-5-(1-methyl-3-(trifluoromethyl)-1H-pyrazol-4-yl)-2-(2-(trifluoromethoxy)phenyl)-3,4-dihydroisoquinolin-1(2H)-one;

2-(2-isopropoxyphenyl)-7-((2-methyl-1H-imidazol-1-yl)methyl)-5-(1-methyl-3-(trifluoromethyl)-1H-pyrazol-4-yl)-3,4-dihydroisoquinolin-1(2H)-one; and (S)-5-(1-ethyl-3-(trifluoromethyl)-1H-pyrazol-4-yl)-2-(1-(4-methoxypyridin-2-yl)ethyl)-7-(1-methyl-1H-imidazol-5-yl)methyl)-3,4-dihydroisoquinolin-1(2H)-one; or a pharmaceutically acceptable salt thereof.

Clause 62. The compound of any of clauses 1-61, or a pharmaceutically acceptable salt thereof, wherein the compound is isotopically labeled.

Clause 63. A pharmaceutical composition comprising the compound of any of clauses 1-62, or a pharmaceutically acceptable salt thereof, and a pharmaceutically acceptable carrier.

Clause 64. A method of treating cancer comprising administering to a subject in need thereof, a therapeutically effective amount of the compound of any of clauses 1-62, or a pharmaceutically acceptable salt thereof, or the pharmaceutical composition of clause 63.

Clause 65. A method of inhibiting cancer cell proliferation, comprising administering to a subject in need thereof, the compound of any of clauses 1-62, or a pharmaceutically acceptable salt thereof, or the pharmaceutical composition of clause 63, in an amount effective to inhibit the cancer cell proliferation.

Clause 66. Use of the compound of any of clauses 1-62, or a pharmaceutically acceptable salt thereof, or the pharmaceutical composition of clause 63, in the manufacture of a medicament for the treatment of cancer.

Clause 67. Use of the compound of any of clauses 1-62, or a pharmaceutically acceptable salt thereof, or the pharmaceutical composition of clause 63, in the manufacture of a medicament for the inhibition of cancer cell proliferation.

Clause 68. The compound of any of clauses 1-62, or a pharmaceutically acceptable salt thereof, or the pharmaceutical composition of clause 63, for use in the treatment of cancer.

Clause 69. The compound of any of clauses 1-62, or a pharmaceutically acceptable salt thereof, or the pharmaceutical composition of clause 63, for use in the inhibition of cancer cell proliferation.

What is claimed is:

1. A compound of formula (I)

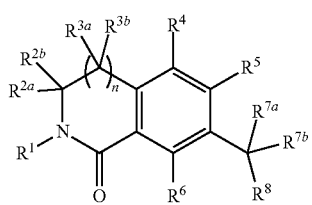

(I)

or a pharmaceutically acceptable salt thereof, wherein:
n is 1;
$R^1$ is —$(CR^aR^b)$-$G^1$;
$G^1$ is a 6 or 5-membered aromatic ring optionally containing 1-2 nitrogen atoms, wherein $G^1$ is substituted with 1-3 substituents independently selected from the group consisting of —$OC_{1-4}$alkyl, $C_{1-4}$alkyl, halogen, and $C_{3-6}$cycloalkyl;

$R^a$ is $C_{1-4}$alkyl, $C_{3-6}$cycloalkyl, or hydrogen;
$R^b$ is hydrogen;
$R^{2a}$, $R^{2b}$, $R^{3a}$, and $R^{3b}$ are each hydrogen;
$R^4$ is a 5 or 6-membered aromatic ring optionally containing 1-2 nitrogen atoms, wherein $R^4$ is substituted with 2, 1, or 3 substituents independently selected from the group consisting of $C_{1-4}$haloalkyl, $C_{1-4}$alkyl, and halogen;
$R^5$ is hydrogen;
$R^6$ is hydrogen;
$R^{7a}$ and $R^{7b}$ are each hydrogen; and
$R^8$ is a 5-membered heterocyclic ring containing 2-3 heteroatoms and 2 or 1 double bonds, wherein one of the 2-3 heteroatoms is a nitrogen and the remaining heteroatoms are independently selected from nitrogen and oxygen, wherein $R^8$ is optionally substituted with 1-3 substituents independently selected from the group consisting of $C_{1-4}$alkyl, imino, $C_{1-4}$haloalkyl, —NH($C_{1-4}$alkyl), halogen, cyano, $NH_2$, —N$(C_{1-4}$alkyl$)_2$, $C_{3-6}$cycloalkyl, and —$C_{1-3}$alkylene-$C_{3-6}$cycloalkyl.

2. The compound of claim 1, or a pharmaceutically acceptable salt thereof, wherein
$R^8$ is imidazolyl or

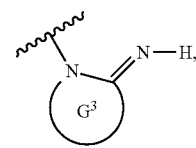

the imidazolyl being optionally substituted with 1-3 substituents independently selected from the group consisting of $C_{1-4}$alkyl, —N$(C_{1-4}$alkyl$)_2$, $C_{1-4}$haloalkyl, —NH$(C_{1-4}$alkyl), halogen, cyano, $NH_2$, $C_{3-6}$cycloalkyl, and —$C_{1-3}$alkylene-$C_{3-6}$cycloalkyl; and $G^3$ is a 5-membered heterocyclic ring containing a first nitrogen at the point of attachment and optionally 1-2 additional heteroatoms selected from the group consisting of nitrogen and oxygen, $G^3$ having the imine substituent =NH adjacent to the first nitrogen and being optionally substituted with 1-3 substituents independently selected from the group consisting of $C_{1-4}$alkyl, $C_{1-4}$haloalkyl, $C_{3-6}$cycloalkyl, and —$C_{1-3}$alkylene-$C_{3-6}$cycloalkyl.

3. The compound of claim 2, or a pharmaceutically acceptable salt thereof, wherein $R^8$ is

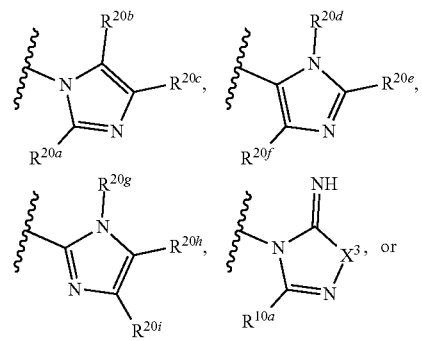

-continued

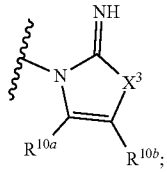

$X^3$ is $NR^{13}$ or O;

$R^{10a}$ and $R^{10b}$ are independently hydrogen, $C_{1-4}$alkyl, or $C_{1-4}$haloalkyl;

$R^{13}$ is $C_{1-4}$alkyl, $C_{1-4}$haloalkyl, $C_{3-6}$cycloalkyl, or —$C_{1-3}$alkylene-$C_{3-6}$cycloalkyl;

$R^{20a}$ is hydrogen, $C_{1-4}$alkyl, —NH($C_{1-4}$alkyl), NH$_2$, —N($C_{1-4}$alkyl)$_2$, or $C_{3-6}$cycloalkyl; and $R^{20b}$, $R^{20c}$, $R^{20d}$, $R^{20e}$, $R^{20f}$, $R^{20g}$, $R^{20h}$, and $R^{20i}$, are each independently hydrogen, $C_{1-4}$alkyl, or $C_{3-6}$cycloalkyl.

4. The compound of claim 3, or a pharmaceutically acceptable salt thereof, wherein $R^8$ is

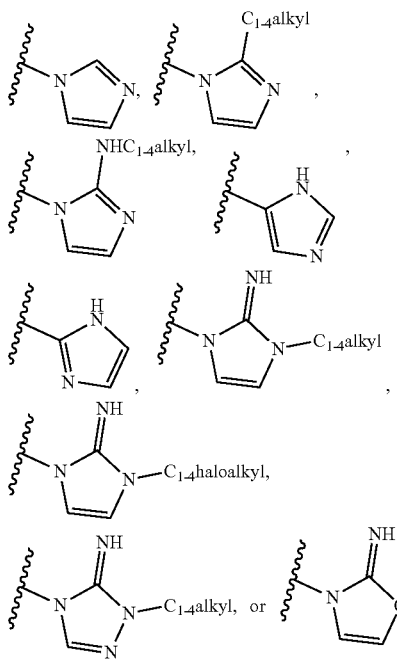

5. The compound of claim 3, or a pharmaceutically acceptable salt thereof, wherein $G^1$ is pyridinyl, phenyl, pyridazinyl, or pyrazolyl, and substituted with 1-3 substituents independently selected from the group consisting of —O$C_{1-4}$alkyl, $C_{1-4}$alkyl, halogen, and $C_{3-6}$cycloalkyl.

6. The compound of claim 4, or a pharmaceutically acceptable salt thereof, wherein $G^1$ is

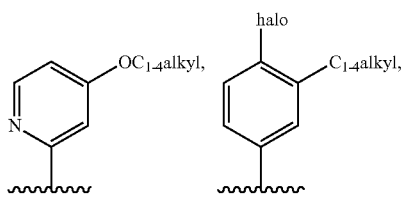

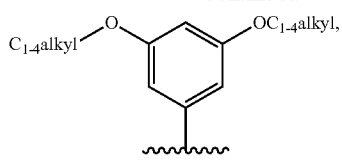

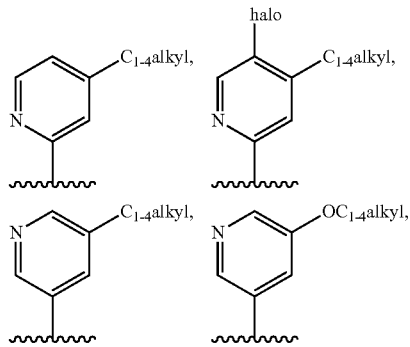

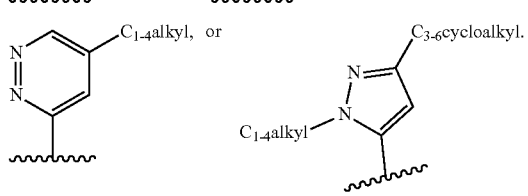

7. The compound of claim 5, or a pharmaceutically acceptable salt thereof, wherein $R^4$ is pyrazolyl, phenyl, or pyridinyl, and substituted with 2, 1, or 3 substituents independently selected from the group consisting of $C_{1-4}$haloalkyl, $C_{1-4}$alkyl, and halogen.

8. The compound of claim 7, or a pharmaceutically acceptable salt thereof, wherein $R^4$ is

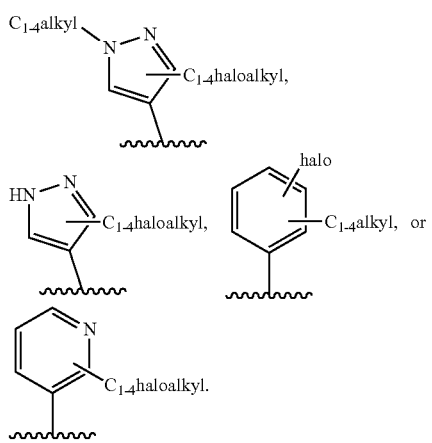

9. The compound of claim 8, or a pharmaceutically acceptable salt thereof, wherein $R^4$ is

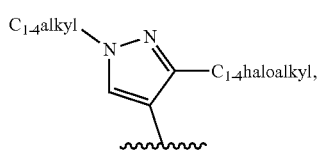

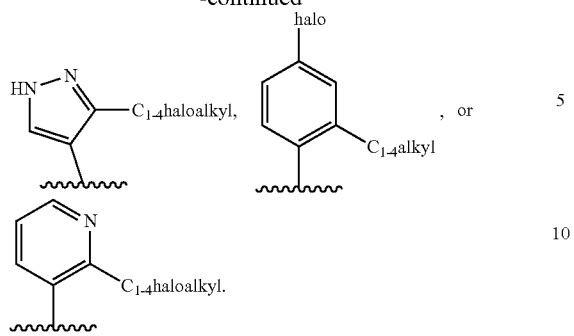

10. A pharmaceutical composition comprising the compound of claim 1, or a pharmaceutically acceptable salt thereof, and a pharmaceutically acceptable carrier.

11. A method of treating cancer comprising administering to a subject in need thereof, a therapeutically effective amount of the compound of claim 1, or a pharmaceutically acceptable salt thereof.

12. A method of inhibiting cancer cell proliferation, comprising administering to a subject in need thereof, the compound of claim 1, or a pharmaceutically acceptable salt thereof, in an amount effective to inhibit the cancer cell proliferation.

* * * * *